(12) United States Patent
Fan et al.

(10) Patent No.: US 8,614,221 B2
(45) Date of Patent: Dec. 24, 2013

(54) INHIBITORS OF AKT ACTIVITY

(75) Inventors: Weiming Fan, Chapel Hill, NC (US); Thomas F. N. Haxell, Morrisville, NC (US); Matthew G. Jenks, Durham, NC (US); Nobuhiko Kawanishi, Moriya (JP); Shuliang Lee, Durham, NC (US); Hao Liu, Raleigh, NC (US); Michael J. Malaska, Chapel Hill, NC (US); Joseph A. Moore, III, Raleigh, NC (US); Yoshio Ogino, Tsukuba (JP); Yu Onozaki, Yokohama (JP); Bharathi Pandi, Cary, NC (US); Michael R. Peel, Chapel Hill, NC (US); Toshihiro Sakamoto, Moriya (JP); Tony Siu, Brookline, MA (US)

(73) Assignees: Merck Sharp & Dohme Corp., Rahway, NJ (US); MSD K.K., Chiyoda-Ku, Tokyo (JP)

( * ) Notice: Subject to any disclaimer, the term of this patent is extended or adjusted under 35 U.S.C. 154(b) by 169 days.

(21) Appl. No.: 13/255,785

(22) PCT Filed: Mar. 10, 2010

(86) PCT No.: PCT/US2010/026796
§ 371 (c)(1), (2), (4) Date: Sep. 9, 2011

(87) PCT Pub. No.: WO2010/104933
PCT Pub. Date: Sep. 16, 2010

(65) Prior Publication Data
US 2012/0004240 A1 Jan. 5, 2012

Related U.S. Application Data

(60) Provisional application No. 61/159,230, filed on Mar. 11, 2009.

(51) Int. Cl.
*A61K 31/519* (2006.01)
*C07D 471/12* (2006.01)

(52) U.S. Cl.
USPC ........... 514/268; 544/242; 544/251; 514/256; 514/267

(58) Field of Classification Search
USPC .......... 544/242, 245, 249, 251; 514/256, 257, 514/267, 268
See application file for complete search history.

(56) References Cited

U.S. PATENT DOCUMENTS

| | | | |
|---|---|---|---|
| 4,072,680 A | 2/1978 | Denzel et al. | |
| 7,544,677 B2 * | 6/2009 | Bilodeau et al. | 514/210.21 |
| 7,910,561 B2 * | 3/2011 | Arruda et al. | 514/43 |
| 8,008,317 B2 * | 8/2011 | Armstrong et al. | 514/290 |
| 8,207,169 B2 * | 6/2012 | Furuyama et al. | 514/250 |
| 2007/0254879 A1 | 11/2007 | Arrington et al. | |
| 2008/0293712 A1 | 11/2008 | Wissner et al. | |

FOREIGN PATENT DOCUMENTS

| | | |
|---|---|---|
| WO | 2004081008 | 9/2004 |
| WO | 2006135627 | 12/2006 |
| WO | 2009148887 | 12/2009 |
| WO | 2009148916 | 12/2009 |

\* cited by examiner

*Primary Examiner* — Golam M M Shameem
(74) *Attorney, Agent, or Firm* — Yong Zhao; Laura M. Ginkel; Matthew A. Leff

(57) ABSTRACT

The instant invention provides for substituted fused naphthyridine derivatives that inhibit Akt activity. In particular, the compounds disclosed selectively inhibit one or two of the Akt isoforms. The invention also provides for compositions comprising such inhibitory compounds and methods of inhibiting Akt activity by administering the compound to a patient in need of treatment of cancer.

5 Claims, No Drawings

SEQUENCE LISTING

<160> NUMBER OF SEQ ID NOS: 16

<210> SEQ ID NO 1
<211> LENGTH: 10
<212> TYPE: DNA
<213> ORGANISM: Artificial Sequence
<220> FEATURE:
<223> OTHER INFORMATION: Completely Synthetic DNA Sequence

<400> SEQUENCE: 1
ctgcggccgc                                                          10

<210> SEQ ID NO 2
<211> LENGTH: 14
<212> TYPE: DNA
<213> ORGANISM: Artificial Sequence
<220> FEATURE:
<223> OTHER INFORMATION: Completely Synthetic DNA Sequence

<400> SEQUENCE: 2
gtacgcggcc gcag                                                     14

<210> SEQ ID NO 3
<211> LENGTH: 39
<212> TYPE: DNA
<213> ORGANISM: Artificial Sequence
<220> FEATURE:
<223> OTHER INFORMATION: Completely Synthetic DNA Sequence

<400> SEQUENCE: 3
cgcgaattca gatctaccat gagcgacgtg gctattgtg                          39

<210> SEQ ID NO 4
<211> LENGTH: 33
<212> TYPE: DNA
<213> ORGANISM: Artificial Sequence
<220> FEATURE:
<223> OTHER INFORMATION: Completely Synthetic DNA Sequence

<400> SEQUENCE: 4
cgctctagag gatcctcagg ccgtgctgct ggc                                33

<210> SEQ ID NO 5
<211> LENGTH: 24
<212> TYPE: DNA
<213> ORGANISM: Artificial Sequence
<220> FEATURE:
<223> OTHER INFORMATION: Completely Synthetic DNA Sequence

<400> SEQUENCE: 5
gtacgatgct gaacgatatc ttcg                                          24

<210> SEQ ID NO 6
<211> LENGTH: 45
<212> TYPE: DNA
<213> ORGANISM: Artificial Sequence
<220> FEATURE:
<223> OTHER INFORMATION: Completely Synthetic DNA Sequence

<400> SEQUENCE: 6
gaatacatgc cgatggaaag cgacggggct gaagagatgg aggtg                   45

<210> SEQ ID NO 7
<211> LENGTH: 45
<212> TYPE: DNA

```
<213> ORGANISM: Artificial Sequence
<220> FEATURE:
<223> OTHER INFORMATION: Completely Synthetic DNA Sequence

<400> SEQUENCE: 7
cccctccatc tcttcagccc cgtcgctttc catcggcatg tattc                45

<210> SEQ ID NO 8
<211> LENGTH: 36
<212> TYPE: DNA
<213> ORGANISM: Artificial Sequence
<220> FEATURE:
<223> OTHER INFORMATION: Completely Synthetic DNA Sequence

<400> SEQUENCE: 8
gaattcagat ctaccatgag cgatgttacc attgtg                          36

<210> SEQ ID NO 9
<211> LENGTH: 30
<212> TYPE: DNA
<213> ORGANISM: Artificial Sequence
<220> FEATURE:
<223> OTHER INFORMATION: Completely Synthetic DNA Sequence

<400> SEQUENCE: 9
tctagatctt attctcgtcc acttgcagag                                 30

<210> SEQ ID NO 10
<211> LENGTH: 48
<212> TYPE: DNA
<213> ORGANISM: Artificial Sequence
<220> FEATURE:
<223> OTHER INFORMATION: Completely Synthetic DNA Sequence

<400> SEQUENCE: 10
ggtaccatgg aatacatgcc gatggaaagc gatgttacca ttgtgaag             48

<210> SEQ ID NO 11
<211> LENGTH: 33
<212> TYPE: DNA
<213> ORGANISM: Artificial Sequence
<220> FEATURE:
<223> OTHER INFORMATION: Completely Synthetic DNA Sequence

<400> SEQUENCE: 11
aagcttagat ctaccatgaa tgaggtgtct gtc                             33

<210> SEQ ID NO 12
<211> LENGTH: 30
<212> TYPE: DNA
<213> ORGANISM: Artificial Sequence
<220> FEATURE:
<223> OTHER INFORMATION: Completely Synthetic DNA Sequence

<400> SEQUENCE: 12
gaattcggat cctcactcgc ggatgctggc                                 30

<210> SEQ ID NO 13
<211> LENGTH: 49
<212> TYPE: DNA
<213> ORGANISM: Artificial Sequence
<220> FEATURE:
<223> OTHER INFORMATION: Completely Synthetic DNA Sequence

<400> SEQUENCE: 13
ggtaccatgg aatacatgcc gatggaaaat gaggtgtctg tcatcaaag            49
```

```
<210> SEQ ID NO 14
<211> LENGTH: 6
<212> TYPE: PRT
<213> ORGANISM: Artificial Sequence
<220> FEATURE:
<223> OTHER INFORMATION: Completely Synthetic Amino Acid Sequence

<400> SEQUENCE: 14

Glu Tyr Met Pro Met Glu
 1               5

<210> SEQ ID NO 15
<211> LENGTH: 13
<212> TYPE: PRT
<213> ORGANISM: Artificial Sequence
<220> FEATURE:
<223> OTHER INFORMATION: Completely Synthetic Amino Acid Sequence

<400> SEQUENCE: 15

Gly Gly Arg Ala Arg Thr Ser Ser Phe Ala Glu Pro Gly
 1               5                  10

<210> SEQ ID NO 16
<211> LENGTH: 15
<212> TYPE: PRT
<213> ORGANISM: Artificial Sequence
<220> FEATURE:
<223> OTHER INFORMATION: Completely Synthetic Amino Acid Sequence

<400> SEQUENCE: 16

Lys Lys Gly Gly Arg Ala Arg Thr Ser Ser Phe Ala Glu Pro Gly
 1               5                  10                  15
```

US 8,614,221 B2

INHIBITORS OF AKT ACTIVITY

REFERENCE TO SEQUENCE LISTING SUBMITTED ELECTRONICALLY

The sequence listing of the present application is being submitted electronically via EFS-Web as an ASCII formatted sequence listing with a file name "BANONC00014USPCT-SEQTXT-09SEP2011.txt", creation date of Sep. 8, 2011 and a size of 3,809 bytes. This sequence listing submitted via EFS-Web is part of the specification and is herein incorporated by reference in its entirety.

BACKGROUND OF THE INVENTION

The present invention relates to substituted naphthyridine compounds which are inhibitors of the activity of one or more of the isoforms of the serine/threonine kinase, Akt (also known as PKB; hereinafter referred to as "Akt"). The present invention also relates to pharmaceutical compositions comprising such compounds and methods of using the instant compounds in the treatment of cancer.

Apoptosis (programmed cell death) plays essential roles in embryonic development and pathogenesis of various diseases, such as degenerative neuronal diseases, cardiovascular diseases and cancer. Recent work has led to the identification of various pro- and anti-apoptotic gene products that are involved in the regulation or execution of programmed cell death. Expression of anti-apoptotic genes, such as Bcl2 or Bcl-xL, inhibits apoptotic cell death induced by various stimuli. On the other hand, expression of pro-apoptotic genes, such as Bax or Bad, leads to programmed cell death (Adams et al. *Science*, 281:1322-1326 (1998)). The execution of programmed cell death is mediated by caspase-1 related proteinases, including caspase-3, caspase-7, caspase-8 and caspase-9 etc (Thornberry et al. *Science*, 281:1312-1316 (1998)).

The phosphatidylinositol 3'-OH kinase (PI3K)/Akt pathway appears important for regulating cell survival/cell death (Kulik et al. *Mol. Cell. Biol.* 17:1595-1606 (1997); Franke et al, *Cell*, 88:435-437 (1997); Kauffmann-Zeh et al. *Nature* 385:544-548 (1997) Hemmings *Science*, 275:628-630 (1997); Dudek et al., *Science*, 275:661-665 (1997)). Survival factors, such as platelet derived growth factor (PDGF), nerve growth factor (NGF) and insulin-like growth factor-1 (IGF-1), promote cell survival under various conditions by inducing the activity of PI3K (Kulik et al. 1997, Hemmings 1997). Activated PI3K leads to the production of phosphatidylinositol (3,4,5)-triphosphate (PtdIns(3,4,5)-P3), which in turn binds to, and promotes the activation of, the serine/threonine kinase Akt, which contains a pleckstrin homology (PH)-domain (Franke et al *Cell*, 81:727-736 (1995); Hemmings *Science*, 277:534 (1997); Downward, *Curr. Opin. Cell Biol.* 10:262-267 (1998), Alessi et al., *EMBO J.* 15: 6541-6551 (1996)). Specific inhibitors of PI3K or dominant negative Akt mutants abolish survival-promoting activities of these growth factors or cytokines. It has been previously disclosed that inhibitors of PI3K (LY294002 or wortmannin) blocked the activation of Akt by upstream kinases. In addition, introduction of constitutively active PI3K or Akt mutants promotes cell survival under conditions in which cells normally undergo apoptotic cell death (Kulik et al. 1997, Dudek et al. 1997).

Three members of the Akt subfamily of second-messenger regulated serine/threonine protein kinases have been identified and termed Akt1/PKBα, Akt2/PKBβ, and Akt3/PKBγ (hereinafter referred to as "Akt1", "Akt2" and "Akt3"), respectively. The isoforms are homologous, particularly in regions encoding the catalytic domains. Akts are activated by phosphorylation events occurring in response to PI3K signaling. PI3K phosphorylates membrane inositol phospholipids, generating the second messengers phosphatidyl-inositol 3,4,5-trisphosphate and phosphatidylinositol 3,4-bisphosphate, which have been shown to bind to the PH domain of Akt. The current model of Akt activation proposes recruitment of the enzyme to the membrane by Y-phosphorylated phosphoinositides, where phosphorylation of the regulatory sites of Akt by the upstream kinases occurs (B. A. Hemmings, *Science* 275:628-630 (1997); B. A. Hemmings, *Science* 276:534 (1997); J. Downward, *Science* 279:673-674 (1998)).

Phosphorylation of Akt1 occurs on two regulatory sites, Thr$^{308}$ in the catalytic domain activation loop and on Ser$^{473}$ near the carboxy terminus (D. R. Alessi et al. *EMBO J.* 15:6541-6551 (1996) and R. Meier et al. *J. Biol. Chem.* 272: 30491-30497 (1997)). Equivalent regulatory phosphorylation sites occur in Akt2 and Akt3. The upstream kinase, which phosphorylates Akt at the activation loop site has been cloned and termed 3'-phosphoinositide-dependent protein kinase 1 (PDK1). PDK1 phosphorylates not only Akt, but also p70 ribosomal S6 kinase, p90RSK, serum and glucocorticoid-regulated kinase (SGK), and protein kinase C. The upstream kinase phosphorylating the regulatory site of Akt near the carboxy terminus has not been identified yet, but recent reports provide evidences indicating that following molecules mediate this event; the rapamycin insensitive mammalian target of rapamycin complex (mTORC2) (D. D. Sarbassov et al. *Science* 307: 1098-1101 (2007)), integrin-linked kinase (ILK-1) (S. Persad et al. *J. Biol. Chem.* 276: 27462-27469 (2001)), PDK1 (A. Balendran et al. *Curr Biol.* 9: 393-404 (1999)), DNA-dependent protein kinase (DNA-PK) (J Feng et al. J. Biol. Chem. 279: 41189-41196 (2004)), and AKT itself (A. Toker and A. C. Newton. *J. Biol. Chem.* 275: 8271-8274 (2000)).

Analysis of Akt levels in human tumors showed that Akt2 is overexpressed in a significant number of ovarian (J. Q. Cheng et al. *Proc. Natl. Acad. Sci. U.S.A.* 89:9267-9271 (1992)) and pancreatic cancers (J. Q. Cheng et al. *Proc. Natl. Acad. Sci. U.S.A.* 93:3636-3641 (1996)). Similarly, Akt3 was found to be overexpressed in breast and prostate cancer cell lines (Nakatani et al. *J. Biol. Chem.* 274:21528-21532 (1999).

The tumor suppressor PTEN, a protein and lipid phosphatase that specifically removes the 3' phosphate of PtdIns (3,4,5)-P3, is a negative regulator of the PI3K/Akt pathway (Li et al. *Science* 275:1943-1947 (1997), Stambolic et al. *Cell* 95:29-39 (1998), Sun et al. *Proc. Natl. Acad. Sci. U.S.A.* 96:6199-6204 (1999)). Germline mutations of PTEN are responsible for human cancer syndromes such as Cowden disease (Liaw et al. *Nature Genetics* 16:64-67 (1997)). PTEN is deleted in a large percentage of human tumors and tumor cell lines without functional PTEN show elevated levels of activated Akt (Li et al. supra, Guldberg et al. *Cancer Research* 57:3660-3663 (1997), Risinger et al. *Cancer Research* 57:4736-4738 (1997)).

These observations demonstrate that the PI3K/Akt pathway plays important roles for regulating cell survival or apoptosis in tumorigenesis.

Inhibition of Akt activation and activity can be achieved by inhibiting PI3K with inhibitors such as LY294002 and wortmannin. However, PI3K inhibition has the potential to indiscriminately affect not just all three Akt isozymes but also other PH domain-containing signaling molecules that are dependent on PdtIns(3,4,5)-P3, such as the Tec family of tyrosine kinases. Furthermore, it has been disclosed that Akt can be activated by growth signals that are independent of PI3K.

Alternatively, Akt activity can be inhibited by blocking the activity of the upstream kinase PDK1. No specific PDK1 inhibitors have been disclosed. Again, inhibition of PDK1 would result in inhibition of multiple protein kinases whose activities depend on PDK1, such as atypical PKC isoforms, SGK, and S6 kinases (Williams et al. Curr. Biol. 10:439-448 (2000)).

It was also reported that deficiency of Akt1 is sufficient to inhibit tumorigenesis in several genetically modified mice tumor models, such as PTEN+/− model as prostate tumors (M. L. Chen et al. Genes & Dev. 20:1569-1574 (2006)), MMTV-ErbB2/Nue and MMTV-polyoma middle T transgenic mice as breast tumor models (I. G. Maroulakou et al. Cancer Res. 67: 167-177 (2007)).

Mice lacking the Akt2 showed diabetes mellitus-like syndrome by the impairment in the ability of insulin to lower blood glucose (J. L. Thorvaldsen et al. Science. 292: 1728-1731 (2001) and R. S. Garofalo et al. J. Clin. Invest. 112:197-208 (2003)).

Inhibitors of Akt are known. WO2005/100344; WO2005/100356; WO2004/096135; WO2004/096129; WO2004/096130; WO2004/096131; WO2006/091395; WO2008/070134; WO2009/148916; WO2008/070016; WO2008/070041; WO2004/041162; WO2009/148887; WO2006/068796; WO2006/065601; WO2006/110638; WO2003/086394; WO2003/086403; WO2003/086404; WO2003/086279; WO2002/083139; WO2002/083675; WO2006/036395; WO2002/083138; WO2006/135627; and WO2002/083140. The compounds disclosed in these patent applications contain mono-, bi- and tri-cyclic core moieties.

Specific Akt inhibitors substituted with a methyl amine moiety are known. WO2006/135627; WO2008/070041; WO2008/070016; WO2008/070134; WO2009/148887; and WO2009/148916.

Specific Akt inhibitors which contain a tri-cyclic core moiety are disclosed in WO2006/135627

The compounds of the instant invention contain a unique tri-cyclic core moiety which has not been previously disclosed.

It is an object of the instant invention to provide novel compounds that are inhibitors of Akt.

It is also an object of the present invention to provide pharmaceutical compositions that comprise the novel compounds that are inhibitors of Akt.

It is also an object of the present invention to provide a method for treating cancer that comprises administering such inhibitors of Akt activity.

SUMMARY OF THE INVENTION

The instant invention provides for fused naphthyridine derivatives that inhibit Akt activity. In particular, the compounds disclosed selectively inhibit one or two of the Akt isoforms. The invention also provides for compositions comprising such inhibitory compounds and methods of inhibiting Akt activity by administering the compound to a patient in need of treatment of cancer.

DETAILED DESCRIPTION OF THE INVENTION

The compounds of the instant invention are useful in the inhibition of the activity of the serine/threonine kinase Akt. In a first embodiment of this invention, the inhibitors of Akt activity are illustrated by the Formula A:

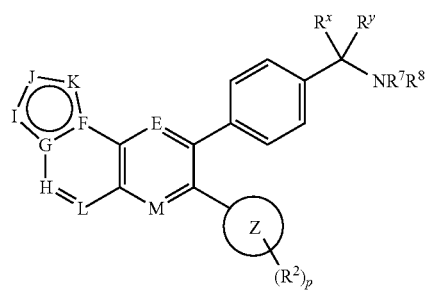

wherein:
E, F, G, H, I, J, K, L and M are independently selected from: C or N, wherein each E, F, G, H, I, J, K, L and M is optionally substituted with $R^1$;
a is 0 or 1; b is 0 or 1; m is 0, 1 or 2; p is independently 0, 1, 2, 3, 4 or 5;
Ring Z is selected from: $(C_3\text{-}C_8)$cycloalkyl, aryl, and heterocyclyl;
$R^1$ is selected from: H, oxo, $(C=O)_aO_b(C_1\text{-}C_{10})$alkyl, $(C=O)_aO_b$-aryl, $(C=O)_aO_b(C_2\text{-}C_{10})$alkenyl, $(C=O)_aO_b(C_2\text{-}C_{10})$alkynyl, $CO_2H$, halo, OH, $O_b(C_1\text{-}C_6)$perfluoroalkyl, $(C=O)_aNR^7R^8$, CN, $(C=O)_aO_b(C_3\text{-}C_8)$cycloalkyl, $S(O)_m$ $NR^7R^8$, SH, $S(O)_m$—$(C_1\text{-}C_{10})$alkyl and $(C=O)_aO_b$-heterocyclyl, said alkyl, aryl, alkenyl, alkynyl, cycloalkyl, and heterocyclyl is optionally substituted with one or more substituents selected from $R^6$;
$R^2$ is independently selected from: oxo, $(C=O)_aO_b(C_1\text{-}C_{10})$alkyl, $(C=O)_aO_b$-aryl, $(=O)_aO_b(C_2\text{-}C_{10})$alkenyl, $(C=O)_aO_b$ $(C_2\text{-}C_{10})$alkynyl, $CO_2H$, halo, OH, $O_b(C_1\text{-}C_6)$ perfluoroalkyl, $(C=O)_aNR^7R^8$, CN, $(C=O)_aO_b(C_3\text{-}C_8)$cycloalkyl, $S(O)_mNR^7R^8$, SH, $S(O)_m$—$(C_1\text{-}C_{10})$alkyl and $(C=O)_aO_b$-heterocyclyl, said alkyl, aryl, alkenyl, alkynyl, cycloalkyl, and heterocyclyl is optionally substituted with one or more substituents selected from $R^6$;
$R^6$ is: $(C=O)_aO_b(C_1\text{-}C_{10})$alkyl, $(C=O)_aO_b$aryl, $(C_2\text{-}C_{10})$alkenyl, $(C_2\text{-}C_{10})$alkynyl, $(C=O)_aO_b$ heterocyclyl, $CO_2H$, halo, CN, OH, $O_b(C_1\text{-}C_6)$perfluoroalkyl, $O_a(C=O)_bNR^7R^8$, oxo, CHO, $(N=O)R^7R^8$, $S(O)_mNR^7R^8$, SH, $S(O)_m$—$(C_1\text{-}C_{10})$alkyl or $(C=O)_aO_b(C_3\text{-}C_8)$cycloalkyl, said alkyl, aryl, alkenyl, alkynyl, heterocyclyl, and cycloalkyl optionally substituted with one or more substituents selected from $R^{6a}$;
$R^{6a}$ is selected from: $(C=O)_aO_b(C_1\text{-}C_{10})$alkyl, $O_a(C_1\text{-}C_3)$ perfluoroalkyl, $(C_0\text{-}C_6)$alkylene-$S(O)_mR^a$, SH, oxo, OH, halo, CN, $(C_2\text{-}C_{10})$alkenyl, $(C_2\text{-}C_{10})$alkynyl, $(C_3\text{-}C_6)$cycloalkyl, $(C_0\text{-}C_6)$alkylene-aryl, $(C_0\text{-}C_6)$alkylene-heterocyclyl, $(C_0\text{-}C_6)$alkylene-$N(R^b)_2$, $C(O)R^a$, $(C_0\text{-}C_6)$alkylene-$CO_2R^a$, $C(O)H$, $(C=O)_aNR^b_2$, and $(C_0\text{-}C_6)$alkylene-$CO_2H$, said alkyl, alkenyl, alkynyl, cycloalkyl, aryl, and heterocyclyl is optionally substituted with up to three substituents selected from $R^b$, OH, halogen, $CO_2H$, CN, $O_a(C=O)_b(C_1\text{-}C_6)$alkyl, oxo, and $N(R^b)_2$;
$R^7$ and $R^8$ are independently selected from: H, $(C=O)_aO_b$ $(C_1\text{-}C_{10})$alkyl, $(C=O)_aO_b(C_3\text{-}C_8)$cycloalkyl, $(C=O)_aO_b$-aryl, $(C=O)_aO_b$-heterocyclyl, $(C_2\text{-}C_{10})$alkenyl, $(C_2\text{-}C_{10})$alkynyl, SH, $SO_2R^a$, and $(C=O)_aNR^b_2$, said alkyl, cycloalkyl, aryl, heterocyclyl, alkenyl, and alkynyl is optionally substituted with one or more substituents selected from $R^{6a}$, or $R^7$ and $R^8$ can be taken together with the nitrogen to which they are attached to form a monocyclic, bicyclic or tricyclic heterocycle with 3-7 members in each ring and optionally containing, in addition to the nitrogen, one or two additional heteroatoms selected from N, O and S, said monocyclic, bicyclic or tricyclic heterocycle is optionally substituted with one or more substituents selected from $R^{6a}$;

$R^a$ is $(C_1-C_6)$alkyl, $(C_3-C_6)$cycloalkyl, aryl, or heterocyclyl, said alkyl, cycloalkyl, aryl, and heterocyclyl is optionally substituted with one or more substituents selected from $R^c$;

$R^b$ is independently: H, $(C=O)_aO_b(C_1-C_6)$alkyl, $(C_2-C_{10})$alkenyl, $S(O)_mR^a$, $(C=O)_aNR^d_2$, $(C=O)_aR^a$, or $S(O)_mNR^e_2$, said alkyl and alkenyl is optionally substituted with one or more substituents selected from $R^a$, $(C=O)_aO_b(C_1-C_6)$alkyl, OH, halo, CN, $CO_2H$, and $(C=O)_aNR^d_2$;

$R^c$ is independently: $(C=O)_aO_b(C_1-C_6)$alkyl, aryl, heterocyclyl, $(C_3-C_6)$cycloalkyl, oxo, OH, halo, CN, $(C=O)_aNR^d_2$, or $S(O)_mR^d$, said alkyl, aryl, heterocyclyl, and cycloalkyl is optionally substituted with one or more substituents selected from $(C=O)_aO_b(C_1-C_6)$alkyl, $O_a(C_1-C_3)$perfluoroalkyl, OH, halo, and CN;

$R^d$ is independently: H, $(C=O)_aO_b(C_1-C_6)$alkyl, aryl, or $S(O)_mR^e$, said alkyl and aryl is optionally substituted with one or more substituents selected from $(C=O)_aO_b(C_1-C_6)$alkyl, OH, halo, and CN;

$R^e$ is independently: H, or $(C_1-C_6)$alkyl; and $R^x$ and $R^y$ are independently selected from: H, $(C_1-C_6)$alkyl, $(C_2-C_6)$alkenyl, and $(C_2-C_6)$alkynyl, wherein said alkyl is optionally substituted with up to three substituents selected from: OH and halo, or $R^x$ and $R^y$ can be taken together to form a monocyclic or bicyclic carbo- or heterocycle with 3-7 members in each ring, said heterocycle is containing one or more heteroatoms selected from N, O and S, and said carbo- or heterocycle is optionally substituted with one or more substituents selected from: $(C_1-C_6)$alkyl, $(C_2-C_6)$alkenyl, $(C_3-C_6)$cycloalkyl, $(C_1-C_6)$alkylidene, $(C_1-C_6)$alkoxy, $CO_2H$, halo, OH, oxo, CN and $NR^7R^8$, said alkyl, cycloalkyl and alkoxy is optionally substituted with one or more substituents selected from halo, CN, OH and $NR^7R^8$;

or a pharmaceutically acceptable salt, stereoisomer or N-oxide derivative thereof.

In a second embodiment of this invention, the inhibitors of Akt activity are illustrated by the Formula A, wherein:

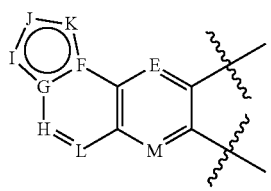

is selected from:

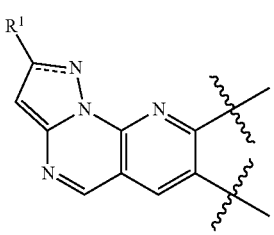

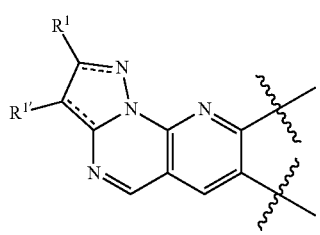

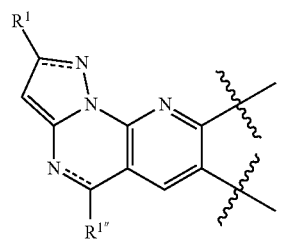

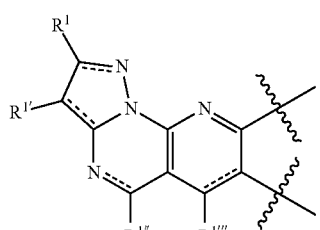

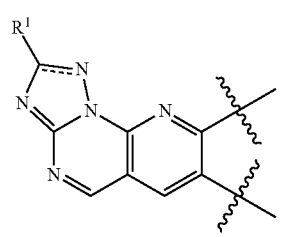

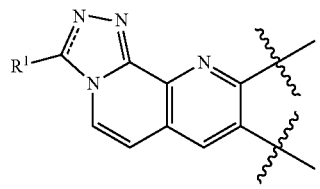

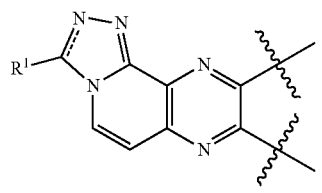

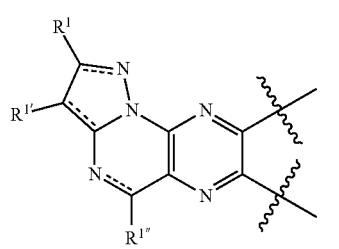

and

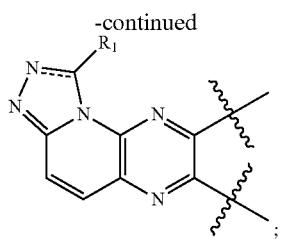

$R^1$, $R^{1'}$, $R^{1''}$ and $R^{1'''}$ are independently selected from: H, oxo, $(C=O)_aO_b(C_1-C_{10})$alkyl, $(C=O)_aO_b$-aryl, $(C=O)_aO_b(C_2-C_{10})$alkenyl, $(C=O)_aO_b(C_2-C_{10})$alkynyl, $CO_2H$, halo, OH, $O_b(C_1-C_6)$perfluoroalkyl, $(C=O)_aNR^7R^8$, CN, $(C=O)_aO_b(C_3-C_8)$cycloalkyl, $S(O)_mNR^7R^8$, SH, $S(O)_m-(C_1-C_{10})$allyl and $(C=O)_aO_b$-heterocyclyl, said alkyl, aryl, alkenyl, alkynyl, cycloalkyl, and heterocyclyl is optionally substituted with one or more substituents selected from $R^6$;

Bond: ------ is a single or double bond, provided that when each $R^1$, $R^{1'}$, $R^{1''}$ and $R^{1'''}$ is oxo, then said bond adjacent to the oxo is a single bond and C or N which is attached to the resulting carbonyl with said single bond bears H; and all other substituents and variables are as defined in the first embodiment;

or a pharmaceutically acceptable salt, stereoisomer or N-oxide derivative thereof.

In a third embodiment of this invention, the inhibitors of Akt activity are illustrated by the Formula B:

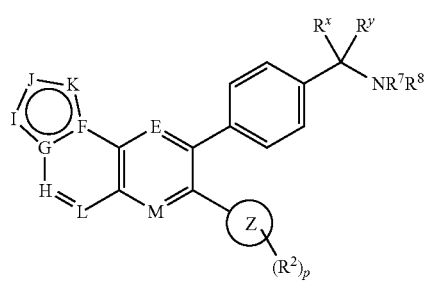

B wherein:

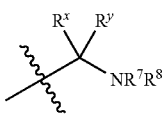

p is 0, 1 or 2;
is selected from:

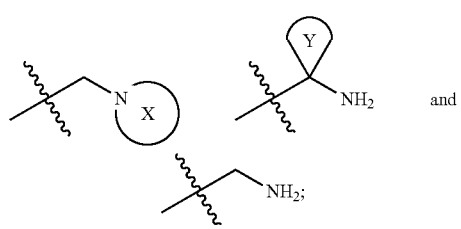

Ring X is a monocyclic, bicyclic or tricyclic heterocycle with 3-7 members in each ring and optionally containing, in addition to the nitrogen, one or two additional heteroatoms selected from N, O and S, said monocyclic, bicyclic or tricyclic heterocycle optionally substituted with one or more substituents selected from $R^{6a}$;

Ring Y is a monocyclic or bicyclic carbo- or heterocycle with 3-7 members in each ring, said heterocycle is containing one or more heteroatoms selected from N, O and S, and said carbo- or heterocycle is optionally substituted with one or more substituents selected from: $(C_1-C_6)$alkyl, $(C_2-C_6)$alkenyl, $(C_3-C_6)$cycloalkyl, $(C_1-C_6)$alkylidene, $(C_1-C_6)$alkoxy, $CO_2H$, halo, OH, oxo, CN and $NR^{7'}R^{8'}$, said alkyl, cycloalkyl and alkoxy is optionally substituted with one or more substituents selected from halo, CN, OH and $NR^{7'}R^{8'}$;

Ring Z is selected from: phenyl, 2-thienyl and 3-thienyl;

$R^2$ is independently selected from: $(C_1-C_6)$alkyl, $(C_1-C_6)$alkoxy, $CO_2H$, halo, OH and $NH_2$;

$R^{6a}$ is selected from: $(C=O)_aO_b(C_1-C_{10})$alkyl, oxo, OH, halo, $(C_0-C_6)$alkylene-heterocyclyl, and $(C=O)_aNR^b{}_2$, said alkyl, and heterocyclyl is optionally substituted with up to three substituents selected from $R^b$;

$R^{7'}$ and $R^{8'}$ are independently selected from: H, and $(C_1-C_6)$alkyl;

$R^a$ is $(C_1-C_6)$alkyl, $(C_3-C_6)$cycloalkyl, aryl, or heterocyclyl, said alkyl, cycloalkyl, aryl, and heterocyclyl is optionally substituted with one or more substituents selected from $R^c$;

$R^b$ is independently: H, $(C=O)_aO_b(C_1-C_6)$alkyl, or $(C=O)_aR^a$, said alkyl is optionally substituted with one or more substituents selected from $(C=O)_aO_b(C_1-C_6)$alkyl, OH, halo, CN, and $(C=O)_aNR^d{}_2$;

$R^c$ is independently: $(C=O)_aO_b(C_1-C_6)$alkyl, oxo, OH, halo, CN, or $(C=O)_aNR^d{}_2$, said alkyl is optionally substituted with one or more substituents selected from $(C_1-C_6)$alkyl, OH, halo, and CN;

$R^d$ is independently: H, or $(C_1-C_6)$alkyl; and all other substituents and variables are as defined in the second embodiment;

or a pharmaceutically acceptable salt, stereoisomer or N-oxide derivative thereof.

In a fourth embodiment the inhibitors of the instant invention are illustrated by the Formula C:

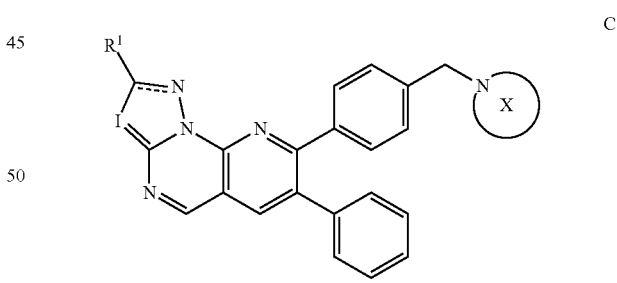

C wherein:
 I is selected from: CH or N;
 a is 0 or 1; b is 0 or 1;
 Ring X is selected from:

-continued

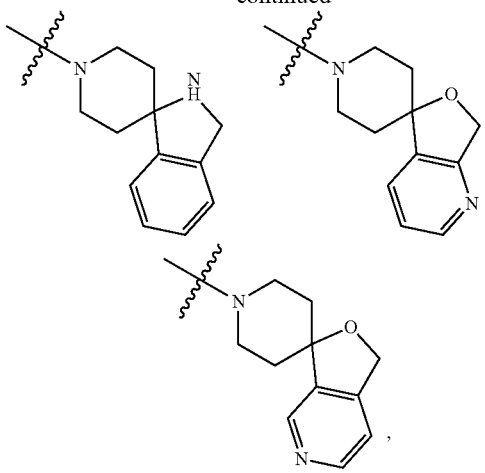

and each of which is optionally substituted with one or more substituents selected from $R^{6a}$;

$R^1$ is selected from: H, oxo, $(C=O)_aO_b(C_1-C_{10})$alkyl, OH, and $(C=O)_aO_b$-heterocyclyl;

$R^{6a}$ is selected from: $(C=O)_aO_b(C_1-C_{10})$alkyl, oxo, OH, halo, $(C_0-C_6)$alkylene-heterocyclyl, and $(C=O)_aNR^b{}_2$, said alkyl, and heterocyclyl is optionally substituted with up to three substituents selected from $R^b$;

$R^a$ is $(C_1-C_6)$alkyl, $(C_3-C_6)$cycloalkyl, aryl, or heterocyclyl, said alkyl, cycloalkyl, aryl, and heterocyclyl is optionally substituted with one or more substituents selected from $R^c$;

$R^b$ is independently: H, $(C=O)_aO_b(C_1-C_6)$alkyl, or $(C=O)_aR^a$, said alkyl is optionally substituted with one or more substituents selected from $(C=O)_aO_b(C_1-C_6)$alkyl, OH, halo, CN, and $(C=O)_aNR^d{}_2$;

$R^c$ is independently: $(C=O)_aO_b(C_1-C_6)$alkyl, oxo, OH, halo, CN, or $(C=O)_aNR^d{}_2$, said alkyl is optionally substituted with one or more substituents selected from $(C_1-C_6)$alkyl, OH, halo, and CN;

$R^d$ is independently: H, or $(C_1-C_6)$alkyl; and

Bond: ------ is a single or double bond, provided that when $R^1$ is oxo, then said bond is a single bond and adjacent N bears H;

or a pharmaceutically acceptable salt, stereoisomer or N-oxide derivative thereof.

In a fifth embodiment the inhibitors of the instant invention are illustrated by the Formula D:

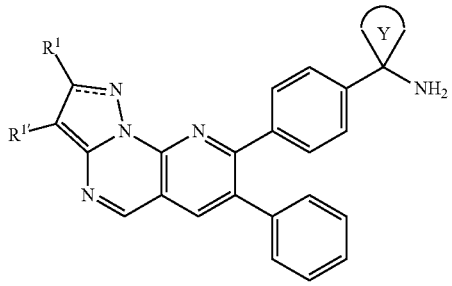

D wherein:
a is 0 or 1; b is 0 or 1;

Ring Y is a group of formula:

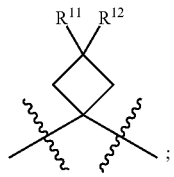

;

$R^1$ is selected from: H; oxo, $(C=O)_aO_b(C_1-C_{10})$alkyl, $(C=O)_aO_b$-aryl, OH, $(C=O)_aO_b(C_3-C_8)$cycloalkyl, and $(C=O)_aO_b$-heterocyclyl, said alkyl, aryl, cycloalkyl, and heterocyclyl is optionally substituted with one or more substituents selected from $R^6$;

$R^{1'}$ is selected from: H, $(C=O)_aO_b(C_1-C_{10})$alkyl, $(C=O)_aO_b$-aryl, halo, CN and $(C=O)_aO_b$-heterocyclyl, said alkyl, aryl, and heterocyclyl is optionally substituted with one or more substituents selected from $R^6$;

$R^6$ is: $(C=O)_aO_b(C_1-C_{10})$alkyl, halo or OH;

$R^7$ and $R^8$ are independently selected from: H, and $(C_1-C_6)$ allyl;

$R^{11}$ and $R^{12}$ are independently selected from: H, $(C_1-C_6)$alkyl, $(C_2-C_6)$alkenyl, $(C_3-C_6)$cycloalkyl, $(C_1-C_6)$alkoxy, $CO_2H$, halo, OH, CN and $NR^7R^8$, said alkyl, cycloalkyl and alkoxy is optionally substituted with one or more substituents selected from halo, CN, OH and $NR^7R^8$, or $R^{11}$ and $R^{12}$ can be taken together to form oxo, $(C_1-C_6)$alkylidene, or a monocyclic carbo- or heterocycle with 3-7 members, said heterocycle is containing one or more heteroatoms selected from N, O and S; and Bond: ------ is a single or double bond, provided that when $R^1$ is oxo, then said bond is a single bond and adjacent N bears H;

or a pharmaceutically acceptable salt, stereoisomer or N-oxide derivative thereof.

In a sixth embodiment the inhibitors of the instant invention are illustrated by the Formula E:

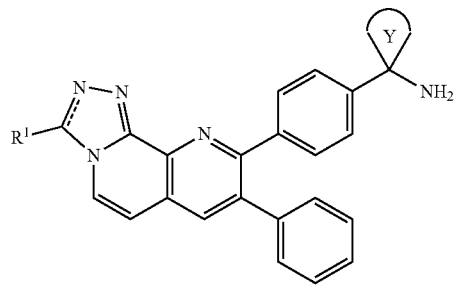

E wherein:
a is 0 or 1; b is 0 or 1;

Ring Y is a group of formula:

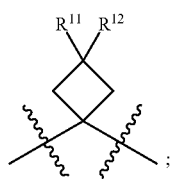

;

$R^1$ is selected from: H, oxo, $(C=O)_aO_b(C_1-C_{10})$alkyl, OH, $(C=O)_aNR^7R^8$, $(C=O)_aO_b(C_3-C_8)$cycloalkyl, and $(C=O)_a$ O$_b$-heterocyclyl, said alkyl, cycloalkyl, and heterocyclyl is optionally substituted with one or more substituents selected from (C$_1$-C$_6$)alkyl, halo, CN, and OH;

R$^7$ and R$^8$ are independently selected from: H, and (C$_1$-C$_6$) alkyl, or R$^7$ and R$^8$ can be taken together with the nitrogen to which they are attached to form a monocyclic heterocycle with 3-7 members and optionally containing, in addition to the nitrogen, one or two additional heteroatoms selected from N, O and S;

R$^{11}$ and R$^{12}$ are independently selected from: H, (C$_1$-C$_6$) alkyl, (C$_2$-C$_6$)alkenyl, (C$_3$-C$_6$)cycloalkyl, (C$_1$-C$_6$)alkoxy, CO$_2$H, halo, OH, CN and NR$^7$R$^8$, said alkyl, cycloalkyl and alkoxy is optionally substituted with one or more substituents selected from halo, CN, OH and NR$^7$R$^8$, or R$^{11}$ and R$^{12}$ can be taken together to form oxo, (C$_1$-C$_6$)alkylidene, or a monocyclic carbo- or heterocycle with 3-7 members, said heterocycle is containing one or more heteroatoms selected from N, O and S; and Bond: ------ is a single or double bond, provided that when R$^1$ is oxo, then said bond is a single bond and adjacent N bears H;

or a pharmaceutically acceptable salt, stereoisomer or N-oxide derivative thereof.

Specific compounds of the instant invention include:
trans-3-amino-1-methyl-3-[4-(2-methyl-7-phenylpyrazolo[1,5-a]pyrido[3,2-e]pyrimidin-8-yl)phenyl]cyclobutanol (1-7);
cis-3-amino-1-methyl-3-[4-(2-methyl-7-phenylpyrazolo[1,5-a]pyrido[3,2-e]pyrimidin-8-yl)phenyl]cyclobutanol (1-8);
trans-3-amino-1-cyclopropyl-3-[4-(2-methyl-7-phenylpyrazolo[1,5-a]pyrido[3,2-e]pyrimidin-8-yl)phenyl]cyclobutanol (1-9);
trans-3-amino-3-[4-(2-methyl-7-phenylpyrazolo[1,5-a]pyrido[3,2-e]pyrimidin-8-yl)phenyl]cyclobutanol (1-10);
trans-3-methoxy-1-[4-(2-methyl-7-phenylpyrazolo[1,5-a]pyrido[3,2-e]pyrimidin-8-yl)phenyl]cyclobutanamine (1-11);
methyl {1-[4-(2-methyl-7-phenylpyrazolo[1,5-a]pyrido[3,2-e]pyrimidin-8-yl)phenyl]-3-oxocyclobutyl}carbamate (1-12);
1-[4-(2-methyl-7-phenylpyrazolo[1,5-a]pyrido[3,2-e]pyrimidin-8-yl)phenyl]methanamine (1-13);
2-methyl-7-phenyl-8-[4-(1H-pyrazol-1-ylmethyl)phenyl]pyrazolo[1,5-a]pyrido[3,2-e]pyrimidine (1-14);
(1R)-1-[4-(2-methyl-7-phenylpyrazolo[1,5-a]pyrido[3,2-e]pyrimidin-8-yl)phenyl]ethanamine (1-15);
trans-3-amino-1-ethyl-3-[4-(2-methyl-7-phenylpyrazolo[1,5-a]pyrido[3,2-e]pyrimidin-8-yl)phenyl]cyclobutanol (1-16);
cis-3-amino-1-ethyl-3-[4-(2-methyl-7-phenylpyrazolo[1,5-a]pyrido[3,2-e]pyrimidin-8-yl)phenyl]cyclobutanol (1-17);
trans-3-amino-1-ethenyl-3-[4-(2-methyl-7-phenylpyrazolo[1,5-a]pyrido[3,2-e]pyrimidin-8-yl)phenyl]cyclobutanol (1-18);
3-methylidene-1-[4-(2-methyl-7-phenylpyrazolo[1,5-a]pyrido[3,2-e]pyrimidin-8-yl)phenyl]cyclobutanamine (1-19);
3,3-difluoro-1-[4-(2-methyl-7-phenylpyrazolo[1,5-a]pyrido[3,2-e]pyrimidin-8-yl)phenyl]cyclobutanamine (1-20);
8-{4-[trans-1-amino-3-(1,2-dihydroxyethyl)-3-hydroxycyclobutyl]phenyl}-2-methyl-7-phenylpyrazolo[1,5-a]pyrido[3,2-e]pyrimidine (1-21);
8-{4-[1-amino-3-hydroxy-3-(hydroxymethyl)cyclobutyl]phenyl}-2-methyl-7-phenylpyrazolo[1,5-a]pyrido[3,2-e]pyrimidine (1-22);
2-[4-(2-methyl-7-phenylpyrazolo[1,5-a]pyrido[3,2-e]pyrimidin-8-yl)phenyl]-5,8-dioxaspiro[3.4]octan-2-amine (1-23);
cis-3-amino-1-cyclopropyl-3-[4-(2-cyclopropyl-7-phenylpyrazolo[1,5-a]pyrido[3,2-e]pyrimidin-8-yl)phenyl]cyclobutanol (2-7);
trans-3-amino-1-cyclopropyl-3-[4-(7-phenylpyrazolo[1,5-a]pyrido[3,2-e]pyrimidin-8-yl)phenyl]cyclobutanol (2-8);
8-[4-(trans-1-amino-3-cyclopropyl-3-hydroxycyclobutyl)phenyl]-7-phenyl-2-(trifluoromethyl)pyrazolo[1,5-a]pyrido[3,2-e]pyrimidine (2-9);
trans-3-cyclopropyl-1-{4-[2-(4-fluorophenyl)-7-phenylpyrazolo[1,5-a]pyrido[3,2-e]pyrimidin-8-yl]phenyl}-3-hydroxycyclobutanamine (2-10);
trans-1-[4-(2-cyclopropyl-7-phenylpyrazolo[1,5-a]pyrido[3,2-e]pyrimidin-8-yl)phenyl]-3-hydroxy-3-methylcyclobutanamine (2-11);
trans-3-amino-3-[4-[2-(1,1-dimethylethyl)-7-phenylpyrazolo[1,5-a]pyrido[3,2-e]pyrimidin-8-yl]phenyl]-1-methyl-cyclobutanol (2-12);
trans-3-amino-1-methyl-3-{4-[2-methyl-7-(thiophen-2-yl)pyrazolo[1,5-a]pyrido[3,2-e]pyrimidin-8-yl]phenyl}cyclobutanol (3-4);
trans-3-amino-3-{4-[7-(2-fluorophenyl)-2-methylpyrazolo[1,5-a]pyrido[3,2-e]pyrimidin-8-yl]phenyl}-1-methylcyclobutanol (3-5);
trans-3-amino-1-methyl-3-{4-[2-methyl-7-(thiophen-3-yl)pyrazolo[1,5-a]pyrido[3,2-e]pyrimidin-8-yl]phenyl}cyclobutanol (3-6);
1-[4-(2-methyl-7-phenylpyrazolo[1,5-a]pyrido[3,2-e]pyrimidin-8-yl)phenyl]cyclobutanamine (4-3);
9-[4-(1-aminocyclobutyl)phenyl]-8-phenyl[1,2,4]triazolo[4,3-h]-1,7-naphthyridin-3(2H)-one (7-6);
9-[4-(1-aminocyclobutyl)phenyl]-8-phenyl[1,2,4]triazolo[4,3-h]-1,7-naphthyridin-3-amine (8-1);
1-[4-(3-methyl-8-phenyl[1,2,4]triazolo[4,3-h]-1,7-naphthyridin-9-yl)phenyl]cyclobutanamine (9-1);
1-{4-[3-cyclopropyl-8-phenyl[1,2,4]triazolo[4,3-h]-1,7-naphthyridin-9-yl)phenyl}cyclobutanamine (9-2);
1-{4-[8-phenyl-3-(pyrimidin-2-yl)[1,2,4]triazolo[4,3-h]-1,7-naphthyridin-9-yl)phenyl}cyclobutanamine (9-3);
trans-3-hydroxy-3-methyl-1-[4-(2-methyl-7-phenylpyrazolo[1,5-a]pteridin-8-yl)phenyl]cyclobutanamine (10-7);
2-methyl-7-phenyl-8-(4-{[4-(5-pyridin-2-yl-4H-1,2,4-triazol-3-yl)piperidin-1-yl]methyl}phenyl)pyrazolo[1,5-a]pyrido[3,2-e]pyrimidine (11-2);
1'-[4-(2-methyl-7-phenylpyrazolo[1,5-a]pyrido[3,2-e]pyrimidin-8-yl)benzyl]-1H-spiro[furo[3,4-c]pyridine-3,4'-piperidin]-1-one (11-3);
2-methyl-1'-[4-(2-methyl-7-phenylpyrazolo[1,5-a]pyrido[3,2-e]pyrimidin-8-yl)benzyl]spiro[isoindole-1,4'-piperidin]-3(2H)-one (11-4);
1'-[4-(2-methyl-7-phenylpyrazolo[1,5-a]pyrido[3,2-e]pyrimidin-8-yl)benzyl]-7H-spiro[furo[3,4-b]pyridine-5,4'-piperidin]-7-one (11-5);
1-[4-(2-methyl-7-phenylpyrazolo[1,5-a]pyrido[3,2-e]pyrimidin-8-yl)benzyl]piperidine-4-carboxamide (11-6);
2-methyl-8-(4-{[4-(2-oxo-2,3-dihydro-1H-benzimidazol-1-yl)piperidin-1-yl]methyl}phenyl)-7-phenylpyrazolo[1,5-a]pyrido[3,2-e]pyrimidine (11-7);
8-(4-[4-{(1,3-benzodioxol-5-ylmethyl)piperazin-1-yl]methyl}phenyl)-2-methyl-7-phenylpyrazolo[1,5-a]pyrido[3,2-e]pyrimidine (11-8);
2-methyl-7-phenyl-8-(4-(piperazin-1-ylmethyl)phenyl]pyrazolo[1,5-a]pyrido[3,2-e]pyrimidine (11-9);
2-methyl-8-{4-[(4-methylpiperazin-1-yl)methyl]phenyl}-7-phenylpyrazolo[1,5-a]pyrido[3,2-e]pyrimidine (11-10);

N-[4-(2-methyl-7-phenylpyrazolo[1,5-a]pyrido[3,2-e]pyrimidin-8-yl)benzyl]-2-(1-methylpyrrolidin-2-yl)ethanamine (11-11);

2-methyl-8-[4-(morpholin-4-ylmethyl)phenyl]-7-phenylpyrazolo[1,5-a]pyrido[3,2-e]pyrimidine (11-12);

3-{1-[4-(2-methyl-7-phenylpyrazolo[1,5-a]pyrido[3,2-e]pyrimidin-8-yl)benzyl]piperidin-4-yl}phenol (11-13);

1-[4-(2-methyl-7-phenylpyrazolo[1,5-a]pyrido[3,2-e]pyrimidin-8-yl)benzyl]piperidin-4-ol (11-14);

2-methyl-7-phenyl-8-[4-(piperidin-1-ylmethyl)phenyl]pyrazolo[1,5-a]pyrido[3,2-e]pyrimidine (11-15);

1-{4-[4-(2-methyl-7-phenylpyrazolo[1,5-a]pyrido[3,2-e]pyrimidin-8-yl)benzyl]piperazin-1-yl}ethanone (11-16);

1-[4-(2-methyl-7-phenylpyrazolo[1,5-a]pyrido pyrimidin-8-yl)benzyl]piperidin-4-amine (11-17);

1-{1-[4-(2-methyl-7-phenylpyrazolo[1,5-a]pyrido[3,2-e]pyrimidin-8-yl)benzyl]piperidin-4-yl}-1,3-dihydro-2H-benzimidazol-2-one (11-18);

4-hydroxy-N-{1-[4-(2-methyl-7-phenylpyrazolo[1,5-a]pyrido[3,2-e]pyrimidin-8-yl)benzyl]piperidin-4-yl}benzamide (11-19);

2-morpholin-4-yl-7-phenyl-8-(4-{[4-(5-pyridin-2-yl-4H-1,2,4-triazol-3-yl)piperidin-1-yl]methyl}phenyl)pyrido[3,2-e][1,2,4]triazolo[1,5-a]pyrimidine (12-3);

ethyl 1-[4-(2-methyl-7-phenylpyrazolo[1,5-a]pyrido[3,2-e]pyrimidin-8-yl)benzyl]piperidine-4-carboxylate (13-1);

methyl 1-[4-(2-methyl-7-phenylpyrazolo[1,5-a]pyrido[3,2-e]pyrimidin-8-yl)benzyl]piperidine-4-carboxylate (13-2);

1-[4-(2-methyl-7-phenylpyrazolo[1,5-a]pyrido[3,2-e]pyrimidin-8-yl)benzyl]piperidine-4-carboxylic acid (14-1);

2-methyl-7-phenyl-8-(4-{[4-(phenylcarbamoyl)piperidin-1-yl]methyl}phenyl)pyrazolo[1,5-a]pyrido[3,2-e]pyrimidine (15-1);

8-[4-({4-[(2-methoxyethyl)carbamoyl]piperidin-1-yl}methyl)phenyl]-2-methyl-7-phenylpyrazolo[1,5-a]pyrido[3,2-e]pyrimidine (15-2);

2-methyl-7-phenyl-8-(4-{[4-(prop-2-en-1-ylcarbamoyl)piperidin-1-yl]methyl}phenyl)pyrazolo[1,5-a]pyrido[3,2-e]pyrimidine (15-3);

8-{4-[(4-{[2-(dimethylamino)ethyl]carbamoyl}piperidin-1-yl)methyl]phenyl}-2-methyl-7-phenylpyrazolo[1,5-a]pyrido[3,2-e]pyrimidine (15-4);

8-{4-[(4-{[3-(1H-imidazol-1-yl)propyl]carbamoyl}piperidin-1-yl)methyl]phenyl}-2-methyl-7-phenylpyrazolo[1,5-a]pyrido[3,2-e]pyrimidine (15-5);

8-[4-({4-[(3,4-dimethoxybenzyl)carbamoyl]piperidin-1-yl}methyl)phenyl}-2-methyl-7-phenylpyrazolo[1,5-a]pyrido[3,2-e]pyrimidine (15-6);

2-methyl-8-{4-[(4-{[2-(1-methylpyrrolidin-2-yl)ethyl]carbamoyl}piperidin-1-yl)methyl]phenyl}-7-phenylpyrazolo[1,5-a]pyrido[3,2-e]pyrimidine (15-7);

{1-[4-(2-methyl-7-phenylpyrazolo[1,5-a]pyrido[3,2-e]pyrimidin-8-yl)benzyl]piperidin-4-yl}(morpholin-4-yl)methanone (15-8);

8-[4-({4-[(1H-benzimidazol-2-ylmethyl)carbamoyl]piperidin-1-yl}methyl)phenyl]-2-methyl-7-phenylpyrazolo[1,5-a]pyrido[3,2-e]pyrimidine (15-9);

N-[2-(1H-imidazol-5-yl)ethyl]-1-[4-(2-methyl-7-phenylpyrazolo[1,5-a]pyrido[3,2-e]pyrimidin-8-yl)benzyl]piperidine-4-carboxamide (15-10);

2-methyl-7-phenyl-8-{4-[(4-{[4-(pyrimidin-2-yl)piperazin-1-yl]carbonyl}piperidin-1-yl)methyl]phenyl}pyrazolo[1,5-a]pyrido[3,2-e]pyrimidine (15-11);

2-methyl-7-phenyl-8-(4-{[4-({4-[5-(trifluoromethyl)pyridin-2-yl]piperazin-1-yl}carbonyl)piperidin-1-yl]methyl}phenyl)pyrazolo[1,5-a]pyrido[3,2-e]pyrimidine (15-12);

2-methyl-7-phenyl-8-{4-[(4-{[4-(pyridin-2-yl)piperazin-1-yl]carbonyl}piperidin-1-yl)methyl]phenyl}pyrazolo[1,5-a]pyrido[3,2-e]pyrimidine (15-13);

2-methyl-7-phenyl-8-{4-[(4-{[2-(pyridin-3-yl)ethyl]carbamoyl}piperidin-1-yl)methyl]phenyl}pyrazolo[1,5-a]pyrido[3,2-e]pyrimidine (15-14);

2-methyl-7-phenyl-8-[4-({4-[(pyridin-2-ylmethyl)carbamoyl]piperidin-1-yl}methyl)phenyl]pyrazolo[1,5-a]pyrido[3,2-e]pyrimidine (15-15);

2-methyl-7-phenyl-8-[4-({4-[(pyridin-4-ylmethyl)carbamoyl]piperidin-1-yl}methyl)phenyl]pyrazolo[1,5-a]pyrido[3,2-e]pyrimidine (15-16);

8-[4-({4-[(3-hydroxyphenyl)carbamoyl]piperidin-1-yl}methyl)phenyl]-2-methyl-7-phenylpyrazolo[1,5-a]pyrido[3,2-e]pyrimidine (15-17);

8-[4-({4-[(trans-4-hydroxycyclohexyl)carbamoyl]piperidin-1-yl}methyl)phenyl]-2-methyl-7-phenylpyrazolo[1,5-a]pyrido[3,2-e]pyrimidine (15-18);

8-{4-[(4-{[2-hydroxy-2-(3-hydroxyphenyl)ethyl]carbamoyl}piperidin-1-yl)methyl]phenyl}-2-methyl-7-phenylpyrazolo[1,5-a]pyrido[3,2-e]pyrimidine (15-19);

8-{4-[(4-{[2-(4-hydroxyphenyl)ethyl]carbamoyl}piperidin-1-yl)methyl]phenyl}-2-methyl-7-phenylpyrazolo[1,5-a]pyrido[3,2-e]pyrimidine (15-20);

8-[4-({4-[(3-hydroxy-4-methoxyphenyl)carbamoyl]piperidin-1-yl}methyl)phenyl]-2-methyl-7-phenylpyrazolo[1,5-a]pyrido[3,2-e]pyrimidine (15-21);

8-{4-[(4-{[2-(3,4-dihydroxyphenyl)ethyl]carbamoyl}piperidin-1-yl)methyl]phenyl}-2-methyl-7-phenylpyrazolo[1,5-a]pyrido[3,2-e]pyrimidine (15-22);

8-[4-({4-[(4-hydroxy-3-methoxybenzyl)carbamoyl]piperidin-1-yl}methyl)phenyl]-2-methyl-7-phenylpyrazolo[1,5-a]pyrido[3,2-e]pyrimidine (15-23);

8-[4-({4-[(3,4-dihydroxybenzyl)carbamoyl]piperidin-1-yl}methyl)phenyl]-2-methyl-7-phenylpyrazolo[1,5-a]pyrido[3,2-e]pyrimidine (15-24);

8-(4-{[4-(benzylcarbamoyl)piperidin-1-yl]methyl}phenyl)-2-methyl-7-phenylpyrazolo[1,5-a]pyrido[3,2-e]pyrimidine (15-25);

8-[4-({4-[benzyl(methyl)carbamoyl]piperidin-1-yl}methyl)phenyl]-2-methyl-7-phenylpyrazolo[1,5-a]pyrido[3,2-e]pyrimidine (15-26);

8-(4-{[4-(cyclohexylcarbamoyl)piperidin-1-yl]methyl}phenyl)-2-methyl-7-phenylpyrazolo[1,5-a]pyrido[3,2-e]pyrimidine (15-27);

8-[4-({4-[(1-methoxypropan-2-yl)carbamoyl]piperidin-1-yl}methyl)phenyl]-2-methyl-7-phenylpyrazolo[1,5-a]pyrido[3,2-e]pyrimidine (15-28);

N-({1-[4-(2-methyl-7-phenylpyrazolo[1,5-a]pyrido[3,2-e]pyrimidin-8-yl)benzyl]piperidin-4-yl}carbonyl)glycinamide (15-29);

2-methyl-7-phenyl-8-[4-({4-[(2,2,2-trifluoroethyl)carbamoyl]piperidin-1-yl}methyl)phenyl]pyrazolo[1,5-a]pyrido[3,2-e]pyrimidine (15-30);

2-methyl-8-(4-{[4-(pentan-3-ylcarbamoyl)piperidin-1-yl]methyl}phenyl)-7-phenylpyrazolo[1,5-a]pyrido[3,2-e]pyrimidine (15-31);

8-(4-{[4-(tert-butylcarbamoyl)piperidin-1-yl]methyl}phenyl)-2-methyl-7-phenylpyrazolo[1,5-a]pyrido[3,2-e]pyrimidine (15-32);

2-methyl-7-phenyl-8-(4-{[4-(propylcarbamoyl)piperidin-1-yl]methyl}phenyl)pyrazolo[1,5-a]pyrido[3,2-e]pyrimidine (15-33);

2-methyl-8-(4-{[4-(methylcarbamoyl)piperidin-1-yl]methyl}phenyl)-7-phenylpyrazolo[1,5-a]pyrido[3,2-e]pyrimidine (15-34);

8-(4-{[4-(ethylcarbamoyl)piperidin-1-yl]methyl}phenyl)-2-methyl-7-phenylpyrazolo[1,5-a]pyrido[3,2-e]pyrimidine (15-35);

8-{4-[(4-{[4-(3-hydroxyphenyl)piperazin-1-yl]carbonyl}piperidin-1-yl)methyl]phenyl}-2-methyl-7-phenylpyrazolo[1,5-a]pyrido[3,2-e]pyrimidine (15-36);

8-{4-[(4-{[(1S)-1-cyclohexylethyl]carbamoyl}piperidin-1-yl)methyl]phenyl}-2-methyl-7-phenylpyrazolo[1,5-a]pyrido[3,2-e]pyrimidine (15-37);

8-(4-{[4-(hexahydrocyclopenta[c]pyrrol-2(1H)-ylcarbonyl)piperidin-1-yl]methyl}phenyl)-2-methyl-7-phenylpyrazolo[1,5-a]pyrido[3,2-e]pyrimidine (15-38);

8-[4-({4-[ethyl(propan-2-yl)carbamoyl]piperidin-1-yl}methyl)phenyl]-2-methyl-7-phenylpyrazolo[1,5-a]pyrido[3,2-e]pyrimidine (15-39);

8-{4-[(4-{[(1S,2S)-2-hydroxycyclohexyl]carbamoyl}piperidin-1-yl)methyl]phenyl}-2-methyl-7-phenylpyrazolo[1,5-a]pyrido[3,2-e]pyrimidine (15-40);

8-[4-({4-[(2-hydroxyethyl)carbamoyl]piperidin-1-yl}methyl)phenyl]-2-methyl-7-phenylpyrazolo[1,5-a]pyrido[3,2-e]pyrimidine (15-41);

2-methyl-7-phenyl-8-[4-({4-[(tetrahydrofuran-2-ylmethyl)carbamoyl]piperidin-1-yl}methyl)phenyl]pyrazolo[1,5-a]pyrido[3,2-e]pyrimidine (15-42);

8-(4-{[4-(cyclobutylcarbamoyl)piperidin-1-yl]methyl}phenyl)-2-methyl-7-phenylpyrazolo[1,5-a]pyrido[3,2-e]pyrimidine (15-43);

2-methyl-7-phenyl-8-(4-{[4-(propan-2-ylcarbamoyl)piperidin-1-yl]methyl}phenyl)pyrazolo[1,5-a]pyrido[3,2-e]pyrimidine (15-44);

N-({1-[4-(2-methyl-7-phenylpyrazolo[1,5-a]pyrido[3,2-e]pyrimidin-8-yl)benzyl]piperidin-4-yl}carbonyl)glycine (15-45);

tert-butyl N-({1-[4-(2-methyl-7-phenylpyrazolo[1,5-a]pyrido[3,2-e]pyrimidin-8-yl)benzyl]piperidin-4-yl}carbonyl)glycinate (15-46);

8-[4-({4-[(4-hydroxyphenyl)carbamoyl]piperidin-1-yl}methyl)phenyl]-2-methyl-7-phenylpyrazolo[1,5-a]pyrido[3,2-e]pyrimidine (15-47);

8-[4-({4-[(3-carbamoylphenyl)carbamoyl]piperidin-1-yl}methyl)phenyl]-2-methyl-7-phenylpyrazolo[1,5-a]pyrido[3,2-e]pyrimidine (15-48);

8-[4-({4-[(3-methoxyphenyl)carbamoyl]piperidin-1-yl}methyl)phenyl]-2-methyl-7-phenylpyrazolo[1,5-a]pyrido[3,2-e]pyrimidine (15-49);

2-methyl-8-(4-{[4-({3-[(methylsulfonyl)amino]phenyl}carbamoyl)piperidin-1-yl]methyl}phenyl)-7-phenylpyrazolo[1,5-a]pyrido[3,2-e]pyrimidine (15-50);

8-[4-({4-[(3-cyanophenyl)carbamoyl]piperidin-1-yl}methyl)phenyl]-2-methyl-7-phenylpyrazolo[1,5-a]pyrido[3,2-e]pyrimidine (15-51);

8-[4-({4-[(3-fluorophenyl)carbamoyl]piperidin-1-yl}methyl)phenyl]-2-methyl-7-phenylpyrazolo[1,5-a]pyrido[3,2-e]pyrimidine (15-52);

8-[4-({4-[(2-hydroxyphenyl)carbamoyl]piperidin-1-yl}methyl)phenyl]-2-methyl-7-phenylpyrazolo[1,5-a]pyrido[3,2-e]pyrimidine (15-53);

8-[4-({4-[(4-carbamoylphenyl)carbamoyl]piperidin-1-yl}methyl)phenyl]-2-methyl-7-phenylpyrazolo[1,5-a]pyrido[3,2-e]pyrimidine (15-54);

2-methyl-7-phenyl-8-[4-({4-[(3-sulfamoylphenyl)carbamoyl]piperidin-1-yl}methyl)phenyl]pyrazolo[1,5-a]pyrido[3,2-e]pyrimidine (15-55);

N-(1,1-dioxido-1-benzothiophen-6-yl)-1-[4-(2-methyl-7-phenylpyrazolo pyrido[3,2-e]pyrimidin-8-yl)benzyl]piperidine-4-carboxamide (15-56);

3-aminobenzyl 1-[4-(2-methyl-7-phenylpyrazolo[1,5-a]pyrido[3,2-e]pyrimidin-8-yl)benzyl]piperidine-4-carboxylate (15-57);

{1-[4-(2-methyl-7-phenylpyrazolo[1,5-a]pyrido[3,2-e]pyrimidin-8-yl)benzyl]piperidin-4-yl}(piperidin-1-yl)methanone (15-58);

(1,1-dioxidothiomorpholin-4-yl){1-[4-(2-methyl-7-phenylpyrazolo[1,5-a]pyrido[3,2-e]pyrimidin-8-yl)benzyl]piperidin-4-yl}methanone (15-59);

1-[4-({1-[4-(2-methyl-7-phenylpyrazolo[1,5-a]pyrido[3,2-e]pyrimidin-8-yl)benzyl]piperidin-4-yl}carbonyl)piperazin-1-yl]ethanone (15-60);

N-(3-chlorophenyl)-1-[4-(2-methyl-7-phenylpyrazolo[1,5-a]pyrido[3,2-e]pyrimidin-8-yl)benzyl]piperidine-4-carboxamide (15-61);

(4-hydroxypiperidin-1-yl){1-[4-(2-methyl-7-phenylpyrazolo[1,5-a]pyrido[3,2-e]pyrimidin-8-yl)benzyl]piperidin-4-yl}methanone (15-62);

N-cyclohexyl-N-methyl-1-[4-(2-methyl-7-phenylpyrazolo[1,5-a]pyrido[3,2-e]pyrimidin-8-yl)benzyl]piperidine-4-carboxamide (15-63);

[4-(hydroxymethyl)piperidin-1-yl]{1-[4-(2-methyl-7-phenylpyrazolo[1,5-a]pyrido[3,2-e]pyrimidin-8-yl)benzyl]piperidin-4-yl}methanone (15-64);

4-tert-butyl-N-{1-[4-(2-methyl-7-phenylpyrazolo[1,5-a]pyrido[3,2-e]pyrimidin-8-yl)benzyl]piperidin-4-yl}benzamide (15-65);

1-(4-fluorophenyl)-3-{1-[4-(2-methyl-7-phenylpyrazolo[1,5-a]pyrido[3,2-e]pyrimidin-8-yl)benzyl]piperidin-4-yl}urea (15-66);

1-(4-tert-butylphenyl)-3-{1-[4-(2-methyl-7-phenylpyrazolo[1,5-a]pyrido[3,2-e]pyrimidin-8-yl)benzyl]piperidin-4-yl}urea (15-67);

N-{1-[4-(2-methyl-7-phenylpyrazolo[1,5-a]pyrido[3,2-e]pyrimidin-8-yl)benzyl]piperidin-4-yl}benzamide (15-68);

1-{1-[4-(2-methyl-7-phenylpyrazolo[1,5-a]pyrido[3,2-e]pyrimidin-8-yl)benzyl]piperidin-4-yl}-3-phenylurea (15-69);

N-(3-aminophenyl)-1-[4-(2-methyl-7-phenylpyrazolo[1,5-a]pyrido[3,2-e]pyrimidin-8-yl)benzyl]piperidine-4-carboxamide (15-70);

N-[3-(hydroxymethyl)phenyl]-1-[4-(2-methyl-7-phenylpyrazolo[1,5-a]pyrido[3,2-e]pyrimidin-8-yl)benzyl]piperidine-4-carboxamide (15-71);

1-[4-(2-methyl-7-phenylpyrazolo[1,5-a]pyrido[3,2-e]pyrimidin-8-yl)benzyl]-N-[3-(methylsulfonyl)phenyl]piperidine-4-carboxamide (15-72);

1-[4-(2-methyl-7-phenylpyrazolo[1,5-a]pyrido[3,2-e]pyrimidin-8-yl)benzyl]-N-(3-oxo-1,3-dihydro-2-benzofuran-5-yl)piperidine-4-carboxamide (15-73);

1-[4-(2-methyl-7-phenylpyrazolo[1,5-a]pyrido[3,2-e]pyrimidin-8-yl)benzyl]-N-(1,3-thiazol-2-yl)piperidine-4-carboxamide (15-74);

1-[4-(2-methyl-7-phenylpyrazolo[1,5-a]pyrido[3,2-e]pyrimidin-8-yl)benzyl]-N-[3-(trifluoromethoxy)phenyl]piperidine-4-carboxamide (15-75);

N-(1,3-benzothiazol-5-yl)-1-[4-(2-methyl-7-phenylpyrazolo[1,5-a]pyrido[3,2-e]pyrimidin-8-yl)benzyl]piperidine-4-carboxamide (15-76);

trans-3-amino-1-cyclopropyl-3-[4-(3-bromo-2-methyl-7-phenylpyrazolo[1,5-a]pyrido[3,2-e]pyrimidin-8-yl)phenyl]cyclobutanol (16-3);

trans-3-amino-3-[4-(3-chloro-2-methyl-7-phenylpyrazolo[1,5-a]pyrido[3,2-e]pyrimidin-8-yl)phenyl]-1-cyclopropylcyclobutanol (16-4);

trans-3-amino-1-cyclopropyl-3-{4-[2-methyl-7-phenyl-3-(pyridin-3-yl)pyrazolo[1,5-a]pyrido[3,2-e]pyrimidin-8-yl]phenyl}cyclobutanol (17-4);
trans-3-amino-1-cyclopropyl-3-[4-(3-cyano-2-methyl-7-phenylpyrazolo[1,5-a]pyrido[3,2-e]pyrimidin-8-yl)phenyl]cyclobutanol (17-5);
trans-3-amino-1-cyclopropyl-3-{4-[2-methyl-7-phenyl-3-(pyridin-4-yl)pyrazolo[1,5-a]pyrido[3,2-e]pyrimidin-8-yl]phenyl}cyclobutanol (17-6);
trans-3-amino-1-cyclopropyl-3-[4-(2-methyl-3,7-diphenylpyrazolo[1,5-a]pyrido[3,2-e]pyrimidin-8-yl)phenyl]cyclobutanol (17-7);
trans-3-amino-1-cyclopropyl-3-{4-[3-(4-methoxyphenyl)-2-methyl-7-phenylpyrazolo[1,5-a]pyrido[3,2-e]pyrimidin-8-yl]phenyl}cyclobutanol (17-8);
8-[4-(trans-1-amino-3-cyclopropyl-3-hydroxycyclobutyl)phenyl]-2,3-dimethyl-7-phenylpyrazolo[1,5-a]pyrido[3,2-e]pyrimidine (18-1);
trans-3-amino-3-[4-(2,5-dimethyl-7-phenylpyrazolo[1,5-a]pyrido[3,2-e]pyrimidin-8-yl)phenyl]-1-methylcyclobutanol (19-3);
trans-3-amino-3-[4-(2,6-dimethyl-7-phenylpyrazolo[1,5-a]pyrido[3,2-e]pyrimidin-8-yl)phenyl]-1-methylcyclobutanol (20-6); and
trans-3-amino-3-[4-(6-chloro-2-methyl-7-phenylpyrazolo[1,5-a]pyrido[3,2-e]pyrimidin-8-yl)phenyl]-1-methylcyclobutanol (20-7);
or a pharmaceutically acceptable salt, stereoisomer or N-oxide derivative thereof.

Specific compounds of the invention include:
trans-3-Amino-1-cyclopropyl-3-[4-(2-methyl-7-phenyl-1,4,9,9b-tetraaza-cyclopenta[a]naphthalen-8-yl)-phenyl]-cyclobutanol;
1-[4-(2-methyl-7-phenyl-1,4,9,9b-tetraaza-cyclopenta[a]naphthalen-8-yl)-phenyl]-cyclobutylamine;
3,3-Difluoro-1-[4-(2-methyl-7-phenyl-1,4,9,9b-tetraaza-cyclopenta[a]naphthalen-8-yl)-phenyl]-cyclobutylamine;
trans-2-[4-(2-Methyl-7-phenyl-1,4,9,9b-tetraaza-cyclopenta[a]naphthalen-8-yl)-phenyl]-5,8-dioxa-spiro[3.4]oct-2-ylamine;
trans-3-Amino-3-[4-(2-methyl-7-phenyl-1,4,9,9b-tetraaza-cyclopenta[a]naphthalen-8-yl)-phenyl]-cyclobutanol;
trans-1-Amino-1-[4-(2-methyl-7-phenyl-1,4,9,9b-tetraaza-cyclopenta[a]naphthalen-8-yl)-phenyl]-3-methoxycyclobutane;
1-[4-(2-methyl-7-phenyl-1,4,9,9b-tetraaza-cyclopenta[a]naphthalen-8-yl)-phenyl]-ethane-1,2-diol;
trans-3-Amino-1-methyl-3-[4-(2-methyl-7-phenyl-1,4,9,9b-tetraaza-cyclopenta[a]naphthalen-8-yl)-phenyl]-cyclobutanol;
cis-3-Amino-1-methyl-3-[4-(2-methyl-7-phenyl-1,4,9,9b-tetraaza-cyclopenta[a]naphthalen-8-yl)-phenyl]-cyclobutanol;
trans-3-Amino-1-cyclopropyl-3-[4-(2-cyclopropyl-7-phenyl-1,4,9,9b-tetraaza-cyclopenta[a]naphthalen-8-yl)-phenyl]-cyclobutanol;
trans-3-Amino-1-cyclopropyl-3-[4-(7-phenyl-1,4,9,9b-tetraaza-cyclopenta[a]naphthalen-8-yl)-phenyl]-cyclobutanol;
trans-3-Amino-1-cyclopropyl-3-[4-(2-(4-fluorophenyl)-7-phenyl-1,4,9,9b-tetraaza-cyclopenta[c]naphthalen-8-yl)-phenyl]-cyclobutanol;
trans-3-Amino-1-cyclopropyl-3-[4-(2-trifluoromethyl-7-phenyl-1,4,9,9b-tetraaza-cyclopenta[a]naphthalen-8-yl)-phenyl]-cyclobutanol;
2-Methyl-8-(4-morpholin-4-ylmethyl-phenyl)-7-phenyl-1,4,9,9b-tetraaza-cyclopenta[a]naphthalene;
4-(2-Methyl-7-phenyl-1,4,9,9b-tetraaza-cyclopenta[c]naphthalen-8-yl)-phenylamine;
N-[4-(2-Methyl-7-phenyl-1,4,9,9b-tetraaza-cyclopenta[a]naphthalen-8-yl)-phenyl]methanesulfonamide;
[4-(2-Methyl-7-phenyl-1,4,9,9b-tetraaza-cyclopenta[a]naphthalen-8-yl)-phenyl]-urea;
Morpholine-4-carboxylic acid [4-(2-methyl-7-phenyl-1,4,9,9b-tetraaza-cyclopenta[a]naphthalen-8-yl)-phenyl]-amide;
3-[4-(2-Methyl-7-phenyl-1,4,9,9b-tetraaza-cyclopenta[a]naphthalen-8-yl)-phenyl]-oxazolidin-2-one;
4-(2-Methyl-7-phenyl-1,4,9,9b-tetraaza-cyclopenta[a]naphthalen-8-yl)-benzylamine;
[4-(2-Methyl-7-phenyl-1,4,9,9b-tetraaza-cyclopenta[a]naphthalen-8-yl)-phenyl]-methanol;
1'-[4-(2-Methyl-7-phenyl-1,4,9,9b-tetraaza-cyclopenta[a]naphthalen-8-yl)-phenylmethyl]-spiro[furo[3,4-c]pyridine-3(1H), 4'-piperidine]-1-one;
1'-[4-(2-Methyl-7-phenyl-1,4,9,9b-tetraaza-cyclopenta[a]naphthalen-8-yl)-phenylmethyl]-spiro[2-methyl-2,3-dihydro-isoindole-3(1H), 4'-piperidine]-1-one;
1'-[4-(2-Methyl-7-phenyl-1,4,9,9b-tetraaza-cyclopenta[a]naphthalen-8-yl)-phenylmethyl]-spiro[furo[3,4-b]pyridine-5(7H), 4'-piperidine]-7-one;
8-[4-(4-Benzo[1,3]dioxol-5-ylmethyl-piperazin-1-ylmethyl)-phenyl]-2-methyl-7-phenyl-1,4,9,9b-tetraaza-cyclopenta[a]naphthalene;
1-[4-(2-Methyl-7-phenyl-1,4,9,9b-tetraaza-cyclopenta[a]naphthalen-8-yl)-benzyl]-piperidine-4-carboxylic acid amide;
3-[4-(2-Methyl-7-phenyl-3-pyridin-3-yl-1,4,9,9b-tetraaza-cyclopenta[a]naphthalen-8-yl)-phenyl]oxazolidin-2-one;
trans-3-Amino-1-cyclopropyl-3-[4-(3-cyano-2-methyl-7-phenyl-1,4,9,9b-tetraaza-cyclopenta[a]naphthalen-8-yl)-phenyl]-cyclobutanol;
3-Amino-3-[4-(3-bromo-2-methyl-7-phenyl-1,4,9,9b-tetraaza-cyclopenta[a]naphthalen-8-yl)-phenyl]-cyclopropyl-cyclobutanol;
3-Amino-3-[4-(3-chloro-2-methyl-7-phenyl-1,4,9,9b-tetraaza-cyclopenta[a]naphthalen-8-yl)-phenyl]-cyclopropyl-cyclobutanol;
3-Amino-3-[4-(2,5-dimethyl-7-phenyl-1,4,9,9b-tetraaza-cyclopenta[a]naphthalen-8-yl)-phenyl]-methyl-cyclobutanol;
3-Amino-1-methyl-3-[4-(2-methyl-7-thiophen-2-yl-8,9-dihydro-1,4,9,9b-tetraaza-cyclopenta[a]naphthalene-8-yl)-phenyl]cyclobutanol;
3-Amino-1-methyl-3-[4-(2-methyl-7-thiophen-3-yl-8,9-dihydro-1,4,9,9b-tetraaza-cyclopenta[a]naphthalene-8-yl)-phenyl]-cyclobutanol;
3-Amino-3-{4-[7-(2-fluoro-phenyl)-2-methyl-1,4,9,9b-tetraaza-cyclopenta[a]naphthalen-8-yl]-phenyl}-1-methyl-cyclobutanol;
3-Amino-1-hydroxymethyl-3-[4-(2-methyl-7-phenyl-1,4,9,9b-tetraaza-cyclopenta[a]naphthalen-8-yl)-phenyl]-cyclobutanol;
3-Methylene-1-[4-(2-methyl-7-phenyl-1,4,9,9b-tetraaza-cyclopenta[a]naphthalen-8-yl)-phenyl]-cyclobutylamine;
1-[4-(2-Methyl-7-phenyl-1,4,9,9b-tetraaza-cyclopenta[a]naphthalen-8-yl)-phenyl]-cyclobutanecarbonitrile;
Methyl-{1-[4-(2-methyl-7-phenyl-1,4,9,9b-tetraaza-cyclopenta[a]naphthalen-8-yl)-phenyl]-cyclobutyl}-amine;
1-Cyclopropyl-3-[4-(2-methyl-7-phenyl-1,4,9,9b-tetraaza-cyclopenta[a]naphthalen-8-yl)-phenyl]-cyclobutanol;
Trans-3-Amino-1-ethyl-3-[4-(2-methyl-7-phenyl-1,4,9,9b-tetraaza-cyclopenta[a]naphthalen-8-yl)-phenyl]-cyclobutanol;

Cis-3-Amino-1-ethyl-3-[4-(2-methyl-7-phenyl-1,4,9,9b-tetraaza-cyclopenta[a]naphthalen-8-yl)-phenyl]-cyclobutanol;

Trans-1-{3-Amino-1-hydroxy-3-[4-(2-methyl-7-phenyl-1,4,9,9b-tetraaza-cyclopenta[a]naphthalen-8-yl)-phenyl]-cyclobutyl}-ethane-1,2-dial;

Trans-3-Amino-3-[4-(2-methyl-7-phenyl-1,4,9,9b-tetraaza-cyclopenta[a]naphthalen-8-yl)-phenyl]-1-vinyl-cyclobutanol;

1-[4-(2-Methyl-7-phenyl-1,4,9,9b-tetraaza-cyclopenta[a]naphthalen-8-yl)-benzyl]-piperidine-4-carboxylic acid ethyl ester;

1-[4-(2-Methyl-7-phenyl-1,4,9,9b-tetraaza-cyclopenta[a]naphthalen-8-yl)-benzyl]-piperidine-4-carboxylic acid;

1-[4-(2-Methyl-7-phenyl-1,4,9,9b-tetraaza-cyclopenta[a]naphthalen-8-yl)-benzyl]-piperidine-4-carboxylic acid phenylamide;

1-[4-(2-Methyl-7-phenyl-1,4,9,9b-tetraaza-cyclopenta[a]naphthalen-8-yl)-benzyl]-piperidine-4-carboxylic acid allylamide;

1-[4-(2-Methyl-7-phenyl-1,4,9,9b-tetraaza-cyclopenta[a]naphthalen-8-yl)-benzyl]-piperidine-4-carboxylic acid (2-dimethylamino-ethyl)-amide;

1-[4-(2-Methyl-7-phenyl-1,4,9,9b-tetraaza-cyclopenta[a]naphthalen-8-yl)-benzyl]-piperidine-4-carboxylic acid (2-methoxy-ethyl)-amide;

1-[4-(2-Methyl-7-phenyl-1,4,9,9b-tetraaza-cyclopenta[a]naphthalen-8-yl)-benzyl]-piperidine-4-carboxylic acid (2-imidazol-1-yl-ethyl)-amide;

1-[4-(2-Methyl-7-phenyl-1,4,9,9b-tetraaza-cyclopenta[a]naphthalen-8-yl)-benzyl]-piperidine-4-carboxylic acid 3,4-dimethoxy-benzylamide;

1-[4-(2-Methyl-7-phenyl-1,4,9,9b-tetraaza-cyclopenta[a]naphthalen-8-yl)-benzyl]-piperidine-4-carboxylic acid [2-(1-methyl-pyrrolidin-2-yl)-ethyl]-amide;

{1-[4-(2-Methyl-7-phenyl-1,4,9,9b-tetraaza-cyclopenta[a]naphthalen-8-yl)-benzyl]-piperidin-4-yl}-morpholin-4-yl-methanone;

1-[4-(2-Methyl-7-phenyl-1,4,9,9b-tetraaza-cyclopenta[a]naphthalen-8-yl)-benzyl]-piperidine-4-carboxylic acid (1H-benzoimidazol-2-ylmethyl)-amide;

1-[4-(2-Methyl-7-phenyl-1,4,9,9b-tetraaza-cyclopenta[a]naphthalen-8-yl)-benzyl]-piperidine-4-carboxylic acid [2-(3H-imidazol-4-yl)-ethyl]-amide;

{1-[4-(2-Methyl-7-phenyl-1,4,9,9b-tetraaza-cyclopenta[a]naphthalen-8-yl)-benzyl]-piperidin-4-yl}-(4-pyrimidin-2-yl-piperazin-1-yl)-methanone;

{1-[4-(2-Methyl-7-phenyl-1,4,9,9b-tetraaza-cyclopenta[a]naphthalen-8-yl)-benzyl]-piperidin-4-yl}-[4-(5-trifluoromethyl-pyridin-2-yl)-piperazin-1-yl]-methanone;

{1-[4-(2-Methyl-7-phenyl-1,4,9,9b-tetraaza-cyclopenta[a]naphthalen-8-yl)-benzyl]-piperidin-4-yl}-(4-pyridin-2-yl-piperazin-1-yl)-methanone;

1-[4-(2-Methyl-7-phenyl-1,4,9,9b-tetraaza-cyclopenta[a]naphthalen-8-yl)-benzyl]-piperidine-4-carboxylic acid (2-pyridin-3-yl-ethyl)-amide;

1-[4-(2-Methyl-7-phenyl-1,4,9,9b-tetraaza-cyclopenta[a]naphthalen-8-yl)-benzyl]-piperidine-4-carboxylic acid (pyridin-2-ylmethyl)-amide;

1-[4-(2-Methyl-7-phenyl-1,4,9,9b-tetraaza-cyclopenta[a]naphthalen-8-yl)-benzyl]-piperidine-4-carboxylic acid (pyridin-4-ylmethyl)-amide;

1-[4-(2-Methyl-7-phenyl-1,4,9,9b-tetraaza-cyclopenta[a]naphthalen-8-yl)-benzyl]-piperidine-4-carboxylic acid (3-hydroxy-phenyl)-amide;

1-[4-(2-Methyl-7-phenyl-1,4,9,9b-tetraaza-cyclopenta[a]naphthalen-8-yl)-benzyl]-piperidine-4-carboxylic acid (4-hydroxy-cyclohexyl)-amide;

1-[4-(2-Methyl-7-phenyl-1,4,9,9b-tetraaza-cyclopenta[a]naphthalen-8-yl)-benzyl]-piperidine-4-carboxylic acid [2-hydroxy-2-(3-hydroxy-phenyl)-ethyl]-amide;

1-[4-(2-Methyl-7-phenyl-1,4,9,9b-tetraaza-cyclopenta[a]naphthalen-8-yl)-benzyl]-piperidine-4-carboxylic acid [2-(4-hydroxy-phenyl)-ethyl]-amide;

1-[4-(2-Methyl-7-phenyl-1,4,9,9b-tetraaza-cyclopenta[a]naphthalen-8-yl)-benzyl]-piperidine-4-carboxylic acid (3-hydroxy-4-methoxy-phenyl)-amide;

1-[4-(2-Methyl-7-phenyl-1,4,9,9b-tetraaza-cyclopenta[a]naphthalen-8-yl)-benzyl]-piperidine-4-carboxylic acid [2-(3,4-dihydroxy-phenyl)-ethyl]amide;

1-[4-(2-Methyl-7-phenyl-1,4,9,9b-tetraaza-cyclopenta[a]naphthalen-8-yl)-benzyl]-piperidine-4-carboxylic acid 4-hydroxy-3-methoxy-benzylamide;

1-[4-(2-Methyl-7-phenyl-1,4,9,9b-tetraaza-cyclopenta[a]naphthalen-8-yl)-benzyl]-piperidine-4-carboxylic acid benzylamide;

1-[4-(2-Methyl-7-phenyl-1,4,9,9b-tetraaza-cyclopenta[a]naphthalen-8-yl)-benzyl]-piperidine-4-carboxylic acid benzyl-methyl-amide;

1-[4-(2-Methyl-7-phenyl-1,4,9,9b-tetraaza-cyclopenta[a]naphthalen-8-yl)-benzyl]-piperidine-4-carboxylic acid cyclohexylamide;

1-[4-(2-Methyl-7-phenyl-1,4,9,9b-tetraaza-cyclopenta[a]naphthalen-8-yl)-benzyl]-piperidine-4-carboxylic acid (2-methoxy-1-methyl-ethyl)-amide;

1-[4-(2-Methyl-7-phenyl-1,4,9,9b-tetraaza-cyclopenta[a]naphthalen-8-yl)-benzyl]-piperidine-4-carboxylic acid carbamoylmethyl-amide;

1-[4-(2-Methyl-7-phenyl-1,4,9,9b-tetraaza-cyclopenta[a]naphthalen-8-yl)-benzyl]-piperidine-4-carboxylic acid (2,2,2-trifluoro-ethyl)-amide;

1-{4-(2-Methyl-7-phenyl-1,4,9,9b-tetraaza-cyclopenta[a]naphthalen-8-yl)-benzyl}-piperidine-4-carboxylic acid (1-ethyl-propyl)-amide;

1-[4-(2-Methyl-7-phenyl-1,4,9,9b-tetraaza-cyclopenta[a]naphthalen-8-yl)-benzyl]piperidine-4-carboxylic acid tert-butylamide;

1-[4-(2-Methyl-7-phenyl-1,4,9,9b-tetraaza-cyclopenta[a]naphthalen-8-yl)-benzyl]-piperidine-4-carboxylic acid propylamide;

1-[4-(2-Methyl-7-phenyl-1,4,9,9b-tetraaza-cyclopenta[a]naphthalen-8-yl)-benzyl]-piperidine-4-carboxylic acid methylamide;

1-[4-(2-Methyl-7-phenyl-1,4,9,9b-tetraaza-cyclopenta[a]naphthalen-8-yl)-benzyl]piperidine-4-carboxylic acid methylamide;

[4-(3-Hydroxy-phenyl)-piperazin-1-yl]-{1-[4-(2-methyl-7-phenyl-1,4,9,9b-tetraaza-cyclopenta[a]naphthalen-8-yl)-benzyl]-piperidin-4-yl}-methanone;

1-[4-(2-Methyl-7-phenyl-1,4,9,9b-tetraaza-cyclopenta[a]naphthalen-8-yl)-benzyl]-piperidine-4-carboxylic acid ((S)-1-cyclohexyl-ethyl)-amide;

(Hexahydro-cyclopenta[c]pyrrol-2-yl)-{1-[4-(2-methyl-7-phenyl-1,4,9,9b-tetraaza-cyclopenta[a]naphthalen-8-yl)-benzyl]-piperidin-4-yl}-methanone;

1-[4-(2-Methyl-7-phenyl-1,4,9,9b-tetraaza-cyclopenta[c]naphthalen-8-yl)-benzyl]-piperidine-4-carboxylic acid ethyl-isopropyl-amide;

1-[4-(2-Methyl-7-phenyl-1,4,9,9b-tetraaza-cyclopenta[a]naphthalen-8-yl)-benzyl]-piperidine-4-carboxylic acid ((1S,2S)-2-hydroxy-cyclohexyl)-amide;

1-[4-(2-Methyl-7-phenyl-1,4,9,9b-tetraaza-cyclopenta[a]
naphthalen-8-yl)-benzyl]piperidine-4-carboxylic acid
(2-hydroxy-ethyl)-amide;

1-[4-(2-Methyl-7-phenyl-1,4,9,9b-tetraaza-cyclopenta[a]
naphthalen-8-yl)-benzyl]-piperidine-4-carboxylic acid
(tetrahydro-furan-2-ylmethyl)-amide;

1-[4-(2-Methyl-7-phenyl-1,4,9,9b-tetraaza-cyclopenta[a]
naphthalen-8-yl)-benzyl]-piperidine-4-carboxylic acid
cyclobutylamide;

1-[4-(2-Methyl-7-phenyl-1,4,9,9b-tetraaza-cyclopenta[a]
naphthalen-8-yl)-benzyl]-piperidine-4-carboxylic acid
isopropylamide;

({1-[4-(2-Methyl-7-phenyl-1,4,9,9b-tetraaza-cyclopenta[a]
naphthalen-8-yl)-benzyl]-piperidine-4-carbonyl}-
amino)-acetic acid;

1-[4-(2-Methyl-7-phenyl-1,4,9,9b-tetraaza-cyclopenta[a]
naphthalen-8-yl)-benzyl]piperidine-4-carboxylic acid
(4-hydroxy-phenyl)-amide;

1-[4-(2-Methyl-7-phenyl-1,4,9,9b-tetraaza-cyclopenta[a]
naphthalen-8-yl)-benzyl]-piperidine-4-carboxylic acid
(3-carbamoyl-phenyl)-amide;

1-[4-(2-Methyl-7-phenyl-1,4,9,9b-tetraaza-cyclopenta[a]
naphthalen-8-yl)-benzyl]-piperidine-4-carboxylic acid
(3-methoxy-phenyl)-amide;

1-[4-(2-Methyl-7-phenyl-1,4,9,9b-tetraaza-cyclopenta[a]
naphthalen-8-yl)-benzyl]-piperidine-4-carboxylic acid
(3-methanesulfonylamino-phenyl)-amide;

1-[4-(2-Methyl-7-phenyl-1,4,9,9b-tetraaza-cyclopenta[a]
naphthalen-8-yl)-benzyl]-piperidine-4-carboxylic acid
(3-cyano-phenyl)-amide;

1-[4-(2-Methyl-7-phenyl-1,4,9,9b-tetraaza-cyclopenta[a]
naphthalen-8-yl)-benzyl]carboxylic acid (3-fluoro-phenyl)-amide;

1-[4-(2-Methyl-7-phenyl-1,4,9,9b-tetraaza-cyclopenta[a]
naphthalen-8-yl)-benzyl]-piperidine-4-carboxylic acid
(2-hydroxy-phenyl)-amide;

1-[4-(2-Methyl-7-phenyl-1,4,9,9b-tetraaza-cyclopenta[a]
naphthalen-8-yl)-benzyl]-piperidine-4-carboxylic acid
(4-carbamoyl-phenyl)-amide;

1-[4-(2-Methyl-7-phenyl-1,4,9,9b-tetraaza-cyclopenta[a]
naphthalen-8-yl)-benzyl]-piperidine-4-carboxylic acid
(3-sulfamoyl-phenyl)-amide;

1-[4-(2-Methyl-7-phenyl-1,4,9,9b-tetraaza-cyclopenta[a]
naphthalen-8-yl)-benzyl]carboxylic acid benzothiazol-5-
ylamide;

1-[4-(2-Methyl-7-phenyl-1,4,9,9b-tetraaza-cyclopenta[a]
naphthalen-8-yl)-benzyl]-piperidine-4-carboxylic acid
(3-trifluoromethoxy-phenyl)-amide;

1-[4-(2-Methyl-7-phenyl-1,4,9,9b-tetraaza-cyclopenta[a]
naphthalen-8-yl)-benzyl]-piperidine-4-carboxylic acid
thiazol-2-ylamide;

1-[4-(2-Methyl-7-phenyl-1,4,9,9b-tetraaza-cyclopenta[a]
naphthalen-8-yl)-benzyl]-piperidine-4-carboxylic acid
(3-oxo-1,3-dihydro-isobenzofuran-5-yl)-amide;

1-[4-(2-Methyl-7-phenyl-1,4,9,9b-tetraaza-cyclopenta[a]
naphthalen-8-yl)-benzyl]-piperidine-4-carboxylic acid
(3-methanesulfonyl-phenyl)-amide;

1-[4-(2-Methyl-7-phenyl-1,4,9,9b-tetraaza-cyclopenta[a]
naphthalen-8-yl)-benzyl]-piperidine-4-carboxylic acid
(3-hydroxymethyl-phenyl)-amide;

1-[4-(2-Methyl-7-phenyl-1,4,9,9b-tetraaza-cyclopenta[a]
naphthalen-8-yl)-benzyl]-piperidine-4-carboxylic acid
3-amino-benzyl ester;

1-[4-(2-Methyl-7-phenyl-1,4,9,9b-tetraaza-cyclopenta[a]
naphthalen-8-yl)-benzyl]-piperidine-4-carboxylic acid
(3-amino-phenyl)-amide;

1-[4-(2-Methyl-7-phenyl-1,4,9,9b-tetraaza-cyclopenta[a]
naphthalen-8-yl)-benzyl]-piperidine-4-carboxylic acid
(1,1-dioxo-1H-1-benzo[b]thiophen-6-yl)amide;

3-Amino-1-methyl-3-[4-(2-methyl-7-phenyl-1,4,6,9,9b-tetraaza-cyclopenta[a]naphthalen-8-yl)-phenyl]-cyclobutanol;

trans-3-Amino-1-methyl-3-[4-(2-t-butyl-7-phenyl-1,4,9,9b-tetraaza-cyclopenta[a]naphthalen-8-yl)-phenyl]-cyclobutanol;

3-Amino-1-cyclopropyl-3-[4-(2,3-dimethyl-7-phenyl-1,4,6,9,9b-pentaaza-cyclopenta[a]naphthalen-8-yl)-phenyl]-cyclobutanol;

trans-3-Amino-1-Methyl-3-[4-(2-cyclopropyl-7-phenyl-1,4,9,9b-tetraaza-cyclopenta[a]naphthalen-8-yl)-phenyl]-cyclobutanol;

3-Amino-3-[4-(6-chloro-2-methyl-7-phenyl-1,4,9,9b-tetraaza-cyclopenta[a]naphthalen-8-yl)-phenyl]-1-methyl-cyclobutanol;

3-Amino-3-[4-(2,6-dimethyl-7-phenyl-1,4,9,9b-tetraaza-cyclopenta[a]naphthalen-8-yl)-phenyl]-1-methyl-cyclobutanol;

trans-3-Amino-1-methyl-3-[4-(2-(4-methoxyphenyl)-7-phenyl-1,4,9,9b-tetraaza-cyclopenta[a]naphthalen-8-yl)-phenyl]-cyclobutanol;

trans-3-Amino-1-methyl-3-[4-(2-isopropyl-7-phenyl-1,4,9,9b-tetraaza-cyclopenta[a]naphthalen-8-yl)-phenyl]-cyclobutanol;

trans-3-Amino-1-methyl-3-[4-(2-cyclobutyl-7-phenyl-1,4,9,9b-tetraaza-cyclopenta[a]naphthalen-8-yl)-phenyl]-cyclobutanol;

3-Amino-1-methyl-3-[4-(7-phenyl-1,4,9,9b-tetraaza-cyclopenta[a]naphthalen-8-yl)-phenyl]-cyclobutanol;

trans-3-Amino-1-methyl-3-[4-(2-(pyridine-4-yl)-7-phenyl-1,4,9,9b-tetraaza-cyclopenta[a]naphthalen-8-yl)-phenyl]-cyclobutanol;

trans-3-Amino-1-methyl-3-[4-(2-(thiophen-3-yl)-7-phenyl-1,4,9,9b-tetraaza-cyclopenta[a]naphthalen-8-yl)-phenyl]-cyclobutanol;

2-Methyl-7-phenyl-8-{4-[4-(5-pyridin-2-yl-4H-[1,2,4]triazol-3-yl)-piperidin-1-ylmethyl]-phenyl}-1,4,9,9b-tetraazacyclopenta[a]naphthalene;

2-Methyl-8-(4-{4-[5-(4-methylpyridin-3-yl)-4H-[1,2,4]triazol-3-yl]-piperidin-1-ylmethyl}phenyl)-7-phenyl-1,4,9,9b-tetraazacyclopenta[a]naphthalene;

2-Methyl-7-phenyl-8-(4-{4-[5-(2-trifluoromethyl-phenyl)-4H-[1,2,4]triazol-3-yl]-piperidin-1-ylmethyl}-phenyl)-1,4,9,9b-tetraaza-cyclopenta[a]naphthalene;

4-(5-{1-[4-(2-Methyl-7-phenyl-1,4,9,9b-tetraaza-cyclopenta[a]naphthalen-8-yl)-benzyl]-piperidin-4-yl}-4H-[1,2,4]triazol-3-yl)-benzamide;

2-Methyl-7-phenyl-8-(4-{4-[5-(3-trifluoromethyl-phenyl)-4H-[1,2,4]triazol-3-yl]-piperidin-1-ylmethyl}-phenyl)-1,4,9,9b-tetraaza-cyclopenta[a]naphthalene;

2-Methyl-7-phenyl-8-{4-[4-(5-pyridin-3-yl-4H-[1,2,4]triazol-3-yl)-piperidin-1-ylmethyl]-phenyl}-1,4,9,9b-tetraaza-cyclopenta[a]naphthalene;

2-Methyl-7-phenyl-8-(4-{4-[5-(4-trifluoromethyl-phenyl)-4H-[1,2,4]triazol-3-yl]-piperidin-1-ylmethyl}-phenyl)-1,4,9,9b-tetraaza-cyclopenta[a]naphthalene;

2-Methyl-8-{4-[4-(5-phenoxymethyl-4H-[1,2,4]triazol-3-yl)-piperidin-1-ylmethyl]-phenyl}-7-phenyl-1,4,9,9b-tetraaza-cyclopenta[a]naphthalene;

2-Methyl-8-(4-{4-[5-(3-methyl-pyridin-2-yl)-4H-[1,2,4]triazol-3-yl]-piperidin-1-ylmethyl}-phenyl)-7-phenyl-1,4,9,9b-tetraaza-cyclopenta[a]naphthalene;

8-(4-{4-[5-(3-Methoxy-phenyl)-4H-[1,2,4]triazol-3-yl]piperidin-1-ylmethyl}-phenyl)-2-methyl-7-phenyl-1,4,9,9b-tetraaza-cyclopenta[a]naphthalene;

8-(4-{4-[5-(4-Methoxy-phenyl)-4H-[1,2,4]triazol-3-yl]-piperidin-1-ylmethyl}-phenyl)-2-methyl-7-phenyl-1,4,9,9b-tetraaza-cyclopenta[a]naphthalene;

2-Methyl-7-phenyl-8-{4-[4-(6,7,8,9-tetrahydro-5H-[1,2,4]triazolo[4,3-a]azepin-3-yl)-piperidin-1-ylmethyl]-phenyl}-1,4,9,9b-tetraaza-cyclopenta[a]naphthalene;

2-Methyl-7-phenyl-8-{4-[4-(5-pyridin-2-yl-4H-[1,2,4]triazol-3-yl)-piperidin-1-ylmethyl]-phenyl}-1,4,9,9b-tetraaza-cyclopenta[a]naphthalene;

2-Methyl-7-phenyl-8-{4-[4-(5-pyridin-4-yl-4H-[1,2,4]triazol-3-yl)-piperidin-1-ylmethyl]-phenyl}-1,4,9,9b-tetraaza-cyclopenta[a]naphthalene;

2-Methyl-8-(4-{4-[5-(4-methyl-pyridin-2-yl)-4H-[1,2,4]triazol-3-yl]-piperidin-1-ylmethyl}-phenyl)-7-phenyl-1,4,9,9b-tetraaza-cyclopenta[a]naphthalene;

2-Methyl-7-phenyl-8-{4-[4-(5-pyridin-2-yl-4H-[1,2,4]triazol-3-yl)-piperidin-1-ylmethyl]-phenyl}-1,4,9,9b-tetraaza-cyclopenta[a]naphthalene;

2-Methyl-7-phenyl-8-(4-{4-[5-(6-trifluoromethyl-pyridin-3-yl)-4H-[1,2,4]triazol-3-yl]-piperidin-1-ylmethyl}-phenyl)-1,4,9,9b-tetraaza-cyclopenta[a]naphthalene;

2-Methyl-8-(4-{4-[5-(6-methyl-pyridin-2-yl)-4H-[1,2,4]triazol-3-yl]-piperidin-1-ylmethyl}-phenyl)-7-phenyl-1,4,9,9b-tetraaza-cyclopenta[a]naphthalene;

1-{1-[4-(2-Methyl-7-phenyl-1,4,9,9b-tetraaza-cyclopenta[a]naphthalen-8-yl)-benzyl]-piperidin-4-yl}-1,3-dihydro-benzoimidazol-2-one;

2-Methyl-8-{4-[4-(4-methyl-4H-[1,2,4]triazol-3-yl)-piperidin-1-ylmethyl]-phenyl}-7-phenyl-1,4,9,9b-tetraaza-cyclopenta[a]naphthalene;

8-[4-(2-Methyl-7-phenyl-1,4,9,9b-tetraaza-cyclopenta[a]naphthalen-8-yl)-benzyl]-1,3,8-triaza-spiro[4.5]decane-2,4-dione;

8-(4-{4-[5-(4-Chloro-phenyl)-1H-pyrazol-3-yl]-piperidin-1-ylmethyl}-phenyl)-2-methyl-7-phenyl-1,4,9,9b-tetraaza-cyclopenta[a]naphthalene;

{1-[4-(2-Methyl-7-phenyl-1,4,9,9b-tetraaza-cyclopenta[a]naphthalen-8-yl)-benzyl]-piperidin-4-yl}-carbamic acid tert-butyl ester;

1-[4-(2-Methyl-7-phenyl-1,4,9,9b-tetraaza-cyclopenta[a]naphthalen-8-yl)-benzyl]-piperidin-4-ylamine;

N-{1-[4-(2-Methyl-7-phenyl-1,4,9,9b-tetraaza-cyclopenta[a]naphthalen-8-yl)-benzyl]-piperidin-4-yl}-isonicotinamide;

N-{1-[4-(2-Methyl-7-phenyl-1,4,9,9b-tetraaza-cyclopenta[a]naphthalen-8-yl)-benzyl]-piperidin-4-yl}-phthalamic acid;

1-{1-[4-(2-Methyl-7-phenyl-1,4,9,9b-tetraaza-cyclopenta[a]naphthalen-8-yl)-benzyl]-piperidin-4-yl}-3-pyridin-4-yl-urea;

1-{1-[4-(2-Methyl-7-phenyl-1,4,9,9b-tetraaza-cyclopenta[a]naphthalen-8-yl)-benzyl]-piperidin-4-yl}-N-morpholinyl-urea;

1-[4-(2-Methyl-7-phenyl-1,4,9,9b-tetraaza-cyclopenta[a]naphthalen-8-yl)-benzyl]-piperidine-4-carboxylic acid pyridin-4-ylamide;

1-[4-(2-Methyl-7-phenyl-1,4,9,9b-tetraaza-cyclopenta[a]naphthalen-8-yl)-benzyl]-piperidine-4-carboxylic acid (2-methoxy-phenyl)-amide;

1-[4-(2-Methyl-7-phenyl-1,4,9,9b-tetraaza-cyclopenta[a]naphthalen-8-yl)-benzyl]-piperidine-4-carboxylic acid (4-carbamoyl-2-methoxy-phenyl)-amide;

1-[4-(2-Methyl-7-phenyl-1,4,9,9b-tetraaza-cyclopenta[a]naphthalen-8-yl)-benzyl]-piperidine-4-carboxylic acid hydrazide trans-3-Amino-3-[4-(2-tert-butyl-7-(thiophen-2-yl)-1,4,9,9b-tetraaza-cyclopenta[a]naphthalen-8-yl)-phenyl]-1-methyl-cyclobutanol;

trans-3-Amino-3-{4-[2-tert-butyl-7-(2-fluoro-phenyl)-1,4,9,9b-tetraaza-cyclopenta[a]naphthalen-8-yl]-phenyl}-1-methyl-cyclobutanol;

trans-3-Amino-3-[4-(2-tert-butyl-7-(thiophen-3-yl)-1,4,9,9b-tetraaza-cyclopenta[a]naphthalen-8-yl)-phenyl]-1-methyl-cyclobutanol;

trans-3-Amino-1-cyclopropyl-3-[4-(7-phenyl-4,5-dihydro-1,4,6,9,9b-pentaaza-cyclopenta[a]naphthalen-8-yl)-phenyl]-cyclobutanol;

trans-3-Amino-1-cyclopropyl-3-[4-(7-phenyl-1,4,6,9,9b-pentaaza-cyclopenta[a]naphthalen-8-yl)-phenyl]-cyclobutanol;

trans-3-Amino-1-methyl-3-[4-(7-phenyl-1,4,6,9,9b-pentaaza-cyclopenta[a]naphthalen-8-yl)-phenyl]-cyclobutanol;

trans-3-Amino-1-methyl-3-[4-(5-methyl-7-phenyl-1,4,9,9b-tetraaza-cyclopenta[a]naphthalen-8-yl)-phenyl]-cyclobutanol;

trans-3-Amino-1-methyl-3-[4-(7-thiophen-2-yl-1,4,9,9b-tetraaza-cyclopenta[a]naphthalen-8-yl)-phenyl]-cyclobutanol;

trans-3-Amino-1-cyclopropyl-3-[4-(2-methyl-3,7-diphenyl-1,4,9,9b-tetraaza-cyclopenta[a]naphthalen-8-yl)-phenyl]-cyclobutanol;

trans-3-Amino-1-cyclopropyl-3-{4-[3-(4-methoxy-phenyl)-2-methyl-7-phenyl-1,4,9,9b-tetraaza-cyclopenta[a]naphthalen-8-yl]-phenyl}-cyclobutanol;

trans-3-Amino-1-cyclopropyl-3-[4-(2-methyl-7-phenyl-3-pyridin-4-yl-1,4,9,9b-tetraaza-cyclopenta[a]naphthalen-8-yl)-phenyl]-cyclobutanol;

trans-3-Amino-1-ethyl-3-[4-(2-methyl-7-phenyl-1,4,9,9b-tetraaza-cyclopenta[a]naphthalen-8-yl)-phenyl]-cyclobutanol;

trans-3-Amino-1-cyclopropyl-3-[4-(3-bromo-2-methyl-7-phenyl-1,4,6,9,9b-pentaaza-cyclopenta[a]naphthalen-8-yl)-phenyl]-cyclobutanol;

trans-3-Amino-1-cyclopropyl-3-[4-(2,3-dimethyl-7-phenyl-1,4,6,9,9b-pentaaza-cyclopenta[a]naphthalen-8-yl)-phenyl]-cyclobutanol;

trans-3-Amino-1-methyl-3-[4-(2-methyl-6,7-diphenyl-1,4,9,9b-tetraaza-cyclopenta[a]naphthalen-8-yl)-phenyl]-cyclobutanol;

trans-8-[4-(1-Amino-3-hydroxy-3-methyl-cyclobutyl)-phenyl]-2-methyl-7-phenyl-1,4,9,9b-tetraaza-cyclopenta[a]naphthalen-6-ol;

trans-3-Amino-3-[4-(6-cyclopropyl-2-methyl-7-phenyl-1,4,9,9b-tetraaza-cyclopenta[a]naphthalen-8-yl)-phenyl]-1-methyl-cyclobutanol;

trans-3-Amino-3-[4-(2-isopropyl-7-thiophen-3-yl-1,4,9,9b-tetraaza-cyclopenta[d]naphthalen-8-yl)-phenyl]-1-methyl-cyclobutanol;

trans-3-Amino-3-[4-(2-isopropyl-7-thiophen-2-yl-1,4,9,9b-tetraaza-cyclopenta[a]naphthalen-8-yl)-phenyl]-1-methyl-cyclobutanol;

trans-3-Amino-3-{4-[7-(2-fluoro-phenyl)-2-isopropyl-1,4,9,9b-tetraaza-cyclopenta[a]naphthalen-8-yl]-phenyl}-1-methyl-cyclobutanol;

trans-3-Amino-3-[4-(2-cyclopropyl-7-phenyl-1,4,9,9b-tetraaza-cyclopenta[a]naphthalen-8-yl)-phenyl]-1-isopropyl-cyclobutanol;

trans-3-Amino-1-isopropyl-3-[4-(2-methyl-7-phenyl-1,4,9,9b-tetraaza-cyclopenta[a]naphthalen-8-yl)-phenyl]-cyclobutanol;
cis-3-Amino-3-[4-(2-cyclopropyl-7-phenyl-1,4,9,9b-tetraaza-cyclopenta[a]naphthalen-8-yl)-phenyl]-1-isopropyl-cyclobutanol;
trans-2-{1-[4-(2-Cyclopropyl-5-methyl-7-phenyl-1,4,9,9b-tetraaza-cyclopenta[a]naphthalen-8-yl)-phenyl]-3-hydroxy-3-methyl-cyclobutyl}-isoindole-1,3-dione;
trans-3-Amino-3-[4-(2-isopropyl-5-methyl-7-phenyl-1,4,9,9b-tetraaza-cyclopenta[a]naphthalen-8-yl)-phenyl]-1-methyl-cyclobutanol;
trans-3-Amino-3-{4-[7-(3-fluoro-phenyl)-2-methyl-1,4,9,9b-tetraaza-cyclopenta[a]naphthalen-8-yl]-phenyl}-1-methyl-cyclobutanol;
trans-3-Amino-3-{4-[7-(4-fluoro-phenyl)-2-methyl-1,4,9,9b-tetraaza-cyclopenta[a]naphthalen-8-yl]-phenyl}-1-methyl-cyclobutanol;
trans-3-Amino-3-{4-[7-(4-chloro-phenyl)-2-methyl-1,4,9,9b-tetraaza-cyclopenta[a]naphthalen-8-yl]-phenyl}-1-methyl-cyclobutanol;
trans-3-Amino-3-{4-[7-(3-chloro-phenyl)-2-methyl-1,4,9,9b-tetraaza-cyclopenta[a]naphthalen-8-yl]-phenyl}-1-methyl-cyclobutanol;
trans-3-Amino-1-methyl-3-[4-(2-methyl-7-o-tolyl-1,4,9,9b-tetraaza-cyclopenta[a]naphthalen-8-yl)-phenyl]-cyclobutanol;
trans-3-Amino-3-{4-[7-(2-methoxy-phenyl)-2-methyl-1,4,9,9b-tetraaza-cyclopenta[a]naphthalen-8-yl]-phenyl}-1-methyl-cyclobutanol;
trans-3-Amino-3-{4-[7-(3-methoxy-phenyl)-2-methyl-1,4,9,9b-tetraaza-cyclopenta[a]naphthalen-8-yl]-phenyl}-1-methyl-cyclobutanol;
trans-3-Amino-3-{4-[7-(2-chloro-phenyl)-2-methyl-1,4,9,9b-tetraaza-cyclopenta[a]naphthalen-8-yl]-phenyl}-1-methyl-cyclobutanol;
trans-3-Amino-1-methyl-3-[4-(2-methyl-7-m-tolyl-1,4,9,9b-tetraaza-cyclopenta[a]naphthalen-8-yl)-phenyl]-cyclobutanol;
trans-3-Amino-3-{4-[7-(4-methoxy-phenyl)-2-methyl-1,4,9,9b-tetraaza-cyclopenta[a]naphthalen-8-yl]-phenyl}-1-methyl-cyclobutanol;
trans-3-Amino-1-methyl-3-{4-[2-methyl-7-(2-trifluoromethyl-phenyl)-1,4,9,9b-tetraaza-cyclopenta[a]naphthalen-8-yl]-phenyl}-cyclobutanol;
trans-3-Amino-1-methyl-3-[4-(2-methyl-7-pyridin-3-yl-1,4,9,9b-tetraaza-cyclopenta[a]naphthalen-8-yl)-phenyl]-cyclobutanol;
trans-3-{8-[4-(1-Amino-3-hydroxy-3-methyl-cyclobutyl)-phenyl]-2-methyl-1,4,9,9b-tetraaza-cyclopenta[a]naphthalen-7-yl}-benzonitrile;
trans-2-{8-[4-(1-Amino-3-hydroxy-3-methyl-cyclobutyl)-phenyl]-2-methyl-1,4,9,9b-tetraaza-cyclopenta[a]naphthalen-7-yl}-benzonitrile;
trans-4-{8-[4-(1-Amino-3-hydroxy-3-methyl-cyclobutyl)-phenyl]-2-methyl-1,4,9,9b-tetraaza-cyclopenta[a]naphthalen-7-yl}-benzonitrile;
4-{8-[4-(1-amino-3-hydroxy-3-methyl-cyclobutyl)-phenyl]-2-methyl-1,4,9,9b-tetraaza-cyclopenta[a]naphthalen-7-yl}-phenyl ester;
trans-4-{8-[4-(1-Amino-3-hydroxy-3-methyl-cyclobutyl)-phenyl]-2-methyl-1,4,9,9b-tetraaza-cyclopenta[a]naphthalen-7-yl}-phenol;
trans-3-{8-[4-(1-Amino-3-hydroxy-3-methyl-cyclobutyl)-phenyl]-2-methyl-1,4,9,9b-tetraaza-cyclopenta[a]naphthalen-7-yl}-phenol;
3-{8-[4-(1-amino-3-hydroxy-3-methyl-cyclobutyl)-phenyl]-2-methyl-1,4,9,9b-tetraaza-cyclopenta[a]naphthalen-7-yl}-phenyl ester;
2-{8-[4-(1-amino-3-hydroxy-3-methyl-cyclobutyl)-phenyl]-2-methyl-1,4,9,9b-tetraaza-cyclopenta[a]naphthalen-7-yl}-phenyl ester;
trans-3-Amino-1-methyl-3-[4-(2-methyl-7-pyridin-4-yl-1,4,9,9b-tetraaza-cyclopenta[a]naphthalen-8-yl)-phenyl]-cyclobutanol;
trans-3-Amino-1-methyl-3-[4-(2-methyl-7-phenyl-6-pyridin-3-yl-1,4,9,9b-tetraaza-cyclopenta[a]naphthalen-8-yl)-phenyl]-cyclobutanol;
trans-3-Amino-1-methyl-3-[4-(2-methyl-7-phenyl-6-pyridin-4-yl-1,4,9,9b-tetraaza-cyclopenta[a]naphthalen-8-yl)-phenyl]-cyclobutanol;
trans-3-Amino-1-methyl-3-[4-(2-methyl-7-phenyl-6-pyridin-5-yl-1,4,9,9b-tetraaza-cyclopenta[a]naphthalen-8-yl)-phenyl]-cyclobutanol;
trans-3-Amino-1-methyl-3-{4-(2-methyl-7-phenyl-6-(1H-pyrazol-3-yl)-1,4,9,9b-tetraaza-cyclopenta[a]naphthalen-8-yl]-phenyl}-cyclobutanol;
trans-8-[4-(1-Amino-3-hydroxy-3-methyl-cyclobutyl)-phenyl]-2-methyl-7-phenyl-1,4,9,9b-tetraaza-cyclopenta[a]naphthalene-6-carbonitrile;
trans-3-Amino-3-[4-(6-methoxy-2-methyl-7-phenyl-1,4,9,9b-tetraaza-cyclopenta[a]naphthalen-8-yl)-phenyl]-1-methyl-cyclobutanol;
trans-3-Amino-3-[4-(6-amino-2-methyl-7-phenyl-1,4,9,9b-tetraaza-cyclopenta[a]naphthalen-8-yl)-phenyl]-1-methyl-cyclobutanol;
trans-3-Amino-3-[4-(3-bromo-7-phenyl-1,4,9,9b-tetraaza-cyclopenta[a]naphthalen-8-yl)-phenyl]-1-methyl-cyclobutanol;
trans-8-[4-(1-Amino-3-hydroxy-3-methyl-cyclobutyl)-phenyl]-2-methyl-7-phenyl-1,4,9,9b-tetraaza-cyclopenta[a]naphthalene-3-carbonitrile;
trans-8-[4-(1-Amino-3-hydroxy-3-methyl-cyclobutyl)-phenyl]-7-phenyl-1,4,9,9b-tetraaza-cyclopenta[a]naphthalene-3-carbonitrile;
trans-3-Amino-1-methyl-3-[4-(3-methyl-7-phenyl-1,4,9,9b-tetraaza-cyclopenta[a]naphthalen-8-yl)-phenyl]-cyclobutanol;
trans-3-Amino-3-[4-(2-isopropenyl-7-phenyl-1,4,6,9,9b-pentaaza-cyclopenta[a]naphthalen-8-yl)-phenyl]-1-methyl-cyclobutanol;
trans-3-Amino-3-[4-(2-cyclopropyl-7-thiophen-2-yl-1,4,9,9b-tetraaza-cyclopenta[a]naphthalen-8-yl)-phenyl]-1-methyl-cyclobutanol;
trans-3-Amino-3-[4-(2-isopropenyl-7-thiophen-2-yl-1,4,6,9,9b-pentaaza-cyclopenta[a]naphthalen-8-yl)-phenyl]-1-methyl-cyclobutanol;
3-Amino-1-methyl-3-[4-(2,5,6-trimethyl-7-phenyl-1,4,9,9b-tetraaza-cyclopenta[a]naphthalen-8-yl)-phenyl]-cyclobutanol; and
1-[4-(2-Methyl-7-phenyl-1,4,9,9b-tetraaza-cyclopenta[a]naphthalen-8-yl)-benzyl]-piperidine-4-carboxylic acid methyl ester;
or a pharmaceutically acceptable salt, stereoisomer or N-oxide derivative thereof.

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119-1190), and occur as racemates, racemic mixtures, and as individual diastereomers, with all possible isomers and mixtures thereof, including optical isomers, all such stereoisomers being included in the present invention.

In addition, the compounds disclosed herein may exist as tautomers and both tautomeric forms are intended to be encompassed by the scope of the invention, even though only one tautomeric structure is depicted.

Tetrazoles exist as a mixture of 1H/2H tautomers. The tautomeric forms of the tetrazol moiety are also within the scope of the instant invention.

This invention is also intended to encompass pro-drugs of the compounds disclosed herein. A prodrug of any of the compounds can be made using well known pharmacological techniques.

When any variable (e.g. $R^2$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is bicyclic, it is intended that the bond be attached to any of the suitable atoms on either ring of the bicyclic moiety.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off target activity, packaging properties, and so on. (Diass, J. O. et al. Organometallics (2006) 5:1188-1198; Showell, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be taken to be equivalent to the phrase "optionally substituted with at least one substituent" and in such cases the preferred embodiment will have from zero to four substituents, and the more preferred embodiment will have from zero to three substituents.

As used herein, "alkyl" is intended to include both branched and straight-chain saturated aliphatic hydrocarbon groups having the specified number of carbon atoms. For example, $C_1$-$C_{10}$, as in "($C_1$-$C_{10}$)alkyl" is defined to include groups having 1, 2, 3, 4, 5, 6, 7, 8, 9 or 10 carbons in a linear or branched arrangement. For example, "($C_1$-$C_{10}$)alkyl" specifically includes methyl, ethyl, n-propyl, i-propyl, n-butyl, t-butyl, i-butyl, pentyl, hexyl, heptyl, octyl, nonyl, decyl, and so on.

The term "cycloalkyl" means a monocyclic saturated aliphatic hydrocarbon group having the specified number of carbon atoms. For example, "cycloalkyl" includes cyclopropyl, methyl-cyclopropyl, 2,2-dimethyl-cyclobutyl, 2-ethyl-cyclopentyl, cyclohexyl, and so on.

"Alkoxy" represents either a cyclic or non-cyclic alkyl group of indicated number of carbon atoms attached through an oxygen bridge. "Alkoxy" therefore encompasses the definitions of alkyl and cycloalkyl above.

The term "alkylidene" refers to both branched and straight-chain divalent hydrocarbon groups having the specified number of carbon atoms. For example, "alkylidene" includes methylene, ethylidene, n-propylidene, i-propylidene, n-butylidene, t-butylidene, i-butylidene, pentylidene, hexylidene, and so on.

If no number of carbon atoms is specified, the term "alkenyl" refers to a non-aromatic hydrocarbon radical, straight, branched or cyclic, containing from 2 to 10 carbon atoms and at least one carbon to carbon double bond. Preferably one carbon to carbon double bond is present, and up to four non-aromatic carbon-carbon double bonds may be present. Thus, "($C_2$-$C_{10}$)alkenyl" means an alkenyl radical having from 2 to 10 carbon atoms. Alkenyl groups include ethenyl, propenyl, butenyl, 2-methylbutenyl and cyclohexenyl. The straight, branched or cyclic portion of the alkenyl group may contain double bonds and may be substituted if a substituted alkenyl group is indicated.

The term "alkynyl" refers to a hydrocarbon radical straight, branched or cyclic, containing from 2 to 10 carbon atoms and at least one carbon to carbon triple bond. Up to three carbon-carbon triple bonds may be present. Thus, "($C_2$-$C_{10}$)alkynyl" means an alkynyl radical having from 2 to 10 carbon atoms. Alkynyl groups include ethynyl, propynyl, butynyl, 3-methylbutynyl and so on. The straight, branched or cyclic portion of the alkynyl group may contain triple bonds and may be substituted if a substituted alkynyl group is indicated.

In certain instances, substituents may be defined with a range of carbons that includes zero, such as ($C_0$-$C_6$)alkylene-aryl. If aryl is taken to be phenyl, this definition would include phenyl itself as well as —$CH_2$Ph, —$CH_2CH_2$Ph, $CH(CH_3)$ $CH_2CH(CH_3)$Ph, and so on.

As used herein, "aryl" is intended to mean any stable monocyclic or bicyclic carbon ring of up to 7 atoms in each ring, wherein at least one ring is aromatic. Examples of such aryl elements include phenyl, naphthyl, tetrahydro-naphthyl, indanyl and biphenyl. In cases where the aryl substituent is bicyclic and one ring is non-aromatic, it is understood that attachment is via the aromatic ring.

The term "carbocycle" or "carbocyclyl" is intended to mean any stable saturated or unsaturated aliphatic monocyclic or bicyclic hydrocarbon group with 3-7 members in each ring. "Carbocyclyl" therefore includes the above mentioned cycloalkyls, as well as spiro-condensed bicyclic ring. Further examples of "carbocyclyl" include, but are not limited to the following: cyclopropyl, methyl-cyclopropyl, cyclobutyl, 2,2-dimethyl-cyclobutyl, 2-ethyl-cyclopentyl, cyclohexyl, or the group selected from:

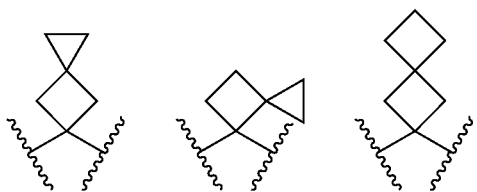

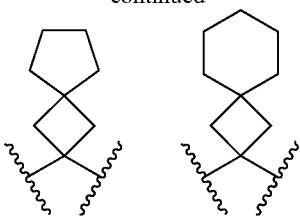

and so on.

The term heteroaryl, as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, quinoxalinyl, pyrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively. Such heteroaryl moieties for substituent Q include but are not limited to: 2-benzimidazolyl, 2-quinolinyl, 3-quinolinyl, 4-quinolinyl, 1-isoquinolinyl, 3-isoquinolinyl and 4-isoquinolinyl.

The term "heterocycle" or "heterocyclyl" as used herein is intended to mean a 3- to 10-membered aromatic or non-aromatic heterocycle containing from 1 to 4 heteroatoms selected from the group consisting of O, N and S, and includes bicyclic or tricyclic groups. "Heterocyclyl" therefore includes the above mentioned heteroaryls, as well as dihydro and tetrahydro analogs thereof. Further examples of "heterocyclyl" include, but are not limited to the following: benzoimidazolyl, benzoimidazolonyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidinyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides or S-oxides thereof. Attachment of a heterocyclyl substituent can occur via a carbon atom or via a heteroatom. In addition, when $R^x$ and $R^y$ in the Formula A are taken together to form a bicyclic heterocycle, the examples of the heterocyclyl include, but are not limited to the group selected from:

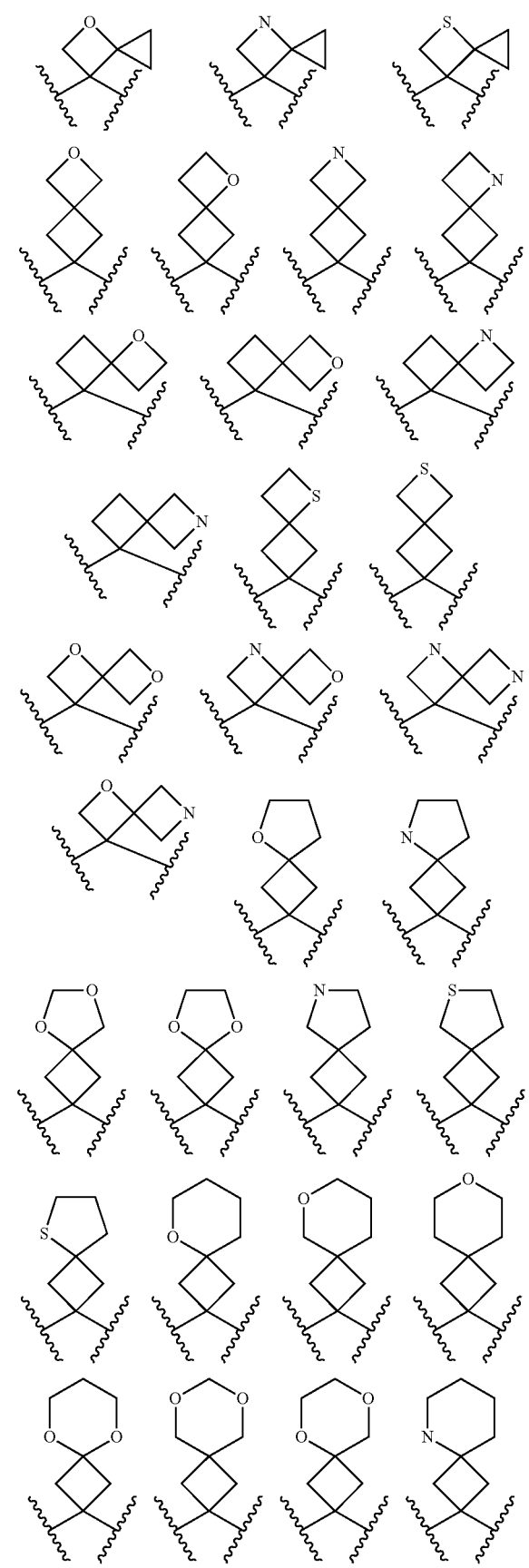

-continued

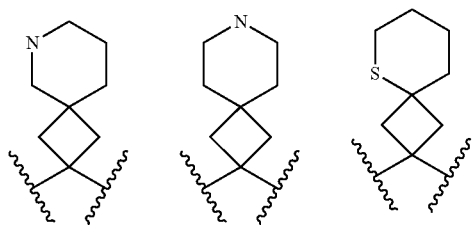

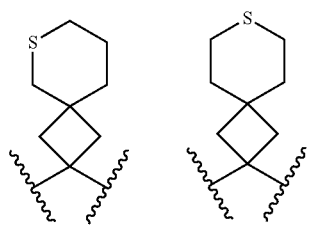

and so on. Further, when $R^7$ and $R^8$ of the formula:

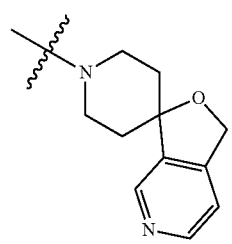

in Formula A and B, are taken together to form a tricyclic heterocycle, the examples of the heterocyclyl include, but are not limited to the group selected from:

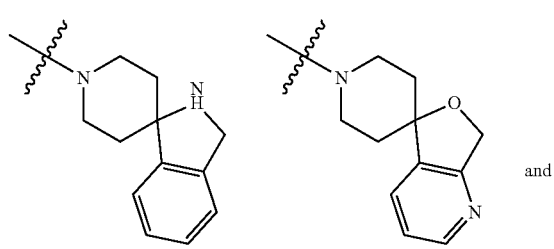

and

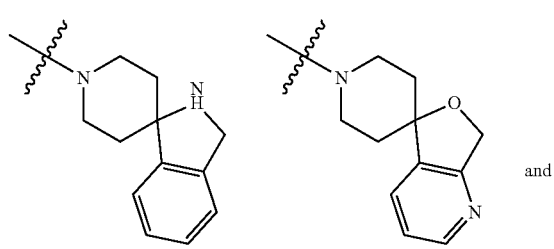

As appreciated by those of skill in the art, "halo" or "halogen" as used herein is intended to include chloro (Cl), fluoro (F), bromo (Br) and iodo (I).

In an embodiment of Formula A and B, the moiety illustrated by the formula:

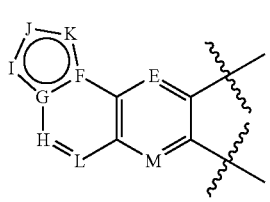

includes the following structures:

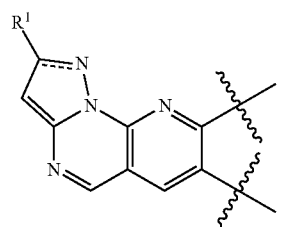

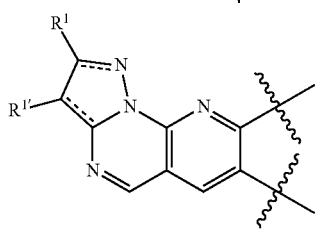

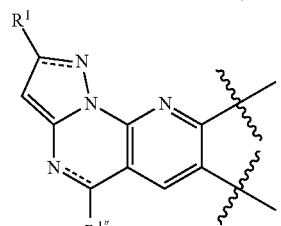

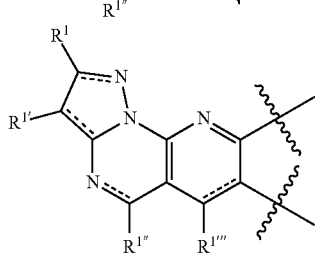

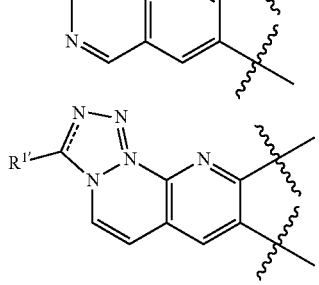

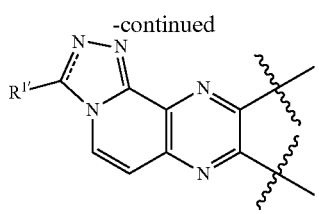
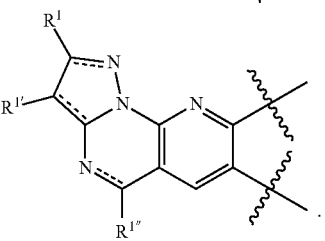
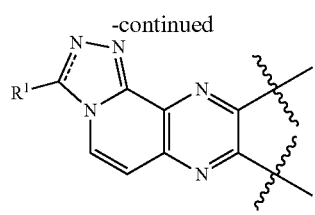
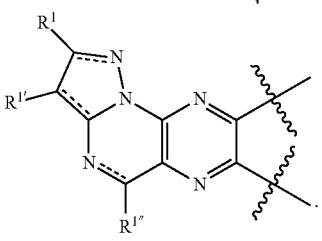
In another embodiment of Formula A and B, the moiety illustrated by the formula:
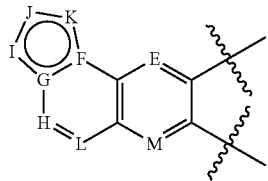
includes the following structures:
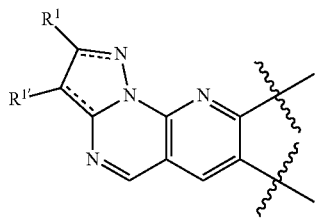
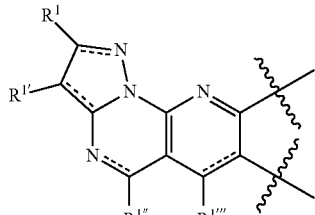
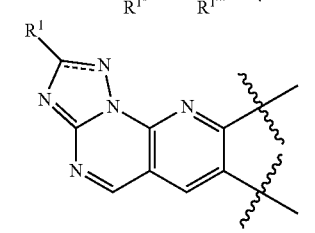
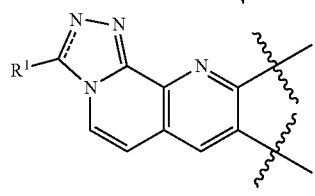
In another embodiment of Formula A and B, the moiety illustrated by the formula:
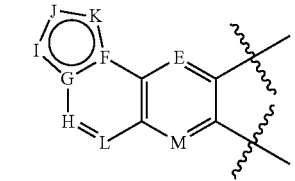
includes the following structures:
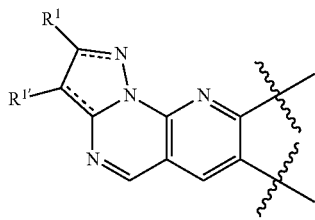
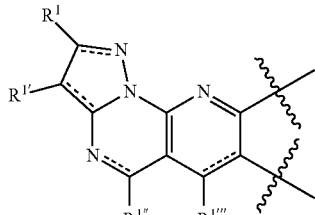
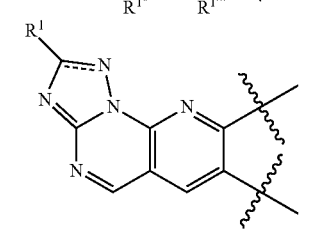
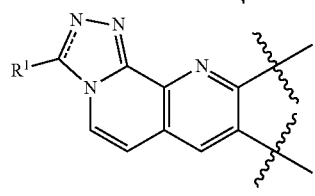

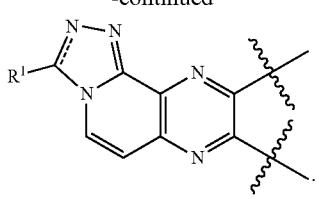
In another embodiment of Formula A and B, the moiety illustrated by the formula:
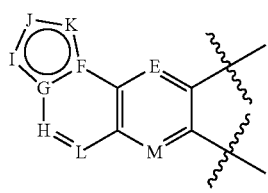
includes the following structures:
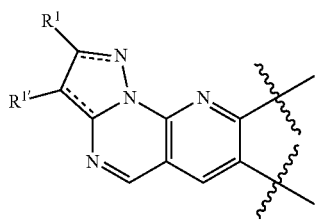
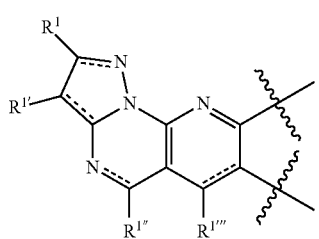
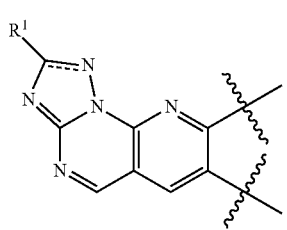
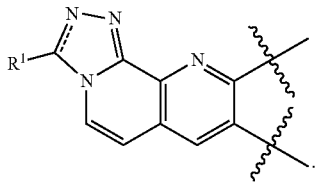
In another embodiment of Formula A and B, the moiety illustrated by the formula:
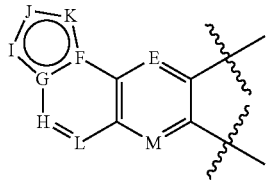
includes the following structures:
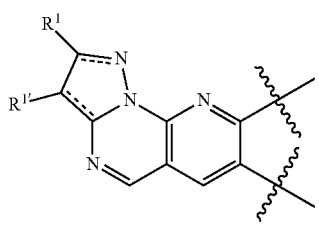
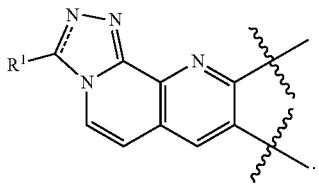
In yet another embodiment of Formula A and B, the moiety illustrated by the formula:
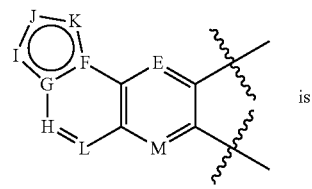 is
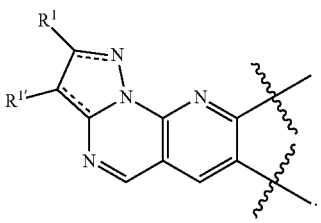

In another embodiment of Formula A and B, the moiety illustrated by the formula:

[chemical structure]

is

[chemical structure with $R^1$, $R^{1'}$, $R^{1''}$, $R^{1'''}$]

In another embodiment of Formula A and B, the moiety illustrated by the formula:

[chemical structure]

is

[chemical structure with $R^1$, $R^{1'}$, $R^{1''}$]

In an embodiment of Formula A, Ring Z is selected from: phenyl and heterocyclyl.

In another embodiment, Ring Z is selected from:

[chemical structures: phenyl, pyrimidyl, thienyl, thienyl and pyrazolyl]

In another embodiment, Ring Z is selected from: phenyl, 2-thienyl, 3-pyridyl, 4-pyridyl and 3-thienyl In yet another embodiment, Ring Z is phenyl.

In an embodiment of Formula B, Ring Z is phenyl.

In an embodiment of Formula B, Ring Z is selected from: 2-thienyl and 3-thienyl.

In an embodiment, p is independently 0, 1, 2 or 3.

In a further embodiment, p is independently 0, 1 or 2.

In another embodiment, p is independently 1.

In yet another embodiment, p is independently 0.

In an embodiment, $R^2$ is independently selected from: ($C_1$-$C_6$)alkyl, O(C=O)($C_1$-$C_6$)alkyl, ($C_1$-$C_6$)alkoxy, CN, $CO_2H$, halo, OH and $NH_2$, wherein said alkyl is optionally substituted with halo.

In an embodiment of Formula A and B, $R^2$ is selected from: H and halogen.

In another embodiment of Formula A and B, $R^2$ is selected from: H and F.

In an embodiment of Formula A, C and E, $R^1$ is H.

In an embodiment of Formula B, $R^1$, $R^{1'}$, $R^{1''}$ and $R^{1'''}$ are H.

In an embodiment of Formula D, $R^1$ and $R^{1'}$ are H.

In an embodiment of Formula A, $R^1$ is selected from: oxo, $(C=O)_aO_b(C_1$-$C_{10})$alkyl, $(C=O)_aO_b$-aryl, halo, OH, $(C=O)_aNR^7R^8$, CN, $(C=O)_aO_b(C_3$-$C_8)$cycloalkyl, and $(C=O)_aO_b$-heterocyclyl, said alkyl, aryl, cycloalkyl, and heterocyclyl is optionally substituted with one or more substituents selected from $R^6$; $R^6$ is: $(C=O)_aO_b(C_1$-$C_{10})$alkyl, halo, OH or $O_a(C=O)_bNR^7R^8$; $R^7$ and $R^8$ in the group of $(C=O)_aNR^7R^8$, are independently H or $(C=O)_aO_b(C_1$-$C_{10})$alkyl; a is 0 or 1; and b is 0 or 1.

In another embodiment of Formula A, $R^1$ is selected from: oxo, $(C=O)_aO_b(C_1$-$C_{10})$alkyl, $(C=O)_aO_b$-aryl, halo, OH, $(C=O)_aNR^7R^8$, CN, $(C=O)_aO_b(C_3$-$C_8)$cycloalkyl, and $(C=O)_aO_b$-heterocyclyl, said alkyl, aryl, cycloalkyl, and heterocyclyl is optionally substituted with one or more substituents selected from $R^6$; $R^6$ is: $(C=O)_aO_b(C_1$-$C_{10})$alkyl, halo, OH or $NR^7R^8$; $R^7$ and $R^8$ in the group of $(C=O)_aNR^7R^8$ or $NR^7R^8$, are independently H or $(C_1$-$C_6)$alkyl; a is 0 or 1; and b is 0 or 1.

In an embodiment of Formula B, $R^1$ is selected from: oxo, $(C=O)_aO_b(C_1$-$C_{10})$alkyl, $(C=O)_aO_b$-aryl, halo, OH, $(C=O)_aNR^7R^8$, CN, $(C=O)_aO_b(C_3$-$C_8)$cycloalkyl, and $(C=O)_aO_b$-heterocyclyl, said alkyl, aryl, cycloalkyl, and heterocyclyl is optionally substituted with one or more substituents selected from $R^6$; $R^{1'}$ is selected from: H, oxo, $(C=O)_aO_b(C_1$-$C_{10})$alkyl, $(C=O)_aO_b$-aryl, halo, OH, $(C=O)_aNR^7R^8$, CN, $(C=O)_aO_b(C_3$-$C_8)$cycloalkyl, and $(C=O)_aO_b$-heterocyclyl, said alkyl, aryl, cycloalkyl, and heterocyclyl is optionally substituted with one or more substituents selected from $R^6$; $R^{1''}$ is selected from: H, oxo, $(C=O)_aO_b(C_1$-$C_{10})$alkyl, $(C=O)_aO_b$-aryl, halo, OH, $(C=O)_aNR^7R^8$, CN, $(C=O)_aO_b(C_3$-$C_8)$cycloalkyl, and $(C=O)_aO_b$-heterocyclyl, said alkyl, aryl, cycloalkyl, and heterocyclyl is optionally substituted with one or more substituents selected from $R^6$; $R^{1'''}$ is selected from: H, oxo, $(C=O)_aO_b(C_1$-$C_{10})$alkyl, $(C=O)_aO_b$-aryl, halo, OH, $(C=O)_aNR^7R^8$, CN, $(C=O)_aO_b(C_3$-$C_8)$cycloalkyl, and $(C=O)_aO_b$-heterocyclyl, said alkyl, aryl, cycloalkyl, and heterocyclyl is optionally substituted with one or more substituents selected from $R^6$; $R^6$ is: $(C=O)_aO_b(C_1$-$C_{10})$alkyl, halo, OH or $O_a(C=O)_bNR^7R^8$; $R^7$ and $R^8$ in the group of $(C=O)_aNR^7R^8$, are independently H or $(C=O)_aO_b(C_1$-$C_{10})$alkyl; a is 0 or 1; and b is 0 or 1.

In another embodiment of Formula B, $R^1$ is selected from: oxo, $(C=O)_aO_b(C_1$-$C_{10})$alkyl, $(C=O)_aO_b$-aryl, halo, OH, $(C=O)_aNR^7R^8$, CN, $(C=O)_aO_b(C_3$-$C_8)$cycloalkyl, and $(C=O)_aO_b$-heterocyclyl, said alkyl, aryl, cycloalkyl, and heterocyclyl is optionally substituted with one or more substituents selected from $R^6$; $R^{1'}$ is selected from: H, $(C=O)_aO_b(C_1$-$C_{10}))$alkyl, $(C=O)_aO_b$-aryl, halo, CN and $(C=O)_aO_b$-heterocyclyl, said alkyl, aryl, and heterocyclyl is optionally substituted with one or more substituents selected from $R^6$; $R^{1''}$ is selected from: H, $(C=O)_aO_b(C_1$-$C_{10})$alkyl and halo, said alkyl is optionally substituted with one or more substituents selected from $R^6$; $R^{1'''}$ is selected from: H, $(C=O)_aO_b$ $(C_1-C_{10})$alkyl and halo, said alkyl is optionally substituted with one or more substituents selected from $R^6$; $R^6$ is: $(C=O)_aO_b(C_1-C_{10})$alkyl, halo, OH or $O_a(C=O)_bNR^7R^8$; $R^7$ and $R^8$ in the group of $(C=O)_aNR^7R^8$, are independently H or $(C=O)_aO_b(C_1-C_{10})$alkyl; a is 0 or 1; and b is 0 or 1.

In yet another embodiment of Formula B, $R^1$ is selected from: oxo, $(C=O)_aO_b(C_1-C_{10})$alkyl, $(C=O)_aO_b$-aryl, OH, $(C=O)_aNR^7R^8$, $(C=O)_aO_b(C_3-C_8)$cycloalkyl, and $(C=O)_aO_b$-heterocyclyl, said alkyl, aryl, cycloalkyl, and heterocyclyl is optionally substituted with one or more substituents selected from $R^6$; $R^{1'}$ is selected from: H, $(C=O)_aO_b(C_1-C_{10})$alkyl, $(C=O)_aO_b$-aryl, halo, CN and $(C=O)_aO_b$-heterocyclyl, said alkyl, aryl, and heterocyclyl is optionally substituted with one or more substituents selected from $R^6$; $R^{1''}$ is selected from: H, $(C=O)_aO_b(C_1-C_{10})$alkyl and halo, said alkyl is optionally substituted with one or more substituents selected from $R^6$; $R^{1'''}$ is selected from: H, $(C=O)_aO_b(C_1-C_{10})$alkyl and halo, said alkyl is optionally substituted with one or more substituents selected from $R^6$; $R^6$ is: $(C=O)_aO_b(C_1-C_{10})$alkyl, halo, OH or $NR^7R^8$; $R^7$ and $R^8$ in the group of $(C=O)_aNR^7R^8$ or $NR^7R^8$, are independently H or $(C_1-C_6)$alkyl; a is 0 or 1; and b is 0 or 1.

In an embodiment of Formula B, $R^{1''}$ is selected from: $(C=O)_aO_b(C_1-C_{10})$alkyl and halo, said alkyl is optionally substituted with one or more substituents selected from $R^6$; $R^{1'''}$ is H; $R^6$ is: $(C=O)_aO_b(C_1-C_{10})$alkyl, halo, OH or $NR^7R^8$; $R^7$ and $R^8$ in the group of $(C=O)_aNR^7R^8$ or $NR^7R^8$, are independently H or $(C_1-C_6)$alkyl; a is 0 or 1; and b is 0 or 1.

In another embodiment of Formula B, $R^{1''}$ is selected from: $(C_1-C_6)$alkyl and halo; and $R^{1'''}$ is H.

In an embodiment of Formula B, $R^{1''}$ is H; $R^{1'''}$ is selected from: $(C=O)_aO_b(C_1-C_{10})$alkyl and halo, said alkyl is optionally substituted with one or more substituents selected from $R^6$; $R^6$ is: $(C=O)_aO_b(C_1-C_{10})$alkyl, halo, OH or $NR^7R^8$; $R^7$ and $R^8$ in the group of $(C=O)_aNR^7R^8$ or $NR^7R^8$, are independently H or $(C_1-C_6)$alkyl; a is 0 or 1; and b is 0 or 1.

In another embodiment of Formula B, $R^{1''}$ is H; and $R^{1'''}$ is selected from: $(C_1-C_6)$alkyl and halo.

In another embodiment of Formula C, $R^1$ is selected from: oxo, $(C=O)_aO_b(C_1-C_{10})$alkyl, OH, and $(C=O)_aO_b$-heterocyclyl; a is 0 or 1; and b is 0 or 1.

In another embodiment of Formula C, $R^1$ is selected from: $(C=O)_aO_b(C_1-C_{10})$alkyl and $(C=O)_aO_b$-heterocyclyl; a is 0 or 1; and b is 0 or 1.

In yet another embodiment of Formula C, $R^1$ is methyl or morpholinyl.

In an embodiment of Formula D, $R^1$ is selected from: oxo, $(C=O)_aO_b(C_1-C_{10})$alkyl, $(C=O)_aO_b$-aryl, OH, $(C=O)_aO_b(C_3-C_8)$cycloalkyl, and $(C=O)_aO_b$-heterocyclyl, said alkyl, aryl, cycloalkyl, and heterocyclyl is optionally substituted with one or more substituents selected from $R^6$; $R^{1'}$ is selected from: H, $(C=O)_aO_b(C_1-C_{10})$alkyl, $(C=O)_aO_b$-aryl, halo, CN and $(C=O)_aO_b$-heterocyclyl, said alkyl, aryl, and heterocyclyl is optionally substituted with one or more substituents selected from $R^6$; $R^6$ is: $(C=O)_aO_b(C_1-C_{10})$alkyl, halo or OH; a is 0 or 1; and b is 0 or 1.

In another embodiment of Formula D, $R^1$ is $(C=O)_aO_b(C_1-C_{10})$alkyl, said alkyl is optionally substituted with one or more substituents selected from $R^6$; $R^{1'}$ is selected from: H, $(C=O)_aO_b(C_1-C_{10})$alkyl, $(C=O)_aO_b$-aryl, halo, CN and $(C=O)_aO_b$-heterocyclyl, said alkyl, aryl, and heterocyclyl is optionally substituted with one or more substituents selected from $R^6$; $R^6$ is: $(C=O)_aO_b(C_1-C_{10})$alkyl, halo or OH; a is 0 or 1; and b is 0 or 1.

In another embodiment of Formula D, $R^1$ is $(C=O)_aO_b$-aryl, said aryl is optionally substituted with one or more substituents selected from $R^6$; $R^{1'}$ is selected from: H, $(C=O)_aO_b(C_1-C_{10})$alkyl, $(C=O)_aO_b$-aryl, halo, CN and $(C=O)_aO_b$-heterocyclyl, said alkyl, aryl, and heterocyclyl is optionally substituted with one or more substituents selected from $R^6$; $R^6$ is: $(C=O)_aO_b(C_1-C_{10})$alkyl, halo or OH; a is 0 or 1; and b is 0 or 1.

In another embodiment of Formula D, $R^1$ is $(C=O)_aO_b(C_3-C_8)$cycloalkyl, said cycloalkyl is optionally substituted with one or more substituents selected from $R^6$; $R^{1'}$ is selected from: H, $(C=O)_aO_b(C_1-C_{10})$alkyl, $(C=O)_aO_b$-aryl, halo, CN and $(C=O)_aO_b$-heterocyclyl, said alkyl, aryl, and heterocyclyl is optionally substituted with one or more substituents selected from $R^6$; $R^6$ is: $(C=O)_aO_b(C_1-C_{10})$alkyl, halo or OH; a is 0 or 1; and b is 0 or 1.

In yet another embodiment of Formula D, $R^1$ is selected from: methyl, ethyl, trifluoromethyl, tert-butyl, phenyl optionally substituted with halo preferably fluoro, and cyclopropyl; and $R^{1'}$ is selected from: H, methyl, phenyl optionally substituted with $O_b(C_1-C_6)$alkyl, halo preferably bromo or chloro, CN and pyridyl, and b is 0 or 1.

In an embodiment of Formula E, $R^1$ is selected from: oxo, $(C=O)_aO_b(C_1-C_{10})$alkyl, OH, $(C=O)_aNR^7R^8$, $(C=O)_aO_b(C_3-C_8)$cycloalkyl, and $(C=O)_aO_b$-heterocyclyl, said alkyl, cycloalkyl, and heterocyclyl is optionally substituted with one or more substituents selected from $(C_1-C_6)$alkyl, halo, CN, and OH; $R^7$ and $R^8$ in the group of $(C=O)_aNR^7R^8$, are independently selected from: H, and $(C_1-C_6)$alkyl; a is 0 or 1; and b is 0 or 1.

In another embodiment of Formula E, $R^1$ is selected from: OH, $(C=O)_aNR^7R^8$, $(C=O)_aO_b(C_3-C_8)$cycloalkyl and $(C=O)_aO_b$-heterocyclyl, said cycloalkyl and heterocyclyl is optionally substituted with one or more substituents selected from $(C_1-C_6)$alkyl, halo, CN, and OH; $R^7$ and $R^8$ in the group of $(C=O)_aNR^7R^8$, are independently selected from: H, and $(C_1-C_6)$alkyl; a is 0 or 1; and b is 0 or 1.

In yet another embodiment of Formula E, $R^1$ is selected from: OH, $NH_2$, cyclopropyl and pyrimidinyl.

In another embodiment of Formula A, B, C, D and E, $(C=O)_aO_b(C_1-C_{10})$alkyl for $R^1$, $R^{1'}$, $R^{1''}$ or $R^{1'''}$ is methyl or ethyl, preferably methyl.

In another embodiment of Formula A, B, C, D and E, $(C=O)_aO_b(C_1-C_{10})$alkyl for $R^1$ is tert-butyl.

In another embodiment of Formula A, B, C, D and E, optionally substituted $(C=O)_aO_b(C_1-C_{10})$alkyl for $R^1$ is trifluoromethyl.

In another embodiment of Formula A, B and E, $(C=O)_aNR^7R^8$ for $R^1$, $R^{1'}$, $R^{1''}$ or $R^{1'''}$ is $NH_2$.

In another embodiment of Formula A, B and E, $(C=O)_aO_b(C_3-C_8)$cycloalkyl for $R^1$, $R^{1'}$, $R^{1''}$ or $R^{1'''}$ is cyclopropyl.

In another embodiment of Formula A, B, C, D and E, heterocyclyl itself in the group of $(C=O)_aO_b$-heterocyclyl for $R^1$, $R^{1'}$, $R^{1''}$ or $R^{1'''}$ is morpholinyl, imidazolyl, pyridyl, or pyrimidinyl; a is 0; and b is 0.

In an embodiment of Formula A, both $R^7$ and $R^8$ in the formula:

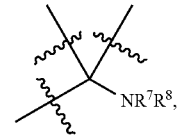

are H.

In an embodiment of Formula A, $R^7$ and $R^8$ are taken together with the nitrogen to which they are attached to form a monocyclic, bicyclic or tricyclic heterocycle with 3-7 members in each ring and optionally containing, in addition to the nitrogen, one or two additional heteroatoms selected from N, O and S, said monocyclic, bicyclic or tricyclic heterocycle is optionally substituted with one or more substituents selected from $R^{6a}$; $R^{6a}$ is selected from: $(C=O)_aO_b(C_1-C_{10})$alkyl, oxo, OH, halo, $(C_0-C_6)$alkylene-heterocyclyl, and $(C=O)_a NR^b{}_2$, said alkyl, and heterocyclyl is optionally substituted with up to three substituents selected from $R^b$; $R^b$ is independently: H, $(C_1-C_6)$alkyl, aryl, heterocyclyl, or $(C_3-C_6)$cycloalkyl, said alkyl, aryl, heterocyclyl, and cycloalkyl is optionally substituted with one or more substituents selected from $(C_1-C_6)$alkyl, OH, halo, and CN; a is 0 or 1; and b is 0 or 1.

In an embodiment of Formula B,

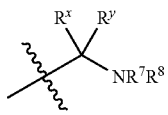

is selected from:

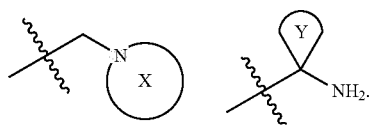

In another embodiment of Formula A and B,

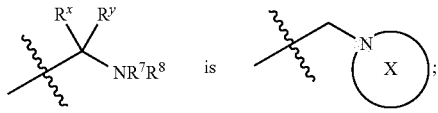

Ring X is selected from:

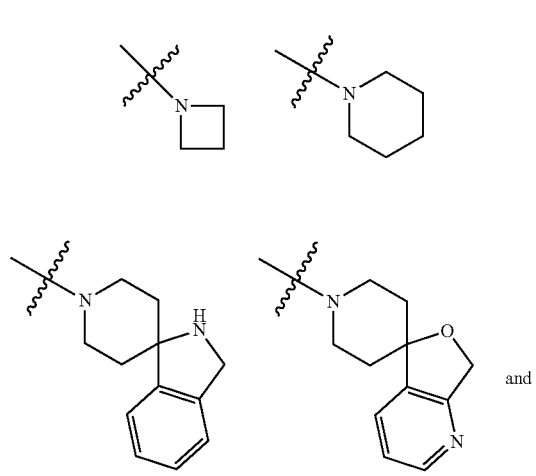

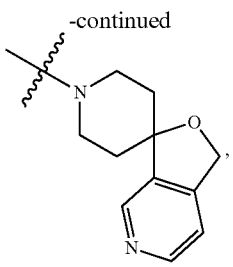

each of which is optionally substituted with one or more substituents selected from $R^{6a}$; $R^{6a}$ is selected from: $(C=O)_aO_b(C_1-C_{10})$alkyl, oxo, OH, halo, $(C_0-C_6)$alkylene-heterocyclyl, and $(C=O)_a NR^b{}_2$, said alkyl, and heterocyclyl is optionally substituted with up to three substituents selected from $R^b$; $R^a$ is $(C_1-C_6)$alkyl, $(C_3-C_6)$cycloalkyl, aryl, or heterocyclyl, said alkyl, cycloalkyl, aryl, and heterocyclyl is optionally substituted with one or more substituents selected from $R^c$; $R^b$ is independently: H, $(C=O)_aO_b(C_1-C_6)$alkyl, or $(C=O)_aR^a$, said alkyl is optionally substituted with one or more substituents selected from $(C=O)_aO_b(C_1-C_6)$alkyl, OH, halo, CN, and $(C=O)_a NR^d{}_2$; $R^c$ is independently: $(C=O)_aO_b(C_1-C_6)$alkyl, oxo, OH, halo, CN, or $(C=O)_a NR^d{}_2$, said alkyl is optionally substituted with one or more substituents selected from $(C_1-C_6)$alkyl, OH, halo, and CN; $R^d$ is independently: H, or $(C_1-C_6)$alkyl; a is 0 or 1; and b is 0 or 1.

In a further embodiment of Formula A and B, above Ring X is selected from:

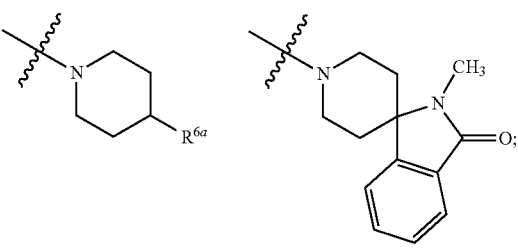

and
$R^{6a}$ is triazolyl substituted with pyridyl.

In an embodiment of Formula C, Ring X is selected from:

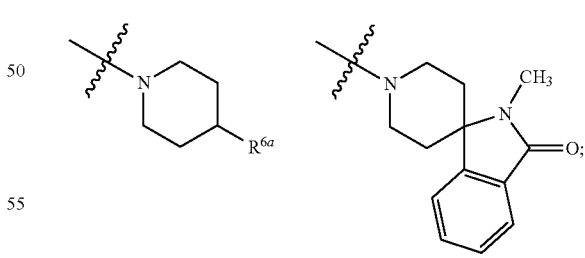

and
$R^{6a}$ is triazolyl substituted with pyridyl.

In an embodiment of Formula A, both $R^x$ and $R^y$ are H.
In an embodiment of Formula A, $R^x$ and $R^y$ are taken together to form a monocyclic or bicyclic carbo- or heterocycle with 3-7 members in each ring, said heterocycle is containing one or more heteroatoms selected from N, O and S, and said carbo- or heterocycle is optionally substituted with one or more substituents selected from: $(C_1-C_6)$alkyl, ($C_2$-$C_6$)alkenyl, ($C_3$-$C_6$)cycloalkyl, ($C_1$-$C_6$)alkylidene, ($C_1$-$C_6$)alkoxy, $CO_2H$, halo, OH, oxo, CN and $NR^7R^8$, said alkyl, cycloalkyl and alkoxy is optionally substituted with one or more substituents selected from halo, CN, OH and $NR^{7'}R^{8'}$; $R^{7'}$ and $R^{8'}$ are independently selected from: H, and ($C_1$-$C_6$) alkyl.

In another embodiment of Formula A and B,

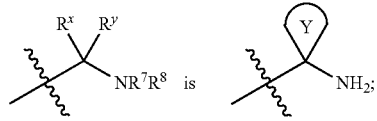

Ring Y is a group of formula:

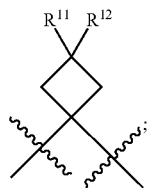

$R^{11}$ and $R^{12}$ are independently selected from: H, ($C_1$-$C_6$) alkyl, ($C_2$-$C_6$)alkenyl, ($C_3$-$C_6$)cycloalkyl, ($C_1$-$C_6$)alkoxy, $CO_2H$, halo, OH, CN and $NR^7R^8$, said alkyl, cycloalkyl and alkoxy is optionally substituted with one or more substituents selected from halo, CN, OH and $NR^7R^8$, or $R^{11}$ and $R^{12}$ can be taken together to form oxo, ($C_1$-$C_6$)alkylidene, or a monocyclic carbo- or heterocycle with 3-7 members, said heterocycle is containing one or more heteroatoms selected from N, O and S; and $R^7$ and $R^8$ in the group of $NR^7R^8$ for $R^{11}$ or $R^{12}$, or for the substituents on alkyl, cycloalkyl or alkoxy of $R^{11}$ and $R^{12}$, are independently selected from: H, and ($C_1$-$C_6$)alkyl.

In a further embodiment of Formula A and B, above $R^{11}$ and $R^{12}$ are independently selected from: H, ($C_1$-$C_6$)alkyl, ($C_2$-$C_6$)alkenyl, ($C_3$-$C_6$)cycloalkyl, ($C_1$-$C_6$)alkoxy, halo, and OH, said alkyl is optionally substituted with one or more OH.

In a further embodiment of Formula A and B, above $R^{11}$ and $R^{12}$ are taken together to form oxo, ($C_1$-$C_6$)alkylidene, or a group of formula:

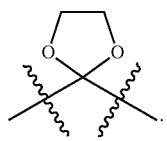 [SMILES: *C1(*)OCCO1]

In another embodiment of Formula D, $R^{11}$ and $R^{12}$ are independently selected from: H, ($C_1$-$C_6$)alkyl, ($C_2$-$C_6$)alkenyl, ($C_3$-$C_6$)cycloalkyl, ($C_1$-$C_6$)alkoxy, halo, and OH, said alkyl is optionally substituted with one or more OH.

In another embodiment of Formula D, $R^{11}$ and $R^{12}$ are taken together to form oxo, ($C_1$-$C_6$)alkylidene, or a group of formula:

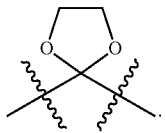 [SMILES: *C1(*)OCCO1]

In another embodiment of Formula E, both $R^{11}$ and $R^{12}$ are H.

Included in the instant invention is the free form of compounds of Formula A, as well as the pharmaceutically acceptable salts and stereoisomers thereof. Some of the isolated specific compounds exemplified herein are the protonated salts of amine compounds. The term "free form" refers to the amine compounds in non-salt form. The encompassed pharmaceutically acceptable salts not only include the isolated salts exemplified for the specific compounds described herein, but also all the typical pharmaceutically acceptable salts of the free form of compounds of Formula A. The free form of the specific salt compounds described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the instant compounds can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the compounds of this invention include the conventional non-toxic salts of the compounds of this invention as formed by reacting a basic instant compound with an inorganic or organic acid. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic (TFA) and the like.

When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,N¹-dibenzylethylenediamine, diethylamin, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

The preparation of the pharmaceutically acceptable salts described above and other typical pharmaceutically acceptable salts is more fully described by Berg et al., "Pharmaceutical Salts," *J. Pharm. Sci.*, 1977:66:1-19.

It will also be noted that the compounds of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

"N-oxide derivatives" of the compounds of the invention are those in which one or two or more arbitrary nitrogen atoms capable of forming N-oxide, existing in the compound, are oxidized to form an N-oxide and which are pharmaceutically acceptable ones.

The process of oxidizing the nitrogen atom to produce an N-oxide derivative may be attained, for example, by the use of an oxidizing agent such as m-chloroperbenzoic acid, dioxirane, sodium periodate, hydrogen peroxide.

The reaction may be attained in a solvent suitably selected in accordance with the oxidizing agent to be used for the reaction. For example, when m-chloroperbenzoic acid is used as the oxidizing agent, then the solvent is preferably methylene chloride or chloroform; and when dioxirane is used as the oxidizing agent, then the solvent is preferably acetone or water.

UTILITY

The compounds of the instant invention are inhibitors of the activity of Akt and are thus useful in the treatment of cancer, in particular cancers associated with irregularities in the activity of Akt and downstream cellular targets of Akt. Such cancers include, but are not limited to, ovarian, pancreatic, breast and prostate cancer, as well as cancers (including glioblastoma) where the tumor suppressor PTEN is mutated (Cheng et al., *Proc. Natl. Acad. Sci.* (1992) 89:9267-9271; Cheng et al., *Proc. Natl. Acad. Sci.* (1996) 93:3636-3641; Bellacosa et al., *Int. J. Cancer* (1995) 64:280-285; Nakatani et al., *J. Biol. Chem.* (1999) 274:21528-21532; Graff, *Expert. Opin. Ther. Targets* (2002) 6(1):103-113; and Yamada and Araki, *J. Cell Science.* (2001) 114:2375-2382; Mischel and Cloughesy, *Brain Pathol.* (2003) 13(1):52-61). Cancers where Akt itself is activated by gene amplification or mutations may also be treated by the compounds.

The compounds, compositions and methods provided herein are particularly deemed useful for the treatment of cancer. Cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: non-small cell lung, bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma), colon, colorectal, rectal; Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepitheliad carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

Cancers that may be treated by the compounds, compositions and methods of the invention include, but are not limited to: breast, prostate, colon, colorectal, lung, non-small cell lung, brain, testicular, stomach, pancreas, skin, small intestine, large intestine, throat, head and neck, oral, bone, liver, bladder, kidney, thyroid and blood.

Cancers that may be treated by the compounds, compositions and methods of the invention include: breast, prostate, colon, ovarian, colorectal, lung and non-small cell lung.

Cancers that may be treated by the compounds, compositions and methods of the invention include: breast, colon, (colorectal) and lung (non-small cell lung).

Cancers that may be treated by the compounds, compositions and methods of the invention include: lymphoma and leukemia.

The compounds of the instant invention are useful for the treatment of breast cancer.

The compounds of the instant invention are useful for the treatment of prostate cancer.

Akt signaling regulates multiple critical steps in angiogenesis. Shiojima and Walsh, *Circ. Res.* (2002) 90:1243-1250. The utility of angiogenesis inhibitors in the treatment of cancer is known in the literature, see J. Rak et al. *Cancer Research,* 55:4575-4580, 1995 and Dredge et al., *Expert Opin. Biol. Ther.* (2002) 2(8):953-966, for example. The role of angiogenesis in cancer has been shown in numerous types of cancer and tissues: breast carcinoma (G. Gasparini and A. L. Harris, *J. Clin. Oncol.,* 1995, 13:765-782; M. Toi et al., *Japan. J. Cancer Res.,* 1994, 85:1045-1049); bladder carcinomas (A. J. Dickinson et al., *Br. J. Urol.,* 1994, 74:762-766); colon carcinomas (L. M. Ellis et al., *Surgery,* 1996, 120(5): 871-878); and oral cavity tumors (J. K. Williams et al., *Am. J. Surg.,* 1994, 168:373-380). Other cancers include, advanced tumors, hairy cell leukemia, melanoma, advanced head and neck, metastatic renal cell, non-Hodgkin's lymphoma, metastatic breast, breast adenocarcinoma, advanced melanoma, pancreatic, gastric, glioblastoma, lung, ovarian, non-small cell lung, prostate, small cell lung, renal cell carcinoma, various solid tumors, multiple myeloma, metastatic prostate, malignant glioma, renal cancer, lymphoma, refractory metastatic disease, refractory multiple myeloma, cervical cancer, Kaposi's sarcoma, recurrent anaplastic glioma, and metastatic colon cancer (Dredge et al., *Expert Opin. Biol. Ther.* (2002) 2(8):953-966). Thus, the Akt inhibitors disclosed in the instant application are also useful in the treatment of these angiogenesis related cancers.

Tumors which have undergone neovascularization show an increased potential for metastasis. In fact, angiogenesis is essential for tumor growth and metastasis. (S. P. Cunningham, et al., *Can. Research,* 61: 3206-3211 (2001)). The Akt inhibitors disclosed in the present application are therefore also useful to prevent or decrease tumor cell metastasis.

Further included within the scope of the invention is a method of treating or preventing a disease in which angiogenesis is implicated, which is comprised of administering to a mammal in need of such treatment a therapeutically effective amount of a compound of the present invention. Ocular neovascular diseases are an example of conditions where much of the resulting tissue damage can be attributed to aberrant infiltration of blood vessels in the eye (see WO 00/30651, published 2 Jun. 2000). The undesirable infiltration can be triggered by ischemic retinopathy, such as that resulting from diabetic retinopathy, retinopathy of prematurity, retinal vein occlusions, etc., or by degenerative diseases, such as the choroidal neovascularization observed in age-related macular degeneration. Inhibiting the growth of blood vessels by administration of the present compounds would therefore prevent the infiltration of blood vessels and prevent or treat diseases where angiogenesis is implicated, such as ocular diseases like retinal vascularization, diabetic retinopathy, age-related macular degeneration, and the like.

Further included within the scope of the invention is a method of treating or preventing a non-malignant disease in which angiogenesis is implicated, including but not limited to: ocular diseases (such as, retinal vascularization, diabetic retinopathy and age-related macular degeneration), atherosclerosis, arthritis, psoriasis, obesity and Alzheimer's disease (Dredge et al., *Expert Opin. Biol. Ther.* (2002) 2(8):953-966). In another embodiment, a method of treating or preventing a disease in which angiogenesis is implicated includes: ocular diseases (such as, retinal vascularization, diabetic retinopathy and age-related macular degeneration), atherosclerosis, arthritis and psoriasis.

Further included within the scope of the invention is a method of treating hyperproliferative disorders such as restenosis, inflammation, autoimmune diseases and allergy/asthma.

Further included within the scope of the instant invention is the use of the instant compounds to coat stents and therefore the use of the instant compounds on coated stents for the treatment and/or prevention of restenosis (WO03/032809).

Further included within the scope of the instant invention is the use of the instant compounds for the treatment and/or prevention of osteoarthritis (WO03/035048).

Further included within the scope of the invention is a method of treating hyperinsulinism.

The compounds of the invention are also useful in preparing a medicament that is useful in treating the diseases described above, in particular cancer.

In an embodiment of the invention, the instant compound is a selective inhibitor whose inhibitory efficacy is dependent on the PH domain. In this embodiment, the compound exhibits a decrease in in vitro inhibitory activity or no in vitro inhibitory activity against truncated Akt proteins lacking the PH domain.

In a further embodiment, the instant compound is selected from the group of a selective inhibitor of Akt1, a selective inhibitor of Akt2 and a selective inhibitor of both Akt1 and Akt2.

In another embodiment, the instant compound is selected from the group of a selective inhibitor of Akt1, a selective inhibitor of Akt2, a selective inhibitor of Akt3 and a selective inhibitor of two of the three Akt isoforms.

In another embodiment, the instant compound is a selective inhibitor of all three Akt isoforms, but is not an inhibitor of one, two or all of such Akt isoforms that have been modified to delete the PH domain, the hinge region or both the PH domain and the hinge region.

The present invention is further directed to a method of inhibiting Akt activity, which comprises administering to a mammal in need thereof a pharmaceutically effective amount of the instant compound.

The compounds of this invention may be administered to mammals, including humans, either alone or, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropylmethyl-cellulose or hydroxypropylcellulose, or a time delay material such as ethyl cellulose, cellulose acetate butyrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethylene glycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavouring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of the present invention are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a composition according to this invention is administered into a human subject, the daily dosage will normally be determined by the prescribing physician with the dosage generally varying according to the age, weight, and response of the individual patient, as well as the severity of the patient's symptoms.

The dosage regimen utilizing the compounds of the instant invention can be selected in accordance with a variety of factors including type, species, age, weight, sex and the type of cancer being treated; the severity (i.e., stage) of the cancer to be treated; the route of administration; the renal and hepatic function of the patient; and the particular compound or salt thereof employed. An ordinarily skilled physician or veterinarian can readily determine and prescribe the effective amount of the drug required to treat, for example, to prevent, inhibit (fully or partially) or arrest the progress of the disease. For example, compounds of the instant invention can be administered in a total daily dose of up to 10,000 mg. Compounds of the instant invention can be administered once daily (QD), or divided into multiple daily doses such as twice daily (BID), and three times daily (TID). Compounds of the instant invention can be administered at a total daily dosage of up to 10,000 mg, e.g., 2,000 mg, 3,000 mg, 4,000 mg, 6,000 mg, 8,000 mg or 10,000 mg, which can be administered in one daily dose or can be divided into multiple daily doses as described above.

For example, compounds of the instant invention can be administered in a total daily dose of up to 1,000 mg. Compounds of the instant invention can be administered once daily (QD), or divided into multiple daily doses such as twice daily (BID), and three times daily (TID). Compounds of the instant invention can be administered at a total daily dosage of up to 1,000 mg, e.g., 200 mg, 300 mg, 400 mg, 600 mg, 800 mg or 1,000 mg, which can be administered in one daily dose or can be divided into multiple daily doses as described above.

In addition, the administration can be continuous, i.e., every day, or intermittently. The terms "intermittent" or "intermittently" as used herein means stopping and starting at either regular or irregular intervals. For example, intermittent administration of a compound of the instant invention may be administration one to six days per week or it may mean administration in cycles (e.g. daily administration for two to eight consecutive weeks, then a rest period with no administration for up to one week) or it may mean administration on alternate days.

In addition, the compounds of the instant invention may be administered according to any of the schedules described above, consecutively for a few weeks, followed by a rest period. For example, the compounds of the instant invention may be administered according to any one of the schedules described above from two to eight weeks, followed by a rest period of one week, or twice daily at a dose of 100-500 mg for three to five days a week. In another particular embodiment, the compounds of the instant invention may be administered three times daily for two consecutive weeks, followed by one week of rest.

Any one or more of the specific dosages and dosage schedules of the compounds of the instant invention, may also be applicable to any one or more of the therapeutic agents to be used in the combination treatment (hereinafter referred to as the "second therapeutic agent").

Moreover, the specific dosage and dosage schedule of this second therapeutic agent can further vary, and the optimal dose, dosing schedule and route of administration will be determined based upon the specific second therapeutic agent that is being used.

Of course, the route of administration of the compounds of the instant invention is independent of the route of administration of the second therapeutic agent. In an embodiment, the administration for a compound of the instant invention is oral administration. In another embodiment, the administration for a compound of the instant invention is intravenous administration. Thus, in accordance with these embodiments, a compound of the instant invention is administered orally or intravenously, and the second therapeutic agent can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form.

In addition, a compound of the instant invention and second therapeutic agent may be administered by the same mode of administration, i.e. both agents administered e.g. orally, by IV. However, it is also within the scope of the present invention to administer a compound of the instant invention by one mode of administration, e.g. oral, and to administer the second therapeutic agent by another mode of administration, e.g. IV or any other ones of the administration modes described hereinabove.

The first treatment procedure, administration of a compound of the instant invention, can take place prior to the second treatment procedure, i.e., the second therapeutic agent, after the treatment with the second therapeutic agent, at the same time as the treatment with the second therapeutic agent, or a combination thereof. For example, a total treatment period can be decided for a compound of the instant invention. The second therapeutic agent can be administered prior to onset of treatment with a compound of the instant invention or following treatment with a compound of the instant invention. In addition, anti-cancer treatment can be administered during the period of administration of a compound of the instant invention but does not need to occur over the entire treatment period of a compound of the instant invention.

The instant compounds are also useful in combination with therapeutic, chemotherapeutic and anti-cancer agents. Combinations of the presently disclosed compounds with therapeutic, chemotherapeutic and anti-cancer agents are within the scope of the invention. Examples of such agents can be found in *Cancer Principles and Practice of Oncology* by V. T. Devita and S. Hellman (editors), $6^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such agents include the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, bisphosphonates, aromatase inhibitors, siRNA therapeutics, γ-secretase inhibitors, agents that interfere with receptor tyrosine kinases (RTKs) and agents that interfere with cell cycle checkpoints. The instant compounds are particularly useful when co-administered with radiation therapy.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell myosis, including alkylating agents, tumor necrosis factors, intercalators, hypoxia activatable compounds, microtubule inhibitors/microtubule-stabilizing agents, inhibitors of mitotic kinesins, histone deacetylase inhibitors, inhibitors of kinases involved in mitotic progression, inhibitors of kinases involved in growth factor and cytokine signal transduction pathways, antimetabolites, biological response modifiers, hormonal/anti-hormonal therapeutic agents, haematopoietic growth factors, monoclonal antibody targeted therapeutic agents, topoisomerase inhibitors, proteosome inhibitors, ubiquitin ligase inhibitors, and aurora kinase inhibitors.

Examples of cytotoxic/cytostatic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755, 4-demethoxy-3-deamino-3-aziridinyl-4-methylsulphonyl-daunorubicin (see WO 00/50032), Raf kinase inhibitors (such as Bay43-9006) and mTOR inhibitors (such as Wyeth's CCI-779).

An example of a hypoxia activatable compound is tirapazamine.

Examples of proteosome inhibitors include but are not limited to lactacystin and MLN-341 (Velcade).

Examples of microtubule inhibitors/microtubule-stabilising agents include paclitaxel, vindesine sulfate, 3',4'-didehydro-4'-deoxy-8'-norvincaleukoblastine, docetaxel, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797. In an embodiment the epothilones are not included in the microtubule inhibitors/microtubule-stabilising agents.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydroxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxybenzo[c]-phenanthridinium, 6,9-bis[(2-aminoethyl)amino]benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl] formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins, and in particular the human mitotic kinesin KSP, are described in Publications WO03/039460, WO03/050064, WO03/050122, WO03/049527, WO03/049679, WO03/049678, WO04/039774, WO03/079973, WO03/099211, WO03/105855, WO03/106417, WO04/037171, WO04/058148, WO04/058700, WO04/126699, WO05/018638, WO05/019206, WO05/019205, WO05/018547, WO05/017190, US2005/0176776. In an embodiment inhibitors of mitotic kinesins include, but are not limited to inhibitors of KSP, inhibitors of MKLP1, inhibitors of CENP-E, inhibitors of MCAK and inhibitors of Rab6-KIFL.

Examples of "histone deacetylase inhibitors" include, but are not limited to, SAHA, TSA, oxamflatin, PXD101, MG98 and scriptaid. Further reference to other histone deacetylase inhibitors may be found in the following manuscript; Miller, T. A. et al. *J. Med. Chem.* 46(24):5097-5116 (2003).

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabin furanosyl cytosine, 3-aminopyridine-2-carboxaldehyde thiosemicarbazone and trastuzumab.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916, 239), pravastatin (PRAVACHOL®; see U.S. Pat. Nos. 4,346, 227, 4,537,859, 4,410,629, 5,030,447 and 5,180,589), fluvastatin (LESCOL®; see U.S. Pat. Nos. 5,354,772, 4,911, 165, 4,929,437, 5,189,164, 5,118,853, 5,290,946 and 5,356, 896), atorvastatin (LIPITOR®; see U.S. Pat. Nos. 5,273,995, 4,681,893, 5,489,691 and 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", *Chemistry & Industry*, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see *European J. of Cancer*, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (PNAS, Vol. 89, p. 7384 (1992); *JNCI*, Vol. 69, p. 475 (1982); *Arch. Opthalmol.*, Vol. 108, p. 573 (1990); *Anat. Rec.*, Vol. 238, p. 68 (1994); *FEBS Letters*, Vol. 372, p. 83 (1995); *Clin, Orthop.* Vol. 313, p. 76 (1995); *J. Mol. Endocrinol.*, Vol. 16, p. 107 (1996); *Jpn. J. Pharmacol.*, Vol. 75, p. 105 (1997); *Cancer Res.*, Vol. 57, p. 1625 (1997); *Cell*, Vol. 93, p. 705 (1998); *Intl. J. Mol. Med.*, Vol. 2, p. 715 (1998); *J. Biol. Chem.*, Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-futnagillol, thalidomide, angiostatin, troponin-1, angiotensin II antagonists (see Fernandez et al., *J. Lab. Clin. Med.* 105:141-145 (1985)), and antibodies to VEGF (see, *Nature Biotechnology*, Vol. 17, pp. 963-968 (October 1999); Kim et al., *Nature,* 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in *Clin. Chem. La. Med.* 38:679-692 (2000)). Examples of such agents that modulate or inhibit the coagulation and fibrinolysis pathways include, but are not limited to, heparin (see *Thromb. Haemost.* 80:10-23 (1998)), low molecular weight heparins and carboxypeptidase U inhibitors (also known as inhibitors of active thrombin activatable fibrinolysis inhibitor [TAFIa]) (see *Thrombosis Res.* 101:329-354 (2001)). TAFIa inhibitors have been described in U.S. Ser. Nos. 60/310,927 (filed Aug. 8, 2001) and 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the CHK11 and CHK12 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include inhibitors of c-Kit, Eph, PDGF, Flt3 and c-Met. Further agents include inhibitors of RTKs as described by Bume-Jensen and Hunter, *Nature,* 411:355-365, 2001.

"Inhibitors of cell proliferation and survival signalling pathway" refer to compounds that inhibit signal transduction cascades downstream of cell surface receptors. Such agents include inhibitors of serine/threonine kinases (including but not limited to inhibitors of Akt such as described in WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670, 469), inhibitors of Raf kinase (for example BAY-43-9006), inhibitors of MEK (for example CI-1040 and PD-098059), inhibitors of mTOR (for example Wyeth CCI-779), and inhibitors of PI3K (for example LY294002).

As described above, the combinations with NSAID's are directed to the use of NSAID's which are potent COX-2 inhibiting agents. For purposes of this specification an NSAID is potent if it possesses an $IC_{50}$ for the inhibition of COX-2 of 1 µM or less as measured by cell or microsomal assays.

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. No. 5,474,995, U.S. Pat. No. 5,861,419, U.S. Pat. No. 6,001,843, U.S. Pat. No. 6,020,343, U.S. Pat. No. 5,409,944, U.S. Pat. No. 5,436,265, U.S. Pat. No. 5,536,752, U.S. Pat. No. 5,550,142, U.S. Pat. No. 5,604,260, U.S. Pat. No. 5,698,584, U.S. Pat. No. 5,710,140, WO 94/15932, U.S. Pat. No. 5,344,991, U.S. Pat. No. 5,134,142, U.S. Pat. No. 5,380,738, U.S. Pat. No. 5,393,790, U.S. Pat. No. 5,466,823, U.S. Pat. No. 5,633,272 and U.S. Pat. No. 5,932,598, all of which are hereby incorporated by reference.

Inhibitors of COX-2 that are particularly useful in the instant method of treatment are: 3-phenyl-4-(4-(methylsulfonyl)phenyl)-2-(5H)-furanone; and 5-chloro-3-(4-methylsulfonyl)phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to, the following: parecoxib, BEXTRA® and CELEBREX® or a pharmaceutically acceptable salt thereof.

Other examples of angiogenesis inhibitors include, but are not limited to, endostatin, ukrain, ranpirnase, IM862, 5-methoxy-4-[2-methyl-3-(3-methyl-2-butenyl)oxiranyl]1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha v\beta 5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl]indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, CI-1033, CDP860, ZR6474, RTK-787, CP549632, and CT53518.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malignancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31:909-913; *J. Biol. Chem.* 1999; 274: 9116-9121; *Invest. Ophthalmol. Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* 2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, G1262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy)phenoxy)propoxy)-2-ethylchromane-2-carboxylic acid (disclosed in U.S. Ser. No. 60/235,708 and 60/244,697).

Another embodiment of the instant invention is the use of the presently disclosed compounds in combination with gene therapy for the treatment of cancer. For an overview of genetic strategies to treating cancer see Hall et al (*Am. J. Hum. Genet.* 61:785-789, 1997) and Kufe et al (Cancer Medicine, 5th Ed, pp 876-889, BC Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," Gene Therapy, August 1998; 5(8):1105-13), and interferon gamma (*J. Immunol.* 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In another embodiment, conjunctive therapy with an anti-emesis agent selected from a neurokinin-1 receptor antagonist, a 5HT3 receptor antagonist and a corticosteroid is disclosed for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232,929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an embodiment, the neurokinin-1 receptor antagonist for use in conjunction with the compounds of the present invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous erythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, isoprinosine and Zadaxin.

A compound of the instant invention may also be useful for treating or preventing cancer in combination with P450 inhibitors including: xenobiotics, quinidine, tyramine, ketoconazole, testosterone, quinine, methyrapone, caffeine, phenelzine, doxorubicin, troleandomycin, cyclobenzaprine, erythromycin, cocaine, furafyline, cimetidine, dextromethorphan, ritonavir, indinavir, amprenavir, diltiazem, terfenadine, verapamil, cortisol, itraconazole, mibefradil, nefazodone and nelfinavir.

A compound of the instant invention may also be useful for treating or preventing cancer in combination with Pgp and/or BCRP inhibitors including: cyclosporin A, PSC833, GF120918, cremophorEL, fumitremorgin C, Ko132, Ko134, Iressa, Imatnib mesylate, EKI-785, Cl1033, novobiocin, diethylstilbestrol, tamoxifen, resperpine, VX-710, tryprostatin A, flavonoids, ritonavir, saquinavir, nelfinavir, omeprazole, quinidine, verapamil, terfenadine, ketoconazole, nifidepine, FK506, amiodarone, XR9576, indinavir, amprenavir, cortisol, testosterone, LY335979, OC144-093, erythromycin, vincristine, digoxin and talinolol.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention may also be useful for treating or preventing breast cancer in combination with aromatase inhibitors. Examples of aromatase inhibitors include but are not limited to: anastrozole, letrozole and exemestane.

A compound of the instant invention may also be useful for treating or preventing cancer in combination with siRNA therapeutics.

The compounds of the instant invention may also be administered in combination with γ-secretase inhibitors and/or inhibitors of NOTCH signaling. Such inhibitors include compounds described in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, U.S. Ser. No. 10/957,251, WO 2004/089911, WO 02/081435, WO 02/081433, WO 03/018543, WO 2004/031137, WO 2004/031139, WO 2004/031138, WO 2004/101538, WO 2004/101539 and WO 02/47671 (including LY-450139).

Inhibitors of Akt, as disclosed in the following publications; WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670,469, and including compounds of the instant invention, are also useful in combination with potassium salts, magnesium salts, beta-blockers (such as atenolol) and endothelin-a (ETa) antagonists with the goal of maintaining cardiovascular homeostasis.

Inhibitors of Akt, as disclosed in the following publications; WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670,469, and including compounds of the instant invention, are also useful in combination with insulin, insulin secretagogues, PPAR-gamma agonists, metformin, somatostatin receptor agonists such as octreotide, DPP4 inhibitors, sulfonylureas and alpha-glucosidase inhibitors with the goal of maintaining glucose homeostasis.

A compound of the instant invention may also be useful for treating or preventing cancer in combination with PARP inhibitors.

A compound of the instant invention may also be useful for treating cancer in combination with the following therapeutic agents: abarelix (Plenaxis Depot®); (Actiq®); aldesleukin (Prokine®); Aldesleukin (Proleukin®); Alemtuzumab (Campath®); alfuzosin HCl (UroXatral®); alitretinoin (Panretin®); allopurinol (Zyloprim®); altretamine (Hexylene); amifostine (Ethyol®); anastrozole (Arimidex®); (Anzemet®); (Anexsia®); aprepitant (Emend®); arsenic trioxide (Trisenox®); asparaginase (Elspar®); azacitidine (Vidaza®); bendamustine hydrochloride (Treanda®); bevacuzimab (Avastin®); bexarotene capsules (Targretin®); bexarotene gel (Targretin®); bleomycin (Blenoxane®); bortezomib (Velcade®); (Brofenac®); busulfan intravenous (Busulflex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cinacalcet (Sensipar®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); dasatinib (Sprycel®); daunorubicin liposomal (DanuoXome®); daunorubicin, daunomycin (Daunorubicin®); daunorubicin, daunomycin (Cerubidine®); decitabine (Dacogen®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (masterone Injection®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); fentanyl citrate (Fentora®); Filgrastim (Neupogen®); floxuridine (intraarterial) (FUDR®); fludarabine (Fludara®); fluorouracil, 5-FU (Adrucil®); flutamide (Eulexin®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); granisetron (Kytril Solution®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); (Kadian®); ixabepilone (Ixempra®); lapatinib (Tykerb®); lenalidomide (Revlimid®); letrozole (Femara®); leucovorin (Wellcovorin®, Leucovorin®); Leuprolide Acetate (Eligard®); (Lupron Depot®); (Viadur®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitomycin C (Mitozytrex®); mitotane (Lysodren®); mitoxantrone (Novantrone®); nandrolone phenpropionate (Durabolin-50®); nelarabine (Arranon®); nilotinib hydrochloride monohydrate (Tasigna®); Nofetumomab (Verluma®); Oprelvekin (Neumega®); (Neupogen®); oxaliplatin (Eloxatin®); paclitaxel (Paxene®); paclitaxel (Taxol®); paclitaxel protein-bound particles (Abraxane®); palifermin (Kepivance®); palonosetron (Aloxi®); pamidronate (Aredia®); panitunnunab (Vectibix®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); (Quadramet®); quadrivalent human papillomavirus (types 6, 11, 16, 18) recombinant vaccine (Gardasil®); quinacrine (Atabrine®); raloxifene hydrochloride (Evista®); Rasburicase (Elitek®); Rituximab (Rituxan®); sargramostim (Leukine®); Sargramostim (Prokine®); secretin (SecreFlo®); sorafenib (Nexavar®); streptozocin (Zanosar®); sunitinib maleate (Sutent®); talc (Sclerosol®); tamoxifen (Nolvadex®); temozolomide (Temodar®); temsirolimus (Torisel®); teniposide, VM-26 (Vumon®); (Temodar®); testolactone (Teslac®); thalidomide (Thalomid®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); (Trelstar LA®); tretinoin, ATRA (Vesanoid®); triptorelin pamoate (Trelstar Depot®); (UltraJect®); Uracil Mustard (Uracil Mustard Capsules®); valrubicin (Valstar®); vinblastine (Velban®); vincristine (Oncovin®); vinorelbine (Navelbine vorinostat (Zolinza®); (Zofran ODT®); and zoledronate (Zometa®).

The compounds of the instant invention are useful for treating cancer in combination with taxanes.

The compounds of the instant invention are useful for treating cancer in combination with docetaxel (Taxotere®).

The compounds of the instant invention are useful for treating cancer in combination with vorinostat (Zolinza®).

The compounds of the instant invention are useful for treating cancer in combination with the aurora kinase inhibitor, MK-0457.

The compounds of the instant invention are useful for treating cancer in combination with the mTOR inhibitor, AP 23573.

The compounds of the instant invention are useful for treating cancer in combination with the IGF1R inhibitor, MK-0646.

The compounds of the instant invention are useful for treating cancer in combination with satraplatin.

The compounds of the instant invention are useful for treating cancer in combination with lapatinib (Tykerb®).

Thus, the scope of the instant invention encompasses the use of the instantly claimed compounds in combination with a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase inhibitors, agents that interfere with receptor tyrosine kinases (RTKs), an agent that interferes with a cell cycle checkpoint and any of the therapeutic agents listed above.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

In an embodiment, the angiogenesis inhibitor to be used as the second compound is selected from a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-α, interleukin-12, pentosan polysulfate, a cyclooxygenase inhibitor, carboxyamidotriazole, combretastatin A-4, squalamine, 6-O-chloroacetyl-carbonyl)-fumagillol, thalidomide, angiostatin, troponin-1, or an antibody to VEGF. In an embodiment, the estrogen receptor modulator is tamoxifen or raloxifene.

Also included in the scope of the claims is a method of treating cancer that comprises administering a therapeutically effective amount of a compound of the instant invention in combination with radiation therapy and/or in combination with a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase inhibitors, agents that interfere with receptor tyrosine kinases (RTKs), an agent that interferes with a cell cycle checkpoint and any of the therapeutic agents listed above.

And yet another embodiment of the invention is a method of treating cancer that comprises administering a therapeutically effective amount of a compound of the instant invention in combination with paclitaxel or trastuzumab.

The invention further encompasses a method of treating or preventing cancer that comprises administering a therapeutically effective amount of a compound of the instant invention in combination with a COX-2 inhibitor.

The instant invention also includes a pharmaceutical composition useful for treating or preventing cancer that comprises a therapeutically effective amount of a compound of the instant invention and a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an inhibitor of cell proliferation and survival signaling, a bisphosphonate, an aromatase inhibitor, an siRNA therapeutic, γ-secretase inhibitors, agents that interfere with receptor tyrosine kinases (RTKs), an agent that interferes with a cell cycle checkpoint and any of the therapeutic agents listed above.

All patents, publications and pending patent applications identified are hereby incorporated by reference.

Abbreviations used in the description of the chemistry and in the Examples that follow are: AcO (acetate); AcOH (acetic acid); Bn (benzyl); BOC (tert-butoxycarbonyl); BSA (bovine serum albumin); BuLi (n-Butyl lithium); t-Bu (tert-butyl); CDI (N,N'-carbonyldiimidazole); DCM (dichloromethane); DEAD (diethyl azodicarboxylate); DIPEA (N,N-diisopropylethylamine); DMF (N,N-dimethylformamide); DMSO (dimethyl sulfoxide); DPPA (diphenylphosphoryl azide); DTT (dithiothreitol); EDC (1-ethyl-3-(3-dimethylaminopropyl) carbodiimide); EDTA (ethylene-diamine-tetra-acetic acid); EGTA (ethylene-glycol-tetra-acetic acid); Et (ethyl); Et$_2$O (diethyl ether); EtOAc (ethyl acetate); EtOH (ethanol); h. (hours); HOBt (1-hydroxybenzotriazole); HPLC (high-performance liquid chromatography); IPA (isopropyl alcohol); KHMDS (potassium bis(trimethylsilyl)amide); LCMS (liquid chromatograph-mass spectrometer); LDA (lithium diisopropyl amide); LiBHEt$_3$ (lithium triethylborohydride); LiHMDS (lithium bis(trimethylsilyl)amide); Me (methyl); MeB(OH)$_2$ (methylboronic acid); MeCN (acetonitrile); MeLi (methyl lithium); MeOH (methanol); min. (minutes); MS (mass spectrum); NaHMDS (sodium bis(trimethylsilyl) amide); NBS (N-bromosuccinimide); NMR (nuclear magnetic resonance); PBS (phosphate buffered saline); PCR (polymerase chain reaction); iPr (iso-propyl); TBAB (tetrabutylammonium bromide); THF (tetrahydrofuran); Tf (trifluoromethylsulfonyl); TFA (trifluoroacteic acid); TLC (thin-layer chromatography); NMP (N-methyl-2-pyrrolidinone); and TMEDA (N,N,N',N'-tetramethylethylenediamine).

The compounds of this invention may be prepared by employing reactions as shown in the following Reaction Schemes, in addition to other standard manipulations that are known in the literature or exemplified in the experimental procedures. The illustrative Reaction Schemes below, therefore, are not limited by the compounds listed or by any particular substituents employed for illustrative purposes. Substituent numbering as shown in the Reaction Schemes does not necessarily correlate to that used in the claims and often, for clarity, a single substituent is shown attached to the compound where multiple substituents are allowed under the definitions of Formula A hereinabove.

Reactions that may be used to generate the compounds of this invention are prepared by employing reactions as shown in the Reaction Schemes I-IX, in addition to other standard manipulations such as ester hydrolysis, cleavage of protecting groups, etc., as may be known in the literature or exemplified in the experimental procedures.

These reactions may be employed in a linear sequence to provide the compounds of the invention or they may be used to synthesize fragments which are subsequently joined by the alkylation reactions described in the Reaction Schemes.

The following Reaction Schemes, Reaction Schemes I-IX, provide useful details for preparing the bicyclic moieties of the instant compounds.

The requisite intermediates are in some cases commercially available, or can be prepared according to literature procedures. As illustrated in Reaction Scheme I, a suitably substituted α-cyano-ketone or its equivalents may be reacted with hydrazine to form the corresponding amino-pyrazole I-1. Intermediate I-1 may then react with a suitably substituted α-cyano-acrylic acid ester such as the ester I-X to provide the 7-amino-pyrazole[1,5-a]pyrimidine-6-carboxylic acid ester I-2. Reduction of ester followed by oxidation with MnO$_2$ provides I-3. Coupling reaction with α-substituted acetate I-a with basic condition provides 1-4. Chlorination of 1-4 provides 1-5. Aryl-aryl coupling reaction, here illustrated by a Suzuki coupling of a suitably substituted boronate 1-6, gives 1-7. Any functional or protecting groups can be transferred appropriately during above reactions.

Reaction Scheme II illustrates the preparation of the compounds, starting with a suitably substituted I-3. This intermediate can be reacted with a suitably substituted methylketone XXX to provide II-1.

Reaction Scheme III illustrates the synthesis of [1,2,4]triazolo[4,3-h][1,7]naphthyridin-3(2H)-one compounds. Boc protection of commercially available amino-pyridine followed by formylation provides aldehyde III-2. Cyclization reaction with suitable substituted methylketone XXX according to scheme H provides chloro-naphthylidine III-4. Chloride is substituted with hydrazine and then cyclized by CDI gives III-6.

Reaction Scheme IV illustrates the preparation of compound IV-1. Cyclization of hydrazide III-5 with bromocyane gives IV-1.

Reaction Scheme V illustrates the preparation of compound V-1. Amidation of hydrazide III-5 with carboxylic acid and following heating of the reaction mixture gives V-1.

Reaction Scheme VI illustrates the synthesis of VI-6 where E=N and M=N. After synthesis of carbohydrazide by reaction with hydrazine with I-2, rearrangement reaction with sodium nitrite gives imidazolone VI-2. Hydrolysis of VI-2 in diluted HCl provides diamine VI-3. Cyclization reaction with suitably substituted ketoester YYY and followed by chlorination provides VI-5. Aryl-aryl coupling reaction, here illustrated by a Suzuki coupling of a suitably substituted boronate 1-6, gives VI-6.

Reaction Scheme VII illustrates the synthesis of amino analogs VII-4. Aryl-aryl coupling reaction of VII-1, here illustrated by a Suzuki coupling of a suitably substituted formyl-arylboronate VII-2, gives VII-3. Reductive amination of VII-3 with suitably substituted secondary or primary amines provides benzylamine VII-4.

Reaction Scheme VIII illustrates the synthesis of compounds with $R^{1'}$ group. Halogenation, here illustrated by a N-bromosuccinimide, gives VIII-1. Following coupling reaction, here illustrated by a Suzuki coupling, gives the compound VIII-2.

Reaction Scheme IX illustrates the synthesis of amino analogs IX-4. Reaction of I-4 with organometallic reagents, here illustrated by alkyllithium, provides IX-1. Oxidation with MnO$_2$ provides IX-2. Chlorination with POCl3 and followed by Suzuki coupling reaction with boronate 1-6 gives IX-4.

Reaction Scheme X illustrates the synthesis of compounds with $R^{1'''}$ group. Amidation of I-2 with a suitably substituted acetic acid or its equivalents, here illustrated by acid chloride, may provide the amide X-1. Cyclizaton reaction in basic condition gives the compound X-2. Chlorination of X-2 provides the dichloride X-3. Aryl-aryl coupling reaction, here illustrated by a Suzuki coupling of a suitably substituted boronate 1-6, gives X-4. Following coupling reaction, here illustrated by a Suzuki coupling, gives the compound X-5. Any functional or protecting groups can be transferred appropriately during above reactions.

Reaction Scheme I

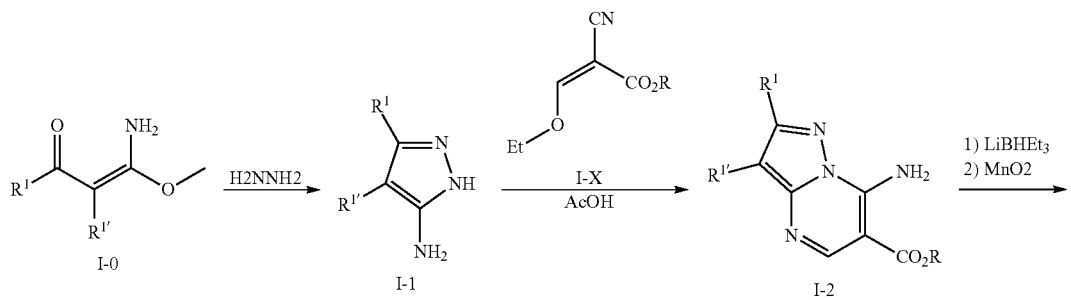

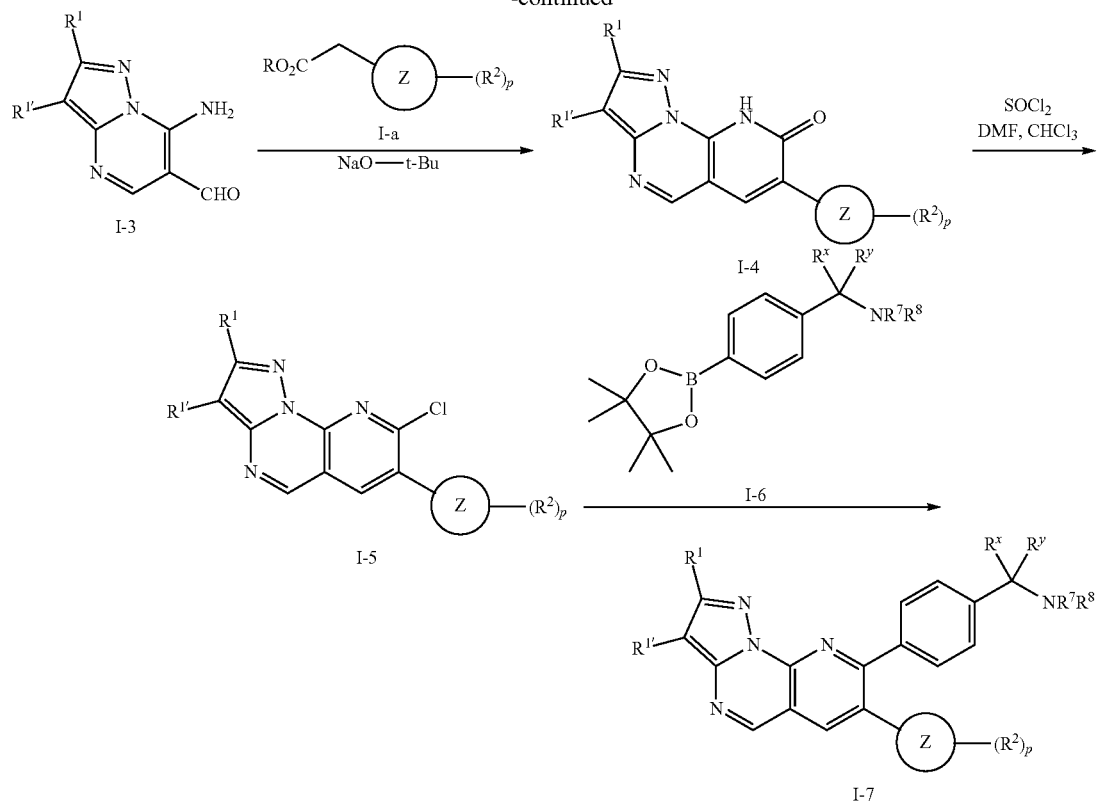
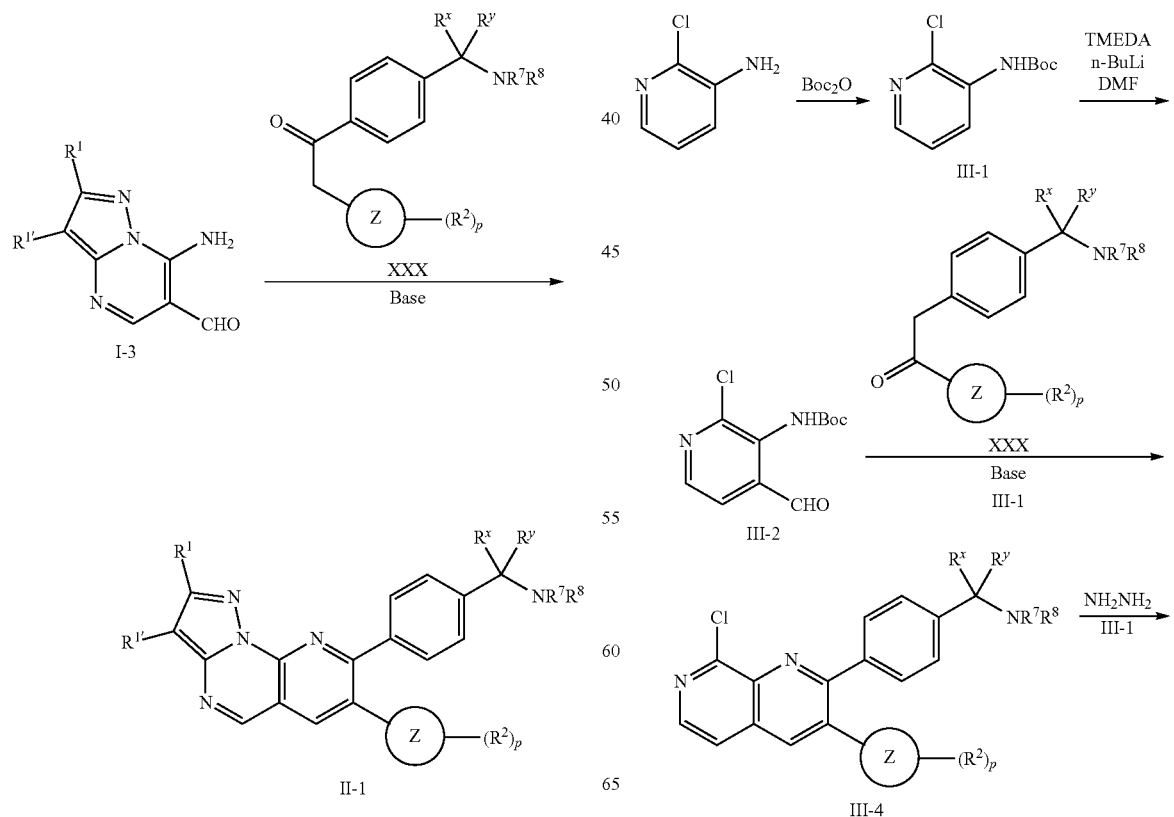

-continued
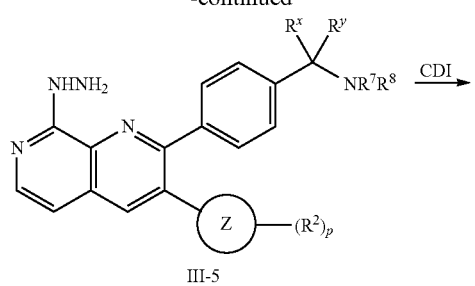
III-5
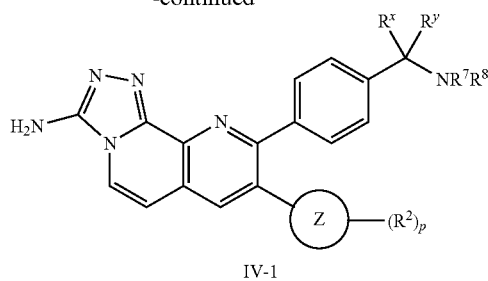
IV-1
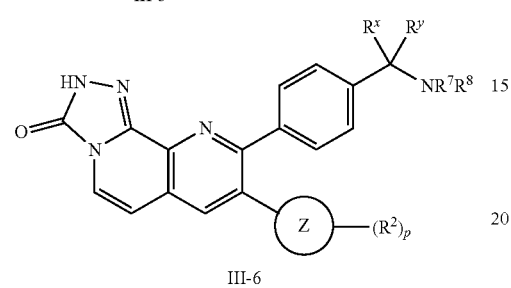
III-6
Reaction Scheme V
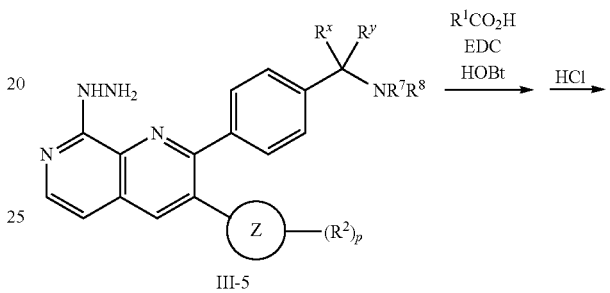
III-5
Reaction Scheme IV
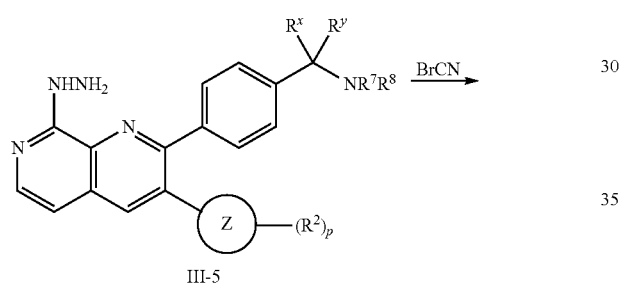
III-5
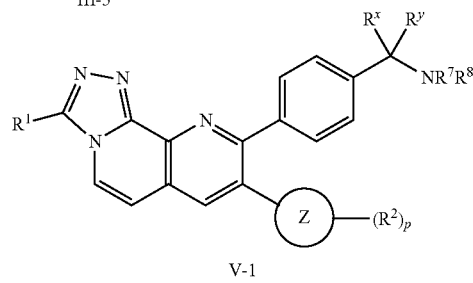
V-1
Reaction Scheme VI
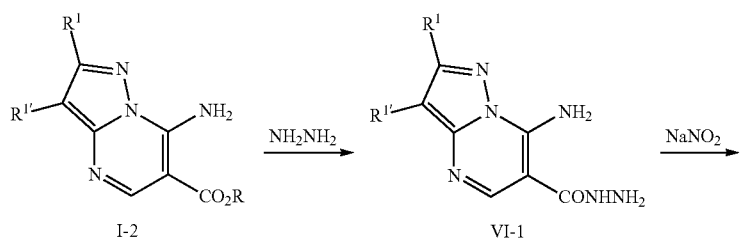
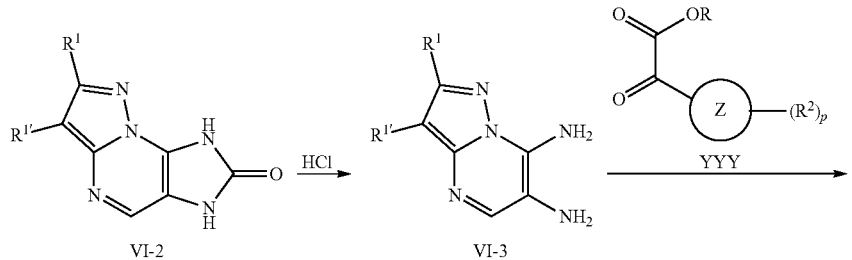

-continued
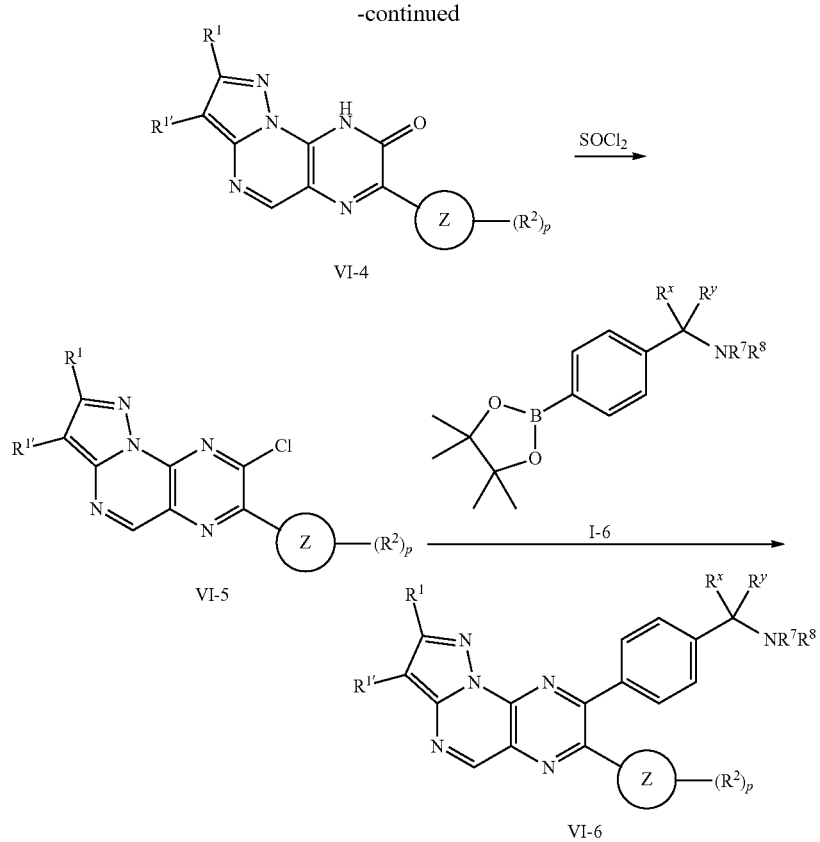
Reaction Scheme VII
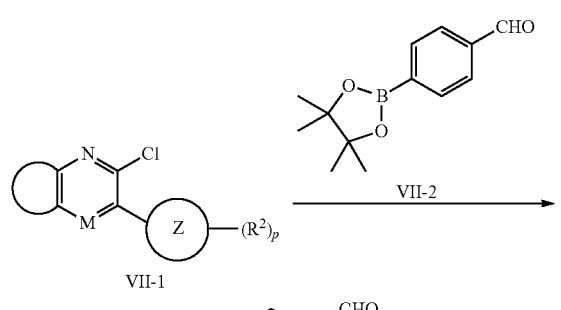
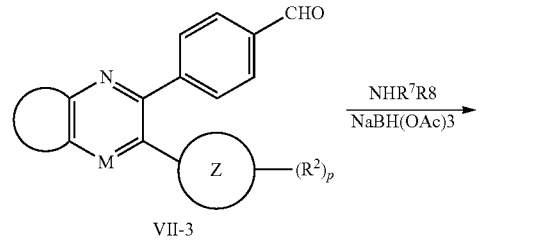
Reaction Scheme VIII
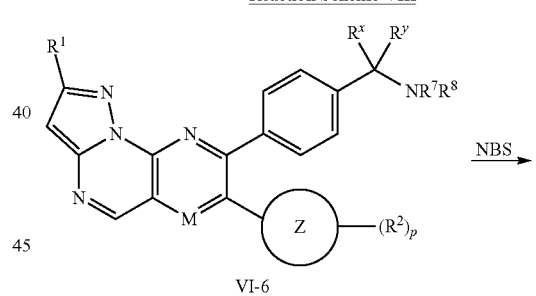
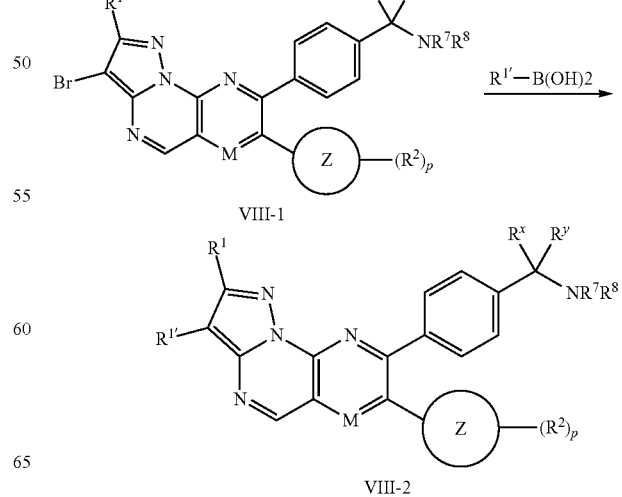

Reaction Scheme IX
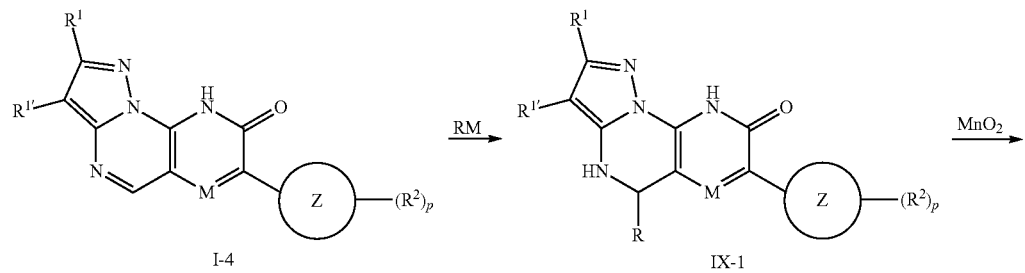
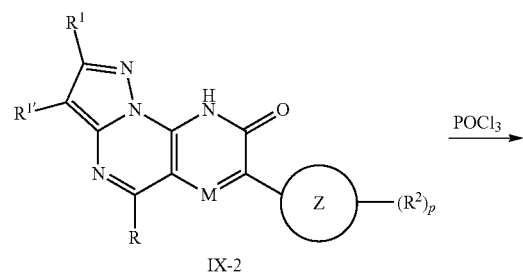
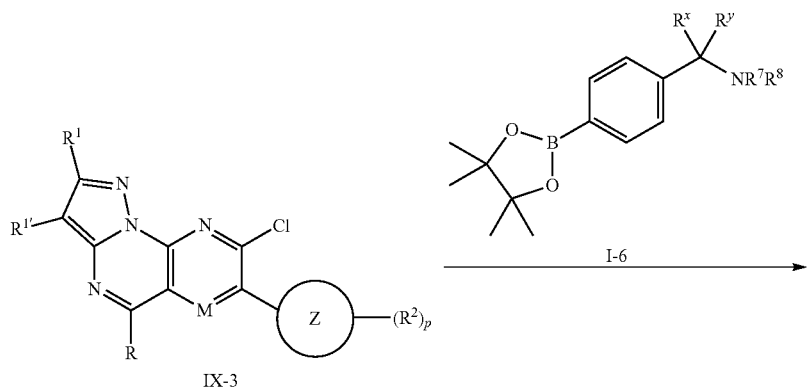
Reaction Scheme X
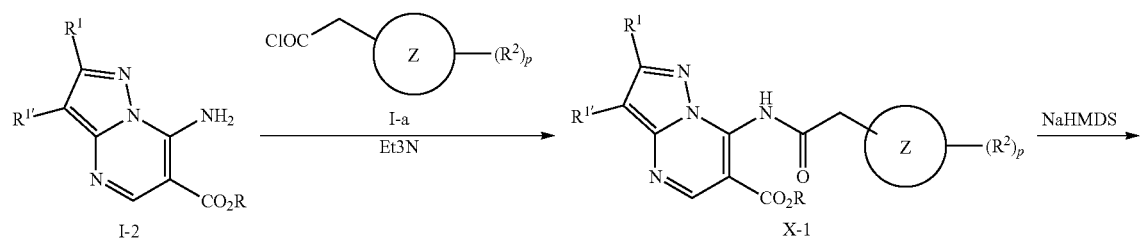

-continued
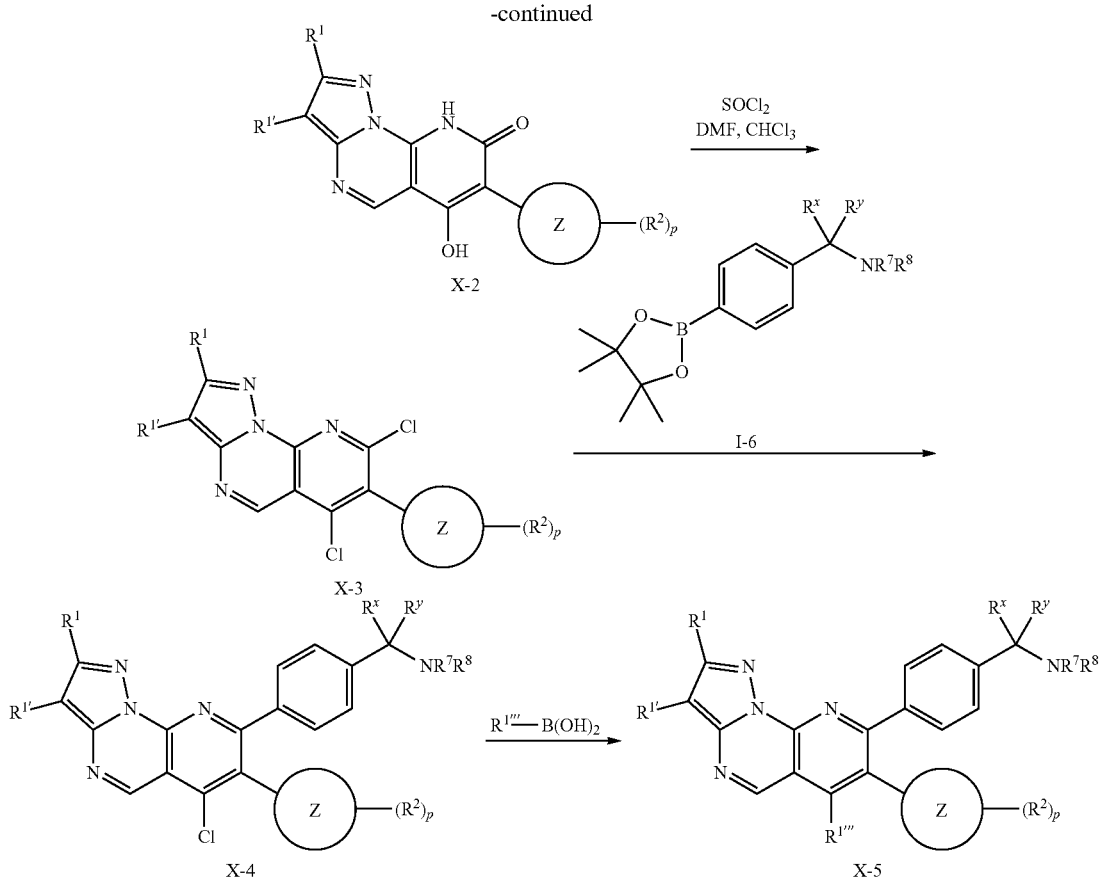
EXAMPLES
Examples and schemes provided are intended to assist in a further understanding of the invention. Particular materials employed, species and conditions are intended to be further illustrative of the invention and do not limit the reasonable scope thereof.
Scheme 1
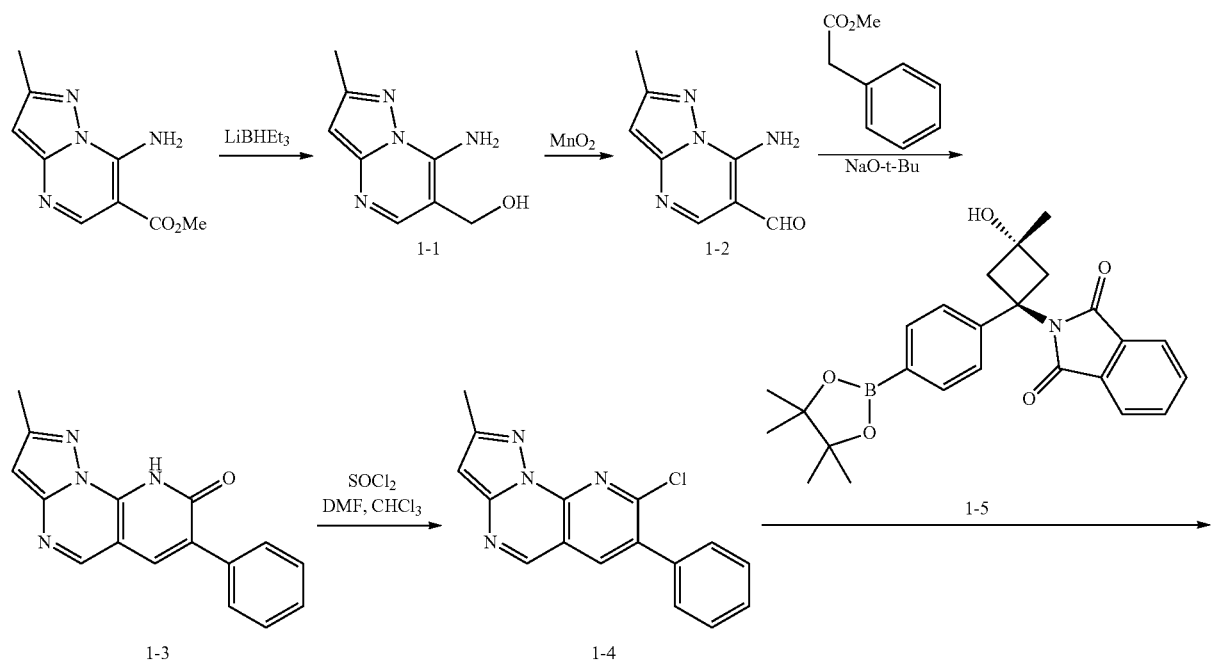

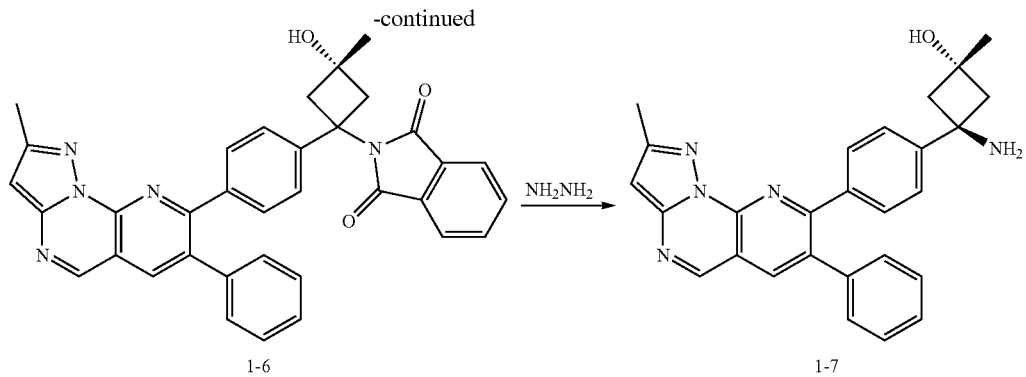

trans-3-amino-1-methyl-3-[4-(2-methyl-7-phenylpyrazolo[1,5-a]pyrido[3,2-e]pyrimidin-8-yl)phenyl]cyclobutanol (1-7)

(7-amino-2-methylpyrazolo[1,5-a]pyrimidin-6-yl)methanol (1-1)

To a 1 L three-necked round bottom flask was added Methyl 7-amino-2-methylpyrazolo[1,5-a]pyrimidine-6-carboxylate (20.6 g, 100 mmol, 1.0 eq.) and THF (400 mL). The mixture was cooled to 0° C. and LiBHEt₃ (315 mL of a 1.0 M solution in THF, 315 mmol, 3.0 eq.) was added slowly through an addition funnel under nitrogen. After addition, the mixture was stirred at room temperature for 4 h. Additional LiBHEt₃ (30 mL of a 1.0 M solution in THF, 30 mmol, 0.3 eq.) was added and the mixture was stirred for an additional 1 h. The mixture was slowly treated with EtOAc (600 mL) and then water (300 mL). The layers were separated and the aqueous phase was extracted with EtOAc (2×300 mL). The combined organic phases were dried over anhydrous Na₂SO₄. After filtration and concentration, the residue was purified by a short silica gel column (2.5 inch in height and 4 inch in diameter) using MeOH in CH₂Cl₂ as the eluent. Concentration by rotary evaporation provided (7-amino-2-methylpyrazolo[1,5-a]pyrimidin-6-yl)methanol (1-1) as a light yellowish solid.

7-amino-2-methylpyrazolo[1,5-a]pyrimidine-6-carbaldehyde (1-2)

(7-amino-2-methylpyrazolo[1,5-a]pyrimidin-6-yl)methanol (1-1) (14.1 g, 79.2 mmol) was dissolved in anhydrous CHCl₃ (500 mL) and TI-IF (250 mL). Activated MnO₂ (68.9 g, 792 mmol) was added to the mixture, and the mixture was stirred for 16 h. After filtration through a plug of Celite pad, the filtrate was evaporated to give 7-amino-2-methylpyrazolo[1,5-a]pyrimidine-6-carbaldehyde (1-2) as a yellowish solid.

2-methyl-7-phenylpyrazolo[1,5-a]pyrido[3,2-e]pyrimidin-8(9H)-one (1-3)

Into a round bottom flask was added 7-amino-2-methylpyrazolo[1,5-a]pyrimidine-6-carbaldehyde (1-2) (5.30 g, 30 mmol), methy phenylacetate (18.0 g, 120 mmol), potassium tert-butoxide (5.80 g, 60 mmol), and toluene (100 mL). The reaction mixture was heated to 105° C. while stirring under an atmosphere of nitrogen for 30 min. Then DMF (100 mL) was added and the mixture was stirred at 100° C. for 3 days. The reaction mixture was cooled to room temperature and concentrated in vacuo. The resulting residue was dissolved in DCM (600 mL) and then water (400 mL) was added to the solution. The precipitated solid was collected by filtration and the solid was washed with water (50 mL) and DCM (100 mL). The solid was dried over an oil pump for 2 days to give 2-methyl-7-phenylpyrazolo[1,5-a]pyrido[3,2-e]pyrimidin-8(9H)-one (1-3) as a yellow solid.

8-chloro-2-methyl-7-phenylpyrazolo[1,5-a]pyrido[3,2-e]pyrimidine (1-4)

To a 250 mL round bottom flask was added 2-methyl-7-phenylpyrazolo[1,5-a]pyrido[3,2-e]pyrimidin-8(9H)-one (1-3) (3 g, 10.9 mmol, 1 eq.), CHCl₃ (120 mL), SOCl₂ (5.17 g, 3.17 mL, 43.5 mmol, 4 eq.) and DMF (158.9 mg, 168.3 uL, 2.17 mmol, 0.2 eq.). The mixture was heated to 70° C. in an oil bath for 1 h. After 1 h, additional SOCl₂ (1.6 mL, 21.8 mmol, 2 eq.) and DMF (168.3 uL, 2.17 mmol, 0.2 eq.) were added. The mixture was maintained at 70° C. for an additional 2 h. After 3 h total, LCMS analysis and TLC analysis (heptane:EtOAc (3:7)) of the resulting light brown solution indicated that the reaction was complete. The reaction was concentrated in vacuo and the residue diluted with EtOAc (100 mL), washed with saturated aqueous NaHCO₃ solution (50 mL), and the aqueous phases re-extracted with EtOAc (3×200 mL). The combined organic phases were dried over MgSO₄, filtered, and concentrated to give 3.2 g of material which was purified by silica gel chromatography using EtOAc/heptane as the eluent to give 8-chloro-2-methyl-7-phenylpyrazolo[1,5-a]pyrido[3,2-e]pyrimidine (1-4) as an yellow solid.

2-{3-hydroxy-3-methyl-1-[4-(2-methyl-7-phenylpyrazolo[1,5-a]pyrido[3,2-e]pyrimidin-8-yl)phenyl]cyclobutyl}-1H-isoindole-1,3(2H)-dione (1-6)

A mixture of 8-chloro-2-methyl-7-phenylpyrazolo[1,5-a]pyrido[3,2-d]pyrimidine (1-4) (206 mg, 0.700 mmol), 2-{trans-3-hydroxy-3-methyl-1-[4-(4,4,5,5-tetramethyl-1,3,2-dioxaborolan-2-yl)phenyl]cyclobutyl}-1H-isoindole-1,3 (2H)-dione (1-5) (364 mg, 0.840 mmol), [1,1'-bis(diphenylphosphino)ferrocene]dichloropalladium (II) complex with dichloromethane (1:1) (114 mg, 0.140 mmol) and 2M aqueous solution of Cs₂CO₃ (1.75 mL, 3.50 mmol) in 1,4-dioxane (15 mL) was stirred at 60° C. for 1 h. The solvent was removed by evaporation, and the residue was diluted with CHCl₃, washed with water and brine, dried (MgSO₄), filtered, and the solvent was removed by evaporation. The residue was purified by silica gel chromatography (CHCl₃-5% MeOH/CHCl₃) to give 2-{3-hydroxy-3-methyl-1-[4-(2-methyl-7-phenylpyrazolo[1,5-a]pyrido[3,2-e]pyrimidin-8-yl)phenyl]cyclobutyl}-1H-isoindole-1,3(2H)-dione (1-6) as pale yellow foam.

trans-3-amino-1-methyl-3-[4-(2-methyl-7-phenylpyrazolo[1,5-a]pyrido[3,2-e]pyrimidin-8-yl)phenyl]cyclobutanol (1-7)

A mixture of 2-{3-hydroxy-3-methyl-1-[4-(2-methyl-7-phenylpyrazolo[1,5-a]pyrido[3,2-e]pyrimidin-8-yl)phenyl]cyclobutyl}-1H-isoindole-1,3(2H)-dione (1-6) (198 mg, 0.350 mmol) and hydrazine monohydrate (1 mL, 20.6 mmol) in MeOH (4 mL) and 1,4-dioxane (4 mL) was heated under microwave irradiation at 130° C. for 30 min. The mixture was diluted with CHCl$_3$, washed with sat. NaHCO$_3$ solution, brine and water, dried (MgSO$_4$), filtered, and the solvent was removed by evaporation. The residue was purified by silica gel chromatography (0-20% MeOH/CHCl$_3$) to give trans-3-amino-1-methyl-3-[4-(2-methyl-7-phenylpyrazolo[1,5-a]pyrido[3,2-e]pyrimidin-8-yl)phenyl]cyclobutanol (1-7) as pale yellow foam. MS (M+H)+: observed=436.2135, calculated=436.2137

The following compounds were prepared in a similar fashion to Example 1-6 and 1-7, but using the appropriate materials:

| # | Compound name | MS (M + H)+: observed | MS (M + H)+: calculated |
|---|---|---|---|
| 1-8 | cis-3-amino-1-methyl-3-[4-(2-methyl-7-phenylpyrazolo[1,5-a]pyrido[3,2-e]pyrimidin-8-yl)phenyl]cyclobutanol | 436 | 436 |
| 1-9 | trans-3-amino-1-cyclopropyl-3-[4-(2-methyl-7-phenylpyrazolo[1,5-a]pyrido[3,2-e]pyrimidin-8-yl)phenyl]cyclobutanol | 462.2287 | 462.2294 |
| 1-10 | trans-3-amino-3-[4-(2-methyl-7-phenylpyrazolo[1,5-a]pyrido[3,2-e]pyrimidin-8-yl)phenyl]cyclobutanol | 462 | 462 |
| 1-11 | trans-3-methoxy-1-[4-(2-methyl-7-phenylpyrazolo[1,5-a]pyrido[3,2-e]pyrimidin-8-yl)phenyl]cyclobutanamine | 436.2141 | 436.2137 |
| 1-12 | methyl {1-[4-(2-methyl-7-phenylpyrazolo[1,5-a]pyrido[3,2-e]primidin-8-yl)phenyl]-3-oxocyclobutyl}carbamate | 478.188 | 478.1879 |
| 1-13 | 1-[4-(2-methyl-7-phenylpyrazolo[1,5-a]pyrido[3,2-e]pyrimidin-8-yl)phenyl]methanamine | 366.1718 | 366.1719 |
| 1-14 | 2-methyl-7-phenyl-8-[4-(1H-pyrazol-1-ylmethyl)phenyl]pyrazolo[1,5-a]pyrido[3,2-e]pyrimidine | 417.1827 | 417.1828 |
| 1-15 | (1R)-1-[4-(2-methyl-7-phenylpyrazolo[1,5-a]pyrido[3,2-e]pyrimidin-8-yl)phenyl]ethanamine | 380.1868 | 380.1875 |
| 1-16 | trans-3-amino-1-ethyl-3-[4-(2-methyl-7-phenylpyrazolo[1,5-a]pyrido[3,2-e]pyrimidin-8-yl)phenyl]cyclobutanol | 450.2296 | 450.2294 |
| 1-17 | cis-3-amino-1-ethyl-3-[4-(2-methyl-7-phenylpyrazolo[1,5-a]pyrido[3,2-e]pyrimidin-8-yl)phenyl]cyclobutanol | 450.2298 | 450.2294 |
| 1-18 | trans-3-amino-1-ethenyl-3-[4-(2-methyl-7-phenylpyrazolo[1,5-a]pyrido[3,2-e]pyrimidin-8-yl)phenyl]cyclobutanol | 448.2129 | 448.2137 |
| 1-19 | 3-methylidene-1-[4-(2-methyl-7-phenylpyrazolo[1,5-a]pyrido[3,2-e]pyrimidin-8-yl)phenyl]cyclobutanamine | 418.2028 | 418.2032 |
| 1-20 | 3,3-difluoro-1-[4-(2-methyl-7-phenylpyrazolo[1,5-a]pyrido[3,2-e]pyrimidin-8-yl)phenyl]cyclobutanamine | 442.183 | 442.1843 |
| 1-21 | 8-{4-[trans-1-amino-3-(1,2-dihydroxyethyl)-3-hydroxycyclobutyl]phenyl}-2-methyl-7-phenylpyrazolo[1,5-a]pyrido[3,2-e]pyrimidine | 482.2206 | 482.2192 |
| 1-22 | 8-{4-[1-amino-3-hydroxy-3-(hydroxymethyl)cyclobutyl]phenyl}-2-methyl-7-phenylpyrazolo[1,5-a]pyrido[3,2-e]pyrimidine | 452.2085 | 452.2087 |
| 1-23 | 2-[4-(2-methyl-7-phenylpyrazolo[1,5-a]pyrido[3,2-e]pyrimidin-8-yl)phenyl]-5,8-dioxaspiro[3.4]octan-2-amine | 464.2093 | 464.2087 |

Scheme 2

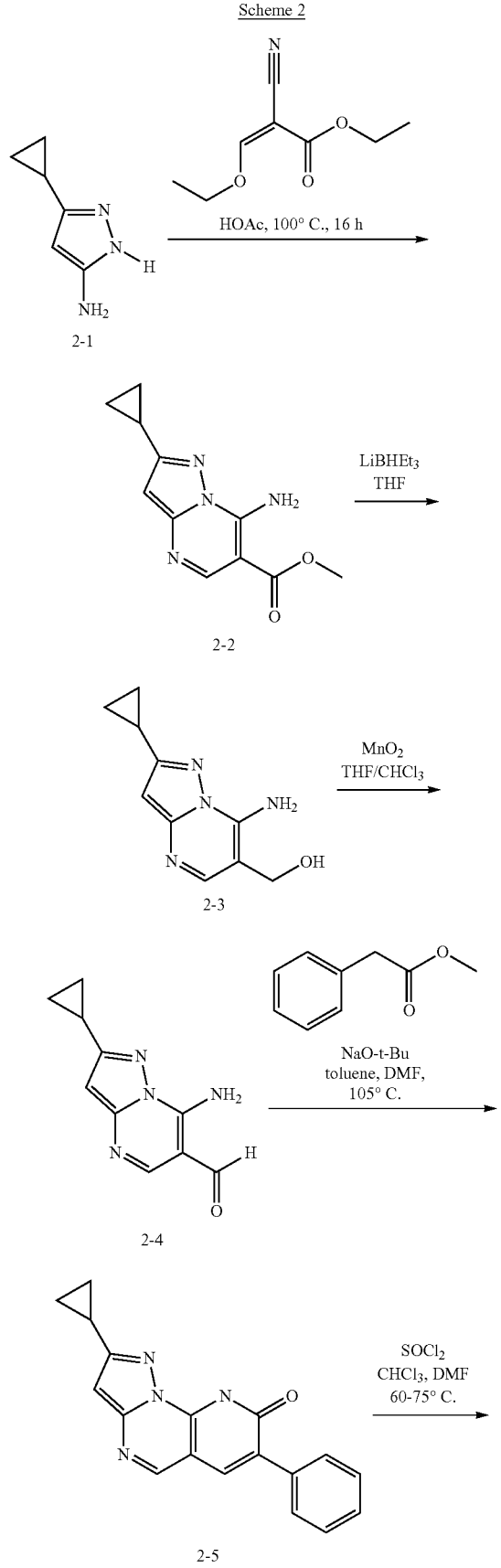

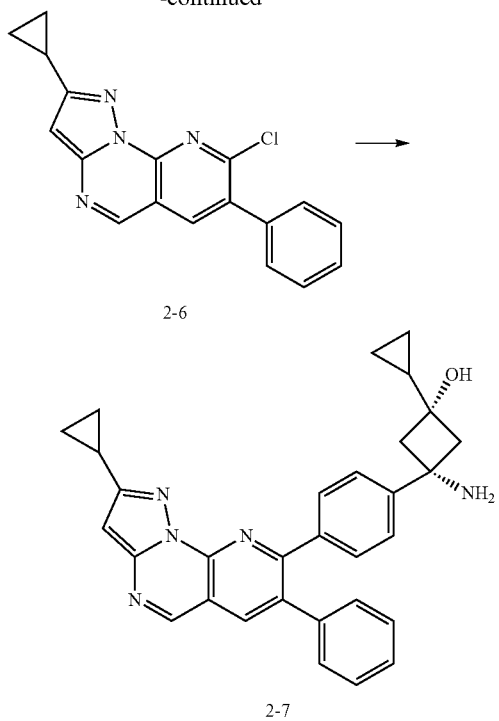

cis-3-amino-1-cyclopropyl-3-[4-(2-cyclopropyl-7-phenylpyrazolo[1,5-a]pyrido[3,2-e]pyrimidin-8-yl)phenyl]cyclobutanol (2-7)

7-Amino-2-cyclopropyl-pyrazolo[1,5-a]pyrimidine-6-carboxylic acid ethyl ester (2-2)

To a 250 mL round bottom flask was added Compound (2-1) (5 g, 40.6 mmol, 1 eq.), ethyl 2-cyano-3-ethoxyacrylate (6.9 g, 40.6 mmol, 1 eq.), and AcOH (100 mL). The mixture was heated at 100° C. for 16 h. The reaction was concentrated and the residue was treated with H₂O (150 mL). The resulting precipitate was filtered, and the precipitate washed with H₂O (3×250 mL). The crude product was dried under high vacuum for 16 h to afford Compound (2-2).

(7-Amino-2-cyclopropyl-pyrazolo[1,5-a]pyrimidin-6-yl)-methanol (2-3)

Compound (2-3) was prepared using a procedure similar to that of Compound (1-1).

7-Amino-2-cyclopropyl-pyrazolo[1,5-a]pyrimidin-6-carbaldehyde (2-4)

Compound (2-4) was prepared using a procedure similar to that of Compound (1-2).

2-Cyclopropyl-7-phenyl-9H-1,4,9,9b-tetraaza-cyclopenta[a]naphthalen-8-one (2-5)

Compound (2-5) was prepared using a procedure similar to that of Compound (1-3).

8-Chloro-2-cyclopropyl-7-phenyl-1,4,9,9b-tetraaza-cyclopenta[a]naphthalene (2-6)

Compound (2-6) was prepared using a procedure similar to that of Compound (1-4).

cis-3-amino-1-cyclopropyl-3-[4-(2-cyclopropyl-7-phenylpyrazolo[1,5-a]pyrido[3,2-e]pyrimidin-8-yl)phenyl]cyclobutanol (2-7)

cis-3-amino-1-cyclopropyl-3-[4-(2-cyclopropyl-7-phenylpyrazolo[1,5-a]pyrido[3,2-e]pyrimidin-8-yl)phenyl]cyclobutanol (2-7) was prepared using a procedure similar to that of Compound (1-6) and (1-7).

MS (M+H)+: observed=488.2448, calculated=488.2450

The following compounds were prepared in a similar fashion to Examples from 2-1 to 2-7, but using the appropriate materials:

| # | Compound name | MS (M + H)+: observed | MS (M + H)+: calculated |
|---|---|---|---|
| 2-8 | trans-3-amino-1-cyclopropyl-3-[4-(7-phenylpyrazolo[1,5-a]pyrido[3,2-e]pyrimidin-8-yl)phenyl]cyclobutanol | 448.2141 | 448.2137 |
| 2-9 | 8-[4-(trans-1-amino-3-cyclopropyl-3-hydroxycyclobutyl)phenyl]-7-phenyl-2-(trifluoromethyl)pyrazolo[1,5-a]pyrido[3,2-e]pyrimidine | 516.2014 | 516.2011 |
| 2-10 | trans-3-cyclopropyl-1-{4-[2-(4-fluorophenyl)-7-phenylpyrazolo[1,5-a]pyrido[3,2-e]pyrimidin-8-yl]phenyl}-3-hydroxycyclobutanamine | 542.2346 | 542.2356 |
| 2-11 | trans-1-[4-(2-cyclopropyl-7-phenylpyrazolo[1,5-a]pyrido[3,2-e]pyrimidin-8-yl)phenyl]-3-hydroxy-3-methylcyclobutanamine | 462.2301 | 462.2294 |
| 2-12 | trans-3-amino-3-[4-[2-(1,1-dimethylethyl)-7-phenylpyrazolo[1,5-a]pyrido[3,2-e]pyrimidin-8-yl]phenyl]-1-methylcyclobutanol | 478.2596 | 478.2607 |

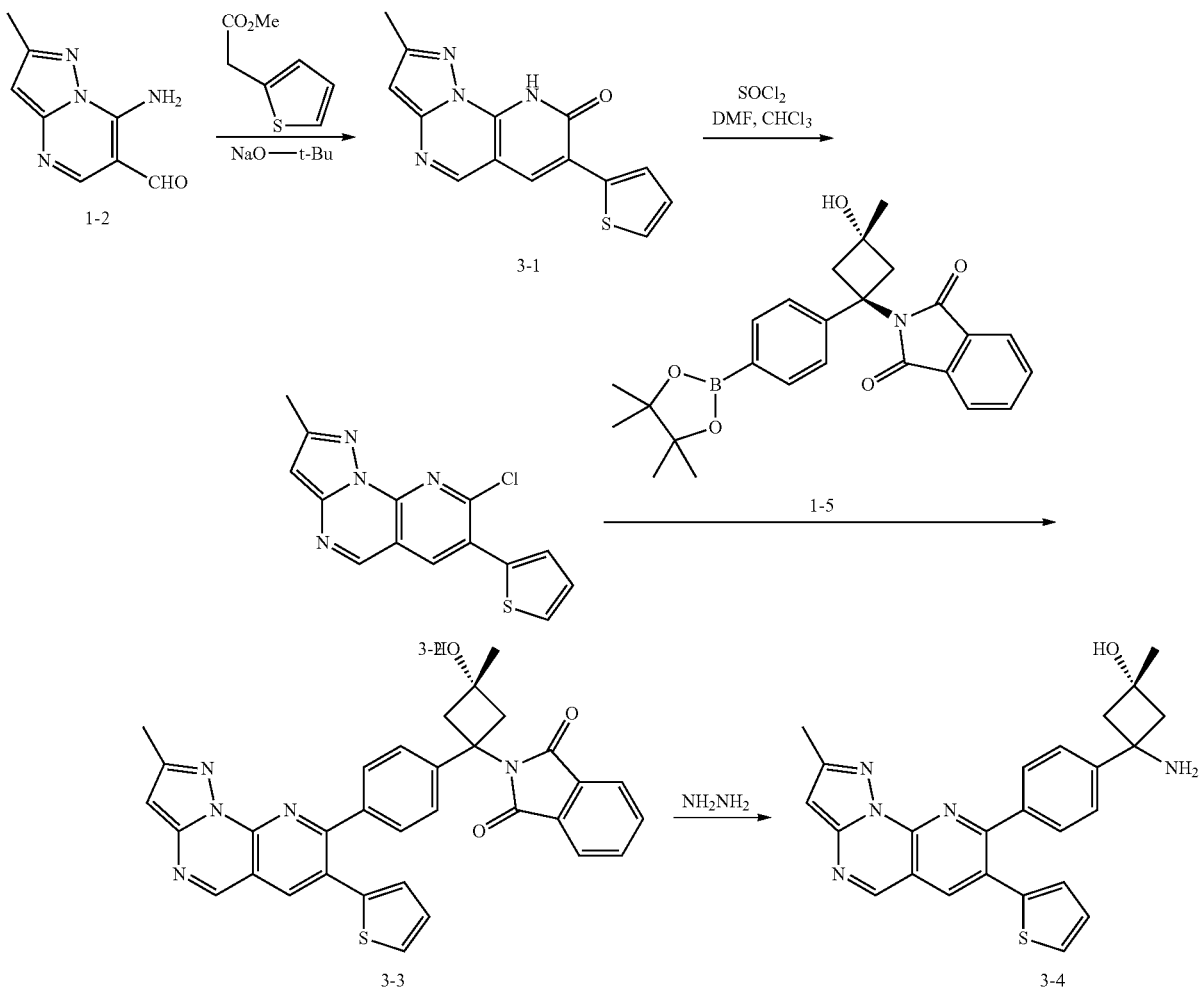

Scheme 3 trans-3-amino-1-methyl-3-{4-[2-methyl-7-(thiophen-2-yl)pyrazolo[1,5-a]pyrido[3,2-e]pyrimidin-8-yl]phenyl}cyclobutanol (3-4)

2-Methyl-7-thiophen-2-yl-9H-1,4,9,9b-tetraaza-cyclopenta[a]naphthalen-8-one 3-1

Compound (3-1) was prepared using a procedure similar to that of Compound (1-3).

8-Chloro-2-methyl-7-thiophen-2-yl-1,4,9,9b-tetraaza-cyclopenta[a]naphthalene (3-2)

Compound (3-2) was prepared using a procedure similar to that of Compound (1-4).

2-{3-Hydroxy-3-methyl-1-[4-(2-methyl-7-thiophen-2-yl-1,4,9,9b-tetraaza-cyclopenta[a]naphthalene-8-yl)-phenyl]cyclobutyl}-isoindole-1,3-dione (3-3)

Compound (3-3) was prepared using a procedure similar to that of Compound (1-6)

trans-3-amino-1-methyl-3-{4-[2-methyl-7-(thiophen-2-yl)pyrazolo[1,5-a]pyrido[3,2-e]pyrimidin-8-yl]phenyl}cyclobutanol (3-4)

Compound (3-4) was prepared using a procedure similar to that of Compound (1-7). MS (M+H)+: observed=442.1701, calculated=442.1702

The following compounds were prepared in a similar fashion to Examples from 1-2 to 3-4, but using the appropriate materials:

| # | Compound name | MS (M + H)+: observed | MS (M + H)+: calculated |
|---|---|---|---|
| 3-5 | trans-3-amino-3-{4-[7-(2-fluorophenyl)-2-methylpyrazolo[1,5-a]pyrido[3,2-e]pyrimidin-8-yl]phenyl}-1-methylcyclobutanol | 453 | 453 |
| 3-6 | trans-3-amino-1-methyl-3-{4-[2-methyl-7-(thiophen-3-yl)pyrazolo[1,5-a]pyrido[3,2-e]pyrimidin-8-yl]phenyl}cyclobutanol | 442.1695 | 442.1702 |

Scheme 4

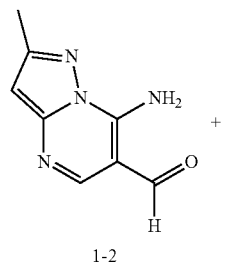

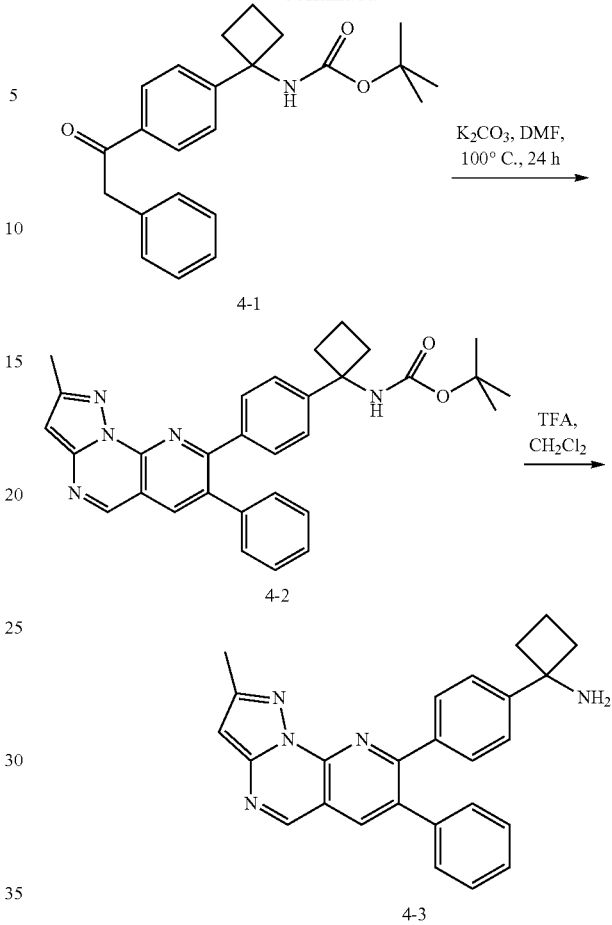

1-[4-(2-methyl-7-phenylpyrazolo[1,5-a]pyrido[3,2-e]pyrimidin-8-yl)phenyl]cyclobutanamine (4-3)

{1-[4-(2-methyl-7-phenyl-1,4,9,9b-tetraaza-cyclopenta[a]naphthalen-8-yl)-phenyl]-cyclobutyl}-carbamic acid tert-butyl ester (4-2)

A mixture of Compound (1-2) (56 mg, 0.32 mmol, 1 eq.), Compound (4-1) (132 mg, 0.36 mmol, 1 eq.), and potassium carbonate (47 mg, 0.36 mmol, 1.1 eq.) in DMF (6 mL) was heated at 100° C. for 24 h. After this time, the mixture was added to aqueous LiCl solution and then extracted three times with EtOAc. The combined organic phases were dried over $Na_2SO_4$ and concentrated under reduced pressure to afford a residue that was further purified by silica gel chromatography using $CH_2Cl_2$:EtOAc as the eluant to provide Compound (4-2). This material was used in the next step without further characterization.

1-[4-(2-methyl-7-phenylpyrazolo[1,5-a]pyrido[3,2-e]pyrimidin-8-yl)phenyl]cyclobutanamine (4-3)

To a solution of Compound (4-2) (7 mg, 0.14 mmol, 1 eq.) in $CH_2Cl_2$ (3 mL) was added trifluoroacetic acid (1 mL) and the mixture stirred at room temperature for 15 minutes. The volatiles were removed under reduced pressure and the residue was purified by reverse phase HPLC using TFA:$CH_3CN$ and water as the eluant to provide Compound (4-3). MS (M+H)+: observed=406.2027, calculated=406.2032

Scheme 7

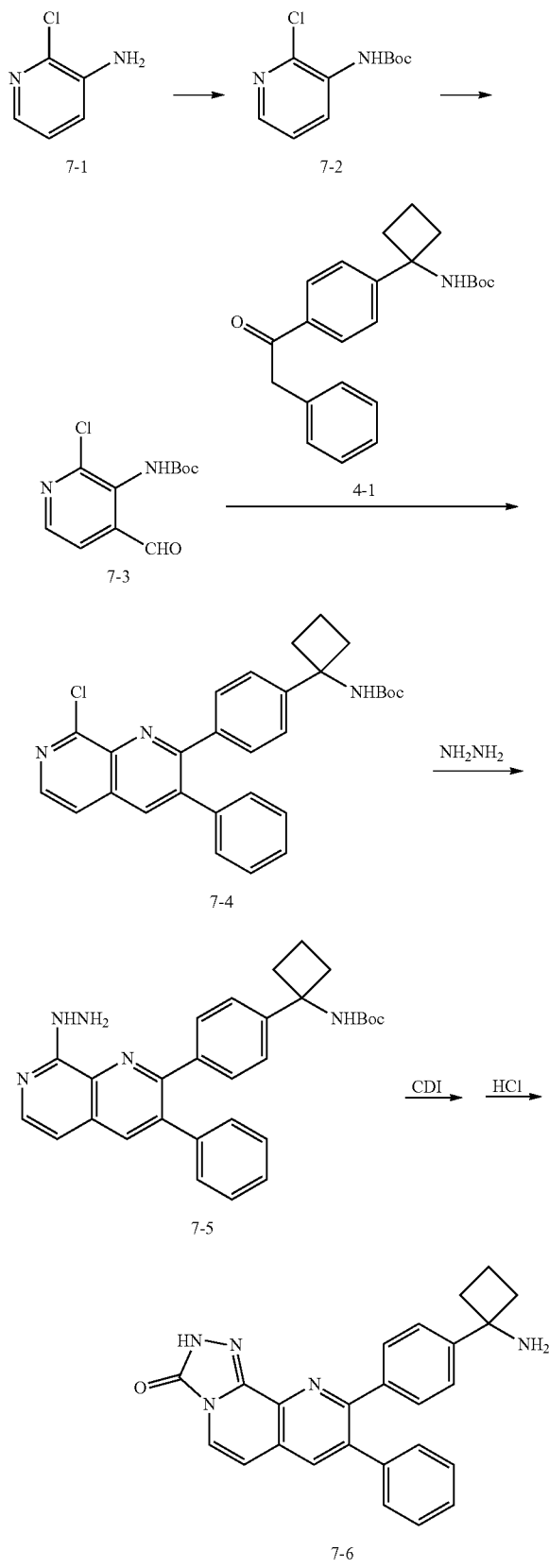

9-[4-(1-aminocyclobutyl)phenyl]-8-phenyl[1,2,4]triazolo[4,3-h]-1,7-naphthyridin-3(2H)-one (7-6)

tert-butyl (2-chloropyridin-3-yl)carbamate (7-2)

To a solution of 2-chloropyridin-3-amine (7-1) (2.00 g, 15.6 mmol) in THF (50 mL) was added a 0.5M solution of KHMDS in THF (68.5 mL) and then di-tert-butyl dicarbonate (3.73 g, 17.1 mmol) and the mixture was stirred at room temperature for 2 hours. The mixture was diluted with ethyl acetate, washed with water, dried over sodium sulfate, filtered and concentrated in vacuo. The residue was purified by silica gel chromatography (0-60% EtOAc/Hexane) to give tert-butyl (2-chloropyridin-3-yl)carbamate (7-2) as a colorless solid.

tert-butyl (2-chloro-4-formylpyridin-3-yl)carbamate (7-3)

To a solution of tert-butyl (2-chloropyridin-3-yl)carbamate (7-2) (3.01 g, 13.2 mmol) and TMEDA (3.37 g, 29 mmol) in THF (50 mL) at −78° C. was added a 2.5 M solution of n-butyllithium in hexane (11.6 mL) dropwise over 10 minutes and the mixture was stirred for 1 hour. The mixture was warmed up to −10° C. and then cooled to −78° C. DMF (3.06 mL) was added to the mixture and then the mixture was warmed to ambient temperature over 3 hours. Saturated aq. $NH_4Cl$ and EtOAc were added to the mixture and the organic layer was washed with $H_2O$ and brine, dried over $MgSO_4$, filtered, concentrated in vacuo, and purified by silica gel chromatography (0-80% EtOAc/hexane) to give tert-butyl (2-chloro-4-formylpyridin-3-yl)carbamate (7-3) as a yellow solid.

tert-butyl {1-[4-(8-chloro-3-phenyl-1,7-naphthyridin-2-yl)phenyl]cyclobutyl}carbamate (7-4)

A mixture of tert-butyl (2-chloro-4-formylpyridin-3-yl)carbamate (7-3) (300 mg, 1.17 mmol), tert-butyl {1-[4-(phenylacetyl)phenyl]cyclobutyl}carbamate (4-1) (427 mg, 1.17 mmol) and potassium carbonate (485 mg, 3.51 mmol) in DMF (10 mL) was stirred at 120° C. for 15 hours. The reaction mixture was cooled to room temperature, diluted with ethyl acetate, washed with water, dried over sodium sulfate, filtered, and concentrated in vacuo. The residue was purified by silica gel chromatography (hexane-EtOAc) to give tert-butyl {1-[4-(8-chloro-3-phenyl-1,7-naphthyridin-2-yl)phenyl]cyclobutyl}carbamate (7-4) as a pale yellow solid.

tert-butyl {1-[4-(8-hydrazino-3-phenyl-1,7-naphthyridin-2-yl)phenyl]cyclobutyl}carbamate (7-5)

To a solution of tert-butyl {1-[4-(8-chloro-3-phenyl-1,7-naphthyridin-2-yl)phenyl]cyclobutyl}carbamate (7-4) (288 mg, 0.593 mmol) in 1,4-dioxane (4 mL) was added hydrazine monohydrate (286 mL, 5.93 mmol). The mixture was stirred at 100° C. for 1 h. The mixture was cooled to room temperature, suspended in ethyl acetate, washed with water, dried over sodium sulfate, filtered, and concentrated in vacuo to give tert-butyl{1-[4-(8-hydrazino-3-phenyl-1,7-naphthyridin-2-yl)phenyl]cyclobutyl}carbamate (7-5) as an orange solid.

9-[4-(1-aminocyclobutyl)phenyl]-8-phenyl[1,2,4]triazolo[4,3-h]-1,7-naphthyridin-3(2H)-one (7-6)

A mixture of tert-butyl {1-[4-(8-hydrazino-3-phenyl-1,7-naphthyridin-2-yl)phenyl]cyclobutyl}carbamate (7-5) (30.0 mg, 0.0620 mmol) and CDI (40.4 mg, 0.249 mmol) in 1,4-dioxane (2 mL) was stirred at 100° C. for 15 h and then cooled to room temperature. The mixture was diluted with EtOAc, washed with water, dried over sodium sulfate, filtered, and concentrated in vacuo. The residue was purified by column chromatography on silica gel. The residue was treated with HCl in MeOH and the mixture was heated in a microwave reactor at 80° C. for 5 min. The solvent was evaporated and the residue was purified by reverse phase (H₂O/0.1% TFAaq.-MeCN/0.1% TFAaq.) HPLC to give 9-[4-(1-aminocyclobutyl)phenyl]-8-phenyl[1,2,4]triazolo[4,3-h]-1,7-naphthyridin-3(2H)-one (7-6) as a colorless solid.

MS (M+H)+: observed=408, calculated=408

Scheme 8

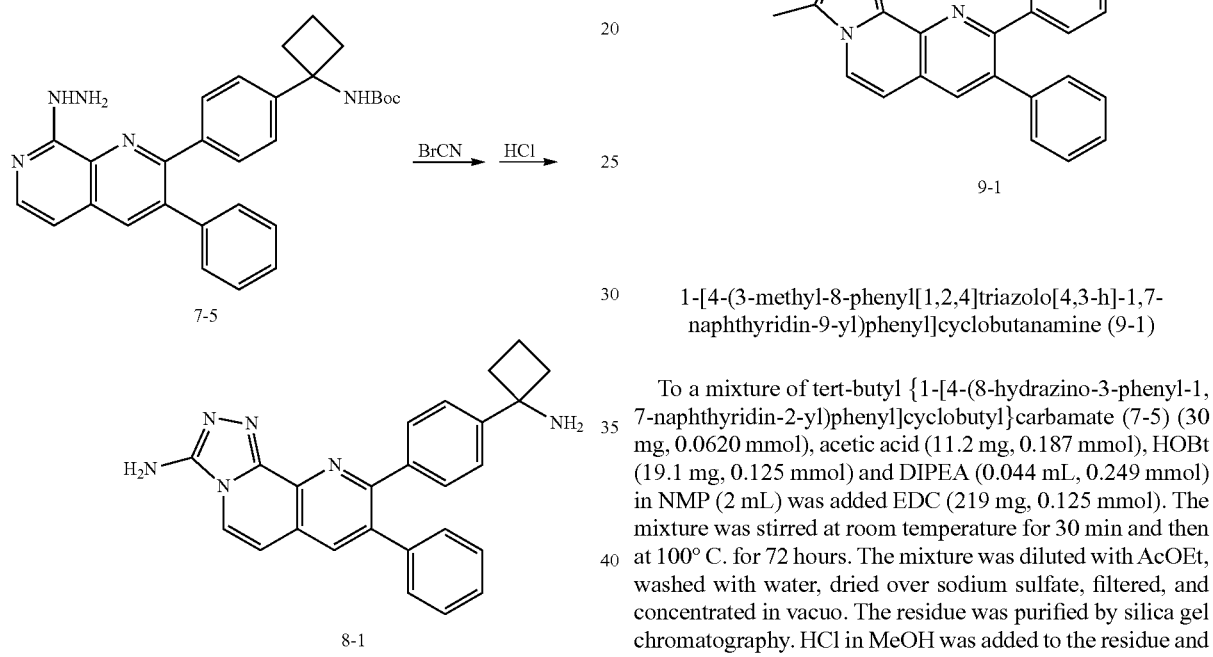

9-[4-(1-aminocyclobutyl)phenyl]-8-phenyl[1,2,4]triazolo[4,3-h]-1,7-naphthyridin-3-amine (8-1)

A mixture of tert-butyl {1-[4-(8-hydrazino-3-phenyl-1,7-naphthyridin-2-yl)phenyl]cyclobutyl}carbamate (7-5) (30 mg, 0.0620 mmol), cyanogen bromide (19.8 mg, 0187 mmol) in ethanol (2 mL) was stirred at 60° C. for 72 hours. The mixture was diluted with AcOEt, washed with water, dried over sodium sulfate, filtered, and concentrated in vacuo. The residue was purified by column chromatography on silica gel. The residue was treated with HCl in MeOH and the mixture was heated in a microwave reactor at 80° C. for 5 min. The solvent was evaporated and the residue was purified by reverse phase HPLC (H₂O/0.1% TFA aq.-MeCN/0.1% TFA aq.) to give 9-[4-(1-aminocyclobutyl)phenyl]-8-phenyl[1,2,4]triazolo[4,3-h]-1,7-naphthyridin-3-amine (8-1) as a pale yellow solid.

MS (M+H)+: observed=407.1974, calculated=407.1984

Scheme 9

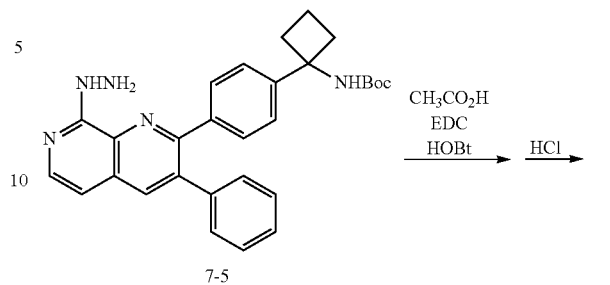

1-[4-(3-methyl-8-phenyl[1,2,4]triazolo[4,3-h]-1,7-naphthyridin-9-yl)phenyl]cyclobutanamine (9-1)

To a mixture of tert-butyl {1-[4-(8-hydrazino-3-phenyl-1,7-naphthyridin-2-yl)phenyl]cyclobutyl}carbamate (7-5) (30 mg, 0.0620 mmol), acetic acid (11.2 mg, 0.187 mmol), HOBt (19.1 mg, 0.125 mmol) and DIPEA (0.044 mL, 0.249 mmol) in NMP (2 mL) was added EDC (219 mg, 0.125 mmol). The mixture was stirred at room temperature for 30 min and then at 100° C. for 72 hours. The mixture was diluted with AcOEt, washed with water, dried over sodium sulfate, filtered, and concentrated in vacuo. The residue was purified by silica gel chromatography. HCl in MeOH was added to the residue and the mixture was heated in a microwave reactor at 80° C. for 5 minutes. The solvent was evaporated and the residue was purified by reverse phase HPLC (H₂O/0.1% TFA aq.-MeCN/0.1% TFA aq.) to give 1-[4-(3-methyl-8-phenyl[1,2,4]triazolo[4,3-h]-1,7-naphthyridin-9-yl)phenyl]cyclobutanamine (9-1) as a pale yellow solid.

MS (M+H)+: observed=406.2028, calculated=406.2032

The following compounds were prepared in a similar fashion to Examples from 2-1 to 2-7, but using the appropriate materials:

| # | Compound name | MS (M + H)+: observed | MS (M + H)+: calculated |
|---|---|---|---|
| 9-2 | 1-{4-[3-cyclopropyl-8-phenyl[1,2,4]triazolo[4,3-h]-1,7-naphthyridin-9-yl)phenyl}cyclobutanamine | 432 | 432 |
| 9-3 | 1-{4-[8-phenyl-3-(pyrimidin-2-yl)[1,2,4]triazolo[4,3-h]-1,7-naphthyridin-9-yl)phenyl}cyclobutanamine | 470 | 470 |

Scheme 10
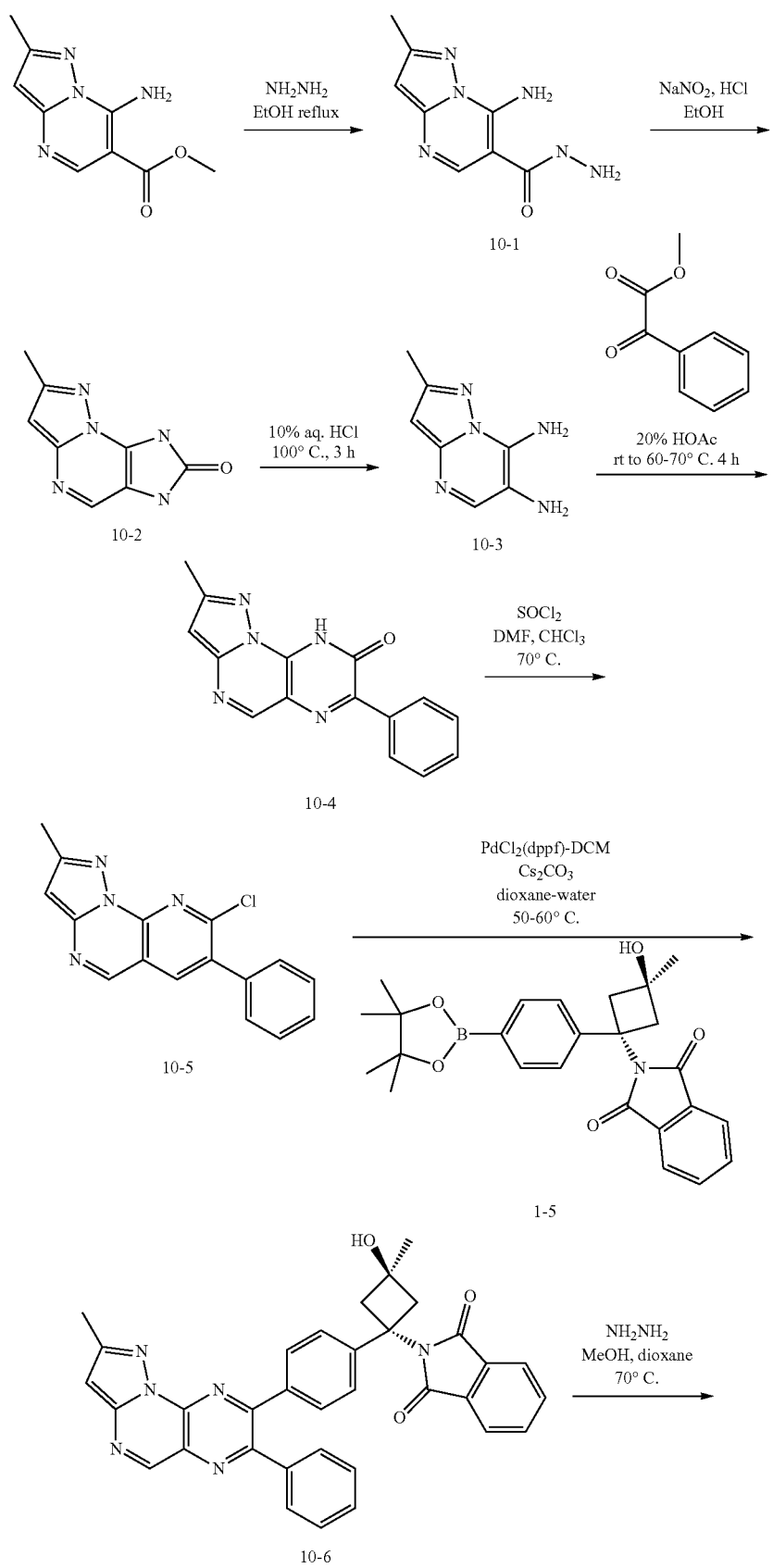

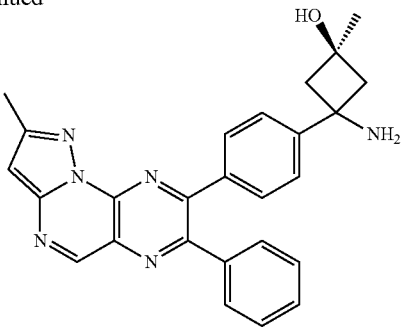

10-7 trans-3-hydroxy-3-methyl-1-[4-(2-methyl-7-phenylpyrazolo[1,5-a]pteridin-8-yl)phenyl]cyclobutan-amine (10-7)

7-Amino-2-methyl-pyrazolo[1,5-a]pyrimidine-6-carboxylic acid hydrazide (10-1)

A 250 mL flask containing the Methyl 7-amino-2-methylpyrazolo[1,5-a]pyrimidine-6-carboxylate (2.1 g, 20 mmol), EtOH (55 mL), and hydrazine hydrate (20 mL) was heated to reflux for 6 hours. The mixture was allowed to cool to room temperature. The precipitated solid was filtered and washed with water (2×10 mL) to provide Compound (10-1) as a white solid.

7-Methyl-1,3-dihydro-pyrazolo[5,1-b]purin-2-one (10-2)

A 100 mL flask containing Compound (10-1) (1.1 g, 5.0 mmol, 1 eq.), EtOH (25 mL), and 10% aqueous HCl (25 mL) was cooled to 0° C. by ice-water bath. Then NaNO$_2$ (0.35 g, 5.0 mmol, 1 eq.) in water (8 mL) was added slowly. The mixture was stirred at that temperature for 2 hours, after which it was heated to 80° C. for 2 hours. After cooling and removal of the volatiles by rotary evaporation, the residue was treated with water (40 mL). The resulting precipitated solid was filtered and washed with water (2×5 mL) to provide Compound (10-2) as a brownish solid.

2-Methyl-pyrazolo[1,5-a]pyrimidine-6,7-diamine (10-3)

A 40 mL scintillation vial containing Compound (10-2) (0.72 g, 3.8 mmol) and 10% aqueous HCl (25 mL) was heated at 100° C. for 3 hours. The mixture was allowed to cool, the solvent was removed in vacuo and water (~40 mL) was added. The resulting solid (starting material) was filtered to recover Compound (10-2). The filtrate was then concentrated and dried to furnish Compound (10-3) as a yellowish solid.

2-Methyl-7-phenyl-1,4,6,9,9b-pentaaza-cyclopenta[a]naphthalen-8-ol (10-4)

A 40-mL scintillation vial containing Compound (10-3) (320 mg, 2.0 mmol, 1 eq.), methyl phenylpyruvate (360 mg, 2.2 mmol, 1.1 eq.), and 20% AcOH (20 mL) was stirred at room temperature for 1.5 hours and at 65° C. for 4 hours. The mixture was allowed to cool and the precipitated solid was filtered and washed successively with water (15 mL) and Et$_2$O (2×10 mL). The solid was dried in vacuo to give Compound (10-4) as a yellowish solid.

8-Chloro-2-methyl-7-phenyl-1,4,6,9,9b-pentaaza-cyclopenta[a]naphthalene (10-5)

A 40 mL scintillation vial containing Compound (10-4) (220 mg, 0.8 mmol, 1 eq.), CHCl$_3$ (12 mL), DMF (12 mg, 0.16 mmol, 2 eq.), and SOCl$_2$ (0.56 g, 3.2 mmol, 4 eq.) was heated at 70° C. under nitrogen for 1.5 hours. Then the mixture was allowed to cool and the solvent was removed in vacuo. The residue was dissolved in CHCl$_3$ (20 mL) and washed with saturated NaHCO$_3$ (5 mL). The water solution was extracted with CHCl$_3$ (2×5 mL). The combined organic phases were dried over MgSO$_4$. After filtration and concentration, the residue was purified by silica gel chromatography using EtOAc and heptane as the mobile phases to furnish Compound (10-5) as a yellowish solid.

2-{3-Hydroxy-3-methyl-1-[4-(2-methyl-7-phenyl-1,4,6,9,9b-pentaaza-cyclopenta[a]naphthalen-8-yl)-phenyl]-cyclobutyl}-isoindole-1,3-dione (10-6)

A 20 mL scintillation vial containing Compound (10-5) (60 mg, 0.20 mmol, 1 eq.), Compound (1-5) (87 mg, 0.20 mmol, 1 eq.), Cs$_2$CO$_3$ (325 mg, 1.0 mmol, 5 eq.), dioxane (3.0 mL) and water (0.6 mL) was evacuated and flushed three times with nitrogen. Then PdCl$_2$(dppf)-CH$_2$Cl$_2$ (24 mg, 0.03 mmol, 0.15 eq.) was added and the resulting solution was evacuated and flushed three times with nitrogen. The mixture was heated at 55° C. for 90 minutes. The mixture was allowed to cool and the solvents removed in vacuo. The residue was dissolved in CH$_2$Cl$_2$ (10 mL). After filtration and concentration, it was purified by silica gel chromatography using MeOH and CH$_2$Cl$_2$ as the mobile phases to furnish Compound (10-6) as a yellowish solid.

trans-3-hydroxy-3-methyl-1-[4-(2-methyl-7-phenylpyrazolo[1,5-a]pteridin-8-yl)phenyl]cyclobutan-amine (10-7)

A 20 mL scintillation vial containing Compound (10-6) (82 mg, 0.145 mmol), MeOH (3 mL), dioxane (3 mL), and hydrazine (1 mL) was heated at 70° C. for 3 hours. Then the solvent was removed in vacuo. The residue was dissolved in 80% MeOH-water (7 mL, some $CH_2Cl_2$) and several drops of AcOH. Then it was purified by reverse-phase preparative HPLC using water-acetonitrile-AcOH [95:5:0.05] and acetonitrile-water-AcOH [95:5:0.05] as the mobile phases to provide Compound (10-7) as a yellow solid.

MS (M+H)+: observed=437.2091, calculated=437.209

Scheme 11

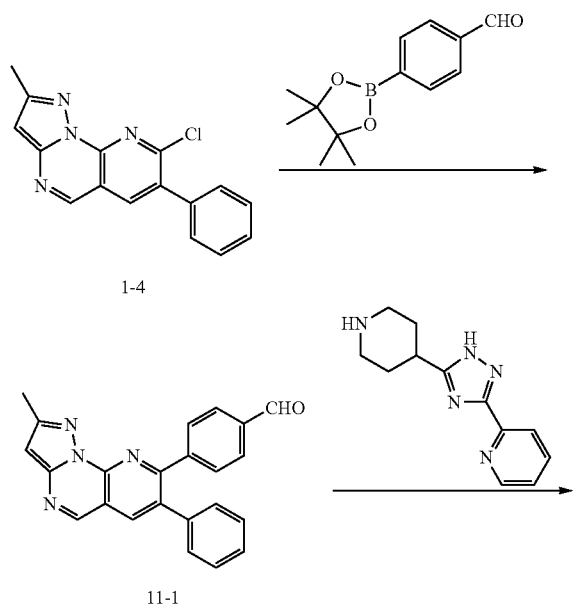

1-4

11-1

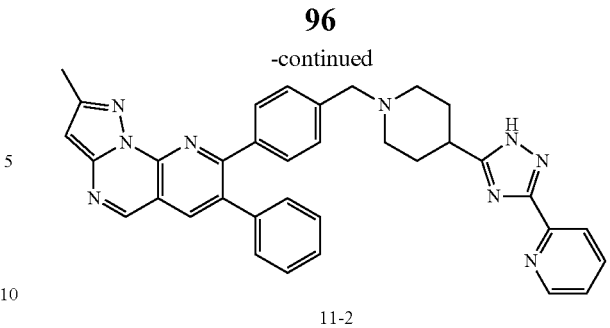

11-2

2-methyl-7-phenyl-8-(4-{[4-(5-pyridin-2-yl-4H-1,2,4-triazol-3-yl)piperidin-1-yl]methyl}phenyl)pyrazolo[1,5-a]pyrido[3,2-e]pyrimidine (11-2)

4-(2-methyl-7-phenylpyrazolo[1,5-a]pyrido[3,2-e]pyrimidin-8-yl)benzaldehyde (11-1)

Compound (11-1) was synthesized in a similar manner to the procedure for example (1-6), but using 4-(4,4,5,5-tetramethyl-1,3,2-dioxaborolan-2-yl)benzaldehyde as a starting material.

2-methyl-7-phenyl-8-(4-{[4-(5-pyridin-2-yl-4H-1,2,4-triazol-3-yl)piperidin-1-yl]methyl}phenyl)pyrazolo[1,5-a]pyrido[3,2-e]pyrimidine (11-2)

Compound (11-2) was synthesized in a similar manner to the procedure for example (1-7) in WO2006091395, but using 4-(2-methyl-7-phenylpyrazolo[1,5-a]pyrido[3,2-e]pyrimidin-8-yl)benzaldehyde (11-1) as a starting material.

MS (M+H)+: observed=578, calculated=578

The following compounds were prepared in a similar fashion to Example 11-2, but using the appropriate materials:

| # | Compound name | MS (M + H)+: observed | MS (M + H)+: calculated |
|---|---|---|---|
| 11-3 | 1'-[4-(2-methyl-7-phenylpyrazolo[1,5-a]pyrido[3,2-e]pyrimidin-8-yl)benzyl]-1H-spiro[furo[3,4-c]pyridine-3,4'-piperidin]-1-one | 553.2341 | 553.2352 |
| 11-4 | 2-methyl-1'-[4-(2-methyl-7-phenylpyrazolo[1,5-a]pyrido[3,2-e]primidin-8-yl)benzyl]spiro[isoindole-1,4'-piperidin]-3(2H)-one | 565.2701 | 565.2716 |
| 11-5 | 1'-[4-(2-methyl-7-phenylpyrazolo[1,5-a]pyrido[3,2-e]pyrimidin-8-yl)benzyl]-7H-spiro[furo[3,4-b]pyridine-5,4'-piperidin]-7-one | 553.2337 | 553.2352 |
| 11-6 | 1-[4-(2-methyl-7-phenylpyrazolo[1,5-a]pyrido[3,2-e]pyrimidin-8-yl)benzyl]piperidine-4-carboxamide | 477.2404 | 477.2403 |
| 11-7 | 2-methyl-8-(4-{[4-(2-oxo-2,3-dihydro-1H-benzimidazol-1-yl)piperidin-1-yl]methyl}phenyl)-7-phenylpyrazolo[1,5-a]pyrido[3,2-e]pyrimidine | 566.2670 | 566.2668 |
| 11-8 | 8-(4-{[4-(1,3-benzodioxol-5-ylmethyl)piperazin-1-yl]methyl}phenyl)-2-methyl-7-phenylpyrazolo[1,5-a]pyrido[3,2-e]pyrimidine | 569.2657 | 569.2665 |
| 11-9 | 2-methyl-7-phenyl-8-[4-(piperazin-1-ylmethyl)phenyl]pyrazolo[1,5-a]pyrido[3,2-e]primidine | 435.2302 | 435.2297 |
| 11-10 | 2-methyl-8-{4-[(4-methylpiperazin-1-yl)methyl]phenyl}-7-phenylpyrazolo[1,5-a]pyrido[3,2-e]pyrimidine | 449.2464 | 449.2454 |
| 11-11 | N-[4-(2-methyl-7-phenylpyrazolo[1,5-a]pyrido[3,2-e]pyrimidin-8-yl)benzyl]-2-(1-methylpyrrolidin-2-yl)ethanamine | 477.2774 | 477.2767 |

-continued

| # | Compound name | MS (M + H)+: observed | MS (M + H)+: calculated |
|---|---|---|---|
| 11-12 | 2-methyl-8-[4-(morpholin-4-ylmethyl)phenyl]-7-phenylpyrazolo[1,5-a]pyrido[3,2-e]pyrimidine | 436.2140 | 436.2137 |
| 11-13 | 3-{1-[4-(2-methyl-7-phenylpyrazolo[1,5-a]pyrido[3,2-e]pyrimidin-8-yl)benzyl]piperidin-4-yl}phenol | 526 | 526 |
| 11-14 | 1-[4-(2-methyl-7-phenylpyrazolo[1,5-a]pyrido[3,2-e]pyrimidin-8-yl)benzyl]piperidin-4-ol | 450 | 450 |
| 11-15 | 2-methyl-7-phenyl-8-[4-(piperidin-1-ylmethyl)phenyl]pyrazolo[1,5-a]pyrido[3,2-e]pyrimidine | 434 | 434 |
| 11-16 | 1-{4-[4-(2-methyl-7-phenylpyrazolo[1,5-a]pyrido[3,2-e]pyrimidin-8-yl)benzyl]piperazin-1-yl}ethanone | 477 | 477 |
| 11-17 | 1-[4-(2-methyl-7-phenylpyrazolo[1,5-a]pyrido[3,2-e]pyrimidin-8-yl)benzyl]piperidin-4-amine | 449 | 449 |
| 11-18 | 1-{1-[4-(2-methyl-7-phenylpyrazolo[1,5-a]pyrido[3,2-e]pyrimidin-8-yl)benzyl]piperidin-4-yl}-1,3-dihydro-2H-benzimidazol-2-one | 566 | 566 |
| 11-19 | 4-hydroxy-N-{1-[4-(2-methyl-7-phenylpyrazolo[1,5-a]prido[3,2-e]pyrimidin-8-yl)benzyl]piperidin-4-yl}benzamide | 569 | 569 |

Scheme 12

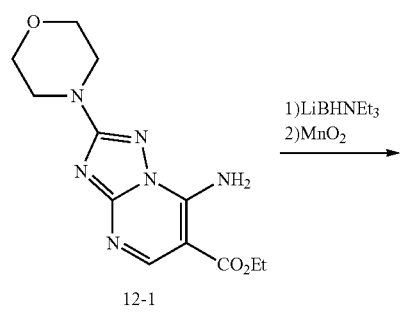

12-1

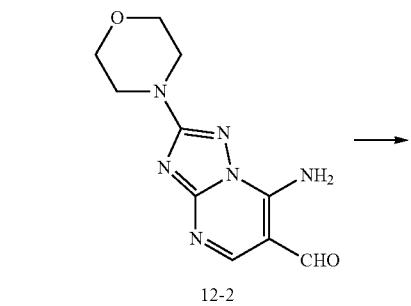

12-2

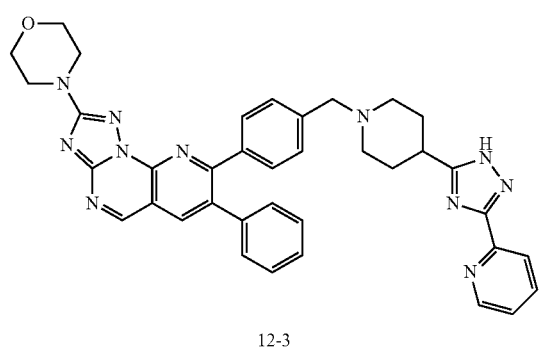

12-3

2-morpholin-4-yl-7-phenyl-8-(4-{[4-(5-pyridin-2-yl-4H-1,2,4-triazol-3-yl)piperidin-1-yl]methyl}phenyl)pyrido[3,2-e][1,2,4]triazolo[1,5-a]pyrimidine (12-3)

7-amino-2-(morpholin-4-yl)[1,2,4]triazolo[1,5-a]pyrimidine-6-carbaldehyde (12-2)

Compound (12-2) was synthesized in a similar manner to the procedure for example (1-1) and (1-2), but using ethyl 7-amino-2-(morpholin-4-yl)[1,2,4]triazolo[1,5-a]pyrimidine-6-carboxylate (12-1) as a starting material.

2-morpholin-4-yl-7-phenyl-8-(4-{[4-(3-pyridin-2-yl-1H-1,2,4-triazol-5-yl)piperidin-1-yl]methyl}phenyl)pyrazolo[1,5-a]pyrido[3,2-e]pyrimidine (12-3)

Compound (12-3) was synthesized in a similar manner to the procedure for example (1-4), (1-5) and (1-7) in WO2006091395, but using 7-amino-2-(morpholin-4-yl)[1,2,4]triazolo[1,5-a]pyrimidine-6-carbaldehyde (12-2) as a starting material.

MS (M+H)$^+$: observed=650, calculated=650.

Scheme 13

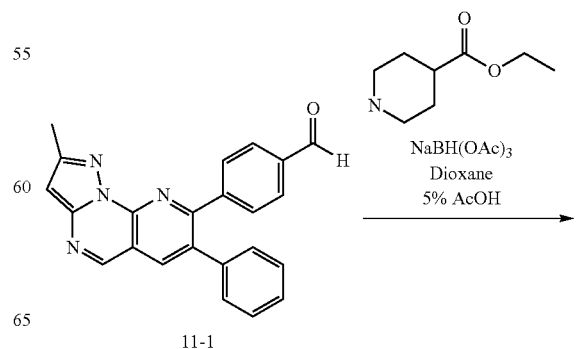

11-1

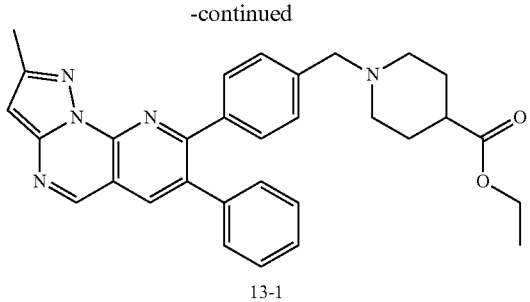

Ethyl 1-[4-(2-methyl-7-phenylpyrazolo[1,5-a]pyrido[3,2-e]pyrimidin-8-yl)benzyl]piperidine-4-carboxylate (13-1)

Compound (11-1) (1.28 g, 3.51 mmol, 1.0 eq) was dissolved in dioxane (38 mL, anhydrous). Ethyl isonipecotate (1.66 g, 10.5 mmol, 3.0 eq), glacial acetic acid (1.90 mL), and NaBH(OAc)$_3$ (2.98 g, 14.1 mmol, 4.0 eq) were added and the reaction stirred at room temperature for 24 hours. The crude reaction was neutralized with NaHCO$_3$ (aq.) and extracted with CHCl$_3$ (×3). The combined organics were dried with brine and Na$_2$SO$_4$, and then concentrated in vacuo. The residue was purified by silica gel chromatography by eluting with a gradient of heptane and EtOAc (20% to 100% EtOAc) to afford Compound (13-1).

MS (M+H)$^+$: observed=506, calculated=506

The following compounds were prepared in a similar fashion to Examples (11-2), but using the appropriate materials:

Methyl 1-[4-(2-methyl-7-phenylpyrazolo[1,5-a]pyrido[3,2-e]pyrimidin-8-yl)benzyl]piperidine-4-carboxylate (13-2)

MS (M+H)$^+$: observed=492, calculated=492.

Scheme 14

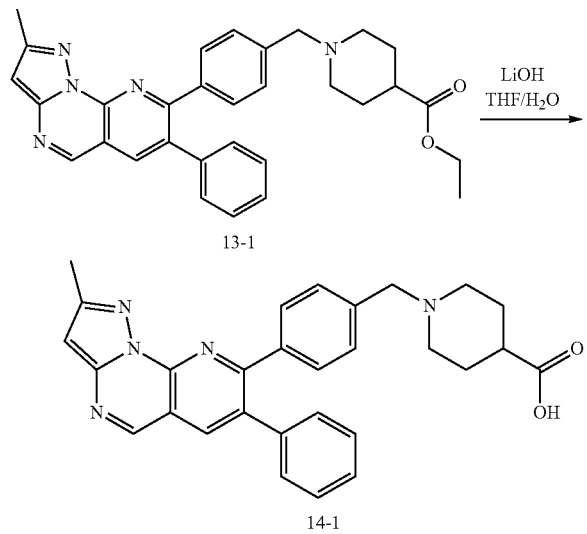

1-[4-(2-methyl-7-phenylpyrazolo[1,5-a]pyrido[3,2-e]pyrimidin-8-yl)benzyl]piperidine-4-carboxylic acid (14-1)

Compound (13-1) (1.78 g, 3.52 mmol, 1.0 eq) was dissolved in THF (35 mL) and then added H$_2$O (35 mL) and LiOH (178 mg, 10% w/w). The reaction was stirred at room temperature for 20 hours. After that time, the THF was removed in vacuo, and the remaining solvent was diluted with additional water and the pH adjusted to 7 with dilute HCl (5% aq). The mixture was extracted with CHCl$_3$/MeOH (4:1, ×5). The combined organic phases were dried with brine and Na$_2$SO$_4$, and then concentrated onto Celite in vacuo. The material was purified by silica gel chromatography by eluting with a gradient of CHCl$_3$ to CHCl$_3$/MeOH (1:1) to give Compound (14-1).

MS (M+H)+: observed=478.2239, calculated=478.2243

Scheme 15

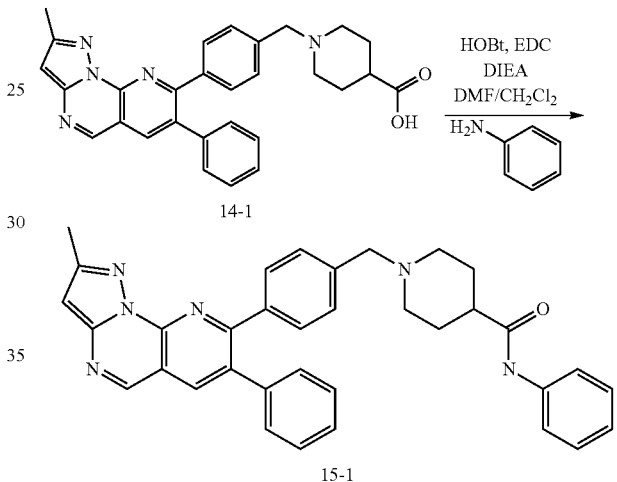

2-methyl-7-phenyl-8-(4-{[4-(phenylcarbamoyl)piperidin-1-yl]methyl}phenyl)pyrazolo[1,5-a]pyrido[3,2-e]pyrimidine (15-1)

Compound (14-1) (20 mg, 0.042 mmol, 1.0 eq), HOBt (11 mg, 0.084 mmol, 2.0 eq), EDC (HCl salt, 12 mg, 0.063 mmol, 1.5 eq) and diisopropylethylamine (22 µL, 0.13 mmol, 3.0 eq) were dissolved in DMF (400 µL, anhydrous) and CH$_2$Cl$_2$ (400 µL, anhydrous). To this solution was added aniline (19 mg, 0.21 mmol, 5.0 eq) and the reaction stirred at room temperature for 16 hours. After that time water was added and the mixture extracted with CHCl$_3$ (×3). The combined organic phases were dried with brine and Na$_2$SO$_4$, and then concentrated in vacuo. The residue was purified by silica gel chromatography by eluting with a gradient of CHCl$_3$ to [CHCl$_3$/MeOH/NH$_4$OH 90:10:1]. The resulting solid was then dissolved in MeOH, added TFA (100 µL), and purified by reverse-phase chromatography (Solvent A H$_2$O/CH$_3$CN/TFA (95:5:0.05), Solvent B CH$_3$CN/H$_2$O/TFA (95:5:0.05)) with a gradient of 5% to 60% B over 5 minutes to give Compound (15-1)

MS (M+H)+: observed=553.2721, calculated=553.2716

The following compounds were prepared in a similar fashion to Example 15-1, but using the appropriate materials:

| # | Compound name | MS (M + H)+: observed | MS (M + H)+: calculated |
|---|---|---|---|
| 15-2 | 8-[4-({4-[(2-methoxyethyl)carbamoyl]piperidin-1-yl}methyl)phenyl]-2-methyl-7-phenylpyrazolo[1,5-a]pyrido[3,2-e]pyrimidine | 535.2823 | 535.2821 |
| 15-3 | 2-methyl-7-phenyl-8-(4-{[4-(prop-2-en-1-ylcarbamoyl)piperidin-1-yl]methyl}phenyl)pyrazolo[1,5-a]pyrido[3,2-e]pyrimidine | 517.2715 | 517.2716 |
| 15-4 | 8-{4-[(4-{[2-(dimethylamino)ethyl]carbamoyl}piperidin-1-yl)methyl]phenyl}-2-methyl-7-phenylpyrazolo[1,5-a]pyrido[3,2-e]pyrimidine | 548.3138 | 548.3138 |
| 15-5 | 8-{4-[(4-{[3-(1H-imidazol-1-yl)propyl]carbamoyl}piperidin-1-yl)methyl]phenyl}-2-methyl-7-phenylpyrazolo[1,5-a]pyrido[3,2-e]pyrimidine | 585.3079 | 585.3090 |
| 15-6 | 8-[4-({4-[(3,4-dimethoxybenzyl)carbamoyl]piperidin-1-yl}methyl)phenyl]-2-methyl-7-phenylpyrazolo[1,5-a]pyrido[3,2-e]pyrimidine | 627.3069 | 627.3084 |
| 15-7 | 2-methyl-8-{4-[(4-{[2-(1-methylpyrrolidin-2-yl)ethyl]carbamoyl}piperidin-1-yl)methyl]phenyl}-7-phenylpyrazolo[1,5-a]pyrido[3,2-e]pyrimidine | 588.3436 | 588.3451 |
| 15-8 | {1-[4-(2-methyl-7-phenylpyrazolo[1,5-a]pyrido[3,2-e]pyrimidin-8-yl)benzyl]piperidin-4-yl}(morpholin-4-yl)methanone | 547.2820 | 547.2821 |
| 15-9 | 8-[4-({4-[(1H-benzimidazol-2-ylmethyl)carbamoyl]piperidin-1-yl}methyl)phenyl]-2-methyl-7-phenylpyrazolo[1,5-a]pyrido[3,2-e]pyrimidine | 607.2919 | 607.2934 |
| 15-10 | N-[2-(1H-imidazol-5-yl)ethyl]-1-[4-(2-methyl-7-phenylpyrazolo[1,5-a]pyrido[3,2-e]pyrimidin-8-yl)benzyl]piperidine-4-carboxamide | 571.2922 | 571.2934 |
| 15-11 | 2-methyl-7-phenyl-8-{4-[(4-{[4-(pyrimidin-2-yl)piperazin-1-yl]carbonyl}piperidin-1-yl)methyl]phenyl}pyrazolo[1,5-a]pyrido[3,2-e]pyrimidine | 624.3198 | 624.3199 |
| 15-12 | 2-methyl-7-phenyl-8-(4-{[4-({4-[5-(trifluoromethyl)pyridin-2-yl]piperazin-1-yl}carbonyl)piperidin-1-yl]methyl}phenyl)pyrazolo[1,5-a]pyrido[3,2-e]pyrimidine | 691.3115 | 691.3121 |
| 15-13 | 2-methyl-7-phenyl-8-{4-[(4-{[4-(pyridin-2-yl)piperazin-1-yl]carbonyl}piperidin-1-yl)methyl]phenyl}pyrazolo[1,5-a]pyrido[3,2-e]primidine | 623.3250 | 623.3247 |
| 15-14 | 2-methyl-7-phenyl-8-{4-[(4-{[2-(pyridin-3-yl)ethyl]carbamoyl}piperidin-1-yl)methyl]phenyl}pyrazolo[1,5-a]pyrido[3,2-e]pyrimidine | 582.2991 | 582.2981 |
| 15-15 | 2-methyl-7-phenyl-8-[4-({4-[(pyridin-2-ylmethyl)carbamoyl]piperidin-1-yl}methyl)phenyl]pyrazolo[1,5-a]pyrido[3,2-e]pyrimidine | 568.2814 | 568.2825 |
| 15-16 | 2-methyl-7-phenyl-8-[4-({4-[(pyridin-4-ylmethyl)carbamoyl]piperidin-1-yl}methyl)phenyl]pyrazolo[1,5-a]pyrido[3,2-e]pyrimidine | 568.2813 | 568.2825 |
| 15-17 | 8-[4-({4-[(3-hydroxyphenyl)carbamoyl]piperidin-1-yl}methyl)phenyl]-2-methyl-7-phenylpyrazolo[1,5-a]pyrido[3,2-e]pyrimidine | 569.2659 | 569.2665 |
| 15-18 | 8-[4-({4-[(trans-4-hydroxycyclohexyl)carbamoyl]piperidin-1-yl}methyl)phenyl]-2-methyl-7-phenylpyrazolo[1,5-a]prido[3,2-e]pyrimidine | 575.3121 | 575.3134 |
| 15-19 | 8-{4-[(4-{[2-hydroxy-2-(3-hydroxyphenyl)ethyl]carbamoyl}piperidin-1-yl)methyl]phenyl}-2-methyl-7-phenylpyrazolo[1,5-a]pyrido[3,2-e]pyrimidine | 613.2937 | 613.2927 |
| 15-20 | 8-{4-[(4-{[2-(4-hydroxyphenyl)ethyl]carbamoyl}piperidin-1-yl)methyl]phenyl}-2-methyl-7-phenylpyrazolo[1,5-a]pyrido[3,2-e]pyrimidine | 597.2968 | 597.2978 |
| 15-21 | 8-[4-({4-[(3-hydroxy-4-methoxyphenyl)carbamoyl]piperidin-1-yl}methyl)phenyl]-2-methyl-7-phenylpyrazolo[1,5-a]pyrido[3,2-e]pyrimidine | 599.2769 | 599.2771 |

-continued

| # | Compound name | MS (M + H)+: observed | MS (M + H)+: calculated |
|---|---|---|---|
| 15-22 | 8-{4-[(4-{[2-(3,4-dihydroxyphenyl)ethyl]carbamoyl}piperidin-1-yl]methyl]phenyl}-2-methyl-7-phenylpyrazolo[1,5-a]pyrido[3,2-e]pyrimidine | 613.2919 | 613.2927 |
| 15-23 | 8-[4-({4-[(4-hydroxy-3-methoxybenzyl)carbamoyl]piperidin-1-yl}methyl)phenyl]-2-methyl-7-phenylpyrazolo[1,5-a]pyrido[3,2-e]pyrimidine | 613.2935 | 613.2927 |
| 15-24 | 8-[4-({4-[(3,4-dihydroxybenzyl)carbamoyl]piperidin-1-yl}methyl)phenyl]-2-methyl-7-phenylpyrazolo[1,5-a]pyrido[3,2-e]pyrimidine | 599.2765 | 599.2771 |
| 15-25 | 8-(4-{[4-(benzylcarbamoyl)piperidin-1-yl]methyl}phenyl)-2-methyl-7-phenylpyrazolo[1,5-a]pyrido[3,2-e]pyrimidine | 567.2863 | 567.2872 |
| 15-26 | 8-(4-({4-[benzyl(methyl)carbamoyl]piperidin-1-yl}methyl)phenyl)-2-methyl-7-phenylpyrazolo[1,5-a]pyrido[3,2-e]pyrimidine | 581.3017 | 581.3029 |
| 15-27 | 8-(4-{[4-(cyclohexylcarbamoyl)piperidin-1-yl]methyl}phenyl)-2-methyl-7-phenylpyrazolo[1,5-a]pyrido[3,2-e]pyrimidine | 559.3182 | 559.3185 |
| 15-28 | 8-[4-({4-[(1-methoxypropan-2-yl)carbamoyl]piperidin-1-yl}methyl)phenyl]-2-methyl-7-phenylpyrazolo[1,5-a]pyrido[3,2-e]pyrimidine | 549.2986 | 549.2978 |
| 15-29 | N-({1-[4-(2-methyl-7-phenylpyrazolo[1,5-a]pyrido[3,2-e]pyrimidin-8-yl)benzyl]piperidin-4-yl}carbonyl)glycinamide | 534.2619 | 534.2617 |
| 15-30 | 2-methyl-7-phenyl-8-[4-({4-[(2,2,2-trifluoroethyl)carbamoyl]piperidin-1-yl}methyl)phenyl]pyrazolo[1,5-a]pyrido[3,2-e]pyrimidine | 559.2425 | 559.2433 |
| 15-31 | 2-methyl-8-(4-{[4-(pentan-3-ylcarbamoyl)piperidin-1-yl]methyl}phenyl)-7-phenylpyrazolo[1,5-a]pyrido[3,2-e]pyrimidine | 547.3176 | 547.3185 |
| 15-32 | 8-(4-{[4-(tert-butylcarbamoyl)piperidin-1-yl]methyl}phenyl)-2-methyl-7-phenylpyrazolo[1,5-a]pyrido[3,2-e]pyrimidine | 533.3022 | 533.3029 |
| 15-33 | 2-methyl-7-phenyl-8-(4-{[4-(propylcarbamoyl)piperidin-1-yl]methyl}phenyl)pyrazolo[1,5-a]pyrido[3,2-e]pyrimidine | 519.2866 | 519.2872 |
| 15-34 | 2-methyl-8-(4-{[4-(methylcarbamoyl)piperidin-1-yl]methyl}phenyl)-7-phenylpyrazolo[1,5-a]pyrido[3,2-e]pyrimidine | 491.2564 | 491.2559 |
| 15-35 | 8-(4-{[4-(ethylcarbamoyl)piperidin-1-yl]methyl}phenyl)-2-methyl-7-phenylpyrazolo[1,5-a]pyrido[3,2-e]pyrimidine | 505.2716 | 505.2716 |
| 15-36 | 8-{4-[(4-{[4-(3-hydroxyphenyl)piperazin-1-yl]carbonyl}piperidin-1-yl)methyl]phenyl}-2-methyl-7-phenylpyrazolo[1,5-a]pyrido[3,2-e]primidine | 638.3219 | 638.3243 |
| 15-37 | 8-{4-[(4-{[(1S)-1-cyclohexylethyl]carbamoyl}piperidin-1-yl)methyl]phenyl}-2-methyl-7-phenylpyrazolo[1,5-a]pyrido[3,2-e]pyrimidine | 587.3493 | 587.3498 |
| 15-38 | 8-(4-{[4-(hexahydrocyclopenta[c]pyrrol-2(1H)-ylcarbonyl)piperidin-1-yl]methyl}phenyl)-2-methyl-7-phenylpyrazolo[1,5-a]pyrido[3,2-e]pyrimidine | 571.3176 | 571.3185 |
| 15-39 | 8-[4-({4-[ethyl(propan-2-yl)carbamoyl]piperidin-1-yl}methyl)phenyl]-2-methyl-7-phenylpyrazolo[1,5-a]pyrido[3,2-e]pyrimidine | 547.3185 | 547.3185 |
| 15-40 | 8-{4-[(4-{[(1S,2S)-2-hydroxycyclohexyl]carbamoyl}piperidin-1-yl)methyl]phenyl}-2-methyl-7-phenylpyrazolo[1,5-a]pyrido[3,2-e]pyrimidine | 575.3121 | 575.3134 |
| 15-41 | 8-[4-({4-[(2-hydroxyethyl)carbamoyl]piperidin-1-yl}methyl)phenyl]-2-methyl-7-phenylpyrazolo[1,5-a]pyrido[3,2-e]pyrimidine | 521.2653 | 521.2665 |
| 15-42 | 2-methyl-7-phenyl-8-[4-({4-[(tetrahydrofuran-2-ylmethyl)carbamoyl]piperidin-1-yl}methyl)phenyl]pyrazolo[1,5-a]pyrido[3,2-e]pyrimidine | 561.2966 | 561.2978 |
| 15-43 | 8-(4-{[4-(cyclobutylcarbamoyl)piperidin-1-yl]methyl}phenyl)-2-methyl-7-phenylpyrazolo[1,5-a]pyrido[3,2-e]pyrimidine | 531.2870 | 531.2872 |

-continued

| # | Compound name | MS (M + H)+: observed | MS (M + H)+: calculated |
|---|---|---|---|
| 15-44 | 2-methyl-7-phenyl-8-(4-{[4-(propan-2-ylcarbamoyl)piperidin-1-yl]methyl}phenyl)pyrazolo[1,5-a]pyrido[3,2-e]pyrimidine | 519.2874 | 519.2872 |
| 15-45 | N-({1-[4-(2-methyl-7-phenylpyrazolo[1,5-a]pyrido[3,2-e]pyrimidin-8-yl)benzyl]piperidin-4-yl}carbonyl)glycine | 535.2458 | 535.2458 |
| 15-46 | tert-butyl N-({1-[4-(2-methyl-7-phenylpyrazolo[1,5-a]pyrido[3,2-e]pyrimidin-8-yl)benzyl]piperidin-4-yl}carbonyl)glycinate | 591.3066 | 591.3084 |
| 15-47 | 8-[4-({4-[(4-hydroxyphenyl)carbamoyl]piperidin-1-yl}methyl)phenyl]-2-methyl-7-phenylpyrazolo[1,5-a]pyrido[3,2-e]pyrimidine | 569.2652 | 569.2665 |
| 15-48 | 8-[4-({4-[(3-carbamoylphenyl)carbamoyl]piperidin-1-yl}methyl)phenyl]-2-methyl-7-phenylpyrazolo[1,5-a]pyrido[3,2-e]pyrimidine | 596.2758 | 596.2774 |
| 15-49 | 8-[4-({4-[(3-methoxyphenyl)carbamoyl]piperidin-1-yl}methyl)phenyl]-2-methyl-7-phenylpyrazolo[1,5-a]pyrido[3,2-e]pyrimidine | 583.2826 | 583.2821 |
| 15-50 | 2-methyl-8-(4-{[4-({3-[(methylsulfonyl)amino]phenyl}carbamoyl)piperidin-1-yl]methyl}phenyl)-7-phenylpyrazolo[1,5-a]pyrido[3,2-e]pyrimidine | 646.2610 | 646.2600 |
| 15-51 | 8-[4-({4-[(3-cyanophenyl)carbamoyl]piperidin-1-yl}methyl)phenyl]-2-methyl-7-phenylpyrazolo[1,5-a]pyrido[3,2-e]pyrimidine | 578.2668 | 578.2668 |
| 15-52 | 8-[4-({4-[(3-fluorophenyl)carbamoyl]piperidin-1-yl}methyl)phenyl]-2-methyl-7-phenylpyrazolo[1,5-a]pyrido[3,2-e]pyrimidine | 571.2613 | 571.2622 |
| 15-53 | 8-[4-({4-[(2-hydroxyphenyl)carbamoyl]piperidin-1-yl}methyl)phenyl]-2-methyl-7-phenylpyrazolo[1,5-a]pyrido[3,2-e]pyrimidine | 569.2649 | 569.2665 |
| 15-54 | 8-[4-({4-[(4-carbamoylphenyl)carbamoyl]piperidin-1-yl}methyl)phenyl]-2-methyl-7-phenylpyrazolo[1,5-a]pyrido[3,2-e]pyrimidine | 596.2763 | 596.2774 |
| 15-55 | 2-methyl-7-phenyl-8-[4-({4-[(3-sulfamoylphenyl)carbamoyl]piperidin-1-yl}methyl)phenyl]pyrazolo[1,5-a]pyrido[3,2-e]pyrimidine | 632.2452 | 632.2444 |
| 15-56 | N-(1,1-dioxido-1-benzothiophen-6-yl)-1-[4-(2-methyl-7-phenylpyrazolo[1,5-a]pyrido[3,2-e]pyrimidin-8-yl)benzyl]piperidine-4-carboxamide | 641.2328 | 641.2335 |
| 15-57 | 3-aminobenzyl 1-[4-(2-methyl-7-phenylpyrazolo[1,5-a]pyrido[3,2-e]pyrimidin-8-yl)benzyl]piperidine-4-carboxylate | 583 | 583 |
| 15-58 | {1-[4-(2-methyl-7-phenylpyrazolo[1,5-a]pyrido[3,2-e]pyrimidin-8-yl)benzyl]piperidin-4-yl}(piperidin-1-yl)methanone | 545 | 545 |
| 15-59 | (1,1-dioxidothiomorpholin-4-yl){1-[4-(2-methyl-7-phenylpyrazolo[1,5-a]pyrido[3,2-e]pyrimidin-8-yl)benzyl]piperidin-4-yl}methanone | 595 | 595 |
| 15-60 | 1-[4-({1-[4-(2-methyl-7-phenylpyrazolo[1,5-a]pyrido[3,2-e]pyrimidin-8-yl)benzyl]piperidin-4-yl}carbonyl)piperazin-1-yl]ethanone | 588 | 588 |
| 15-61 | N-(3-chlorophenyl)-1-[4-(2-methyl-7-phenylpyrazolo[1,5-a]pyrido[3,2-e]pyrimidin-8-yl)benzyl]piperidine-4-carboxamide | 587 | 587 |
| 15-62 | (4-hydroxypiperidin-1-yl){1-[4-(2-methyl-7-phenylpyrazolo[1,5-a]pyrido[3,2-e]pyrimidin-8-yl)benzyl]piperidin-4-yl}methanone | 561 | 561 |
| 15-63 | N-cyclohexyl-N-methyl-1-[4-(2-methyl-7-phenylpyrazolo[1,5-a]pyrido[3,2-e]pyrimidin-8-yl)benzyl]piperidine-4-carboxamide | 573 | 573 |
| 15-64 | [4-(hydroxymethyl)piperidin-1-yl]{1-[4-(2-methyl-7-phenylpyrazolo[1,5-a]pyrido[3,2-e]pyrimidin-8-yl)benzyl]piperidin-4-yl}methanone | 575 | 575 |
| 15-65 | 4-tert-butyl-N-{1-[4-(2-methyl-7-phenylpyrazolo[1,5-a]pyrido[3,2-e]pyrimidin-8-yl)benzyl]piperidin-4-yl}benzamide | 609 | 609 |

-continued

| # | Compound name | MS (M + H)+: observed | MS (M + H)+: calculated |
|---|---|---|---|
| 15-66 | 1-(4-fluorophenyl)-3-{1-[4-(2-methyl-7-phenylpyrazolo[1,5-a]pyrido[3,2-e]pyrimidin-8-yl)benzyl]piperidin-4-yl}urea | 586 | 586 |
| 15-67 | 1-(4-tert-butylphenyl)-3-{1-[4-(2-methyl-7-phenylpyrazolo[1,5-a]pyrido[3,2-e]pyrimidin-8-yl)benzyl]piperidin-4-yl}urea | 624 | 624 |
| 15-68 | N-{1-[4-(2-methyl-7-phenylpyrazolo[1,5-a]pyrido[3,2-e]pyrimidin-8-yl)benzyl]piperidin-4-yl}benzamide | 553 | 553 |
| 15-69 | 1-{1-[4-(2-methyl-7-phenylpyrazolo[1,5-a]pyrido[3,2-e]pyrimidin-8-yl)benzyl]piperidin-4-yl}-3-phenylurea | 568 | 568 |
| 15-70 | N-(3-aminophenyl)-1-[4-(2-methyl-7-phenylpyrazolo[1,5-a]pyrido[3,2-e]pyrimidin-8-yl)benzyl]piperidine-4-carboxamide | 568 | 568 |
| 15-71 | N-[3-(hydroxymethyl)phenyl]-1-[4-(2-methyl-7-phenylpyrazolo[1,5-a]pyrido[3,2-e]pyrimidin-8-yl)benzyl]piperidine-4-carboxamide | 583 | 583 |
| 15-72 | 1-[4-(2-methyl-7-phenylpyrazolo[1,5-a]pyrido[3,2-e]pyrimidin-8-yl)benzyl]-N-[3-(methylsulfonyl)phenyl]piperidine-4-carboxamide | 631 | 631 |
| 15-73 | 1-[4-(2-methyl-7-phenylpyrazolo[1,5-a]pyrido[3,2-e]pyrimidin-8-yl)benzyl]-N-(3-oxo-1,3-dihydro-2-benzofuran-5-yl)piperidine-4-carboxamide | 609 | 609 |
| 15-74 | 1-[4-(2-methyl-7-phenylpyrazolo[1,5-a]pyrido[3,2-e]pyrimidin-8-yl)benzyl]-N-(1,3-thiazol-2-yl)piperidine-4-carboxamide | 560 | 560 |
| 15-75 | 1-[4-(2-methyl-7-phenylpyrazolo[1,5-a]pyrido[3,2-e]pyrimidin-8-yl)benzyl]-N-[3-(trifluoromethoxy)phenyl]piperidine-4-carboxamide | 637 | 637 |
| 15-76 | N-(1,3-benzothiazol-5-yl)-1-[4-(2-methyl-7-phenylpyrazolo[1,5-a]pyrido[3,2-e]pyrimidin-8-yl)benzyl]piperidine-4-carboxamide | 610 | 610 |

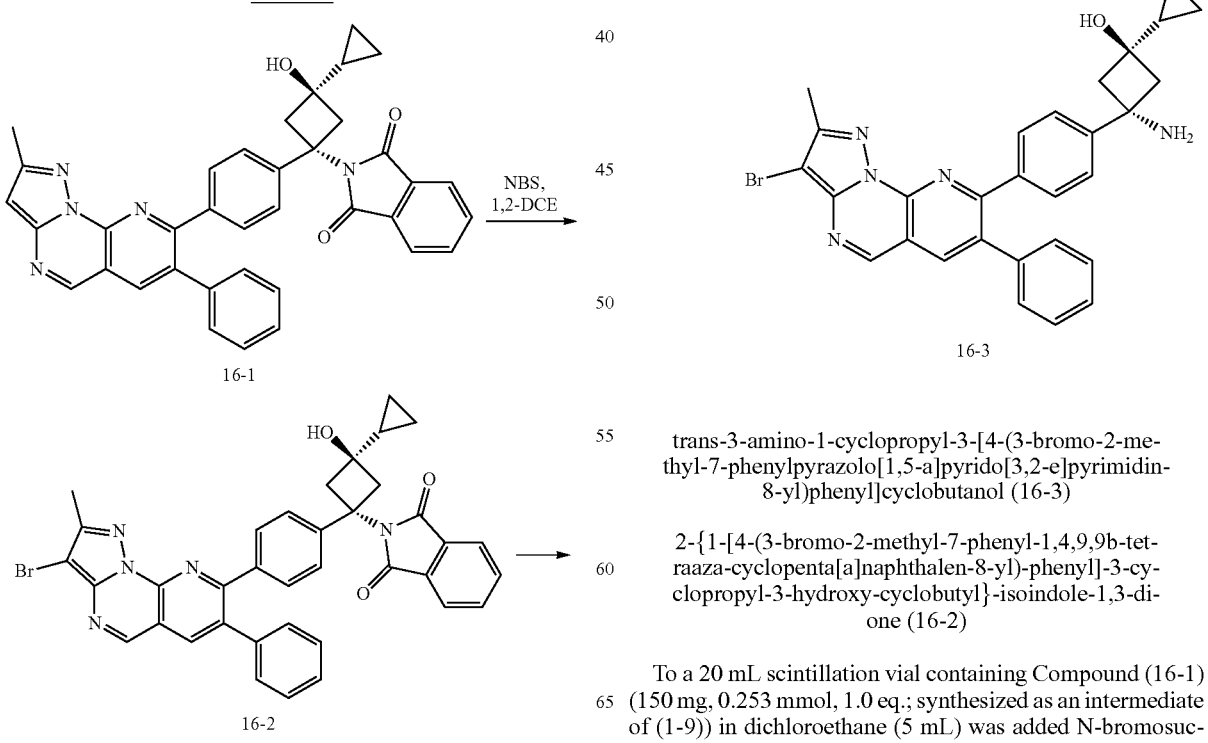

trans-3-amino-1-cyclopropyl-3-[4-(3-bromo-2-methyl-7-phenylpyrazolo[1,5-a]pyrido[3,2-e]pyrimidin-8-yl)phenyl]cyclobutanol (16-3)

2-{1-[4-(3-bromo-2-methyl-7-phenyl-1,4,9,9b-tetraaza-cyclopenta[a]naphthalen-8-yl)-phenyl]-3-cyclopropyl-3-hydroxy-cyclobutyl}-isoindole-1,3-dione (16-2)

To a 20 mL scintillation vial containing Compound (16-1) (150 mg, 0.253 mmol, 1.0 eq.; synthesized as an intermediate of (1-9)) in dichloroethane (5 mL) was added N-bromosuccinimide (54 mg, 0.305 mmol, 1.2 eq.). The mixture was stirred at room temperature for 25 minutes. The solvent was then evaporated under reduced pressure. The residue was dissolved in MeOH/CHCl₃ and purified by silica gel chromatography using CHCl₃ and MeOH [90:10] as the mobile phases to provide Compound (16-2) as a pale yellow solid.

trans-3-amino-1-cyclopropyl-3-[4-(3-bromo-2-methyl-7-phenylpyrazolo[1,5-a]pyrido[3,2-e]pyrimidin-8-yl)phenyl]cyclobutanol (16-3)

Compound (16-3) was prepared using a procedure similar to that of Compound (1-6) and (1-7).
MS (M+H)+: observed=540, 5420, calculated=540, 5420
The following compounds were prepared in a similar fashion to Examples 16-2 and 16-3, but using the appropriate materials:

| # | Compound name | MS (M + H)+: observed | MS (M + H)+: calculated |
|---|---|---|---|
| 16-4 | trans-3-amino-3-[4-(3-chloro-2-methyl-7-phenylpyrazolo[1,5-a]pyrido[3,2-e]pyrimidin-8-yl)phenyl]-1-cyclopropylcyclobutanol | 496 | 496 | trans-3-amino-1-cyclopropyl-3-{4-[2-methyl-7-phenyl-3-(pyridin-3-yl)pyrazolo[1,5-a]pyrido[3,2-e]pyrimidin-8-yl]phenyl}cyclobutanol (17-4)

3-Iodo-2-methyl-7-phenyl-1,4,9,9b-tetraaza-cyclopenta[a]naphthalen-8-ol (17-1)

To a solution of Compound (1-3) (0.2 g, 0.73 mmol, 1 eq.) in DMF (10 mL) was added N-iodosuccinimide (0.18 g, 0.8 mmol, 1.1 eq.) and the mixture stirred for 2 hours and concentrated. The residue was purified by silica gel chromatography using CHCl₃/MeOH (10%) as eluant to give Compound (17-1)

2-Methyl-7-phenyl-3-pyridin-3-yl-1,4,9,9b-tetraaza-cyclopenta[a]naphthalen-8-ol (17-2)

Compound (17-2) was prepared using a procedure similar to that of Compound (1-6).

8-Chloro-2-methyl-7-phenyl-3-pyridin-3-yl-1,4,9,9b-tetraaza-cyclopenta[a]naphthalene (17-3)

Compound (17-3) was prepared using a procedure similar to that of Compound (1-4).

Scheme 17

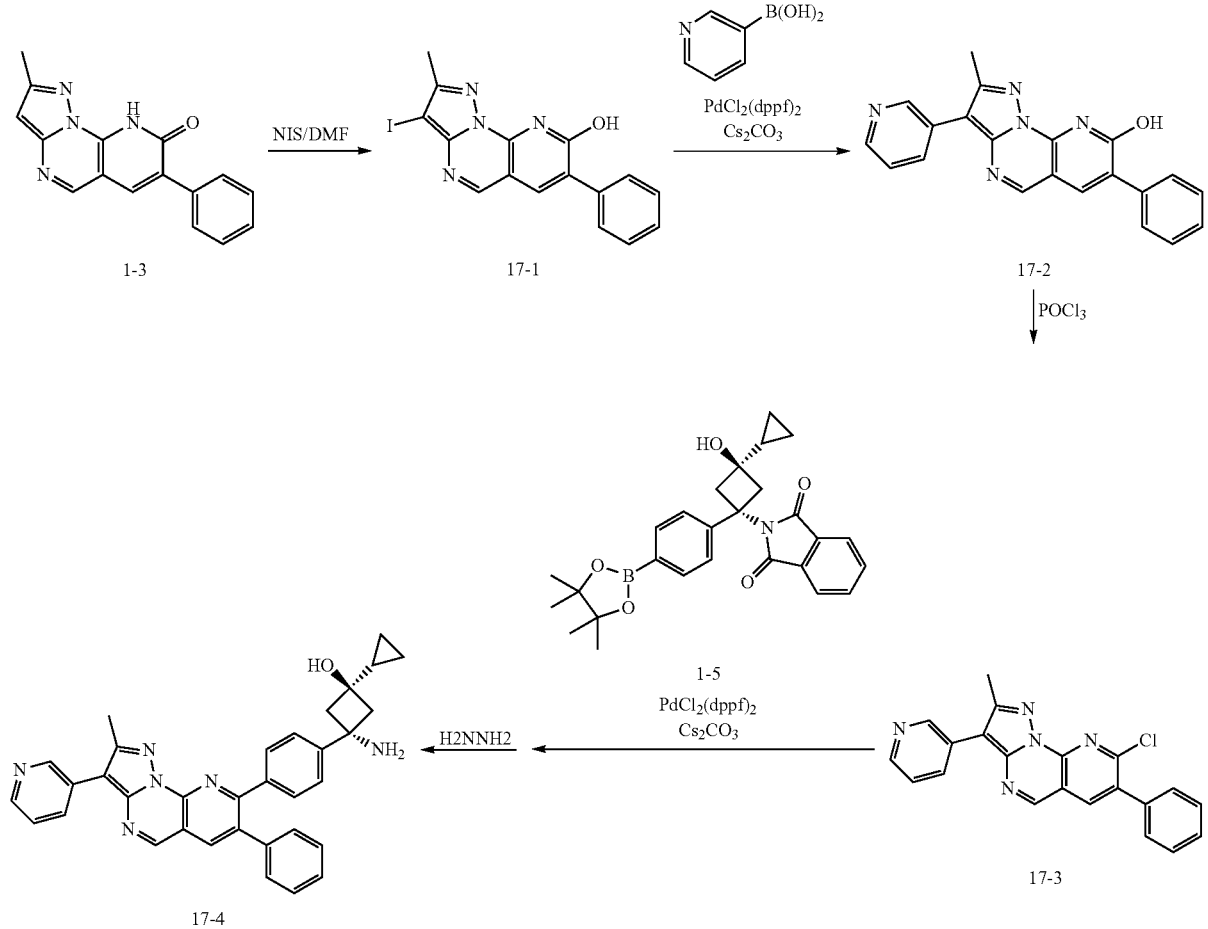

trans-3-amino-1-cyclopropyl-3-{4-[2-methyl-7-phenyl-3-(pyridin-3-yl)pyrazolo[1,5-a]pyrido[3,2-e]pyrimidin-8-yl]phenyl}cyclobutanol (17-4)

Compound (17-4) was prepared using a procedure similar to that of Compound (1-6) and (1-7). MS (M+H)+: observed=539.2549, calculated=539.2559.

trans-3-amino-1-cyclopropyl-3-[4-(3-cyano-2-methyl-7-phenylpyrazolo[1,5-a]pyrido[3,2-e]pyrimidin-8-yl)phenyl]cyclobutanol (17-5)

trans-3-amino-1-cyclopropyl-3-[4-(3-cyano-2-methyl-7-phenylpyrazolo[1,5-a]pyrido[3,2-e]pyrimidin-8-yl)phenyl]cyclobutanol (17-5) was prepared using a procedure similar to that of Compound (17-4). MS (M+H)+: observed=487.2253, calculated=487.2246

The following compounds were prepared in a similar fashion to Examples from 17-2 to 17-4 but using the appropriate materials:

8-[4-(trans-1-amino-3-cyclopropyl-3-hydroxycyclobutyl)phenyl]-2,3-dimethyl-7-phenylpyrazolo[1,5-a]pyrido[3,2-e]pyrimidine (18-1)

A 20 mL scintillation vial containing Compound (16-2) (12 mg, 0.03 mmol, 1 eq.), MeB(OH)$_2$ (50 mg, 0.30 mmol, 10 eq.), Cs$_2$CO$_3$ (96 mg, 0.30 mmol, 10 eq.), and dioxane (2 mL) was evacuated and flushed three times with nitrogen. Then, Pd(P-t-Bu$_3$)$_2$ (2.3 mg, 0.0045 mmol, 0.15 eq.) was added and the resulting solution was evacuated and flushed three times with nitrogen. The mixture was heated at 80° C. for 2 hours. Then it was allowed to cool and diluted with MeOH (2 mL). After filtration, the filtrate was purified by reverse-phase preparative HPLC using water-acetonitrile-TFA [95:5:0.05] and acetonitrile-water-TFA [95:5:0.05] as the mobile phases to provide Compound (18-1) as a yellow solid.

MS (M+H)+: observed=476.2461, calculated=476.2450

| # | Compound name | MS (M + H)+: observed | MS (M + H)+: calculated |
|---|---|---|---|
| 17-6 | trans-3-amino-1-cyclopropyl-3-{4-[2-methyl-7-phenyl-3-(pyridin-4-yl)pyrazolo[1,5-a]pyrido[3,2-e]pyrimidin-8-yl]phenyl}cyclobutanol | 539 | 539 |
| 17-7 | trans-3-amino-1-cyclopropyl-3-[4-(2-methyl-3,7-diphenylpyrazolo[1,5-a]pyrido[3,2-e]pyrimidin-8-yl)phenyl]cyclobutanol | 538 | 538 |
| 17-8 | trans-3-amino-1-cyclopropyl-3-{4-[3-(4-methoxyphenyl)-2-methyl-7-phenylpyrazolo[1,5-a]pyrido[3,2-e]pyrimidin-8-yl]phenyl}cyclobutanol | 568 | 568 |

Scheme 18

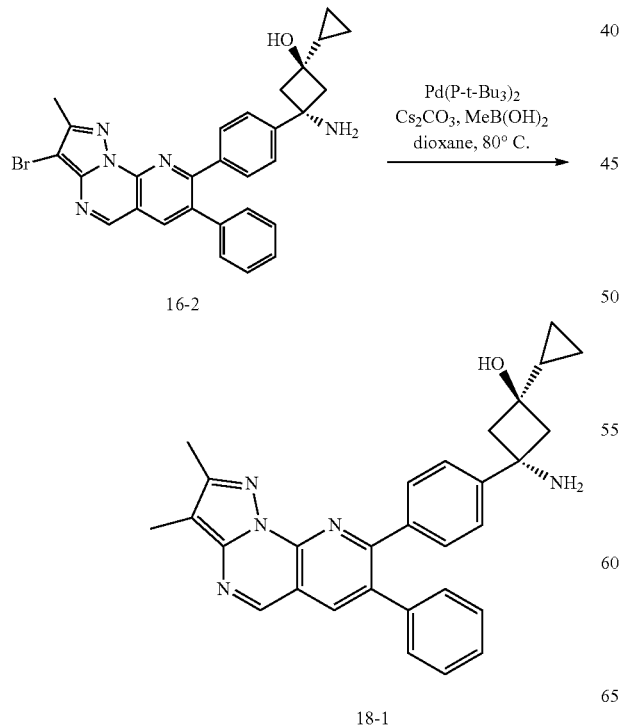

18-1

Scheme 19

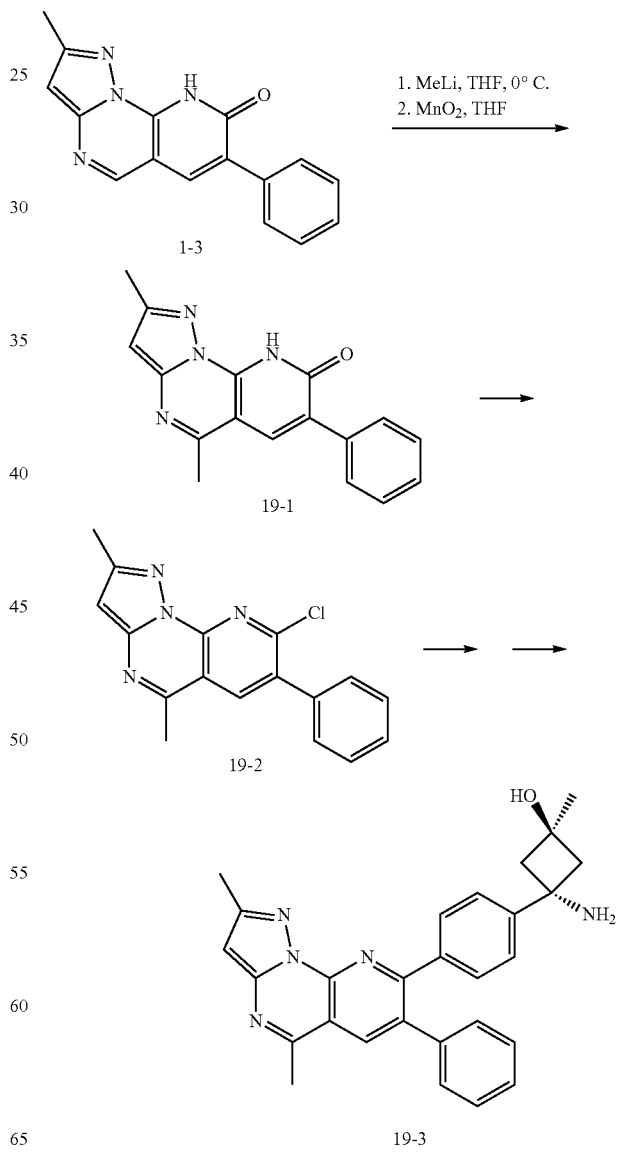

trans-3-amino-3-[4-(2,5-dimethyl-7-phenylpyrazolo[1,5-a]pyrido[3,2-e]pyrimidin-8-yl)phenyl]-1-methylcyclobutanol (19-3)

2,5-dimethyl-7-phenylpyrazolo[1,5-a]pyrido[3,2-e]pyrimidin-8(9H)-one (19-1)

In a 20 mL scintillation vial, Compound (1-3) (0.15 g, 0.543 mmol, 1.0 eq.) was dissolved in THF (10 mL). The solution was cooled to −78° C. and MeLi (15 mL of 1.6 M THF solution, 24 mmol, 44.19 eq.) was added dropwise and the reaction mixture was stirred for 16 hours at 0-20° C. The reaction mixture was carefully and slowly poured into ethyl acetate 20 (mL) and stirred for 10 minutes. The quenched reaction mixture was concentrated. The residue was treated with 100 mL of THF and the THF solution was separated from the solid by filtration. The organic solution was stirred with $MnO_2$ (0.47 g, 5.4 mmol, 10 eq.) for 4 hours at room temperature. The reaction was filtered and the solids washed with $CHCl_3$/MeOH (10%) (50 mL). The combined organic solution was concentrated and the crude was purified by silica gel chromatography using $CHCl_3$/MeOH (10%) as the eluant to give Compound (19-1).

8-chloro-2,5-dimethyl-7-phenylpyrazolo[1,5-a]pyrido[3,2-e]pyrimidine (19-2)

In a 20 mL scintillation vial Compound (19-1) (0.08 g, 0.275 mmol, 1.0 eq.) was heated with 2 mL of $POCl_3$ at 80° C. for 2 hours. The reaction was cooled and concentrated and the residue by silica gel chromatography using $CHCl_3$/MeOH (10%) as eluant to give Compound (19-2).

trans-3-amino-3-[4-(2,5-dimethyl-7-phenylpyrazolo[1,5-a]pyrido[3,2-e]pyrimidin-8-yl)phenyl]-1-methylcyclobutanol (19-3)

Compound (19-3) was prepared using procedures similar to those of Compound (1-6) and (1-7). MS (M+H)+: observed=450.2291, calculated=450.2294

Scheme 20

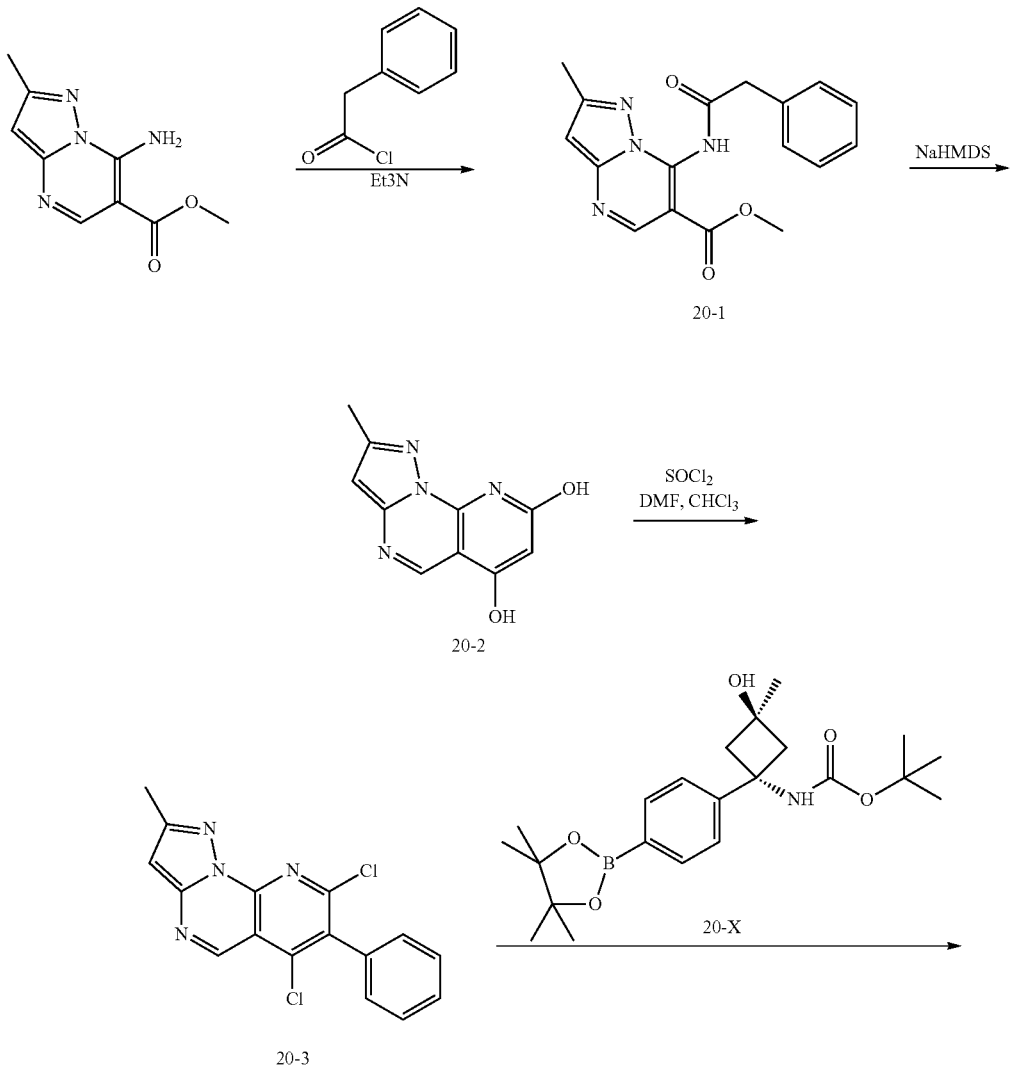

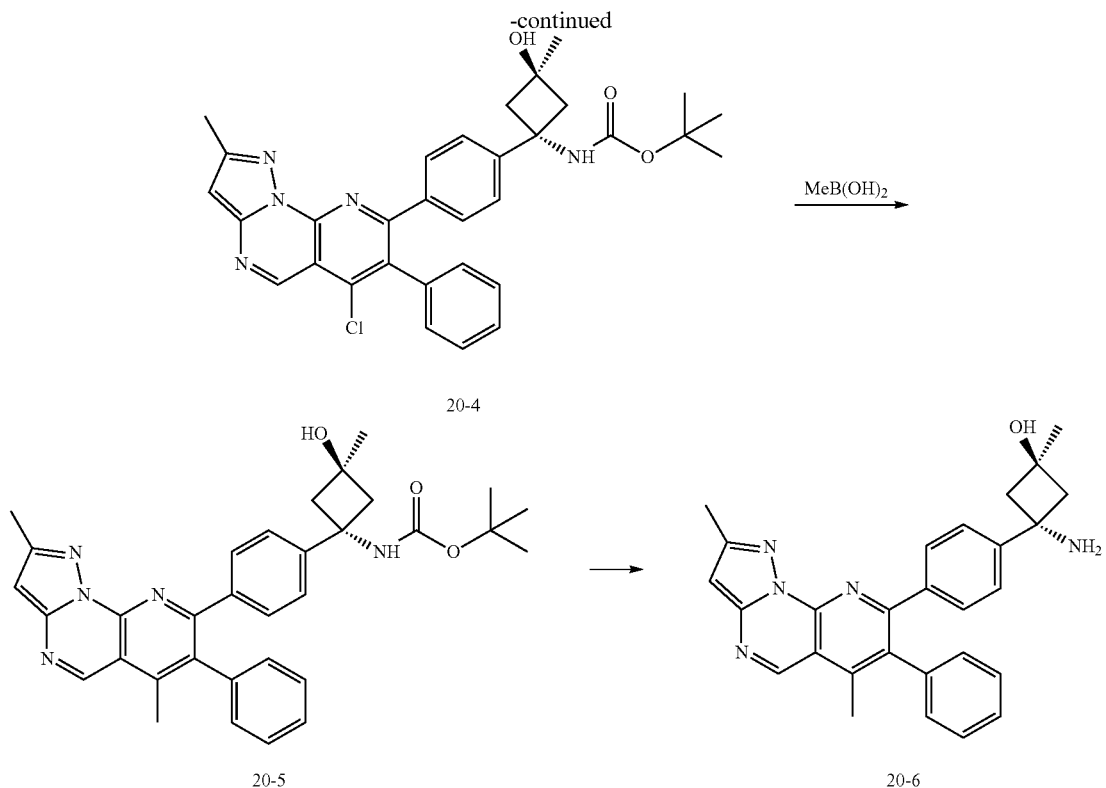

trans-3-amino-3-[4-(2,6-dimethyl-7-phenylpyrazolo[1,5-a]pyrido[3,2-e]pyrimidin-8-yl)phenyl]-1-methylcyclobutanol (20-6)

2-Methyl-7-phenylacetylamino-pyrazolo[1,5-a]pyrimidine-6-carboxylic acid methyl ester (20-1)

A 250 mL round-bottomed flask containing methyl 7-amino-2-methylpyrazolo[1,5-a]pyrimidine-6-carboxylate (1.10 g, 5.0 mmol, 1 eq.), CH$_2$Cl$_2$ (40 mL), and Et$_3$N (2.04 g, 20 mmol, 4 eq.) was added slowly phenylacetyl chloride (6.16 g, 40 mmol, 8 eq.). Then the mixture was heated at 80° C. for 4 h. The mixture was allowed to cool and the solvent was removed in vacuo. The residue was dissolved in CH$_2$Cl$_2$ (40 mL) and water (25 mL). The aqueous phase was extracted with CH$_2$Cl$_2$ (2×15 mL). The combined organic solution was dried over Na$_2$SO$_4$. After filtration and concentration, the residue was purified by silica gel chromatography using MeOH and CH$_2$Cl$_2$ as the mobile phases to furnish Compound (20-1) as a yellowish solid.

2-Methyl-1,4,9,9b-tetraaza-cyclopenta[a]naphthalene-6,8-diol (20-2)

A 250 mL round bottom flask containing Compound (20-1) (1.62 g, 5.0 mmol, 1 eq.), THF (30 mL), and NaHMDS (7.5 mL, 7.5 mmol, 1.5 eq.) was stirred at room temperature for 2 h. The reaction was treated with CH$_2$Cl$_2$ (30 mL) and water (40 mL). The aqueous phase was extracted with CH$_2$Cl$_2$ (2×15 mL). The water layer was acidified with concentrated HCl (~10 mL). The precipitated solid was filtered and washed with CH$_2$Cl$_2$ (4 mL) to furnish Compound (20-2) as a yellowish solid. The acidified water layer was extracted with 5% MeOH in CH$_2$Cl$_2$ (3×25 mL). The combined organic phases were dried over Na$_2$SO$_4$. After filtration and concentration, the residue was purified by silica gel chromatography using MeOH and CH$_2$Cl$_2$ as the mobile phases to furnish Compound (20-2) as a yellowish solid.

6,8-Dichloro-2-methyl-7-phenyl-1,4,9,9b-tetraaza-cyclopenta[a]naphthalene (20-3)

Compound (20-3) was prepared using procedures similar to those of Compound (1-4).

{1-[4-(6-Chloro-2-methyl-7-phenyl-1,4,9,9b-tetraaza-cyclopenta[a]naphthalen-8-yl)-phenyl]-3-hydroxy-3-methyl-cyclobutyl}-carbamic acid tert-butyl ester (20-4)

Compound (20-4) was prepared using procedures similar to those of Compound (1-5).

{1-[4-(2,6-Dimethyl-7-phenyl-1,4,9,9b-tetraaza-cyclopenta[a]naphthalen-8-yl)-phenyl]-3-hydroxy-3-methyl-cyclobutyl}-carbamic acid tert-butyl ester (20-5)

A 20 ml scintillation vial containing Compound (20-4) (40 mg, 0.07 mmol, 1 eq.), methylboronic acid (84 mg, 1.4 mmol, 2 eq.), Cs$_2$CO$_3$ (226 mg, 0.70 mmol, 1 eq.), and dioxane (5.0 ml) was evacuated and flushed three times with nitrogen. Then PdCl$_2$(dppf)-CH$_2$Cl$_2$ (24 mg, 0.03 mmol, 0.5 eq.) was added and the resulting solution was evacuated and flushed three times with nitrogen. The mixture was heated at 80° C. for 2.5 h. Then it was allowed to cool. The solvent was removed in vacuo. The residue was dissolved in CH$_2$Cl$_2$ (10 mL). After filtration and concentration, it was purified by silica gel chromatography by using MeOH and CH$_2$Cl$_2$ as the mobile phases to furnish Compound (20-5) as a yellowish solid.

trans-3-amino-3-[4-(2,6-dimethyl-7-phenylpyrazolo [1,5-a]pyrido[3,2-e]pyrimidin-8-yl)phenyl]-1-methylcyclobutanol (20-6)

Compound (20-6) was prepared using procedures similar to those of Compound (9-1). MS (M+H)+: observed=450, calculated=450 trans-3-amino-3-[4-(6-chloro-2-methyl-7-phenylpyrazolo[1,5-a]pyrido[3,2-e]pyrimidin-8-yl)phenyl]-1-methylcyclobutanol (20-7)

Compound (20-7) was prepared using procedures similar to those of Compound (9-1), but using Compound (20-4). MS (M+H)+: observed=470, calculated=470

Continuing Experimental Schemes and Compounds

7-Aryl-tetraaza- and 7-aryl-pentaaza-cyclopenta[a]napthalene Benzene Derivatives as Alai Allosteric Inhibitors

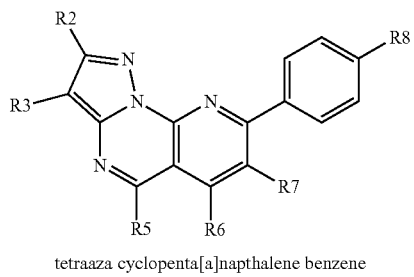

tetraaza cyclopenta[a]napthalene benzene

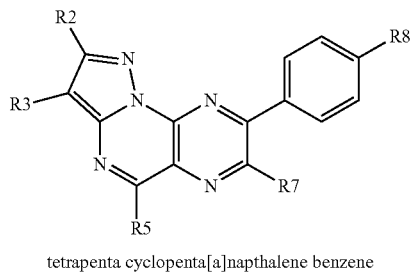

tetrapenta cyclopenta[a]napthalene benzene

Key Transformations
Synthesis of Pyridone Intermediate

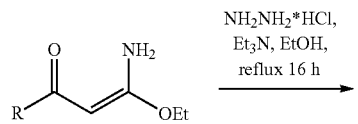

R = CF$_3$: XXIV

-continued

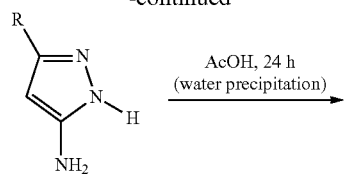

R = CF$_3$: XXV
R = cPr: VI

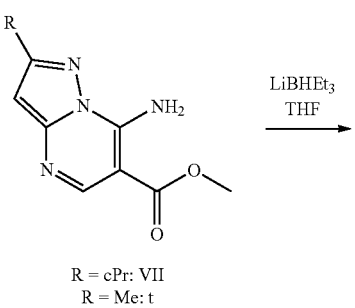

R = cPr: VII
R = Me: t

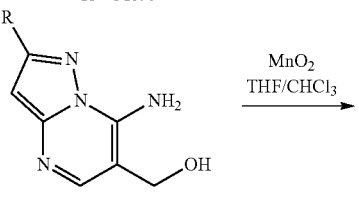

R = Me: II

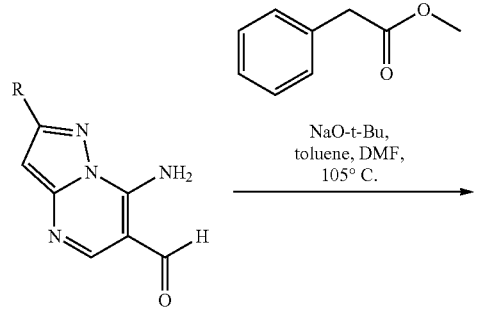

R = Me: III

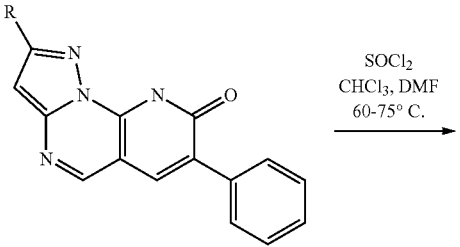

R = Me: IV

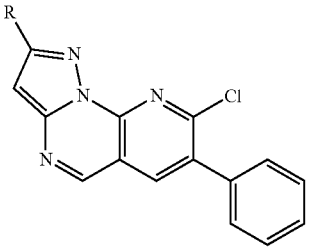

R = Me: V

Chlorination of Pyridone (SOCl₂ Procedure)
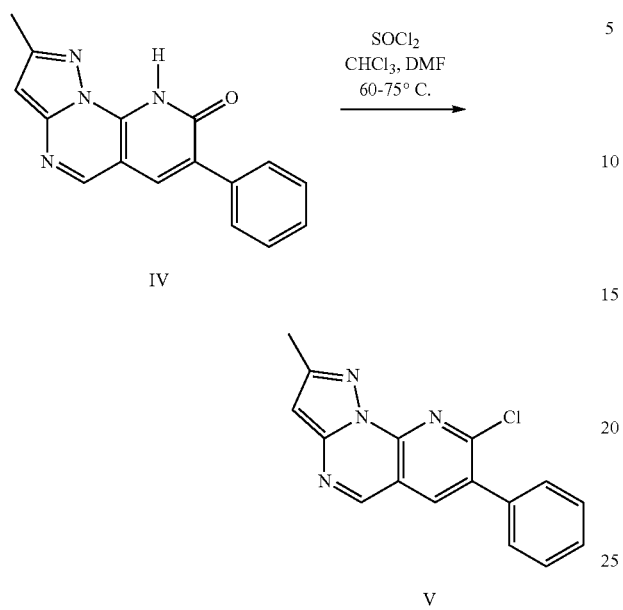
Chlorination of Pyridone (POCl₃ Procedure)
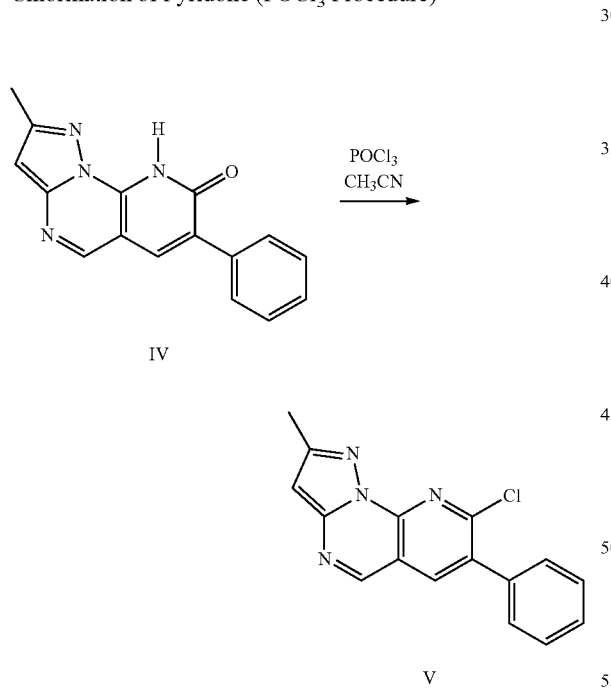
Synthesis of Cyclobutylamine Headgroup (Scheme VI)
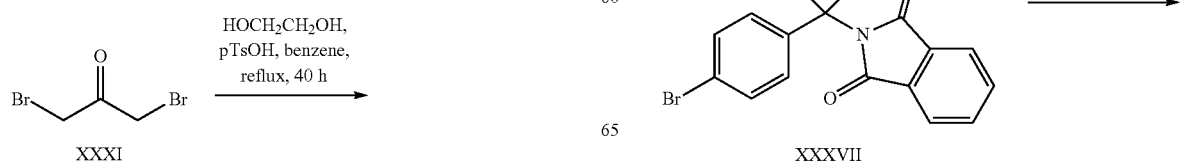
-continued
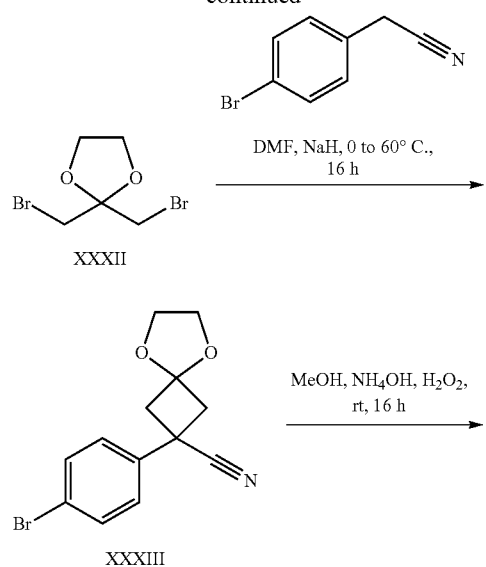
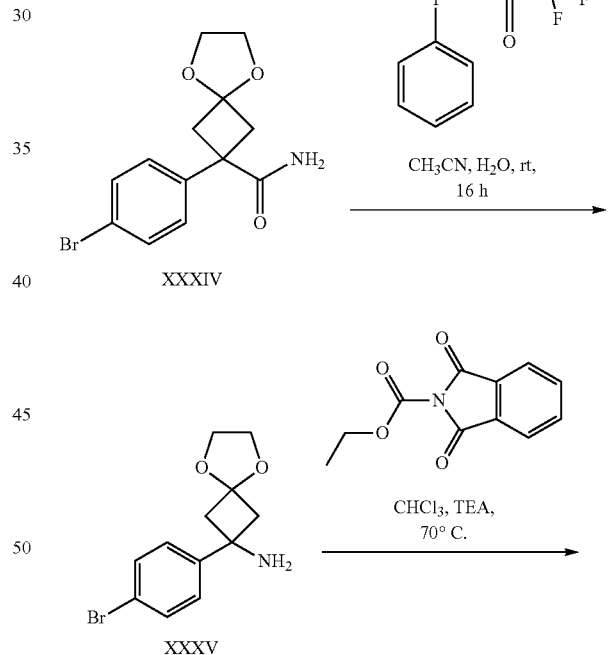

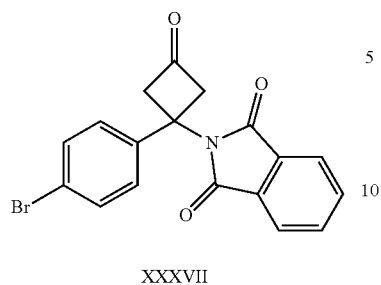
XXXVII
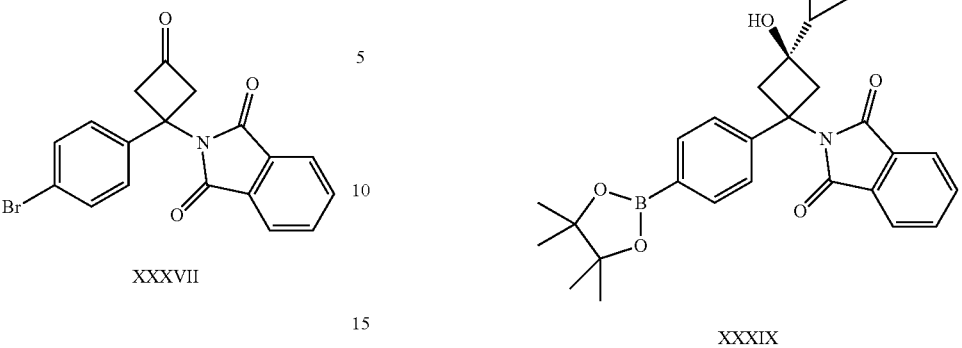
XXXIX
Conversion of Cyclobutanone to Alkylcyclobutanol (Scheme VII)
Suzuki (Pd Coupling) of Core Chloride to Headgroup Boronic Acid:
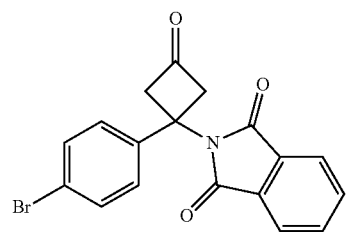
XXXVII
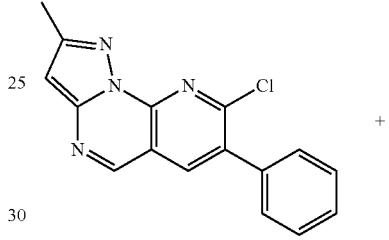
V
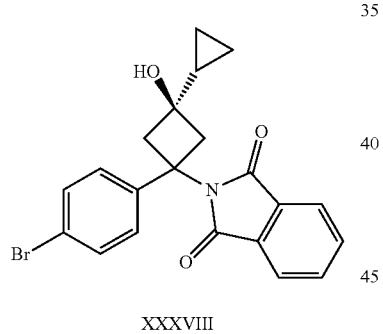
XXXVIII
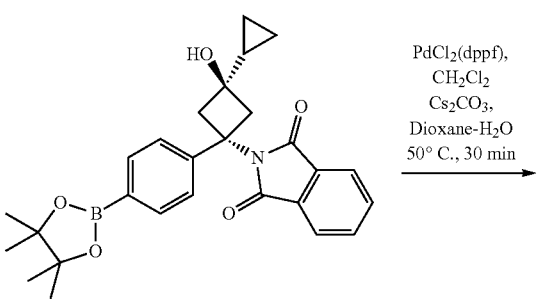
XXXIX
Br→B(OR)$_2$ Conversion
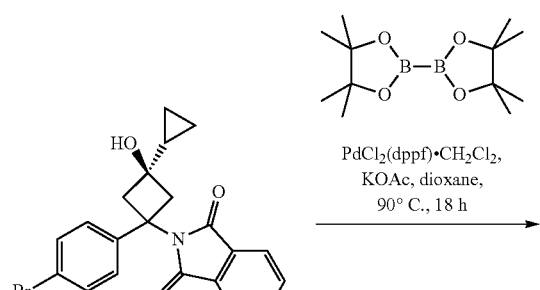
XXXVIII
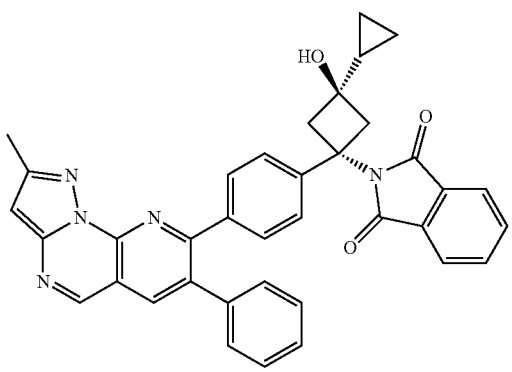
XL

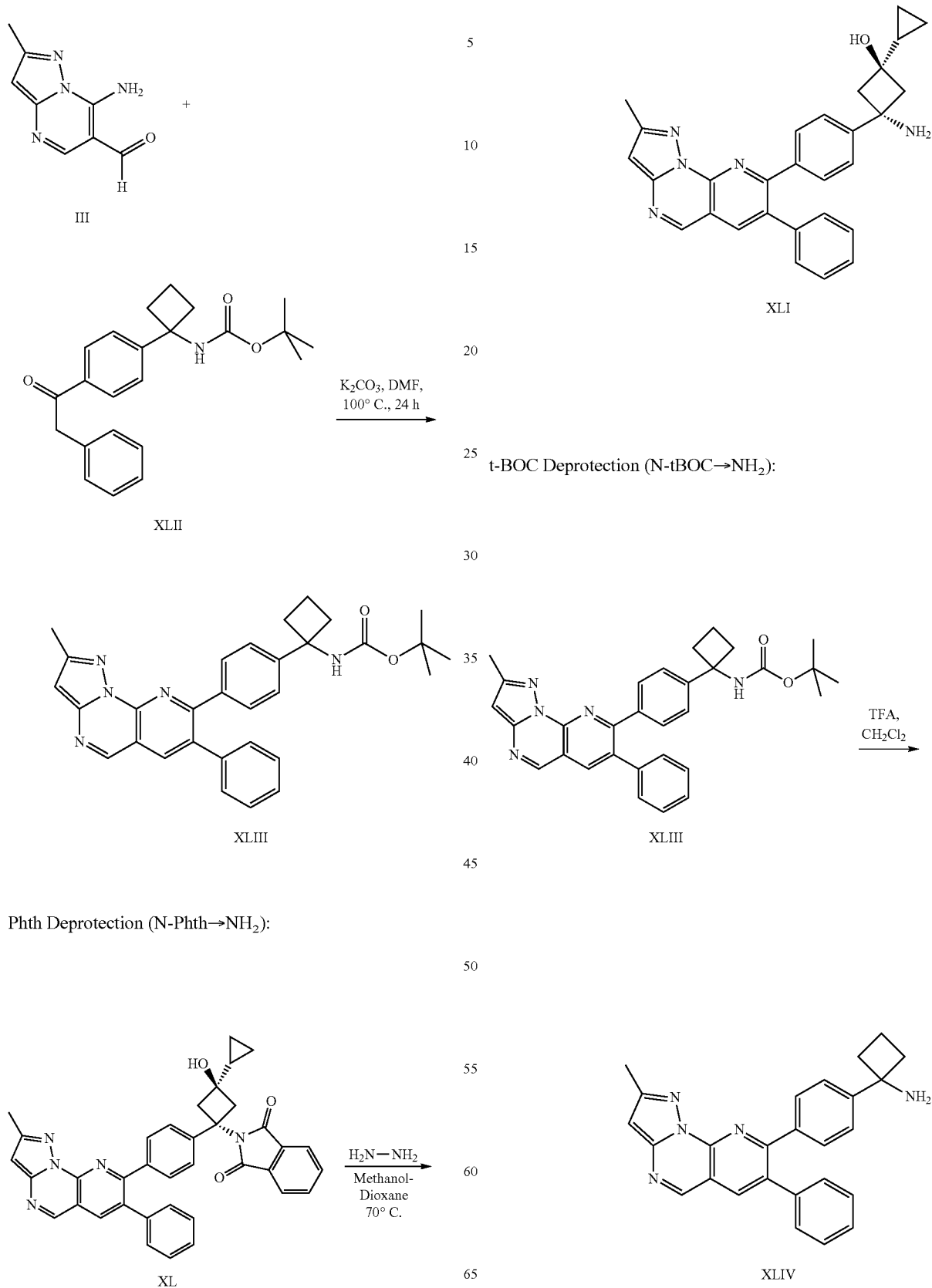

Scheme VIII-Iodination and coupling of pyridone
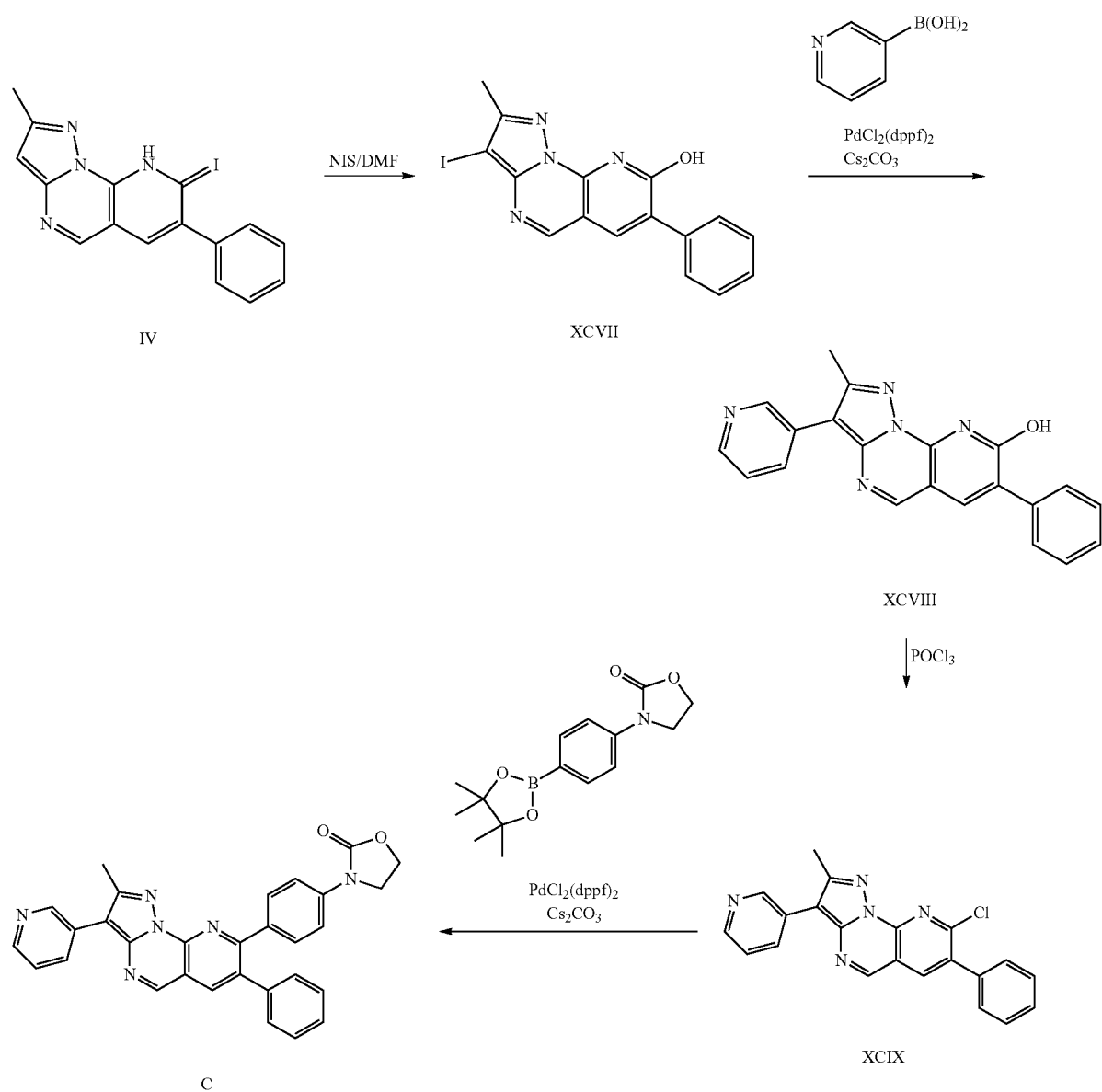
Bromination of 3-Position
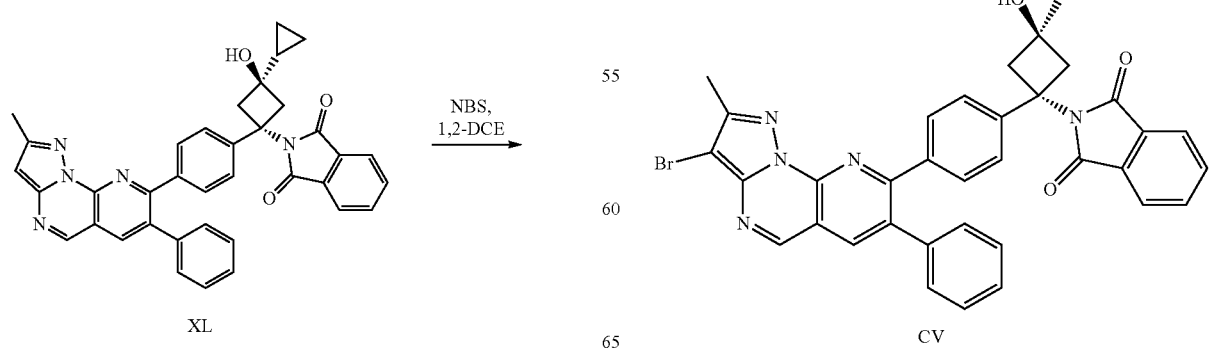
-continued Suzuki Reaction at the 3-Position
5-Methylation
Scheme IX - Synthesis of 4-piperidine carboxamides
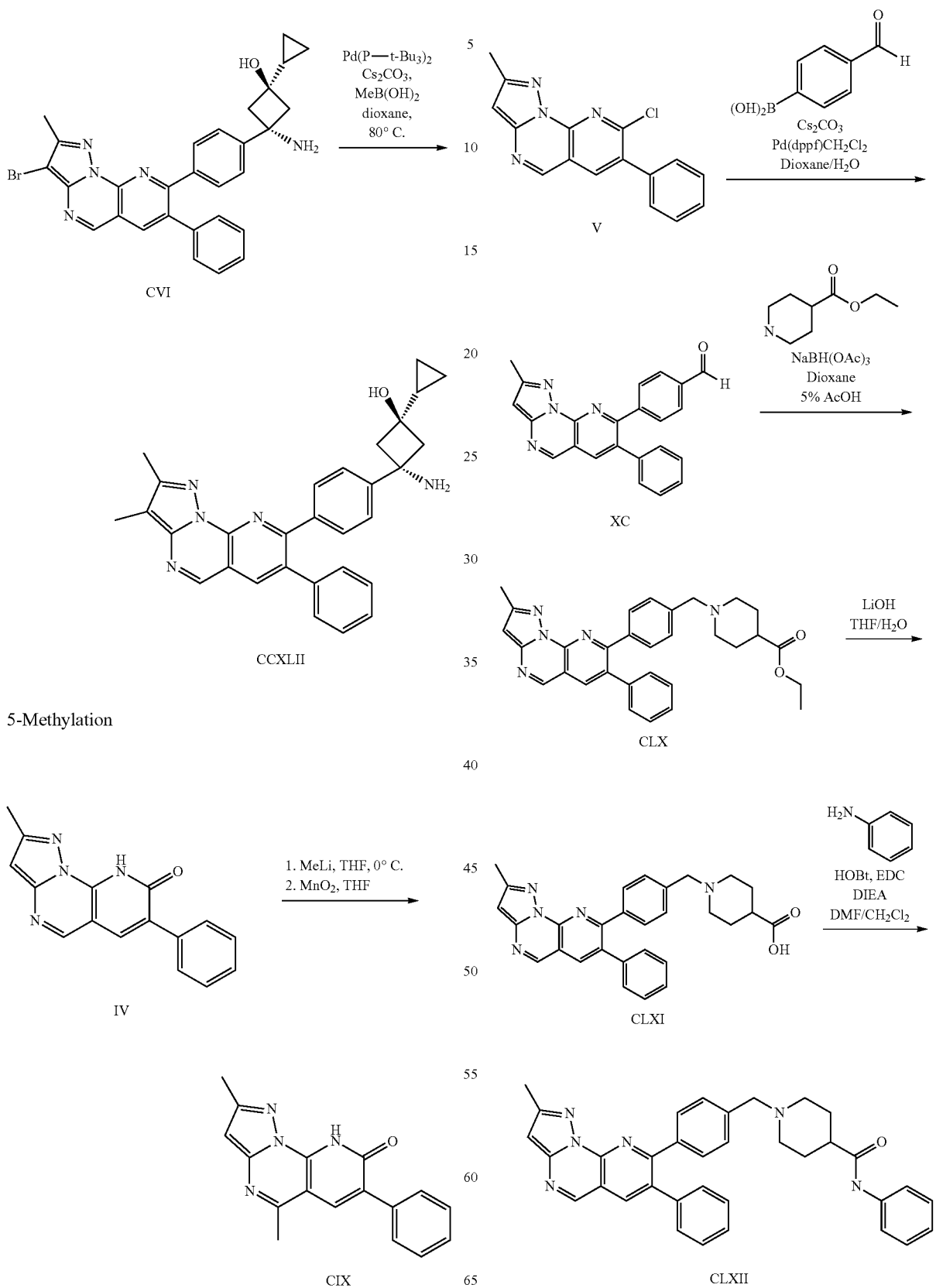

Scheme X - Synthesis of Pyridazine compound
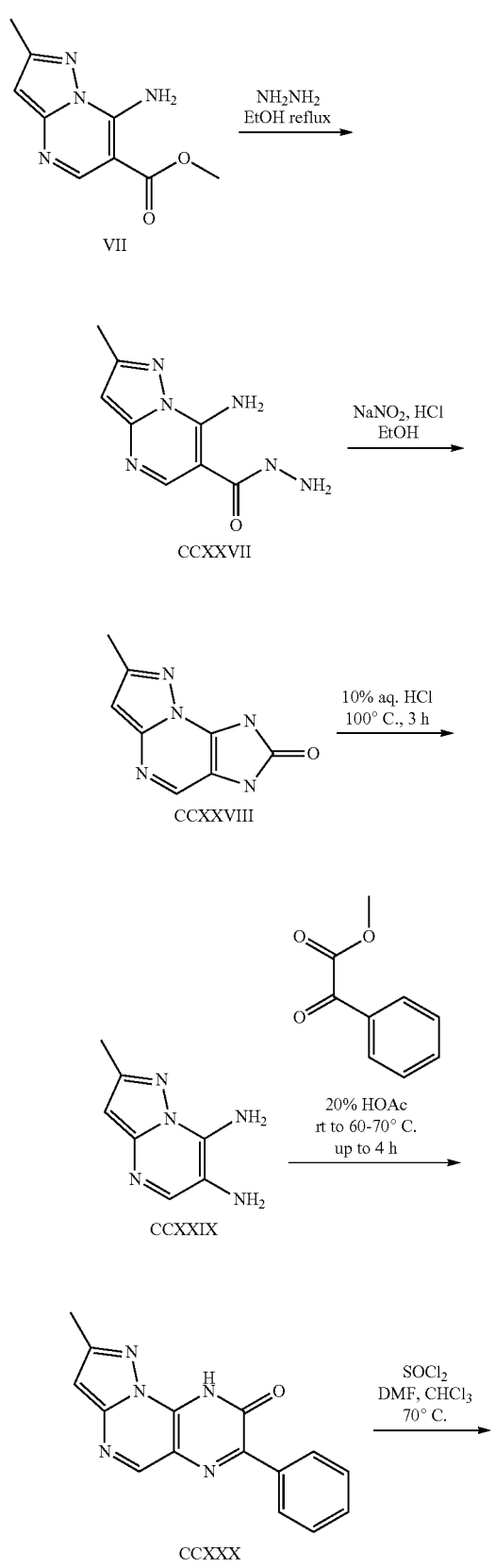
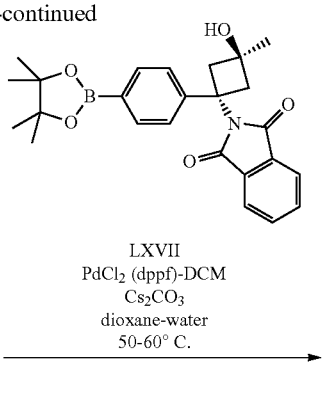
List of Key Reference Compounds for Experimental Procedures
2-Methyl-7-phenyl-9H-1,4,9,9b-tetraaza-cyclopenta[a]naphthalen-8-one [IV]
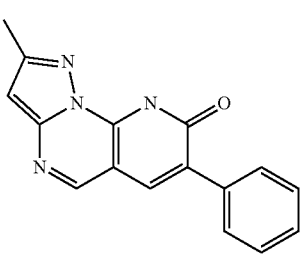

8-Chloro-2-methyl-7-phenyl-1,4,9,9b-tetraaza-cyclo-penta[a]naphthalene [V]

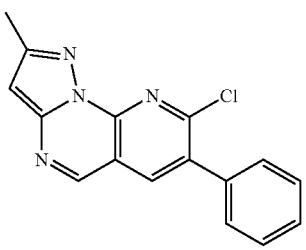

7-Amino-2-methyl-pyrazolo[1,5-a]pyrimidin-6-car-baldehyde [III]

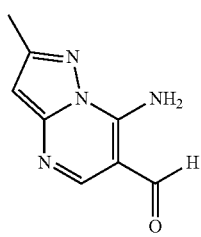

2-[1-(4-Bromo-phenyl)-3-oxo-cyclobutyl]-isoindole-1,3-dione [XXXVII]

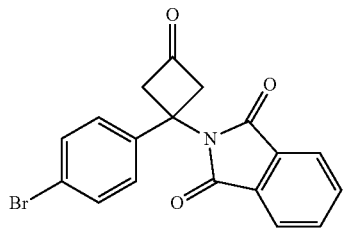

trans-2-{3-Cyclopropyl-3-hydroxy-1-[4-(4,4,5,5-tetramethyl-[1,3,2]dioxaborolan-2-yl)-phenyl]-cyclobutyl}-isoindole-1,3-dione [XXXIX]

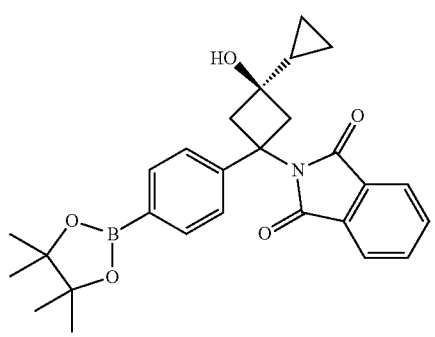

trans-2-[1-(4-Bromo-phenyl)-3-hydroxy-3-methyl-cyclobutyl]-isoindole-1,3-dione [LXVII]

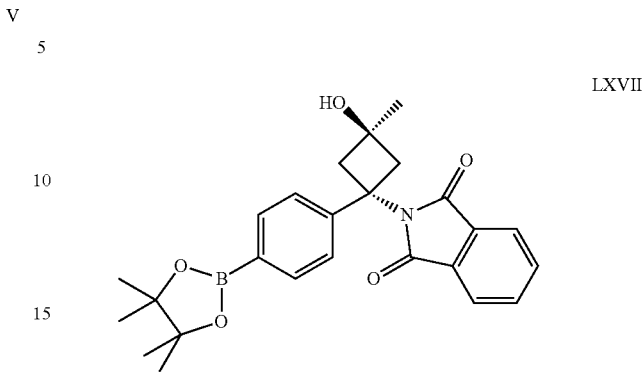

trans-3-Amino-1-cyclopropyl-3-[4-(2-methyl-7-phenyl-1,4,9,9b-tetraaza-cyclopenta[a]naphthalen-8-yl)-phenyl]-cyclobutanol [XLI]

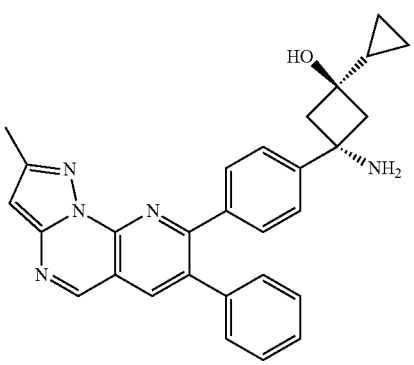

trans-3-Amino-t-methyl-3-[4-(2-methyl-7-phenyl-1,4,9,9b-tetraaza-cyclopenta[a]naphthalen-8-yl)-phenyl]-cyclobutanol [LXIX]

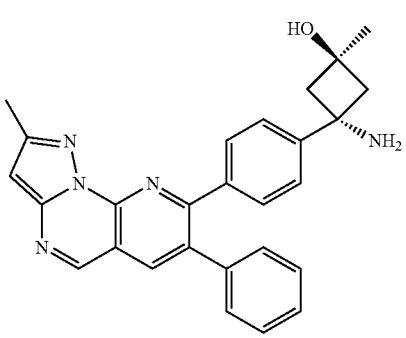

133 cis-3-Amino-1-methyl-3-[4-(2-methyl-7-phenyl-1,4,9,9b-tetraaza-cyclopenta[a]naphthalen-8-yl)-phenyl]-cyclobutanol [LXXII]

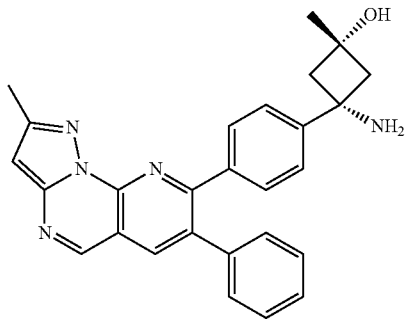

LXXII trans-3-Amino-1-cyclopropyl-3-[4-(2-cyclopropyl-7-phenyl-1,4,9,9b-tetraaza-cyclopenta[a]naphthalen-8-yl)-phenyl]-cyclobutanol [LXXIV]

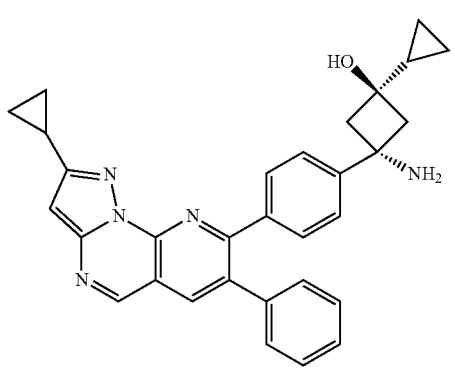

LXXIV trans-3-Amino-1-cyclopropyl-3-[4-(7-phenyl-1,4,9,9b-tetraaza-cyclopenta[a]naphthalen-8-yl)-phenyl]-cyclobutanol [LXXVI]

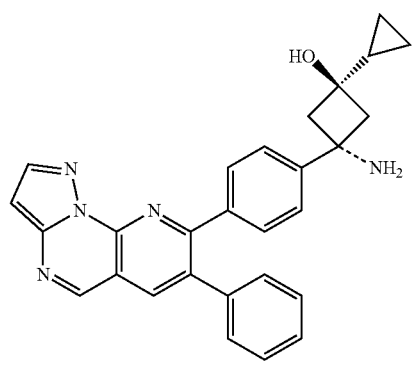

LXXVI

134 trans-3-Amino-1-Methyl-3-[4-(2-cyclopropyl-7-phenyl-4,4,9,9b-tetraaza-cyclopenta[a]naphthalen-8-yl)-phenyl]-cyclobutanol [CCXLIV]

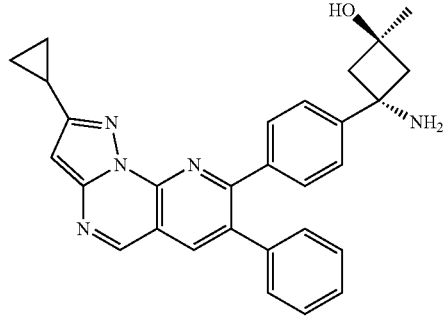

CCXLIV trans-3-Amino-4-cyclopropyl-3-[4-(2-(4-fluorophenyl)-7-phenyl-1,4,9,9b-tetraaza-cyclopenta[a]naphthalen-8-yl)-phenyl]-cyclobutanol [LXXVIII]

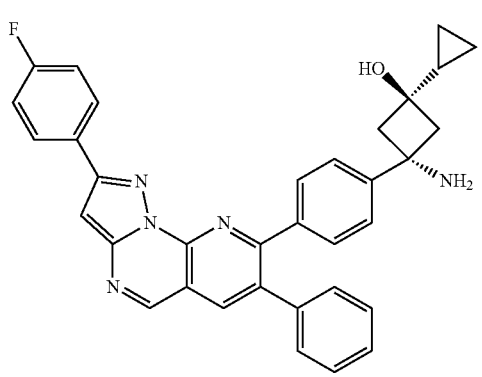

LXXVIII trans-3-Amino-1-cyclopropyl-3-[4-(2-trifluoromethyl-7-phenyl-1,4,9,9b-tetraaza-cyclopenta[a]naphthalen-8-yl)-phenyl]-cyclobutanol [LXXX]

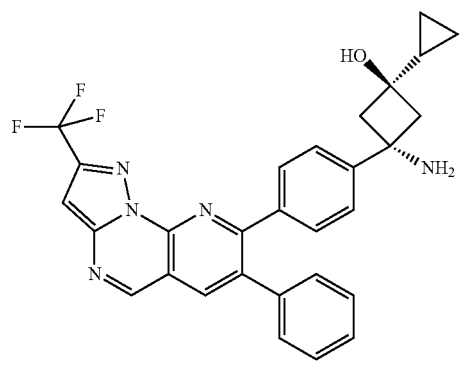

LXXX trans-3-Amino-1-methyl-3-[4-(2-t-butyl-7-phenyl-1,4,9,9b-tetraaza-cyclopenta[a]naphthalen-8-yl)-phenyl]-cyclobutanol [CCXLI]

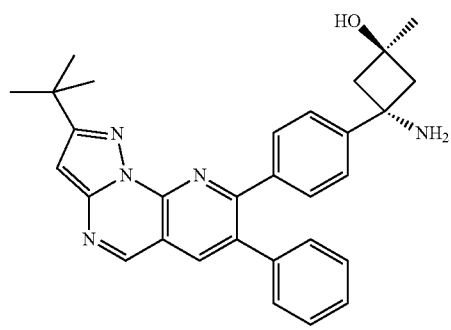

CCLXI trans-3-Amino-1-cyclopropyl-3-[4-(3-cyano-2-methyl-7-phenyl-1,4,9,9b-tetraaza-cyclopenta[a]naphthalen-8-yl)-phenyl]-cyclobutanol [CIV]

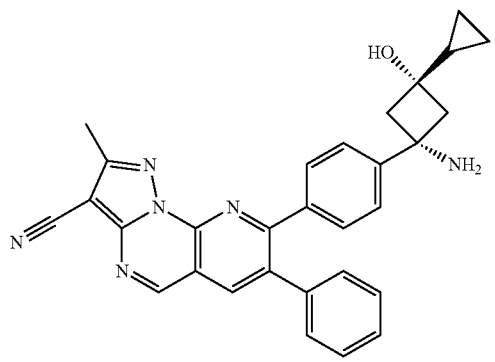

CIV

3-Amino-3-[4-(3-bromo-2-methyl-7-phenyl-1,4,9,9b-tetraaza-cyclopenta[a]naphthalen-8-yl)-phenyl]-cyclopropyl-cyclobutanol [CVI]

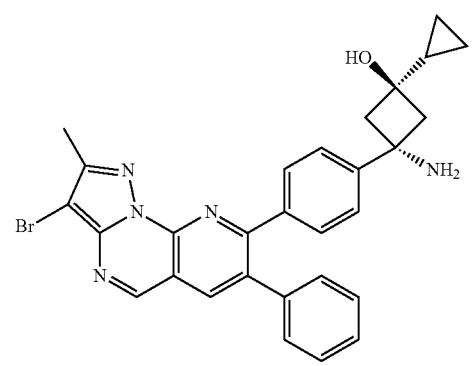

CVI

3-Amino-1-cyclopropyl-3-[4-(2,3-dimethyl-7-phenyl-1,4,6,9,9b-pentaaza-cyclopenta[a]naphthalen-8-yl)-phenyl]-cyclobutanol [CCXLII]

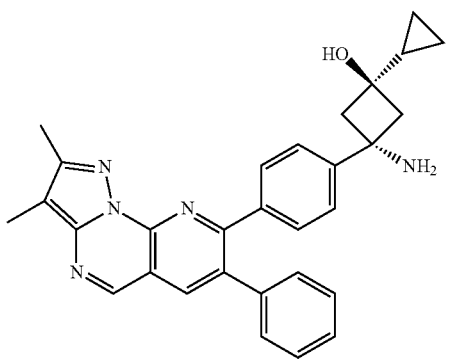

CCXLII

3-Amino-3-[4-(3-chloro-2-methyl-7-phenyl-1,4,9,9b-tetraaza-cyclopenta[a]naphthalen-8-yl)-phenyl]-cyclopropyl-cyclobutanol [CVIII]

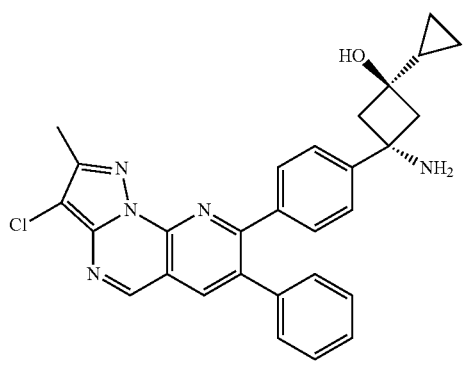

CVIII

3-[4-(2-Methyl-7-phenyl-3-pyridin-3-yl-1,4,9,9b-tetraaza-cyclopenta[a]naphthalen-8-yl)-phenyl]-oxazolidin-2-one [C]

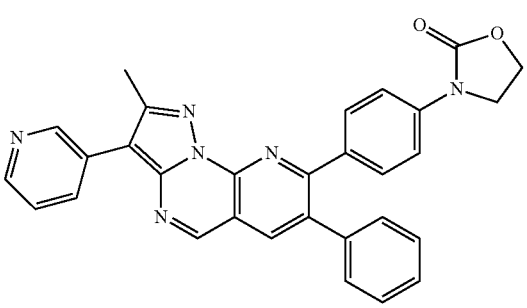

C

137

3-Amino-3-[4-(2,5-dimethyl-7-phenyl-1,4,9,9b-tetraaza-cyclopenta[a]naphthalen-8-yl)-phenyl]-methyl-cyclobutanol [CXII]

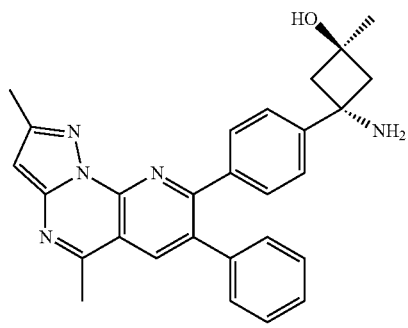

CXII

3-Amino-1-methyl-3-[4-(2-methyl-7-thiophen-2-yl-8,9-dihydro-1,4,9,9b-tetraaza-cyclopenta[a]naphthalene-8-yl)-phenyl]-cyclobutanol [CXVI]

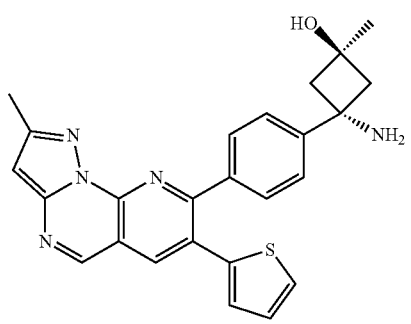

CXVI

3-Amino-1-methyl-3-[4-(2-methyl-7-thiophen-3-yl-8,9-dihydro-1,4,9,9b-tetraaza-cyclopenta[a]naphthalene-8-yl)-phenyl]-cyclobutanol [CXX]

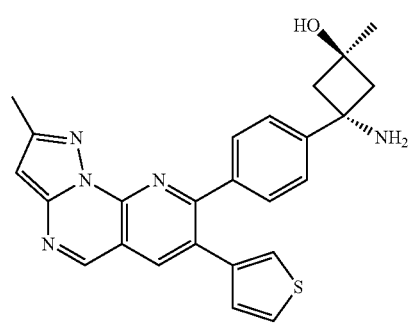

CXX

138

3-Amino-3-{4-[7-(2-fluoro-phenyl)-2-methyl-1,4,9,9b-tetraaza-cyclopenta[a]naphthalen-8-yl]-phenyl}-1-methyl-cyclobutanol [CXXIV]

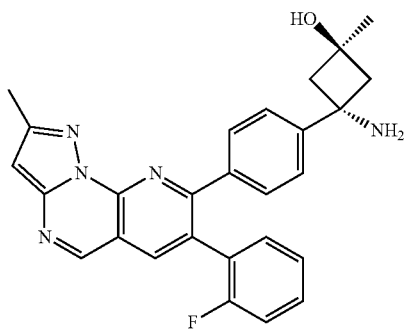

CXXIV trans-1-Amino-1-[4-(2-methyl-7-phenyl-1,4,9,9b-tetraaza-cyclopenta[a]naphthalen-8-yl)-phenyl]-3-methoxycyclobutane [LII]

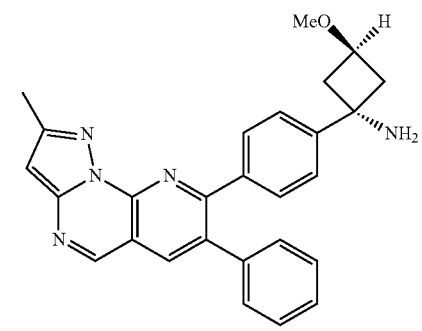

LVI

3-Amino-1-hydroxymethyl-3-[4-(2-methyl-7-phenyl-1,4,9,9b-tetraaza-cyclopenta[a]naphthalen-8-yl)-phenyl]-cyclobutanol [CXXX]

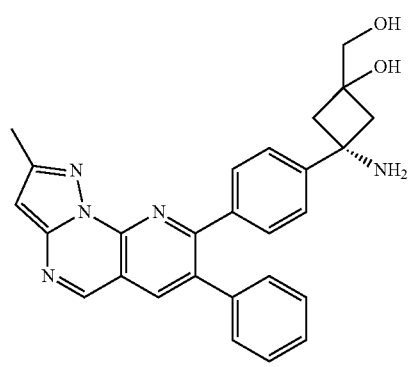

CXXX

1-[4-(2-methyl-7-phenyl-1,4,9,9b-tetraaza-cyclopenta[a]naphthalen-8-yl)-phenyl]-ethane-1,2-diol [LXIV]

1'-[4-(2-Methyl-7-phenyl-1,4,9,9b-tetraaza-cyclopenta[a]naphthalen-8-yl)-phenylmethyl]-spiro[furo[3,4-c]pyridine-3(1H),4'-piperidine]-1-one [XCII]

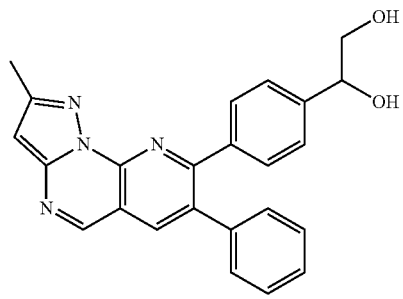
LXIV

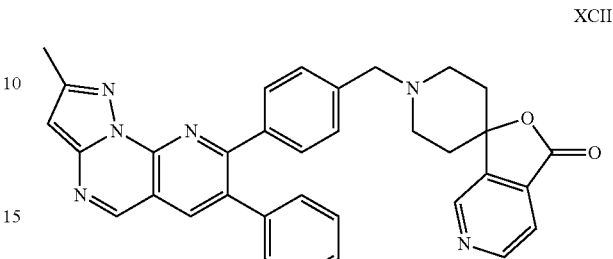
XCII

3-[4-(2-Methyl-7-phenyl-1,4,9,9b-tetraaza-cyclopenta[a]naphthalen-8-yl)-phenyl]-oxazolidin-2-one [LXXXVI]

1-[4-(2-Methyl-7-phenyl-1,4,9,9b-tetraaza-cyclopenta[a]naphthalen-8-yl)-benzyl]-piperidine-4-carboxylic acid ethyl ester [CLX]

LXXXVI

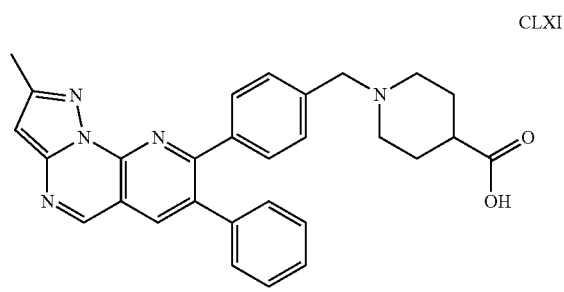 [SMILES: Cc1cc2ncc3cc(-c4ccccc4)c(-c4ccc(CN5CCC(C(=O)O)CC5)cc4)nc3n2n1]
CLX

[4-(2-Methyl-7-phenyl-1,4,9,9b-tetraaza-cyclopenta[a]naphthalen-8-yl)-phenyl]-carboxaldehyde [XC]

1-[4-(2-Methyl-7-phenyl-4,4,9,9b-tetraaza-cyclopenta[a]naphthalen-8-yl)-benzyl]-piperidine-4-carboxylic acid [CLXI]

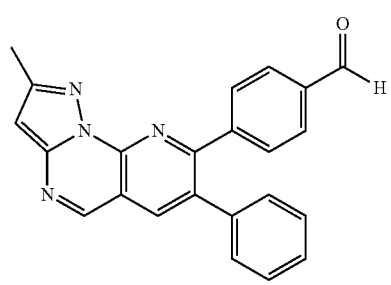
XC

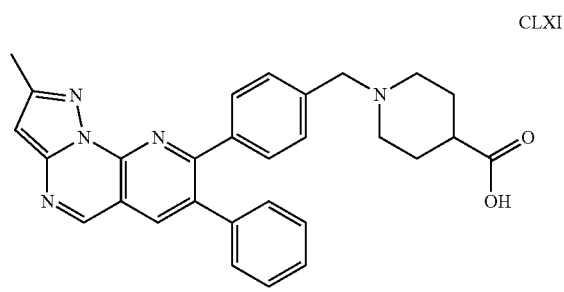 [SMILES: Cc1cc2ncc3cc(-c4ccccc4)c(-c4ccc(CN5CCC(C(=O)O)CC5)cc4)nc3n2n1]
CLXI

| 141 | 142 |
|---|---|
| 1-[4-(2-Methyl-7-phenyl-4,4,9,9b-tetraaza-cyclopenta[a]naphthalen-8-yl)-benzyl]-piperidine-4-carboxylic acid phenylamide [CLXII] | 3-Amino-3-[4-(2,6-dimethyl-7-phenyl-1,4,9,9b-tetraaza-cyclopenta[a]naphthalen-8-yl)-phenyl]-1-methyl-cyclobutanol [CCLI] |

CLXII

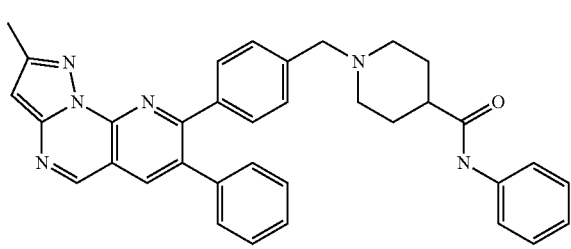

CCLI

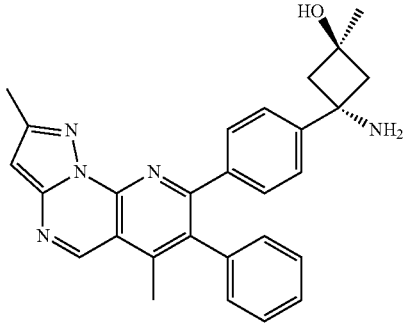

1-[4-(2-Methyl-7-phenyl-1,4,9,9b-tetraaza-cyclopenta[a]naphthalen-8-yl)-benzyl]-piperidine-4-carboxylic acid methylamide [CXCV]

trans-3-Amino-1-methyl-3-[4-(2-(4-methoxyphenyl)-7-phenyl-1,4,9,9b-tetraaza-cyclopenta[a]naphthalen-8-yl)-phenyl]-cyclobutanol [CCLXXVI]

CXCV

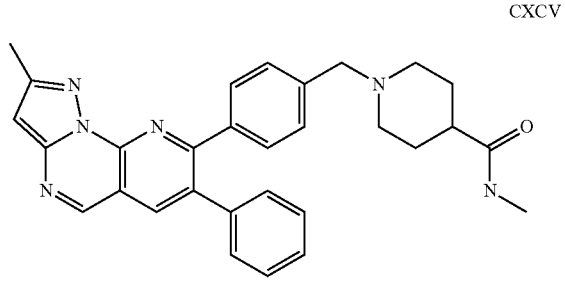

CCLXXVI

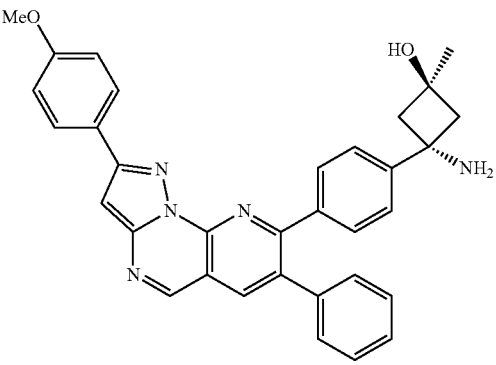

3-Amino-1-methyl-3-[4-(2-methyl-7-phenyl-1,4,6,9,9b-pentaaza-cyclopenta[a]naphthalen-8-yl)-phenyl]-cyclobutanol [CCXXXIII]

trans-3-Amino-1-methyl-3-[4-(2-isopropyl-7-phenyl-1,4,9,9b-tetraaza-cyclopenta[a]naphthalen-8-yl)-phenyl]-cyclobutanol [CCLXXVIII]

CCXXXIII

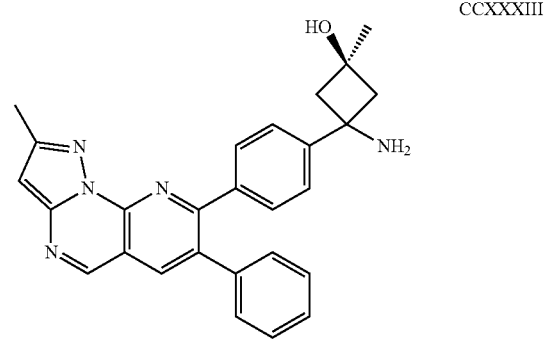

CCLXXVIII

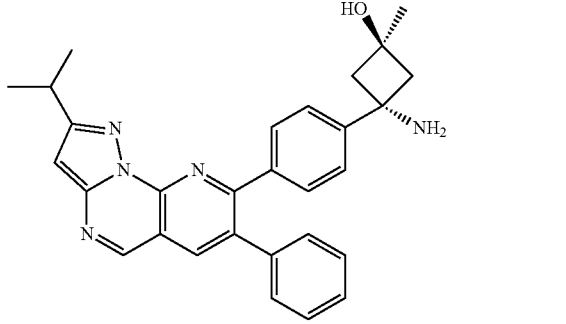

143 trans-3-Amino-1-methyl-3-[4-(2-cyclobutyl-7-phenyl-1,4,9,9b-tetraaza-cyclopenta[a]naphthalen-8-yl)-phenyl]-cyclobutanol [CCLXXX]

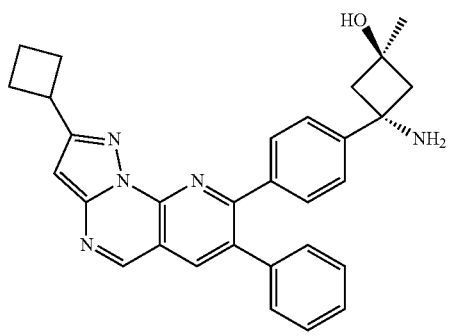

CCLXXX trans-3-Amino-1-methyl-3-[4-(2-(pyridine-4-yl)-7-phenyl-1,4,9,9b-tetraaza-cyclopenta[a]naphthalen-8-yl)-phenyl]-cyclobutanol [CCXCIX]

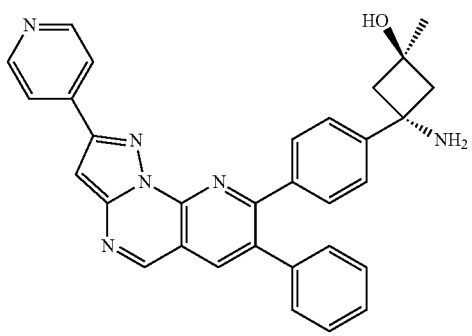

CCXCIX trans-3-Amino-1-methyl-3-[4-(2-(thiophen-3-yl)-7-phenyl-1,4,9,9b-tetraaza-cyclopenta[a]naphthalen-8-yl)-phenyl]-cyclobutanol [CCCX]

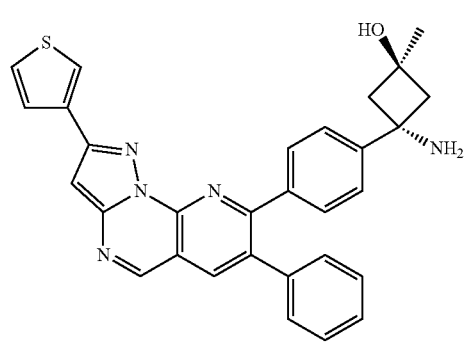

CCCX

144 trans-3-Amino-1-methyl-3-[4-(7-phenyl-1,4,6,9,9b-pentaaza-cyclopenta[a]naphthalen-8-yl)-phenyl]-cyclobutanol [CCCLXXXII]

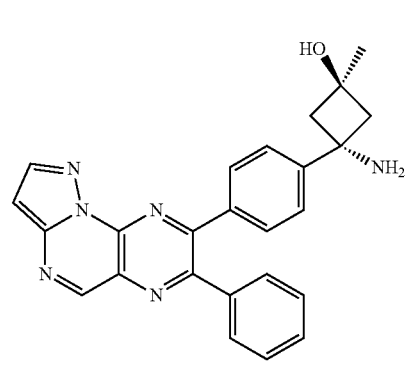

CCCXXXII trans-3-Amino-1-methyl-3-[4-(5-methyl-7-phenyl-1,4,9,9b-tetraaza-cyclopenta[a]naphthalen-8-yl)-phenyl]-cyclobutanol [CCCLXXXIX]

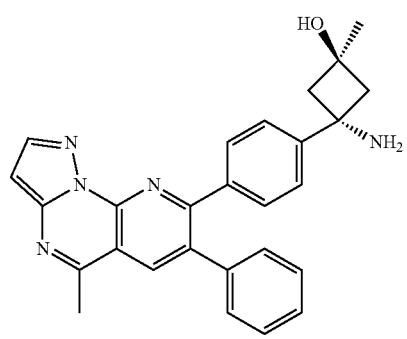

CCCLXXXIX trans-3-Amino-1-cyclopropyl-3-[4-(2-methyl-3,7-diphenyl-1,4,9,9b-tetraaza-cyclopenta[a]naphthalen-8-yl)-phenyl]-cyclobutanol [CCCXCIV]

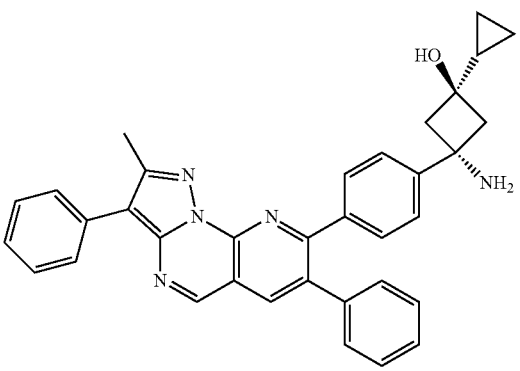

CCCXCIV

145
trans-{3-Ethyl-3-hydroxy-1-[4-(4,4,5,5-tetramethyl-[1,3,2]dioxaborolan-2-yl)-phenyl]-cyclobutyl}-isoindole-1,3-dione [CCCXCVIII]
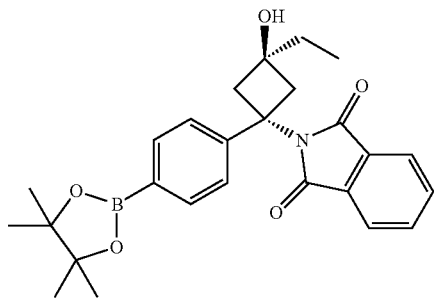
CCCXCVIII
trans-3-Amino-1-ethyl-3-[4-(2-methyl-7-phenyl-1,4,9,9b-tetraaza-cyclopenta[a]naphthalen-8-yl)-phenyl]-cyclobutanol [CD]
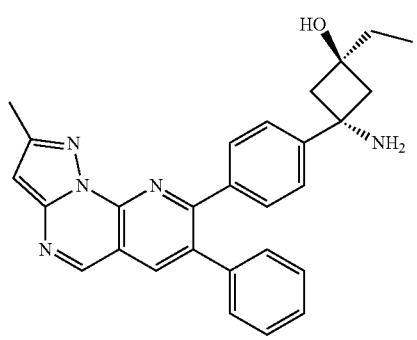
CD
Scheme-Synthesis of [XI]
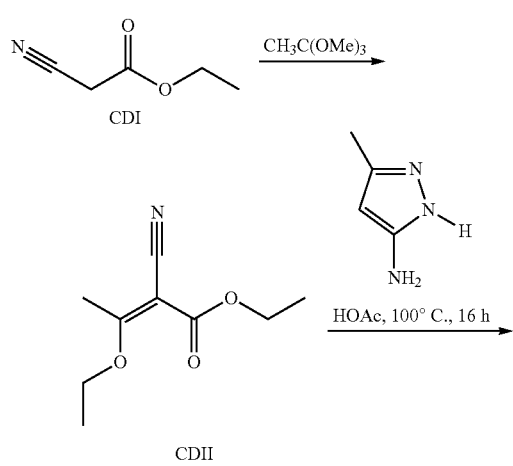
CDI
CDII
146
-continued
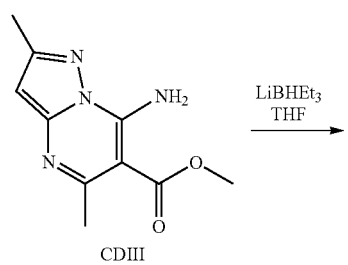
CDIII
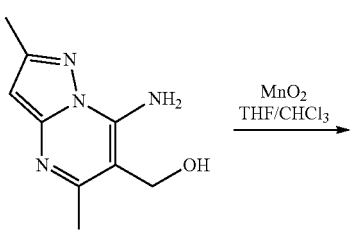
CDIV
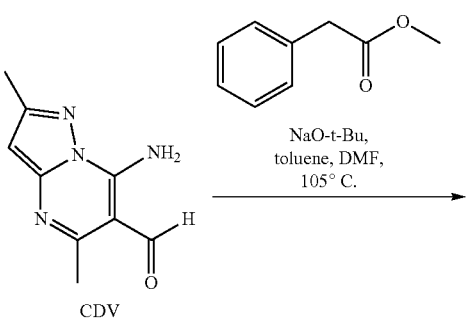
CDV
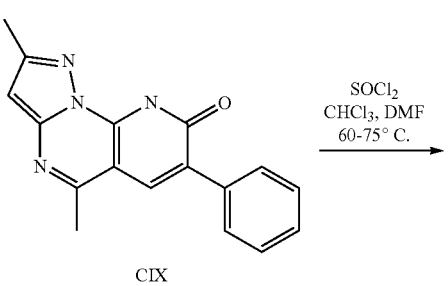
CIX
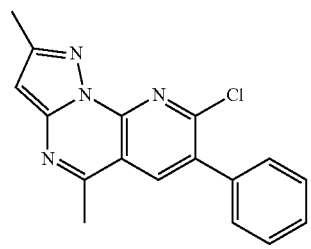
CX

147 trans-3-Amino-1-methyl-3-[4-(2-methyl-6,7-diphenyl-1,4,9,9b-tetraaza-cyclopenta[a]naphthalen-8-yl)-phenyl]-cyclobutanol [CDIX]

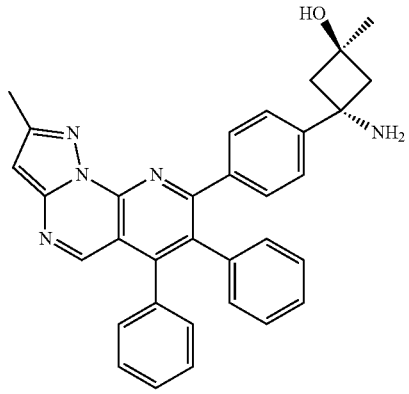

CDIX trans-2-{3-Hydroxy-3-isopropyl-1-[4-(4,4,5,5-tetramethyl-[1,3,2]dioxaborolan-2-yl)-phenyl]-cyclobutyl}-isoindole-1,3-dione [CDXXVIII]

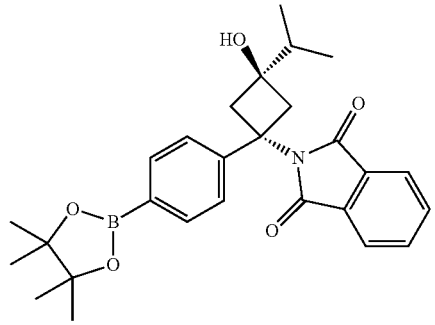

CDXXVIII trans-3-Amino-1-isopropyl-3-[4-(2-methyl-7-phenyl-1,4,9,9b-tetraaza-cyclopenta[a]naphthalen-8-yl)-phenyl]-cyclobutanol [CDXXXII]

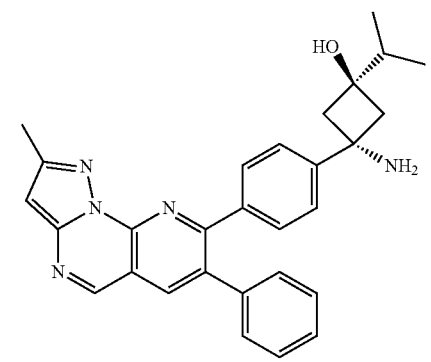

CDXXXII

148 trans-3-Amino-1-methyl-3-[4-(2-methyl-7-pyridin-4-yl-1,4,9,9b-tetraaza-cyclopenta[a]naphthalen-8-yl)-phenyl]-cyclobutanol [DXXXVII]

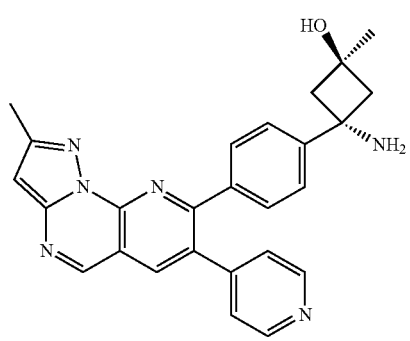

DXXXVII trans-8-[4-(1-Amino-3-hydroxy-3-methyl-cyclobutyl)-phenyl]-2-methyl-7-phenyl-1,4,9,9b-tetraaza-cyclopenta[a]naphthalene-6-carbonitrile [DXLVII]

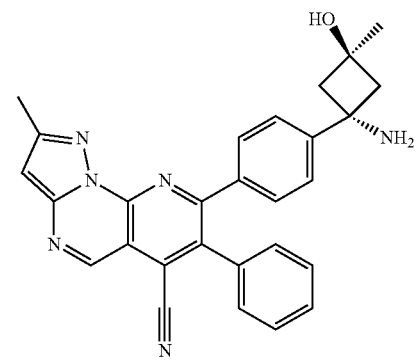

DXLVII trans-3-Amino-3-[4-(2-isopropenyl-7-thiophen-2-yl-1,4,6,9,9b-pentaaza-cyclopenta[a]naphthalen-8-yl)-phenyl]-1-methyl-cyclobutanol [DLXXIV]

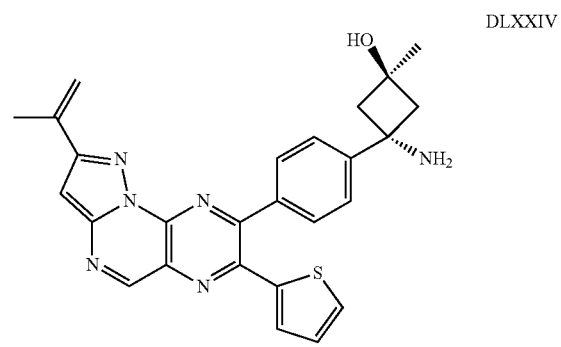 [SMILES: C=C(C)c1cc2ncc3nc(-c4cccs4)c(-c4ccc([C@]5(N)C[C@](C)(O)C5)cc4)nc3n2n1]

DLXXIV

Scheme showing synthesis of Compound [DLXXIX]

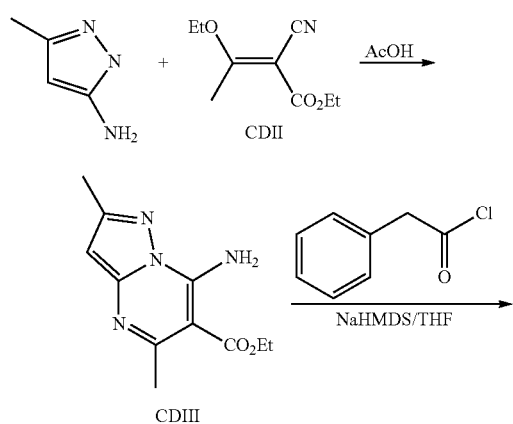

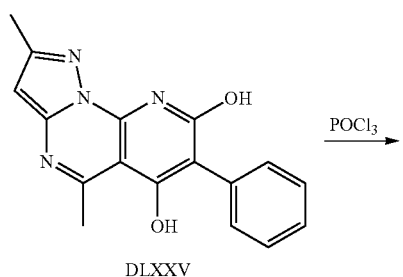

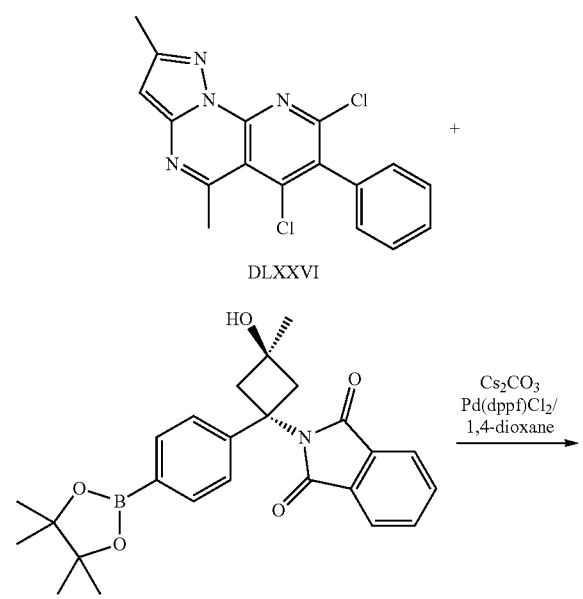

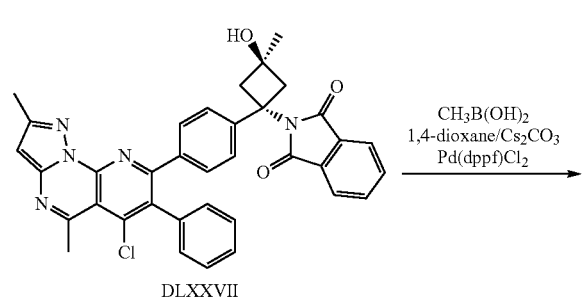

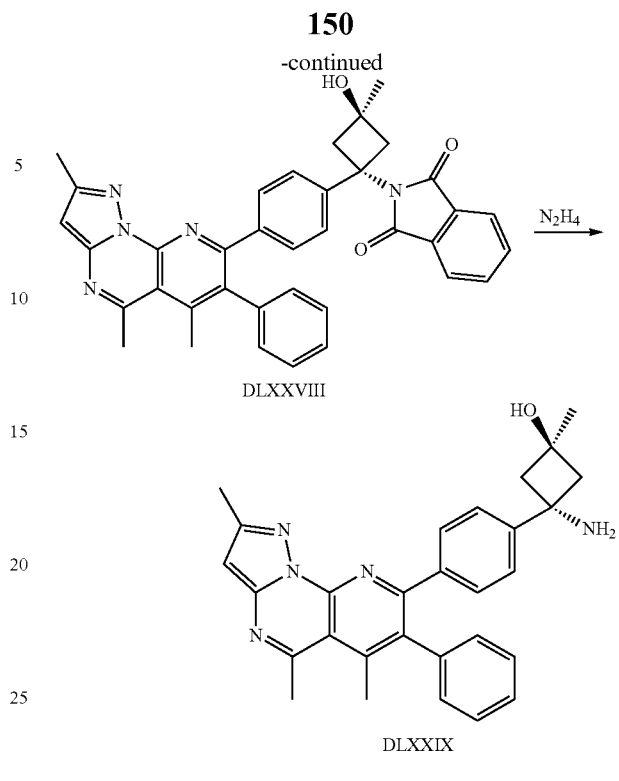

3-Amino-1-methyl-3-[4-(2,5,6-trimethyl-7-phenyl-1,4,9,9b-tetraaza-cyclopenta[a]naphthalen-8-yl)-phenyl]-cyclobutanol [DLXXIX]

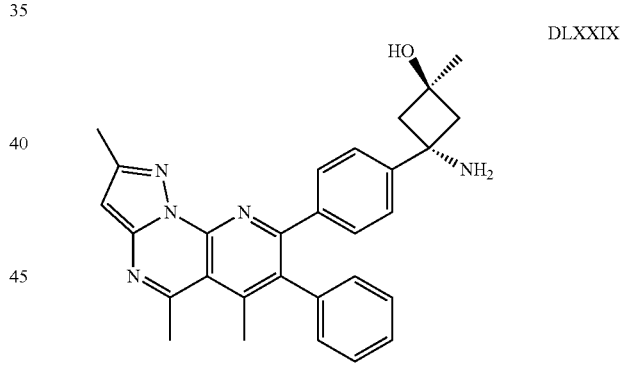

Examples

The following preparations illustrate methods for the preparation of compounds according to the present invention, as well as those for the preparation of intermediates. It should be evident to those skilled in the art that appropriate substitution of both the materials and methods disclosed herein will produce the examples illustrated below and those encompassed by the scope of the invention.

Before describing each preparation of intermediates and compounds according to the present invention, the following should be noted in general:

All temperatures are given in degrees Celsius. Reagents were purchased from commercial sources or prepared in accordance with literature procedures.

Unless otherwise noted, HPLC purification was performed by redissolving a residue in a small volume of $CH_3OH$ or other appropriate solvent. The solution was then purified via preparatory reverse-phase purification system using a Varian Dynamax HPLC 21.4 mm Microsorb Guard-8 $C_{18}$ column. In general, Solvent A was a mixture of 5% $CH_3CN$: 95% $H_2O$: 0.1% $CF_3COOH$ while Solvent B was a mixture of 95% $CH_3CN$: 5% $H_2O$: 0.1% $CF_3COOH$. Details are as follows: A typical run would be from 0% Solvent B: 100% Solvent A to 100% Solvent B: 0% Solvent A over a period of 5 minutes, followed by a hold at 100% Solvent B, before it was re-equilibrated back to the initial starting gradient. Total run time was 7 minutes. The resulting fractions were analyzed, combined as appropriate, and then evaporated to provide purified material. Unless otherwise noted, all compounds resulting from the reverse-phase HPLC purification were characterized as the corresponding TFA salts.

Proton magnetic resonance ($^1H$ NMR) spectra were recorded on either a Varian INOVA 400 MHz ($^1H$) NMR spectrometer, or Varian INOVA 500 MHz ($^1H$) NMR spectrometer. All spectra were determined in the solvents indicated below. Although chemical shifts are reported in parts per million (ppm) downfield of tetramethylsilane, they are referenced to the residual proton peak of the respective solvent peak for $^1H$ NMR. Interproton coupling constants are reported in Hertz (Hz). LCMS spectra were obtained using a ThermoFinnigan AQA MS ESI instrument. The samples were sent through a Phenomenex Aqua 5 micron $C_{18}$ 125 Å 50×4.60 mm column. For purity analysis, Solvent C was $H_2O$ with 0.1% formic acid, and Solvent D was $CH_3OH$ with 0.1% formic acid. For purity analysis of the freebase intermediates a gradient of 45% D:C to 95% D:C over 5 minutes and then a 3-minute hold at 95% D:C was used. For purity analysis of the trifluoroacetate salts, a gradient of 5% D:C to 95% D:C over 5 minutes and then a 1 minute hold at 95% D:C was used. The spray setting for the MS probe was at 350 μL/min with a cone voltage at 3 kV and a probe temperature at 450° C.

Abbreviations used herein are: HPLC (high-performance liquid chromatography); TFA (trifluoroacetic acid); $^1H$ NMR (proton nuclear magnetic resonance); LCMS (liquid chromatograph-mass spectrometer); MS (mass spectrometer); THF (tetrahydrofuran); eq (equivalents); $NH_4Cl$ (ammonium chloride); DMF (N,N-dimethylformamide); NaCl (sodium chloride)1 NaOMe (sodium methoxide); EtOH (ethanol); Pd/C (palladium on carbon); $Et_3N$ (triethylamine); AcOH (acetic acid); DMSO (dimethyl sulfoxide); DCM (dichloromethane); EtOAc (ethyl acetate); LC/MS (liquid chromatogram-mass spectrometer); BINAP (2,2'-bis(diphenylphosphino)-1,1'-binapthyl); NaO-t-Bu (sodium t-butoxide); $Pd_2(dba)_3$ (tris(dibenzylideneacetone)dipalladium); $BnCH_2Br$ (benzyl bromide); rt (room temperature); n-(normal); ESI (electrospray ionization) x-phos, xantphos (4,5-bis(diphenylphosphino)-9,9-dimethylxanthene); DIAD (diisopropyl azodicarboxylate); NBS (N-bromosuccinimide); EDCI (1-ethyl-3-(3-dimethylaminopropyl) carbodiimide); dppf (1,1'-bis(diphenylphosphanyl)ferrocene); HATU (o-(7-azabenzotriazol-1-yl)-N,N,N',N'-tetramethyluronium hexafluorophosphate); DIPEA (diisopropylethylamine); $Tf_2O$ (trifluoromethanesulfonic anhydride); MS (N-iodosuccinimide); TsCl (p-toluenesulfonyl chloride); TBAF (tetrabutylammonium fluoride); DMAP (dimethylaminopyridine); ACN (acetonitrile); DMA (dimethylacetoamide); MCPBA (m-chloroperbenzoic acid); TBAB (tetrabutylammonium bromide); DIBAL-H (diisobutylaluminium hydride); NCS (N-chlorosuccinimide); dppe (1,2-Bis(diphenylphosphino)ethane); HOBT (1-hydroxybenzotriazole); 18-crown-6 (1,4,7,10,13,16-hexaoxacyclooctadecane).

Experimental Procedures

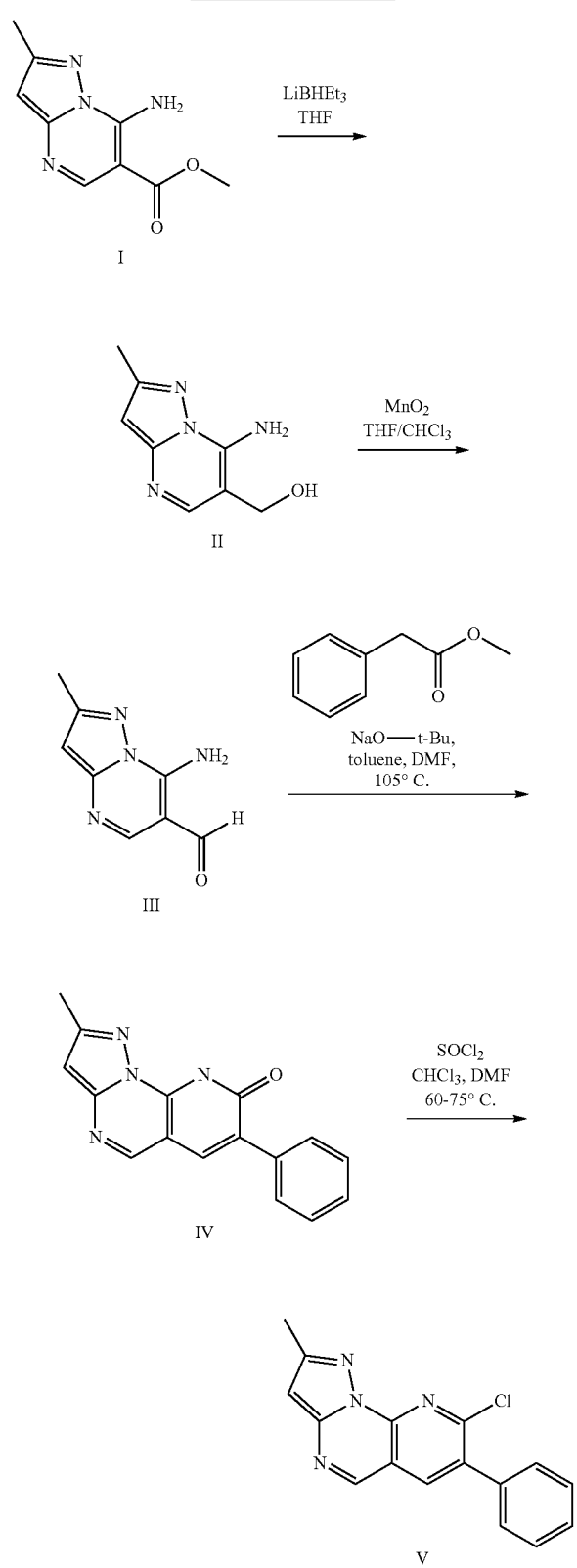

Scheme I - Synthesis of [V]

(7-Amino-2-methyl-pyrazolo[1,5-a]pyrimidin-6-yl)-methanol [II]

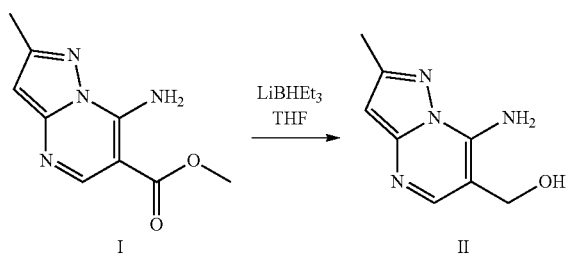

To a 1 L three-necked round bottom flask was added compound [I] (20.6 g, 100 mmol, 1.0 eq.) and THF (400 mL). The mixture was cooled to 0° C. and LiBHEt₃ (315 mL of a 1.0 M solution in THF, 315 mmol, 3.0 eq.) was added slowly through an addition funnel under nitrogen. After addition, the mixture was stirred at room temperature for 4 hours. Analysis of the reaction mixture by TLC indicated that a small amount of starting material was still present. Additional LiBHEt₃ (30 mL of a 1.0 M solution in THF, 30 mmol, 0.3 eq.) was added and the mixture was stirred for an additional 1 hour. The mixture was slowly treated with EtOAc (600 mL) and then water (300 mL). The layers were separated and the aqueous phase was extracted with EtOAc (2×300 mL). The combined organic phases were dried over anhydrous Na$_2$SO$_4$. After filtration and concentration, the residue was purified by a short silica gel column (2.5 inch in height and 4 inch in diameter) using MeOH in CH$_2$Cl$_2$ as the eluant. Concentration by rotary evaporation provided Compound [II] as a light yellowish solid (14.0 g): LCMS m/e 179 (M+H); $^1$H NMR (400 MHz, METHANOL-d$_4$) δ ppm 2.43 (s, 3H) 4.66 (s, 2H) 6.16 (s, 1H) 8.01 (s, 1H).

7-Amino-2-methyl-pyrazolo[1,5-a]pyrimidin-6-carbaldehyde

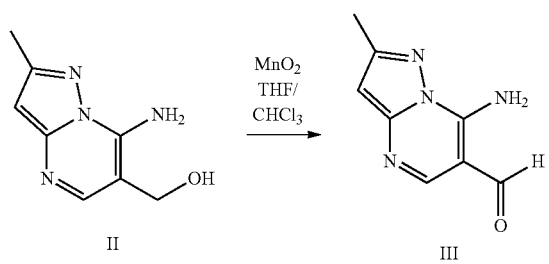

To a 1 L three-necked round bottom flask containing Compound [II] (14.1 g, 79.2 mmol, 1.0 eq.) was added CHCl$_3$ (500 mL) and THF (250 mL) followed by MnO$_2$ (68.9 g, 792 mmol, 10 eq.). The mixture was stirred at room temperature for 16 hours. Analysis of the reaction mixture by TLC indicated that the reaction was complete. The mixture was filtered through a 2.5 cm thick layer of layer of Celite and the filtered material washed with 15% MeOH in CHCl$_3$ (~1000 mL) and 30% MeOH in CHCl$_3$ (~1500 mL) until no additional product was observed through analysis of the filtrates by TLC. Removal of solvents in vacuo provided Compound [III] as a yellowish solid (13.9 g, 98%). LCMS m/e 177 (M+H); $^1$H NMR (400 MHz, METHANOL-d$_4$) δ ppm 2.45 (s, 3H) 6.31 (s, 1H) 8.41 (s, 1H) 9.82 (s, 1H).

2-Methyl-7-phenyl-9H-1,4,9,9b-tetraaza-cyclopenta[a]naphthalen-8-one [IV]

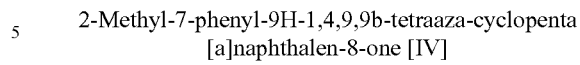

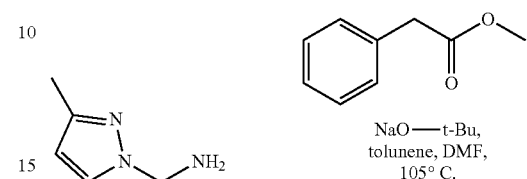

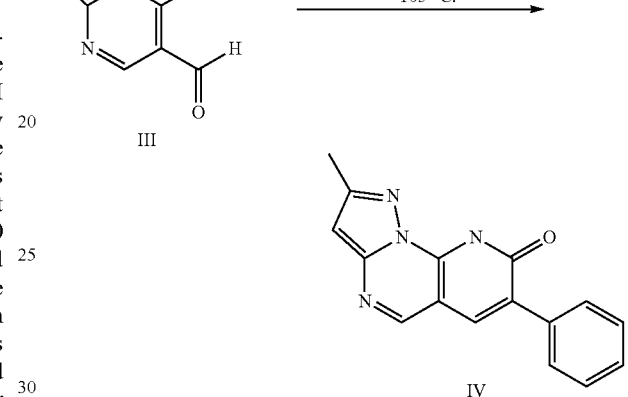

To a 1 L three necked round bottom flask was added Compound [III] (5.3 g, 30 mmol, 1 eq.), methyl phenylacetate (18 g, 120 mmol, 4.0 eq.), toluene (100 mL), and NaO-t-Bu (5.8 g, 60 mmol, 2.0 eq.). The mixture was heated at 105° C. for 30 min and the formation of large amounts of solid was noted. DMF (100 mL) was added and the solid was observed to go into solution. The mixture was heated for 3 days. After this time, the heat was removed and the mixture allowed to cool to room temperature. The reaction mixture was concentrated and the residue dissolved in CH$_2$Cl$_2$ (600 mL), followed by the addition of water (400 mL) to form a yellowish precipitate. The solid was filtered and washed with water (50 mL) and CH$_2$Cl$_2$ (100 mL). The collected solid was dried under vacuum to furnish Compound [IV] as a yellowish solid (7.8 g, 94%): LCMS (m/e) 277 (M+H), $^1$H NMR (400 MHz, DMSO-d$_6$) δ ppm 2.36 (s, 3H) 6.23 (s, 1H) 7.16-7.25 (m, 1H) 7.33 (t, J=7.58 Hz, 2H) 7.74 (d, J=7.22 Hz, 2H) 7.83 (s, 1H) 8.41 (s, 1H).

8-Chloro-2-methyl-7-phenyl-1,4,9,9b-tetraaza-cyclopenta[a]naphthalene [V]: (SOCl$_2$ procedure)

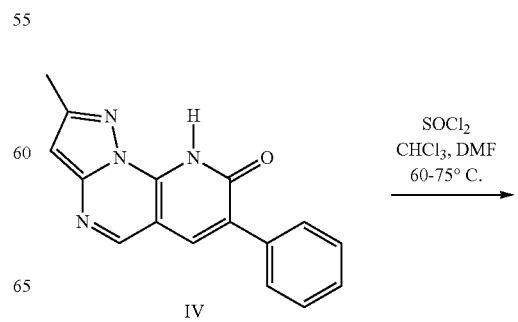

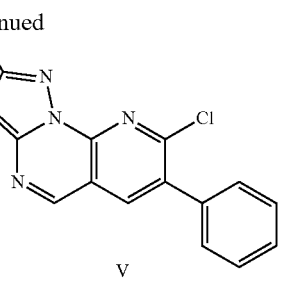

V

To a 250 mL round bottom flask was added Compound [IV] (3 g, 10.9 mmol, 1 eq.), CHCl₃ (120 mL), SOCl₂ (5.17 g, 3.17 mL, 43.5 mmol, 4 eq.) and DMF (158.9 mg, 168.3 uL, 2.17 mmol, 0.2 eq.). The mixture was heated to 70° C. in an oil bath for 1 hour. At this time, additional SOCl₂ (1.6 mL, 21.8 mmol, 2 eq.) and DMF (168.3 uL, 2.17 mmol, 0.2 eq.) were added. The mixture was maintained at 70° C. for an additional 2 hours. After 3 hours total, LCMS analysis and TLC analysis (heptane:EtOAc (3:7)) of the resulting light brown solution indicated that the reaction was complete. The reaction was concentrated in vacuo and the residue diluted with EtOAc (100 mL), washed with saturated aqueous NaHCO₃ solution (50 mL), and the aqueous phases re-extracted with EtOAc (3×200 mL). The combined organic phases were dried over MgSO₄, filtered, and concentrated to give 3.2 g of material which was purified by silica gel chromatography using EtOAc/heptane as the eluant to give Compound [V]: LCMS (m/e) 295 (M+H); ¹H NMR (400 MHz, METHANOL-d₄) δ ppm 2.60 (s, 3H) 6.79 (s, 1H) 7.43-7.67 (m, 5H) 8.57 (s, 1H) 9.04 (s, 1H).

8-Chloro-2-methyl-7-phenyl-1,4,9,9b-tetraaza-cyclopenta[a]naphthalene [V]: (POCl₃ procedure)

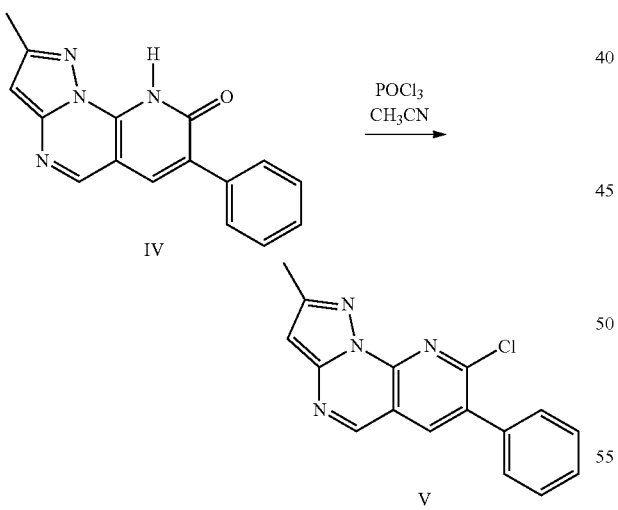

To a 40 mL scintillation vial was added Compound [IV] (0.275 g, 1 mmol, 1 eq.), CH₃CN (5 mL), and POCl₃ (3.5 g, 20 mmol, 20 eq.). The reaction mixture was heated at 65-70° C. for 12 hours under a nitrogen atmosphere. The heat was removed and the mixture was allowed to cool to room temperature. The reaction was concentrated under reduced pressure and the residue re-dissolved in CH₃CN (5 mL) and treated with two drops of water. The mixture was then concentrated onto Celite (0.5 g) and purified by silica gel chromatography using MeOH:CH₂Cl₂ as the eluant to furnish Compound [V] as a viscous yellowish solid with the same spectral characteristics as determined previously.

Scheme II - Synthesis of [XI]

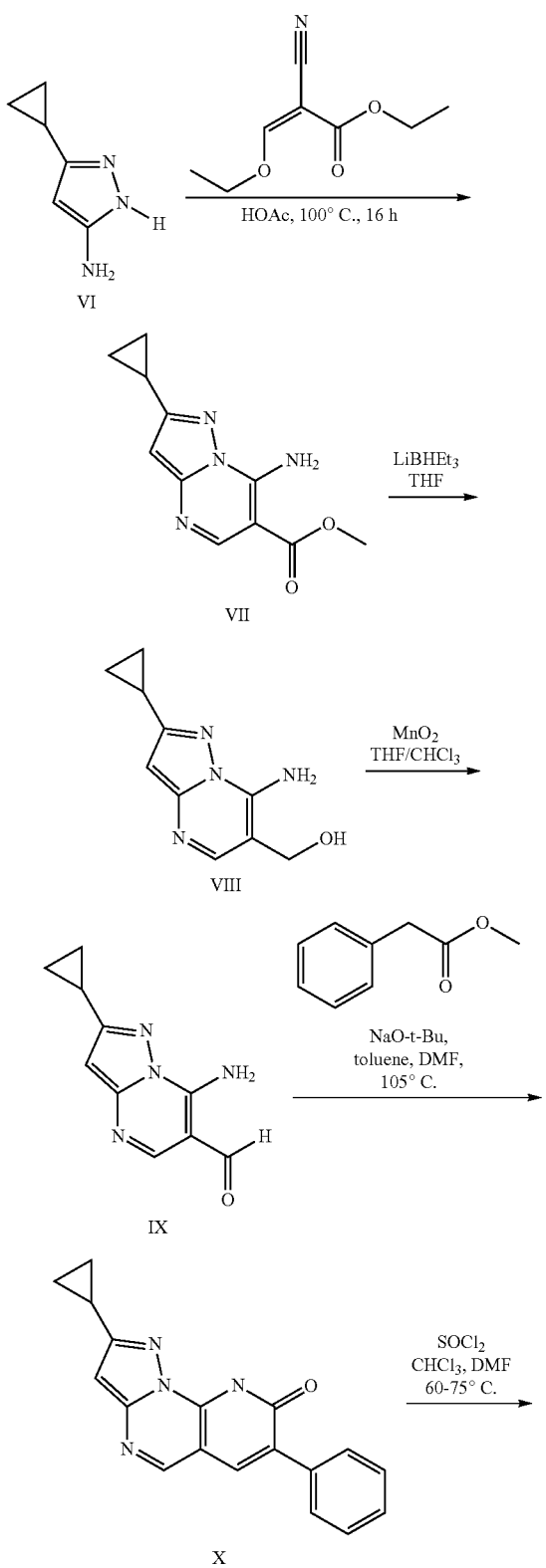

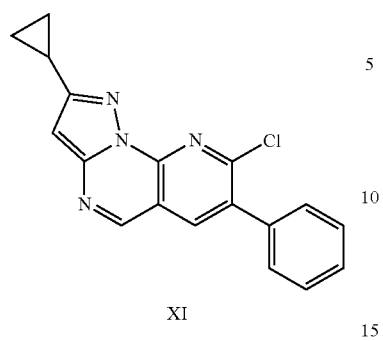

XI

7-Amino-2-cyclopropyl-pyrazolo[1,5-a]pyrimidine-
6-carboxylic acid ethyl ester [VII]

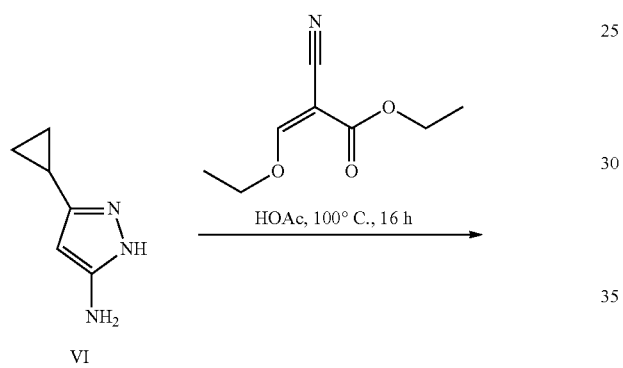

VII

To a 250 mL round bottom flask was added Compound [VI] (5 g, 40.6 mmol, 1 eq.), ethyl-2-cyano-3-ethoxyacrylate (6.9 g, 40.6 mmol, 1 eq.), and HOAc (100 mL). The mixture was heated at 100° C. for 16 hours. The reaction was concentrated and the residue was treated with $H_2O$ (150 mL). The resulting precipitate was filtered, and the precipitate washed with $H_2O$ (3×250 mL). The crude product was dried under high vacuum for 16 hours to afford 8.4 g (yield=84%) of Compound [VII]: LCMS (m/e) 247 (M+H); $^1$H NMR (400 MHz, METHANOL-$d_4$) δ ppm 0.92-1.02 (m, 2H) 1.03-1.14 (m, 2H) 1.42 (t, J=7.10 Hz, 3H) 2.13 (t, J=8.30 Hz, 1H) 4.28-4.47 (m, 2H) 6.21 (s, 1H) 8.61 (s, 1H).

(7-Amino-2-cyclopropyl-pyrazolo[1,5-a]pyrimidin-6-yl)-methanol [VIII]

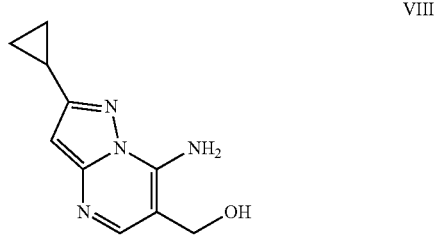 [SMILES: Nc1c(CO)cnc2cc(C3CC3)nn12]

VIII

Compound [VIII] was prepared using a procedure similar to that of Compound [II]. Data for Compound [VIII]: LCMS (m/e) 205 (M+H); $^1$H NMR (400 MHz, METHANOL-$d_4$) δ ppm 0.86-0.99 (m, 2H) 1.03-1.12 (m, 2H) 2.00-2.16 (m, 1H) 4.68 (s, 2H) 6.07 (s, 1H) 8.02 (s, 1H).

7-Amino-2-cyclopropyl-pyrazolo[1,5-a]pyrimidin-6-carbaldehyde [IX]

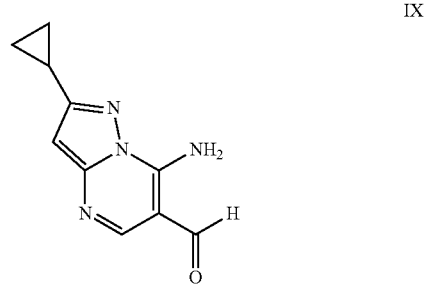 [SMILES: Nc1c(C=O)cnc2cc(C3CC3)nn12]

IX

Compound [IX] was prepared using a procedure similar to that of Compound [III].

Data for Compound [IX]: LCMS (rule) 203 (M+H); $^1$H NMR, (400 MHz, METHANOL-$d_4$) δ ppm 0.93 (m, 2H) 1.07 (m, 2H) 2.00-2.19 (m, 2H) 6.07 (s, 1H) 8.02 (s, 1H) 9.85 (s, 1H).

2-Cyclopropyl-7-phenyl-9H-1,4,9,9b-tetraaza-cyclopenta[a]naphthalen-8-one [X]

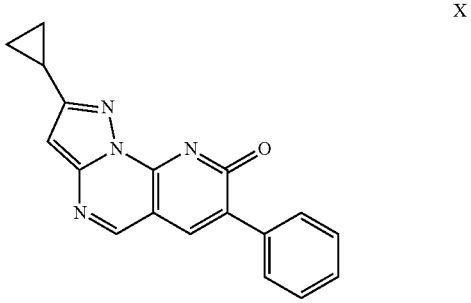

X

Compound [X] was prepared using a procedure similar to that of Compound [IV]. Data for Compound [X]: LCMS (m/e) 303 (M+H); $^1$H NMR (400 MHz, DMSO-$d_6$) δ ppm 0.86-0.96 (m, 2H) 1.00-1.10 (m, 2H) 2.07-2.18 (m, 1H) 6.50 (s, 1H) 7.36 (t, 1H) 7.44 (t, J=7.44 Hz, 2H) 7.69 (d, J=7.22 Hz, 2H) 8.32 (s, 1H) 8.74 (s, 1H).

8-Chloro-2-cyclopropyl-7-phenyl-1,4,9,9b-tetraaza-cyclopenta[a]naphthalene [XI]

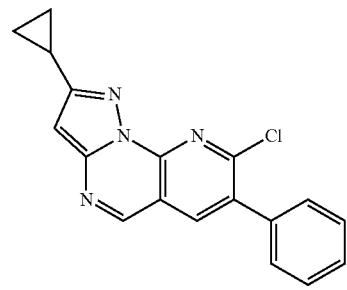

Compound [XI] was prepared using a procedure similar to that of Compound [V](SOCl₂ procedure). Data for Compound [XI]: LCMS (m/e) 321 (M+H).

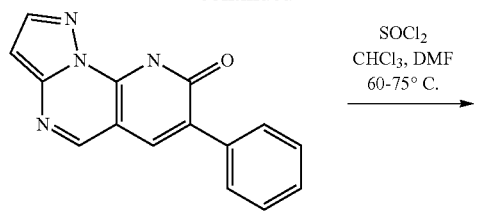

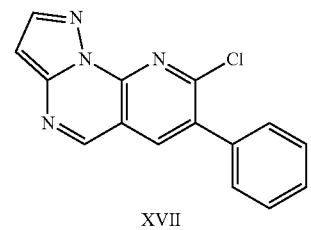

7-Amino-pyrazolo[1,5-a]pyrimidine-6-carboxylic acid ethyl ester [XIII]

Compound [XIII] was prepared using a procedure similar to that of Compound [VII]. Data for Compound [XIII]: LCMS (m/e) 207 (M+H); ¹H NMR (400 MHz, METHANOL-d₄) δ ppm 1.43 (t, J=7.13 Hz, 3H) 4.43 (q, J=7.13 Hz, 2H) 6.51 (d, J=2.15 Hz, 1H) 8.14 (d, J=2.10 Hz, 1H) 8.70 (s, 1H).

(7-Amino-pyrazolo[1,5-a]pyrimidin-6-yl)-methanol [XIV]

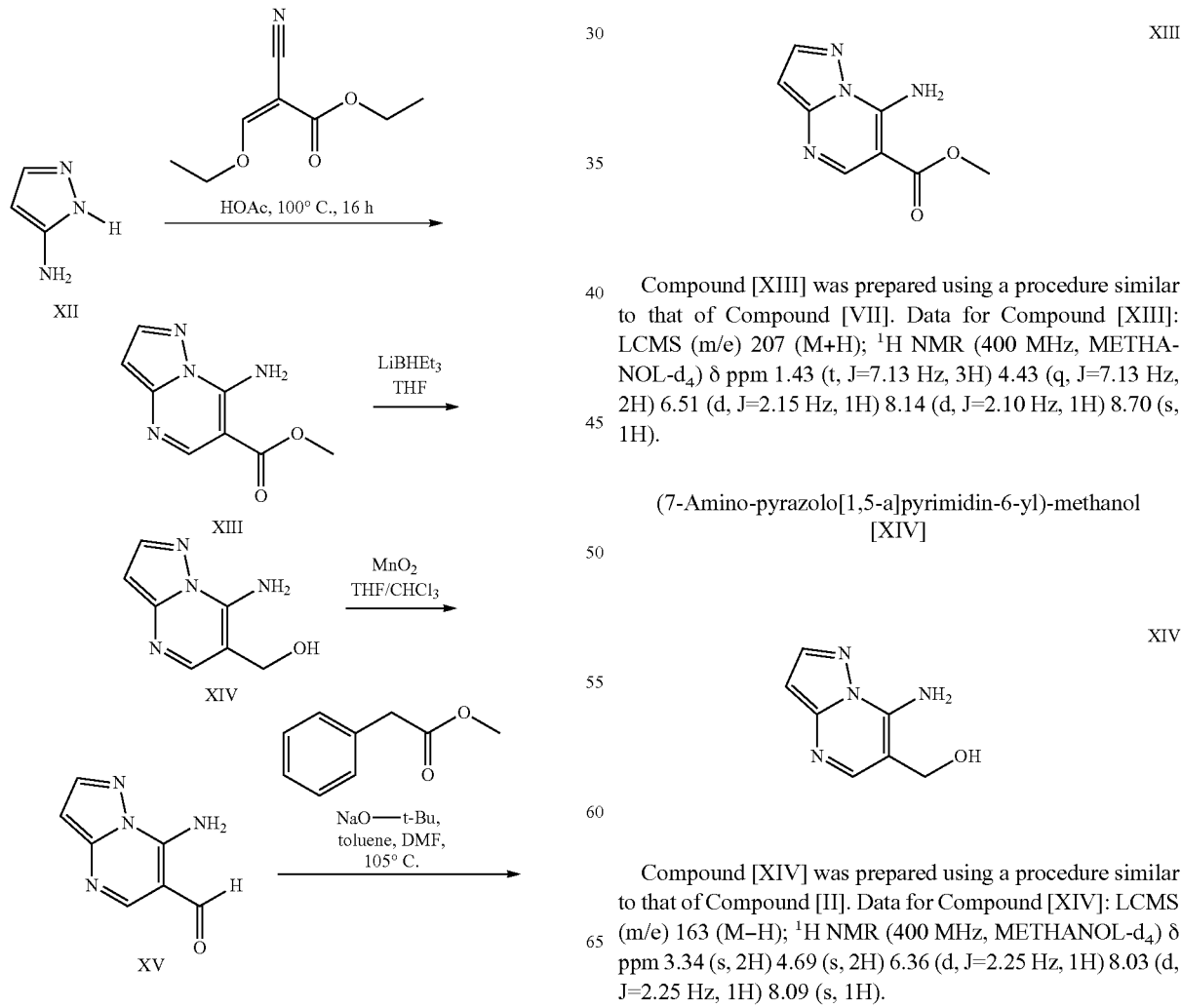

Compound [XIV] was prepared using a procedure similar to that of Compound [II]. Data for Compound [XIV]: LCMS (m/e) 163 (M−H); ¹H NMR (400 MHz, METHANOL-d₄) δ ppm 3.34 (s, 2H) 4.69 (s, 2H) 6.36 (d, J=2.25 Hz, 1H) 8.03 (d, J=2.25 Hz, 1H) 8.09 (s, 1H).

7-Amino-pyrazolo[1,5-a]pyrimidin-6-carbaldehyde [XV]

Compound [XV] was prepared using a procedure similar to that of Compound [III]. Data for Compound [XV]: LCMS (m/e) 163 (M+H); $^1$H NMR (400 MHz, METHANOL-$d_4$) δ ppm 6.51 (d, J=2.10 Hz, 1H) 8.15 (d, J=2.05 Hz, 1H) 8.50 (s, 1H) 9.88 (s, 1H).

7-Phenyl-9H-1,4,9,9b-tetraaza-cyclopenta[a]naphthalen-8-one [XVI]

Compound [XVI] was prepared using a procedure similar to that of Compound [IV]. Data for Compound [XVI]: LCMS (m/e) 263 (M+H).

8-Chloro-2-cyclopropyl-7-phenyl-1,4,9,9b-tetraaza-cyclopenta[a]naphthalene [XVII]

Compound [XVII] was prepared using a procedure similar to that of Compound [V] (SOCl$_2$ procedure). Data for Compound [XVII]: LCMS (m/e) 281 (M+H); $^1$H NMR (400 MHz, METHANOL-$d_4$) δ ppm 6.96 (d, J=2.10 Hz, 1H) 7.44-7.63 (, 5H) 8.27 (d, J=2.10 Hz 1H) 8.59 (s, 1H) 9.07 (s, 1H).

Scheme IV- Synthesis of [XXIII]

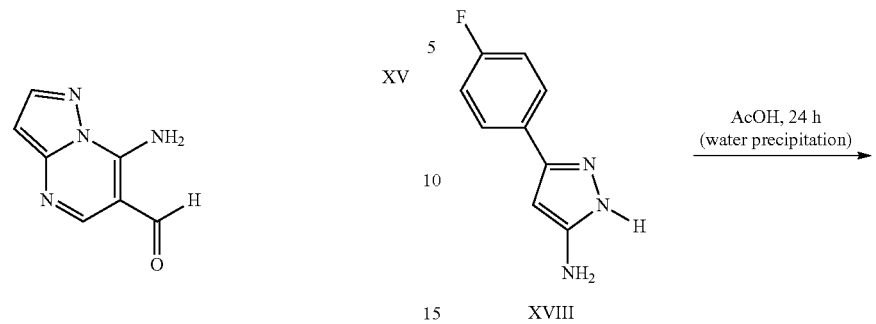

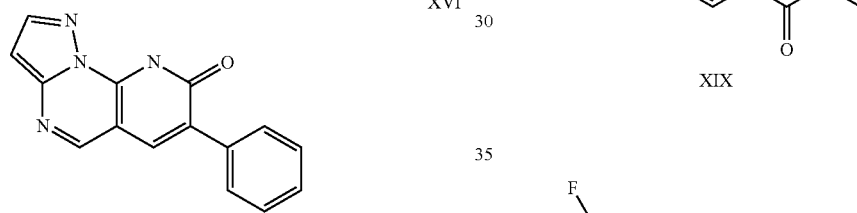

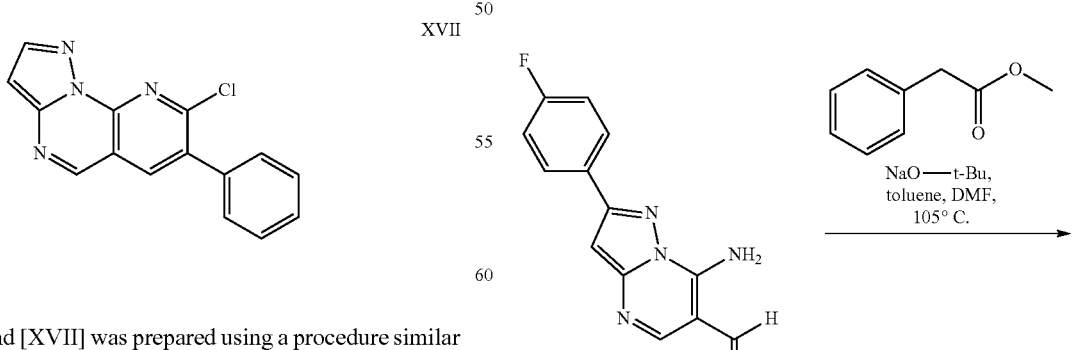

-continued

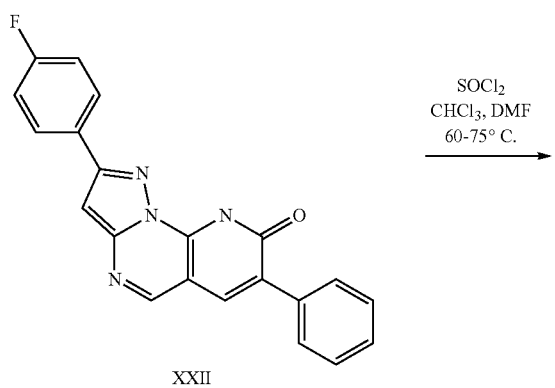

XXII

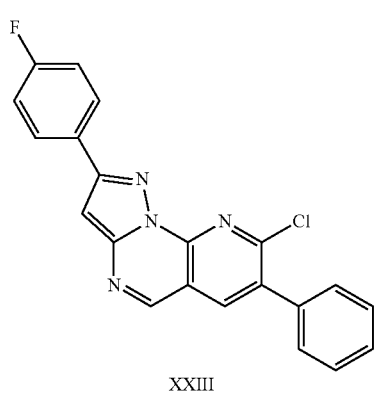

XXIII

7-Amino-2-(4-fluorophenyl)-pyrazolo[1,5-a]pyrimidine-6-carboxylic acid ethyl ester [XIX]

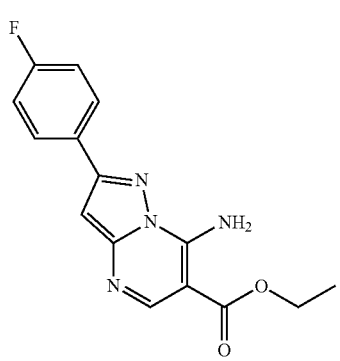

XIX

Compound [XX] was prepared using a procedure similar to that of Compound [VII]. Data for Compound [XIX]: LCMS m/e 301 (M+H); $^1$H NMR (400 MHz, DMSO-d$_6$) δ ppm 1.32 (t, J=7.08 Hz, 3H) 4.31 (q, J=7.08 Hz, 2H) 7.05 (s, 1H) 7.33 (t, J=8.83 Hz, 2H) 8.13 (dd, J=8.57, 5.64 Hz, 2H) 8.48 (br. s., 1H) 8.59 (s, 1H) 8.68 (br. s., 1H).

[7-Amino-2-(4-fluorophenyl)cyclopropyl-pyrazolo[1,5-a]pyrimidin-6-yl]-methanol [XX]

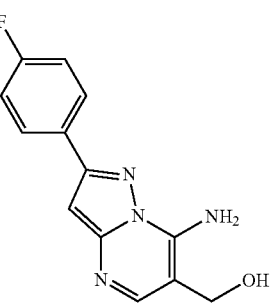

XX

Compound [XX] was prepared using a procedure similar to that of Compound [II]. Data for Compound [XX]: LCMS m/e 259 (M+H); $^1$H NMR (400 MHz, METHANOL-d$_4$) δ ppm 4.70 (s, 2H) 6.69 (s, 1H) 7.18 (t, J=8.79 Hz, 2H) 8.03-8.06 (m, 2H) 8.07 (s, 1H).

7-Amino-2-(4-fluorophenyl)-pyrazolo[1,5-a]pyrimidin-6-carbaldehyde [XXI]

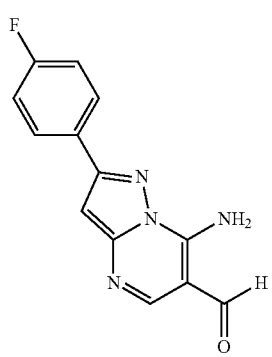

XXI

Compound [XXI] was prepared using a procedure similar to that of Compound [III]. Data for Compound [XXI]: LCMS m/e 257 (M+H); $^1$H NMR (400 MHz, METHANOL-d$_4$) δ ppm 6.88 (s, 1H) 7.21 (t, J=8.81 Hz, 2H) 8.10 (dd, J=8.81, 5.39 Hz, 2H) 8.50 (s, 1H).

2-(4-Fluorophenyl)-7-phenyl-9H-1,4,9,9b-tetraaza-cyclopenta[a]naphthalen-8-one [XXII]

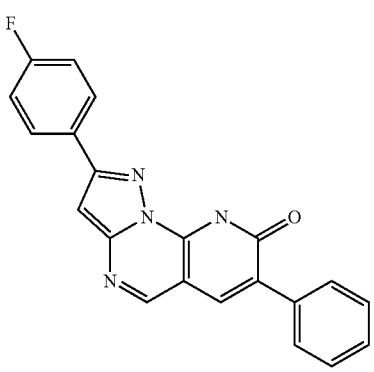

XXII

Compound [XXII] was prepared using a procedure similar to that of Compound [IV]. Data for Compound [XXII]: LCMS m/e 357 (M+H).

8-Chloro-2-(4-fluorophenyl)-7-phenyl-1,4,9,9b-tetraaza-cyclopenta[a]naphthalene [XXIII]

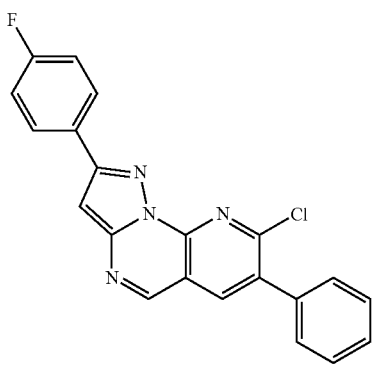

XXIII

Compound [XXIII] was prepared using a procedure similar to that of Compound [V] (POCl₃ procedure). Data for Compound [XXIII]: LCMS m/e 375 (M+H); ¹H NMR (400 MHz, CHLOROFORM-d) δ ppm 7.14-7.21 (m, 3H) 7.50-7.54 (m, 5H) 8.10-8.15 (m, 2H) 8.23 (s, 1H) 8.87 (s, 1H).

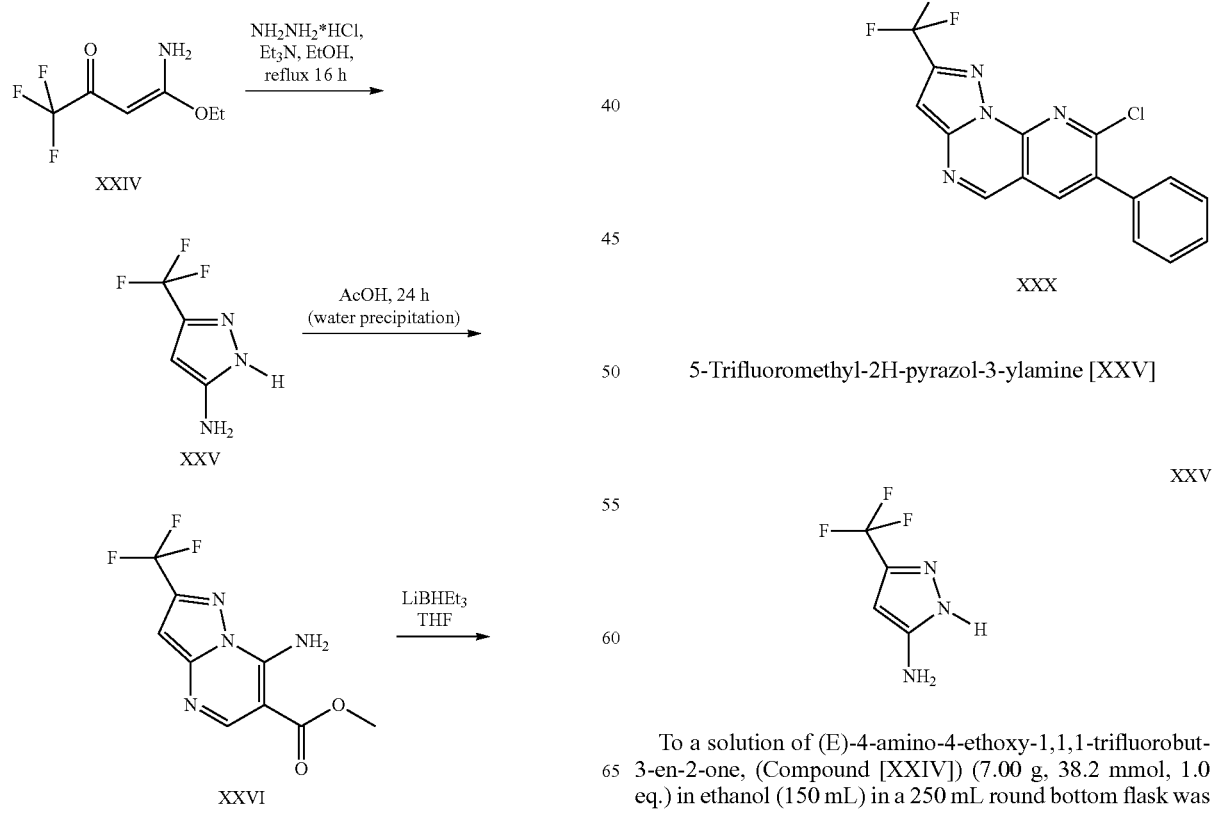

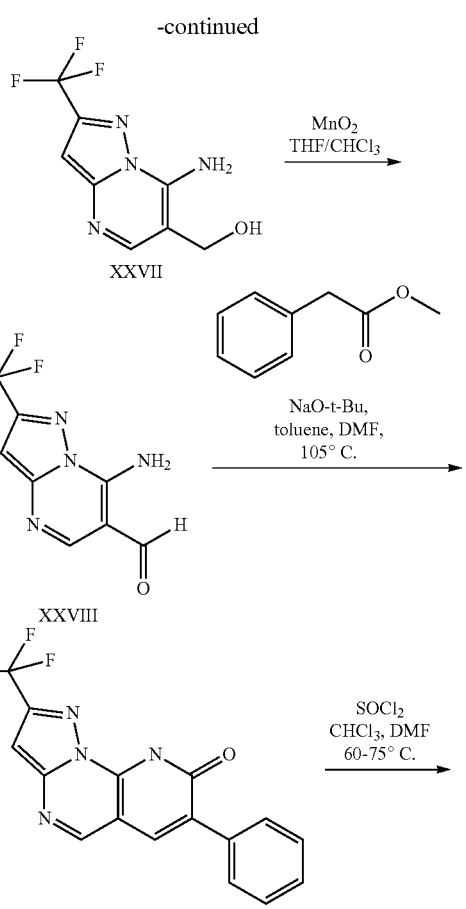

5-Trifluoromethyl-2H-pyrazol-3-ylamine [XXV]

To a solution of (E)-4-amino-4-ethoxy-1,1,1-trifluorobut-3-en-2-one, (Compound [XXIV]) (7.00 g, 38.2 mmol, 1.0 eq.) in ethanol (150 mL) in a 250 mL round bottom flask was added hydrazine hydrochloride (2.75 g, 40.16 mmol, 1.05 eq.) followed by triethylamine (4.05 g, 40.16 mmol, 1.05 eq.). The reaction mixture was heated to reflux for 16 hours. After cooling and concentration, the residue was purified by silica gel chromatography using CHCl₃-MeOH (10%) as the eluant to give Compound [XXV]: LCMS m/e 152 (M+H); ¹H NMR (400 MHz, DMSO-d₆) δ ppm 5.32 (s, 2H) 5.51 (s, 1H) 12.12 (br. s., 1H).

7-Amino-2-trifluoromethyl-pyrazolo[1,5-a]pyrimidine-6-carboxylic acid ethyl ester [XXVI]

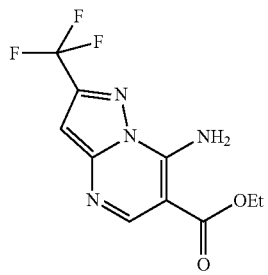

Compound [XXVI] was prepared using a procedure similar to that of Compound [VII]. Data for Compound [XXVI]: LCMS m/e 275 (M+H); ¹H NMR (400 MHz, CHLOROFORM-d) δ ppm 1.45 (t, J=7.15 Hz, 3H) 4.44 (q, J=7.13 Hz, 2H) 6.81 (s, 1H) 6.99 (br. s., 1H) 8.62 (br. s., 1H) 8.87 (s, 1H).

[7-Amino-2-trifluoromethyl-pyrazolo[1,5-a]pyrimidin-6-yl]-methanol [XXVII]

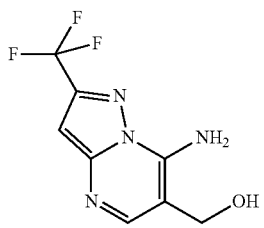

Compound [XXVII] was prepared using a procedure similar to that of Compound [III]. Data for Compound [XXVII]: LCMS m/e 233 (M+H); ¹H NMR (400 MHz, CHLOROFORM-d) δ ppm 4.88 (s, 2H) 6.75 (s, 1H) 8.17 (s, 1H).

7-Amino-2-trifluoromethyl-pyrazolo[1,5-a]pyrimidin-6-carbaldehyde [XXVIII]

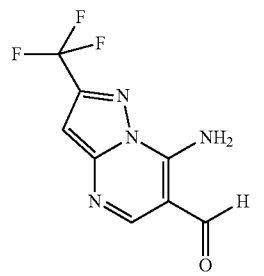

Compound [XXVIII] was prepared using a procedure similar to that of Compound [III]. Data for Compound [XX-VIII]: LCMS m/e 231 (M+H); ¹H NMR (400 MHz, CHLOROFORM-d) δ ppm 6.83 (s, 1H) 8.60 (s, 1H) 9.99 (s, 1H).

2-trifluoromethyl-7-phenyl-9H-1,4,9,9b-tetraaza-cyclopenta[a]naphthalen-8-one [XXIX]

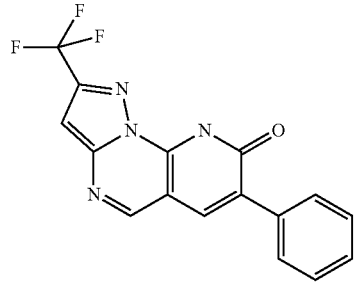

Compound [XXIX] was prepared using a procedure similar to that of Compound [IV]. Data for Compound [XXIX]: LCMS m/e 331 (M+H); ¹H NMR (400 MHz, DMSO-d₆) δ ppm 7.33 (s, 1H) 7.38-7.44 (m, 1H) 7.48 (t, J=7.42 Hz, 2H) 7.71 (d, J=7.22 Hz, 2H) 8.54 (s, 1H) 9.05 (s, 1H).

8-Chloro-2-trifluoromethyl-7-phenyl-1,4,9,9b-tetraaza-cyclopenta[a]naphthalene [XXX]

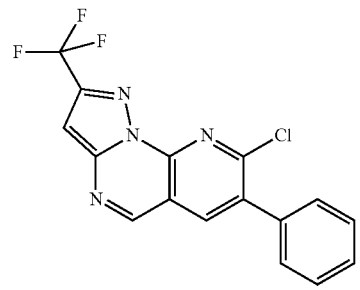

Compound [XXX] was prepared using a procedure similar to that of Compound [V] (POCl₃ procedure). Data for Compound [XXX]: LCMS m/e 349 (M+H); ¹H NMR (400 MHz, METHANOL-d₄) δ ppm 7.28 (s, 1H) 7.46-7.64 (m, 5H) 8.66 (s, 1H) 9.19 (s, 1H).

Synthesis of Cyclobutylamine Headgroup

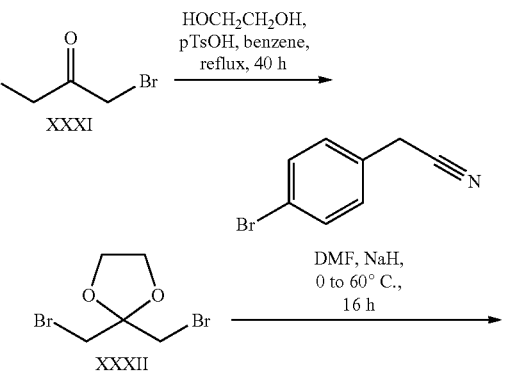

2,2-Bis-bromomethyl-1,3-dioxolane [XXXI]

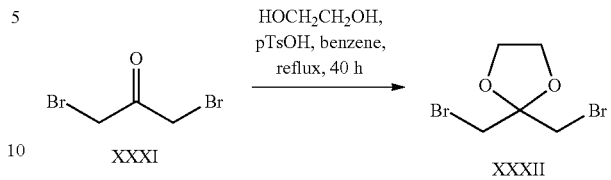

Compound [XXXI] (46.3 g, 215 mmol, 1.0 eq.), ethylene glycol (310 mL, 4.29 mol, 20 eq.), p-toluenesulfonic acid (408 mg, 2.15 mmol, 0.01 eq.), and benzene (1.40 L, anhydrous) were added to a 2 L round bottom flask, which as fitted with a Dean-Stark apparatus. The reaction was heated to 125° C. for 40 hours with azeotropic removal of water. After the collection of water ceased, the reaction was cooled, and poured into saturated aqueous NaHCO₃ solution. The aqueous layer was extracted with ether (×3). The combined organic layers were dried and concentrated and the residue purified by silica gel chromatography by eluting with ethyl acetate and heptane (using a gradient of 0% to 25% ethyl acetate) to give Compound [XXXII]: ¹H NMR (400 MHz, CHLOROFORM-d) δ ppm 3.61 (s, 4H) 4.14 (s, 4H).

2-(4-Bromo-phenyl)-5,8-dioxa-spiro[3.4]octane-2-carbonitrile [XXXIII]

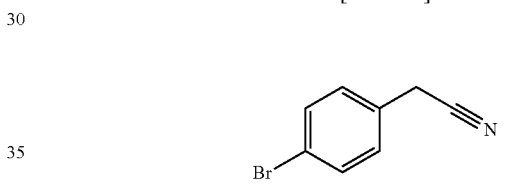

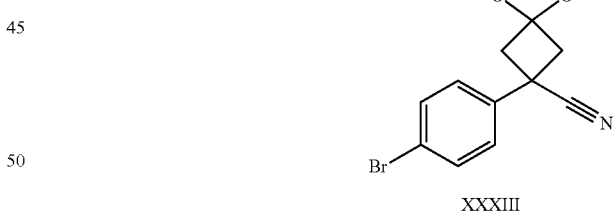

4-Bromobenzylnitrile (78.7 g, 402 mmol, 2.0 eq.) was dissolved in DMF (425 mL, anhydrous) and cooled to 0° C. To this mixture was slowly added NaH (portionwise, 24.1 g, 60% dispersion in mineral oil, 1.00 mol, 5 eq.) and the reaction stirred at 0° C. for 20 min. Then Compound [XXXII] (52.2 g, 201 mmol, 1.0 eq.) was added and the mixture stirred at 0° C. for 20 min, and then warmed to 60° C. for 16 hours. After 16 hours at 60° C., the reaction was cooled to 0° C. and slowly quenched with MeOH, diluted with water, and extracted with ethyl acetate (×3). The combined organic phases were washed with water (×2), dried over Na₂SO₄, and concentrated. The resulting oil was diluted with ethyl acetate and heptane and placed onto a silica pad, which was then eluted with heptane/ethyl acetate (4:1). The collected frac-

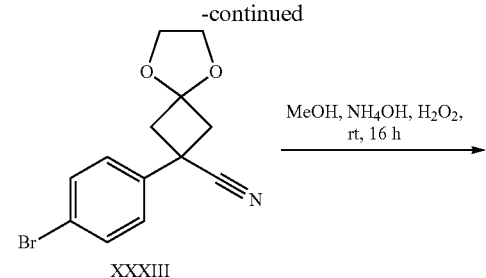

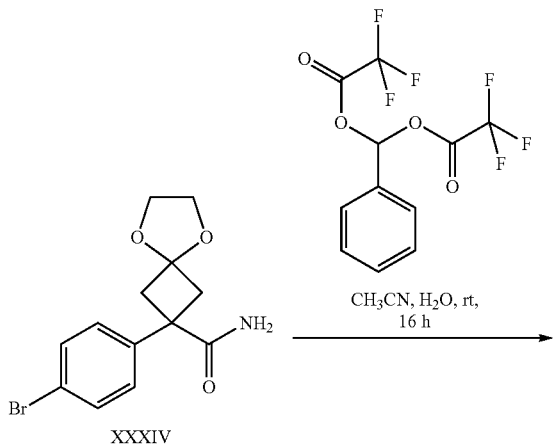

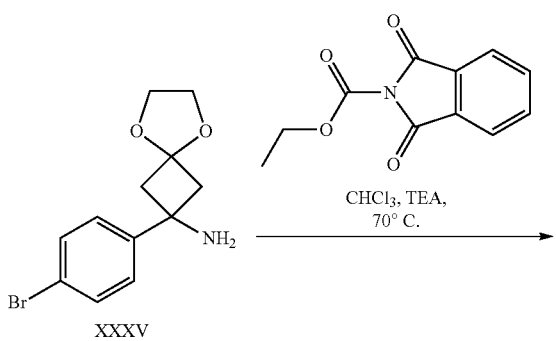

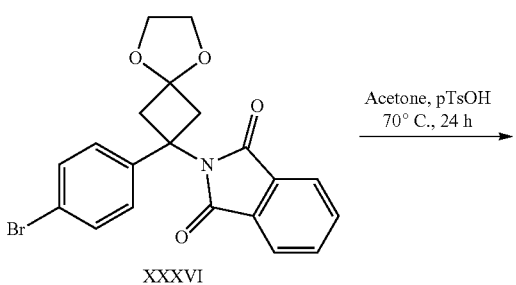

tions were concentrated, and the resulting oil purified by silica gel chromatography eluting with heptane and ethyl acetate (gradient of 0% to 50% EtOAc) to provide Compound [XXXIII]: $^1$H NMR (400 MHz, CHLOROFORM-d) δ ppm 2.89-3.01 (m, 2H) 3.21-3.33 (m, 2H) 3.91-3.97 (m, 2H) 3.98-4.06 (m, 2H) 7.41 (m, 2H) 7.48-7.60 (m, 2H).

2-(4-Bromo-phenyl)-5,8-dioxa-spiro[3,4]octane-2-carboxylic acid amide [XXXIV]

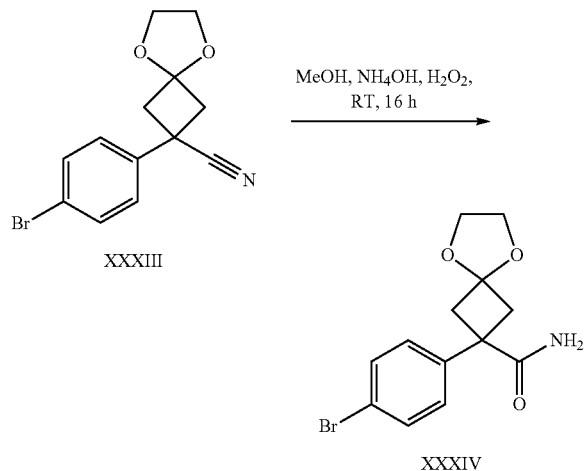

To a mixture of Compound [XXXIII] (13.0 g, 44.2 mmol, 1.0 eq.) in MeOH (520 mL) was added H$_2$O$_2$ (13.7 mL, 33% in water, 133 mmol, 3.00 eq.), and NH$_4$OH (52 mL). The resulting mixture was stirred for 16 hours at room temperature, then diluted with additional water and extracted with ethyl acetate (×3). The combined organics were washed with Na$_2$S$_2$O$_3$ (10% in water), dried, and concentrated. The residue was purified by silica gel chromatography by eluting with heptane and ethyl acetate (gradient of 0% to 100% EtOAc) to give Compound [XXXIV]: LCMS (m/e) 312, 314 (M+H); $^1$H NMR (400 MHz, CHLOROFORM-d) δ ppm 2.78-2.87 (m, 2H) 3.22-3.29 (m, 2H) 3.84-3.91 (m, 2H) 3.91-3.99 (m, 2H) 5.42 (br. s., 2H) 7.19-7.25 (m, 2H) 7.48-7.55 (m, 2H).

2-(4-Bromo-phenyl)-5,8-dioxa-spiro[3.4]oct-2-ylamine [XXXV]

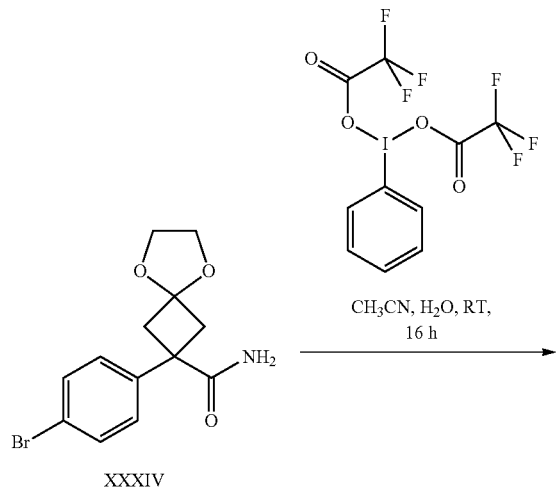

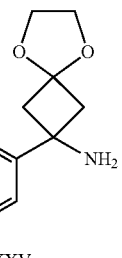

To a solution of Compound [XXXIV] (8.40 g, 26.9 mmol, 1.0 eq.) in CH$_3$CN (26 mL) and water (26 mL) was added [bis(trifluoroacetoxy)iodo]benzene (17.4 g, 40.4 mmol, 1.5 eq.) and the resulting mixture stirred at room temperature. After 16 hours the reaction was slowly poured into NaHCO$_3$ (aq sat) and extracted with ethyl acetate (×3). The combined organic layers were dried, concentrated, and the residue purified by silica gel chromatography by eluting with CHCl$_3$ to CHCl$_3$/MeOH/NH$_4$OH (95:5:1) to give Compound [XXXV]: $^1$H NMR (400 MHz, ACETONITRILE-d$_3$) δ ppm 2.40-2.50 (m, 2H) 2.73-2.82 (m, 2H) 3.77-3.85 (m, 2H) 3.85-3.93 (m, 2H) 7.37-7.44 (m, 2H) 7.45-7.52 (m, 2H).

2-[2-(4-Bromo-phenyl)-5,8-dioxa-spiro[3.4]oct-2-yl]-isoindole-1,3-dione [XXXVI]

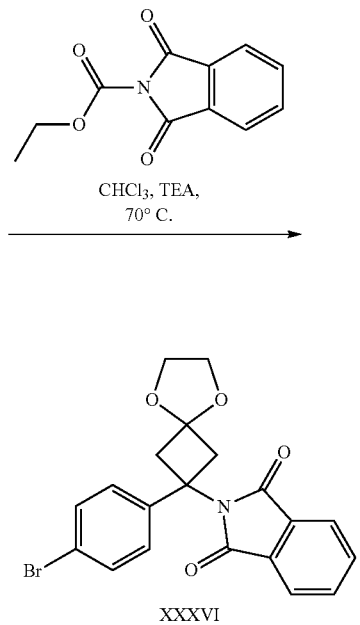

To a solution of Compound [XXXV] (6.03 g, 21.2 mmol, 1.0 eq.) in CHCl$_3$ (100 mL, anhydrous) was added N-ethoxy-carbonylphthalimide (5.12 g, 23.3 mmol, 1.1 eq.) and triethylamine (11.8 mL, 84.9 mmol, 4.0 eq.). The mixture was then heated to 70° C. for 24 hours. The reaction was then cooled and concentrated. Methanol was added to the residue, and the mixture concentrated, then methanol was added again, and the resulting solid collected by filtration to provide Compound [XXXVI] as a light tan solid: $^1$H NMR (400 MHz, CHLOROFORM-d) δ ppm 3.30-3.39 (m, 2H) 3.44-3.53 (m, 2H) 3.89 (s, 4H) 7.42-7.49 (m, 2H) 7.50-7.58 (m, 2H) 7.69 (dd, J=5.34, 3.10 Hz, 2H) 7.78 (dd, J=5.54, 3.00 Hz, 2H).

2-[1-(4-Bromo-phenyl)-3-oxo-cyclobutyl]-isoindole-1,3-dione [XXXVII]

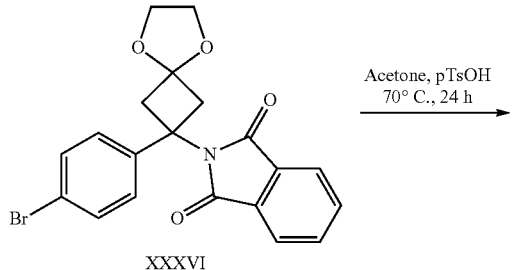

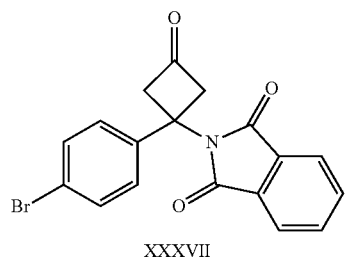

To a mixture of Compound [XXXVI] (3.25 g, 7.85 mmol, 1.0 eq.) in acetone (300 mL), was added p-toluenesulfonic acid (1.49 g, 7.85 mmol, 1.0 eq.) with stirring and heated to 70° C. After 64 hours at 70° C., the reaction was cooled and poured into saturated aqueous NaHCO₃ and extracted with ethyl acetate (×3). The combined organic phases were concentrated and the resulting residue purified by silica gel chromatography eluting with heptane and ethyl acetate (gradient of 0% to 40% ethyl acetate) to give Compound [XXXVII]: $^1$H NMR (400 MHz, CHLOROFORM-d) δ ppm 3.92-4.01 (m, 2H) 4.20-4.33 (m, 2H) 7.44-7.52 (m, 4H) 7.74 (dd, J=5.37, 3.12 Hz, 2H) 7.84 (dd, J=5.54, 3.00 Hz, 2H).

Scheme VII. Conversion of cyclobutanone to alkylcyclobutanol

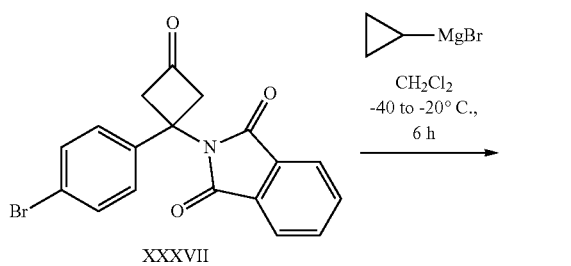

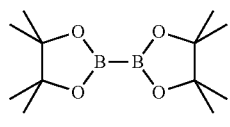

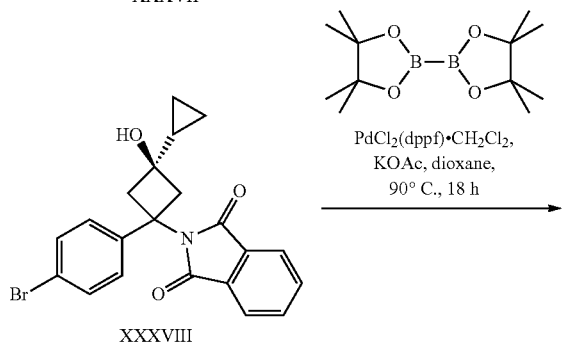

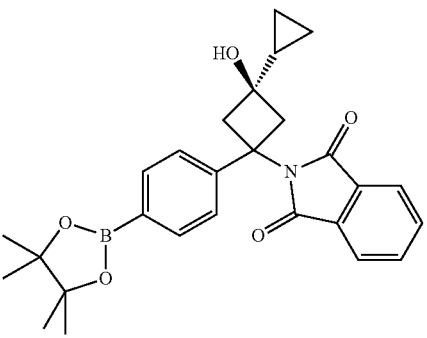

trans-2-[1-(4-Bromo-phenyl)-3-cyclopropyl-3-hydroxy-cyclobutyl]-isoindole-1,3-dione [XXXVIII]

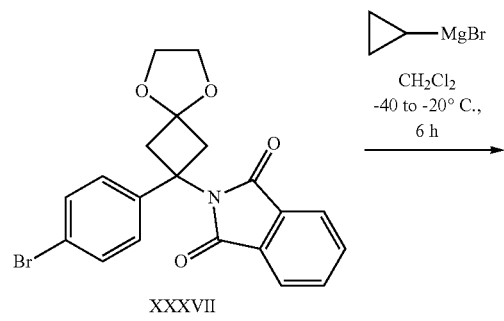

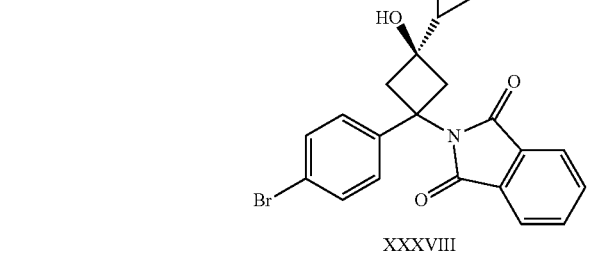

To a solution of Compound [XXXVII] (122 mg, 0.3 mmol, 1 eq.) in CH₂Cl₂ (6 mL) at −40° C. was added dropwise a solution of cyclopropylmagnesium bromide (0.6 mL of a 0.5 M solution in THY, 0.3 mmol, 1 eq.). The mixture was held at −20° C. for 6 hours and then quenched by the addition of saturated aqueous NH₄Cl solution. The mixture was extracted three times with CH₂Cl₂. The combined organic phases were dried over Na₂SO₄ and the material concentrated under reduced pressure. Purification of the residue using silica gel chromatography with ethyl acetate:heptane as the eluant provided Compound [XXXVIII]: $^1$H NMR (400 MHz, CHLOROFORM-d) δ ppm 0.23-0.36 (m, 2H) 0.40-0.54 (m, 2H) 1.08-1.20 (m, 1H) 2.97-3.07 (m, 2H) 3.06-3.16 (m, 2H) 7.42-7.49 (m, 2H) 7.55-7.63 (m, 2H) 7.68 (dd, J=5.42, 3.08 Hz, 1H) 7.72-7.82 (m, 2H) 7.88 (dd, J=5.52, 3.03 Hz, 1H).

trans-2-{3-Cyclopropyl-3-hydroxy-1-[4-(4,4,5,5-tetramethyl-[1,3,2]dioxaborolan-2-yl)-phenyl]-cyclobutyl}-isoindole-1,3-dione [XXXIX]

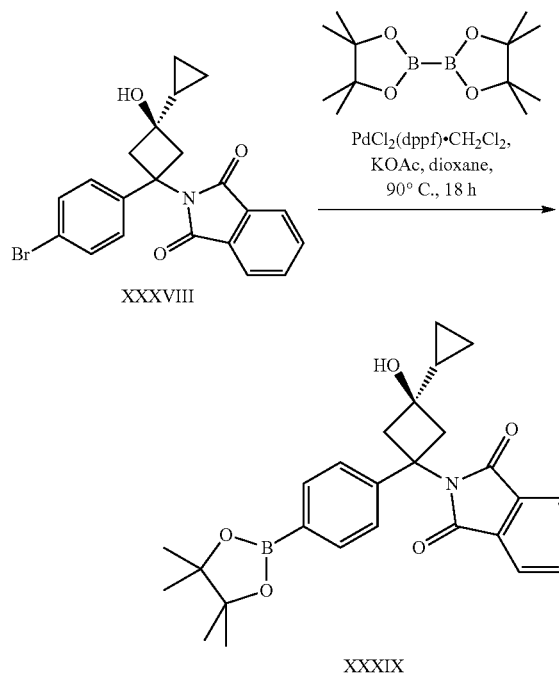

A flask containing mixture of Compound [XXXVIII] (82 mg, 0.20 mmol, 1 eq.), bis(pinacolato)diboron (51 mg, 0.20 mmol, 1 eq.), and KOAc (98 mg, 1.0 mmol, 1 eq.) in dioxane (4 mL) was evacuated and refilled with a nitrogen atmosphere three times. Then PdCl₂(dppt) (16 mg, 0.02 mmol, 0.1 eq.) was added and the flask was again evacuated and refilled three times with a nitrogen atmosphere. The resulting mixture was heated at 90° C. for 18 hours. The volatiles were removed under reduced pressure and the resulting residue purified by silica gel chromatography using ethyl acetate:heptane as the eluants to provide Compound [XXXIX]: LCMS (m/e) 442 (M−H₂O); ¹H NMR (400 MHz, CHLOROFORM-d) δ ppm 2.64 (s, 3H) 3.42-3.52 (m, 2H) 3.90-4.00 (m, 2H) 5.25 (br. s., 1H) 5.44 (br. s., 1H) 6.75 (s, 1H) 7.22-7.26 (m, 1H) 7.27-7.28 (m, 1H) 7.31 (d, J=8.20 Hz, 2H) 7.35-7.39 (m, 3H) 7.64 (d, J=8.15 Hz, 2H) 8.29 (s, 1H) 8.90 (s, 1H).

Coupling and Deprotection trans-2-{3-Cyclopropyl-3-hydroxy-1-[4-(2-methyl-7-phenyl-1,4,9,9b-tetraaza-cyclopenta[a]naphthalen-8-yl)-phenyl]-cyclobutyl}-isoindole-1,3-dione [XL]

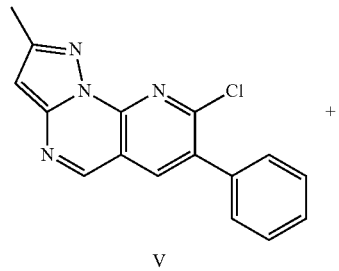

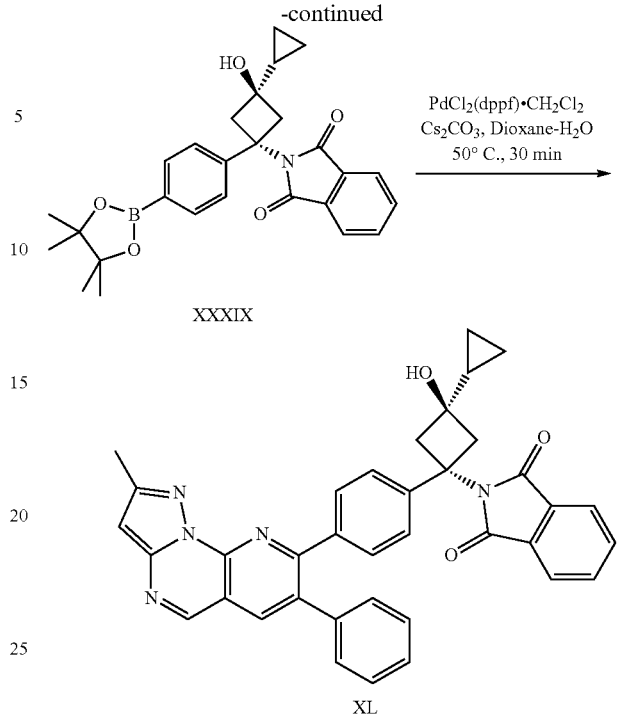

A 20 mL scintillation vial containing a mixture of Compound [V] (133 mg, 0.45 mmol, 1.5 eq.), Compound [XXXIX] (138 mg, 0.30 mmol, 1.0 eq.), Cs₂CO₃ (489 mg, 1.5 mmol, 5.0 eq.)) and dioxane-water [3:1] (8 mL) was evacuated and flushed three times with argon. Then PdCl₂(dppf).CH₂Cl₂ (49 mg, 0.06 mmol, 20%) was added and the resulting solution again evacuated and flushed with argon three times. The mixture was heated at 50° C. for 1 hour. The mixture was allowed to cool, water (25 mL) was added, and the resulting mixture was extracted with EtOAc (3×25 mL). The combined organic phases were dried over Na₂SO₄ and the material concentrated under reduced pressure. The residue was purified by silica gel chromatography using CH₂Cl₂ and [CH₂Cl₂—CH₃OH—NH₄OH 90:9:1] as the mobile phases to furnish Compound [XL] as a pale yellow solid: LCMS (m/e): 592 (M+H); ¹H NMR. (400 MHz, CHLOROFORM-d) δ ppm 0.02 (q, J=5.27 Hz, 2H) 0.15-0.21 (m, 2H) 0.81-0.89 (m, 1H) 2.29 (s, 3H) 2.71-2.78 (m, 2H) 2.81-2.88 (m, 2H) 6.40 (s, 1H) 6.93-6.97 (m, 2H) 6.98-7.03 (m, 3H) 7.21-7.25 (m, 2H) 7.29-7.34 (m, 2H) 7.37-7.42 (m, 2H) 7.45-7.50 (m, 2H) 7.92 (s, 1H) 8.55 (s, 1H).

trans-3-Amino-1-cyclopropyl-3-[4-(2-methyl-7-phenyl-1,4,9,9b-tetraaza-cyclopenta[a]naphthalen-8-yl)-phenyl]-cyclobutanol [XLI]

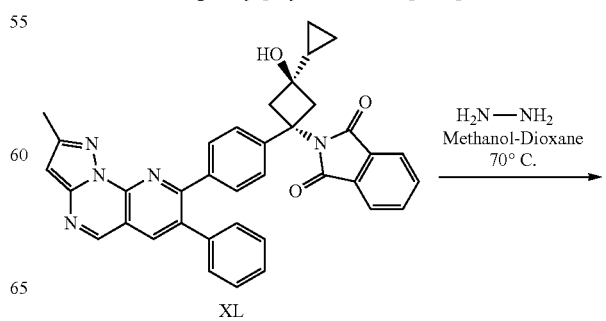

-continued

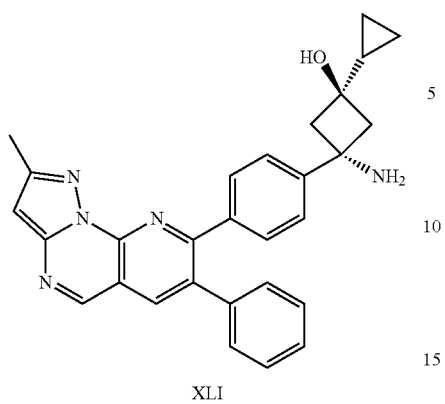

XLI

To a 20 mL scintillation vial containing Compound [XL] (200 mg, 0.34 mmol) in methanol-dioxane (1:1) (10 mL) was added hydrazine (1.3 mL, 40 mmol, 120 eq.). The mixture was heated at 70° C. for 2 hours. The solvent was then evaporated under reduced pressure. The residue was dissolved in MeOH/Water/TFA and purified by reverse-phase preparative HPLC using water-acetonitrile-TFA [95:5:0.05] and acetonitrile-water-TFA [95:5:0.05] as the mobile phases to provide Compound [XLI] as a pale yellow solid: LCMS (m/e) 462 (M+H); $^1$H NMR (400 MHz, METHANOL-$d_4$) δ ppm 0.39-0.44 (m, 2H) 0.45-0.51 (m, 2H) 1.15-1.23 (m, 1H) 2.59 (s, 3H) 2.61-2.66 (m, 2H) 2.76-2.82 (m, 2H) 6.77 (s, 1H) 7.32-7.37 (m, 5H) 7.53-7.56 (m, 2H) 7.72-7.75 (m, 2H) 8.56 (s, 1H) 9.05 (s, 1H).

Friedlander Cyclization

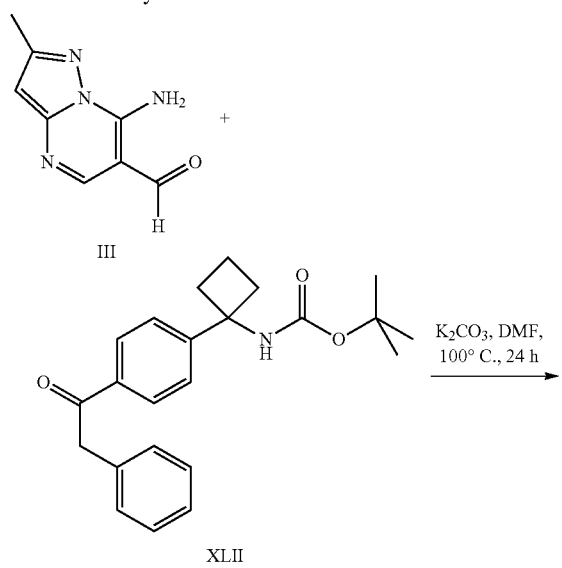

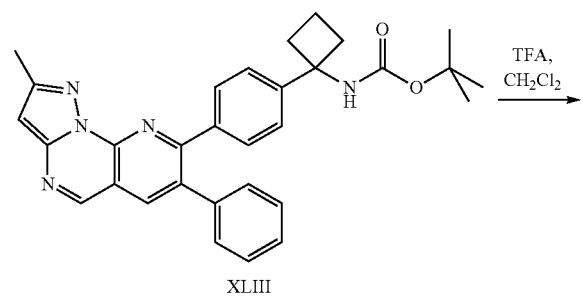

-continued

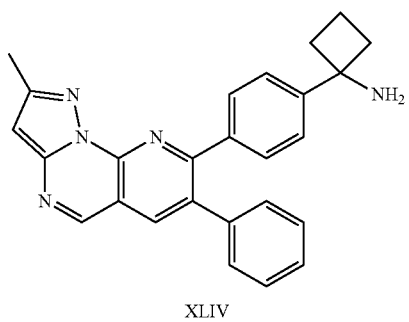

XLIV

{1-[4-(2-methyl-7-phenyl-1,4,9,9b-tetraaza-cyclopenta[a]naphthalen-8-yl)-phenyl]-cyclobutyl}-carbamic acid tert-butyl ester [XLIII]

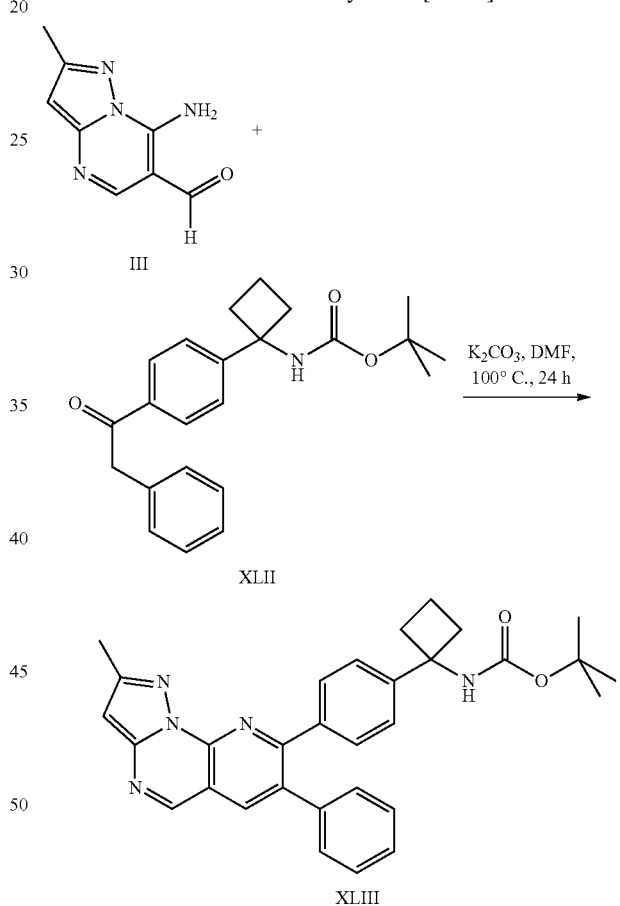

A mixture of Compound [III] (56 mg, 0.32 mmol, 1 eq.), Compound [XLII] (132 mg, 0.36 mmol, 1 eq.), K$_2$CO$_3$ (132 mg, 0.36 mmol, 1.1 eq.) in DMF (6 mL) was heated at 100° C. for 24 hours. After this time, the mixture was added to aqueous LiCl solution and then extracted three times with EtOAc. The combined organic phases were dried over Na$_2$SO$_4$ and concentrated under reduced pressure to afford a residue that was further purified by silica gel chromatography using CH$_2$Cl$_2$:EtOAc as the eluant to provide Compound [XLIII]. This material was used in the next step without further characterization.

1-[4-(2-methyl-7-phenyl-1,4,9,9b-tetraaza-cyclopenta[a]naphthalen-8-yl)-phenyl]-cyclobutylamine [XLIV]

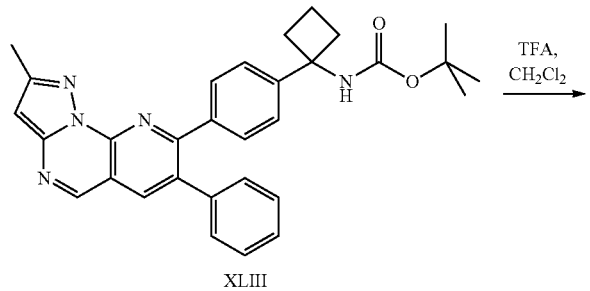

XLIII

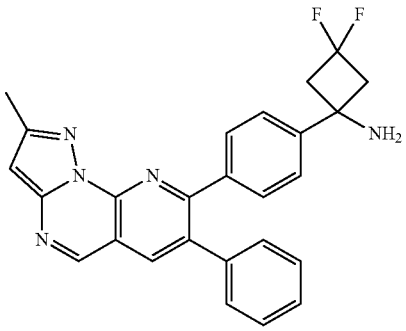

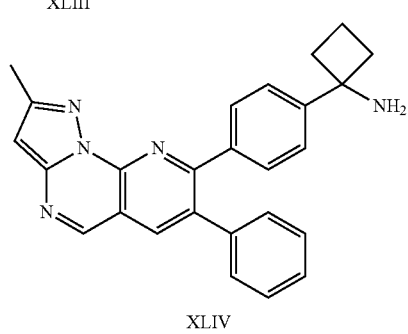

XLIV

To a solution of Compound [XLIII] (7 mg, 0.14 mmol, 1 eq.) in CH$_2$Cl$_2$ (3 mL) was added trifluoroacetic acid (1 mL) and the mixture stirred at room temperature for 15 minutes. The volatiles were removed under reduced pressure and the residue was purified by reverse phase HPLC using TFA:CH$_3$CN and water as the eluant to provide Compound [XLIV]: LCMS (m/e) 406 (M+H), $^1$H NMR (400 MHz, METHANOL-d$_4$) δ ppm 1.91-2.05 (m, 1H) 2.19-2.31 (m, 1H) 2.53-2.64 (m, 5H) 2.73-2.83 (m, 2H) 7.31-7.39 (m, 5H) 7.47 (d, 2H) 7.72 (d, 2H) 8.62 (s, 1H) 9.12 (s, 1H).

{3,3-Difluoro-1-[4-(2-methyl-7-phenyl-1,4,9,9b-tetraaza-cyclopenta[a]naphthalen-8-yl)-phenyl]-cyclobutyl}-carbamic acid tert-butyl ester [XLV]

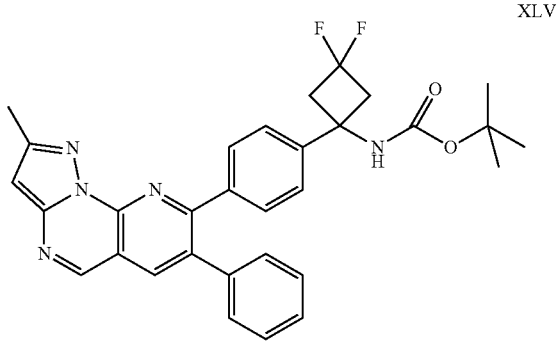 [SMILES: Cc1cc2ncc3cc(-c4ccccc4)c(-c4ccc(C5(NC(=O)OC(C)(C)C)CC(F)(F)C5)cc4)nc3n2n1]

XLV

Compound [XLV] was prepared using a procedure similar to that of Compound [XLIII]. This compound was carried on to the next step without further characterization.

3,3-Difluoro-1-[4-(2-methyl-7-phenyl-1,4,9,9b-tetraaza-cyclopenta[a]naphthalen-8-yl)-phenyl]-cyclobutylamine [XLVI]

XLVI

Compound [XLV] was prepared using a procedure similar to that of Compound [XLIV]. Data for Compound [XLIV]: LCMS (m/e) 442 (M+H); $^1$H NMR (400 MHz, METHANOL-d$_4$) δ ppm 2.59 (s, 3H) 3.41-3.52 (m, 2H) 6.78 (s, 1H) 7.32-7.38 (m, 5H) 7.52 (d, J=8.49 Hz, 2H) 7.76 (d, J=8.47 Hz, 2H) 8.58 (s, 1H) 9.06 (s, 1H).

{2-[4-(2-Methyl-7-phenyl-1,4,9,9b-tetraaza-cyclopenta[a]naphthalen-8-yl)-phenyl]-5,8-dioxa-spiro[3.4]oct-2-yl}-carbamic acid tert-butyl ester [XLVII]

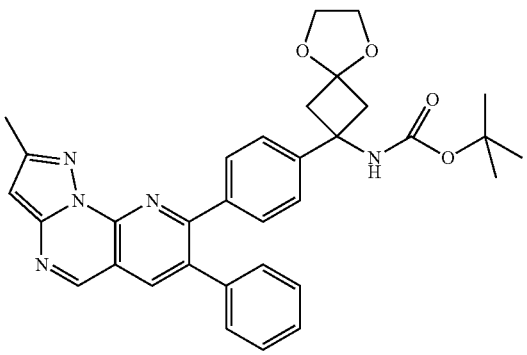

XLVII

Compound [XLVII] was prepared using a procedure similar to that of Compound [XLIII]. Data for Compound [XLVII]: LCMS (m/e) 564 (M+H); $^1$H NMR (400 MHz, CHLOROFORM-d) δ ppm 1.37 (br. s., 9H) 2.63 (s, 3H) 2.86-2.92 (m, 2H) 3.87-3.99 (m, 4H) 6.72 (s, 1H) 7.25-7.29 (m, 2H) 7.30-7.37 (m, 5H) 7.51-7.56 (m, 2H) 8.23 (s, 2H) 8.86 (s, 2H) 9.89 (s, 1H).

trans-2-[4-(2-Methyl-7-phenyl-1,4,9,9b-tetraaza-cyclopenta[a]naphthalen-8-yl)-phenyl]-5,8-dioxa-spiro[3.4]oct-2-ylamine

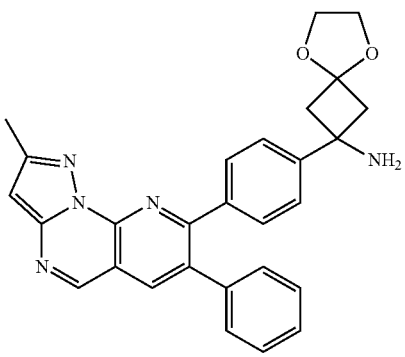

XLVIII

Compound [XLVIII] was prepared using a procedure similar to that of Compound [XLIV]. Data for Compound [XLVIII]: LCMS (m/e) 464 (M+H); ¹H NMR (400 MHz, METHANOL-d₄) d ppm 2.58 (d, J=5.61 Hz, 3H) 2.93-3.00 (m, 2H) 3.06-3.12 (m, 2H) 3.89-3.94 (m, 2H) 3.97-4.02 (m, 2H) 6.72-6.84 (m, 1H) 7.31-7.39 (m, 5H) 7.47 (d, J=7.22 Hz, 2H) 7.72 (t, J=8.19 Hz, 2H) 8.59 (d, 1H) 9.09 (d, J=16.74 Hz, 1H).

trans-2-[1-(4-Bromo-phenyl)-3-hydroxy-cyclobutyl]-isoindole-1,3-dione [XLIX]

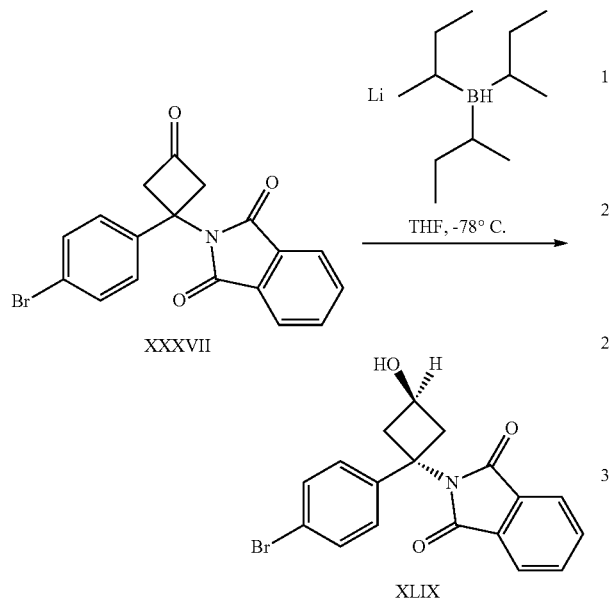

To a −78° C. solution of Compound [XXVII] (92 mg, 0.25 mmol, 1 eq.) in THF (2.5 mL) was added a solution of L-selectride (0.25 mL of a 1.0 M solution in THF, 0.25 mmol, 1 eq.). The mixture was allowed to stir 1 hour and then the mixture was quenched with the addition of saturated aqueous NaHCO₃ solution while the mixture was still at −78° C. The mixture was extracted three times with EtOAc and the combined organic phases were dried over Na₂SO₄ and the material concentrated under reduced pressure. The residue was purified by silica gel chromatography using EtOAc and heptane as the eluant to provide Compound [XLIX]: ¹H NMR (400 MHz, CHLOROFORM-d) δ ppm 2.72-2.85 (m, 2H) 3.75-3.86 (m, 2H) 4.47-4.57 (m, 1H) 7.42-7.47 (m, 2H) 7.47-7.52 (m, 2H) 7.65-7.72 (m, 2H) 7.73-7.82 (m, 2H).

trans-2-{3-Hydroxy-1-[4-(4,4,5,5-tetramethyl-[1,3,2]dioxaborolan-2-yl)-phenyl]-cyclobutyl}-isoindole-1,3-dione [L]

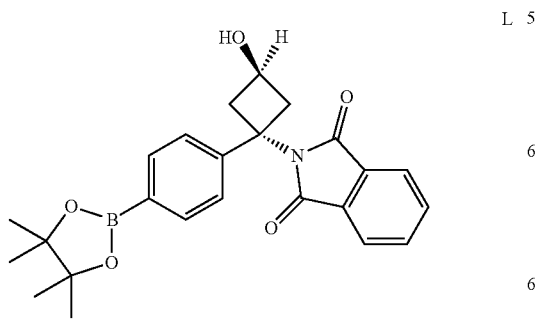

Compound [L] was prepared using a procedure similar to that of Compound [XXXIX]. Data for Compound [L]: ¹H NMR (400 MHz, CHLOROFORM-d) δ ppm 1.31 (s, 12H) 2.78-2.87 (m, 2H) 3.79-3.88 (m, 2H) 4.47-4.56 (m, 1H) 7.58-7.63 (m, 2H) 7.64-7.69 (m, 2H) 7.73-7.81 (m, 4H).

trans-2-{3-hydroxy-1-[4-(2-methyl-7-phenyl-1,4,9,9b-tetraaza-cyclopenta[a]naphthalen-8-yl)-phenyl]-cyclobutyl}-isoindole-1,3-dione [LI]

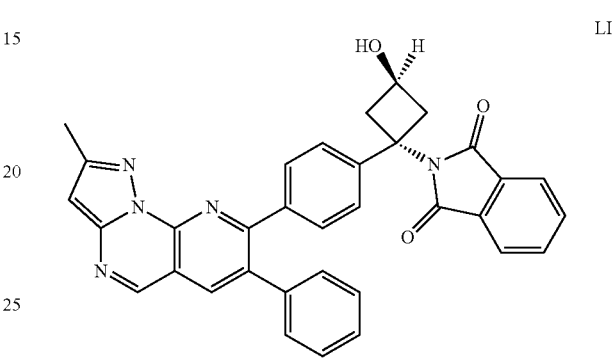

Compound [LI] was prepared in a similar way to that of Compound [XL]. Data for Compound [LI]: LCMS (m/e) 552 (M+H); ¹H NMR (400 MHz, CHLOROFORM-d) δ ppm 2.59 (s, 3H) 2.74-2.84 (m, 2H) 3.79-3.89 (m, 2H) 4.47-4.56 (m, 1H) 6.69 (s, 1H) 7.23-7.27 (m, 2H) 7.29-7.35 (m, 3H) 7.47-7.54 (m, 4H) 7.69 (dd, J=5.44, 3.10 Hz, 2H) 7.75-7.80 (m, 2H) 8.22 (s, 1H) 8.84 (s, 1H).

trans-3-Amino-3-[4-(2-methyl-7-phenyl-1,4,9,9b-tetraaza-cyclopenta[a]naphthalen-8-yl)-phenyl]-cyclobutanol [LII]

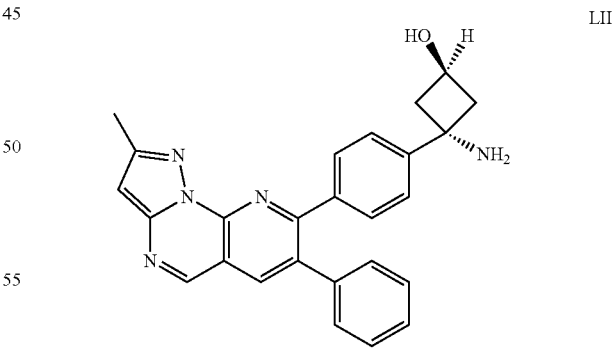

Compound [LI] was prepared in a similar way to that of Compound [XII]. Data for Compound [LI]: LCMS (m/e) 422 (M+H); ¹H NMR (400 MHz, METHANOL-d₄) δ ppm 2.57-2.66 (m, 5H) 2.95-3.03 (m, 2H) 4.60-4.70 (m, 1H) 6.77 (s, 1H) 7.29-7.41 (m, 7H) 7.72 (d, J=8.44 Hz, 2H) 8.57 (s, 1H) 9.06 (s, 1H).

trans-2-[1-(4-Bromo-phenyl)-3-methoxy-cyclobutyl]-isoindole-1,3-dione [LIII]

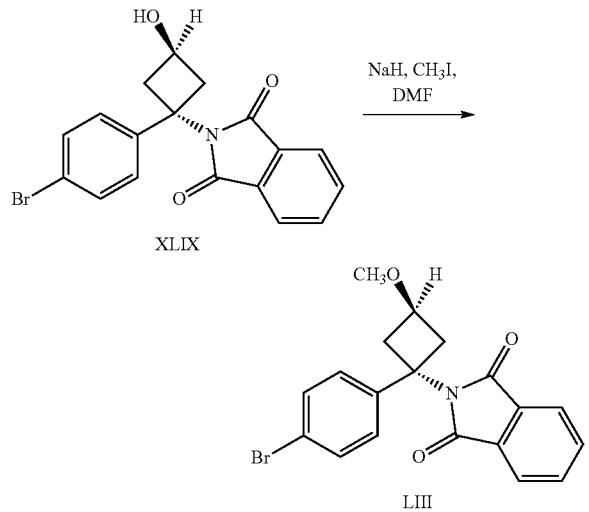

To a room temperature solution of Compound [XLIX] (56 mg, 0.15 mmol, 1 eq.) in DMF (1.5 mL) was added NaH (7.2 mg of a 60% dispersion in mineral oil, 0.18 mmol, 1.2 eq.) and the mixture stirred for 30 minutes. Then iodomethane (0.01 mL, 0.23 mmol, 1.5 eq.) was added and the mixture allowed to stir 1 hour. The mixture was quenched with the addition of aqueous ammonium chloride and the resulting mixture extracted three times with EtOAc. The combined organic phases were dried over $Na_2SO_4$ and the material concentrated under reduced pressure. The residue was purified by silica gel chromatography using EtOAc and heptane as the eluant to provide Compound [LIII]: $^1$H NMR (400 MHz, CHLOROFORM-d) δ ppm 2.75-2.84 (m, 2H) 3.24 (s, 3H) 3.68-3.78 (m, 2H) 4.01-4.10 (m, 1H) 7.41-7.49 (m, 4H) 7.66-7.72 (m, 2H) 7.75-7.81 (m, 2H).

trans-2-{3-Methoxy-1-[4-(4,4,5,5-tetramethyl-[1,3,2]dioxaborolan-2-yl)-phenyl]-cyclobutyl}-isoindole-1,3-dione [LIV]

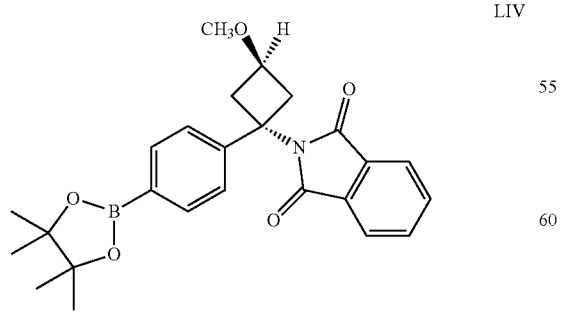

Compound [LIV] was prepared using a procedure similar to that of Compound [XXXIX].

trans-2-{3-methoxy-1-[4-(2-methyl-7-phenyl-1,4,9,9b-tetraaza-cyclopenta[a]naphthalen-8-yl)-phenyl]-cyclobutyl}-isoindole-1,3-dione [LV]

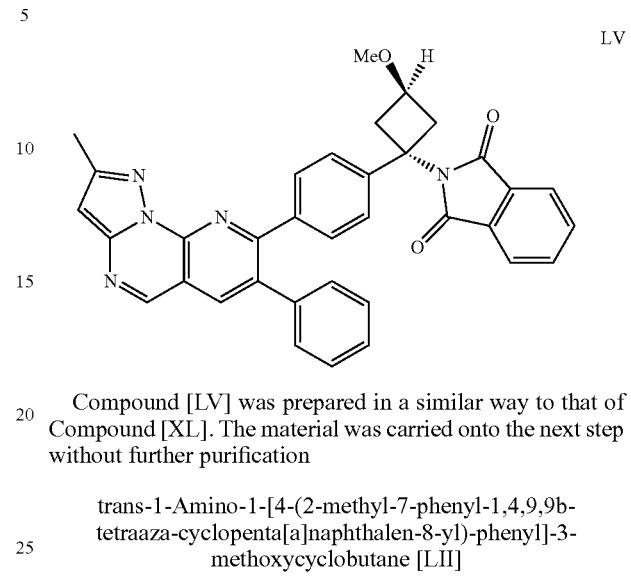

Compound [LV] was prepared in a similar way to that of Compound [XL]. The material was carried onto the next step without further purification trans-1-Amino-1-[4-(2-methyl-7-phenyl-1,4,9,9b-tetraaza-cyclopenta[a]naphthalen-8-yl)-phenyl]-3-methoxycyclobutane [LII]

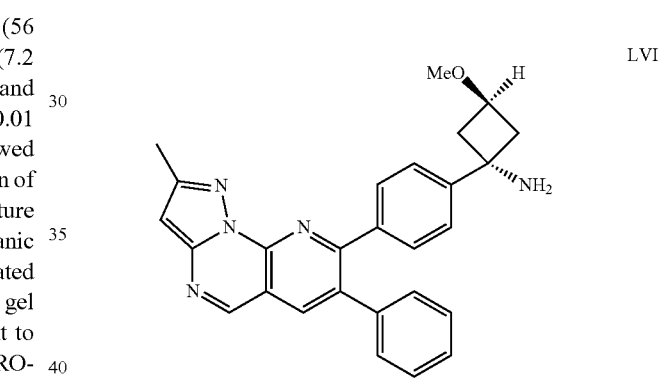

Compound [LVI] was prepared in a similar way to that of Compound [XL]. Data for Compound [LVI]: LCMS (m/e) 436 (M+H); $^1$H NMR (400 MHz, CHLOROFORM-d) δ ppm 2.47 (dd, J=12.10, 5.17 Hz, 4H) 2.54 (s, 3H) 2.98-3.07 (m, 2H) 3.21 (s, 3H) 4.28-4.38 (m, 1H) 6.70 (s, 1H) 7.00-7.06 (m, 2H) 7.17-7.26 (m, 4H) 7.30-7.35 (m, 3H) 8.61 (s, 1H) 8.93 (s, 1H).

2-[4-(4,4,5,5-Tetramethyl-[1,3,2]dioxaborolan-2-yl)-phenyl]-5,8-dioxa-spiro[3.4]octane-2-carbonitrile [LVII]

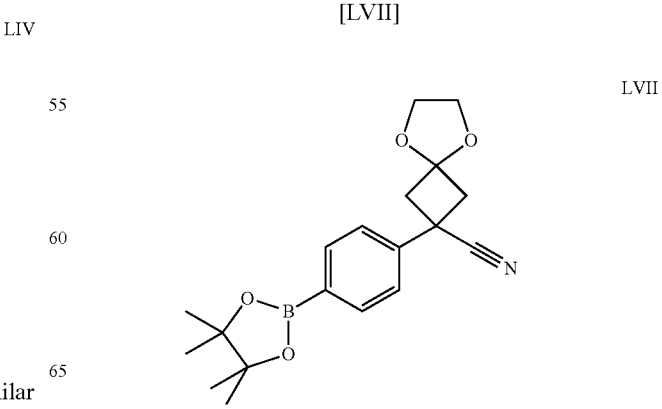

Compound [LVII] was prepared in a similar way to that of Compound [XXXIX] using Compound [XXXIII] as the starting material. Data for Compound [LVII]: $^1$H NMR (400 MHz, CHLOROFORM-d) δ ppm 1.36 (s, 12H) 2.98-3.04 (m, 2H) 3.22-3.28 (m, 2H) 3.90-3.97 (m, 2H) 3.99-4.07 (m, 2H) 7.52 (d, J=8.30 Hz, 2H) 7.85 (d, Hz, 2H).

2-[4-(2-methyl-7-phenyl-1,4,9,9b-tetraaza-cyclopenta[a]naphthalen-8-yl)-phenyl]-5,8-dioxa-spiro[3.4]octane-2-carbonitrile [LVIII]

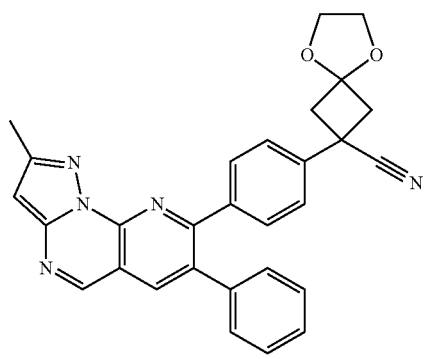

Compound [LVIII] was prepared in a similar way to that of Compound [XL]. Data for Compound [LVIII]: LCMS (m/e) 474 (M+H); $^1$H NMR (400 MHz, CHLOROFORM-d) δ ppm 2.64 (s, 3H) 2.93-2.98 (m, 2H) 3.22-3.27 (m, 2H) 3.92-3.96 (m, 2H) 4.00-4.05 (m, 2H) 6.73 (s, 1H) 7.24-7.26 (m, 1H) 7.27-7.29 (m, 1H) 7.35-7.38 (m, 3H) 7.43 (d, J=8.44 Hz, 2H) 7.60 (d, J=8.49 Hz, 2H) 8.27 (s, 1H) 8.88 (s, 1H).

[1-{4-(2-methyl-7-phenyl-1,4,9,9b-tetraaza-cyclopenta[a]naphthalen-8-yl)-phenyl}-3,3-dimethoxy-cyclobutyl]-carbamic acid methyl ester [LIX]

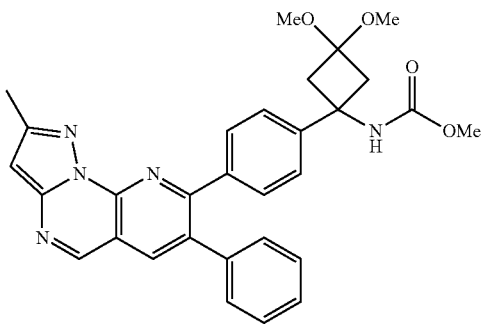

Compound [LIX] was prepared in a similar way to that of Compound [XL]. Data for Compound [LIX]: LCMS (mile) 524 (M+H); $^1$H NMR (400 MHz, CHLOROFORM-d) d ppm 2.63 (s, 3H) 2.66-2.76 (m, 4H) 3.14 (s, 3H) 3.22 (s, 3H) 3.60 (s, 3H) 5.23 (s, 1H) 6.72 (s, 1H) 7.27-7.30 (m, 2H) 7.31-7.32 (m, 1H) 7.32-7.37 (m, 4H) 7.52-7.56 (m, 2H) 8.24 (s, 1H) 8.86 (s, 1H).

[1-{4-(2-methyl-7-phenyl-1,4,9,9b-tetraaza-cyclopenta[a]naphthalen-8-yl)-phenyl}-3-oxo-cyclobutyl]-carbamic acid methyl ester [LX]

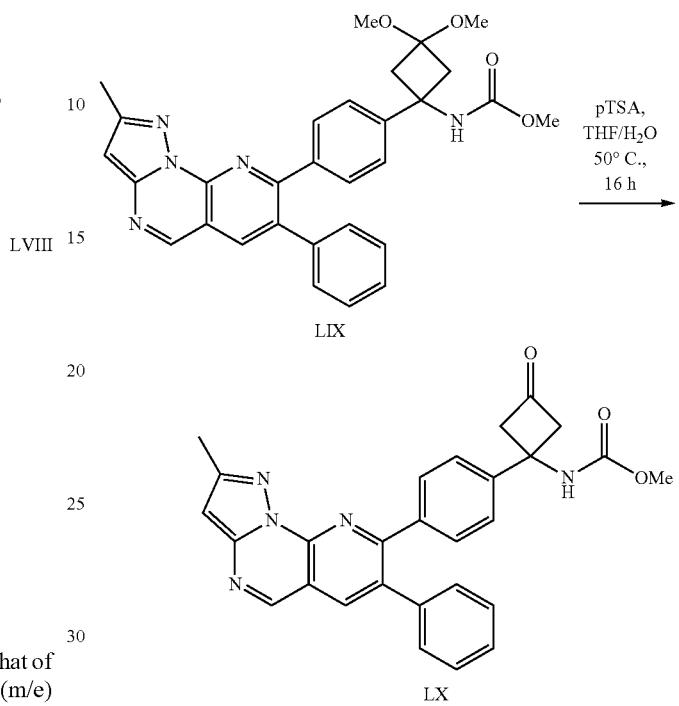

To Compound [LIX] (105 mg, 0.2 mmol, 1 eq.) in THF:H$_2$O [1:1] (20 mL) was added para-toluenesulfonic acid (38 mg, 0.2 mmol, 1 eq.) and the mixture heated to 50° C. After 16 hours, the mixture was added to saturated aqueous NaHCO$_3$ solution and then extracted three times with EtOAc. The combined organics were dried over Na$_2$SO$_4$, concentrated, and subjected to reverse phase chromatography using TFA acidified H$_2$O:CH$_3$CN as the eluant to furnish Compound [LX]: LCMS (m/e) 478 (M+H); $^1$H NMR (400 MHz, ACETONITRILE-d$_3$) δ ppm 2.54 (s, 3H) 3.52-3.55 (m, 4H) 3.56 (s, 3H) 6.57 (br. s., 1H) 6.70 (s, 1H) 7.28-7.33 (m, 2H) 7.35-7.39 (m, 4H) 7.40-7.41 (m, 1H) 7.45-7.48 (m, 2H) 8.41 (s, 1H) 8.93 (s, 1H).

1-(4-Bromo-phenyl)-ethane-1,2-diol [LXII]

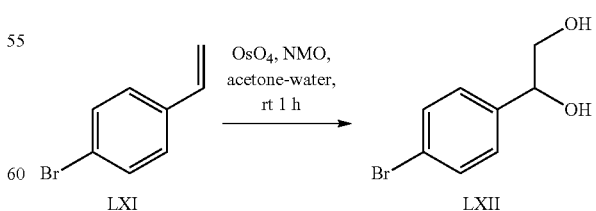

To 4-bromostyrene (Compound [LXI], 366 mg, 2 mmol, 1 eq.) in acetone (10 mL) was added morpholine N-oxide (953 mg of a 50% solution in H$_2$O, 4.0 mmol, 2.0 eq.) and then OsO$_4$ (1.3 g for a 4% OsO$_4$ in H$_2$O, 0.2 mmol, 0.1 eq). The mixture was allowed to stir at room temperature for 1 hour. The reaction mixture was then added to an aqueous solution of sodium thiosulfate and then extracted three times with EtOAc. The combined organics were dried over Na$_2$SO$_4$, concentrated, and subjected to silica gel chromatography using EtOAc-heptane as the eluant to provide Compound [LXII]: $^1$H NMR (400 MHz, METHANOL-d$_4$) δ ppm 3.54-3.66 (m, 2H) 4.66 (dd, J=6.76, 5.10 Hz, 1H) 7.24-7.35 (m, 2H) 7.41-7.53 (m, 2H).

1-[4-(4,4,5,5-Tetramethyl-[1,3,2]dioxaborolan-2-yl)-phenyl]-ethane-1,2-diol [LXIII]

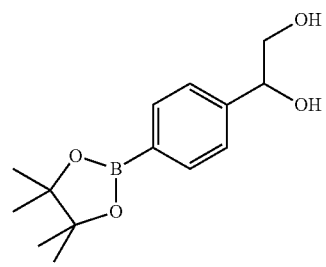

Compound [LXIII] was prepared in a similar way to that of Compound [XXXIX] using Compound [LXII] as the starting material.

Data for Compound [LXIII]: $^1$H NMR (400 MHz, CHLOROFORM-d) δ ppm 1.35 (s, 12H) 3.63-3.70 (m, 1H) 3.74-3.82 (m, 1H) 4.83-4.89 (m, 1H) 7.39 (d, J=7.76 Hz, 2H) 7.82 (d, J=8.00 Hz, 2H).

1-[4-(2-methyl-7-phenyl-1,4,9,9b-tetraaza-cyclopenta[a]naphthalen-8-yl)-phenyl]-ethane-1,2-diol [LXIV]

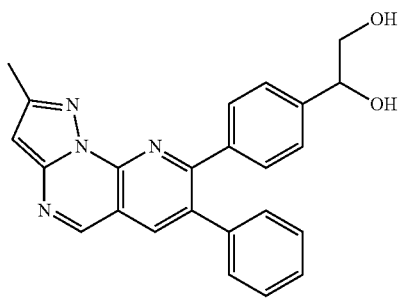

Compound [LXIV] was prepared in a similar way to that of Compound [XL]. Data for Compound [LXIV]: LCMS (m/e) 397 (M+H); $^1$H NMR (400 MHz, METHANOL-d$_4$) δ ppm 2.58 (s, 3H) 2.66 (s, 1H) 3.55-3.65 (m, 2H) 4.69 (dd, j=7.32, 4.59 Hz, 1H) 6.74 (s, 1H) 7.27-7.36 (m, 7H) 7.57 (d, J=8.30 Hz, 2H) 8.50 (s, 1H) 9.01 (s, 1H).

trans-2-[1-(4-Bromo-phenyl)-3-hydroxy-3-methyl-cyclobutyl]-isoindole-1,3-dione [LXV] and cis-2-[1-(4-bromo-phenyl)-3-hydroxy-3-methyl-cyclobutyl]-isoindole-1,3-dione [LXVI]

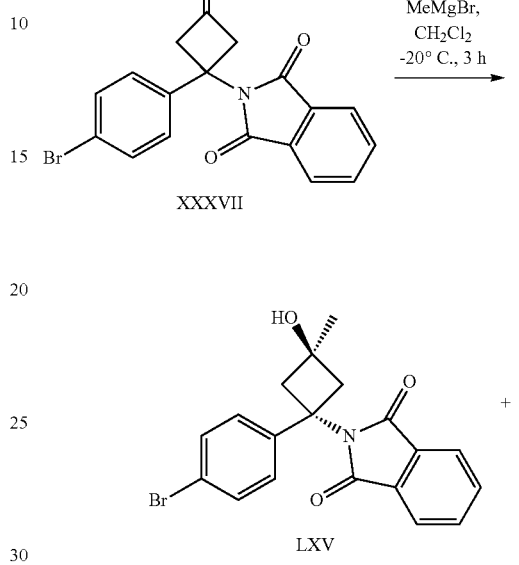

To a solution of Compound [XXXVII] (370 mg, 1 mmol, 1 eq.) in CH$_2$Cl$_2$ (10 mL) at −20° C. was added dropwise a solution of methylmagnesium bromide (0.33 mL of a 3.0 M solution in THF, 1 mmol, 1 eq.). The mixture was held at −20° C. for 3 hours and then quenched by the addition of saturated aqueous NH$_4$Cl solution before being allowed to warm to room temperature. The mixture was extracted with CH$_2$Cl$_2$ and the combined organic phases were dried over Na$_2$SO$_4$ and concentrated under reduced pressure. Purification of the residue using silica gel chromatography with ethyl acetate:heptane as the eluant provided Compound [LXV] and Compound [LXVI].

Data for Compound [LXV]: $^1$H NMR (400 MHz, CHLOROFORM-d) δ ppm 1.44 (s, 3H) 3.08-3.16 (m, 2H) 3.29-3.36 (m, 2H) 7.44-7.49 (m, 2H) 7.55-7.60 (m, 2H) 7.65-7.71 (m, 2H) 7.73-7.80 (m, 2H).

Data for Compound [LXVI]: $^1$H NMR (400 MHz, CHLOROFORM-d) δ ppm 1.15 (s, 3H) 3.08-3.16 (m, 2H) 3.28-3.35 (m, 2H) 7.45-7.50 (m, 2H) 7.59-7.64 (m, 2H) 7.64-7.69 (m, 2H) 7.71-7.78 (m, 2H).

trans-2-[1-(4-Bromo-phenyl)-3-hydroxy-3-methyl-cyclobutyl]-isoindole-1,3-dione [LXVII]

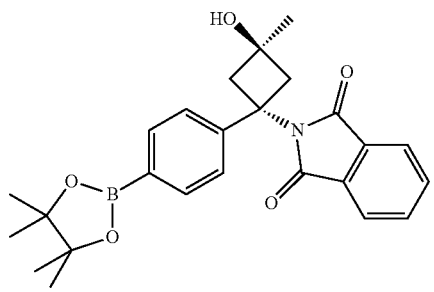

Compound [LXVII] was prepared in a similar way to that of Compound [XXXIX] using Compound [LXV] as the starting material.

Data for Compound [LXVII]: LCMS (m/e) 434 (M+H); $^1$H NMR (400 MHz, CHLOROFORM-d) δ ppm 1.31 (s, 12H) 1.44 (s, 3H) 3.15-3.22 (m, 2H) 3.32-3.39 (m, 2H) 7.64-7.67 (m, 2H) 7.69-7.72 (m, 2H) 7.73-7.77 (m, 2H) 7.78-7.82 (m, 2H).

trans-2-{3-Hydroxy-3-methyl-1-[4-(2-methyl-7-phenyl-1,4,9,9b-tetraaza-cyclopenta[a]naphthalen-8-yl)-phenyl]-cyclobutyl}-isoindole-1,3-dione [LXVIII]

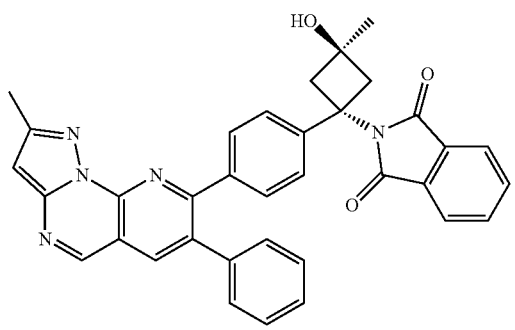

Compound [LXVIII] was prepared in a similar way to that of Compound [XL]. Data for Compound [LXVIII]: LCMS (m/e) 566 (M+H); $^1$H NMR (400 MHz, CHLOROFORM-d) δ ppm 1.44 (s, 3H) 1.56 (s, 1H) 2.59 (s, 3H) 3.10-3.16 (m, 2H) 3.33-3.39 (m, 2H) 6.69 (s, 1H) 7.23-7.26 (m, 2H) 7.28-7.33 (m, 3H) 7.51-7.55 (m, 2H) 7.57-7.61 (m, 2H) 7.67-7.72 (m, 2H) 7.75-7.79 (m, 2H) 8.22 (s, 1H) 8.84 (s, 1H).

trans-3-Amino-1-methyl-3-[4-(2-methyl-7-phenyl-4,4,9,9b-tetraaza-cyclopenta[a]naphthalen-8-yl)-phenyl]-cyclobutanol [LXIX]

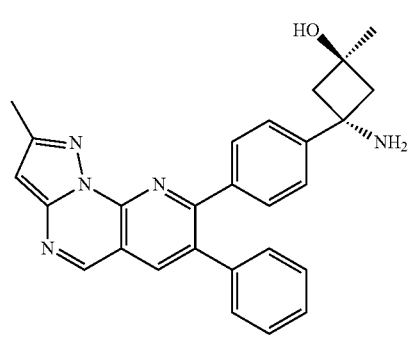

Compound [LXIX] was prepared in a similar way to that of Compound [XLI]. Data for Compound [LXIX]: LCMS (m/e) 436 (M+H); $^1$H NMR (400 MHz, CHLOROFORM-d) δ ppm 1.43 (s, 3H) 2.40 (s, 3H) 2.58-2.65 (m, 2H) 2.65-2.71 (m, 2H) 6.59 (s, 1H) 7.10-7.15 (m, 2H) 7.21-7.27 (m, 5H) 7.28-7.32 (m, 2H) 8.31 (s, 1H) 8.82 (s, 1H).

cis-2-[1-(4-Bromo-phenyl)-3-hydroxy-3-methyl-cyclobutyl]-isoindole-1,3-dione [LXX]

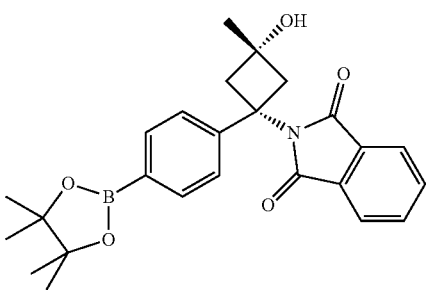

Compound [LXX] was prepared in a similar way to that of Compound [XXXIX] using Compound [LXVI] as the starting material.

Data for Compound [LXX]: LCMS (m/e) 434 (M+H).

cis-2-{3-Hydroxy-3-methyl-1-[4-(2-methyl-7-phenyl-1,4,9,9b-tetraaza-cyclopenta[a]naphthalen-8-yl)-phenyl]-cyclobutyl}-isoindole-1,3-dione [LXXI]

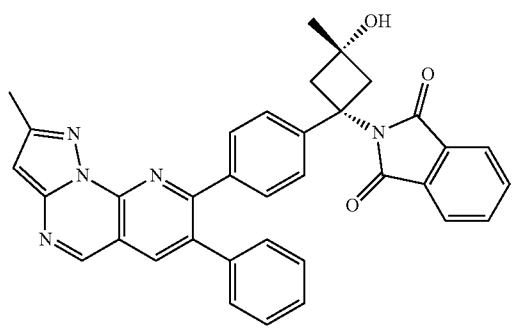

Compound [LXXI] was prepared in a similar way to that of Compound [XL]. Data for Compound [LXXI]: LCMS (m/e) 566 (M+H); $^1$H NMR (400 MHz, CHLOROFORM-d) δ ppm 1.15 (s, 3H) 2.61 (s, 3H) 3.08-3.15 (m, 2H) 3.30-3.37 (m, 2H) 6.71 (s, 1H) 7.20-7.26 (m, 4H) 7.29-7.31 (m, 1H) 7.51-7.55 (m, 2H) 7.62-7.70 (m, 4H) 7.76 (dd, J=5.52, 2.98 Hz, 2H) 8.24 (s, 1H) 8.87 (s, 1H).

cis-3-Amino-1-methyl-3-[4-(2-methyl-7-phenyl-1,4,9,9b-tetraaza-cyclopenta[a]naphthalen-8-yl)-phenyl]-cyclobutanol [LXXII]

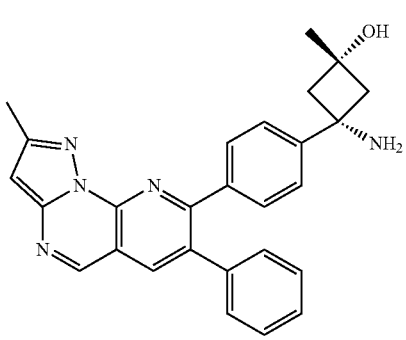

Compound [LXXII] was prepared in a similar way to that of Compound [XLI]. Data for Compound [LXXII]: LCMS (m/e) 436 (M+H); ¹H NMR (400 MHz, CHLOROFORM-d) δ ppm 1.22 (s, 3H) 2.49 (s, 3H) 2.63 (d, J=13.76 Hz, 2H) 2.78 (d, J=13.72 Hz, 2H) 6.70 (s, 1H) 7.17-7.23 (m, 4H) 7.28-7.35 (m, 3H) 7.38 (d, J=8.30 Hz, 2H) 8.46 (s, 1H) 8.94 (s, 1H).

trans-2-{3-Cyclopropyl-3-hydroxy-1-[4-(2-cyclopropyl-7-phenyl-1,4,9,9b-tetraaza-cyclopenta[a]naphthalen-8-yl)-phenyl]-cyclobutyl}-isoindole-1,3-dione [LXXIII]

LXXIII

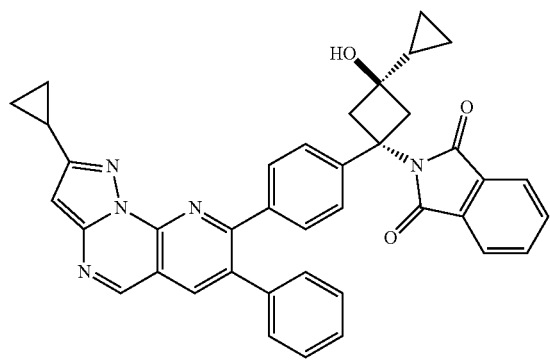

Compound [LXXIII] was prepared in a similar way to that of Compound [XL]. Data for Compound [LXXIII]: LCMS (m/e) 618 (M+H); ¹H NMR. (400 MHz, CHLOROFORM-d) □ ppm 0.01 (q, J=5.30 Hz, 2H) 0.12-0.21 (m, 2H) 0.60-0.68 (m, 2H) 0.73-0.79 (m, 2H) 0.84 (t, J=8.32 Hz, 1H) 1.98 (t, J=8.42 Hz, 1H) 2.73 (d, 2H) 2.84 (d, 2H) 6.17 (s, 1H) 6.92-6.95 (m, 2H) 6.98-7.02 (m, 3H) 7.23 (d, 2H) 7.30 (d, 2H) 7.36-7.40 (m, 2H) 7.43-7.49 (m, 2H) 7.89 (s, 1H) 8.51 (s, 1H).

trans-3-Amino-1-cyclopropyl-3-[4-(2-cyclopropyl-7-phenyl-1,4,9,9b-tetraaza-cyclopenta[a]naphthalen-8-yl)-phenyl]-cyclobutanol [LXXIV]

LXXIV

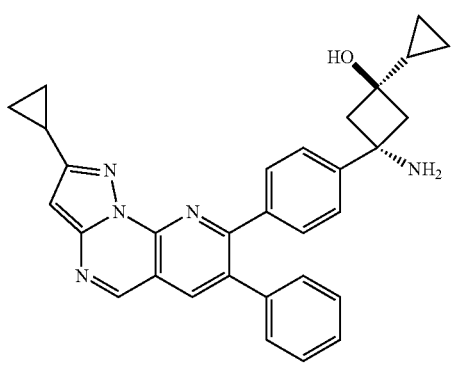

Compound [LXXIV] was prepared in a similar way to that of Compound [XLI]. Data for Compound [LXXIV]: LCMS (m/e) 488 (M+H); ¹H NMR (400 MHz, METHANOL-d₄) δ ppm 0.41 (t, J=4.78 Hz, 2H) 0.47 (d, J=8.30 Hz, 2H) 0.96-1.04 (m, 2H) 1.09-1.15 (m, 2H) 1.15-1.22 (m, 1H) 2.24 (t, J=5.05 Hz, 1H) 2.61 (d, J=14.25 Hz, 2H) 2.78 (d, j=14.35 Hz, 2H) 6.61 (s, 1H) 7.33 (s, 5H) 7.53 (d, J=8.35 Hz, 2H) 7.72 (d, J=8.40 Hz, 2H) 8.55 (s, 1H) 9.03 (s, 1H).

trans-2-{3-Cyclopropyl-3-hydroxy-1-[4-(7-phenyl-1,4,9,9b-tetraaza-cyclopenta[a]naphthalen-8-yl)-phenyl]-cyclobutyl}-isoindole-4,3-dione [LXXV]

LXXV

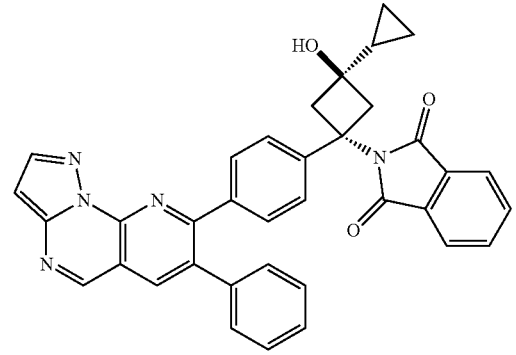

Compound [LXXV] was prepared in a similar way to that of Compound [XL]. Data for Compound [LXXV]: LCMS (m/e)=578 (M+H). This material was used in the next step without further characterization.

trans-3-Amino-1-cyclopropyl-3-[4-(7-phenyl-1,4,9,9b-tetraaza-cyclopenta[a]naphthalen-8-yl)-phenyl]-cyclobutanol [LXXVI]

LXXVI

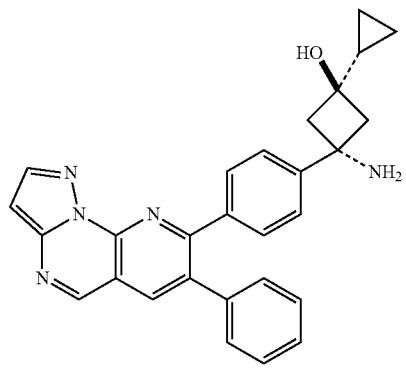

Compound [LXXVI] was prepared in a similar way to that of Compound [XLI]. Data for Compound [LXXVI]: LCMS (m/e) 448 (M+H); ¹H NMR (400 MHz, METHANOL-d₄) δ ppm 0.40-0.46 (m, 2H) 0.47-0.55 (m, 2H) 1.16-1.25 (m, 1H) 2.59-2.69 (m, 2H) 2.76-2.86 (m, 2H) 7.01 (d, J=2.17 Hz, 1H) 7.33-7.43 (m, 2H) 7.57 (d, J=8.44 Hz, 1H) 7.76 (d, J=8.47 Hz, 1H) 8.30 (d, J=2.12 Hz, 1H) 8.65 (s, 1H) 9.15 (s, 1H).

trans-2-{3-Cyclopropyl-3-hydroxy-1-[4-(2-(4-fluorophenyl)-7-phenyl-1,4,9,9b-tetraaza-cyclopenta[a]naphthalen-8-yl)-phenyl]-cyclobutyl}-isoindole-1,3-dione [LXXVII]

LXXVII

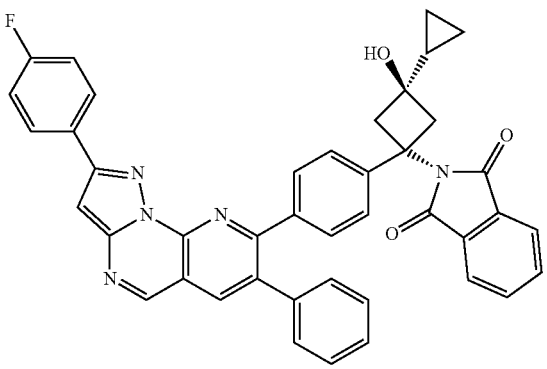

Compound [LXXVII] was prepared in a similar way to that of Compound [XL]. Data for Compound [LXXVII]: LCMS m/e 672 (M+H). This material was carried on to the next step without further characterization.

trans-3-Amino-1-cyclopropyl-3-[4-(2-(4-fluorophenyl)-7-phenyl-1,4,9,9b-tetraaza-cyclopenta[a]naphthalen-8-yl)-phenyl]-cyclobutanol [LXXVIII]

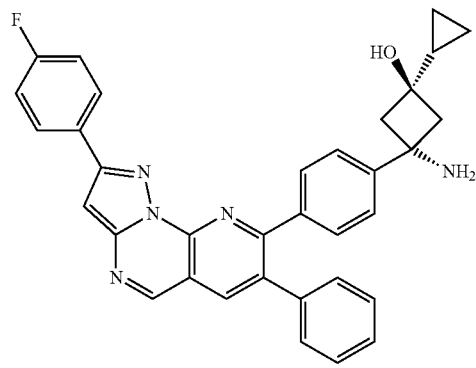

LXXVIII

Compound [LXXVIII] was prepared in a similar way to that of Compound [XLI]. Data for Compound [LXXVIII]: LCMS m/e 542 (M+H); $^1$H NMR (400 MHz, METHANOL-$d_4$) δ ppm 0.37-0.44 (m, 2H) 0.45-0.51 (m, 2H) 1.13-1.22 (m, 1H) 2.58-2.66 (m, 2H) 2.79 (d, J=14.30 Hz, 2H) 7.24 (t, J=8.76 Hz, 2H) 7.31 (s, 1H) 7.34 (s, 5H) 7.56 (d, J=8.40 Hz, 2H) 7.73 (d, J=8.35 Hz, 2H) 8.17 (dd, J=8.69, 5.42 Hz, 2H) 8.60 (s, 1H) 9.11 (s, 1H).

trans-2-{3-Cyclopropyl-3-hydroxy-1-[4-(2-trifluoromethyl-7-phenyl-1,4,9,9b-tetraaza-cyclopenta[a]naphthalen-8-yl)-phenyl]-cyclobutyl}-isoindole-1,3-dione [LXXIX]

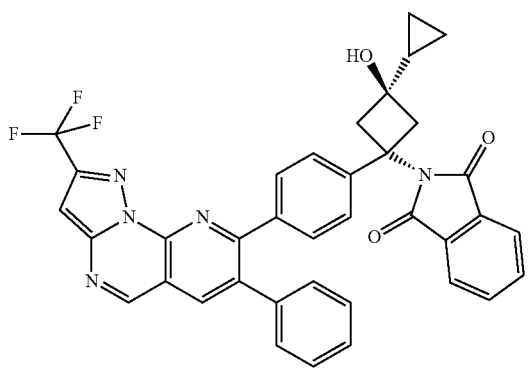

LXXIX

Compound [LXXIX] was prepared in a similar way to that of Compound [XL]. Data for Compound [LXXIX]: LCMS m/e 672 (M+H). This compound was used directly in the next step without further purification or characterization.

trans-3-Amino-1-cyclopropyl-3-[4-(2-trifluoromethyl-7-phenyl-1,4,9,9b-tetraaza-cyclopenta[a]naphthalen-8-yl)-phenyl]-cyclobutanol [LXXX]

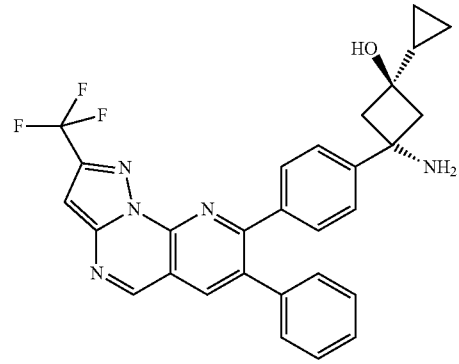

LXXX

Compound [LXXX] was prepared in a similar way to that of Compound [XLI]. Data for Compound [LXXV]: LCMS m/e 516 (M+H); $^1$H NMR (400 MHz, METHANOL-$d_4$) δ ppm 0.41 (dd, 2H) 0.44-0.52 (m, 2H) 1.12-1.22 (m, 1H) 2.58-2.66 (m, 2H) 2.74-2.82 (m, 2H) 7.29 (s, 1H) 7.36 (s, 5H) 7.55 (d, J=8.40 Hz, 2H) 7.73 (d, J=8.40 Hz, 2H) 8.68 (s, 1H) 9.24 (s, 1H).

2-Methyl-8-(4-morpholin-4-ylmethyl-phenyl)-7-phenyl-1,4,9,9b-tetraaza-cyclopenta[a]naphthalene [LXXXI]

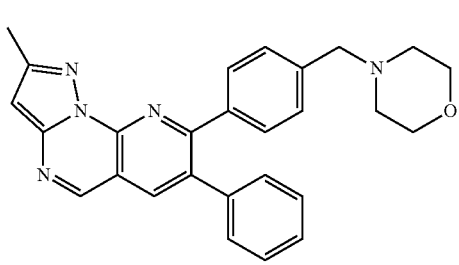

LXXXI

[LXXXI] was prepared in a similar way to that of Compound [XL]. Data for Compound [LXXXI]: LCMS m/e 436 (M+H);

1H NMR (400 MHz, METHANOL-$d_4$) δ ppm 2.58 (s, 3H) 3.13-3.32 (m, 4H) 3.63-3.87 (m, 2H) 3.95-4.14 (m, 2H) 4.37 (s, 2H) 6.77 (s, 1H) 7.27-7.38 (m, 5H) 7.46 (d, J=8.15 Hz, 2H) 7.71 (d, J=8.15 Hz, 2H) 8.58 (s, 1H) 9.06 (s, 1H).

4-(2-Methyl-7-phenyl-1,4,9,9b-tetraaza-cyclopenta[a]naphthalen-8-yl)-phenylamine [LXXXII]

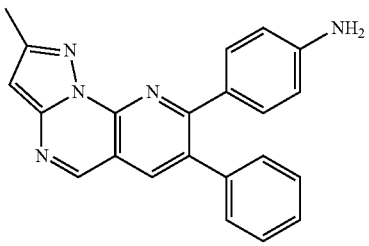

LXXXII

Compound [LXXXII] was prepared using a procedure similar to that of xyxXL]. Data for Compound [LXXXII]: LCMS m/e 352 (M+H); 1H NMR (400 MHz, METHANOL-d4) □ ppm 2.57 (s, 3H) 6.74 (s, 1H) 7.09 (d, J=8.61 Hz, 2H) 7.28-7.40 (m, 5H) 7.64 (d, J=8.64 Hz, 2H) 8.51 (s, 1H) 9.02 (s, 1H).

N-[4-(2-Methyl-7-phenyl-1,4,9,9b-tetraaza-cyclopenta[a]naphthalen-8-yl)-phenyl]-methanesulfonamide [LXXXIII]

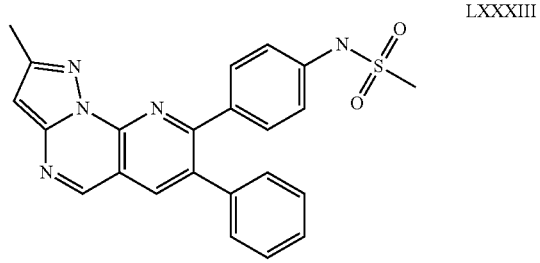

Compound [LXXXIII] was prepared using a procedure similar to that of Compound [XL]. Data for Compound [LXXXIII]: LCMS m/e 430 (M+H); $^1$H NMR (400 MHz, METHANOL-d$_4$) δ ppm 2.57 (s, 3H) 2.96 (s, 3H) 6.70 (s, 1H) 7.13 (d, J=8.40 Hz, 2H) 7.23-7.40 (m, 4H) 7.56 (d, J=8.40 Hz, 2H) 7.66 (d, J=4.22 Hz, 1H) 8.41 (s, 1H) 8.96 (s, 1H).

[4-(2-Methyl-7-phenyl-1,4,9,9b-tetraaza-cyclopenta[a]naphthalen-8-yl)-phenyl]urea [LXXXIV]

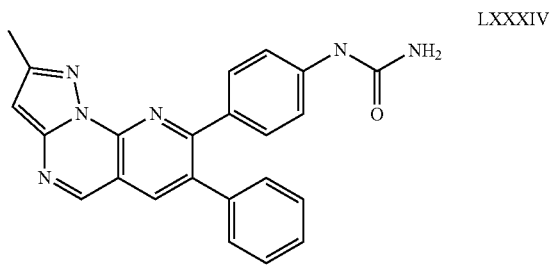 [SMILES: Cc1cc2ncc3cc(-c4ccccc4)c(-c4ccc(NC(N)=O)cc4)nc3n2n1]

Compound [LXXXIV] was prepared using a procedure similar to that of Compound [XL]. Data for Compound [LXXXIV]: LCMS m/e 395 (M+H); $^1$H NMR (400 MHz, METHANOL-d$_4$) δ ppm 2.57 (s, 3H) 6.71 (s, 1H) 7.27-7.39 (m, 7H) 7.51 (d, J=8.71 Hz, 2H) 8.44 (s, 1H) 8.98 (s, 1H).

Morpholine-4-carboxylic acid [4-(2-methyl-7-phenyl-1,4,9,9b-tetraaza-cyclopenta[a]naphthalen-8-yl)-phenyl]-amide [LXXXV]

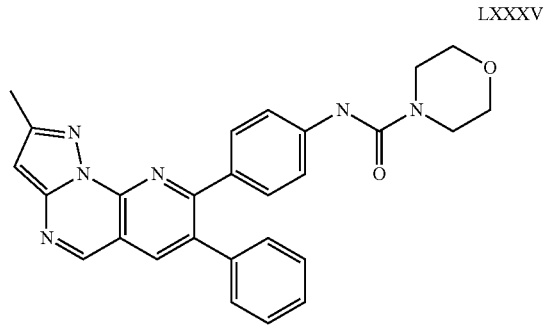 [SMILES: Cc1cc2ncc3cc(-c4ccccc4)c(-c4ccc(NC(=O)N5CCOCC5)cc4)nc3n2n1]

Compound [LXXXV] was prepared using a procedure similar to that of Compound [XL]. Data for Compound [LXXXV]: LCMS m/e 465 (M+H); $^1$H NMR (400 MHz, METHANOL-d$_4$) δ ppm 2.57 (s, 3H) 3.45-3.55 (m, 4H) 3.61-3.78 (m, 4H) 6.73 (s, 1H) 7.27-7.42 (m, 7H) 7.47-7.61 (m, 2H) 8.47 (s, 1H) 9.00 (s, 1H).

3-[4-(2-Methyl-7-phenyl-1,4,9,9b-tetraaza-cyclopenta[a]naphthalen-8-yl)-phenyl]-oxazolidin-2-one [LXXXVI]

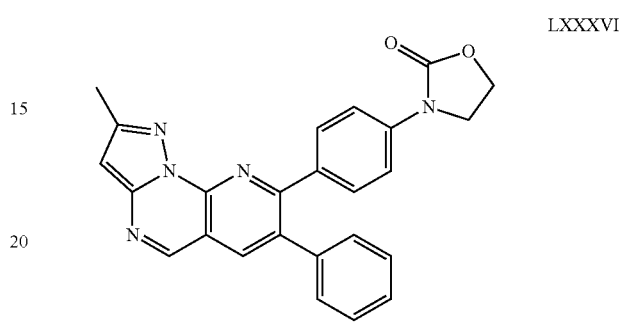

Compound [LXXXVI] was prepared using a procedure similar to that of Compound [XL]. Data for Compound [LXXXVI]: LCMS m/e 422 (M+H); $^1$H NMR (400 MHz, METHANOL-d$_4$) δ ppm 2.63 (s, 3H) 4.05 (t, J=7.83 Hz, 2H) 4.49 (t, J=7.86 Hz, 2H) 6.72 (s, 1H) 7.20-7.29 (m, 2H) 7.32-7.37 (m, 3H) 7.45 (d, J=8.57 Hz, 2H) 7.56-7.62 (m, 2H) 8.23 (s, 1H) 8.87 (s, 1H).

4-(2-Methyl-7-phenyl-1,4,9,9b-tetraaza-cyclopenta[a]naphthalen-8-yl)-benzylamine [LXXXVII]

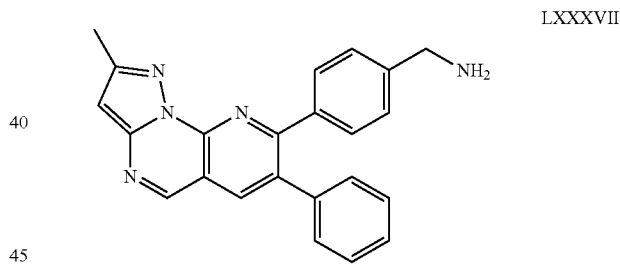

Compound [LXXXVII] was prepared using a procedure similar to that of Compound [XL]. Data for Compound [LXXXVII]: LCMS m/e 366 (M+H); $^1$H NMR (400 MHz, METHANOL-d$_4$) δ ppm 2.58 (s, 3H) 4.12 (s, 2H) 6.76 (s, 1H) 7.28-7.35 (m, 5H) 7.39 (d, J=8.27 Hz, 2H) 7.67 (d, J=8.27 Hz, 2H) 8.56 (s, 1H) 9.05 (s, 1H).

[4-(2-Methyl-7-phenyl-1,4,9,9b-tetraaza-cyclopenta[a]naphthalen-8-yl)-phenyl]-methanol [LXXXIX]

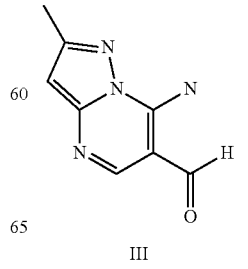

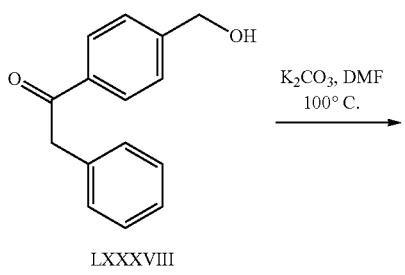

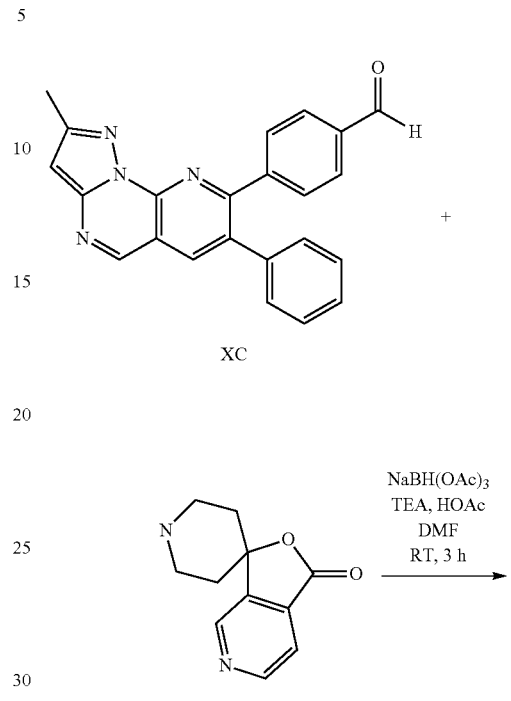

A 20 mL scintillation vial containing Compound [III] (35 mg, 0.20 mmol, 1 eq.), DMF (1 mL), K$_2$CO$_3$ (84 mg, 0.60 mmol, 3 eq.), and Compound [LXXXVIII] (55 mg, 0.25 mmol, 1.25 eq.) was heated at 100° C. for 16 hours. The mixture was allowed to cool. After filtration, the resultant solution was purified by reverse-phase preparative HPLC using water-acetonitrile-TFA [95:5:0.05] and acetonitrile-water-TFA [95:5:0.05] as the mobile phases to provide Compound [LXXXIX] as a solid: LCMS m/e 367 (M+H); $^1$H NMR (400 MHz, METHANOL-d$_4$) δ ppm 2.57 (s, 3H) 4.61 (s, 2H) 6.74 (s, 1H) 7.27-7.36 (m, 7H) 7.54-7.59 (m, 2H) 8.52 (s, 1H) 9.03 (s, 1H).

[4-(2-Methyl-7-phenyl-1,4,9,9b-tetraaza-cyclopenta[a]naphthalen-8-yl)-phenyl]-carboxaldehyde [XC]

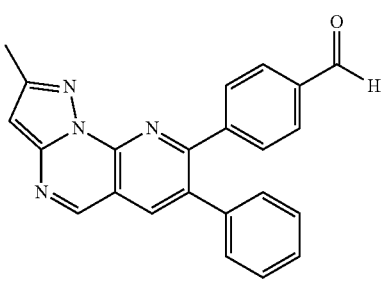

Compound [XC] was prepared using a procedure similar to that of Compound [XL]. Data for Compound [XC]: LCMS m/e 365 (M+H); $^1$H NMR (400 MHz, CHLOROFORM-d) δ ppm 2.67 (br. s., 3H) 6.83 (br. s., 1H) 7.01-8.09 (m, 9H) 8.21-8.52 (s, 1H) 9.10 (br. s., 1H) 10.04 (br. s., 1H).

1'-[4-(2-Methyl-7-phenyl-1,4,9,9b-tetraaza-cyclopenta[a]naphthalen-8-yl)-phenylmethyl]-spiro[furo[3,4-c]pyridine-3(1H),4'-piperidine]-1-one [XCII]

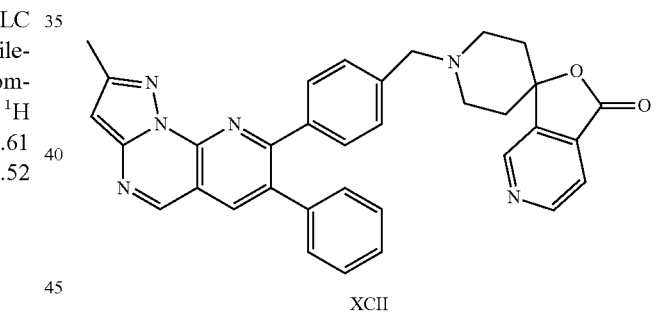

To a 20 mL scintillation vial containing Compound [XC] (18 mg, 0.05 mmol, 1 eq.) in 5% HOAc-DMF (0.5 mL), TEA (7.7 mg, 0.075 mmol, 1.5 eq.), and Compound [XCI] (12 mg, 0.05 mmol, 1 eq.) was added NaBH(OAc)$_3$ (21 mg, 0.1 mmol, 2 eq.). The mixture was stirred at room temperature for 3 hours. The reaction mixture was diluted with MeOH (1 mL) and purified by reverse-phase preparative HPLC using water-acetonitrile-TFA [95:5:0.05] and acetonitrile-water-TFA [95:5:0.05] as the mobile phases to provide Compound [XCII] as a pale yellow solid: LCMS m/e 553 (M+H); $^1$H NMR (400 MHz, CHLOROFORM-d) δ ppm 1.94 (d, J=14.62 Hz, 2H) 2.63 (s, 3H) 2.92-3.03 (m, 2H) 3.16-3.27 (m, 6H) 3.65 (d, J=10.93 Hz, 2H) 4.27 (s, 2H) 6.76 (s, 1H) 7.21-7.25 (m, 2H) 7.33-7.43 (m, 5H) 7.64 (d, J=8.08 Hz, 2H) 7.82 (d, J=4.81 Hz, 1H) 8.32 (s, 1H) 8.94 (s, 1H) 8.95 (d, J=5.03 Hz, 1H) 9.02 (s, 1H).

1'-[4-(2-Methyl-7-phenyl-1,4,9,9b-tetraaza-cyclopenta[a]naphthalen-8-yl)-phenylmethyl]-spiro[2-methyl-2,3-dihydro-isoindole-3(1H),4'-piperidine]-1-one [XCIII]

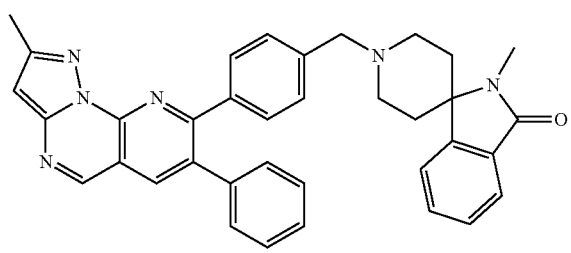

XCIII

Compound [XCIII] was prepared using a procedure similar to that of Compound [XCII]. Data for Compound [XCIII]: LCMS m/e 565 (M+H); $^1$H NMR (400 MHz, METHANOL-$d_4$) δ ppm 1.30 (t, J=7.28 Hz, 1H) 1.66-1.83 (m, 1H) 2.46-2.57 (m, 1H) 2.58 (s, 3H) 3.05 (br. s., 3H) 3.20 (q, J=7.31 Hz, 1H) 3.66-3.75 (m, 4H) 4.60 (s, 2H) 6.77 (s, 1H) 7.29-7.39 (m, 5H) 7.57 (d, J=8.22 Hz, 2H) 7.59-7.66 (m, 1H) 7.68-7.81 (m, 3H) 7.86 (d, J=7.37 Hz, 1H) 8.06 (br. s., 1H) 8.59 (s, 1H) 9.06 (s, 1H).

1'-[4-(2-Methyl-7-phenyl-1,4,9,9b-tetraaza-cyclopenta[a]naphthalen-8-yl)-phenylmethyl]-spiro[furo[3,4-b]pyridine-5(7H),4'-piperidine]-7-one [XCIV]

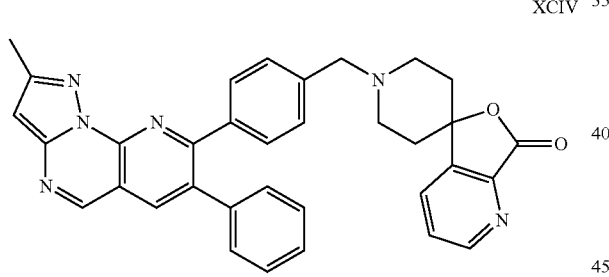

XCIV

Compound [XCIV] was prepared using a procedure similar to that of Compound Data for Compound [XCIV]: LCMS m/e 553 (M+H); $^1$H NMR (400 MHz, METHANOL-$d_4$) δ ppm 2.13 (d, J=14.57 Hz, 2H) 2.50-2.56 (m, 2H) 2.58 (s, 3H) 3.45-3.70 (m, 4H) 4.51 (br. s., 2H) 6.77 (s, 1H) 7.27-7.38 (m, 5H) 7.54 (d, J=8.08 Hz, 2H) 7.74 (d, J=8.13 Hz, 2H) 7.78 (dd, J=7.82, 4.97 Hz, 1H) 8.08-8.18 (m, 1H) 8.59 (s, 1H) 8.89 (d, J=4.05 Hz, 1H) 9.06 (s, 1H).

8-[4-(4-Benzo[1,3]-dioxol-5-ylmethyl-piperazin-1-ylmethyl)-phenyl]-2-methyl-7-phenyl-1,4,9,9b-tetraaza-cyclopenta[a]naphthalene [XCV]

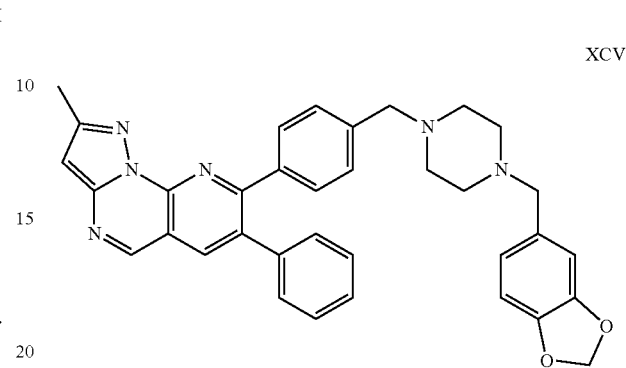

XCV

Compound [XCV] was prepared using a procedure similar to that of Compound [XCII]. Data for Compound [XCV]: LCMS m/e 569 (M+H); 1H NMR (400 MHz, METHANOL-$d_4$) δ ppm 2.58 (s, 3H) 2.83-2.97 (m, 4H) 3.07-3.19 (m, 4H) 3.86 (s, 2H) 4.05 (s, 2H) 5.98 (s, 2H) 6.75 (s, 1H) 6.83-6.96 (m, 3H) 7.26-7.37 (m, 7H) 8.55 (s, 1H) 9.04 (s, 1H).

1-[4-(2-Methyl-7-phenyl-1,4,9,9b-tetraaza-cyclopenta[a]naphthalen-8-yl)-benzyl]-piperidine-4-carboxylic acid amide [XCVI]

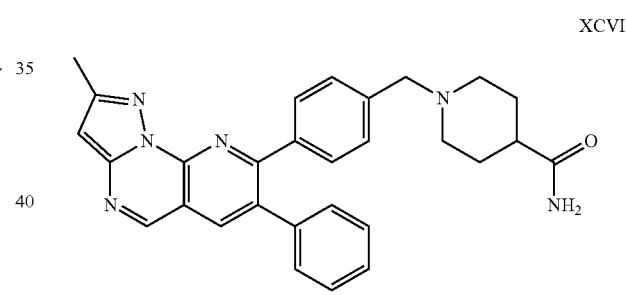

XCVI

Compound [XCVI] was prepared using a procedure similar to that of Compound [XCII]. Data for Compound [XCVI]: LCMS m/e 477 (M+H); 1H NMR (400 MHz, METHANOL-$d_4$) δ ppm 1.81-1.97 (m, 2H) 2.01-2.15 (m, 2H) 2.58 (s, 3H) 2.94-3.08 (m, 2H) 3.43-3.59 (m, 2H) 4.32 (s, 1H) 6.77 (s, 1H) 7.27-7.37 (m, 5H) 7.45 (d, J=8.10 Hz, 2H) 7.70 (d, J=8.05 Hz, 2H) 8.58 (s, 1H) 9.06 (s, 1H).

Scheme VI - Synthesis of C

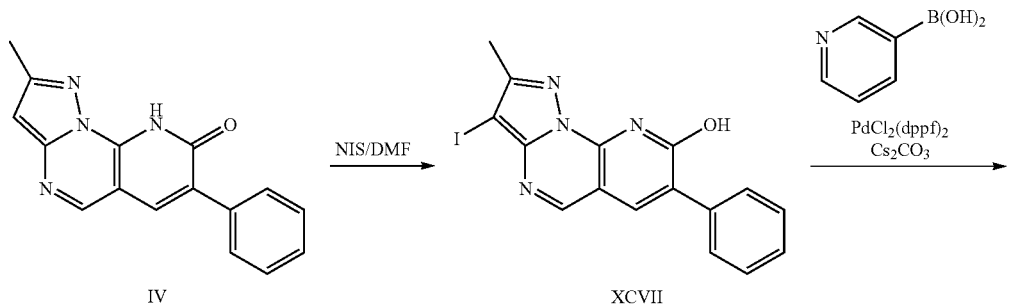

-continued
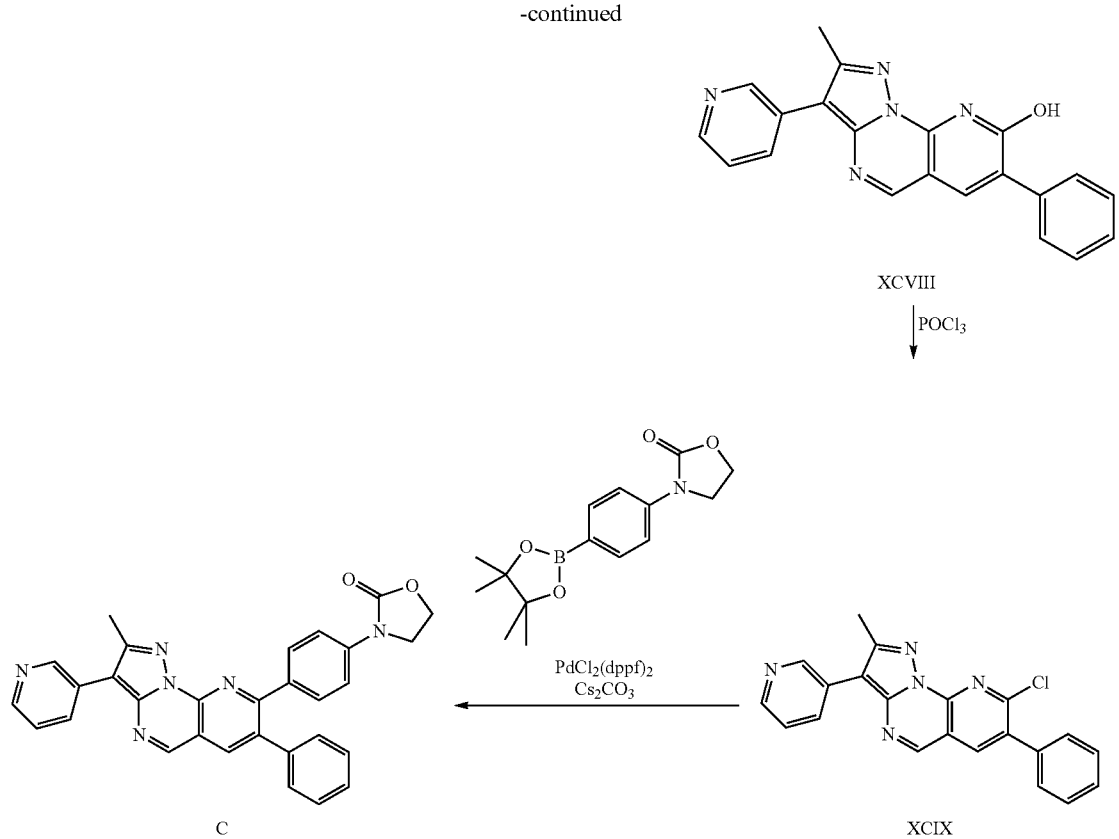
3-Iodo-2-methyl-7-phenyl-1,4,9,9b-tetraaza-cyclo- 35
penta[a]naphthalen-8-ol [XCVII]
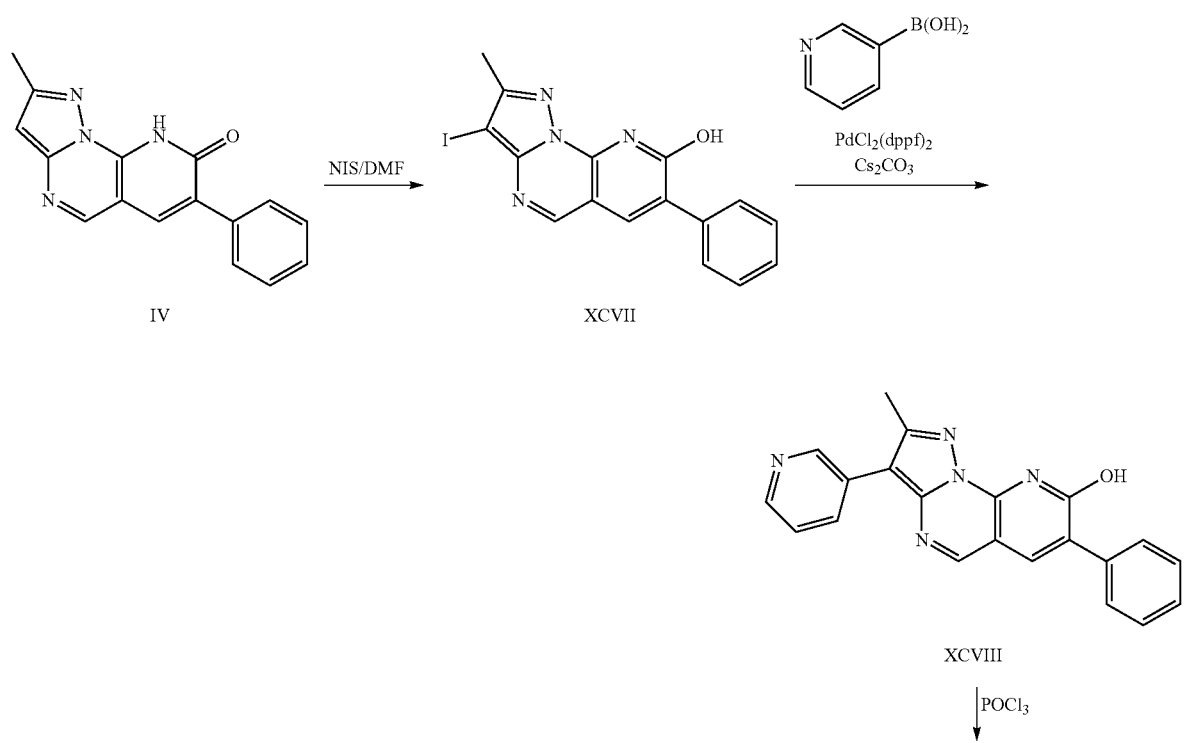

-continued

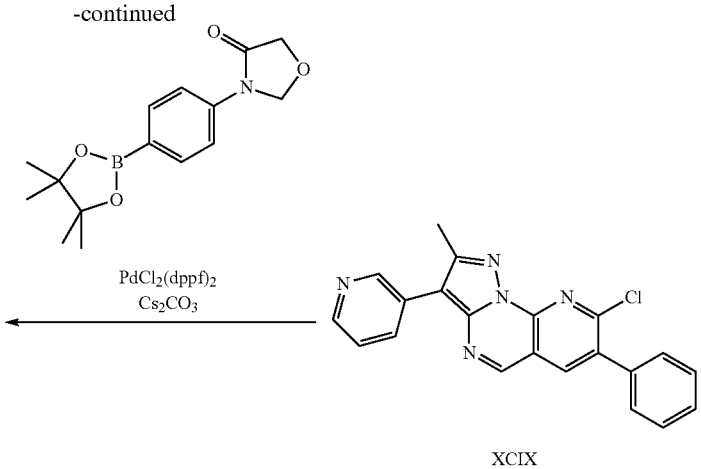

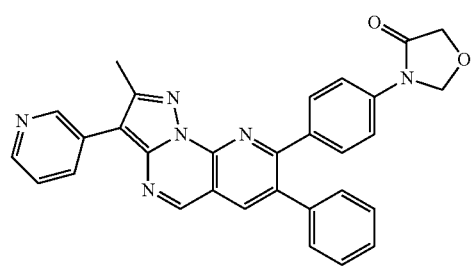

To a solution of Compound [IV] (0.2 g, 0.73 mmol, 1 eq.) in DMF (10 mL) was added N-iodosuccinimide (0.18 g, 0.8 mmol, 1.1 eq.) and the mixture stirred for 2 hours and concentrated. The residue was purified by silica gel chromatography using CHCl$_3$/MeOH (10%) as eluant to give Compound [XCVII]: LCMS ink 403 (M+H); $^1$H NMR (400 MHz, DMSO-d$_6$) δ ppm 7.33-7.40 (m, 1H) 7.44 (t, J=7.42 Hz, 2H) 7.69 (d, J=7.22 Hz, 2H) 8.37 (s, 1H) 8.83 (s, 1H).

2-Methyl-7-phenyl-3-pyridin-3-yl-1,4,9,9b-tetraaza-cyclopenta[a]naphthalen-8-ol [XCVIII]

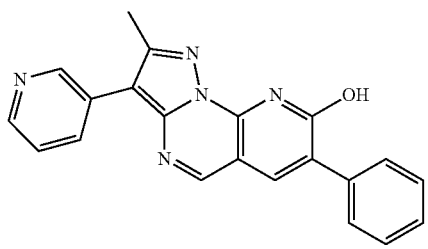

Compound [XCVIII] was prepared using a procedure similar to that of Compound [XL]. Data for Compound [XCVIII]: LCMS m/e 354 (M+H); $^1$H NMR (400 MHz, METHANOL-d$_4$) δ ppm 2.81 (s, 3H) 7.35-7.51 (m, 3H) 7.73 (d, J=7.08 Hz, 2H) 8.07 (dd, J=8.05, 5.66 Hz, 1H) 8.27 (s, 1H) 8.69 (d, J=5.32 Hz, 1H) 8.90 (s, 1H) 8.97 (d, J=8.20 Hz, 1H) 9.39 (s, 1H).

8-Chloro-2-methyl-7-phenyl-3-pyridin-3-yl-1,4,9,9b-tetraaza-cyclopenta[a]naphthalene [XCIX]

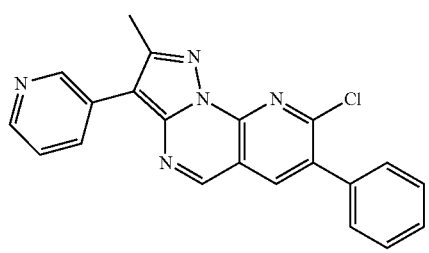

Compound [XCIX] was prepared using a procedure similar to that of Compound [V]. Data for Compound [XCIX]:

LCMS m/e 372 (M+H); $^1$H NMR (400 MHz, METHANOL-d$_4$) δ ppm 2.79 (s, 3H) 7.46-7.63 (m, 5H) 8.03 (dd, J=8.05, 5.56 Hz, 1H) 8.63 (s, 1H) 8.72 (d, J=5.08 Hz, 1H) 8.87 (d, J=8.20 Hz, 1H) 9.19 (s, 1H) 9.31 (s, 1H).

3-[4-(2-Methyl-7-phenyl-3-pyridin-3-yl-1,4,9,9b-tetraaza-cyclopenta[a]naphthalen-8-yl)-phenyl]-oxazolidin-2-one [C]

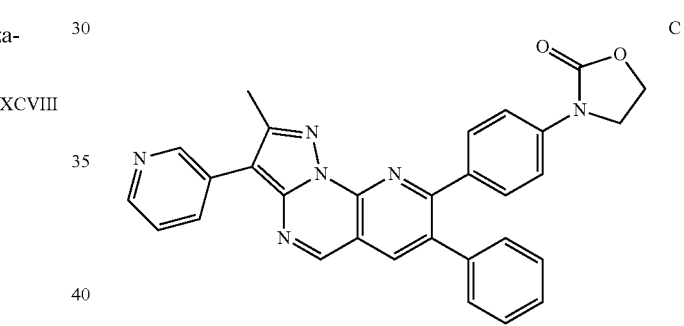

Compound [C] was prepared using a procedure similar to that of Compound [XL]. Data for Compound [C]: LCMS m/e 499 (M+H); $^1$H NMR (400 MHz, METHANOL-d$_4$) δ ppm 2.83 (s, 3H) 4.12 (t, J=8.00 Hz, 2H) 4.47-4.55 (m, 2H) 7.31-7.41 (m, 5H) 7.52-7.61 (m, 2H) 7.63-7.71 (m, 2H) 8.11-8.20 (m, 1H) 8.62 (s, 1H) 8.76 (d, J=5.52 Hz, 1H) 9.06 (d, J=8.30 Hz, 1H) 9.24 (s, 1H) 9.42 (s, 1H).

3-Cyano-2-methyl-7-phenyl-1,4,9,9b-tetraaza-cyclopenta[a]naphthalen-8-ol [CI]

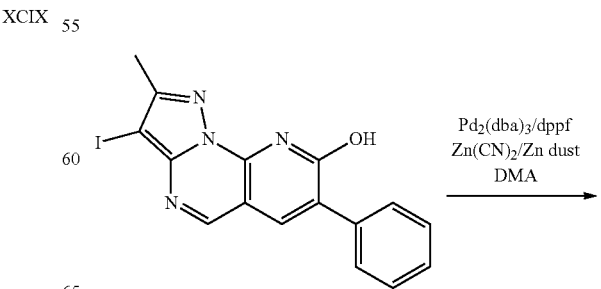

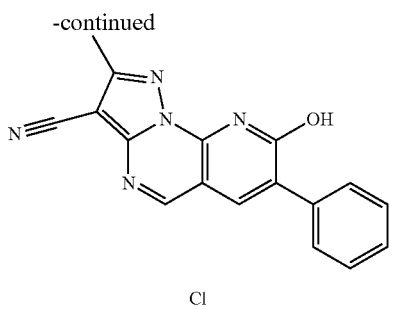

CI

In a 20 mL scintillation vial Pd$_2$(dba)$_3$ (0.032 g, 0.035 mmol, 0.05 eq.) and DPPF (0.04 g, 0.0704 mmol, 0.1 eq.) were taken in 10 mL of N,N-dimethylacetamide. Zn(CN)$_2$ (0.082 g, 0.704 mmol, 1.0 equiv.) and Zn (0.0091 g, 0.1408 mmol, 0.2 equiv.) were added to this followed Compound [XCVIII] (0.25 g, 0.704 mmol, 1.0 eq.). The solution was degassed for several minutes and stirred at 90° C. for 16 hours. The reaction was then cooled, concentrated, and the crude purified by silica gel chromatography using CHCl$_3$/MeOH (1:10) as the eluant to give Compound [CI] as a greenish solid: LCMS m/e 302 (M+H). This material was used in the next step without further purification.

8-Chloro-3-cyano-2-methyl-7-phenyl-1,4,9,9b-tetraaza-cyclopenta[a]naphthalene [CI]

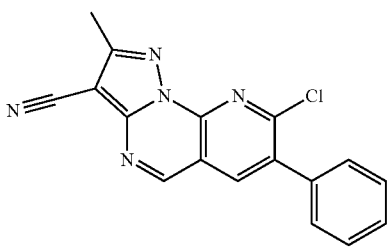

CII

Compound [CII] was prepared using a procedure similar to that of Compound [V]. Data for Compound [CII]: LCMS m/e 320 (M+H). This material was used directly in the next step without further purification.

trans-2-{3-Cyclopropyl-3-hydroxy-1-[4-(3-cyano-2-methyl-7-phenyl-1,4,9,9b-tetraaza-cyclopenta[a]naphthalen-8-yl)-phenyl]-cyclobutyl}-isoindole-1,3-dione [XL]

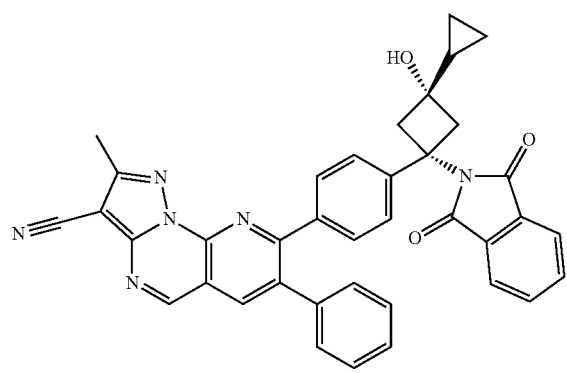

CIII

Compound [CIII] was prepared using a procedure similar to that of Compound [XL]. Data for Compound [CIII]: LCMS m/e 617 (M+H); $^1$H NMR (400 MHz, CHLOROFORM-d) δ ppm 0.23-0.33 (m, 2H) 0.40-0.52 (m, 2H) 1.17 (m, 1H) 2.69 (s, 3H) 2.96-3.05 (m, 2H) 3.09-3.16 (m, 2H) 7.28-7.35 (m, 4H) 7.47-7.54 (m, 3H) 7.61 (d, J=8.40 Hz, 2H) 7.68 (dd, J=5.34, 3.10 Hz, 2H) 7.72-7.78 (m, 2H) 8.33 (s, 1H) 9.09 (s, 1H).

trans-3-Amino-1-cyclopropyl-3-[4-(3-cyano-2-methyl-7-phenyl-1,4,9,9b-tetraaza-cyclopenta[a]naphthalen-8-yl)-phenyl]-cyclobutanol [CIV]

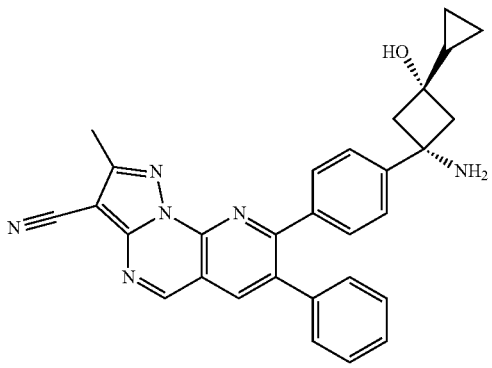

CIV

Compound [CIV] was prepared using a procedure similar to that of Compound [XLI]. Data for Compound [CIV]: LCMS m/e 487 (M+H); $^1$H NMR (400 MHz, METHANOL-d$_4$) δ ppm 0.37-0.43 (m, 2H) 0.43-0.51 (m, 2H) 1.17 (m, 1H) 2.58-2.65 (m, 2H) 2.68 (s, 3H) 2.74-2.81 (m, 2H) 7.28-7.41 (m, 5H) 7.55 (d, J=8.40 Hz, 2H) 7.72 (d, J=8.40 Hz, 2H) 8.70 (s, 1H) 9.33 (s, 1H).

2-{1-[4-(3-bromo-2-methyl-7-phenyl-1,4,9,9b-tetraaza-cyclopenta[a]naphthalen-8-yl)-phenyl]-3-cyclopropyl-3-hydroxy-cyclobutyl}-isoindole-1,3-dione [CV]

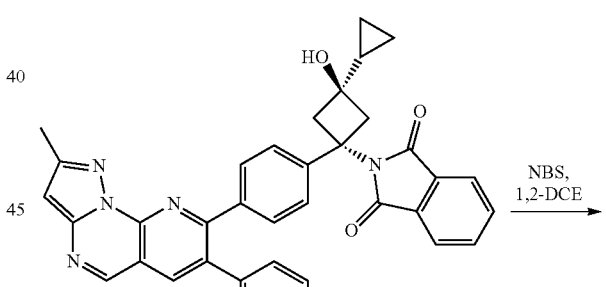

XL

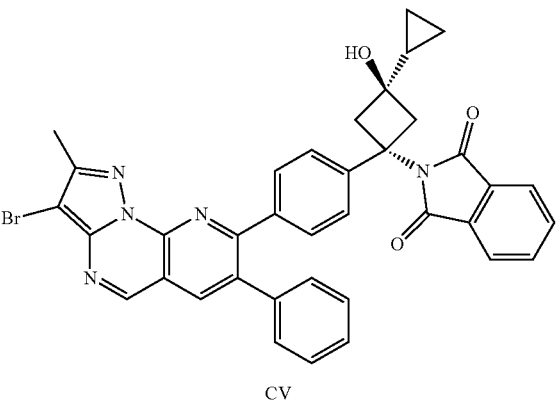

CV

To a 20 mL scintillation vial containing Compound [XL] (150 mg, 0.253 mmol, 1.0 eq.) in dichloroethane (5 mL) was added N-bromosuccinitnide (54 mg, 0.305 mmol, 1.2 eq.). The mixture was stirred at room temperature for 25 minutes. The solvent was then evaporated under reduced pressure. The residue was dissolved in MeOH/CHCl$_3$ and purified by silica gel chromatography using CHCl$_3$ and MeOH [90:10] as the mobile phases to provide Compound [CV] as a pale yellow solid: LCMS (m/e) 672 (M+2); $^1$H NMR (400 MHz, CHLOROFORM-d) δ ppm 0.02 (d, J=5.08 Hz, 2H) 0.19 (d, J=7.71 Hz, 2H) 0.85 (m, 1H) 1.27 (m, 5H) 2.29 (s, 3H) 2.74 (d, J=14.50 Hz, 2H) 2.85 (d, J=14.50 Hz, 2H) 7.23 (d, J=8.40 Hz, 2H) 7.32 (d, J=8.40 Hz, 2H) 7.39-7.41 (m, 2H) 7.47-7.49 (m, 2H) 7.96 (s, 1H) 8.63 (s, 1H).

3-Amino-3-[4-(3-bromo-2-methyl-7-phenyl-1,4,9, 9b-tetraaza-cyclopenta[a]naphthalen-8-yl)-phenyl]-cyclopropyl-cyclobutanol [CVI]

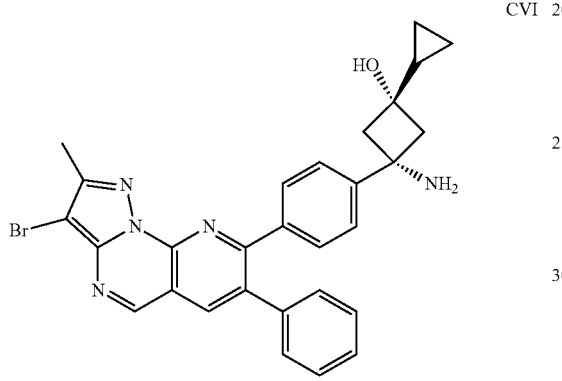

CVI

Compound [CVI] was prepared using a procedure similar to that of Compound [XLI]. Data for Compound [CVI]: LCMS (m/e) 542; $^1$H NMR (400 MHz, METHANOL-d$_4$) δ ppm 0.41 (d, J=4.10 Hz, 2H) 0.47 (d, J=8.00 Hz, 2H) 1.23 (m, 1H) 2.35 (d, J=13.47 Hz, 2H) 2.56 (s, 3H) 2.62 (d, J=13.47 Hz, 2H) 7.33 (m, 5H) 7.46 (d, J=8.40 Hz, 2H) 7.60 (d, J=8.40 Hz, 2H) 8.54 (s, 1H) 9.08 (s, 1H).

2-{1-[4-(3-Chloro-2-methyl-7-phenyl-1,4,9,9b-tetraaza-cyclopenta[a]naphthalen-8-yl)-phenyl]-3-cyclopropyl-3-hydroxy-cyclobutyl}-isoindole-1,3-dione

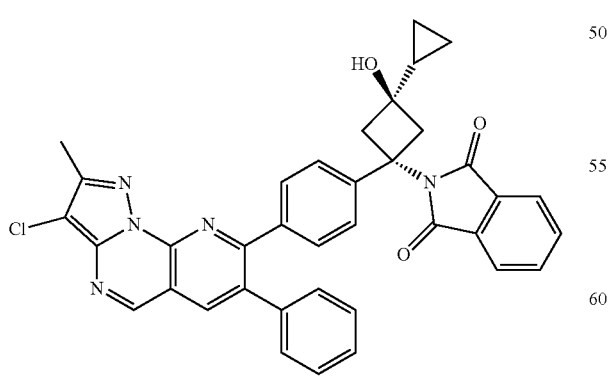

CVII

To a 20 mL scintillation vial containing Compound [XL] (47.3 mg, 0.08 mmol, 1.0 eq.) in dichloromethane (5 mL) was added N-chlorosuccinimide (9.9 mg, 0.074 mmol, 1.1 eq.). The mixture was stirred at room temperature for 3 hours. The solvent was then evaporated under reduced pressure. The residue was dissolved in MeOH/CHCl$_3$ and purified by silica gel chromatography using CHCl$_3$ and MeOH [90:10] as the mobile phases to provide Compound [CVII] as a pale yellow solid: LCMS (m/e) 626 (M+H); $^1$H NMR (400 MHz, METHANOL-d$_4$) δ ppm 0.29 (d, J=4.69 Hz, 2H) 0.40 (d, J=7.61 Hz, 2H) 1.09 (m, 1H) 2.52 (s, 3H) 2.93 (d, J=14.45 Hz, 2H) 3.17 (d, J=14.45 Hz, 2H) 7.27 (m, 5H) 7.53 (d, J=8.59 Hz, 2H) 7.57 (d, J=8.59 Hz, 2H) 7.78 (m, 4H) 8.52 (s, 1H) 9.05 (s, 1H).

3-Amino-3-[4-(3-chloro-2-methyl-7-phenyl-1,4,9, 9b-tetraaza-cyclopenta[a]naphthalen-8-yl)-phenyl]-cyclopropyl-cyclobutanol [CVIII]

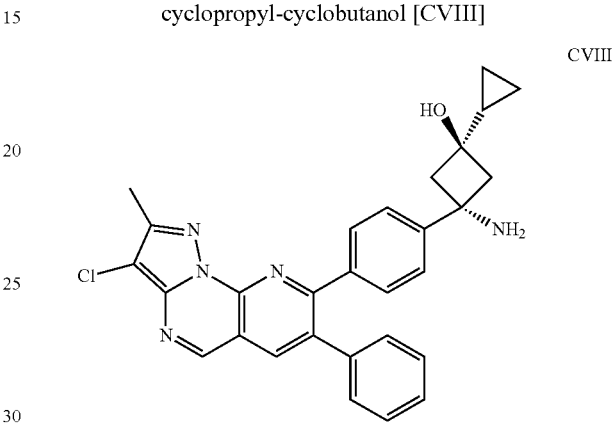

CVIII

Compound [CVIII] was prepared using a procedure similar to that of Compound [XLI]. Data for Compound [CVIII]: LCMS (m/e) 496 (M+H); $^1$H NMR (400 MHz, METHANOL-d$_4$) δ ppm 0.41 (d, J=4.88 Hz, 2H) 0.47 (d, J=8.20 Hz, 2H) 1.21 (m, 1H) 2.47 (d, J=13.67 Hz, 2H) 2.57 (s, 3H) 2.70 (d, J=14.076 Hz, 2H) 7.34 (m, 5H) 7.50 (d, J=8.40 Hz, 2H) 7.66 (d, J=8.00 Hz, 2H) 8.57 (s, 1H) 9.09 (s, 1H).

2,5-Dimethyl-7-phenyl-1,4,9,9b-tetraaza-cyclopenta[a]naphthalen-8-ol [CIX]

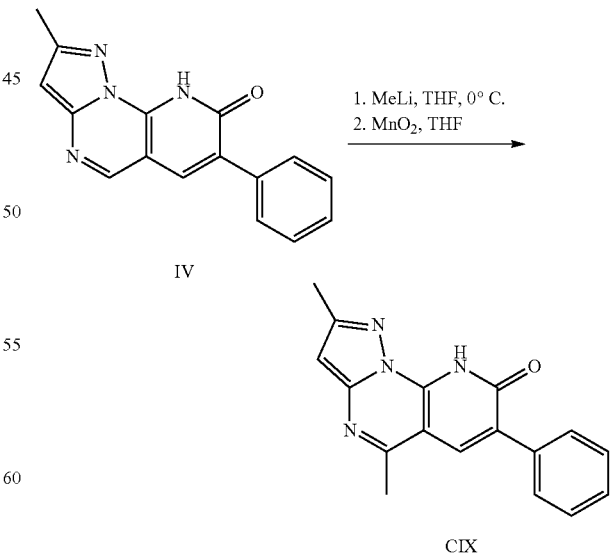

In a 20 mL scintillation vial, Compound [IV] (0.15 g, 0.543 mmol, 1.0 eq.) was dissolved in THF (10 mL). The solution was cooled to −78° C. and MeLi (15 mL of 1.6 M THF solution, 24 mmol, 44.19 eq.) was added dropwise and the reaction mixture was stirred for 16 hours at 0-20° C. The reaction mixture was carefully and slowly poured into ethyl acetate 20 (mL) and stirred for 10 minutes. The quenched reaction mixture was concentrated. The residue was treated with 100 mL of THF and the THF solution was separated from the solid by filtration. The organic solution was stirred with MnO$_2$ (0.47 g, 5.4 mmol, 10 eq.) for 4 hours at room temperature. The reaction was filtered and the solids washed with CHCl$_3$/MeOH (10%) (50 mL). The combined organic solution was concentrated and the crude was purified by silica gel chromatography using CHCl$_3$/MeOH (10%) as the eluant to give Compound [CIX]: LCMS m/e 291 (M+H); $^1$H NMR (400 MHz, CHLOROFORM-d) δ ppm 2.51 (s, 3H) 2.77 (s, 3H) 6.40 (s, 1H) 7.36-7.51 (m, 3H) 7.71 (d, J=7.22 Hz, 2H) 7.97 (s, 1H).

8-Chloro-2,5-dimethyl-7-phenyl-1,4,9,9b-tetraaza-cyclopenta[a]naphthalene [CX]

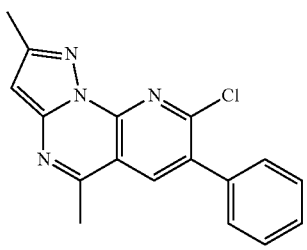

In a 20 mL scintillation vial Compound [CIX] (0.08 g, 0.275 mmol, 1.0 eq.) was heated with 2 mL of POCl$_3$ at 80° C. for 2 hours. The reaction was cooled and concentrated and the residue by silica gel chromatography using CHCl$_3$/MeOH (10%) as eluant to give Compound [CX]: LCMS m/e 309 (M+H); $^1$H NMR (400 MHz, CHLOROFORM-d) δ ppm 2.60 (s, 3H) 2.84 (s, 3H) 6.57 (s, 1H) 7.43-7.61 (m, 5H) 8.22 (s, 1H).

2-{1-[4-(2,5-Dimethyl-7-phenyl-1,4,9,9b-tetraaza-cyclopenta[a]naphthalen-8-yl)-phenyl]-3-methyl-3-hydroxy-cyclobutyl}-isoindole-1,3-dione [CXI]

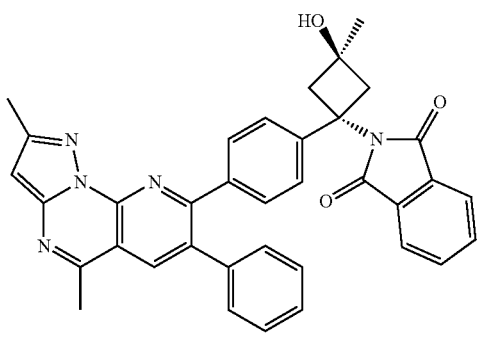

Compound [CXI] was prepared using a procedure similar to that of Compound [XL]. Data for Compound [CXI]: LCMS m/e 580 (M+H); $^1$H NMR (400 MHz, METHANOL-d$_4$) δ ppm 1.36 (s, 3H) 2.50 (s, 3H) 2.86 (s, 3H) 2.97 (d, J=13.86 Hz, 2H) 3.36-3.43 (m, 2H) 6.55 (s, 1H) 7.24-7.30 (m, 5H) 7.48-7.56 (m, 4H) 7.74-7.82 (m, 4H) 8.46 (s, 1H).

3-Amino-3-[4-(2,5-dimethyl-7-phenyl-1,4,9,9b-tetraaza-cyclopenta[a]naphthalen-8-yl)-phenyl]-methyl-cyclobutanol [CXII]

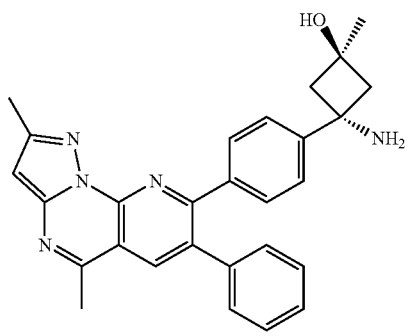

Compound [CXII] was prepared using a procedure similar to that of Compound [XLI]. Data for Compound [CXII]: LCMS m/e 450 (M+H); $^1$H NMR (400 MHz, METHANOL-d$_4$) δ ppm 1.54 (s, 3H) 2.37 (d, J=13.52 Hz, 2H) 2.54 (s, 3H) 2.65 (d, J=13.42 Hz, 2H) 2.89 (s, 3H) 6.58 (s, 1H) 7.30-7.36 (m, 5H) 7.39 (d, J=8.35 Hz, 2H) 7.59 (d, Hz, 2H) 8.49 (s, 1H).

2-Methyl-7-thiophen-2-yl-9H-1,4,9,9b-tetraaza-cyclopenta[a]naphthalen-8-one [CXIII]

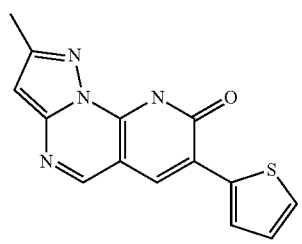

Compound [CXIII] was prepared using a procedure similar to that of Compound [IV]. Data for Compound [CXIII]: LCMS (m/e): 283 (M+H); $^1$H NMR (400 MHz, METHANOL-d$_4$) δ ppm 2.49 (s, 3H) 6.36 (s, 1H) 7.08 (t, J=4.20 Hz, 1H) 7.36 (d, J=4.69 Hz, 1H) 7.71 (d, J=3.12 Hz, 1H) 8.32 (s, 1H) 8.53 (s, 1H).

8-Chloro-2-methyl-7-thiophen-2-yl-1,4,9,9b-tetraaza-cyclopenta[a]naphthalene [CXIV]

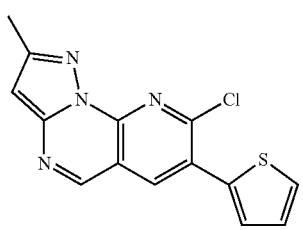

Compound [CXIV] was prepared using a procedure similar to that of Compound [V] (POCl$_3$ procedure). Data for Compound [CXIV]: LCMS (m/e): 301 (M+H); $^1$H NMR (400 MHz, CHLOROFORM-d) δ ppm 2.63 (s, 3H) 6.72 (s, 1H) 7.16-7.22 (m, 1H) 7.49 (d, J=3.51 Hz, 1H) 7.52 (d, J=5.08 Hz, 1H) 8.34 (s, 1H) 8.82 (s, 1H).

2-{3-Hydroxy-3-methyl-1-[4-(2-methyl-7-thiophen-2-yl-8,9-dihydro-1,4,9,9b-tetraaza-cyclopenta[a]naphthalene-8-yl)-phenyl]-cyclobutyl}-isoindole-4,3-dione [CXV]

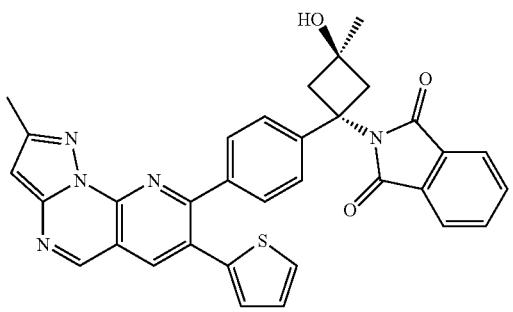

CXV

Compound [CXV] was prepared using a procedure similar to that of Compound [XL]. Data for Compound [CXV]: LCMS (m/e): 573 (M+H); $^1$H NMR (400 MHz, CHLOROFORM-d) δ ppm 1.44 (s, 3H) 2.56 (s, 3H) 3.15 (d, J=14.25 Hz, 2H) 3.38 (d, J=14.25 Hz, 2H) 6.67 (d, 1H) 6.86 (d, J=2.73 Hz, 1H) 6.93 (t, J=3.71 Hz, 1H) 7.25 (s, 3H) 7.30 (d, J=5.08 Hz, 1H) 7.57 (d, J=8.60 Hz, 2H) 7.65 (d, J=8.60 Hz, 2H) 7.68 (dd, J=5.47, 2.93 Hz, 2H) 7.77 (dd, J=5.47, 3.12 Hz, 2H) 8.29 (s, 1H) 8.82 (s, 1H).

3-Amino-1-methyl-3-[4-(2-methyl-7-thiophen-2-yl-8,9-dihydro-1,4,9,9b-tetraaza-cyclopenta[a]naphthalene-8-yl)-phenyl]-cyclobutanol [CXVI]

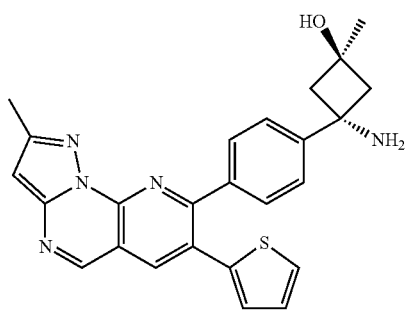

CXVI

Compound [CXVI] was prepared using a procedure similar to that of Compound [XLI]. Data for Compound [CXVI]: LCMS (m/e): 442 (M+H); $^1$H NMR (400 MHz, METHANOL-d$_4$) δ ppm 1.55 (s, 3H) 2.45 (d, J=13.47 Hz, 2H) 2.56 (s, 3H) 2.72 (d, J=13.28 Hz, 2H) 6.75 (s, 1H) 7.00-7.03 (m, 2H) 7.46 (d, J=3.32 Hz, 1H) 7.48 (d, J=8.40 Hz, 2H) 7.67 (d, Hz, 2H) 8.62 (s, 1H) 9.02 (s, 1H).

2-Methyl-7-thiophen-3-yl-9H-1,4,9,9b-tetraaza-cyclopenta[a]naphthalen-8-one [CXIII]

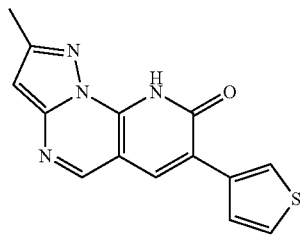

CXVII

Compound [CXVII] was prepared using a procedure similar to that of Compound [IV]. Data for Compound [CXVII]:

LCMS (m/e) 283 (M+H); $^1$H NMR (400 MHz, DMSO-d$_6$) δ ppm 2.45 (s, 3H) 6.39 (s, 1H) 8.31 (br. s., 1H) 8.40 (br. s., 1H) 8.49 (s, 1H) 8.59 (s, 1H) 9.86 (s, 1H).

Amount obtained: 0.493 g, 61% yield.

8-Chloro-2-methyl-7-thiophen-3-yl-1,4,9,9b-tetraaza-cyclopenta[a]naphthalene [CXVIII]

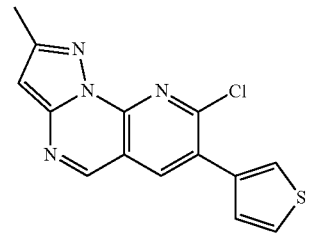

CXVIII

Compound [CXVIII] was prepared using a procedure similar to that of Compound [V]. Data for Compound [CXVIII]: LCMS (m/e) 301 (M+H); $^1$H NMR (400 MHz, CHLOROFORM-d) δ ppm 2.64 (s, 3H) 6.73 (s, 1H) 7.40 (dd, J=5.00, 1.20 Hz, 1H) 7.49 (dd, J=5.00, 3.00 Hz, 1H) 7.62 (dd, J=2.93, 1.22 Hz, 1H) 8.27 (s, 1H) 8.83 (s, 1H).

2-{3-Hydroxy-3-methyl-1-[4-(2-methyl-7-thiophen-3-yl-8,9-dihydro-1,4,9,9b-tetraaza-cyclopenta[a]naphthalene-8-yl)-phenyl]-cyclobutyl}-isoindole-4,3-dione [CXIX]

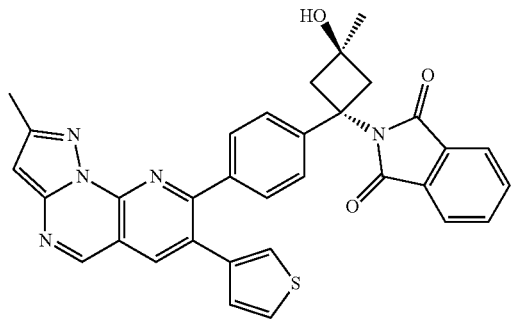

CXIX

Compound [CXIX] was prepared using a procedure similar to that of Compound [XL]. Data for Compound [CXIX]: LCMS (m/e) 572 (M+H); $^1$H NMR (400 MHz, CHLOROFORM-d) δ ppm 1.46 (s, 3H) 2.59 (s, 3H) 3.16 (d, 2H) 3.37 (d, 2H) 6.69 (s, 1. H) 7.23 (s, 1H) 7.48-7.80 (m, 8H) 8.26 (s, 1H) 8.84 (s, 1H).

3-Amino-1-methyl-3-[4-(2-methyl-7-thiophen-3-yl-8,9-dihydro-1,4,9,9b-tetraaza-cyclopenta[a]naphthalene-8-yl)-phenyl]-cyclobutanol [CXX]

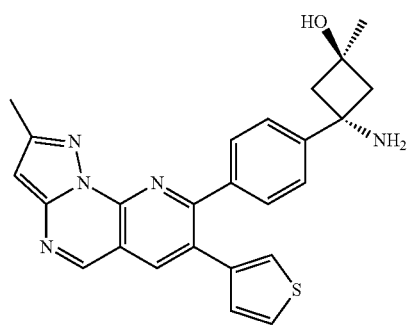

CXX

Compound [CXX] was prepared using a procedure similar to that of Compound [XL]. Data for Compound [CXX]: LCMS (m/e) 442 (M+H); ¹H NMR (400 MHz, METHANOL-d₄) δ ppm 1.78 (s, 3H) 2.84 (s, 3H) 2.94 (d, J=14.25 Hz, 2H) 3.14 (d, J=14.30 Hz, 2H) 7.02 (s, 1H) 7.15 (d, J=3.90 Hz, 1H) 7.61-7.68 (m, 1H) 7.65 (d, J=4.98 Hz, 1H) 7.71 (s, 1H) 7.81 (d, J=8.40 Hz, 2H) 8.01 (d, J=8.39 Hz, 2H) 8.87 (s, 1H) 9.30 (s, 1H).

7-(2-Fluoro-phenyl)-2-methyl-9H-4,4,9,9b-tetraaza-cyclopenta[a]naphthalen-8-one [CXXI]

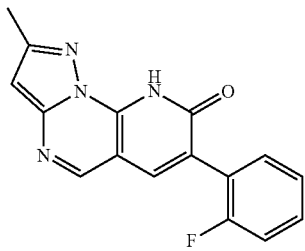

Compound [CXXI] was prepared using a procedure similar to that of Compound [IV]. Data for Compound [CXXI]: LCMS (m/e) 295 (M+H). This material was used directly in the next step without further purification or characterization.

8-Chloro-7-(2-fluoro-phenyl)-2-methyl-1,4,9,9b-tetraaza-cyclopenta[a]naphthalene [CXXII]

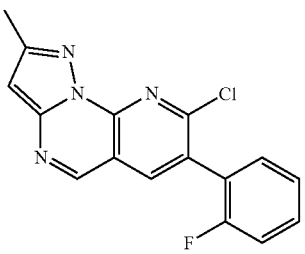

Compound [CXXII] was prepared using a procedure similar to that of Compound [V]. Data for Compound [CXXII]: LCMS (m/e) 313 (M+H). This material was used directly in the next step without further purification or characterization.

2-(1-{4-[7-(2-Fluoro-phenyl)-2-methyl-1,4,9,9b-tetraaza-cyclopenta[a]naphthalen-8-yl]-phenyl}-3-hydroxy-3-methyl-cyclobutyl)-isoindole-1,3-dione [CXXIII]

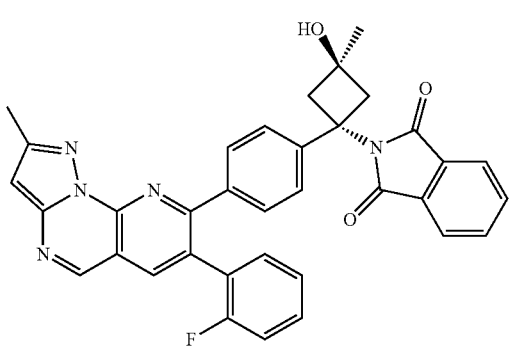

Compound [CXXIII] was prepared using a procedure similar to that of Compound [XL]. Data for Compound [CXXIII]:

LCMS (m/e) 584 (M+H). This material was used directly in the next step without further purification or characterization.

3-Amino-3-{4-[7-(2-fluoro-phenyl)-2-methyl-1,4,9,9b-tetraaza-cyclopenta[a]naphthalen-8-yl]-phenyl}-1-methyl-cyclobutanol [CXXIV]

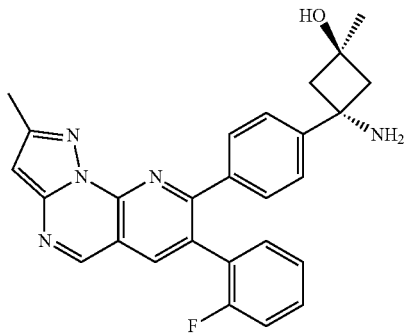

Compound [CXXIV] was prepared using a procedure similar to that of Compound [XLI]. Data for Compound [CXXIV]: LCMS (m/e) 454 (M+H); NMR (400 MHz, METHANOL-d₄) δ ppm 1.49 (s, 3H) 1.98 (s, 2H) 2.59 (s, 3H) 2.70 (d, J=14.64 Hz, 2H) 2.87 (d, J=14.25 Hz, 2H) 6.78 (s, 1H) 7.04 (t, J=9.08 Hz, 2H) 7.26 (t, J=7.42 Hz, 2H) 7.39-7.49 (m, 2H) 7.52 (d, J=8.20 Hz, 2H) 7.74 (d, J=8.20 Hz, 2H) 8.09 (s, 1H) 8.59 (s, 1H) 9.05 (s, 1H).

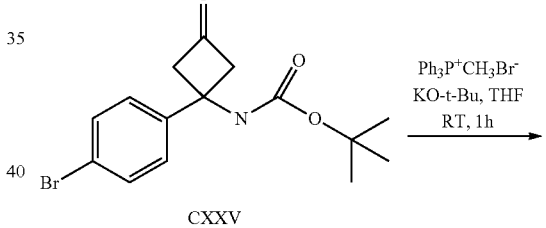

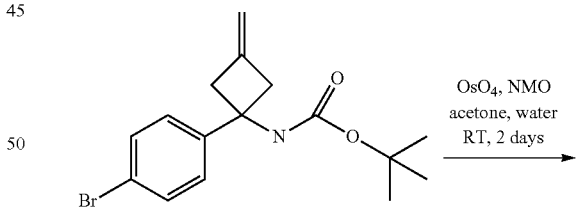

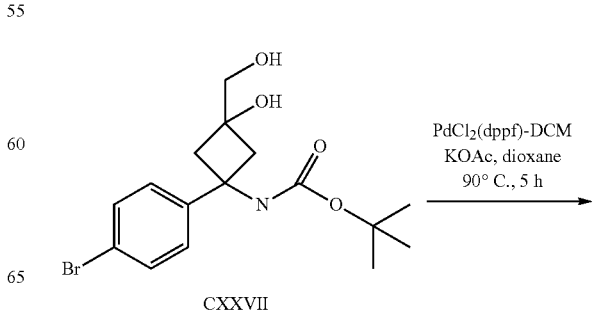

-continued

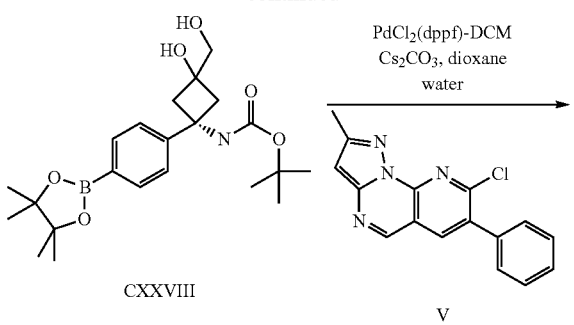

CXXVIII

V

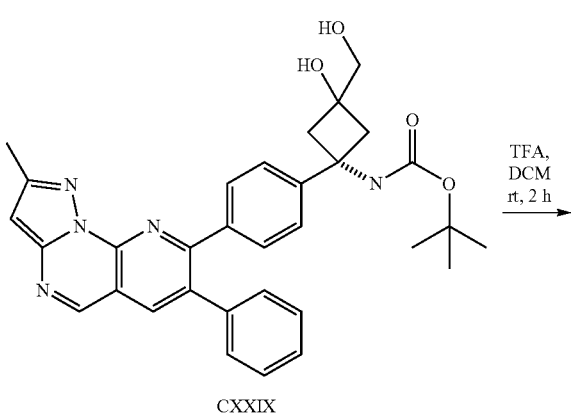

CXXIX

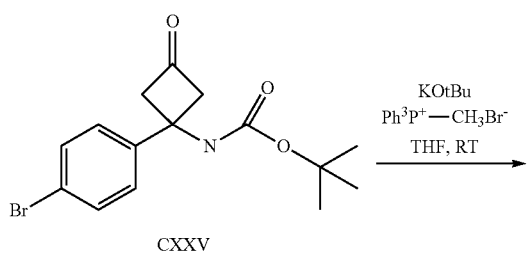

CXXX

[1-(4-Bromo-phenyl)-3-methylene-cyclobutyl]-carbamic acid tert-butyl ester [CXXVI]

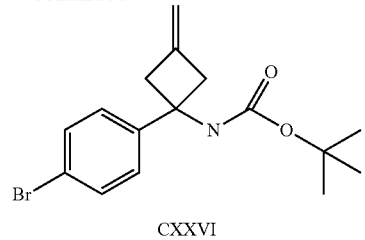

CXXVI

To a 40 mL scintillation vial containing Ph$_3$P$^+$CH$_3$Br$^-$ (1.45 g, 4.0 mmol, 2.8 eq.) and THF (12 mL) under Argon was added KO-t-Bu (0.45 g, 4.0 mmol, 2.8 eq.) in three portions. The reaction mixture was stirred at room temperature for 1 hour to form a solution of the ylide.

To a 20 mL scintillation vial containing Compound [CCXV] (0.49 mg, 1.42 mmol, 1 eq.) and THF (4.5 mL) under Argon was added the above ylide (4.26 mL of the above ylide solution, 1.42 mmol, 1 eq.) slowly at room temperature. After the addition, the reaction mixture was stirred for 1 hour. The reaction was quenched with water (5 mL) and the resulting solution was extracted with EtOAc (3×8 mL). The combined organic solution was dried over Na$_2$SO$_4$. After filtration and concentration, the residue was purified by silica gel chromatography using EtOAc and heptanes as the mobile phases to furnish Compound [CCXVI] as a yellowish solid: LCMS m/e 339 (M+H); $^1$H NMR (400 MHz, CHLOROFORM-d) δ ppm 1.38 (s, 9H) 3.14 (br. s., 4H) 4.90-5.01 (m, 2H) 5.19 (s, 1H) 7.00-7.59 (m, 4H).

[1-(4-Bromo-phenyl)-3-hydroxy-3-hydroxymethyl-cyclobutyl]-carbamic acid tert-butyl ester [CXXVII]

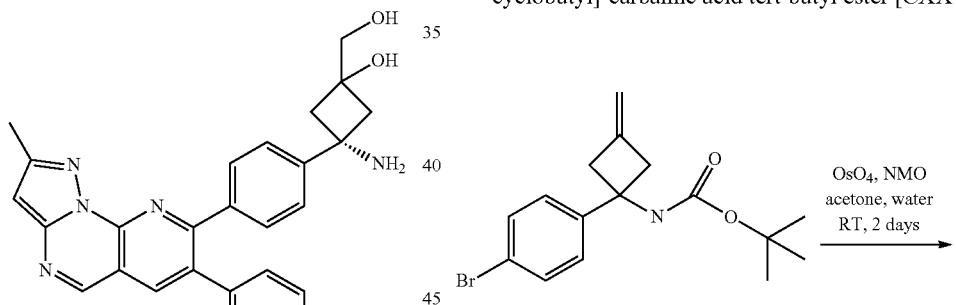

CXXVI

CXXVII

To a 20 mL scintillation vial containing Compound [CXXVI] (68 mg, 0.2 mmol, 1 eq.) and acetone (2 mL) and N-methylmorpholine-N-oxide (46 mg, 0.4 mmol, 2 eq.) was added OsO$_4$ (126 mg of a 4% solution in H$_2$O, 126 mg, 0.02 mmol, 0.1 eq.). The reaction mixture was stirred for 5 hours at room temperature. Then additional N-methylmorpholine-N-oxide (184 mg, 1.6 mmol, 8 eq.) and OsO$_4$ (504 mg of a 4% solution in H$_2$O, 0.08 mmol, 0.4 eq.) were added. The reaction mixture was stirred for 2 days at room temperature. Then it was quenched with saturated Na$_2$SO$_3$ (10 mL) and the resulting solution was extracted with EtOAc (3×10 mL) and CHCl₃ (3×10 mL). The combined organic solution was dried over Na₂SO₄. After filtration and concentration, the residue was purified by silica gel chromatography using MeOH and CH₂Cl₂ as the mobile phases to furnish Compound [CXXVII] as a yellowish solid: LCMS m/e 373 (M+H); ¹H NMR (400 MHz, METHANOL-d₄) δ ppm 1.35 (br. 2 s., 9H) 2.34-2.49 (m, 2H) 2.63-2.74 (m, 1H) 2.78-2.88 (m, 1H) 3.25 (s, 1H) 3.34 (s, 1H) 3.65 (s, 1H) 7.31-7.49 (m, 4H).

{3-Hydroxy-3-hydroxymethyl-1-[4-(4,4,5,5-tetramethyl-[1,3,2]dioxaborolan-2-yl)-phenyl-cyclobutyl}-carbamic acid tert-butyl ester [CXXVIII]

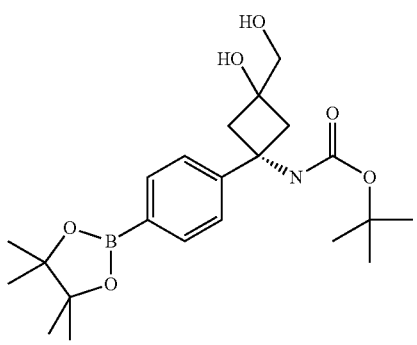

CXXVIII

Compound [CXXVIII] was prepared using a procedure similar to that of Compound [XXXIX]. Data for Compound [CXXVIII]: LCMS m/e 420 (M+H); ¹H NMR (400 MHz, CHLOROFORM-d) δ ppm 1.11-1.64 (m, 21H) 1.91-2.12 (m, 1H) 2.31-3.10 (m, 4H) 3.34 (d, J=5.76 Hz, 1H) 3.82 (d, J=4.93 Hz, 1H) 4.69-5.19 (m, 1H) 7.30-7.87 (m, 4H).

[1-(4-{7-[(Z)-1-Eth-(E)-ylidene-penta-2,4-dienyl]-2-methyl-1,4,9,9b-tetraaza-cyclopenta[a]naphthalen-8-yl}-phenyl)-3-hydroxy-3-hydroxymethyl-cyclobutyl]-carbamic acid tert-butyl ester [CXXIX]

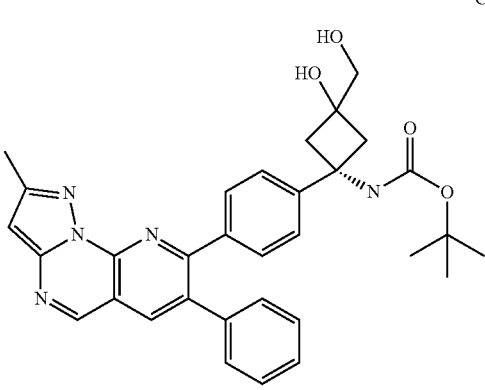

CXXIX

Compound [CXXIX] was prepared using a procedure similar to that of Compound [XL]. Data for Compound [CXXIX]: LCMS m/e 552 (M+H); ¹H NMR (400 MHz, CHLOROFORM-d) δ ppm 1.44 (br. s., 9H) 2.62 (s, 3H) 2.74-3.04 (m, 4H) 3.34 (s, 1H) 3.78 (br. s., 1H) 4.78-5.17 (m, 1H) 6.71 (2 s, 1H) 7.16-7.67 (m, 9H) 8.24 (2 s, 1H) 8.86 (2 s, 1H).

3-Amino-1-hydroxymethyl-3-[4-(2-methyl-7-phenyl-1,4,9,9b-tetraaza-cyclopenta[a]naphthalen-8-yl)-phenyl]-cyclobutanol [CXXX]

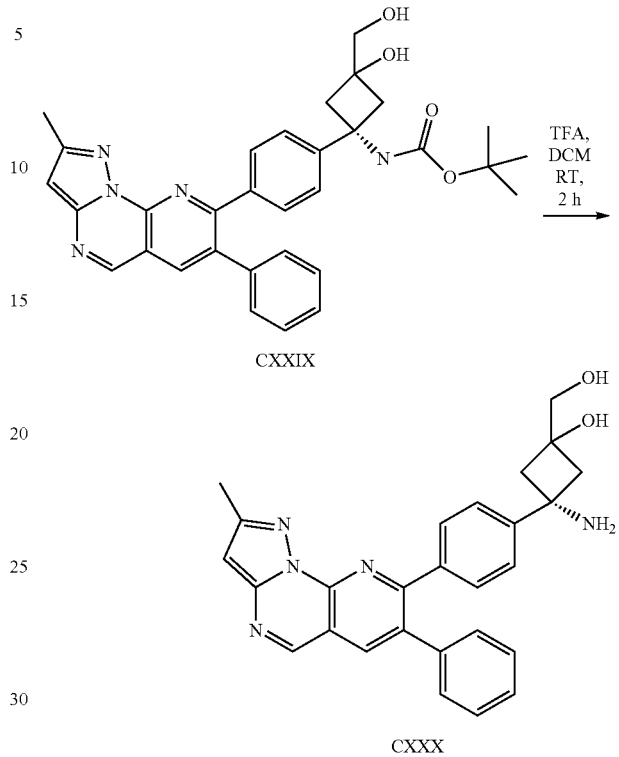

To a 20 mL scintillation vial containing Compound [CXXIX] (22 mg, 0.04 mmol, 1 eq.) and CH₂Cl₂ (2 mL) was added TFA (0.2 mL). The reaction mixture was stirred for 2 hours at room temperature. Then the solvent was removed and the residue was dissolved in 80% MeOH:H₂O (2 mL). Then it was purified by reverse-phase preparative HPLC using water-acetonitrile-TFA [95:5:0.05] and acetonitrile-water-TFA [95:5:0.05] as the mobile phases to provide Compound [CXXX] as a yellow solid: LCMS m/e 452 (M+H); ¹H NMR (400 MHz, METHANOL-d₄) δ ppm 2.47-2.55 (m, 1H) 2.58 (s, 3H) 2.75-2.86 (m, 1H) 2.90-3.03 (m, 2H) 3.28 (br. s., 1H) 3.57 (s, 1H) 6.77 (s, 1H) 7.25-7.38 (m, 5H) 7.40-7.48 (m, 2H) 7.63-7.77 (m, 2H) 8.57 (2 s, 1H) 9.05 (s, 1H).

{3-Methylene-1-[4-(4,4,5,5-tetramethyl-[1,3,2]dioxaborolan-2-yl)-phenyl]-cyclobutyl}-carbamic acid tert-butyl ester [CXXXI]

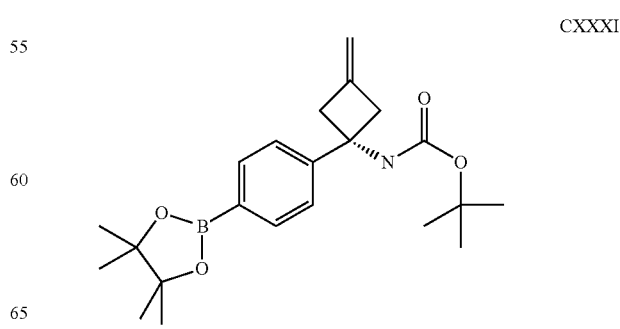

CXXXI

Compound [CXXXI] was prepared using a procedure similar to that of Compound [XXXIX]. Data for Compound [CXXXI]: LCMS m/e 386 (M+H); $^1$H NMR (400 MHz, CHLOROFORM-d) δ ppm 1.34 (br. s., 21H) 3.18 (br. s., 4H) 4.94 (t, J=2.33 Hz, 2H) 5.13 (br. s., 1H) 7.42 (d, J=8.20 Hz, 2H) 7.77 (d, J=8.13 Hz, 2H).

{3-Methylene-1-[4-(2-methyl-7-phenyl-1,4,9,9b-tetraaza-cyclopenta[a]naphthalen-8-yl)-phenyl]-cyclobutyl}-carbamic acid tert-butyl ester [CXXXII]

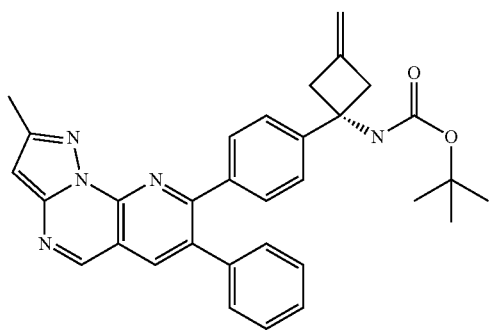

CXXXII

Compound [CXXXII] was prepared using a procedure similar to that of Compound [XL]. Data for Compound [CXXXII]: LCMS m/e 519 (M+H); $^1$H NMR (400 MHz, METHANOL-d$_4$) δ ppm 1.40 (br. s., 9H) 2.57 (s, 3H) 3.11 (br. s., 4H) 4.88-4.94 (m, 2H) 6.74 (s, 1H) 7.27-7.43 (m, 7H) 7.57 (d, J=8.44 Hz, 2H) 8.51 (s, 1H) 9.02 (s, 1H).

3-Methylene-1-[4-(2-methyl-7-phenyl-1,4,9,9b-tetraaza-cyclopenta[a]naphthalen-8-yl)-phenyl]-cyclobutylamine [CXXXIII]

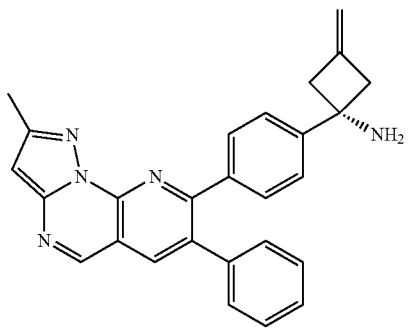

CXXXIII

Compound [CXXXIII] was prepared using a procedure similar to that of Compound [XLIV]. Data for Compound [CXXXIII]: LCMS m/e 418 (M+H); $^1$H NMR (400 MBz, METHANOL-d$_4$) δ ppm 2.58 (s, 3H) 3.26-3.29 (m, 1H) 3.31-3.34 (m, 1H) 3.36-3.50 (m, 2H) 5.09 (t, J=2.34 Hz, 2H) 6.76 (s, 1H) 7.24-7.39 (m, 5H) 7.45 (d, J=8.47 Hz, 1H) 7.71 (d, J=8.44 Hz, 1H) 8.55 (s, 1H) 9.04 (s, 1H).

1-(4-Bromo-phenyl)-cyclobutanecarbonitrile [CXXXIV]

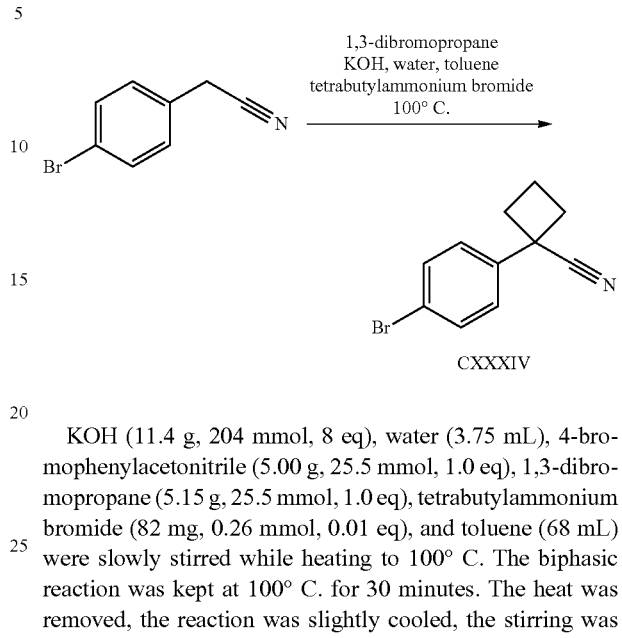

CXXXIV

KOH (11.4 g, 204 mmol, 8 eq), water (3.75 mL), 4-bromophenylacetonitrile (5.00 g, 25.5 mmol, 1.0 eq), 1,3-dibromopropane (5.15 g, 25.5 mmol, 1.0 eq), tetrabutylammonium bromide (82 mg, 0.26 mmol, 0.01 eq), and toluene (68 mL) were slowly stirred while heating to 100° C. The biphasic reaction was kept at 100° C. for 30 minutes. The heat was removed, the reaction was slightly cooled, the stirring was then increased to rapid, and then heating continued up to reflux, 115° C. After 1.5 hours at 115° C., the reaction was cooled, diluted with water, and extracted with EtOAc (×3). The combined organics were dried with brine and Na$_2$SO$_4$, and then concentrated in vacuo onto Celite. The resulting material was purified by silica gel chromatography by eluting with a gradient of heptane and EtOAc (0% to 35% EtOAc) to provide Compound [CXXXIV]: $^1$H NMR (400 MHz, CHLOROFORM-d) δ ppm 1.99-2.15 (m, J=11.52, 9.02, 9.02, 4.40, 4.40 Hz, 1H) 2.34-2.51 (m, 1H) 2.51-2.65 (m, 2H) 2.74-2.89 (m, 2H) 7.21-7.36 (m, 2H) 7.45-7.57 (m, 2H).

1-[4-(4,4,5,5-Tetramethyl-[1,3,2]dioxaborolan-2-yl)-phenyl]-cyclobutanecarbonitrile [CXXXV]

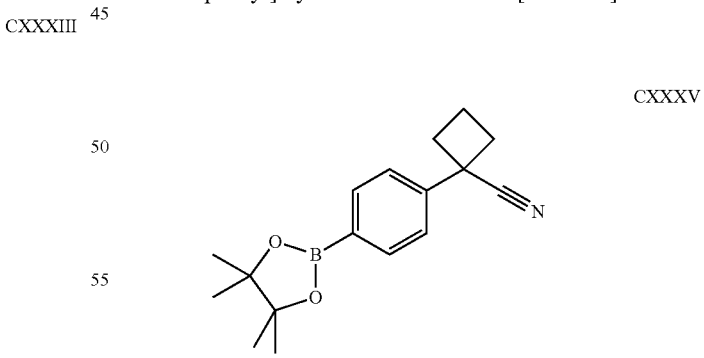

CXXXV

Compound [CXXXV] was prepared in a similar way to that of Compound [XXXIX]. Data for Compound [CXXXV]: LCMS (m/e) 306 (M+Na); $^1$H NMR (400 MHz, CHLOROFORM-d) δ ppm 1.28 (s, 12H) 1.93-2.09 (m, J=11.57, 9.05, 9.05, 4.47, 4.47 Hz, 1H) 2.29-2.45 (m, 1H) 2.50-2.62 (m, 2H) 2.71-2.82 (m, 2H) 7.35 (d, J=8.30 Hz, 2H) 7.77 (d, J=8.30 Hz, 2H).

1-[4-(2-Methyl-7-phenyl-1,4,9,9b-tetraaza-cyclopenta[a]naphthalen-8-yl)-phenyl]-cyclobutanecarbonitrile [CXXXVI]

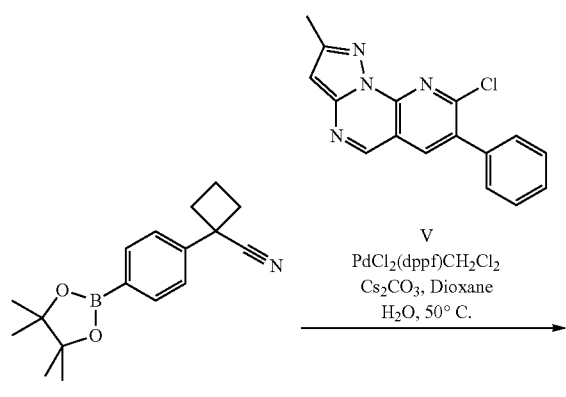

Compound [V] (20 mg, 0.07 mmol, 1.0 eq), Cs$_2$CO$_3$ (110 mg, 0.34 mmol, 5.00 eq), PdCl$_2$(dppf)CH$_2$Cl$_2$ (8.0 mg, 0.01 mmol, 0.15 eq), and Compound [CXXXV] (29 mg, 0.10 mmol, 1.5 eq) were dissolved in dioxane (1.5 mL, degassed) and water (0.5 mL, degassed). The reaction was again degassed and heated to 50° C. for 1 hour. After that time, additional water was added and extracted with CH$_2$Cl$_2$ (×3). The combined organics were dried with brine and Na$_2$SO$_4$, and then concentrated in vacuo. The residue was purified by silica gel chromatography by eluting with a gradient of CHCl$_3$ to [CHCl$_3$/MeOH/NH$_4$OH 95:5:1]. The resulting solid was then dissolved in MeOH with added TEA (100 μL) and purified by reverse-phase chromatography (Solvent A H$_2$O/CH$_3$CN/TFA (95:5:0.05), Solvent B CH$_3$CN/H$_2$O/TFA (95:5:0.05)) with a gradient of 5% to 60% B over 5 minutes to give Compound [CXXXVI] as the TFA salt: LCMS (m/e) 416 (M+H); $^1$H NMR (400 MHz, METHANOL-d$_4$) δ ppm 2.02-2.15 (m, 1H) 2.31-2.47 (m, 1H) 2.56 (s, 3H) 2.59-2.70 (m, 2H) 2.70-2.82 (m, 2H) 6.72.

1-(4-Bromo-phenyl)-cyclobutanecarboxylic acid amide [CXXXVII]

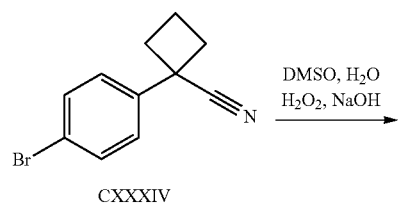

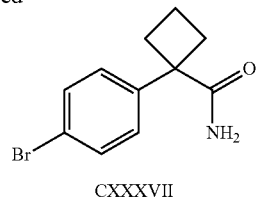

Compound [CXXXIV] (2.90 g, 12.3 mmol, 1.0 eq) was dissolved in DMF (30 mL). Next, NaOH (5.0 N aq, 3.28 mL), water (3.28 mL), H$_2$O$_2$ (30%, 6.56 mL), and DMSO (2.98 mL) were added and the reaction heated to 50° C. for 30 minutes. The mixture was cooled, water was added, and the layers separated. The aqueous phase was extracted with EtOAc (×3). The combined organic phases were washed with water (×2), dried with brine and Na$_2$SO$_4$, and concentrated. The residue was purified by silica gel chromatography by eluting with a gradient of heptane and EtOAc (0% to 100% EtOAc). Collected [CXXXVII]: $^1$H NMR (400 MHz, CHLOROFORM-d) δ ppm 1.78-1.96 (m, J=11.18, 9.27, 9.27, 5.62, 5.62 Hz, 1H) 2.07-2.22 (m, J=9.13, 9.13, 9.13, 9.13, 7.22 Hz, 1H) 2.35-2.49 (m, 2H) 2.82 (ddd, J=12.06, 9.18, 5.66 Hz, 2H) 5.07 (br. s., 1H) 5.31 (br. s., 1H) 7.16-7.22 (m, 2H) 7.45-7.52 (m, 2H).

1-(4-Bromo-phenyl)-cyclobutylamine [CXXXVIII]

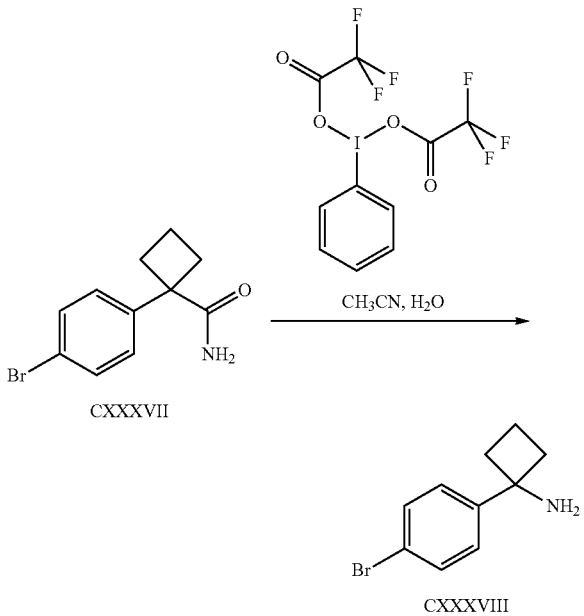

To a solution of Compound [CXXXVII] (2.80 g, 11.0 mmol, 1.0 eq.) in CH$_3$CN (12 mL) and water (12 mL) was added [bis(trifluoroacetoxy)iodo]benzene (7.11 g, 16.5 mmol, 1.5 eq.) and the resulting mixture stirred at room temperature. After 24 hours, the reaction was slowly poured into saturated aqueous NaHCO$_3$ and extracted with ethyl acetate (×3). The combined organic layers were dried with brine and Na$_2$SO$_4$, concentrated, and the residue purified by silica gel chromatography by eluting with CHCl$_3$ to CHCl$_3$/MeOH/NH$_4$OH (90:10:1) to give Compound [CXXXVIII]: LCMS (m/e) 226 (M+H); $^1$H NMR (400 MHz, CHLOROFORM-d) δ ppm 1.65 (br. s., 2H) 1.68-1.80 (m, 1H) 1.97-2.09

(m, 1H) 2.10-2.20 (m, 2H) 2.50 (ddd, J=11.93, 8.93, 6.08 Hz, 2H) 7.26-7.33 (m, 2H) 7.41-7.51 (m, 2H).

[1-(4-Bromo-phenyl)-cyclobutyl]-methyl-carbamic acid tert-butyl ester [CXXXIX]

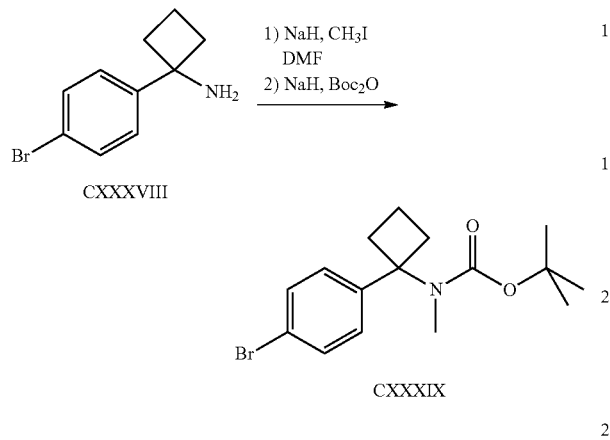

To as solution of Compound [CXXXVIII] (226 mg, 1.0 mmol, 1.0 eq) in DMF (10 mL, anhydrous) was added NaH (60% in oil, 40 mg, 1.0 mmol, 1.0 eq), and the mixture stirred at room temperature for 1 hour. $CH_3I$ (62 μL, 1.0 mmol, 1.0 eq) was added and the mixture stirred for an additional 7 hours at room temperature. After that time, the reaction was placed under vacuum to remove the unreacted $CH_3I$. Next, NaH (60% in oil, 80 mg, 2.0 mmol, 2.0 eq) and $Boc_2O$ (327 mg, 1.5 mmol, 1.5 eq) were added and the reaction stirred at room temperature for 16 hours. After that time the reaction was quenched by the addition of MeOH, followed by water. The mixture was then extracted with EtOAc (×3). The combined organic layers were dried, concentrated, and the residue purified by silica gel chromatography by eluting with heptane and EtOAc (0% to 100% EtOAc) to give Compound [CXXXIX]: LCMS (m/e) 396 (M+Na). This material was used directly in the next step.

Methyl-{1-[4-(4,4,5,5-tetramethyl-[1,3,2]dioxaborolan-2-yl)-phenyl]-cyclobutyl}-carbamic acid tert-butyl ester [CXL]

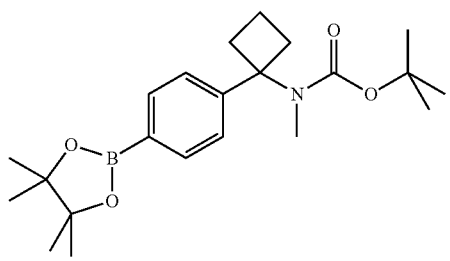

Compound [CXL] was prepared in a similar way to that of Compound [XXXIX]. Data for Compound [CXL]: LCMS (m/e) 410 (M+Na); $^1H$ NMR (400 MHz, CHLOROFORM-d) δ ppm 1.33 (d, J=2.00 Hz, 12H) 1.55 (s, 3H) 1.69-1.92 (m, 1H) 2.44-2.66 (m, 3H) 2.76 (br. s., 1H) 7.38-7.45 (m, 1H) 7.45-7.55 (m, 1H) 7.69-7.86 (m, 2H).

Methyl-{1-[4-(2-methyl-7-phenyl-1,4,9,9b-tetraazacyclopenta[a]naphthalen-8-yl)-phenyl]-cyclobutyl}-amine [CXLI]

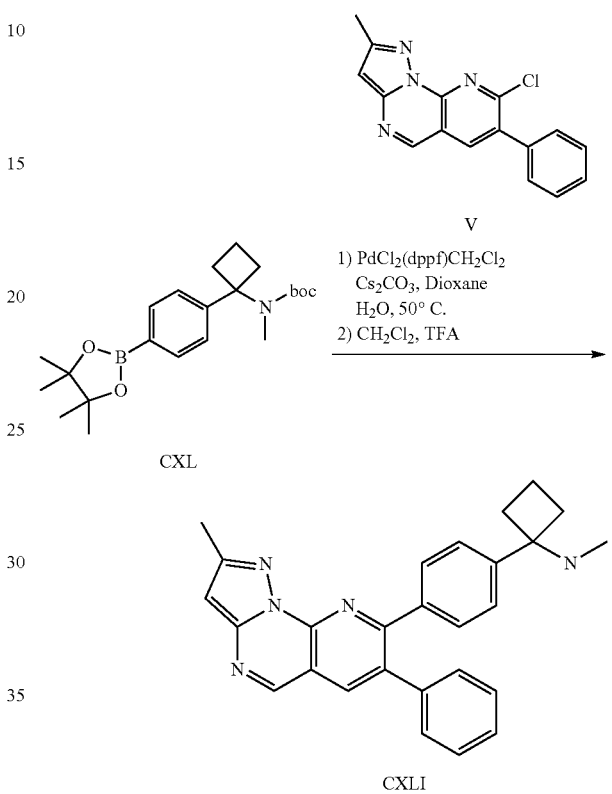

Compound [CXL] (99 mg, 0.25 mmol) was reacted under similar conditions to that of Compound [XL]. After purification on silica gel the intermediate was dissolved in $CH_2Cl_2$ (1.0 mL) and reacted with TFA (0.5 mL) to remove the BOC protecting group. Then the final compound was blown down to dryness, redissolved in MeOH, and purified by reverse-phase chromatography (Solvent A $H_2O/CH_3CN/TFA$ (95:5:0.05), Solvent B $CH_3CN/H_2O/TFA$ (95:5:0.05)) with a gradient of 5% to 60% B over 5 minutes to give [CXLI] as the TFA salt: LCMS (m/e) 420 (M+H); $^1H$ NMR (400 MHz, METHANOL-$d_4$) δ ppm 1.84-1.99 (m, 1H) 2.11-2.25 (m, 1H) 2.34 (s, 3H) 2.59 (s, 3H) 2.60-2.71 (m, 2H) 2.71-2.86 (m, 2H) 6.78 (s, 1H) 7.28-7.40 (m, 5H) 7.49 (d, J=8.54 Hz, 2H) 7.74 (d, J=8.44 Hz, 2H) 8.59 (s, 1H) 9.06 (s, 1H).

3-(4-Bromo-phenyl)-2,2-dichloro-cyclobutanone [CXLII]

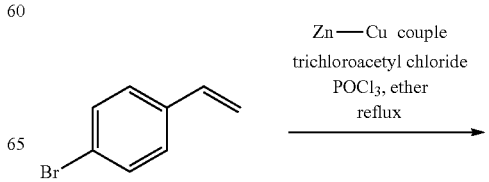

-continued

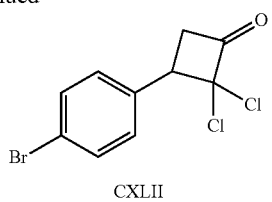

4-Bromosytrene (40.0 g, 219 mmol, 1.0 eq) was dissolved in anhydrous Et$_2$O (320 mL). Then Zn—Cu couple (28.6 g, 437 mmol, 2.0 eq) was added to the ether solution. To the resulting mixture was slowly added a mixture of trichloroacetyl chloride (24 mL, 218 mmol, 1.0 eq), POCl$_3$ (20 mL, 218 mmol, 1.0 eq), and ether (160 mL, anhydrous) over 30 minutes. The reaction was then heated to reflux for 16 hours. After that time the reaction was cooled, filtered through Celite, and quenched by slowly pouring into water. The water layer was removed and the remaining organic layer was washed with NaHCO$_3$ (aq sat), dried with brine and Na$_2$SO$_4$, and then concentrated in vacuo. This material was used directly in the next step without further purification. Data for Compound [CXLII]: $^1$H NMR (400 MHz, CHLOROFORM-d) δ ppm 3.49-3.60 (m, 1H) 3.60-3.73 (m, 1H) 4.18 (t, J=10.30 Hz, 1H) 7.18 (d, J=8.59 Hz, 2H) 7.56 (d, J=8.40 Hz, 2H).

3-(4-Bromo-phenyl)-cyclobutanone [CXLIII]

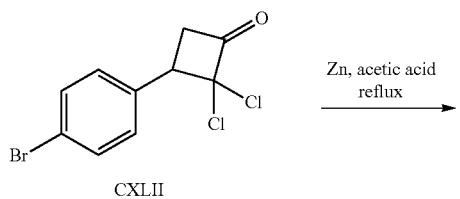

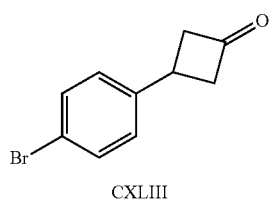

Compound [CXLII] (30.0 g, 102 mmol, 1.0 eq) was dissolved, in glacial acetic acid (75 mL), then Zn (30.0 g, 450 mmol, 4.5 eq) was slowly added in small portions. The slurry was stirred at room temperature for 30 minutes then heated to 115° C. for 16 hours. After that time, the reaction was cooled, diluted with EtOAc, filtered through Celite, and concentrated. The resulting oil was purified by silica gel chromatography by eluting with heptane and EtOAc (0% to 25% EtOAc) to give Compound [CXLIII]: $^1$H NMR (400 MHz, CHLOROFORM-d) δ ppm 3.07-3.21 (m, 2H) 3.37-3.50 (m, 2H) 3.51-3.64 (m, 1H) 7.08-7.13 (m, 2H) 7.38-7.44 (m, 2H).

3-(4-Bromo-phenyl)-1-cyclopropyl-cyclobutanol [CXLIV]

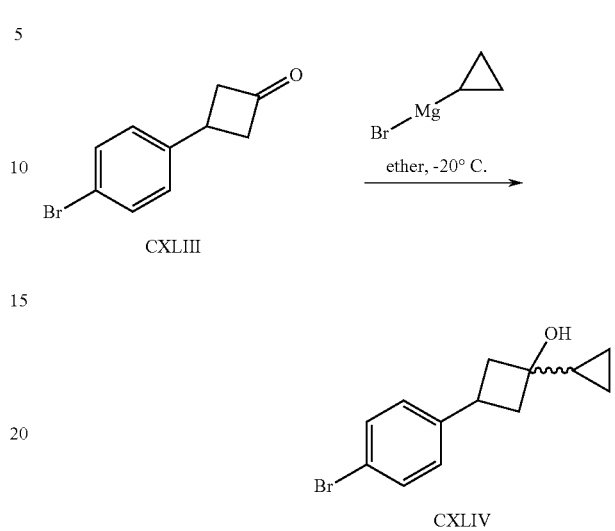

Compound [CXLIII] (50 mg, 0.22 mmol, 1.0 eq) was dissolved in anhydrous Et$_2$O (2.5 mL) and cooled to −40° C. Cyclopropyl magnesium bromide (666 μL of a 0.50 M solution in THF, 0.33 mmol, 1.5 eq) was then added and the reaction stirred at −20° C. for 4 hours. The reaction was quenched with NH$_4$Cl (aq sat) and extracted with ether (×3). The combined organic layers were dried with brine and Na$_2$SO$_4$ and concentrated in vacuo. The resulting oil was purified by silica gel chromatography by eluting with heptane and EtOAc (0% to 40% EtOAc) to give Compound [CXLIV]: $^1$H NMR (400 MHz, CHLOROFORM-d) δ ppm 0.39-0.48 (m, 2H) 0.54-0.66 (m, 2H) 1.16-1.35 (m, 1H) 1.81 (s, 1H) 2.08-2.20 (m, 2H) 2.44 (ddd, J=9.58, 8.31, 2.81 Hz, 2H) 2.93 (dq, J=9.15, 8.97 Hz, 1H) 7.12 (d, J=8.30 Hz, 2H) 7.38-7.47 (m, 2H).

1-Cyclopropyl-3-[4-(4,4,5,5-tetramethyl-[1,3,2]dioxaborolan-2-yl)-phenyl]-cyclobutanol [CXLV]

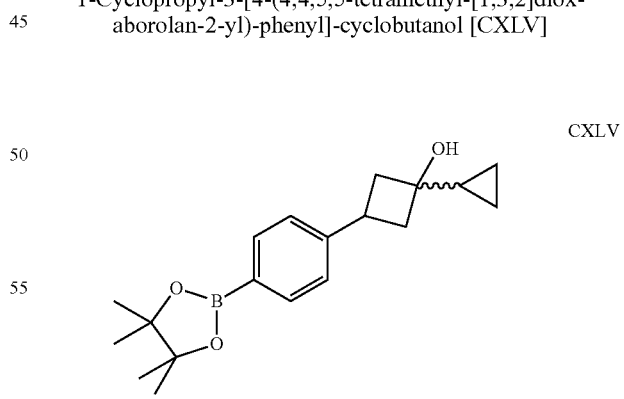

Compound [CXLV] was prepared in a similar way to that of Compound [XXXIX]. Data for Compound [CXLV]: LCMS (m/e) 337 (M+Na); $^1$H NMR (400 MHz, CHLOROFORM-d) δ ppm 0.12-0.23 (m, 2H) 0.27-0.37 (m, 2H) 0.93-0.99 (m, 1H) 1.03-1.13 (m, 12H) 1.87-1.97 (m, 2H) 2.11-2.24 (m, 2H) 7.00 (d, 2H) 7.49 (d, J=8.00 Hz, 2H).

1-Cyclopropyl-3-[4-(2-methyl-7-phenyl-1,4,9,9b-tetraaza-cyclopenta[a]naphthalen-8-yl)-phenyl]-cyclobutanol [CXLVI]

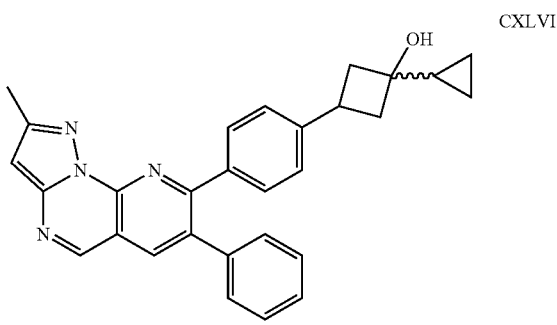 [SMILES: Cc1cc2ncc3cc(-c4ccccc4)c(-c4ccc(C5CC(O)(C6CC6)C5)cc4)nc3n2n1]

Compound [CXLVI] was prepared in a similar way to that of Compound [XL]. Data for Compound [CXLVI] (as the TFA salt): LCMS (m/e) 447 (M+H); $^1$H NMR (400 MHz, METHANOL-$d_4$) δ ppm 0.39-0.48 (m, 2H) 0.52 (d, J=8.20 Hz, 1H) 1.12-1.25 (m, 1H) 2.06-2.18 (m, 2H) 2.43 (td, J=8.96, 2.68 Hz, 2H) 2.58 (s, 3H) 3.00 (quin, J=9.03 Hz, 1H) 6.73 (s, 1H) 7.18 (d, J=8.20 Hz, 2H) 7.25-7.31 (m, 2H) 7.34 (d, J=2.83 Hz, 3H) 7.51 (d, J=8.25 Hz, 2H) 8.47 (s, 1H) 9.00 (s, 1H).

Trans-2-[1-(4-Bromo-phenyl)-3-hydroxy-3-vinyl-cyclobutyl]-isoindole-1,3-dione [CXLVII] and Cis-2-[1-(4-Bromo-phenyl)-3-hydroxy-3-vinyl-cyclobutyl]-isoindole-1,3-dione [CXLVIII]

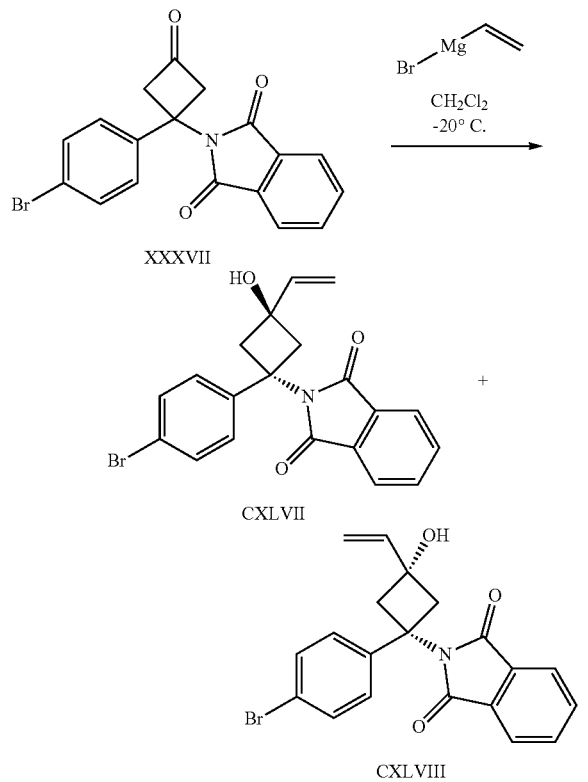

Compound [XXXVII] (250 mg, 0.68 mmol, 1.0 eq) was dissolved in $CH_2Cl_2$ (7.0 mL, anhydrous) and cooled to −40° C. Then vinylmagnesium bromide (1.0 mL of a 1.0 M in THF, 1.0 mmol, 1.5 eq) was added, the reaction was warmed to −20° C., and held for 1.5 hours. The reaction was quenched with the addition of aqueous saturated $NH_4Cl$ solution. The mixture was diluted with $H_2O$, then extracted with EtOAc (×3). The combined organic layers were dried with brine and $Na_2SO_4$ and concentrated in vacuo. The residue was purified by silica gel chromatography by eluting with heptane and EtOAc (0% to 50% EtOAc) to give Compound [CXLVII] and Compound [CXLVIII].

Data for Compound [CXLVII]: $^1$H NMR (400 MHz, CHLOROFORM-d) δ ppm 3.10-3.21 (m, 2H) 3.39-3.49 (m, 2H) 5.07 (dd, J=10.64, 0.83 Hz, 1H) 5.25 (dd, J=17.23, 0.88 Hz, 1H) 6.05 (dd, J=17.23, 10.59 Hz, 1H) 7.46 (t, J=4.64 Hz, 2H) 7.54-7.61 (m, 2H) 7.62-7.70 (m, 2H) 7.70-7.79 (m, 2H).

Data for Compound [CXLVIII] $^1$H NMR (400 MHz, CHLOROFORM-d) δ ppm 3.20-3.31 (m, 2H) 3.39-3.49 (m, 2H) 4.94 (dd, J=10.69, 0.63 Hz, 1H) 5.10 (dd, J=17.25, 0.66 Hz, 1H) 5.77 (dd, J=17.25, 10.66 Hz, 1H) 7.40-7.47 (m, 2H) 7.53-7.59 (m, 2H) 7.61-7.69 (m, 2H) 7.70-7.77 (m, 2H).

Trans-2-{3-Hydroxy-1-[4-(4,4,5,5-tetramethyl-[1,3,2]dioxaborolan-2-yl)-phenyl]-3-vinyl-cyclobutyl}-isoindole-1,3-dione [CXLIX]

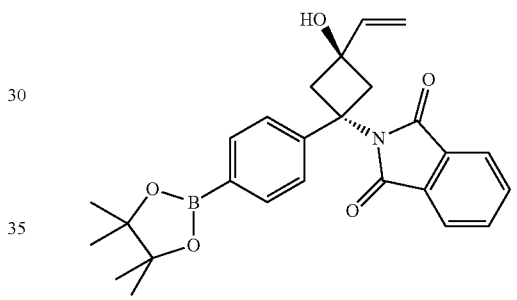

Compound [CXLIX] was prepared in a similar way to that of Compound [XXXIX]. This material was used directly in the next step without father purification or characterization.

Trans-2-{3-Hydroxy-1-[4-(2-methyl-7-phenyl-1,4,9,9b-tetraaza-cyclopenta[a]naphthalen-8-yl)-phenyl]-3-vinyl-cyclobutyl}-isoindole-1,3-dione

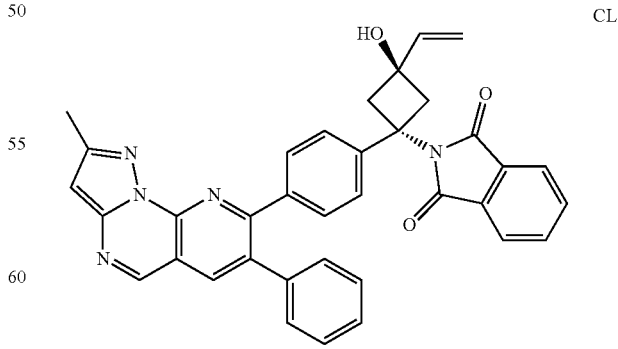

Compound [CL] was prepared in a similar way to that of Compound Ng. Data for Compound [CL]: LCMS (rule) 578 (M+H).

Trans-3-Amino-1-ethyl-3-[4-(2-methyl-7-phenyl-1,4,9,9b-tetraaza-cyclopenta[a]naphthalen-8-yl)-phenyl]-cyclobutanol [CLI]

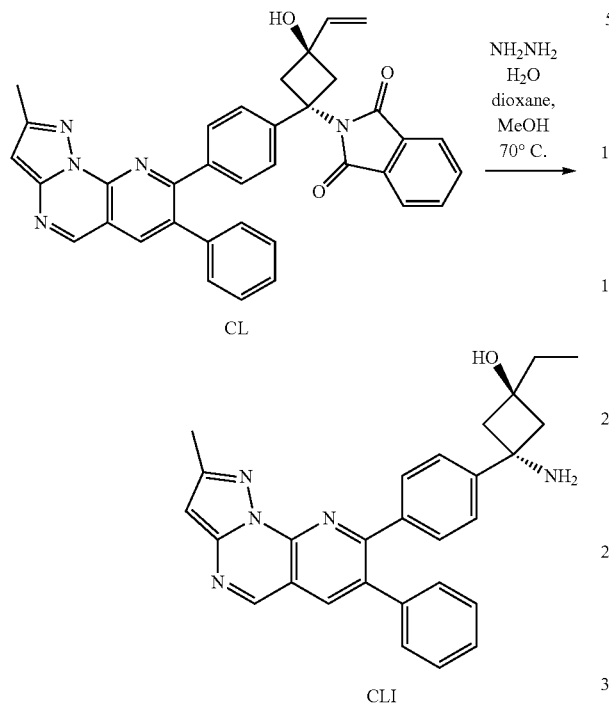

To Compound [CL] (28 mg, 0.05 mmol, 1.0 eq) was added MeOH (500 μL), dioxane (500 μL), and hydrazine monohydrate (250 μL). The reaction was heated to 70° C. for 2 hours. After that time the reaction was blown to dryness with $N_2$ and the resulting solid was dissolved in MeOH. Following addition of TFA (100 μL), the material was purified by reverse-phase chromatography (Solvent A: $H_2O/CH_3CN/TFA$ (95:5:0.05), Solvent B: $CH_3CN/H_2O/TFA$ (95:5:0.05)) with a gradient of 5% to 60% B over 5 minutes to give Compound [CLI] as the TFA salt: LCMS (m/e) 450 (M+H); $^1$H NMR (400 MHz, METHANOL-$d_4$) δ ppm 0.95 (t, J=7.37 Hz, 3H) 1.76 (q, J=7.32 Hz, 2H) 2.59 (s, 3H) 2.62-2.73 (m, 2H) 2.75-2.89 (m, 2H) 6.77 (s, 1H) 7.35 (t, J=3.10 Hz, 5H) 7.54 (d, J=8.40 Hz, 2H) 7.74 (d, J=8.40 Hz, 2H) 8.56 (s, 1H) 9.05 (s, 1H).

Cis-2-{3-Hydroxy-1-[4-(4,4,5,5-tetramethyl-[1,3,2]dioxaborolan-2-yl)-phenyl]-3-vinyl-cyclobutyl}-isoindole-1,3-dione [CLII]

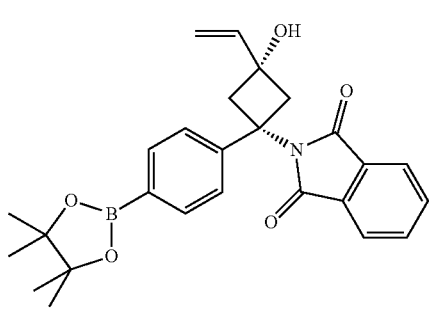

Compound [CLII] was prepared in a similar way to that of Compound [XXXIX]. This material was used directly in the next step without father purification or characterization.

Cis-2-{3-Hydroxy-1-[4-(2-methyl-7-phenyl-1,4,9,9b-tetraaza-cyclopenta[a]naphthalen-8-yl)-phenyl]-3-vinyl-cyclobutyl}-isoindole-1,3-dione [CLIII]

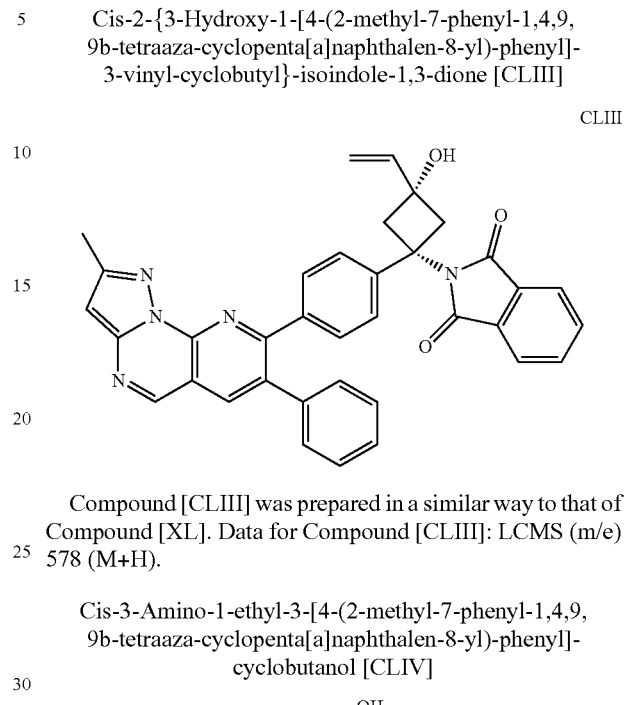

Compound [CLIII] was prepared in a similar way to that of Compound [XL]. Data for Compound [CLIII]: LCMS (m/e) 578 (M+H).

Cis-3-Amino-1-ethyl-3-[4-(2-methyl-7-phenyl-1,4,9,9b-tetraaza-cyclopenta[a]naphthalen-8-yl)-phenyl]-cyclobutanol [CLIV]

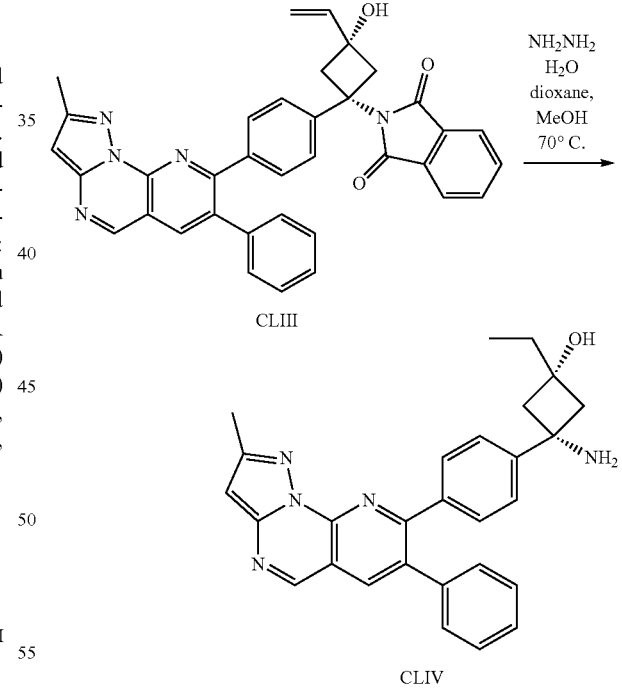

To Compound [CLIII] (31 mg, 0.05 mmol, 1.0 eq) was added MeOH (500 μL), dioxane (500 μL), and hydrazine monohydrate (250 μL). The reaction was heated to 70° C. for 2 hours. After that time the reaction was blown to dryness with $N_2$, the resulting solid was dissolved in MeOH. Then added TFA (100 μL), and purified by reverse-phase chromatography (Solvent A $H_2O/CH_3CN/TFA$ (95:5:0.05), Solvent B $CH_3CN/H_2O/TFA$ (95:5:0.05)) with a gradient of 5% to 60% B over 5 minutes to give Compound [CLIV] as the TFA salt: LCMS (m/e) 450 (M+H); $^1$H NMR (400 MHz, METHA- NOL-d₄) δ ppm 0.85 (t, J=7.37 Hz, 3H) 1.44 (q, J=7.32 Hz, 2H) 2.51-2.64 (m, 5H) 2.84 (d, J=13.52 Hz, 2H) 6.77 (s, 1H) 7.27-7.39 (m, 5H) 7.45 (d, J=8.49 Hz, 2H) 7.71 (d, J=8.49 Hz, 2H) 8.57 (s, 1H) 9.05 (s, 1H).

Trans-2-[1-(4-Bromo-phenyl)-3-(1,2-dihydroxy-ethyl)-3-hydroxy-cyclobutyl]-isoindole-1,3-dione [CLV]

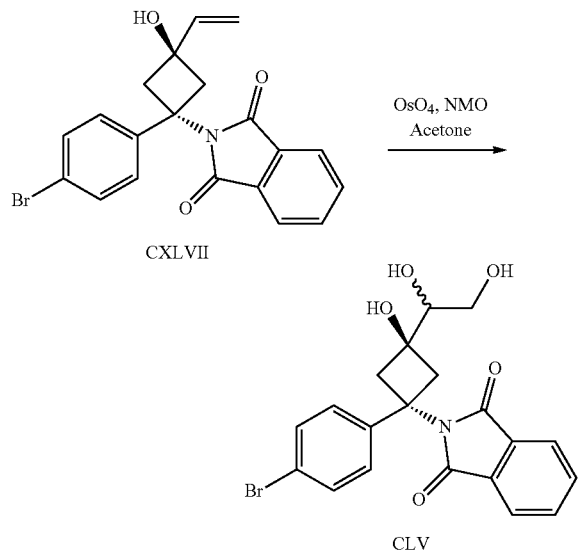

Compound [CXLVII] (50 mg, 0.13 mmol, 1.0 eq.) was dissolved in acetone (2.0 mL). To that solution was added a solution of 4-methylmorpholine N-oxide (29 mg, 0.25 mmol, 2.0 eq) in water (30 μL). Then added OsO₄ (4% in water, 80 μL, 0.013 mmol, 0.1 eq) and stirred 1 hour at room temperature. The reaction was quenched with Na₂S₂O₅ (aq) and extracted with CH₂Cl₂ (×3). The combined organic layers were dried with brine and Na₂SO₄, concentrated, and the residue purified by silica gel chromatography by eluting with CHCl₃/MeOH/NH₄OH (95:5:1) to CHCl₃/MeOH/NH₄OH (90:10:1) to give Compound [CLV]: LCMS (m/e) 455 (M+Na); ¹H NMR (400 MHz, CHLOROFORM-d) δ ppm 2.42 (br. s., 3H) 3.02-3.15 (m, 2H) 3.25-3.45 (m, 2H) 3.60 (t, J=4.34 Hz, 1H) 3.77 (d, J=4.34 Hz, 2H) 7.45 (d, J=8.59 Hz, 2H) 7.56 (d, J=8.59 Hz, 2H) 7.62-7.70 (m, 2H) 7.70-7.79 (m, 2H).

Trans-2-{3-(1,2-Dihydroxy-ethyl)-3-hydroxy-1-[4-(4,4,5,5-tetramethyl-[1,3,2]dioxaborolan-2-yl)-phenyl]-cyclobutyl}-isoindole-1,3-dione [CLVI]

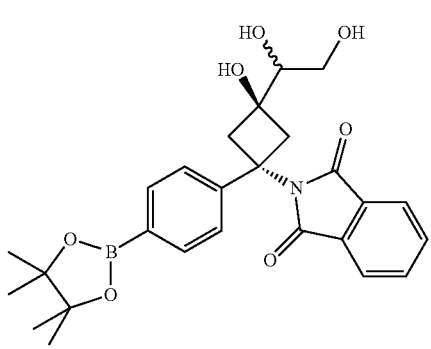

Compound [CLVI] was prepared in a similar way to that of Compound [XXXIX]. This material was used directly in the next step without father purification or characterization.

Trans-2-{3-(1,2-Dihydroxy-ethyl)-3-hydroxy-1-[4-(2-methyl-7-phenyl-1,4,9,9b-tetraaza-cyclopenta[a]naphthalen-8-yl)-phenyl]-cyclobutyl}-isoindole-1,3-dione [CLVII]

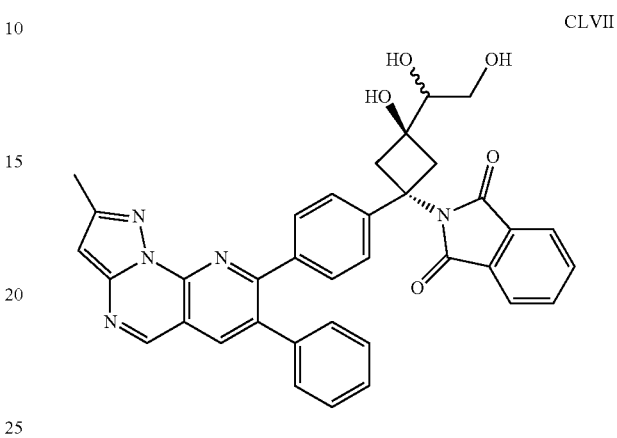

Compound [CLVII] was prepared in a similar way to that of Compound [XL]. Data for Compound [CLVII]: LCMS (m/e) 612 (M+H).

Trans-1-{3-Amino-1-hydroxy-3-[4-(2-methyl-7-phenyl-1,4,9,9b-tetraaza-cyclopenta[a]naphthalen-8-yl)-phenyl]-cyclobutyl}-ethane-1,2-diol [CLVIII]

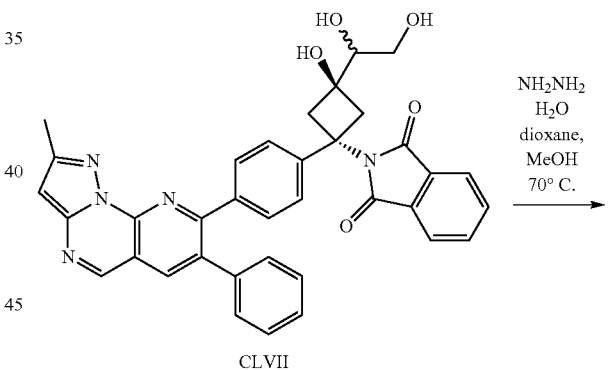

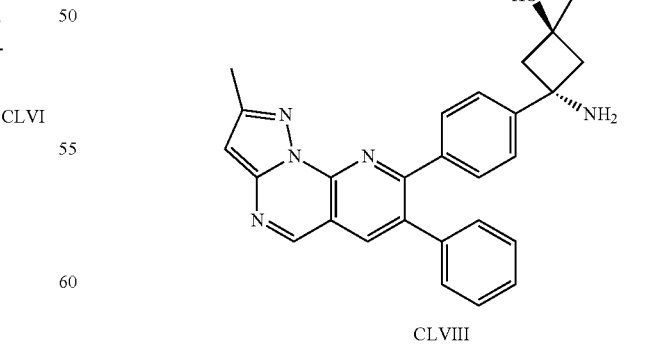

To Compound [CLVII] (16 mg, 0.03 mmol, 1.0 eq) was added MeOH (500 μL), dioxane (500 μL), and hydrazine monohydrate (250 μL). The reaction was heated to 70° C. for 2 hours. After that time the reaction was blown to dryness with N$_2$, the resulting solid was dissolved in MeOH. Then TFA (100 μL) was added, and the material purified by reverse-phase chromatography (Solvent A H$_2$O/CH$_3$CN/TFA (95:5:0.05), Solvent B CH$_3$CN/H$_2$O/TFA (95:5:0.05)) with a gradient of 5% to 60% B over 5 minutes to give [CLVIII] as the TFA salt: LCMS (m/e) 482 (M+H); $^1$H NMR (400 MHz, METHANOL-d$_4$) δ ppm 2.59 (s, 3H) 2.69-2.86 (m, 2H) 3.02-3.16 (m, 2H) 3.56-3.72 (m, 2H) 3.83 (dd, J=10.81, 3.10 Hz, 1H) 6.77 (s, 1H) 7.29-7.40 (m, 5H) 7.43 (d, J=8.44 Hz, 2H) 7.72 (d, J=8.44 Hz, 2H) 8.57 (s, 1H) 9.06 (s, 1H).

Trans-3-Amino-3-[4-(2-methyl-7-phenyl-1,4,9,9b-tetraaza-cyclopenta[a]naphthalen-8-yl)-phenyl]-1-vinyl-cyclobutanol [CLIX]

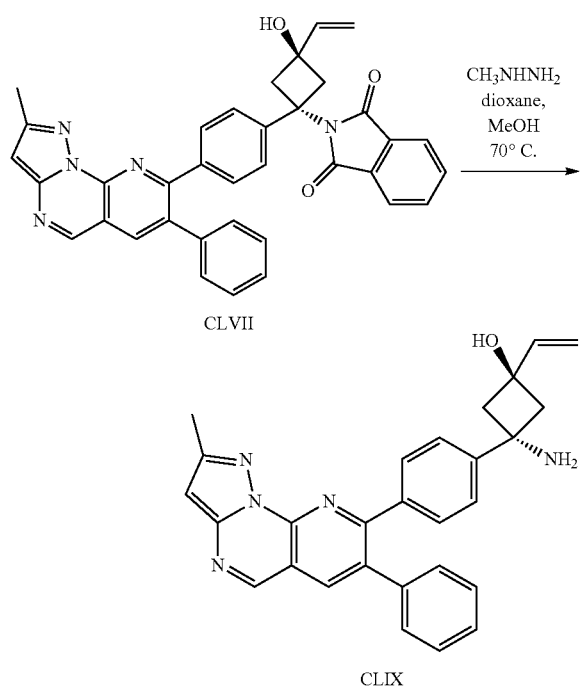

To compound [CLVII] (50 mg, 0.09 mmol, 1.0 eq) was added MeOH (1.0 mL), dioxane (1.0 mL), and methylhydrazine (500 μL). The reaction was heated to 70° C. for 6 hours. After that time the reaction was blown to dryness with N$_2$. The residue was purified by silica gel chromatography by eluting with CHCl$_3$ to CHCl$_3$/MeOH/NH$_4$OH (90:10:1). Further purification was effected by dissolving the material in MeOH, then adding TFA (100 μL), and subjecting to reverse-phase chromatography (Solvent A H$_2$O/CH$_3$CN/TFA (95:5:0.05), Solvent B CH$_3$CN/H$_2$O/TFA (95:5:0.05)) with a gradient of 5% to 60% B over 5 minutes to give [CLIX] as the TFA salt: LCMS (m/e) 448 (M+H); $^1$H NMR (400 MHz, METHANOL-d$_4$) δ ppm 2.59 (s, 3H) 2.79-2.99 (m, 4H) 5.18 (dd, J=10.62, 1.15 Hz, 1H) 5.34 (dd, J=17.18, 1.12 Hz, 1H) 6.17 (dd, J=17.20, 10.62 Hz, 1H) 6.78 (s, 1H) 7.35 (d, J=1.90 Hz, 5H) 7.56 (d, J=8.49 Hz, 2H) 7.75 (d, J=8.49 Hz, 2H) 8.57 (s, 1H) 9.06 (s, 1H).

Scheme VIII - Synthesis of 4-piperidine carboxamides

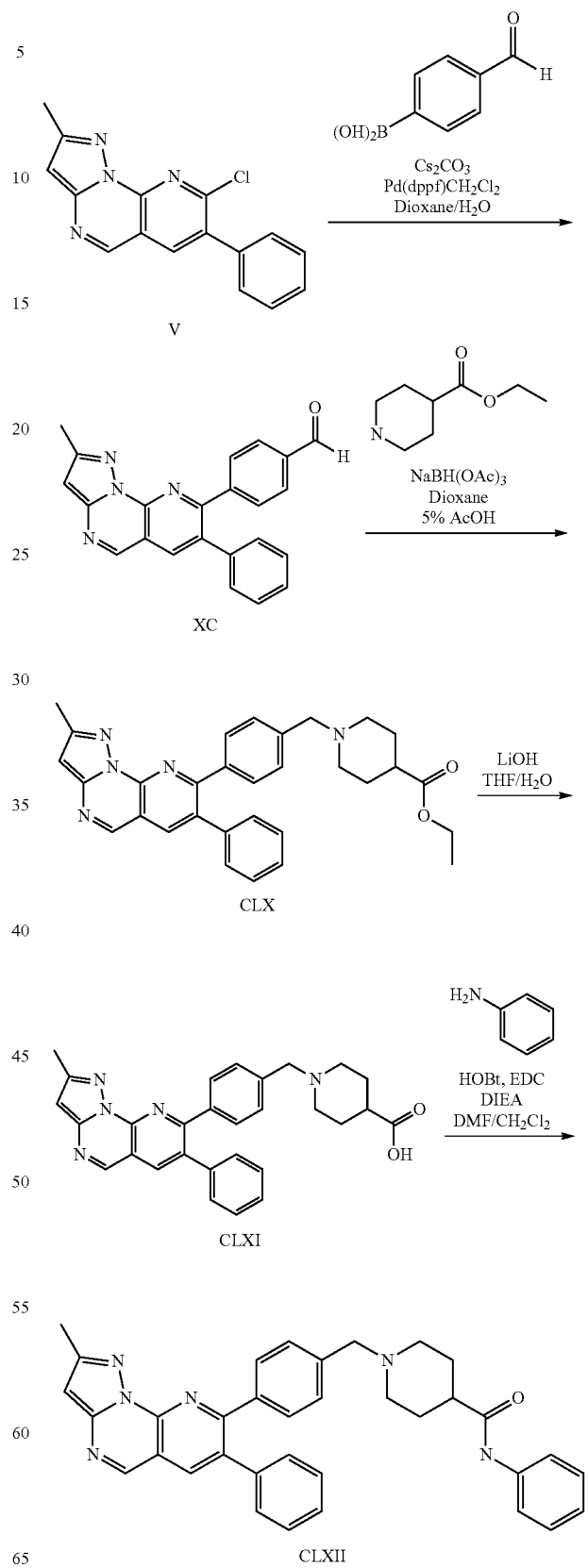

4-(2-Methyl-7-phenyl-1,4,9,9b-tetraaza-cyclopenta[a]naphthalen-8-yl)-benzaldehyde [XC] (CHCl₃ extraction procedure)

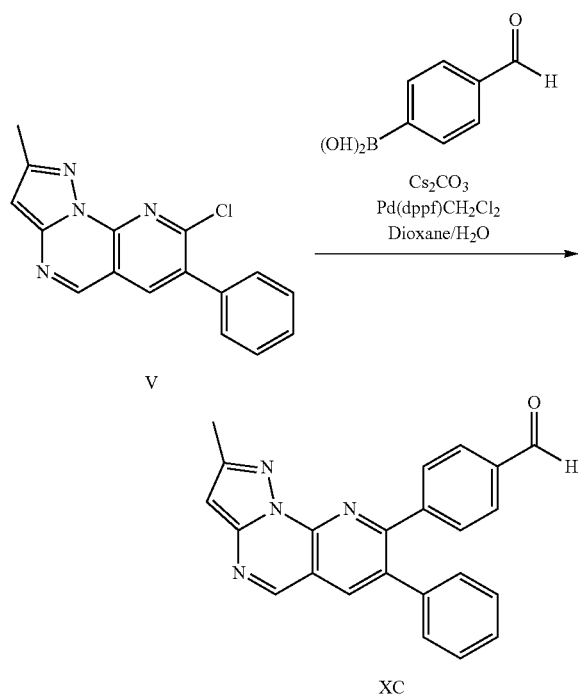

Compound [V] (1.00 g, 3.39 mmol. 1.0 eq), Cs₂CO₃ (5.53 g, 17.0 mmol, 5.0 eq), Pd(dppf)CH₂Cl₂ (208 mg, 0.250 mmol, 0.075 eq), and 4-formylphenylboronic acid (763 mg, 5.09 mmol, 1.5 eq) were dissolved in dioxane (17.0 mL, degassed) and H₂O (4.25 mL, degassed). The reaction was again degassed and then warmed to 50° C. for 45 minutes. Next the reaction was cooled, water was added, and the mixture extracted with CHCl₃ (×3). The combined organic phases were dried with brine and Na₂SO₄, and then concentrated in vacuo. The residue was purified by silica gel chromatography by eluting with a gradient of heptane and EtOAc (30% to 100% EtOAc) to provide Compound [XC]: LCMS (m/e) 365 (M+H); ¹H NMR (400 MHz, CHLOROFORM-d) δ ppm 2.64 (s, 3H) 6.76 (s, 1H) 7.19-7.26 (m, 2H) 7.31-7.39 (m, 3H) 7.66-7.75 (m, 2H) 7.75-7.85 (m, 2H) 8.31 (s, 1H) 8.90 (s, 1H) 10.03 (s, 1H).

1-[4-(2-Methyl-7-phenyl-1,4,9,9b-tetraaza-cyclopenta[a]naphthalen-8-yl)-benzyl]-piperidine-4-carboxylic acid ethyl ester [CLX]

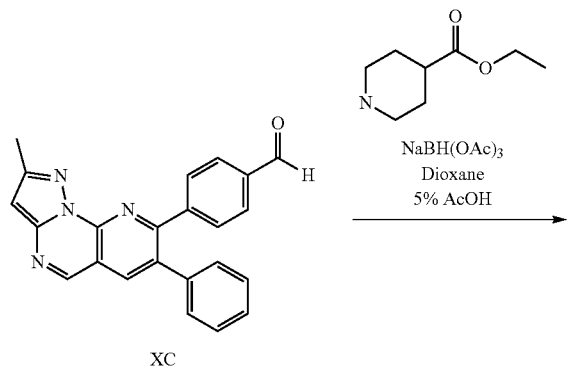

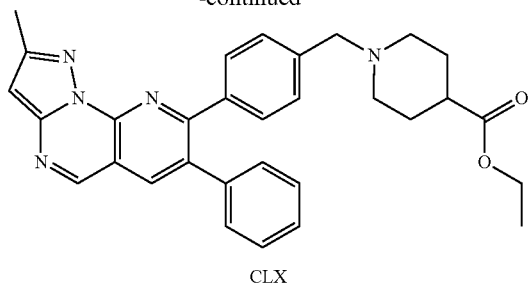

Compound [XC] (1.28 g, 3.51 mmol, 1.0 eq) was dissolved in dioxane (38 mL, anhydrous). Ethyl isonipecotate (1.66 g, 10.5 mmol, 3.0 eq), glacial acetic acid (1.90 mL), and NaBH(OAc)₃ (2.98 g, 14.1 mmol, 4.0 eq) were added and the reaction stirred at room temperature for 24 hours. The crude reaction was neutralized with NaHCO₃ (aq.) and extracted with CHCl₃ (×3). The combined organics were dried with brine and Na₂SO₄, and then concentrated in vacuo. The residue was purified by silica gel chromatography by eluting with a gradient of heptane and EtOAc (20% to 100% EtOAc) to afford Compound [CLX]: LCMS (m/e) 506 (M+H); ¹H NMR (400 MHz, CHLOROFORM-d) δ ppm 1.24 (t, J=7.13 Hz, 3H) 1.78 (t, J=10.59 Hz, 2H) 1.83-1.96 (m, 2H) 2.07 (s, 2H) 2.27 (t, j=10.98 Hz, 1H) 2.62 (s, 3H) 2.76-2.89 (m, 2H) 3.52 (s, 2H) 4.12 (q, J=7.13 Hz, 2H) 6.71 (s, 1H) 7.16-7.24 (m, 4H) 7.28-7.37 (m, 3H) 7.48 (d, J=8.15 Hz, 2H) 8.23 (s, 1H) 8.86 (s, 1H).

1-[4-(2-Methyl-7-phenyl-1,4,9,9b-tetraaza-cyclopenta[a]naphthalen-8-yl)-benzyl]-piperidine-4-carboxylic acid [CLXI]

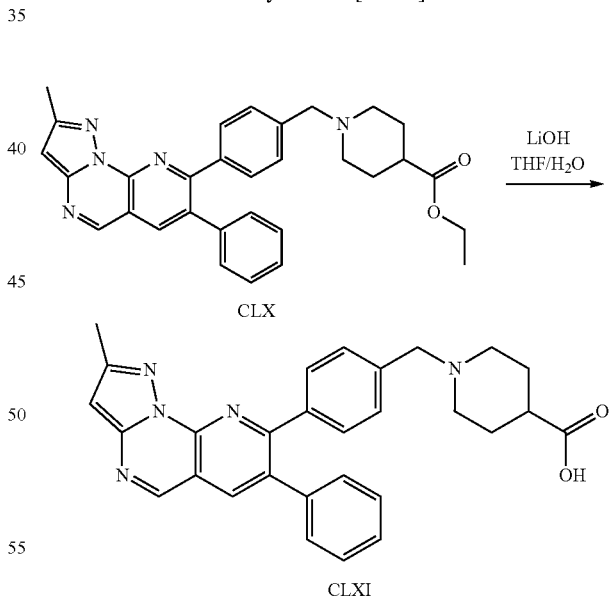

Compound [CLX] (1.78 g, 3.52 mmol, 1.0 eq) was dissolved in THF (35 mL) and then added H₂O (35 mL) and LiOH (178 mg, 10% w/w). The reaction was stirred at room temperature for 20 hours. After that time, the THF was removed in vacuo, and the remaining solvent was diluted with additional water and the pH adjusted to 7 with dilute HCl (5% aq). The mixture was extracted with CHCl₃/MeOH (4:1, ×5). The combined organic phases were dried with brine and Na₂SO₄, and then concentrated onto Celite in vacuo. The material was purified by silica gel chromatography by eluting with a gradient of CHCl₃ to CHCl₃/MeOH (1:1) to give Compound [CLXI] (data of the TFA salt): LCMS (m/e) 478 (M+H); ¹H NMR (400 MHz, METHANOL-d₄) δ ppm 1.76-2.09 (m, 2H) 2.18-2.40 (m, 2H) 2.59 (s, 3H) 2.61-2.75 (m, 1H) 2.98-3.24 (m, 2H) 3.34-3.60 (m, 2H) 4.30-4.38 (m, 2H) 6.77 (s, 1H) 7.27-7.33 (m, 2H) 7.33-7.38 (m, 3H) 7.46 (d, J=8.25 Hz, 2H) 7.71 (d, J=8.00 Hz, 2H) 8.58 (s, 1H) 9.06 (s, 1H).

1-[4-(2-Methyl-7-phenyl-1,4,9,9b-tetraaza-cyclopenta[a]naphthalen-8-yl)-benzyl]-piperidine-4-carboxylic acid phenylamide [CLXII]

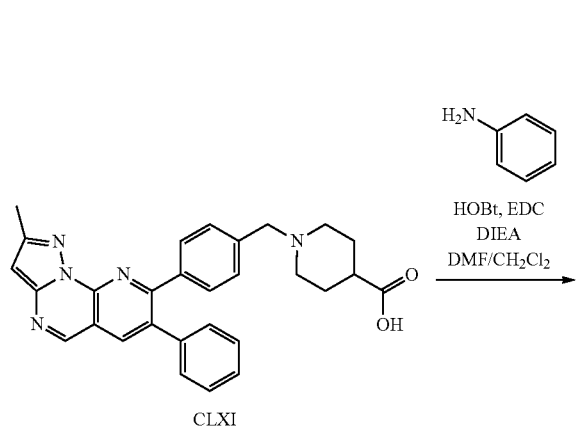

CLXI

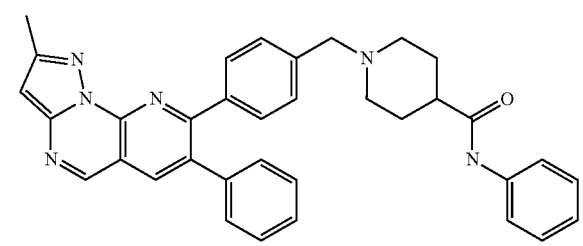

CLXII

Compound [CLXI] (20 mg, 0.042 mmol, 1.0 eq), HOBt (11 mg, 0.084 mmol, 2.0 eq), EDC (HCl salt, 12 mg, 0.063 mmol, 1.5 eq) and diisopropylethylamine (22 μL, 0.13 mmol, 3.0 eq) were dissolved in DMF (400 μL, anhydrous) and CH₂Cl₂ (400 μL, anhydrous). To this solution was added aniline (19 mg, 0.21 mmol, 5.0 eq) and the reaction stirred at room temperature for 16 hours. After that time water was added and the mixture extracted with CHCl₃ (×3). The combined organic phases were dried with brine and Na₂SO₄, and then concentrated in vacuo. The resulting impure intermediate was purified by silica gel chromatography by eluting with a gradient of CHCl₃ to [CHCl₃/MeOH/NH₄OH 90:10:1]. The resulting solid was then dissolved in MeOH, added TFA (100 μL), and purified by reverse-phase chromatography (Solvent A H₂O/CH₃CN/TFA (95:5:0.05), Solvent B CH₃CN/H₂O/TFA (95:5:0.05)) with a gradient of 5% to 60% B over 5 minutes to give Compound [CLXII] as the TFA salt: LCMS (m/e) 553 (M+H); ¹H NMR (400 MHz, METHANOL-d₄) δ ppm 1.94-2.10 (m, 2H) 2.11-2.22 (m, 2H) 2.59 (s, 3H) 2.63-2.77 (m, 1H) 3.02-3.16 (m, 2H) 3.51-3.64 (m, 2H) 4.31-4.45 (m, 2H) 6.77 (s, 1H) 7.10 (t, J=7.42 Hz, 1H) 7.25-7.40 (m, 7H) 7.48 (d, J=8.25 Hz, 2H) 7.54 (d, J=8.00 Hz, 2H) 7.72 (d, J=8.10 Hz, 2H) 8.58 (s, 1H) 9.06 (s, 1H).

1-[4-(2-Methyl-7-phenyl-1,4,9,9b-tetraaza-cyclopenta[a]naphthalen-8-yl)-benzyl]-piperidine-4-carboxylic acid allylamide [CLXIII]

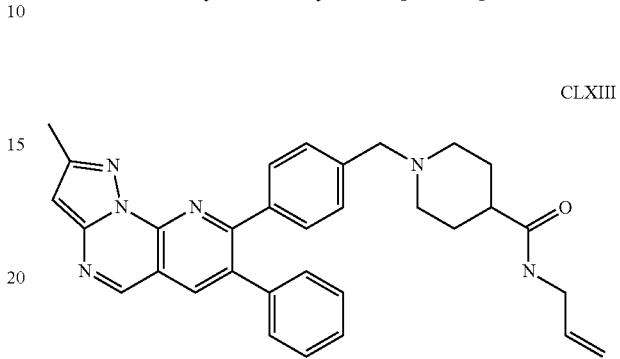

CLXIII

Compound [CLXIII] was prepared in a similar way to that of Compound [CLXII]. Data for Compound [CLXIII] (as the TFA salt): LCMS (m/e) 517 (M+H); ¹H NMR (400 MHz, METHANOL-d₄) δ ppm 1.95 (t, J=13.67 Hz, 2H) 2.01-2.13 (m, 2H) 2.54 (td, J=11.97, 3.49 Hz, 1H) 2.59 (s, 3H) 3.04 (d, J=1.90 Hz, 2H) 3.53 (d, J=12.06 Hz, 2H) 3.80 (d, J=5.42 Hz, 2H) 4.26-4.44 (m, 2H) 5.11 (dd, J=10.27, 1.29 Hz, 1H) 5.17 (dd, J=17.18, 1.42 Hz, 1H) 5.83 (dt, J=17.07, 5.23 Hz, 1H) 6.78 (s, 1H) 7.35 (t, J=7.17 Hz, 5H) 7.46 (d, J=8.20 Hz, 2H) 7.71 (d, J=8.20 Hz, 2H) 8.59 (s, 1H) 9.06 (s, 1H).

1-[4-(2-Methyl-7-phenyl-1,4,9,9b-tetraaza-cyclopenta[a]naphthalen-8-yl)-benzyl]-piperidine-4-carboxylic acid (2-dimethylamino-ethyl)-amide [CLXIV]

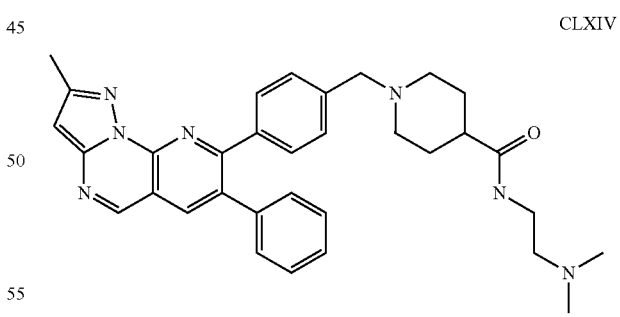

CLXIV

Compound [CLXIV] was prepared in a similar way to that of Compound [CLXII]. Data for Compound [CLXIV] (as the TFA salt): LCMS (m/e) 548 (M+H); ¹H NMR (400 MHz, METHANOL-d₄) δ ppm 1.84-2.02 (m, 2H) 2.05-2.16 (m, 2H) 2.49-2.57 (m, 1H) 2.59 (s, 3H) 2.93 (s, 6H) 3.05 (t, J=13.01 Hz, 2H) 3.27 (t, J=5.95 Hz, 2H) 3.46-3.61 (m, 4H) 4.29-4.41 (m, 2H) 6.78 (s, 1H) 7.28-7.39 (m, 5H) 7.46 (d, J=8.20 Hz, 2H) 7.71 (d, J=8.25 Hz, 2H) 8.59 (s, 1H) 9.06 (s, 1H).

1-[4-(2-Methyl-7-phenyl-1,4,9,9b-tetraaza-cyclopenta[a]naphthalen-8-yl)-benzyl]-piperidine-4-carboxylic acid (2-methoxy-ethyl)-amide [CLXV]

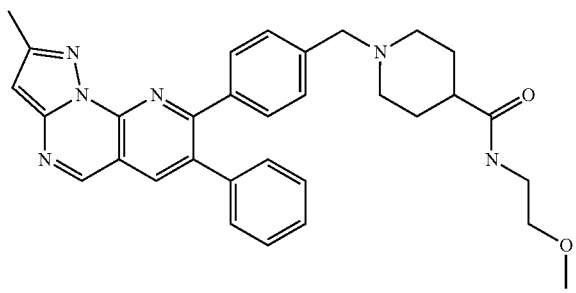

CLXV

Compound [CLXV] was prepared in a similar way to that of Compound [CLXII]. Data for Compound [CLXV] (as the TFA salt): LCMS (m/e) 535 (M+H); $^1$H NMR (400 MHz, METHANOL-$d_4$) δ ppm 1.83-1.99 (m, 2H) 2.00-2.11 (m, 2H) 2.52 (dd, J=14.81, 6.32 Hz, 1H) 2.59 (s, 3H) 3.03 (td, J=13.00, 2.61 Hz, 2H) 3.36 (d, J=5.27 Hz, 5H) 3.45 (t, J=5.34 Hz, 2H) 3.53 (d, J=12.01 Hz, 2H) 4.33 (s, 2H) 6.78 (s, 1H) 7.28-7.39 (m, 5H) 7.46 (d, J=8.05 Hz, 2H) 7.71 (d, J=8.20 Hz, 2H) 8.58 (s, 1H) 9.06 (s, 1H).

1-[4-(2-Methyl-7-phenyl-1,4,9,9b-tetraaza-cyclopenta[a]naphthalen-8-yl)-benzyl]-piperidine-4-carboxylic acid (2-imidazol-1-yl-ethyl)-amide [CLXVI]

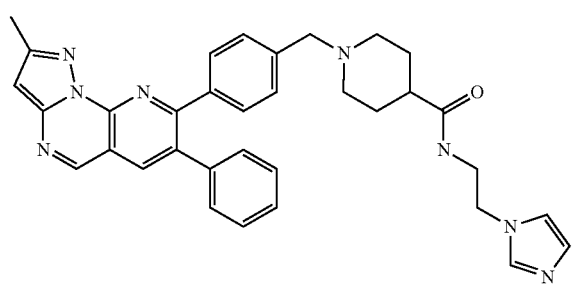

CLXVI

Compound [CLXVI] was prepared in a similar way to that of Compound [CLXVI]. Data for Compound [CLXVI] (as the TFA salt): LCMS (m/e) 585 (M+H); $^1$H NMR (400 MHz, METHANOL-$d_4$) δ ppm 1.84-2.02 (m, 2H) 2.01-2.17 (m, 4H) 2.53 (t, J=12.13 Hz, 1H) 2.59 (s, 3H) 3.05 (t, J=12.08 Hz, 2H) 3.23 (t, J=6.61 Hz, 2H) 3.54 (d, J=12.89 Hz, 2H) 4.28 (t, J=6.96 Hz, 2H) 4.31-4.43 (m, 2H) 6.78 (s, 1H) 7.28-7.39 (m, 5H) 7.47 (d, J=8.25 Hz, 2H) 7.59 (t, J=1.68 Hz, 1H) 7.69 (t, J=1.66 Hz, 1H) 7.71 (d, J=8.30 Hz, 2H) 8.59 (s, 1H) 8.97 (s, 1H) 9.07 (s, 1H).

1-[4-(2-Methyl-7-phenyl-1,4,9,9b-tetraaza-cyclopenta[a]naphthalen-8-yl)-benzyl]-piperidine-4-carboxylic acid 3,4-dimethoxy-benzylamide [CLXVII]

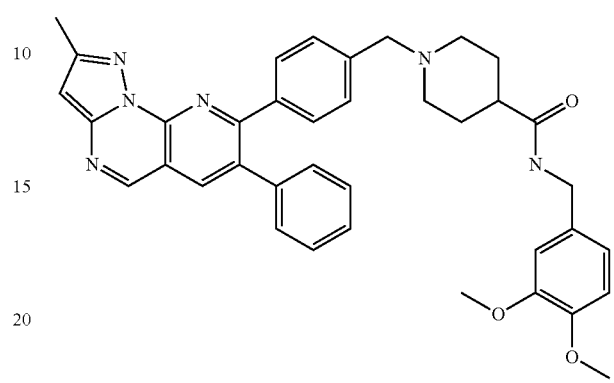

CLXVII

Compound [CLXVII] was prepared in a similar way to that of Compound [CLXII]. Data for Compound [CLXVII] (as the TFA salt): LCMS (m/e) 627 (M+H); $^1$H NMR (400 MHz, METHANOL-$d_4$) δ ppm 1.86-2.02 (m, 2H) 2.02-2.14 (m, 2H) 2.48-2.58 (m, 1H) 2.59 (s, 3H) 2.96-3.10 (m, 2H) 3.53 (d, J=12.74 Hz, 2H) 3.80 (s, 3H) 3.81 (s, 3H) 4.25-4.42 (m, 4H) 6.78 (s, 1H) 6.80-6.94 (m, 3H) 7.35 (t, J=7.03 Hz, 5H) 7.46 (d, J=8.20 Hz, 2H) 7.71 (d, J=8.15 Hz, 2H) 8.59 (s, 1H) 9.06 (s, 1H).

1-[4-(2-Methyl-7-phenyl-1,4,9,9b-tetraaza-cyclopenta[a]naphthalen-8-yl)-benzyl]-piperidine-4-carboxylic acid [2-(1-methyl-pyrrolidin-2-yl)-ethyl]-amide [CLXVIII]

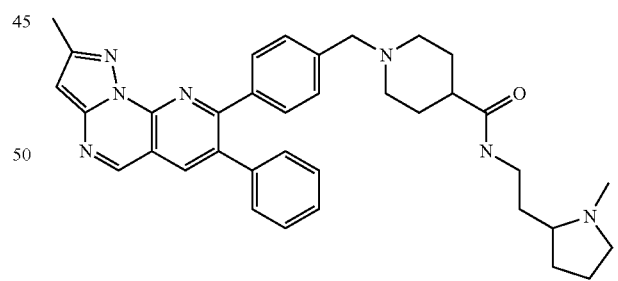

CLXVIII

Compound [CLXVIII] was prepared in a similar way to that of Compound [CLXII]. Data for Compound [CLXVIII] (as the TFA salt): LCMS (m/e) 588 (M+H); $^1$H NMR (400 MHz, METHANOL-$d_4$) δ ppm 1.67-1.85 (m, 2H) 1.85-2.02 (m, 2H) 2.02-2.11 (m, 3H) 2.11-2.22 (m, 2H) 2.35-2.47 (m, 1H) 2.47-2.57 (m, 1H) 2.59 (s, 3H) 2.92 (s, 3H) 2.98-3.10 (m, 2H) 3.10-3.21 (m, 1H) 3.54 (d, J=13.47 Hz, 2H) 3.61-3.74 (m, 1H) 4.29-4.43 (m, 2H) 6.78 (s, 1H) 7.27-7.40 (m, 5H) 7.46 (d, J=8.20 Hz, 2H) 7.71 (d, J=8.30 Hz, 2H) 8.59 (s, 1H) 9.07 (s, 1H).

241

{1-[4-(2-Methyl-7-phenyl-1,4,9,9b-tetraaza-cyclopenta[a]naphthalen-8-yl)-benzyl]-piperidin-4-yl}-morpholin-4-yl-methanone [CLXIX]

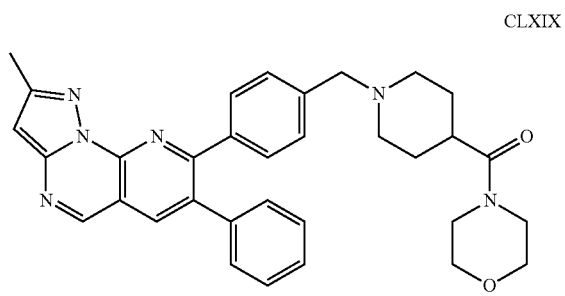 [SMILES: Cc1cc2ncc3cc(-c4ccccc4)c(-c4ccc(CN5CCC(C(=O)N6CCOCC6)CC5)cc4)nc3n2n1]

CLXIX

Compound [CLXIX] was prepared in a similar way to that of Compound [CLXII]. Data for Compound [CLXIX] (as the TFA salt): LCMS (m/e) 546 (M+H); $^1$H NMR (400 MHz, METHANOL-$d_4$) δ ppm 1.85-2.12 (m, 4H) 2.59 (s, 3H) 2.92-3.22 (m, 3H) 3.47-3.74 (m, 10H) 4.29-4.43 (m, 2H) 6.78 (s, 1H) 7.28-7.39 (m, 5H) 7.46 (d, J=8.20 Hz, 2H) 7.72 (d, J=8.15 Hz, 2H) 8.59 (s, 1H) 9.06 (s, 1H).

1-[4-(2-Methyl-7-phenyl-1,4,9,9b-tetraaza-cyclopenta[a]naphthalen-8-yl)-benzyl]-piperidine-4-carboxylic acid (1H-benzoimidazol-2-ylmethyl)-amide [CLXX]

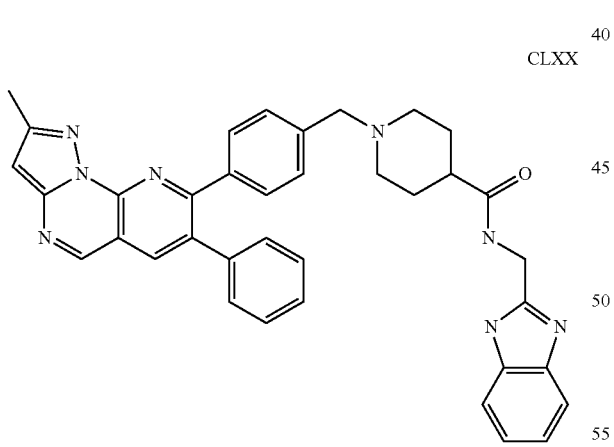

CLXX

Compound [CLXX] was prepared in a similar way to that of Compound [CLXII]. Data for Compound [CLXX] (as the TFA salt): LCMS (m/e) 607 (M+H); $^1$H NMR (400 MHz, METHANOL-$d_4$) δ ppm 1.83-2.06 (m, 2H) 2.11-2.25 (m, 2H) 2.59 (s, 3H) 2.64-2.78 (m, 1H) 3.00-3.18 (m, 2H) 3.55 (d, J=13.03 Hz, 2H) 4.34 (s, 2H) 4.84 (s, 2H) 6.78 (s, 1H) 7.23-7.39 (m, 5H) 7.40-7.50 (m, 2H) 7.50-7.63 (m, 2H) 7.64-7.81 (m, 4H) 8.59 (s, 1H) 9.07 (s, 1H).

242

1-[4-(2-Methyl-7-phenyl-1,4,9,9b-tetraaza-cyclopenta[a]naphthalen-8-yl)-benzyl]-piperidine-4-carboxylic acid [2-(3H-imidazol-4-yl)-ethyl]-amide [CLXXI]

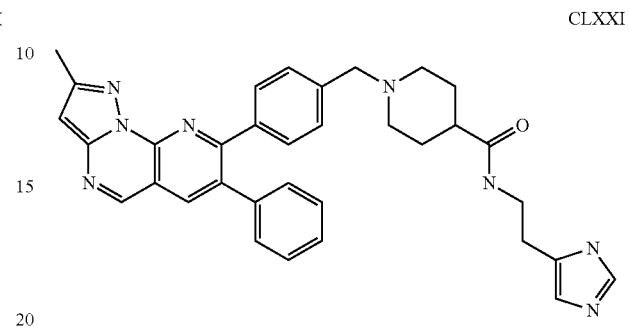

CLXXI

Compound [CLXXI] was prepared in a similar way to that of Compound [CLXII]. Data for Compound [CLXXI] (as the TFA salt): LCMS (m/e) 571 (M+H); $^1$H NMR (400 MHz, METHANOL-$d_4$) δ ppm 1.80-1.96 (m, 2H) 1.95-2.08 (m, 2H) 2.41-2.55 (m, 1H) 2.59 (s, 3H) 2.92 (t, J=6.86 Hz, 2H) 2.96-3.10 (m, 2H) 3.43-3.59 (m, 4H) 4.32 (s, 2H) 6.78 (s, 1H) 7.28-7.40 (m, 6H) 7.46 (d, J=8.20 Hz, 2H) 7.71 (d, J=8.20 Hz, 2H) 8.59 (s, 1H) 8.81 (br. s., 1H) 9.07 (s, 1H).

{1-[4-(2-Methyl-7-phenyl-1,4,9,9b-tetraaza-cyclopenta[a]naphthalen-8-yl)-benzyl]-piperidin-4-yl}-(4-pyrimidin-2-yl-piperazin-1-yl)-methanone [CLXXII]

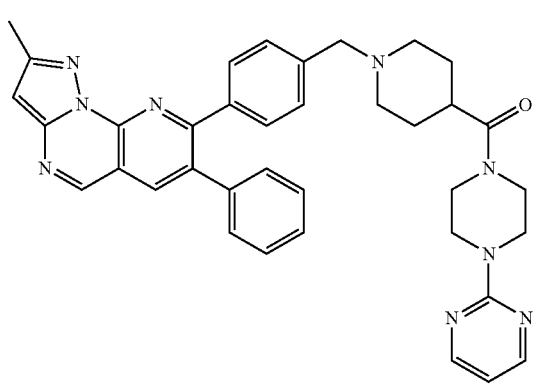

CLXXII

Compound [CLXXII] was prepared in a similar way to that of Compound [CLXII]. Data for Compound [CLXXII] (as the TFA salt): LCMS (m/e) 624 (M+H); $^1$H NMR (400 MHz, METHANOL-$d_4$) δ ppm 1.86-2.10 (m, 4H) 2.59 (s, 3H) 2.99-3.18 (m, 3H) 3.49-3.62 (m, 2H) 3.62-3.76 (m, 4H) 3.78-3.86 (m, 2H) 3.85-3.94 (m, 2H) 4.29-4.44 (m, 2H) 6.66 (t, J=4.81 Hz, 1H) 6.78 (s, 1H) 7.27-7.41 (m, 5H) 7.47 (d, J=8.20 Hz, 2H) 7.72 (d, J=8.15 Hz, 2H) 8.37 (d, J=4.83 Hz, 2H) 8.59 (s, 1H) 9.07 (s, 1H).

{1-[4-(2-Methyl-7-phenyl-1,4,9,9b-tetraaza-cyclopenta[a]naphthalen-8-yl)-benzyl]-piperidin-4-yl}-[4-(5-trifluoromethyl-pyridin-2-yl)-piperazin-1-yl]-methanone [CLXXIII]

CLXXIII

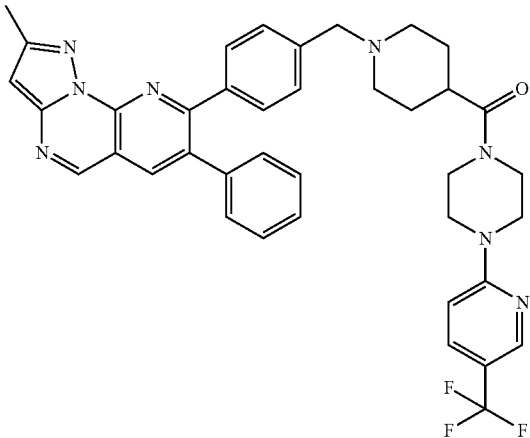

Compound [CLXXIII] was prepared in a similar way to that of Compound [CLXII]. Data for Compound [CLXXIII] (as the TFA salt): LCMS (m/e) 691 (M+H); $^1$H NMR (400 MHz, METHANOL-$d_4$) δ ppm 1.86-2.12 (m, 4H) 2.59 (s, 3H) 3.00-3.18 (m, 3H) 3.50-3.61 (m, 2H) 3.62-3.84 (m, 8H) 4.30-4.43 (m, 2H) 6.78 (s, 1H) 6.92 (d, J=9.13 Hz, 1H) 7.28-7.40 (m, 5H) 7.47 (d, J=8.25 Hz, 2H) 7.72 (d, J=8.10 Hz, 2H) 7.77 (dd, J=9.13, 2.49 Hz, 1H) 8.37 (d, J=1.66 Hz, 1H) 8.59 (s, 1H) 9.07 (s, 1H).

{1-[4-(2-Methyl-7-phenyl-1,4,9,9b-tetraaza-cyclopenta[a]naphthalen-8-yl)-benzyl]-piperidin-4-yl}-(4-pyridin-2-yl-piperazin-1-yl)-methanone [CLXXIV]

CLXXIV

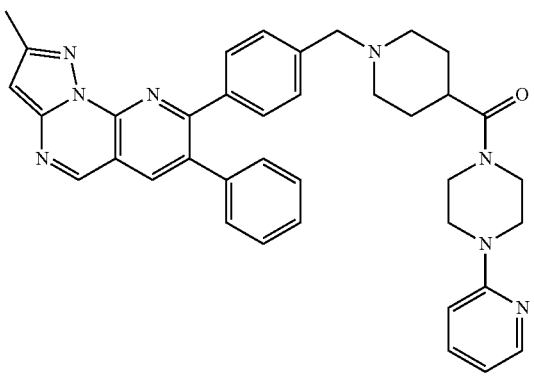

Compound [CLXXIV] was prepared in a similar way to that of Compound [CLXII].

Data for Compound [CLXXIV] (as the TFA salt): LCMS (m/e) 623 (M+H); $^1$H NMR (400 MHz, METHANOL-$d_4$) δ ppm 1.88-2.13 (m, 4H) 2.59 (s, 3H) 3.01-3.20 (m, 3H) 3.49-3.61 (m, 2H) 3.70-3.99 (m, 8H) 4.30-4.44 (m, 2H) 6.78 (s, 1H) 7.03 (t, J=6.69 Hz, 1H) 7.26-7.40 (m, 6H) 7.48 (d, J=8.25 Hz, 2H) 7.72 (d, J=8.20 Hz, 2H) 8.01 (dd, J=6.27, 1.15 Hz, 1H) 8.05 (ddd, J=9.15, 7.17, 1.78 Hz, 1H) 8.59 (s, 1H) 9.07 (s, 1H).

1-[4-(2-Methyl-7-phenyl-1,4,9,9b-tetraaza-cyclopenta[a]naphthalen-8-yl)-benzyl]-piperidine-4-carboxylic acid (2-pyridin-3-yl-ethyl)-amide [CLXXV]

CLXXV

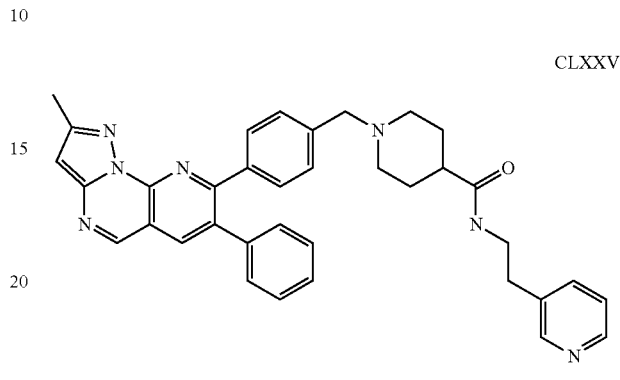

Compound [CLXXV] was prepared in a similar way to that of Compound [CLXII]. Data for Compound [CLXXV] (as the TFA salt): LCMS (m/e) 582 (M+H); $^1$H NMR (400 MHz, METHANOL-$d_4$) δ ppm 1.76-1.91 (m, 2H) 1.92-2.05 (m, 2H) 2.39-2.52 (m, 1H) 2.59 (s, 3H) 2.92-3.09 (m, 4H) 3.43-3.60 (m, 4H) 4.24-4.41 (m, 2H) 6.78 (s, 1H) 7.27-7.40 (m, 5H) 7.45 (d, J=8.25 Hz, 2H) 7.71 (d, J=8.15 Hz, 2H) 7.95 (dd, J=7.96, 5.76 Hz, 1H) 8.43 (dt, J=8.05, 1.46 Hz, 1H) 8.59 (s, 1H) 8.65-8.83 (m, 2H) 9.07 (s, 1H).

1-[4-(2-Methyl-7-phenyl-1,4,9,9b-tetraaza-cyclopenta[a]naphthalen-8-yl)-benzyl]-piperidine-4-carboxylic acid (pyridin-2-ylmethyl)-amide [CLXXVI]

CLXXVI

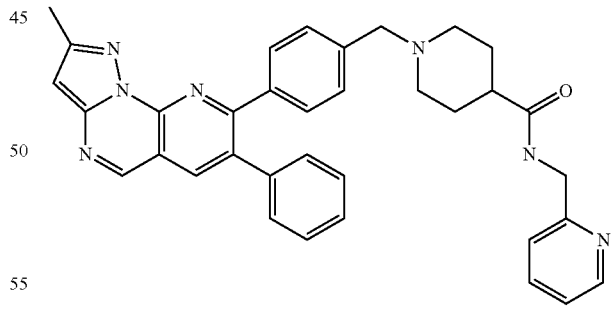

Compound [CLXXVI] was prepared in a similar way to that of Compound [CLXII]. Data for Compound [CLXXVI] (as the TFA salt): LCMS (m/e) 568 (M+H); $^1$H NMR (400 MHz, METHANOL-$d_4$) δ ppm 1.84-2.02 (m, 2H) 2.09-2.20 (m, 2H) 2.59 (s, 3H) 2.60-2.73 (m, 1H) 3.00-3.13 (m, 2H) 3.48-3.62 (m, 2H) 4.34 (s, 2H) 4.63 (s, 2H) 6.78 (s, 1H) 7.26-7.40 (m, 5H) 7.46 (d, J=8.30 Hz, 2H) 7.66-7.80 (m, 4H) 8.27 (t, J=8.00 Hz, 1H) 8.59 (s, 1H) 8.67 (d, J=5.27 Hz, 1H) 9.06 (s, 1H).

1-[4-(2-Methyl-7-phenyl-1,4,9,9b-tetraaza-cyclopenta[a]naphthalen-8-yl)-benzyl]-piperidine-4-carboxylic acid (pyridin-4-ylmethyl)-amide [CLXXVII]

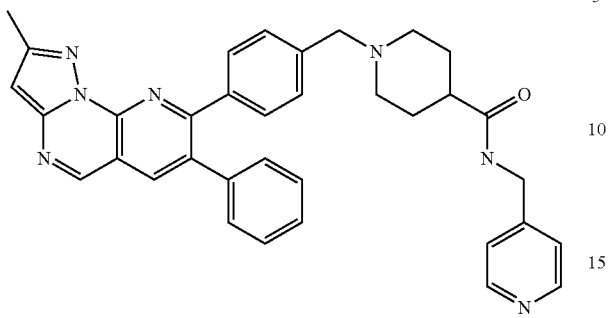

CLXXVII

Compound [CLXXVII] was prepared in a similar way to that of Compound [CLXII]. Data for Compound [CLXXVII] (as the TFA salt): LCMS (m/e) 568 (M+H); $^1$H NMR (400 MHz, METHANOL-d$_4$) δ ppm 1.86-2.07 (m, 2H) 2.09-2.23 (m, 2H) 2.59 (s, 3H) 2.62-2.76 (m, 1H) 3.01-3.17 (m, 2H) 3.48-3.65 (m, 2H) 4.35 (s, 2H) 4.64 (s, 2H) 6.78 (s, 1H) 7.25-7.40 (m, 5H) 7.47 (d, J=8.10 Hz, 2H) 7.71 (d, J=8.00 Hz, 2H) 7.91 (d, J=6.49 Hz, 2H) 8.59 (s, 1H) 8.76 (d, J=5.66 Hz, 2H) 9.07 (s, 1H).

1-[4-(2-Methyl-7-phenyl-1,4,9,9b-tetraaza-cyclopenta[a]naphthalen-8-yl)-benzyl]-piperidine-4-carboxylic acid (3-hydroxy-phenyl)-amide [CLXXVIII]

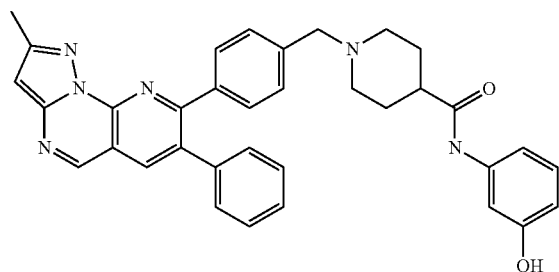

CLXXVIII

Compound [CLXXVIII] was prepared in a similar way to that of Compound [CLXII]. Data for Compound [CLXXVIII] (as the TFA salt): LCMS (m/e) 569 (M+H); $^1$H NMR (400 MHz, METHANOL-d$_4$) δ ppm 1.90-2.10 (m, 2H) 2.09-2.20 (m, 2H) 2.59 (s, 3H) 2.62-2.73 (m, 1H) 3.00-3.17 (m, 2H) 3.52-3.64 (m, 2H) 4.30-4.45 (m, 2H) 6.54 (dd, J=8.08, 2.32 Hz, 1H) 6.78 (s, 1H) 6.94 (d, J=8.15 Hz, 1H) 7.10 (t, J=8.10 Hz, 1H) 7.14 (t, J=1.73 Hz, 1H) 7.28-7.40 (m, 5H) 7.48 (d, J=8.25 Hz, 2H) 7.73 (d, J=8.10 Hz, 2H) 8.59 (s, 1H) 9.07 (s, 1H).

1-[4-(2-Methyl-7-phenyl-1,4,9,9b-tetraaza-cyclopenta[a]naphthalen-8-yl)-benzyl]-piperidine-4-carboxylic acid (4-hydroxy-cyclohexyl)-amide [CLXXIX]

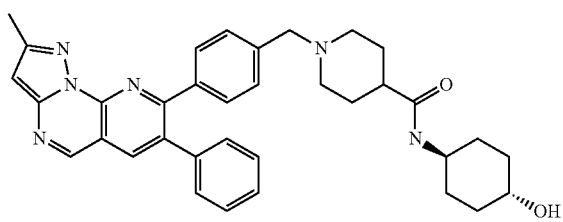

CLXXIX

Compound [CLXXIX] was prepared in a similar way to that of Compound [CLXII]. Data for Compound [CLXXIX] (as the TFA salt): LCMS (m/e) 575 (M+H); $^1$H NMR (400 MHz, METHANOL-d$_4$) δ ppm 1.18-1.45 (m, 4H) 1.81-2.20 (m, 8H) 2.45 (t, J=3.76 Hz, 1H) 2.59 (s, 3H) 3.02 (td, J=12.87, 2.56 Hz, 2H) 3.44-3.67 (m, 4H) 4.27-4.42 (m, 2H) 6.78 (s, 1H) 7.28-7.40 (m, 5H) 7.46 (d, J=8.15 Hz, 2H) 7.71 (d, J=8.20 Hz, 2H) 8.59 (s, 1H) 9.06 (s, 1H).

1-[4-(2-Methyl-7-phenyl-1,4,9,9b-tetraaza-cyclopenta[a]naphthalen-8-yl)-benzyl]-piperidine-4-carboxylic acid [2-hydroxy-2-(3-hydroxy-phenyl)-ethyl]-amide [CLXXX]

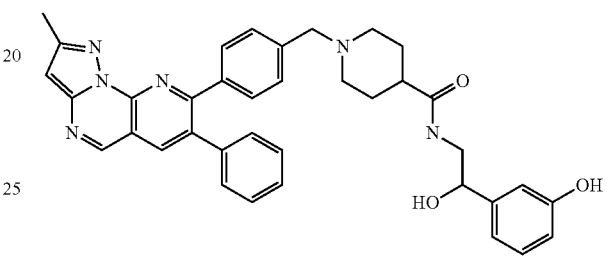

CLXXX

Compound [CLXXX] was prepared in a similar way to that of Compound [CLXII]. Data for Compound [CLXXX] (as the TFA salt): LCMS (m/e) 613 (M+H); $^1$H NMR (400 MHz, METHANOL-d$_4$) δ ppm 1.77-2.19 (m, 4H) 2.43-2.55 (m, 1H) 2.59 (s, 3H) 3.01 (td, J=13.06, 2.44 Hz, 2H) 3.34-3.46 (m, 2H) 3.46-3.57 (m, 2H) 4.31 (s, 2H) 4.68 (dd, J=6.81, 5.44 Hz, 1H) 6.68 (dd, J=7.32, 1.90 Hz, 1H) 6.78 (s, 1H) 6.79-6.86 (m, 2H) 7.14 (t, J=7.88 Hz, 1H) 7.28-7.39 (m, 5H) 7.45 (d, J=8.25 Hz, 2H) 7.71 (d, J=8.25 Hz, 2H) 8.59 (s, 1H) 9.06 (s, 1H).

1-[4-(2-Methyl-7-phenyl-1,4,9,9b-tetraaza-cyclopenta[a]naphthalen-8-yl)-benzyl]-piperidine-4-carboxylic acid [2-(4-hydroxy-phenyl)-ethyl]-amide [CLXXXI]

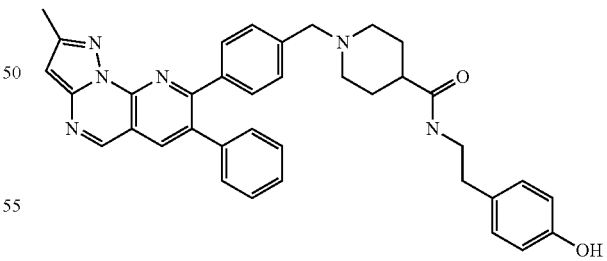

CLXXXI

Compound [CLXXXI] was prepared in a similar way to that of Compound [CLXII]. Data for Compound [CLXXXI] (as the TFA salt): LCMS (m/e) 597 (M+H); $^1$H NMR (400 MHz, METHANOL-d$_4$) δ ppm 1.77-2.15 (m, 4H) 2.35-2.50 (m, 1H) 2.59 (s, 3H) 2.69 (t, J=7.10 Hz, 2H) 3.00 (td, 2H) 3.37 (t, J=7.17 Hz, 2H) 3.46-3.56 (m, 2H) 4.31 (s, 2H) 6.69 (d, J=8.40 Hz, 2H) 6.78 (s, 1H) 7.01 (d, J=8.40 Hz, 2H) 7.28-7.40 (m, 5H) 7.45 (d, J=8.25 Hz, 2H) 7.71 (d, J=8.25 Hz, 2H) 8.59 (s, 1H) 9.06 (s, 1H).

1-[4-(2-Methyl-7-phenyl-1,4,9,9b-tetraaza-cyclopenta[a]naphthalen-8-yl)-benzyl]-piperidine-4-carboxylic acid (3-hydroxy-4-methoxy-phenyl)-amide [CLXXXII]

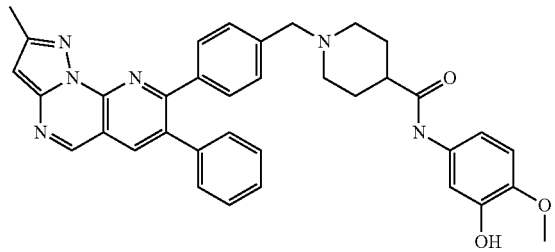

Compound [CLXXXII] was prepared in a similar way to that of Compound [CLXII]. Data for Compound [CLXXXII] (as the TFA salt): LCMS (m/e) 599 (M+H); $^1$H NMR (400 MHz, METHANOL-$d_4$) δ ppm 1.90-2.20 (m, 4H) 2.59 (s, 3H) 2.60-2.72 (m, 1H) 2.99-3.16 (m, 2H) 3.50-3.63 (m, 2H) 3.82 (s, 3H) 4.35 (s, 2H) 6.77 (s, 1H) 6.85 (d, 1H) 6.93 (dd, 1H) 7.10 (d, J=2.10 Hz, 1H) 7.27-7.40 (m, 5H) 7.47 (d, J=8.25 Hz, 2H) 7.72 (d, J=8.10 Hz, 2H) 8.58 (s, 1H) 9.06 (s, 1H).

1-[4-(2-Methyl-7-phenyl-1,4,9,9b-tetraaza-cyclopenta[a]naphthalen-8-yl)-benzyl]-piperidine-4-carboxylic acid [2-(3,4-dihydroxy-phenyl)-ethyl]-amide [CLXXXIII]

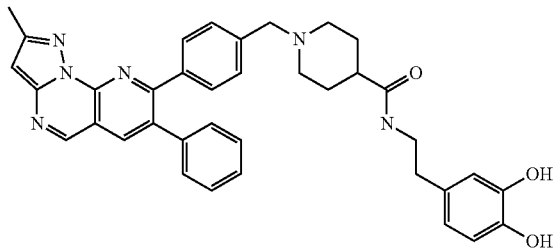

Compound [CLXXXIII] was prepared in a similar way to that of Compound [CLXII]. Data for Compound [CLXXXIII] (as the TFA salt): LCMS (m/e) 613 (M+H); $^1$H NMR (400 MHz, METHANOL-$d_4$) δ ppm 1.79-2.15 (m, 4H) 2.37-2.52 (m, 1H) 2.59 (s, 3H) 2.64 (t, J=7.15 Hz, 2H) 3.00 (td, J=12.92, 2.51 Hz, 2H) 3.35 (t, J=7.10 Hz, 2H) 3.46-3.55 (m, 2H) 4.25-4.34 (m, 2H) 6.46-6.56 (m, 1H) 6.61 (d, J=1.42 Hz, 1H) 6.67 (d, J=7.96 Hz, 1H) 6.78 (s, 1H) 7.26-7.40 (m, 5H) 7.45 (d, J=8.20 Hz, 2H) 7.71 (d, J=8.20 Hz, 2H) 8.59 (s, 1H) 9.06 (s, 1H).

1-[4-(2-Methyl-7-phenyl-1,4,9,9b-tetraaza-cyclopenta[a]naphthalen-8-yl)-benzyl]-piperidine-4-carboxylic acid 4-hydroxy-3-methoxy-benzylamide [CLXXXIV]

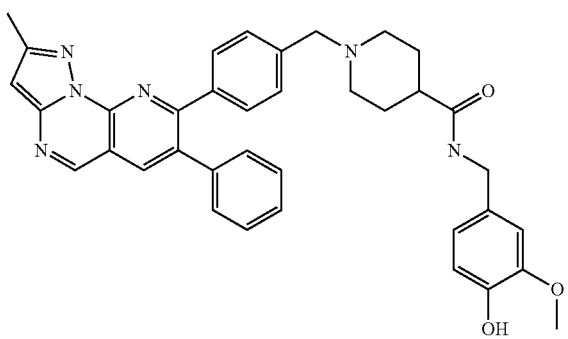

Compound [CLXXXIV] was prepared in a similar way to that of Compound [CLXIII]. Data for Compound [CLXXXIV] (as the TFA salt): LCMS (m/e) 613 (M+H); $^1$H NMR. (400 MHz, METHANOL-$d_4$) δ ppm 1.84-2.13 (m, 4H) 2.45-2.56 (m, 1H) 2.59 (s, 3H) 2.93-3.07 (m, 2H) 3.45-3.56 (m, 2H) 3.83 (s, 3H) 4.26 (s, 2H) 4.28-4.39 (m, 2H) 6.70 (dd, 1H) 6.74 (d, 1H) 6.76 (s, 1H) 6.83 (d, J=1.32 Hz, 1H) 7.26-7.32 (m, 2H) 7.32-7.37 (m, 3H) 7.43 (d, J=8.25 Hz, 2H) 7.70 (d, J=8.25 Hz, 2H) 8.56 (s, 1H) 9.04 (s, 1H).

1-[4-(2-Methyl-7-phenyl-1,4,9,9b-tetraaza-cyclopenta[a]naphthalen-8-yl)-benzyl]-piperidine-4-carboxylic acid 3,4-dihydroxy-benzylamide [CLXXXV]

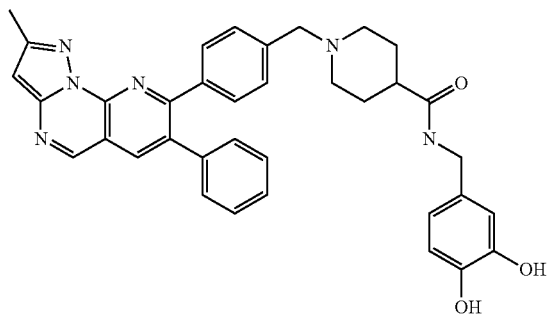

Compound [CLXXXV] was prepared in a similar way to that of Compound [CLXII]. Data for Compound [CLXXXV] (as the TFA salt): LCMS (m/e) 599 (M+H); $^1$H NMR (400 MHz, METHANOL-$d_4$) δ ppm 2.55-2.82 (m, 4H) 3.16-3.28 (m, 1H) 3.29 (s, 3H) 3.72 (td, J=12.70, 2.81 Hz, 2H) 4.00-4.08 (m, 1H) 4.13-4.24 (m, 2H) 4.85-4.95 (m, 2H) 5.03-5.16 (m, 2H) 7.29 (dd, J=8.05, 2.05 Hz, 1H) 7.39-7.48 (m, 2H) 7.55 (s, 1H) 8.08 (d, J=3.66 Hz, 2H) 8.10-8.16 (m, 3H) 8.24 (d, J=8.25 Hz, 2H) 8.37 (d, J=8.30 Hz, 2H) 9.41 (s, 1H) 9.86 (s, 1H).

1-[4-(2-Methyl-7-phenyl-1,4,9,9b-tetraaza-cyclopenta[a]naphthalen-8-yl)-benzyl]-piperidine-4-carboxylic acid benzylamide [CLXXXVI]

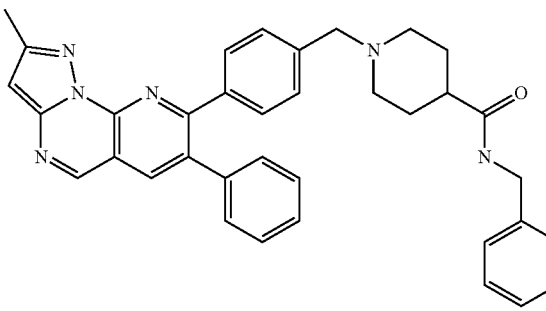

Compound [CLXXXVI] was prepared in a similar way to that of Compound [CLXII]. Data for Compound [CLXXXVI] (as the TFA salt): LCMS (m/e) 567 (M+H); $^1$H NMR (400 MHz, METHANOL-$d_4$) δ ppm 1.86-2.03 (m, 2H) 2.03-2.15 (m, 2H) 2.50-2.57 (m, 1H) 2.59 (s, 3H) 3.04 (td, J=12.96, 2.88 Hz, 2H) 3.49-3.59 (m, 2H) 4.30-4.35 (m, 2H) 4.36 (s, 2H) 6.78 (s, 1H) 7.20-7.39 (m, 10H) 7.46 (d, J=8.25 Hz, 2H) 7.71 (d, J=8.20 Hz, 2H) 8.59 (s, 1H) 9.07 (s, 1H).

1-[4-(2-Methyl-7-phenyl-1,4,9,9b-tetraaza-cyclopenta[a]naphthalen-8-yl)-benzyl]-piperidine-4-carboxylic acid benzyl-methyl-amide [CLXXXVII]

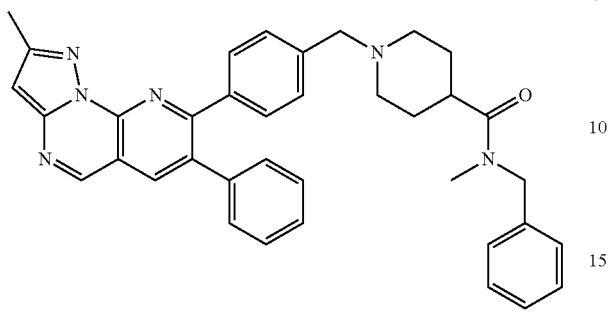

Compound [CLXXXVII] was prepared in a similar way to that of Compound [CLXII]. Data for Compound [CLXXXVII] (as the TFA salt): LCMS (m/e) 581 (M+H); $^1$H NMR (400 MHz, METHANOL-$d_4$) δ ppm 1.87-2.16 (m, 4H) 2.59 (s, 3H) 2.91-3.18 (m, 6H) 3.41-3.62 (m, 2H) 4.24-4.46 (m, 2H) 4.55-4.77 (m, 2H) 6.78 (s, 1H) 7.17-7.53 (m, 12H) 7.66-7.75 (m, 2H) 8.56-8.61 (m, 1H) 9.04-9.08 (m, 1H).

1-[4-(2-Methyl-7-phenyl-1,4,9,9b-tetraaza-cyclopenta[a]naphthalen-8-yl)-benzyl]-piperidine-4-carboxylic acid cyclohexylamide [CLXXXVIII]

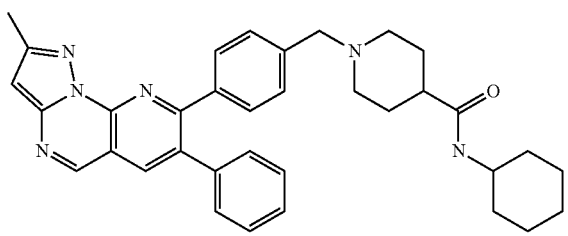

Compound [CLXXXVIII] was prepared in a similar way to that of Compound [CLXII]. Data for Compound [CLXXXVIII] (as the TFA salt): LCMS (m/e) 559 (M+H); $^1$H NMR (400 MHz, METHANOL-$d_4$) δ ppm 1.12-1.28 (m, 3H) 1.28-1.43 (m, 2H) 1.59-1.70 (m, 1H) 1.70-1.80 (m, 2H) 1.80-1.88 (m, 2H) 1.88-1.98 (m, 2H) 1.98-2.08 (m, 2H) 2.40-2.53 (m, 1H) 2.59 (s, 3H) 3.02 (td, J=13.00, 3.25 Hz, 2H) 3.48-3.56 (m, 2H) 3.56-3.67 (m, 1H) 4.28-4.42 (m, 2H) 6.78 (s, 1H) 7.35 (t, J=7.15 Hz, 5H) 7.46 (d, J=8.15 Hz, 2H) 7.71 (d, J=8.20 Hz, 2H) 8.59 (s, 1H) 9.06 (s, 1H).

1-[4-(2-Methyl-7-phenyl-1,4,9,9b-tetraaza-cyclopenta[a]naphthalen-8-yl)-benzyl]-piperidine-4-carboxylic acid (2-methoxy-1-methyl-ethyl)-amide [CLXXXIX]

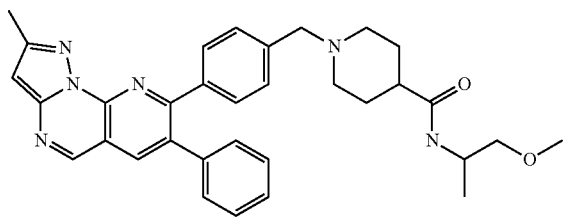

Compound [CLXXXIX] was prepared in a similar way to that of Compound [CLXII]. Data for Compound [CLXXXIX] (as the TFA salt): LCMS (m/e) 549 (M+H); $^1$H NMR (400 MHz, METHANOL-$d_4$) δ ppm 1.12 (d, J=6.78 Hz, 3H) 1.81-2.10 (m, 4H) 2.42-2.55 (m, 1H) 2.59 (s, 3H) 3.03 (td, J=13.03, 2.29 Hz, 2H) 3.32-3.37 (m, 5H) 3.53 (d, J=12.74 Hz, 2H) 3.99-4.13 (m, 1H) 4.29-4.42 (m, 2H) 6.78 (s, 1H) 7.26-7.40 (m, 5H) 7.46 (d, J=8.15 Hz, 2H) 7.71 (d, J=8.20 Hz, 2H) 8.59 (s, 1H) 9.06 (s, 1H).

1-[4-(2-Methyl-7-phenyl-1,4,9,9b-tetraaza-cyclopenta[a]naphthalen-8-yl)-benzyl]-piperidine-4-carboxylic acid carbamoylmethyl-amide [CXC]

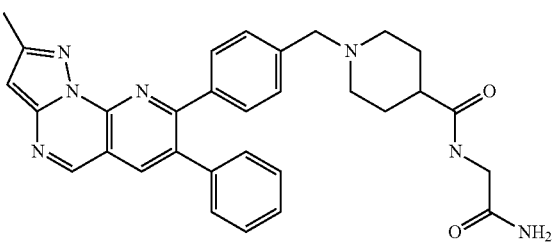

Compound [CXC] was prepared in a similar way to that of Compound [CLXII]. Data for Compound [CXC] (as the TFA salt): LCMS (m/e) 534 (M+H); $^1$H NMR (400 MHz, METHANOL-$d_4$) δ ppm 1.82-2.07 (m, 2H) 2.08-2.31 (m, 2H) 2.53-2.65 (m, 4H) 2.99-3.11 (m, 2H) 3.49-3.58 (m, 2H) 3.85 (s, 2H) 4.33 (s, 2H) 6.78 (s, 1H) 7.35 (t, J=7.25 Hz, 5H) 7.46 (d, J=8.20 Hz, 2H) 7.71 (d, J=8.15 Hz, 2H) 8.59 (s, 1H) 9.06 (s, 1H).

1-[4-(2-Methyl-7-phenyl-1,4,9,9b-tetraaza-cyclopenta[a]naphthalen-8-yl)-benzyl]-piperidine-4-carboxylic acid (2,2,2-trifluoro-ethyl)-amide [CXCI]

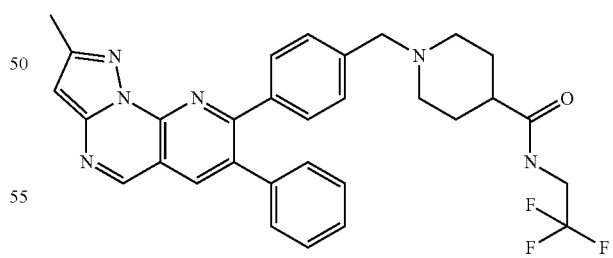

Compound [CXCI] was prepared in a similar way to that of Compound [CLXII]. Data for Compound [CXCI] (as the TFA, salt): LCMS (m/e) 559 (M+H); $^1$H NMR (400 MHz, METHANOL-$d_4$) δ ppm 1.83-2.14 (m, 4H) 2.51-2.66 (m, 4H) 2.99-3.11 (m, 2H) 3.36 (br. s., 1H) 3.47-3.60 (m, 2H) 3.91 (q, J=9.42 Hz, 2H) 4.27-4.43 (m, 2H) 6.78 (s, 1H) 7.28-7.39 (m, 5H) 7.46 (d, J=8.15 Hz, 2H) 7.71 (d, J=8.15 Hz, 2H) 8.59 (s, 1H) 9.06 (s, 1H).

1-[4-(2-Methyl-7-phenyl-1,4,9,9b-tetraaza-cyclopenta[a]naphthalen-8-yl)-benzyl]-piperidine-4-carboxylic acid (1-ethyl-propyl)-amide [CXCII]

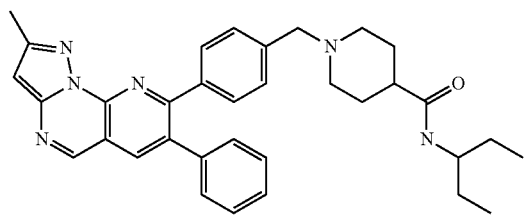

Compound [CXCII] was prepared in a similar way to that of Compound [CLXII]. Data for Compound [CXCII] (as the TFA salt): LCMS (m/e) 547 (M+H); $^1$H NMR (400 MHz, METHANOL-d$_4$) δ ppm 0.89 (t, J=7.42 Hz, 6H) 1.31-1.46 (m, 2H) 1.48-1.64 (m, 2H) 1.87-2.01 (m, 2H) 2.00-2.10 (m, 2H) 2.47-2.57 (m, J=11.87, 11.87, 4.27, 4.06 Hz, 1H) 2.59 (s, 3H) 3.04 (td, J=12.84, 2.73 Hz, 2H) 3.49-3.58 (m, 2H) 3.64 (spt, 1H) 4.28-4.43 (m, 2H) 6.78 (s, 1H) 7.27-7.39 (m, 5H) 7.46 (d, J=8.20 Hz, 2H) 7.71 (d, J=8.25 Hz, 2H) 8.59 (s, 1H) 9.06 (s, 1H).

1-[4-(2-Methyl-7-phenyl-1,4,9,9b-tetraaza-cyclopenta[a]naphthalen-8-yl)-benzyl]-piperidine-4-carboxylic acid tert-butylamide [CXCIII]

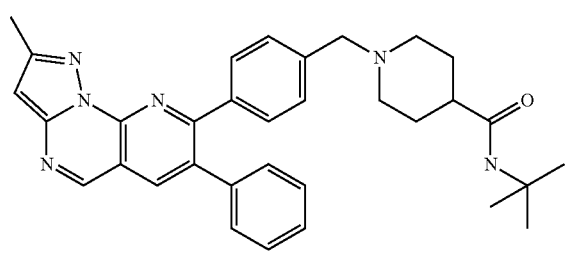

Compound [CXCIII] was prepared in a similar way to that of Compound [CLXII]. Data for Compound [CXCIII] (as the TFA salt): LCMS (m/e) 533 (M+H); $^1$H NMR (400 MHz, METHANOL-d$_4$) δ ppm 1.32 (s, 9H) 1.80-1.95 (m, 2H) 1.95-2.04 (m, 2H) 2.37-2.51 (m, 1H) 2.59 (s, 3H) 3.00 (td, J=12.75, 2.46 Hz, 2H) 3.45-3.58 (m, 4H) 4.28-4.43 (m, 2H) 6.78 (s, 1H) 7.29-7.38 (m, 5H) 7.46 (d, J=8.20 Hz, 2H) 7.71 (d, J=8.25 Hz, 2H) 8.59 (s, 1H) 9.06 (s, 1H).

1-[4-(2-Methyl-7-phenyl-1,4,9,9b-tetraaza-cyclopenta[a]naphthalen-8-yl)-benzyl]-piperidine-4-carboxylic acid propylamide [CXCIV]

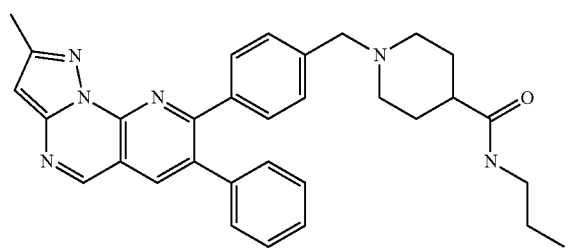

Compound [CXCIV] was prepared in a similar way to that of Compound [CLXII]. Data for Compound [CXCIV] (as the TFA salt): LCMS (m/e) 519 (M+H); $^1$H NMR (400 MHz, METHANOL-d$_4$) δ ppm 0.92 (t, J=7.42 Hz, 3H) 1.52 (sxt, J=7.27 Hz, 2H) 1.83-1.99 (m, 2H) 1.99-2.10 (m, 2H) 2.43-2.55 (m, J=12.12, 12.12, 3.78, 3.56 Hz, 1H) 2.59 (s, 3H) 3.03 (td, J=12.71, 2.10 Hz, 2H) 3.14 (t, J=7.10 Hz, 2H) 3.47-3.58 (m, 2H) 4.33 (s, 2H) 6.78 (s, 1H) 7.27-7.39 (m, 5H) 7.46 (d, J=8.20 Hz, 2H) 7.71 (d, J=8.25 Hz, 2H) 8.59 (s, 1H) 9.06 (s, 1H).

1-[4-(2-Methyl-7-phenyl-1,4,9,9b-tetraaza-cyclopenta[a]naphthalen-8-yl)-benzyl]-piperidine-4-carboxylic acid methylamide [CXCV]

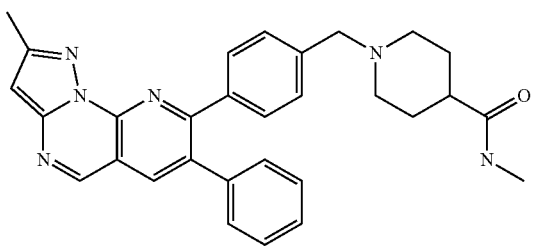

Compound [CXCV] was prepared in a similar way to that of Compound [CLXII]. Data for Compound [CXCV] (as the TFA salt): LCMS (m/e) 491 (M+H); $^1$H NMR. (400 MHz, METHANOL-d$_4$) δ ppm 1.83-1.99 (m, 2H) 2.00-2.11 (m, 2H) 2.47 (d, J=13.57 Hz, 1H) 2.59 (s, 3H) 2.70-2.77 (m, 3H) 3.03 (td, J=13.02, 2.90 Hz, 2H) 3.49-3.57 (m, 2H) 4.28-4.42 (m, 2H) 6.78 (s, 1H) 7.28-7.39 (m, 5H) 7.46 (d, J=8.25 Hz, 2H) 7.72 (d, J=8.20 Hz, 2H) 8.60 (s, 1H) 9.07 (s, 1H).

1-[4-(2-Methyl-7-phenyl-1,4,9,9b-tetraaza-cyclopenta[a]naphthalen-8-yl)-benzyl]-piperidine-4-carboxylic acid ethylamide [CXCVI]

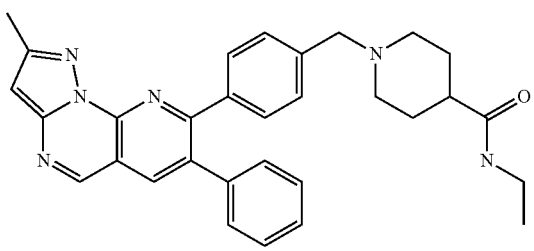

Compound [CXCVI] was prepared in a similar way to that of Compound [CLXII]. Data for Compound [CXCVI] (as the TFA salt): LCMS (m/e) 505 (M+H); $^1$H NMR (400 MHz, METHANOL-d$_4$) δ ppm 1.12 (t, J=7.30 Hz, 3H) 1.82-1.99 (m, 2H) 1.99-2.10 (m, 2H) 2.40-2.53 (m, 1H) 2.59 (s, 3H) 3.03 (td, J=13.08, 2.93 Hz, 2H) 3.20 (q, J=7.16 Hz, 2H) 3.49-3.58 (m, 2H) 4.28-4.43 (m, 2H) 6.78 (s, 1H) 7.28-7.40 (m, 5H) 7.46 (d, J=8.20 Hz, 2H) 7.72 (d, J=8.20 Hz, 2H) 8.59 (s, 1H) 9.07 (s, 1H).

253

[4-(3-Hydroxy-phenyl)-piperazin-1-yl]-{1-[4-(2-methyl-7-phenyl-1,4,9,9b-tetraaza-cyclopenta[a]naphthalen-8-yl)-benzyl]-piperidin-4-yl}-methanone [CXCVII]

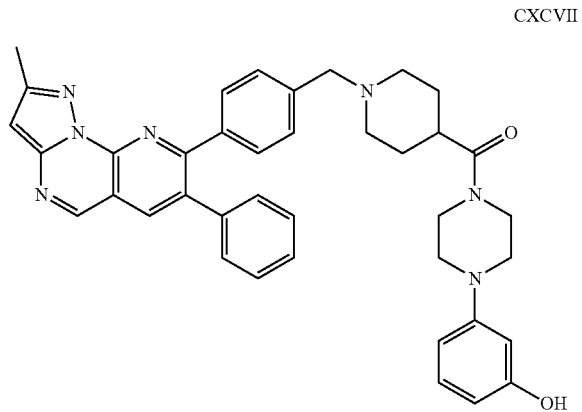 [SMILES: Cc1cc2ncc3cc(-c4ccccc4)c(-c4ccc(CN5CCC(C(=O)N6CCN(c7cccc(O)c7)CC6)CC5)cc4)nc3n2n1]

Compound [CXCVII] was prepared in a similar way to that of Compound [CLXII]. Data for Compound [CXCVII] (as the TFA salt): LCMS (m/e) 638 (M+H); $^1$H NMR (400 MHz, METHANOL-$d_4$) δ ppm 1.85-2.10 (m, 4H) 2.59 (s, 3H) 2.99-3.19 (m, 4H) 3.20-3.28 (m, 2H) 3.35-3.45 (m, 1H) 3.48-3.62 (m, 2H) 3.67-3.85 (m, 4H) 4.25-4.46 (m, 2H) 6.34-6.61 (m, 2H) 6.78 (s, 1H) 7.08 (quip, J=4.06 Hz, 1H) 7.35 (t, J=7.13 Hz, 5H) 7.47 (d, J=8.25 Hz, 2H) 7.72 (d, J=8.05 Hz, 2H) 8.59 (s, 1H) 9.06 (s, 1H).

1-[4-(2-Methyl-7-phenyl-1,4,9,9b-tetraaza-cyclopenta[a]naphthalen-8-yl)-benzyl]-piperidine-4-carboxylic acid ((S)-1-cyclohexyl-ethyl)-amide [CXCVIII]

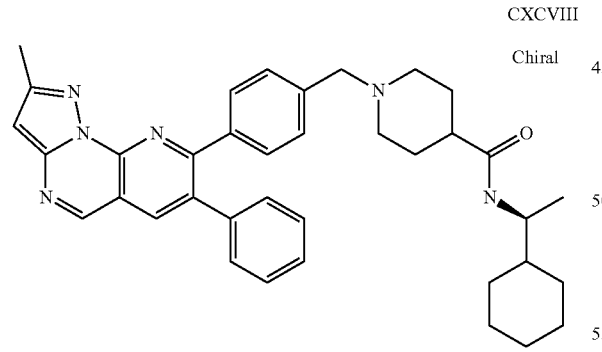

Compound [CXCVIII] was prepared in a similar way to that of Compound [CLXII]. Data for Compound [CXCVIII] (as the TFA salt): LCMS (m/e) 587 (M+H); $^1$H NMR (400 MHz, METHANOL-$d_4$) δ ppm 0.90-1.05 (m, 2H) 1.08 (d, J=6.78 Hz, 3H) 1.12-1.40 (m, 4H) 1.62-1.70 (m, 1H) 1.70-1.82 (m, 4H) 1.84-2.10 (m, 4H) 2.43-2.56 (m, 1H) 2.59 (s, 3H) 2.96-3.10 (m, 2H) 3.48-3.59 (m, 2H) 3.63-3.77 (m, 1H) 4.26-4.43 (m, 2H) 6.77 (s, 1H) 7.28-7.40 (m, 5H) 7.46 (d, J=8.10 Hz, 2H) 7.71 (d, J=8.20 Hz, 2H) 8.58 (s, 1H) 9.06 (s, 1H).

254

(Hexahydro-cyclopenta[c]pyrrol-2-yl)-{1-[4-(2-methyl-7-phenyl-1,4,9,9b-tetraaza-cyclopenta[a]naphthalen-8-yl)-benzyl]-piperidin-4-yl}-methanone [CXCIX]

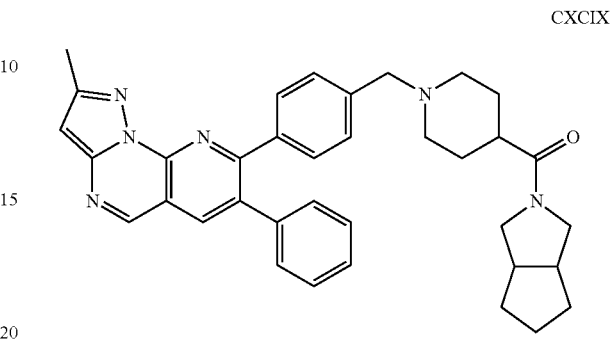

Compound [CXCIX] was prepared in a similar way to that of Compound [CLXII]. Data for Compound [CXCIX] (as the TFA salt): LCMS (m/e) 571 (M+H); $^1$H NMR (400 MHz, METHANOL-$d_4$) δ ppm 1.49 (tt, J=12.50, 6.34 Hz, 2H) 1.59-1.72 (m, 1H) 1.72-1.82 (m, 1H) 1.82-1.98 (m, 4H) 1.98-2.08 (m, 2H) 2.59 (s, 3H) 2.62-2.73 (m, 1H) 2.73-2.91 (m, 2H) 3.07 (t, J=12.89 Hz, 2H) 3.25 (dd, J=12.59, 4.78 Hz, 1H) 3.40 (dd, J=10.96, 4.76 Hz, 1H) 3.47-3.56 (m, 2H) 3.61 (dd, J=12.59, 8.40 Hz, 1H) 3.80 (dd, J=10.79, 8.25 Hz, 1H) 4.32 (s, 2H) 6.77 (s, 1H) 7.28-7.39 (m, 5H) 7.46 (d, J=8.20 Hz, 2H) 7.71 (d, J=8.20 Hz, 2H) 8.58 (s, 1H) 9.06 (s, 1H).

1-[4-(2-Methyl-7-phenyl-1,4,9,9b-tetraaza-cyclopenta[a]naphthalen-8-yl)-benzyl]-piperidine-4-carboxylic acid ethyl-isopropyl-amide [CC]

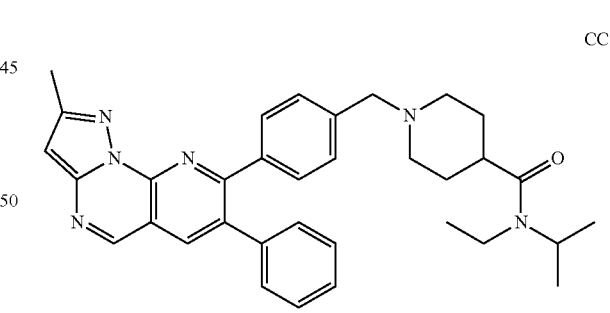

Compound [CC] was prepared in a similar way to that of Compound [CLXII]. Data for Compound [CC] (as the TFA salt): LCMS (m/e) 547 (M+H); $^1$H NMR (400 MHz, METHANOL-$d_4$) δ ppm 1.12 (t, J=6.98 Hz, 1H) 1.17 (d, J=6.83 Hz, 3H) 1.21-1.31 (m, 5H) 1.87-2.18 (m, 4H) 2.59 (s, 3H) 2.82-3.16 (m, 3H) 3.23-3.43 (m, 2H) 3.46-3.58 (m, 2H) 4.18-4.62 (m, 3H) 6.77 (s, 1H) 7.28-7.40 (m, 5H) 7.47 (d, J=8.20 Hz, 2H) 7.71 (d, J=8.20 Hz, 2H) 8.58 (s, 1H) 9.06 (s, 1H).

255

1-[4-(2-Methyl-7-phenyl-1,4,9,9b-tetraaza-cyclopenta[a]naphthalen-8-yl)-benzyl]-piperidine-4-carboxylic acid ((1S,2S)-2-hydroxy-cyclohexyl)-amide [CCI]

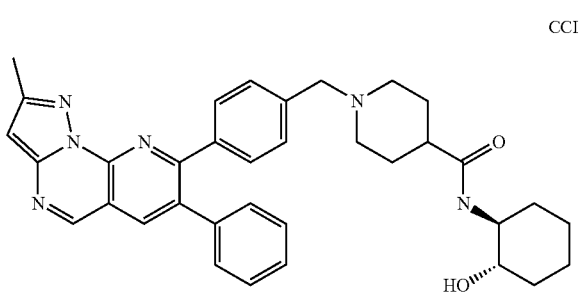 [SMILES: Cc1cc2ncc3cc(-c4ccccc4)c(-c4ccc(CN5CCC(C(=O)N[C@H]6CCCC[C@@H]6O)CC5)cc4)nc3n2n1]

Compound [CC] was prepared in a similar way to that of Compound [CLXII]. Data for Compound [CC] (as the TFA salt): LCMS (m/e) 575 (M+H); $^1$H NMR (400 MHz, METHANOL-$d_4$) δ ppm 1.12-1.42 (m, 4H) 1.61-1.80 (m, 2H) 1.82-2.17 (m, 6H) 2.44-2.56 (m, 1H) 2.59 (s, 3H) 3.03 (td, J=12.86, 2.73 Hz, 2H) 3.33-3.39 (m, 1H) 3.46-3.60 (m, 3H) 4.25-4.41 (m, 2H) 6.78 (s, 1H) 7.28-7.40 (m, 5H) 7.46 (d, J=8.20 Hz, 2H) 7.71 (d, J=8.20 Hz, 2H) 8.59 (s, 1H) 9.06 (s, 1H).

1-[4-(2-Methyl-7-phenyl-1,4,9,9b-tetraaza-cyclopenta[a]naphthalen-8-yl)-benzyl]-piperidine-4-carboxylic acid (2-hydroxy-ethyl)-amide [CCII]

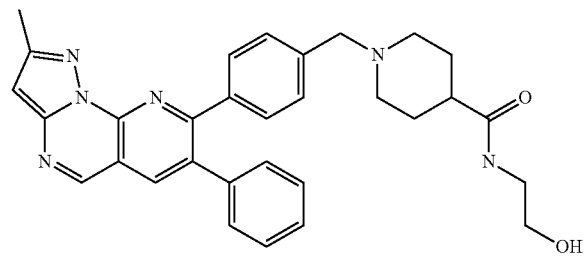

Compound [CCII] was prepared in a similar way to that of Compound [CLXII]. Data for Compound [CCII] (as the TFA salt): LCMS (rule) 521 (M+H); $^1$H NMR (400 MHz, METHANOL-$d_4$) δ ppm 1.83-2.01 (m, 2H) 2.00-2.13 (m, 2H) 2.46-2.57 (m, 1H) 2.59 (s, 3H) 3.03 (td, J=13.01, 2.73 Hz, 2H) 3.27-3.29 (m, 2H) 3.49-3.57 (m, 2H) 3.59 (t, J=5.66 Hz, 2H) 4.27-4.43 (m, 2H) 6.78 (s, 1H) 7.35 (t, J=6.88 Hz, 5H) 7.46 (d, J=8.20 Hz, 2H) 7.72 (d, J=8.20 Hz, 2H) 8.59 (s, 1H) 9.07 (s, 1H).

256

1-[4-(2-Methyl-7-phenyl-1,4,9,9b-tetraaza-cyclopenta[a]naphthalen-8-0)-benzyl]-piperidine-4-carboxylic acid (tetrahydro-furan-2-ylmethyl)-amide [CCIII]

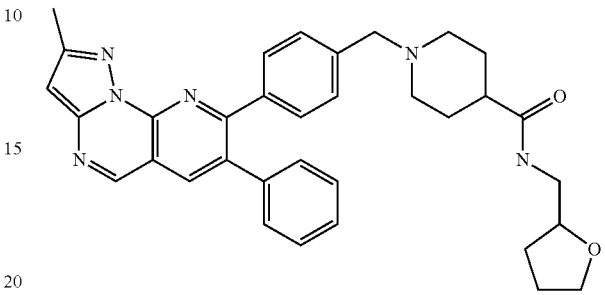

Compound [CCIII] was prepared in a similar way to that of Compound [CLXII]. Data for Compound [CCIII] (as the TFA salt): LCMS (m/e) 561 (M+H); $^1$H NMR (400 MHz, METHANOL-$d_4$) δ ppm 1.48-1.63 (m, 1H) 1.82-2.12 (m, 7H) 2.48-2.58 (m, 1H) 2.59 (s, 3H) 3.03 (td, J=12.87, 2.03 Hz, 2H) 3.16-3.26 (m, 1H) 3.47-3.59 (m, 2H) 3.74 (q, J=7.44 Hz, 1H) 3.80-3.90 (m, 1H) 3.90-4.01 (m, 1H) 4.27-4.42 (m, 2H) 6.77 (s, 1H) 7.27-7.39 (m, 5H) 7.46 (d, J=8.20 Hz, 2H) 7.71 (d, J=8.20 Hz, 2H) 8.58 (s, 1H) 9.06 (s, 1H).

1-[4-(2-Methyl-7-phenyl-1,4,9,9b-tetraaza-cyclopenta[a]naphthalen-8-yl)-benzyl]-piperidine-4-carboxylic acid cyclobutylamide [CCIV]

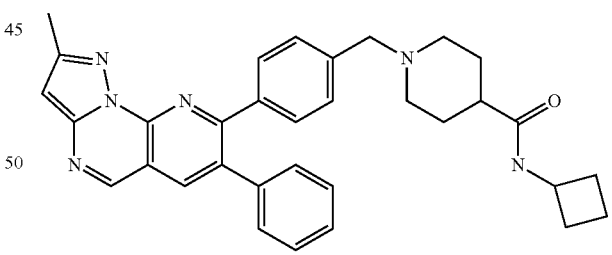

Compound [CCIV] was prepared in a similar way to that of Compound [CLXII]. Data for Compound [CCIV] (as the TFA salt): LCMS (m/e) 531 (M+H); $^1$H NMR (400 MHz, METHANOL-$d_4$) δ ppm 1.65-1.80 (m, 2H) 1.82-1.98 (m, 4H) 1.98-2.08 (m, 2H) 2.21-2.33 (m, 2H) 2.45 (ft, J=11.95, 3.43 Hz, 1H) 2.59 (s, 3H) 3.02 (td, J=12.84, 2.20 Hz, 2H) 3.47-3.57 (m, 2H) 4.20-4.30 (m, 1H) 4.32 (s, 2H) 6.77 (s, 1H) 7.26-7.40 (m, 5H) 7.46 (d, J=8.15 Hz, 2H) 7.71 (d, J=8.15 Hz, 2H) 8.58 (s, 1H) 9.06 (s, 1H).

1-[4-(2-Methyl-7-phenyl-1,4,9,9b-tetraaza-cyclopenta[a]naphthalen-8-yl)-benzyl]-piperidine-4-carboxylic acid isopropylamide [CCV]

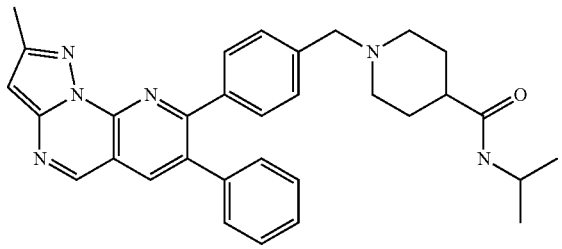

CCV

Compound [CCV] was prepared in a similar way to that of Compound [CLXII]. Data for Compound [CCV] (as the TFA salt): LCMS (m/e) 519 (M+H); $^1$H NMR (400 MHz, METHANOL-$d_4$) δ ppm 1.13 (d, J=6.54 Hz, 6H) 1.83-1.98 (m, 2H) 1.98-2.08 (m, 2H) 2.38-2.53 (m, 1H) 2.59 (s, 3H) 3.02 (td, J=12.82, 2.32 Hz, 2H) 3.48-3.58 (m, 2H) 3.94 (dt, J=13.20, 6.63 Hz, 1H) 4.27-4.43 (m, 2H) 6.78 (s, 1H) 7.35 (t, J=7.13 Hz, 5H) 7.46 (d, J=8.10 Hz, 2H) 7.71 (d, J=8.20 Hz, 2H) 8.59 (s, 1H) 9.06 (s, 1H).

({1-[4-(2-Methyl-7-phenyl-1,4,9,9b-tetraaza-cyclopenta[a]naphthalen-8-yl)-benzyl]-piperidine-4-carbonyl}-amino)-acetic acid tert-butyl ester [CCVI]

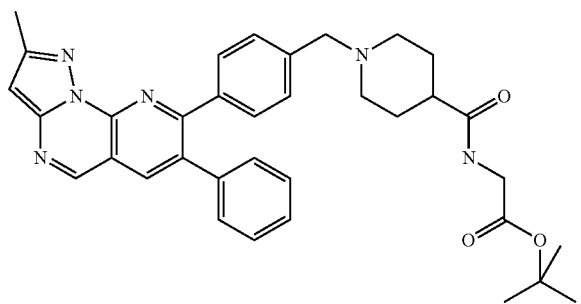

CCVI

Compound [CCVI] was prepared in a similar way to that of Compound [CLXII]. Data for Compound [CCVI] (as the TFA salt): LCMS (m/e) 591 (M+H); $^1$H NMR (400 MHz, METHANOL-$d_4$) δ ppm 1.46 (s, 9H) 1.84-2.01 (m, 2H) 2.06-2.17 (m, 2H) 2.52-2.64 (m, 4H) 2.99-3.11 (m, 2H) 3.50-3.59 (m, 2H) 3.82 (s, 2H) 4.29-4.41 (m, 2H) 6.78 (s, 1H) 7.26-7.40 (m, 5H) 7.46 (d, J=8.25 Hz, 2H) 7.72 (d, J=8.20 Hz, 2H) 8.60 (s, 1H) 9.07 (s, 1H).

({1-[4-(2-Methyl-7-phenyl-1,4,9,9b-tetraaza-cyclopenta[a]naphthalen-8-yl)-benzyl]-piperidine-4-carbonyl}-amino)-acetic acid [CCVII]

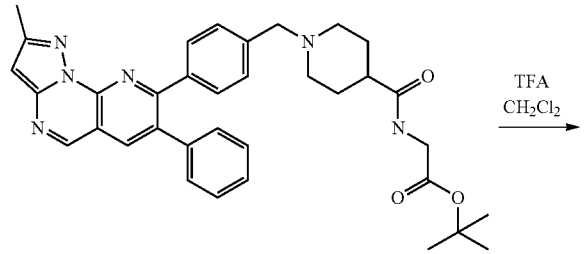

$\xrightarrow{\text{TFA}}{\text{CH}_2\text{Cl}_2}$

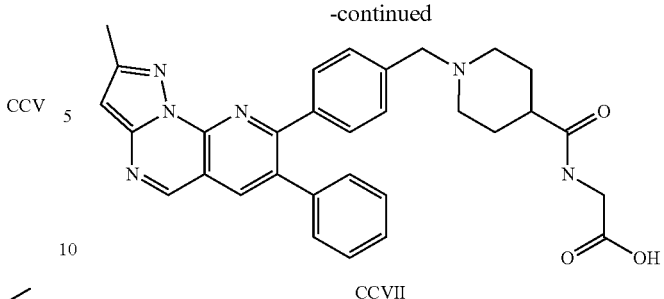

CCVII

Compound [CCVI] (10 mg, 0.017 mmol) was dissolved in CH$_2$Cl$_2$ (2 mL) and then TFA (500 μL) was added. The reaction was stirred at room temperature for 4 hours, and then blown to dryness with N$_2$. The residue was dissolved in MeOH and purified by reverse-phase chromatography (Solvent A H$_2$O/CH$_3$CN/TFA (95:5:0.05), Solvent B CH$_3$CN/H$_2$O/TFA (95:5:0.05)) with a gradient of 5% to 60% B over 5 minutes to give Compound [CCVII] as the TFA salt: LCMS (m/e) 535 (M+H); $^1$H NMR (400 MHz, METHANOL-$d_4$) δ ppm 1.81-2.00 (m, 2H) 2.04-2.17 (m, 2H) 2.51-2.64 (m, 4H) 2.96-3.10 (m, 2H) 3.48-3.59 (m, 2H) 3.90 (s, 2H) 4.32 (s, 2H) 6.77 (s, 1H) 7.34 (t, J=6.86 Hz, 5H) 7.45 (d, J=8.25 Hz, 2H) 7.70 (d, J=8.15 Hz, 2H) 8.58 (s, 1H) 9.06 (s, 1H).

1-[4-(2-Methyl-7-phenyl-1,4,9,9b-tetraaza-cyclopenta[a]naphthalen-8-yl)-benzyl]-piperidine-4-carboxylic acid (4-hydroxy-phenyl)-amide [CCVIII]

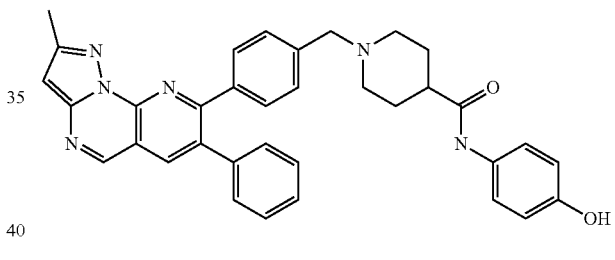

CCVIII

Compound [CCVIII] was prepared in a similar way to that of Compound [CLXII]. Data for Compound [CCVIII] (as the TFA salt): LCMS (m/e) 569 (M+H); $^1$H NMR (400 MHz, METHANOL-$d_4$) δ ppm 1.92-2.08 (m, 2H) 2.08-2.21 (m, 2H) 2.59 (s, 3H) 2.61-2.72 (m, 1H) 3.00-3.17 (m, 2H) 3.50-3.63 (m, 2H) 4.26-4.44 (m, 2H) 6.69-6.76 (m, 2H) 6.77 (s, 1H) 7.25-7.40 (m, 7H) 7.47 (d, J=8.25 Hz, 2H) 7.72 (d, J=8.15 Hz, 2H) 8.58 (s, 1H) 9.06 (s, 1H).

1-[4-(2-Methyl-7-phenyl-1,4,9,9b-tetraaza-cyclopenta[a]naphthalen-8-yl)-benzyl]-piperidine-4-carboxylic acid (3-carbamoyl-phenyl)-amide [CCIX]

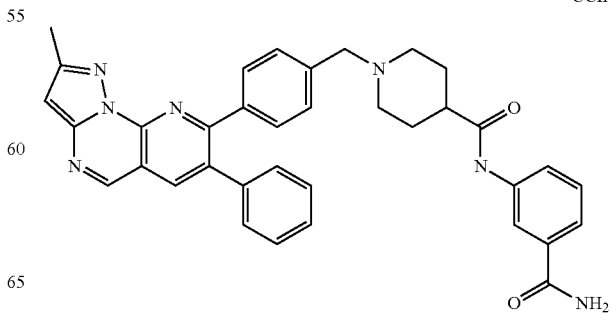

CCIX

Compound [CCIX] was prepared in a similar way to that of Compound [CLXII]. Data for Compound [CCIX] (as the TFA salt): LCMS (m/e) 596 (M+H); $^1$H NMR (400 MHz, METHANOL-$d_4$) δ ppm 1.94-2.11 (m, 2H) 2.12-2.26 (m, 2H) 2.59 (s, 3H) 2.64-2.81 (m, 1H) 3.01-3.17 (m, 2H) 3.49-3.66 (m, 2H) 4.37 (s, 2H) 6.78 (s, 1H) 7.34 (d, J=7.17 Hz, 5H) 7.41 (t, J=7.93 Hz, 1H) 7.48 (d, J=8.25 Hz, 2H) 7.59 (d, J=7.81 Hz, 1H) 7.67-7.78 (m, 3H) 8.05 (br. s., 1H) 8.59 (s, 1H) 9.06 (s, 1H).

1-[4-(2-Methyl-7-phenyl-1,4,9,9b-tetraaza-cyclopenta[a]naphthalen-8-yl)-benzyl]-piperidine-4-carboxylic acid (3-methoxy-phenyl)-amide [CCX]

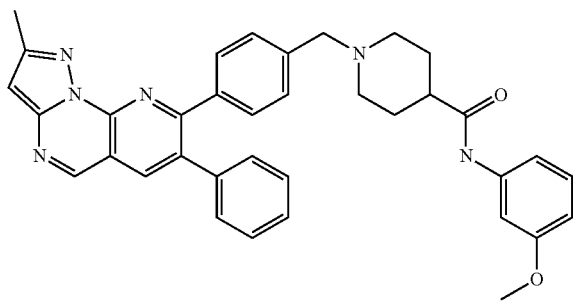

CCX

Compound [CCX] was prepared in a similar way to that of Compound [CLXII]. Data for Compound [CCX] (as the TFA salt): LCMS (m/e) 583 (M+H); $^1$H NMR (400 MHz, METHANOL-$d_4$) δ ppm 1.92-2.09 (m, 2H) 2.10-2.21 (m, 2H) 2.59 (s, 3H) 2.62-2.77 (m, 1H) 2.99-3.17 (m, 2H) 3.49-3.63 (m, 2H) 3.77 (s, 3H) 4.29-4.46 (m, 2H) 6.67 (dd, J=8.10, 2.34 Hz, 1H) 6.77 (s, 1H) 7.05 (d, J=8.20 Hz, 1H) 7.20 (t, J=8.18 Hz, 1H) 7.34 (d, J=9.47 Hz, 6H) 7.47 (d, J=8.25 Hz, 2H) 7.71 (d, J=8.05 Hz, 2H) 8.57 (s, 1H) 9.05 (s, 1H).

1-[4-(2-Methyl-7-phenyl-1,4,9,9b-tetraaza-cyclopenta[a]naphthalen-8-yl)-benzyl]-piperidine-4-carboxylic acid (3-methanesulfonylamino-phenyl)-amide [CCXI]

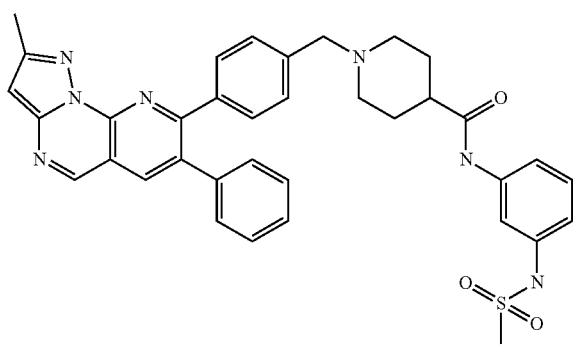

CCXI

Compound [CCXI] was prepared in a similar way to that of Compound [CLXII]. Data for Compound [CCXI] (as the TFA salt): LCMS (m/e) 646 (M+H); $^1$H NMR (400 MHz, METHANOL-$d_4$) δ ppm 1.94-2.08 (m, 2H) 2.09-2.23 (m, 2H) 2.59 (s, 3H) 2.63-2.76 (m, 1H) 2.96 (s, 3H) 3.01-3.16 (m, 2H) 3.50-3.63 (m, 2H) 4.30-4.45 (m, 2H) 6.78 (s, 1H) 6.95 (d, J=7.42 Hz, 1H) 7.27 (t, 1H) 7.29-7.39 (m, 6H) 7.48 (d, J=8.20 Hz, 2H) 7.60-7.69 (m, 1H) 7.72 (d, J=8.05 Hz, 2H) 8.59 (s, 1H) 9.06 (s, 1H).

1-[4-(2-Methyl-7-phenyl-1,4,9,9b-tetraaza-cyclopenta[a]naphthalen-8-yl)-benzyl]-piperidine-4-carboxylic acid (3-cyano-phenyl)-amide [CCXII]

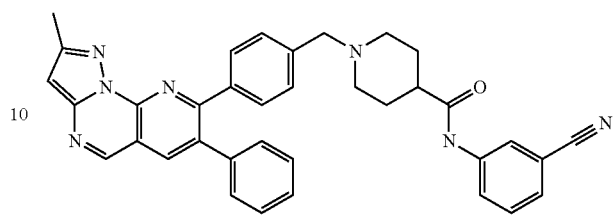

CCXII

Compound [CCXII] was prepared in a similar way to that of Compound [CLXII]. Data for Compound [CCXII] (as the TFA salt): LCMS (m/e) 578 (M+H); $^1$H NMR (400 MHz, METHANOL-$d_4$) δ ppm 1.95-2.10 (m, 2H) 2.11-2.25 (m, 2H) 2.59 (s, 3H) 2.64-2.77 (m, 1H) 3.02-3.18 (m, 2H) 3.52-3.64 (m, 2H) 4.29-4.46 (m, 2H) 6.78 (s, 1H) 7.27-7.39 (m, 5H) 7.40-7.54 (m, 4H) 7.72 (d, J=8.10 Hz, 2H) 7.77 (d, J=8.10 Hz, 1H) 8.00-8.17 (m, 1H) 8.59 (s, 1H) 9.06 (s, 1H).

1-[4-(2-Methyl-7-phenyl-1,4,9,9b-tetraaza-cyclopenta[a]naphthalen-8-yl)-benzyl]-piperidine-4-carboxylic acid (3-fluoro-phenyl)-amide [CCXIII]

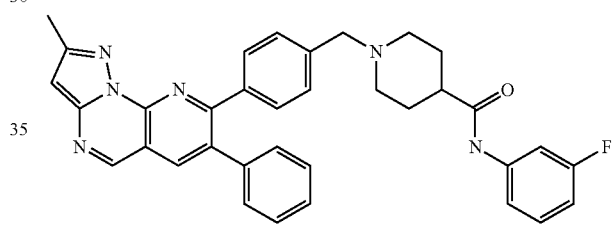

CCXIII

Compound [CCXIII] was prepared in a similar way to that of Compound [CLXII]. Data for Compound [CCXIII] (as the TFA salt): LCMS (m/e) 571 (M+H); $^1$H NMR (400 MHz, METHANOL-$d_4$) δ ppm 1.94-2.10 (m, 2H) 2.10-2.22 (m, 2H) 2.59 (s, 3H) 2.62-2.76 (m, 1H) 3.02-3.16 (m, 2H) 3.51-3.65 (m, 2H) 4.28-4.44 (m, 2H) 6.77 (s, 1H) 6.82 (td, J=8.13, 2.39 Hz, 1H) 7.20-7.26 (m, 1H) 7.26-7.40 (m, 6H) 7.48 (d, J=8.20 Hz, 2H) 7.53 (d, J=10.84 Hz, 1H) 7.72 (d, J=8.15 Hz, 2H) 8.58 (s, 1H) 9.06 (s, 1H).

1-[4-(2-Methyl-7-phenyl-1,4,9,9b-tetraaza-cyclopenta[a]naphthalen-8-yl)-benzyl]-piperidine-4-carboxylic acid (2-hydroxy-phenyl)-amide [CCXIV]

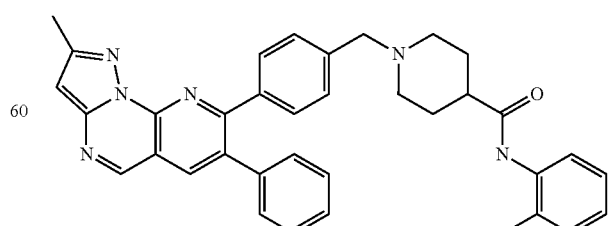

CCXIV

Compound [CCXIV] was prepared in a similar way to that of Compound [CLXII]. Data for Compound [CCXIV] (as the TFA salt): LCMS (m/e) 569 (M+H); $^1$H NMR (400 MHz, METHANOL-d$_4$) δ ppm 1.92-2.11 (m, 2H) 2.12-2.26 (m, 2H) 2.59 (s, 3H) 2.74-2.89 (m, 1H) 3.02-3.16 (m, 2H) 3.51-3.63 (m, 2H) 4.28-4.45 (m, 2H) 6.75-6.84 (m, 2H) 6.86 (d, J=7.37 Hz, 1H) 7.00 (t, J=7.52 Hz, 1H) 7.29-7.40 (m, 5H) 7.48 (d, J=8.25 Hz, 2H) 7.69 (d, J=8.00 Hz, 1H) 7.73 (d, J=8.00 Hz, 2H) 8.60 (s, 1H) 9.07 (s, 1H).

1-[4-(2-Methyl-7-phenyl-1,4,9,9b-tetraaza-cyclopenta[a]naphthalen-8-yl)-benzyl]-piperidine-4-carboxylic acid (4-carbamoyl-phenyl)-amide [CCXV]

CCXV

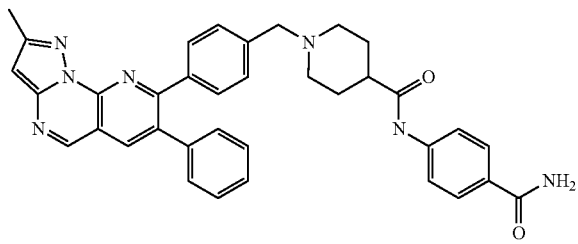

Compound [CCXV] was prepared in a similar way to that of Compound [CLXII]. Data for Compound [CCXV] (as the TFA salt): LCMS (m/e) 596 (M+H); $^1$H NMR (400 MHz, METHANOL-d$_4$) δ ppm 1.92-2.09 (m, 2H) 2.09-2.23 (m, 2H) 2.58 (s, 3H) 2.64-2.78 (m, 1H) 3.00-3.15 (m, 2H) 3.50-3.63 (m, 2H) 4.28-4.43 (m, 2H) 6.77 (s, 1H) 7.26-7.39 (m, 5H) 7.47 (d, J=8.20 Hz, 2H) 7.62-7.75 (m, 4H) 7.84 (d, J=8.74 Hz, 2H) 8.58 (s, 1H) 9.05 (s, 1H).

1-[4-(2-Methyl-7-phenyl-1,4,9,9b-tetraaza-cyclopenta[a]naphthalen-8-yl)-benzyl]-piperidine-4-carboxylic acid (3-sulfamoyl-phenyl)-amide [CCXVI]

CCXVI

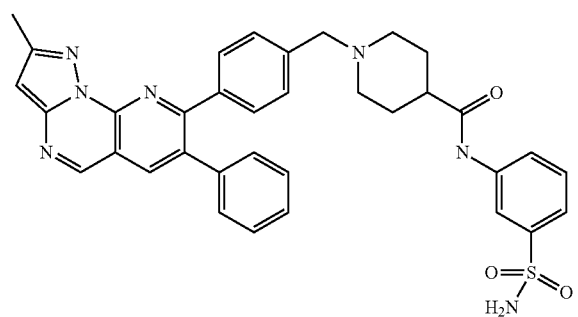

Compound [CCXVI] was prepared in a similar way to that of Compound [CLXII]. Data for Compound [CCXVI] (as the TFA salt): LCMS (m/e) 632 (M+H); $^1$H NMR (400 MHz, METHANOL-d$_4$) δ ppm 1.95-2.12 (m, 2H) 2.11-2.24 (m, 2H) 2.59 (s, 3H) 2.65-2.78 (m, 1H) 3.02-3.17 (m, 2H) 3.52-3.63 (m, 2H) 4.36 (s, 2H) 6.78 (s, 1H) 7.26-7.40 (m, 5H) 7.44-7.53 (m, 3H) 7.63 (ddd, J=8.05, 1.22, 0.83 Hz, 1H) 7.72 (d, J=8.00 Hz, 3H) 8.19-8.30 (m, 1H) 8.59 (s, 1H) 9.06 (s, 1H).

1-[4-(2-Methyl-7-phenyl-1,4,9,9b-tetraaza-cyclopenta[a]naphthalen-8-0)-benzyl]-piperidine-4-carboxylic acid benzothiazol-5-ylamide [CCXVII]

CCXVII

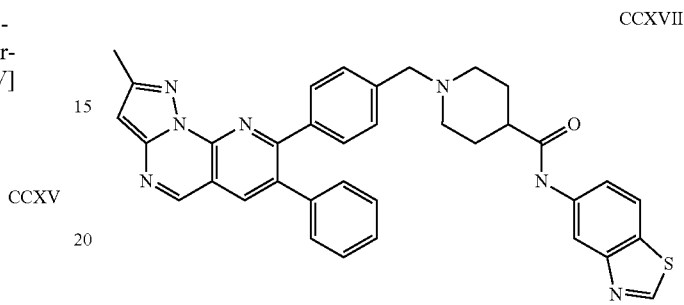

Compound [CCXVII] was prepared in a similar way to that of Compound [CLXII]. Data for Compound [CCXVII] (as the TFA salt): LCMS (m/e) 610 (M+H); $^1$H NMR (400 MHz, METHANOL-d$_4$) δ ppm 1.96-2.15 (m, 2H) 2.15-2.28 (m, 2H) 2.59 (s, 3H) 2.68-2.83 (m, 1H) 3.05-3.19 (m, 2H) 3.53-3.66 (m, 2H) 4.33-4.47 (m, 2H) 6.78 (s, 1H) 7.27-7.41 (m, 5H) 7.49 (d, J=8.20 Hz, 2H) 7.62 (dd, J=8.74, 2.00 Hz, 1H) 7.73 (d, J=8.00 Hz, 2H) 8.00 (d, J=8.74 Hz, 1H) 8.42-8.53 (m, 1H) 8.59 (s, 1H) 9.06 (s, 1H) 9.24 (s, 1H).

1-[4-(2-Methyl-7-phenyl-1,4,9,9b-tetraaza-cyclopenta[a]naphthalen-8-yl)-benzyl]-piperidine-4-carboxylic acid (3-trifluoromethoxy-phenyl)-amide [CCXVIII]

CCXVIII

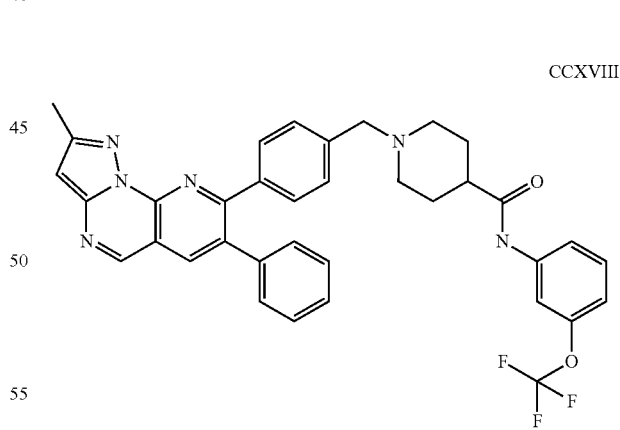

Compound [CCXVIII] was prepared in a similar way to that of Compound [CLXII]. Data for Compound [CCXVIII] (as the TFA salt): LCMS (mile) 637 (M+H); $^1$H NMR (400 MHz, METHANOL-d$_4$) δ ppm 1.93-2.10 (m, 2H) 2.10-2.25 (m, 2H) 2.59 (s, 3H) 2.63-2.77 (m, 1H) 3.02-3.16 (m, 2H) 3.51-3.64 (m, 2H) 4.32-4.45 (m, 2H) 6.78 (s, 1H) 7.00 (d, J=8.00 Hz, 1H) 7.29-7.38 (m, 5H) 7.40 (d, J=8.05 Hz, 1H) 7.42-7.46 (m, 1H) 7.48 (d, J=8.20 Hz, 2H) 7.66-7.82 (m, 3H) 8.59 (s, 1H) 9.07 (s, 1H).

1-[4-(2-Methyl-7-phenyl-1,4,9,9b-tetraaza-cyclopenta[a]naphthalen-8-yl)-benzyl]-piperidine-4-carboxylic acid thiazol-2-ylamide [CCXIX]

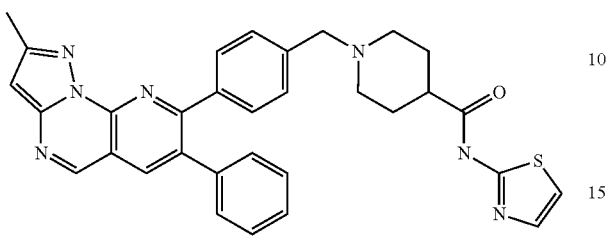

CCXIX

Compound [CCXIX] was prepared in a similar way to that of Compound [CLXII]. Data for Compound [CCXIX] (as the TFA salt): LCMS (m/e) 560 (M+H); $^1$H NMR (400 MHz, METHANOL-$d_4$) δ ppm 1.91-2.11 (m, 2H) 2.11-2.28 (m, 2H) 2.59 (s, 3H) 2.75-2.90 (m, 1H) 3.03-3.17 (m, 2H) 3.52-3.64 (m, 2H) 4.33-4.44 (m, 2H) 6.78 (s, 1H) 7.12 (d, J=3.61 Hz, 1H) 7.28-7.40 (m, 5H) 7.44 (d, J=3.61 Hz, 1H) 7.48 (d, J=8.30 Hz, 2H) 7.72 (d, J=8.05 Hz, 2H) 8.59 (s, 1H) 9.06 (s, 1H).

1-[4-(2-Methyl-7-phenyl-1,4,9,9b-tetraaza-cyclopenta[a]naphthalen-8-yl)-benzyl]-piperidine-4-carboxylic acid (3-oxo-1,3-dihydro-isobenzofuran-5-yl)-amide [CCXX]

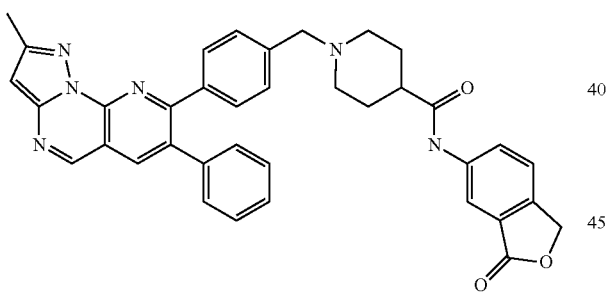

CCXX

Compound [CCXX] was prepared in a similar way to that of Compound [CLXII].

Data for Compound [CCXX] (as the TFA salt): LCMS (m/e) 609 (M+H); $^1$H NMR (400 MHz, METHANOL-$d_4$) δ ppm 1.93-2.12 (m, 2H) 2.12-2.27 (m, 2H) 2.59 (s, 3H) 2.65-2.84 (m, 1H) 3.02-3.20 (m, 2H) 3.52-3.67 (m, 2H) 4.25-4.46 (m, 2H) 5.34 (s, 2H) 6.77 (s, 1H) 7.26-7.41 (m, 5H) 7.48 (d, J=8.20 Hz, 2H) 7.56 (d, J=8.35 Hz, 1H) 7.72 (d, J=8.10 Hz, 2H) 7.83 (d, J=9.57 Hz, 1H) 8.15-8.29 (m, 1H) 8.58 (s, 1H) 9.06 (s, 1H).

1-[4-(2-Methyl-7-phenyl-1,4,9,9b-tetraaza-cyclopenta[a]naphthalen-8-yl)-benzyl]-piperidine-4-carboxylic acid (3-methanesulfonyl-phenyl)-amide [CCXXI]

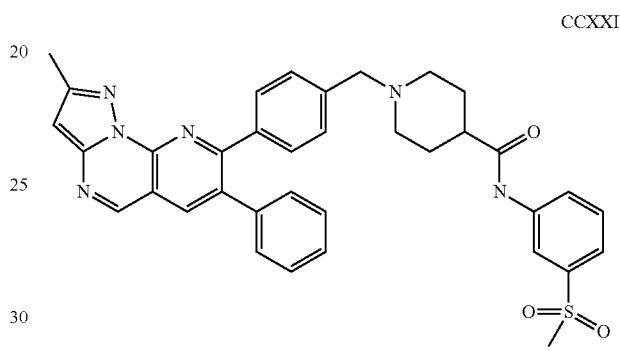

CCXXI

Compound [CCXXI] was prepared in a similar way to that of Compound [CLXII]. Data for Compound [CCXXI] (as the TFA salt): LCMS (m/e) 631 (M+H); $^1$H NMR (400 MHz, METHANOL-$d_4$) δ ppm 1.94-2.14 (m, 2H) 2.14-2.39 (m, 2H) 2.59 (s, 3H) 2.66-2.79 (m, 1H) 3.02-3.17 (m, 5H) 3.51-3.65 (m, 2H) 4.30-4.46 (m, 2H) 6.78 (s, 1H) 7.28-7.41 (m, 5H) 7.48 (d, J=8.25 Hz, 2H) 7.58 (t, J=7.96 Hz, 1H) 7.68 (d, J=7.96 Hz, 1H) 7.72 (d, J=8.05 Hz, 2H) 7.82 (d, J=8.00 Hz, 1H) 8.25-8.40 (m, 1H) 8.59 (s, 1H) 9.06 (s, 1H).

1-[4-(2-Methyl-7-phenyl-1,4,9,9b-tetraaza-cyclopenta[a]naphthalen-8-yl)-benzyl]-piperidine-4-carboxylic acid (3-hydroxymethyl-phenyl)-amide [CCXXII] 1-[4-(2-Methyl-7-phenyl-1,4,9,9b-tetraaza-cyclopenta[a]naphthalen-8-yl)-benzyl]-piperidine-4-carboxylic acid 3-amino-benzyl ester [CCXXIII]

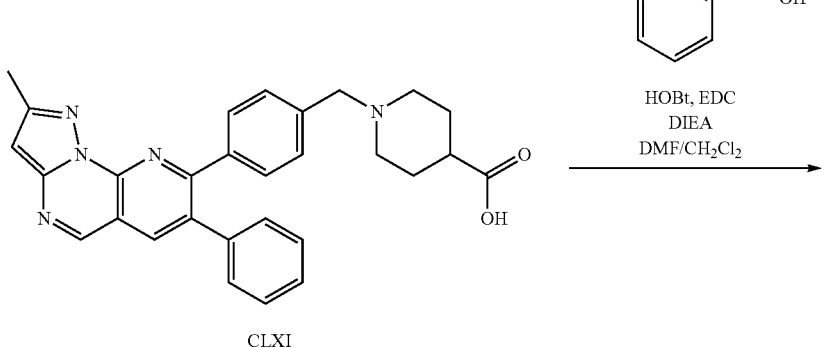

CLXI

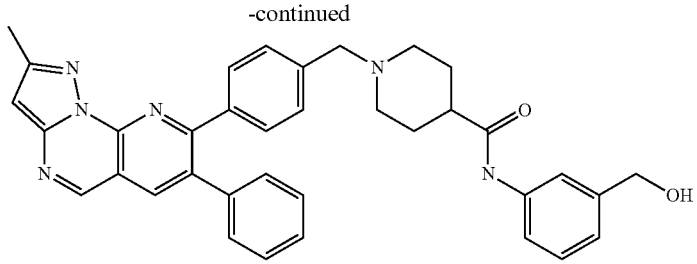

CCXXII

+

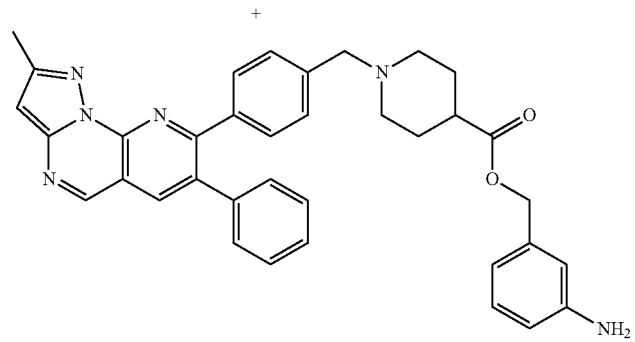

CCXXIII

Compound [CLXI] (20 mg, 0.042 mmol) was reacted with (3-aminophenyl)methanol (26 mg, 0.21 mmol, 5.0 eq) under similar conditions as for the synthesis of Compound [CLXII] to give Compound [CCXXII] and Compound [CCXXIII] as the TFA salts: Data for [CCXXII]: LCMS (m/e) 583 (M+H); $^1$H NMR (400 MHz, METHANOL-4) δ ppm 1.93-2.12 (m, 2H) 2.12-2.37 (m, 2H) 2.59 (s, 3H) 2.64-2.76 (m, 1H) 3.01-3.17 (m, 2H) 3.51-3.64 (m, 2H) 4.30-4.44 (m, 2H) 4.58 (s, 2H) 6.78 (s, 1H) 7.10 (d, J=7.61 Hz, 1H) 7.28 (t, J=7.86 Hz, 1H) 7.31-7.40 (m, 5H) 7.42-7.52 (m, 3H) 7.56 (s, 1H) 7.72 (d, J=8.05 Hz, 2H) 8.59 (s, 1H) 9.06 (s, 1H);

for [CCXXIII] LCMS (m/e) 583 (M+H); $^1$H NMR (400 MHz, METHANOL-d$_4$) δ ppm 1.74-2.10 (m, 2H) 2.13-2.37 (m, 2H) 2.59 (s, 3H) 2.67-2.82 (m, 1H) 2.98-3.16 (m, 2H) 3.44-3.62 (m, 2H) 4.33 (s, 2H) 5.19 (br. s., 2H) 6.78 (s, 1H) 7.17-7.25 (m, 1H) 7.27 (s, 1H) 7.29-7.40 (m, 6H) 7.41-7.49 (m, 3H) 7.71 (d, J=8.30 Hz, 2H) 8.59 (s, 1H) 9.07 (s, 1H).

1-[4-(2-Methyl-7-phenyl-1,4,9,9b-tetraaza-cyclopenta[a]naphthalen-8-yl)-benzyl]-piperidine-4-carboxylic acid (3-amino-phenyl)-amide [CCXXIV]

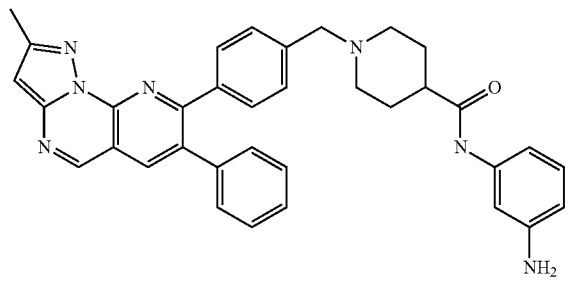

CCXXIV

Compound [CCXXIV] was prepared in a similar way to that of Compound [CLXII]. Data for Compound [CCXXIV] (as the TFA salt): LCMS (m/e) 568 (M+H); $^1$H NMR (400 MHz, METHANOL-d$_4$) δ ppm 1.94-2.10 (m, 2H) 2.11-2.24 (m, 2H) 2.59 (s, 3H) 2.64-2.82 (m, 1H) 3.01-3.19 (m, 2H) 3.52-3.65 (m, 2H) 4.36 (s, 2H) 6.78 (s, 1H) 7.01 (dd, J=8.93, 2.10 Hz, 1H) 7.35 (t, J=6.83 Hz, 7H) 7.48 (d, J=8.25 Hz, 2H) 7.72 (d, J=8.20 Hz, 2H) 7.83-7.89 (m, 1H) 8.59 (s, 1H) 9.07 (s, 1H).

1-[4-(2-Methyl-7-phenyl-1,4,9,9b-tetraaza-cyclopenta[a]naphthalen-8-yl)-benzyl]-piperidine-4-carboxylic acid methyl ester [CCXXV]

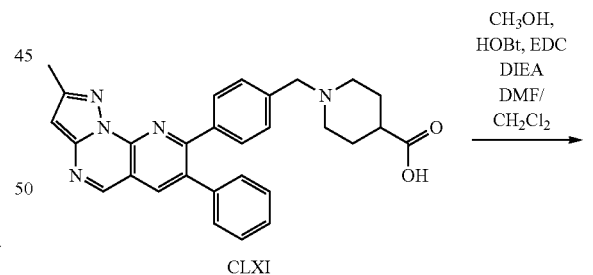

CLXI $\xrightarrow{\text{CH}_3\text{OH, HOBt, EDC, DIEA, DMF/CH}_2\text{Cl}_2}$

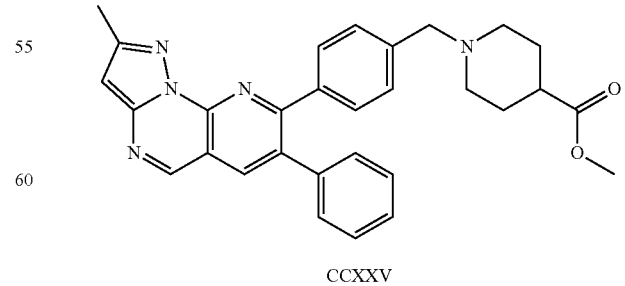

CCXXV

Compound [CLXI] (20 mg, 0.042 mmol) was reacted with methanol (7 mg, 0.21 mmol, 5.0 eq) under similar conditions and purified under similar conditions to that of Compound [CLXII] to give Compound [CCXXV] as the TFA salt: LCMS (m/e) 492 (M+H); $^1$H NMR (400 MHz, METHANOL-d$_4$) δ ppm 1.74-2.10 (m, 2H) 2.16-2.38 (m, 2H) 2.59 (s, 3H) 2.63-2.76 (m, 1H) 2.99-3.11 (m, 2H) 3.47-3.58 (m, 2H) 3.66-3.82 (m, 3H) 4.28-4.40 (m, 2H) 6.78 (s, 1H) 7.27-7.40 (m, 5H) 7.46 (d, j=8.30 Hz, 2H) 7.71 (d, J=8.20 Hz, 2H) 8.59 (s, 1H) 9.06 (s, 1H).

1-[4-(2-Methyl-7-phenyl-1,4,9,9b-tetraaza-cyclopenta[a]naphthalen-8-yl)-benzyl]-piperidine-4-carboxylic acid (1,1-dioxo-1H-1lambda*6*-benzo[b]thiophen-6-yl)amide [CCXXVI]

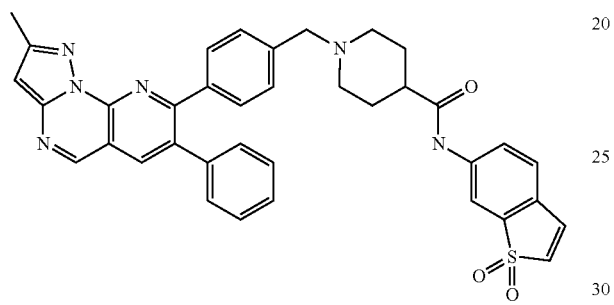

CCXXVI

Compound [CCXXVI] was prepared in a similar way to that of Compound [CLXII]. Data for Compound [CCXXVI] (as the TFA salt): LCMS (m/e) 641 (M+H); $^1$H NMR (400 MHz, METHANOL-d$_4$) δ ppm 1.92-2.11 (m, 2H) 2.11-2.28 (m, 2H) 2.59 (s, 3H) 2.65-2.79 (m, 1H) 3.02-3.18 (m, 2H) 3.52-3.65 (m, 2H) 4.28-4.46 (m, 2H) 6.78 (s, 1H) 6.91 (d, J=6.88 Hz, 1H) 7.29-7.39 (m, 5H) 7.40 (dd, J=6.91, 0.81 Hz, 1H) 7.45 (d, J=8.30 Hz, 1H) 7.48 (d, J=8.30 Hz, 2H) 7.66-7.77 (m, 3H) 8.06-8.24 (m, 1H) 8.59 (s, 1H) 9.07 (s, 1H).

Scheme IX - Synthesis of Pyridazine compound

7-Amino-2-methyl-pyrazolo[1,5-a]pyrimidine-

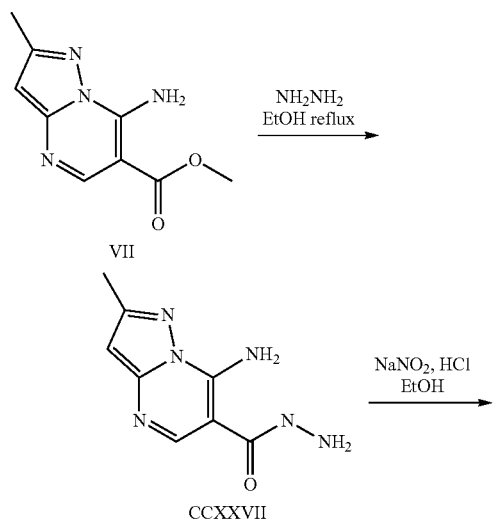

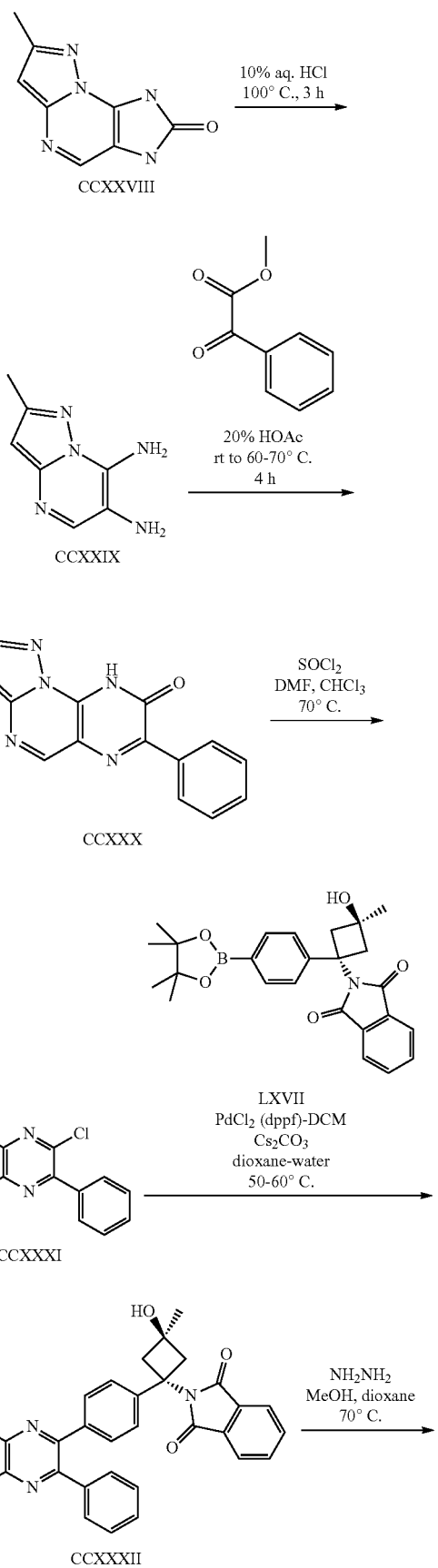

269

-continued

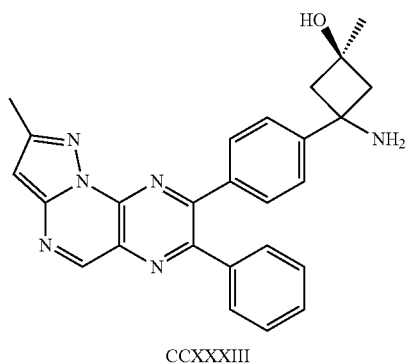

CCXXXIII 6-carboxylic acid hydrazide [CCXXVII]

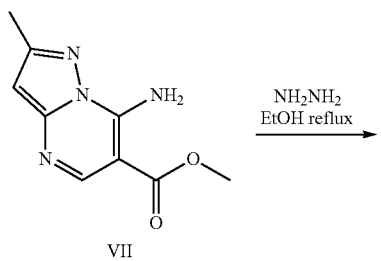

A 250 mL flask was containing the Compound [VII] (2.1 g, 20 mmol), EtOH (55 mL), and hydrazine hydrate (20 mL) was heated to reflux for 6 hours. The mixture was allowed to cool to room temperature. The precipitated solid was filtered and washed with water (2×10 mL) to provide Compound [CCXXVII] as a white solid: LCMS (m/e) 207 (M+H); $^1$H NMR (400 MHz, DMSO-d$_6$) δ ppm 2.38 (s, 3H) 4.40 (s, 2H) 6.27 (s, 1H) 8.52 (s, 1H) 8.76 (br. s., 1H) 9.66 (br. s., 1H).

7-Methyl-1,3-dihydro-pyrazolo[5,1-h]purin-2-one [CCXXVIII]

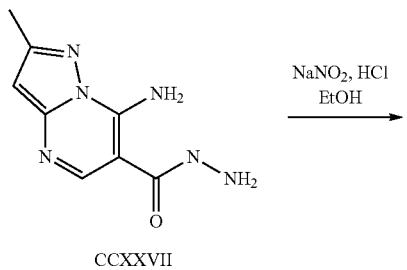

270

-continued

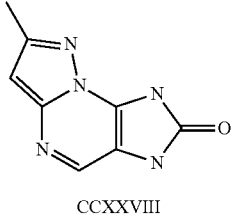

CCXXVIII

A 100 mL flask containing Compound [CCXXVII] (1.1 g, 5.0 mmol, 1 eq.), EtOH (25 mL), and 10% aqueous HCl (25 mL) was cooled to 0° C. by ice-water bath. Then NaNO$_2$ (0.35 g, 5.0 mmol, 1 eq.) in water (8 mL) was added slowly. The mixture was stirred at that temperature for 2 hours, after which it was heated to 80° C. for 2 hours. After cooling and removal of the volatiles by rotary evaporation, the residue was treated with water (40 mL). The resulting precipitated solid was filtered and washed with water (2×5 mL) to provide Compound [CCXXVIII] as a brownish solid: LCMS (m/e) 190 (M+H); $^1$H NMR (400 MHz, DMSO-d$_6$) δ ppm 2.42 (s, 3H) 6.37 (s, 1H) 8.20 (s, 1H) 11.13 (s, 1H).

2-Methyl-pyrazolo[1,5-a]pyrimidine-6,7-diamine [CCXXIX]

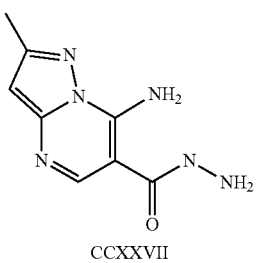

A 40 mL scintillation vial containing Compound [CCXXVIII] (0.72 g, 3.8 mmol) and 10% aqueous HCl (25 mL) was heated at 100° C. for 3 hours. The mixture was allowed to cool, the solvent was removed in vacuo and water (~40 mL) was added. The resulting solid (starting material) was filtered and dried to recover Compound [CCXXVIII] (0.2 g, 28% recovery). The filtrate was then concentrated and dried to furnish Compound [CCXXIX] as a yellowish solid: LCMS (m/e) 164 (M+H); $^1$H NMR. (400 MHz, DMSO-d$_6$) δ ppm 2.41 (s, 3H) 6.28 (s, 1H) 8.01 (s, 1H) 9.42 (br. s., 1H).

2-Methyl-7-phenyl-1,4,6,9,9b-pentaaza-cyclopenta[a]naphthalen-8-ol [CCXXX]

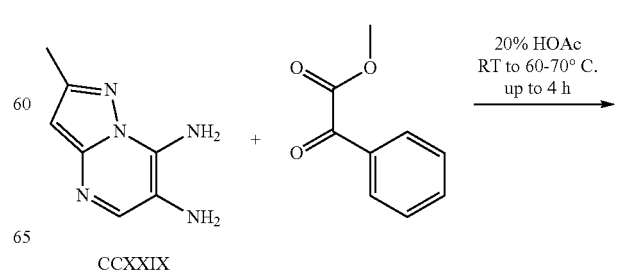

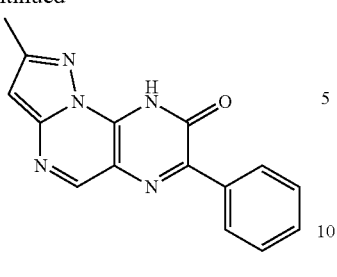

CCXXX

A 40-mL scintillation vial containing Compound [CCXXIX] (320 mg, 2.0 mmol, 1 eq.), methyl phenylpyruvate (360 mg, 2.2 mmol, 1.1 eq.), and 20% HOAc (20 mL) was stirred at room temperature for 1.5 hours and at 65° C. for 4 hours. The mixture was allowed to cool and the precipitated solid was filtered and washed successively with water (15 mL) and Et$_2$O (2×10 mL). The solid was dried in vacuo to give Compound [CCXXX] as a yellowish solid: LCMS (m/e) 278 (M+H); $^1$H NMR (400 MHz, DMSO-d$_6$) δ ppm 2.48 (s, 3H) 6.64 (s, 1H) 7.35-7.57 (m, 4H) 8.07-8.29 (m, 2H) 8.85 (s, 1H).

8-Chloro-2-methyl-7-phenyl-1,4,6,9,9b-pentaaza-cyclopenta[a]naphthalene [CCXXXI]

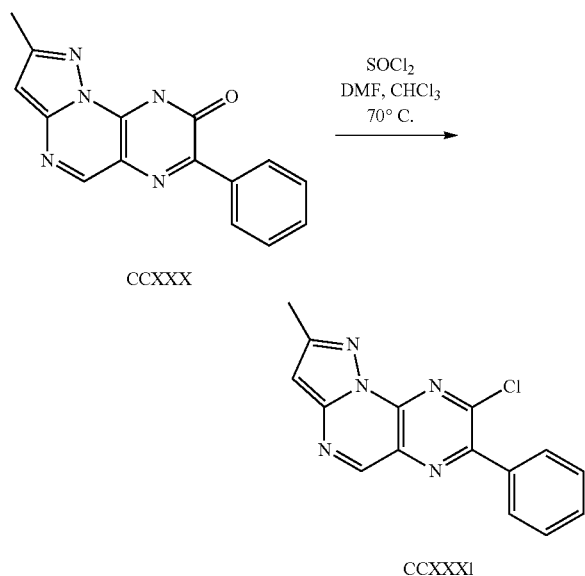

A 40 mL scintillation vial containing Compound [CCXXX] (220 mg, 0.8 mmol, 1 eq.), CHCl$_3$ (12 mL), DMF (12 mg, 0.16 mmol, 2 eq.), and SOCl$_2$ (0.56 g, 3.2 mmol, 4 eq.) was heated at 70° C. under nitrogen for 1.5 hours. Then the mixture was allowed to cool and the solvent was removed in vacuo. The residue was dissolved in CHCl$_3$ (20 mL) and washed with saturated NaHCO$_3$ (5 mL). The water solution was extracted with CHCl$_3$ (2×5 mL). The combined organic phases were dried over MgSO$_4$. After filtration and concentration, the residue was purified by silica gel chromatography using EtOAc and heptanes as the mobile phases to furnish Compound [CCXXXI] as a yellowish solid: LCMS (m/e) 296 (M+H); $^1$H NMR (400 MHz, CHLOROFORM-d) δ ppm 2.57 (s, 3H) 6.71 (s, 1H) 7.46-7.52 (m, 3H) 7.79 (dd, J=6.61, 3.00 Hz, 2H) 9.02 (s, 1H).

2-{3-Hydroxy-3-methyl-[4-(2-methyl-7-phenyl-1,4,6,9,9b-pentaaza-cyclopenta[a]naphthalen-8-yl)-phenyl]-cyclobutyl}-isoindole-1,3-dione [CCXXXII]

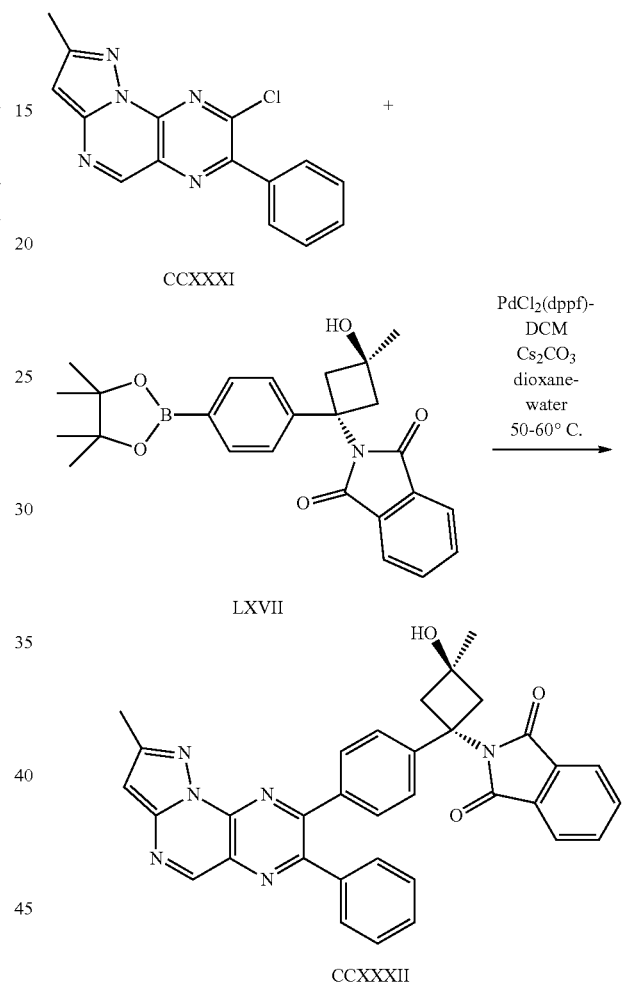

A 20 ml scintillation vial containing Compound [CCXXXI] (60 mg, 0.20 mmol, 1 eq.), Compound [LXVII] (87 mg, 0.20 mmol, 1 eq.), Cs$_2$CO$_3$ (325 mg, 1.0 mmol, 5 eq.), dioxane (3.0 ml), and water (0.6 ml) was evacuated and flushed three times with nitrogen. Then PdCl$_2$(dppf)-CH$_2$Cl$_2$ (24 mg, 0.03 mmol, 0.15 eq.) was added and the resulting solution was evacuated and flushed three times with nitrogen. The mixture was heated at 55° C. for 90 minutes. The mixture was allowed to cool and the solvents removed in vacuo. The residue was dissolved in CH$_2$Cl$_2$ (10 mL). After filtration and concentration, it was purified by silica gel chromatography using MeOH and CH$_2$Cl$_2$ as the mobile phases to furnish Compound [CXXXII] as a yellowish solid: LCMS (m/e) 567 (M+H); $^1$H NMR (400 MHz, CHLOROFORM-d) δ ppm 1.44 (s, 3H) 2.59 (s, 3H) 3.09-3.17 (m, 2H) 3.32-3.40 (m, 2H) 6.73 (s, 1H) 7.28-7.41 (m, 3H) 7.46-7.54 (m, 2H) 7.58-7.82 (m, 9H) 9.10 (s, 1H).

3-Amino-1-methyl-3-[4-(2-methyl-7-phenyl-1,4,6,9,9b-pentaaza-cyclopenta[a]naphthalen-8-yl)-phenyl]-cyclobutanol [CCXXXIII]

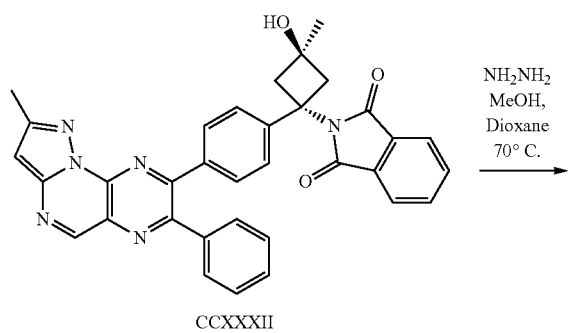

CCXXXII

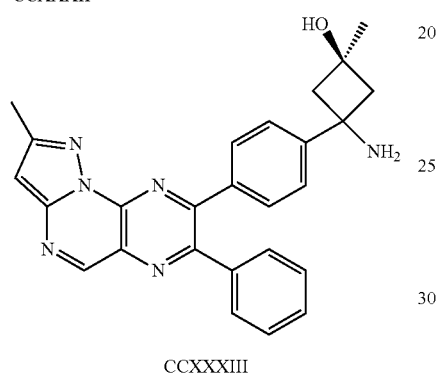

CCXXXIII

A 20 mL scintillation vial containing Compound [CCXXXII] (82 mg, 0.145 mmol), MeOH (3 mL), dioxane (3 mL), and hydrazine (1 mL) was heated at 70° C. for 3 hours. Then the solvent was removed in vacuo. The residue was dissolved in 80% MeOH-water (7 mL, some CH$_2$Cl$_2$) and several drops of HOAc. Then it was purified by reverse-phase preparative HPLC using water-acetonitrile-HOAc [95:5:0.05] and acetonitrile-water-HOAc [95:5:0.05] as the mobile phases to provide Compound [CCXXXIII] as a yellow solid (acetate salt): LCMS (m/e) 437 (M+H); $^1$H NMR (400 MHz, MeOH-d$_4$) δ ppm 1.50 (s, 3H) 1.97 (s, 3H, HOAc) 2.60 (s, 3H) 2.65-2.72 (m, 2H) 2.82-2.91 (m, 2H) 6.84 (s, 1H) 7.33-7.44 (m, 3H) 7.52-7.61 (m, 4H) 7.78-7.83 (m, 2H) 9.14 (s, 1H).

Scheme VIII-Synthesis of [CCXXXIX]

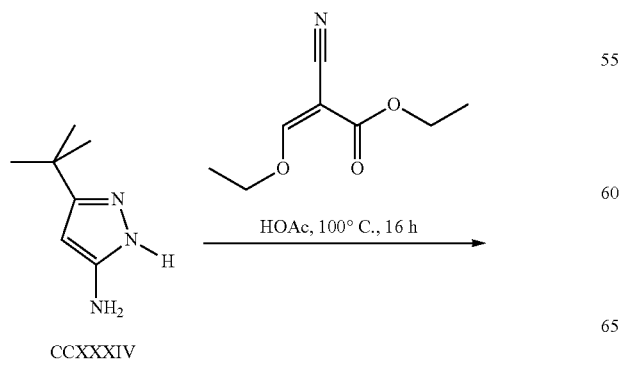

CCXXXIV

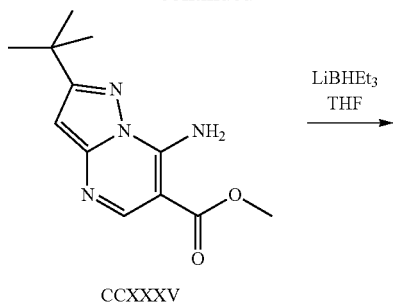

CCXXXV

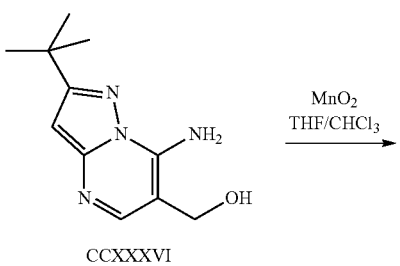

CCXXXVI

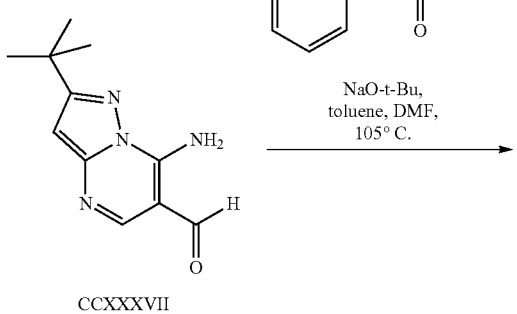

CCXXXVII

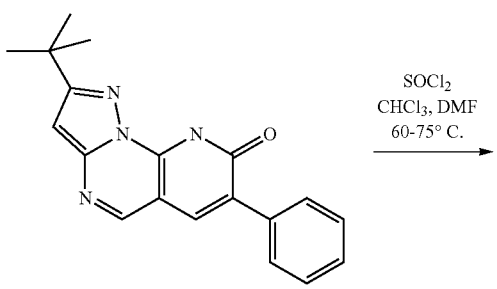

CCXXXVIII

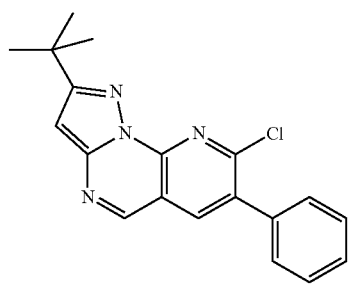

CCXXXIX

7-Amino-2-t-butyl-pyrazolo[1,5-a]pyrimidine-6-carboxylic acid ethyl ester [CCXXXV]

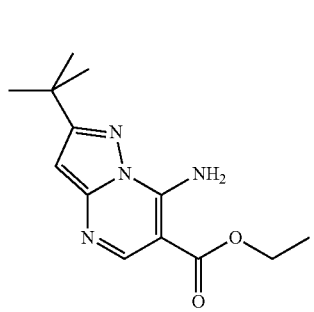

CCXXXV

Compound [CCXXXV] was prepared using a procedure similar to that of Compound [VII]. Data for Compound [CCXXXV]: LCMS (m/e) 263 (M+H); $^1$H NMR (400 MHz, CHLOROFORM-d) δ ppm 1.36-1.48 (m, 12H) 4.40 (q, J=7.13 Hz, 2H) 6.40 (s, 1H) 6.90 (br. s., 1H) 8.40 (br. s., 1H) 8.71 (s, 1H).

(7-Amino-2-t-butyl-pyrazolo[1,5-a]pyrimidin-6-yl)-methanol [CCXXXVI]

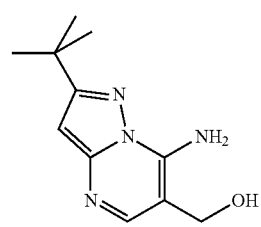

CCXXXVI

Compound [CCXXXVI] was prepared using a procedure similar to that of Compound [III]. Data for Compound [CCXXXVI]: LCMS (m/e) 221 (M+H); $^1$H NMR (400 MHz, METHANOL-d$_4$) δ ppm 1.85 (s, 9H) 5.11 (s, 2H) 6.67 (s, 1H) 8.46 (s, 1H).

7-Amino-2-t-butyl-pyrazolo[1,5-a]pyrimidin-6-carbaldehyde CCXXXVII

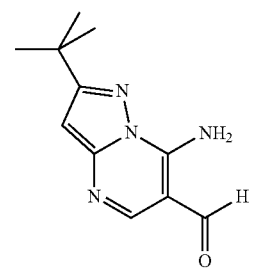

CCXXXVII

Compound [CCXXXVII] was prepared using a procedure similar to that of Compound [III]. Data for Compound [CCXXXVII]: LCMS (m/e) 219 (M+H); $^1$H NMR (400 MHz, METHANOL-d$_4$) δ ppm 1.86 (s, 9H) 6.86 (s, 1H) 8.88 (s, 1H) 10.29 (s, 1H).

2-t-Butyl-7-phenyl-3-yl-9H-1,4,9,9b-tetraaza-cyclopenta[a]naphthalen-8-one [CCXXXVIII]

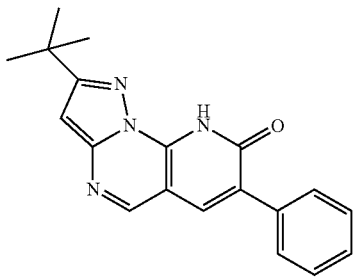

CCXXXVIII

Compound [CCXXXVIII] was prepared using a procedure similar to that of Compound [IV]. Data for Compound [CCXXXVIII]: LCMS 319 (M+H); $^1$H NMR (400 MHz, METHANOL-d$_4$) δ ppm 1.90 (s, 9H) 6.88 (s, 1H) 7.75 (t, 1H) 7.84 (t, J=7.64 Hz, 2H) 8.13 (d, J=7.32 Hz, 2H) 8.18 (none, 1H) 8.36 (s, 1H) 8.95 (s, 1H)

8-Chloro-2-t-butyl-7-phenyl-3-yl-1,4,9,9b-tetraaza-cyclopenta[a]naphthalene [CCXXXIX]

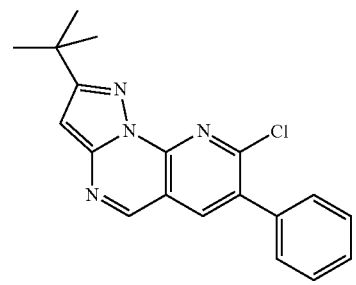

CCXXXIX

Compound [CCXXXIX] was prepared using a procedure similar to that of Compound [V]. Data for Compound [CCXXXIX]: LCMS (m/e) 337 (M+H); $^1$H NMR (400 MHz, CHLOROFORM-d) δ ppm 1.52 (s, 9H) 6.82 (s, 1H) 7.52 (d, J=6.25 Hz, 5H) 8.20 (s, 1H) 8.82 (s, 1H).

trans-2-{3-Methyl-3-hydroxy-1-[4-(2-t-butyl-7-phenyl-1,4,9,9b-tetraaza-cyclopenta[a]naphthalen-8-yl)-phenyl]-cyclobutyl}-isoindole-1,3-dione [CCXL]

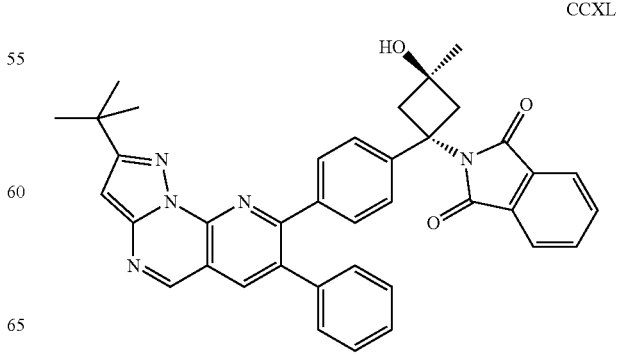

CCXL

Compound [CCXL] was prepared in a similar way to that of Compound [XL]. Data for Compound [CCXL]: LCMS (m/e) 608 (M+H); $^1$H NMR (400 MHz, CHLOROFORM-d) δ ppm 1.44 (s, 3H) 1.48 (s, 9H) 3.14 (d, J=14.40 Hz, 2H) 3.37 (d, J=14.40 Hz, 2H) 6.77 (s, 1H) 7.24 (d, J=4.39 Hz, 1H) 7.30-7.34 (m, 3H) 7.56-7.63 (m, 5H) 7.66-7.72 (m, 2H) 7.74-7.80 (m, 2H) 8.20 (s, 1H) 8.82 (s, 1H).

trans-3-Amino-1-methyl-3-[4-(2-t-butyl-7-phenyl-1,4,9,9b-tetraaza-cyclopenta[a]naphthalen-8-yl)-phenyl]-cyclobutanol [CCXLI]

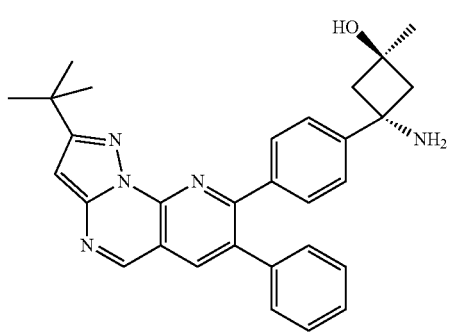

CCXLI

Compound [CCXLI] was prepared in a similar way to that of Compound [XLI]. Data for Compound [CCXLI]: LCMS (m/e) 478 (M+H); $^1$H NMR (400 MHz, METHANOL-d$_4$) δ ppm 1.75 (s, 12H) 2.95 (d, J=14.54 Hz, 2H) 3.13 (d, J=14.55 Hz, 1H) 7.10 (s, 1H) 7.59 (s, 5H) 7.78 (d, J=8.40 Hz, 2H) 7.97 (d, J=8.40 Hz, 2H) 8.83 (s, 1H) 9.30 (s, 1H).

3-Amino-1-cyclopropyl-3-[4-(2,3-dimethyl-7-phenyl-1,4,6,9,9b-pentaaza-cyclopenta[a]naphthalen-8-0)-phenyl]-cyclobutanol [CCXLII]

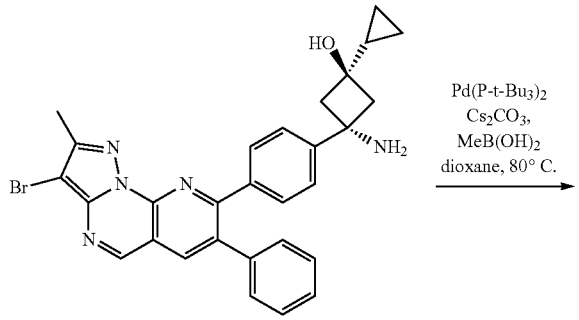

A 20 mL scintillation vial containing Compound [CVI] (12 mg, 0.03 mmol, 1 eq.), MeB(OH)$_2$ (50 mg, 0.30 mmol, 10 eq.), Cs$_2$CO$_3$ (96 mg, 0.30 mmol, 10 eq.), and dioxane (2 ml) was evacuated and flushed three times with nitrogen. Then, Pd(P-t-Bu$_3$)$_2$ (2.3 mg, 0.0045 mmol, 0.15 eq.) was added and the resulting solution was evacuated and flushed three times with nitrogen. The mixture was heated at 80° C. for 2 hours. Then it was allowed to cool and diluted with MeOH (2 mL). After filtration, the filtrate was purified by reverse-phase preparative HPLC using water-acetonitrile-TFA [95:5:0.05] and acetonitrile-water-TFA [95:5:0.05] as the mobile phases to provide Compound [CCXLII] as a yellow solid: LCMS (m/e) 476 (M+H); $^1$H NMR (400 MHz, MeOH-d$_4$) δ ppm 0.33-0.54 (m, 4H) 1.11-1.23 (m, 1H) 2.37 (s, 3H) 2.52 (s, 3H) 2.56-2.66 (m, 2H) 2.73-2.83 (m, 2H) 7.28-7.38 (m, 5H) 7.52 (d, J=8.44 Hz, 2H) 7.72 (d, J=8.44 Hz, 2H) 8.51 (s, 1H) 8.97 (s, 1H).

trans-2-{3-methyl-3-hydroxy-1-[4-(2-cyclopropyl-7-phenyl-1,4,9,9b-tetraaza-cyclopenta[a]naphthalen-8-yl)-phenyl]-cyclobutyl}-isoindole-1,3-dione [CCXLIII]

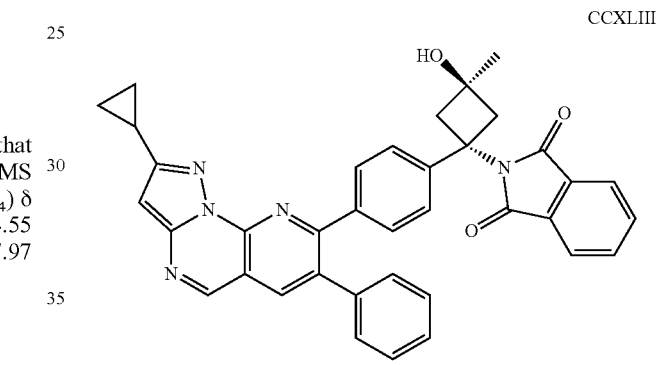

CCXLIII

Compound [CCXLIII] was prepared in a similar way to that of Compound [XL]. Data for Compound [CCXLIII]: LCMS (m/e) 592 (M+H); $^1$H NMR (400 MHz, CHLOROFORM-d) δ ppm 0.89-0.99 (m, 2H) 1.04-1.13 (m, 2H) 1.44 (s, 3H) 2.29 (t, J=5.00 Hz, 1H) 3.14 (d, J=14.40 Hz, 2H) 3.36 (d, J=14.40 Hz, 2H) 7.25 (br. s., 3H) 7.30-7.33 (m, 3H) 7.70 (dd, 2H) 7.78 (dd, 2H) 8.20 (s, 1H) 8.82 (s, 1H).

trans-3-Amino-1-Methyl-3-[4-(2-cyclopropyl-7-phenyl-1,4,9,9b-tetraaza-cyclopenta[a]naphthalen-8-yl)-phenyl]-cyclobutanol [CCXLIV]

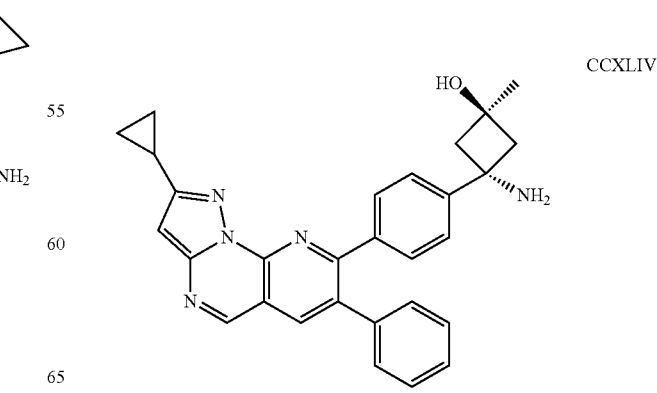

CCXLIV

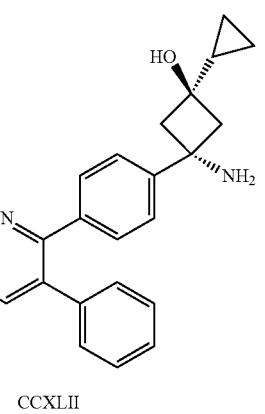

CCXLII

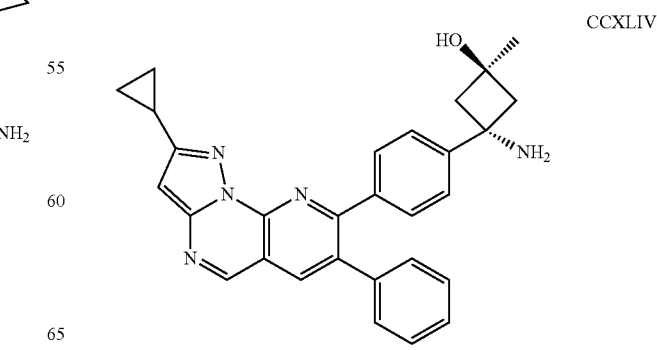

Pd(P-t-Bu$_3$)$_2$
Cs$_2$CO$_3$,
MeB(OH)$_2$
dioxane, 80° C.

CVI

Compound [CCXLIV] was prepared in a similar way to that of Compound [XLI]. Data for Compound [CCXLIV]: LCMS (trite) 462 (M+H); $^1$H NMR (400 MHz, METHANOL-d$_4$) δ ppm 1.00-1.07 (m, 2H) 1.13-1.19 (m, 2H) 1.53 (s, 3H) 2.22-2.33 (m, 1H) 2.72 (d, J=14.50 Hz, 2H) 2.91 (d, 2H) 6.65 (s, 1H) 7.37 (s, 5H) 7.54 (d, J=8.44 Hz, 2H) 7.75 (d, J=8.44 Hz, 2H) 8.58 (s, 1H) 9.07 (s, 1H).

2-Methyl-7-phenylacetylamino-pyrazolo[1,5-a]pyrimidine-6-carboxylic acid methyl ester [CCXLV]

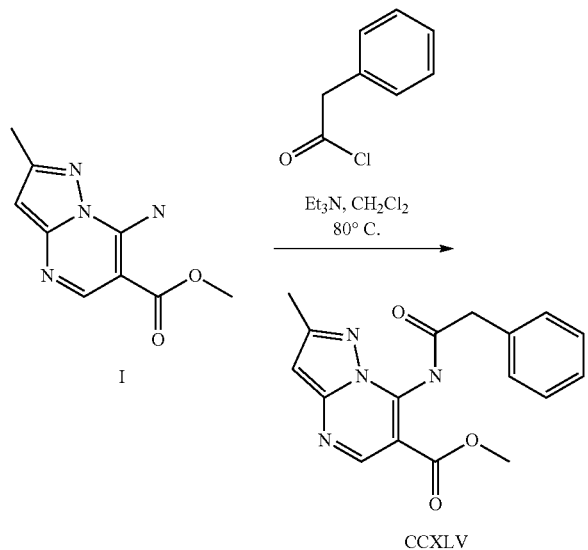

A 250 mL round-bottomed flask containing Compound [I] (1.10 g, 5.0 mmol, 1 eq.), CH$_2$Cl$_2$ (40 mL), and Et$_3$N (2.04 g, 20 mmol, 4 eq.) was added slowly phenylacetyl chloride (6.16 g, 40 mmol, 8 eq.). Then the mixture was heated at 80° C. for 4 h. The mixture was allowed to cool and the solvent was removed in vacuo. The residue was dissolved in CH$_2$Cl$_2$ (40 mL) and water (25 mL). The aqueous phase was extracted with CH$_2$Cl$_2$ (2×15 mL). The combined organic solution was dried over Na$_2$SO$_4$. After filtration and concentration, the residue was purified by silica gel chromatography using MeOH and CH$_2$Cl$_2$ as the mobile phases to furnish Compound [CCXLV] as a yellowish solid (1.7 g, 90%, crude). The small amount of pure sample was purified by reverse-phase preparative HPLC using water-acetonitrile-TFA [95:5:0.05] and acetonitrile-water-TFA [95:5:0.05] as the mobile phases to provide the analytic sample for characterization of Compound [CCXLV]: LCMS m/e 325 (M+H); $^1$H NMR (400 MHz, CHLOROFORM-d) δ ppm 2.46 (s, 3H) 3.80 (s, 3H) 3.92 (s, 2H) 6.50 (s, 1H) 7.28-7.51 (m, 5H) 8.72 (s, 1H) 9.22 (br. s., 1H).

2-Methyl-7-phenyl-1,4,9,9b-tetraaza-cyclopenta[a]naphthalene-6,8-diol [CCXLVI]

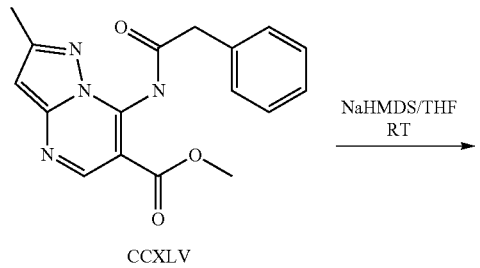

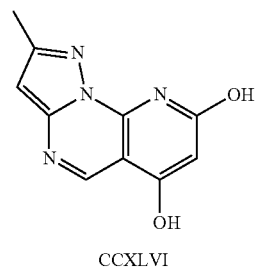

A 250 mL round bottom flask containing Compound [CCXLV] (1.62 g, 5.0 mmol, 1 eq.), THF (30 mL), and NaHMDS (7.5 mL, 7.5 mmol, 1.5 eq.) was stirred at room temperature for 2 h. The reaction was treated with CH$_2$Cl$_2$ (30 mL) and water (40 mL). The aqueous phase was extracted with CH$_2$Cl$_2$ (2×15 mL). The water layer was acidified with concentrated HCl (~10 mL). The precipitated solid was filtered and washed with CH$_2$Cl$_2$ (4 mL) to furnish Compound [CCXLVI] as a yellowish solid (0.53 g). The acidified water layer was extracted with 5% MeOH in CH$_2$Cl$_2$ (3×25 mL). The combined organic phases were dried over Na$_2$SO$_4$. After filtration and concentration, the residue was purified by silica gel chromatography using MeOH and CH$_2$Cl$_2$ as the mobile phases to furnish Compound [CCXLVI] as a yellowish solid (0.46 g). The total yield is 0.99 g (68%) for Compound [CCXLVI]: LCMS m/e 293 (M+H); $^1$H NMR (400 MHz, DMSO-d) δ ppm 2.45 (s, 3H) 6.55 (s, 1H) 7.07-7.56 (m, 5H) 8.91 (s, 1H) 10.99 (br. s., 1H).

6,8-Dichloro-2-methyl-7-phenyl-1,4,9,9b-tetraaza-cyclopenta[a]naphthalene [CCXLVII]

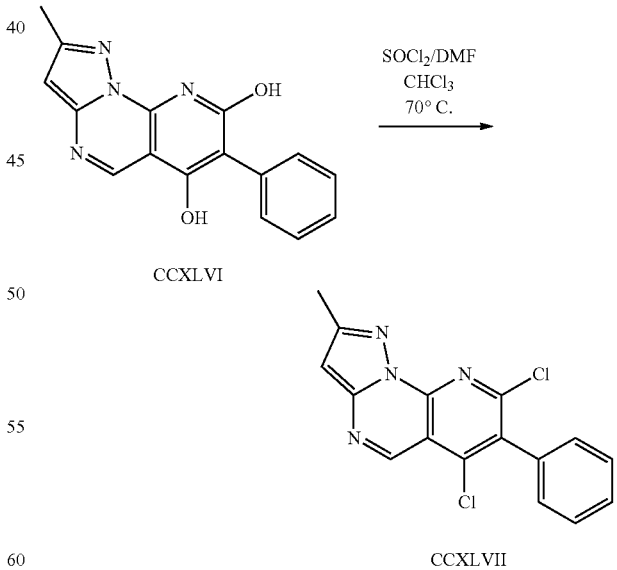

Compound [CCXLVII] was prepared using a procedure similar to that of Compound [V] (SOCl$_2$ procedure). Data for Compound [CCXLVII]: LCMS m/e 329 (M+H); $^1$H NMR (400 MHz, CHLOROFORM-d) δ ppm 2.63 (s, 3H) 6.75 (s, 1H) 7.27-7.42 (m, 2H) 7.42-7.66 (m, 3H) 9.16 (s, 1H).

281

{1-[4-(6-Chloro-2-methyl-7-phenyl-1,4,9,9b-tetraaza-cyclopenta[a]naphthalen-8-yl)-phenyl]-3-hydroxy-3-methyl-cyclobutyl}-carbamic acid tert-butyl ester [CCXLVIII]

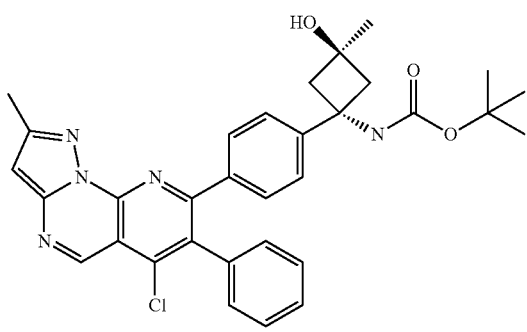

CCXLVIII

Compound [CCXLVIII] was prepared using a procedure similar to that of Compound [XL]. Data for Compound [CCXLVIII]: LCMS m/e 570 (M+H).

282

3-Amino-3-[4-(6-chloro-2-methyl-7-phenyl-1,4,9,9b-tetraaza-cyclopenta[a]naphthalen-8-yl)-phenyl]-1-methyl-cyclobutanol [CCXLIX]

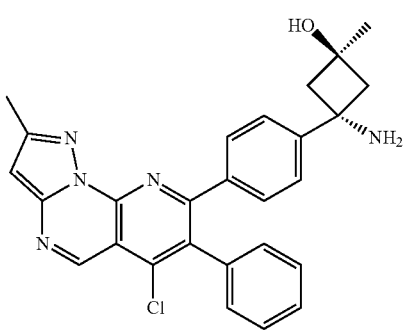

CCXLIX

Compound [CCXLIX] was prepared using a procedure similar to that of Compound [XLIV]. Data for Compound [CCXLIX]: LCMS m/e 470 (M+H); $^1$H NMR (400 MHz, METHANOL-d4) δ ppm 1.46 (s, 3H) 2.57 (s, 3H) 2.61-2.69 (m, 2H) 2.76-2.85 (m, 2H) 6.80 (s, 1H) 7.22-7.29 (m, 2H) 7.34-7.39 (m, 3H) 7.41-7.47 (m, 2H) 7.60-7.66 (m, 2H) 9.30 (s, 1H).

{1-[4-(2,6-Dimethyl-7-phenyl-1,4,9,9b-tetraaza-cyclopenta[a]naphthalen-8-yl)-phenyl]-3-hydroxy-3-methyl-cyclobutyl}-carbamic acid tert-butyl ester [CCL]

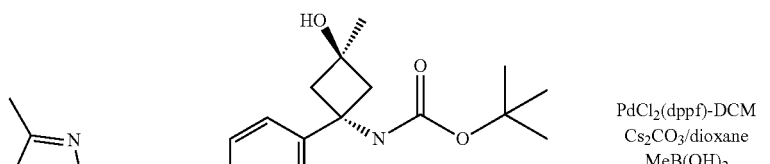

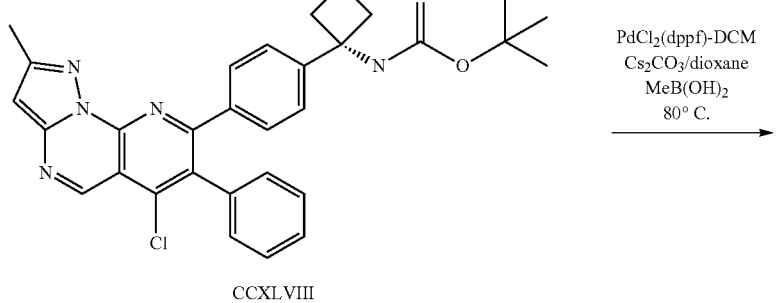

A 20 ml scintillation vial containing Compound [CCX-LVIII] (40 mg, 0.07 mmol, 1 eq.), the borate (84 mg, 1.4 mmol, 2 eq.), Cs₂CO₃ (226 mg, 0.70 mmol, 1 eq.), and dioxane (5.0 ml) was evacuated and flushed three times with nitrogen. Then PdCl₂(dppf)-CH₂Cl₂ (24 mg, 0.03 mmol, 0.5 eq.) was added and the resulting solution was evacuated and flushed three times with nitrogen. The mixture was heated at 80° C. for 2.5 h. Then it was allowed to cool. The solvent was removed in vacuo. The residue was dissolved in CH₂Cl₂ (10 mL). After filtration and concentration, it was purified by silica gel chromatography by using MeOH and CH₂Cl₂ as the mobile phases to furnish Compound [CCL] as a yellowish solid (20 mg, 50%): LCMS (m/e) 550 (M+H).

3-Amino-3-[4-(2,6-dimethyl-7-phenyl-1,4,9,9b-tetraaza-cyclopenta[a]naphthalen-8-yl)-phenyl]-1-methyl-cyclobutanol [CCLI]

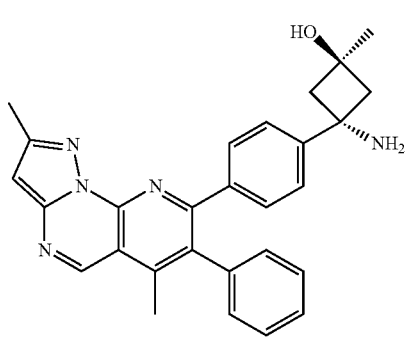

Compound [CCLI] was prepared using a procedure similar to that of Compound [XLIV]. Data for Compound [CCLI]: LCMS m/e 450 (M+H); ¹H NMR (400 MHz, METHANOL-d4) δ ppm 1.46 (s, 3H) 2.55 (s, 3H) 2.61 (s, 3H) 2.62-2.70 (m, 2H) 2.77-2.86 (m, 2H) 6.73 (s, 1H) 7.20 (dd, J=7.55, 1.77 Hz, 2H) 7.29-7.37 (m, 3H) 7.41 (d, J=8.49 Hz, 2H) 7.59 (d, J=8.49 Hz, 2H) 9.28 (s, 1H).

8-Chloro-2-tert-butyl-7-phenyl-1,4,9,9b-tetraaza-cyclopenta[a]naphthalene 3-tert-Butyl-1H-pyrazol-5-amine [CCXXXIV]

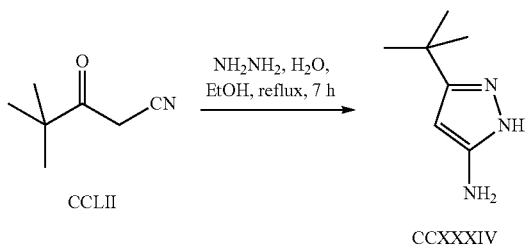

A solution of 4,4-dimethyl-3-oxopentanenitrile (Compound [CCLII]) (7 g, 55.9 mmol, 1.00 equiv) and NH₂NH₂·H₂O (4.5 g, 140 mmol, 2.00 equiv) in EtOH (100 mL) was stirred for 7 h at 110° C. under nitrogen. The reaction progress was monitored by TLC (ethyl acetate/petroleum ether=1:2). After cooling, the resulting solution was concentrated under vacuum and diluted with 50 mL of water. The resulting solution was extracted with CH₂Cl₂, dried and concentrated under reduced pressure. The residue was loaded onto a silica gel column with ethyl acetate/petroleum ether as the eluent to Compound [CCXXXIV] as a yellowish oil: LCMS (m/e) 140 (M+H); ¹H NMR (300 MHz, DMSO-d₆) δ ppm 5.18 (s, 1H), 1.19 (s, 9H). Amount obtained: 7.6 g, 97% yield.

Compound [CCXXXIV] to Compound [CCXXXV]

Previously Described

Ethyl 7-amino-2-tert-butylpyrazolo[1,5-a]pyrimidine-6-carboxylate [CCXXXV]

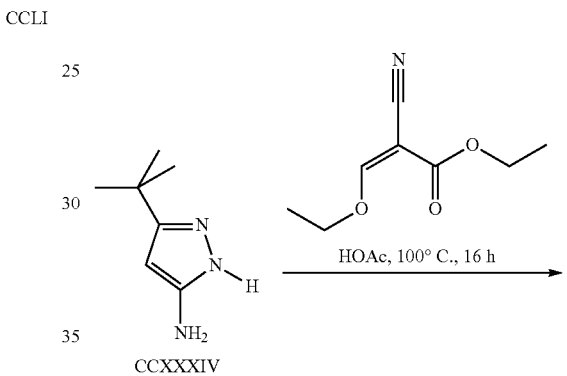

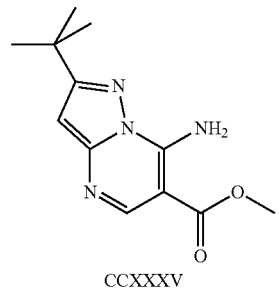

A solution of 3-tert-butyl-1H-pyrazol-5-amine (484 mg, 3.48 mmol, 1 eq.) and ethyl 2-cyano-3-ethoxyacrylate (590 mg, 3.49 mmol, 1.00 eq.) in acetic acid (10 mL) was stirred for 16 h at 100° C. under nitrogen. After cooling, the resulting mixture was concentrated under vacuum. The pH value of the solution was adjusted to 8 with saturated aqueous NaHCO₃ solution and extracted with ethyl acetate (100 mL×3). The organic layers were combined, dried and concentrated under reduced pressure. The residue was applied onto a silica gel column with CH₂Cl₂/MeOH (30:1) as an eluent to obtain the corresponding product as a white solid: LCMS (m/e) 263 (M+H); ¹H NMR (300 MHz, DMSO-d₆) δ ppm 8.56 (s, 1H), 8.40-8.38 (broad, d, J=6.0 Hz, 2H), 6.48 (s, 1H), 4.33 (q, J=7.2 Hz, 2H), 1.37-1.31 (m, 12H).

(7-Amino-2-tert-butylpyrazolo[1,5-a]pyrimidin-6-yl)methanol [CCXXXVI]

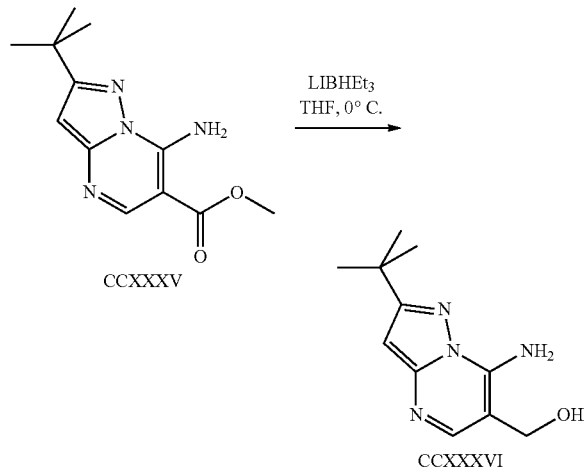

A solution of ethyl 7-amino-2-tert-butylpyrazolo[1,5-a]pyrimidine-6-carboxylate (740 mg, 2.82 mmol, 1.00 equiv) in tetrahydrofuran (12 mL) was added dropwise LiBHEt$_3$ (8.5 mL of a 1 M solution in THF, 3.0 eq.) at 0° C. under nitrogen. After addition, the resulting solution was stirred for 4 h at 25° C. Additional LiBHEt$_3$ (0.85 mL of a 1 M solution in THF, 0.85 mmol, 0.3 eq.) was added and the mixture was stirred for another 1 h. After a total of 3 h, the reaction was then quenched with water and extracted with ethyl acetate (100 mL×3). The organic layers were combined, dried and concentrated. The residue was loaded onto a silica gel column with CH$_2$Cl$_2$/MeOH (30:1) as an eluent to give Compound [CCXXXVI] as a white solid: LCMS (m/e) 221 (M+H); $^1$H NMR (300 MHz, DMSO-d$_6$) δ ppm 8.02 (s, 1H), 7.32 (s, 2H), 6.22 (s, 1H), 4.94 (t, J=5.7 Hz, 1H), 4.53 (d, J=5.7 Hz, 2H), 1.36 (s, 9H).

7-Amino-2-tert-butylpyrazolo[1,5-a]pyrimidine-6-carbaldehyde [CCXXXVII]

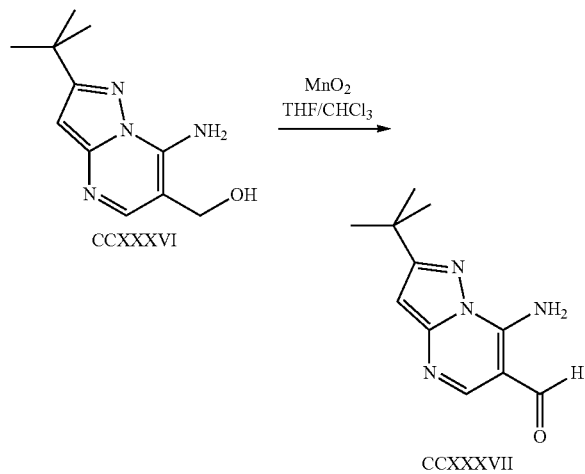

A solution of (7-amino-2-tert-butylpyrazolo[1,5-a]pyrimidin-6-yl)methanol (380 mg, 1.73 mmol, 1 eq.) and MnO$_2$ (1.5 g, 17.25 mmol, 10 eq.) in THF (6 mL) and CHCl$_3$ (12 ml) was stirred for about 36 h at 25° C. under nitrogen. MnO$_2$ was filtered and washed with 15% MeOH in CHCl$_3$ (~100 mL) and 30% MeOH in CHCl$_3$ (~100 mL) until no additional product was observed through analysis of the filtrates by TLC. The filtrates were combined and concentrated under vacuum to give Compound [CCXXXVII] as a yellow solid: LCMS (m/e) 219 (M+H); $^1$H NMR (300 MHz, DMSO, δ, ppm) 9.87 (s, 1H), 8.99-8.82 (s, 2H), 8.50 (s, 1H), 6.52 (s, 1H), 1.38 (s, 9H).

2-tert-Butyl-7-phenyl-9H-1,4,9,9b-tetraaza-cyclopenta[a]naphthalen-8-one [CCXXXVIII]

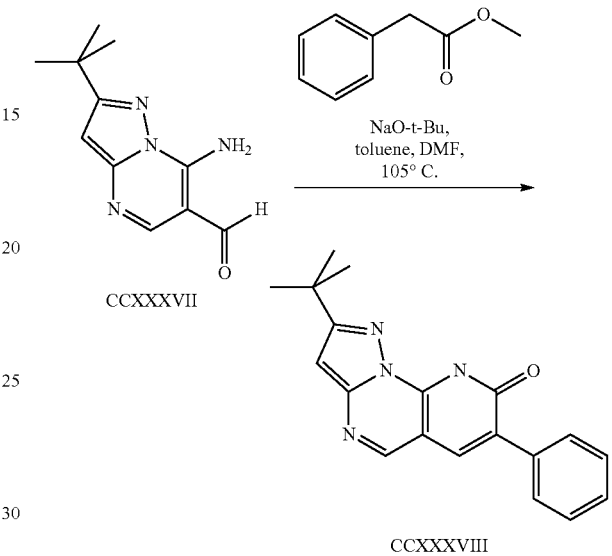

A solution of 7-amino-2-tert-butylpyrazolo[1,5-a]pyrimidine-6-carbaldehyde (1.5 g, 6.87 mmol, 1.00 eq.), methyl 2-phenylacetate (4.1 g, 27.30 mmol, 4.00 eq.) and NaO$^t$Bu (1.3 g, 13.53 mmol, 2.00 eq.) in toluene (30 mL) was stirred at 105° C. for about 30 min under nitrogen. Then the reaction mixture was added 30 mL of DMF and the mixture was stirred for about 2 days at 105° C. After concentrating under vacuum, the residue was diluted with water and extracted with ethyl acetate. The organic layers were combined and dried over anhydrous sodium sulfate and concentrated under vacuum. The residue was applied onto a silica gel column with ethyl acetate/petroleum ether (1:6) to give the resulted product (1 g, 46%) as a yellow solid. LCMS (m/e)=319 (M+H); $^1$H NMR (300 MHz, DMSO, δ, ppm) 8.82 (s, 1H), 8.42 (s, 1H), 7.72 (d, J=6.9 Hz, 2H), 7.50-7.38 (m, 3H), 6.72 (s, 1H), 1.42 (s, 9H).

8-Chloro-2-tert-butyl-7-phenyl-1,4,9,9b-tetraazacyclopenta[a]naphthalene [CCXXXIX]

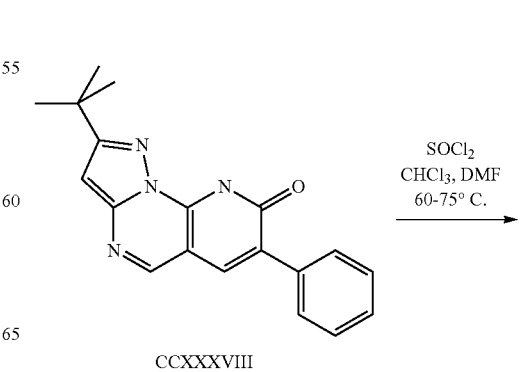

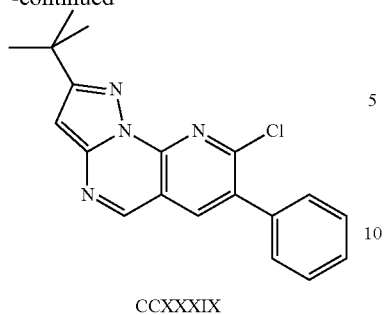

CCXXXIX

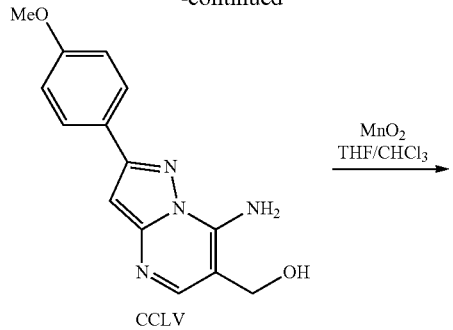

To a 100 mL three necked round bottom flask was added 2-tert-butyl-7-phenyl-9H-1,4,9,9b-tetraaza-cyclopenta[a]naphthalen-8-one (1 g, 3.14 mmol, 1.00 equiv), CHCl$_3$ (20 mL), thionyl chloride (0.94 mL, 4.00 equiv) and DMF (48 µL, 0.20 equiv) and the resulting solution was stirred for 1 h at 70° C. under nitrogen. After 1 h, additional thionyl chloride (0.47 mL, 2.00 equiv) and DMF (48 µL, 0.20 equiv) was added and the resulting solution was stirred for an additional 2 h at 70° C. After a total of 3 h, the resulting mixture was concentrated under vacuum and the pH value of the solution was adjusted to 7 with saturated aqueous NaHCO$_3$ solution. The resulting solution was extracted with ethyl acetate and the organic layers were combined and dried and concentrated under vacuum. The residue was loaded onto a silica gel column with ethyl acetate/petroleum ether as the eluent to give the Compound [CCXXXIX] as a yellow solid. $^1$H NMR (300 MHz, DMSO, δ, ppm) 9.09 (s, 1H), 8.74 (s, 1H), 7.60-7.52 (m, 5H), 6.97 (s, 1H), 1.44 (s, 91-1); LC-MS: m/z=337 (M+H)$^+$.

Scheme: 2-Methoxyphenyl substituent:

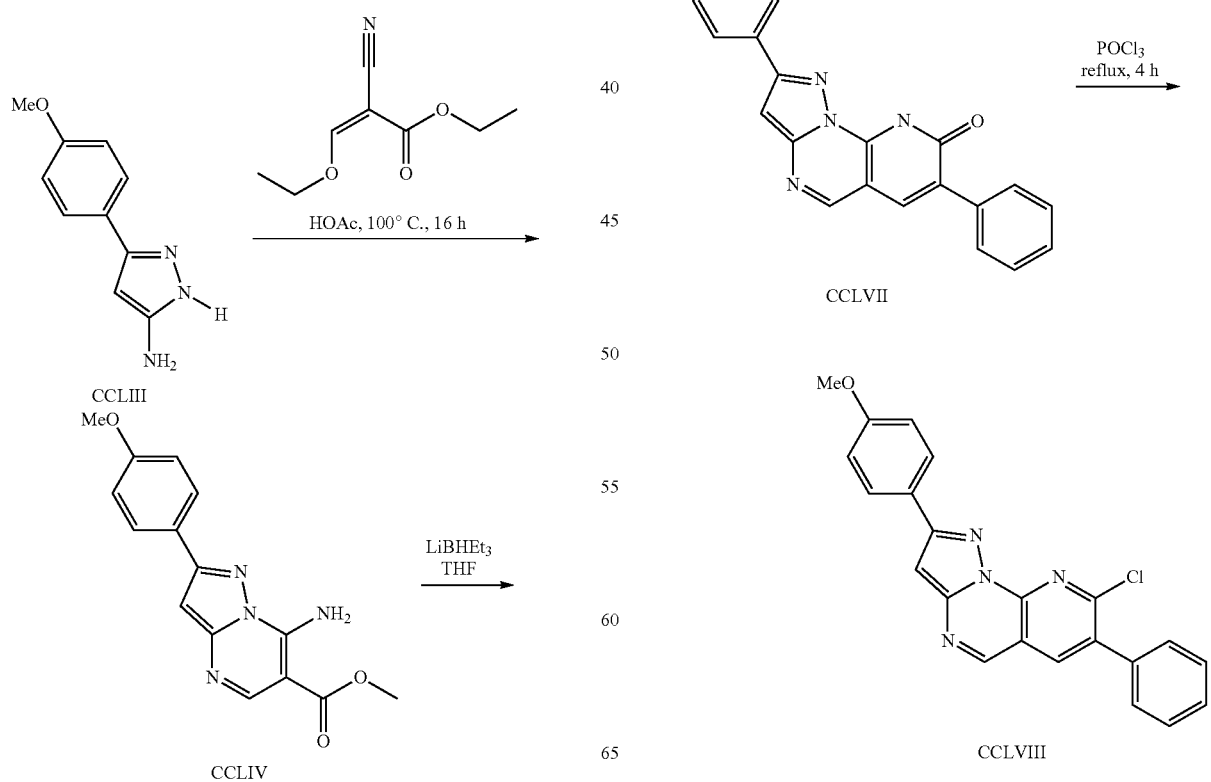

Ethyl 7-amino-2-(4-methoxyphenyl)pyrazolo[1,5-a]pyrimidine-6-carboxylate [CCLIV]

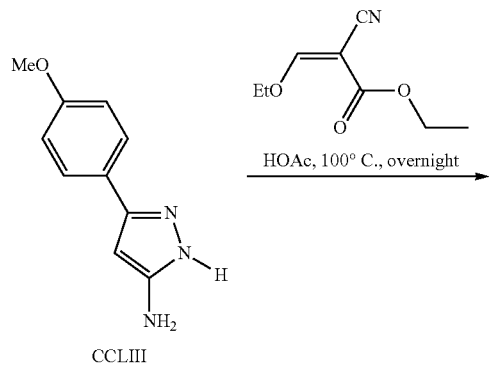

To a 50 mL round-bottom flask was added Compound [CCLIII] (1 g, 5.29 mmol, 1.05 eq.), ethyl-2-cyano-3-ethoxyacrylate (0.85 g, 5.02 mmol, 1.00 eq.), and HOAc (20 mL). The mixture was heated at 100° C. for 16 h. The reaction was concentrated and the residue was treated with H$_2$O (20 mL). The resulting precipitate was filtered, and the precipitate washed with H$_2$O (3×50 mL). The crude product was dried in an oven to afford of Compound [CCLIV]: LCMS (m/e) 313 (M+H); $^1$H NMR (300 MHz, DMSO-d$_6$) δ ppm 1.35 (t, J=7.2 Hz, 3H) 3.83 (s, 3H) 4.34 (q, J=7.2 Hz, 2H) 7.01 (s, 1H) 7.08 (d, J=8.7 Hz, 2H) 8.05 (d, J=8.7 Hz, 2H) 8.49 (s, 1H) 8.60 (s, 1H) 8.68 (s, 1H).

(7-Amino-2-(4-methoxyphenyl)pyrazolo[1,5-a]pyrimidin-6-yl)methanol [CCLV]

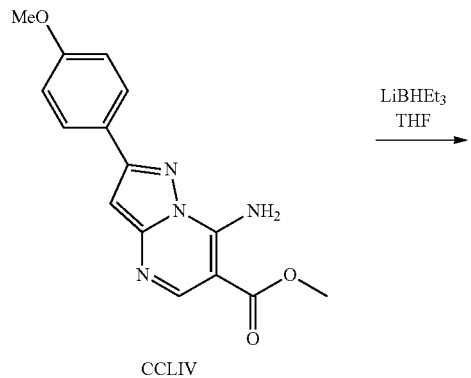

To a 100 mL three-necked round bottom flask was added Compound [CCLV] (1.38 g, 4.42 mmol, 1.00 eq.) and THF (35 mL). The mixture was cooled to 0° C. and LiBHEt$_3$ (13.3 mL of a 1.0 M solution in THF, 13.3 mmol, 3.00 eq.) was added slowly through an addition funnel under nitrogen. After addition, the mixture was stirred at room temperature for 4 h. Additional LiBHEt$_3$ (1.3 mL of a 1.0 M solution in THF, 1.3 mmol, 0.30 eq.) was added and the mixture was stirred for an additional 1 h. The mixture was slowly treated with EtOAc (30 mL) and then water (15 mL). The layers were separated and the aqueous phase was extracted with EtOAc (2×30 mL). The combined organic phases were dried over anhydrous Na$_2$SO$_4$. After filtration and concentration, the residue was purified by a silica gel column using dichloromethane/methanol as the eluent. Concentration by rotary evaporation provided Compound [CCLV] as a light yellowish solid: LCMS (m/e) 271 (M+H); $^1$H NMR (300 MHz, DMSO-d$_6$) δ ppm 3.83 (s, 3H) 4.55 (d, J=5.4 Hz, 2H) 5.00 (t, J=5.7 Hz, 1H) 6.77 (s, 1H) 7.05 (d, J=9 Hz, 2H) 7.55 (s, 1H) 8.01 (d, J=8.7 Hz, 2H) 8.08 (s, 1H).

7-Amino-2-(4-methoxyphenyl)pyrazolo[1,5-a]pyrimidine-6-carbaldehyde [CCLVI]

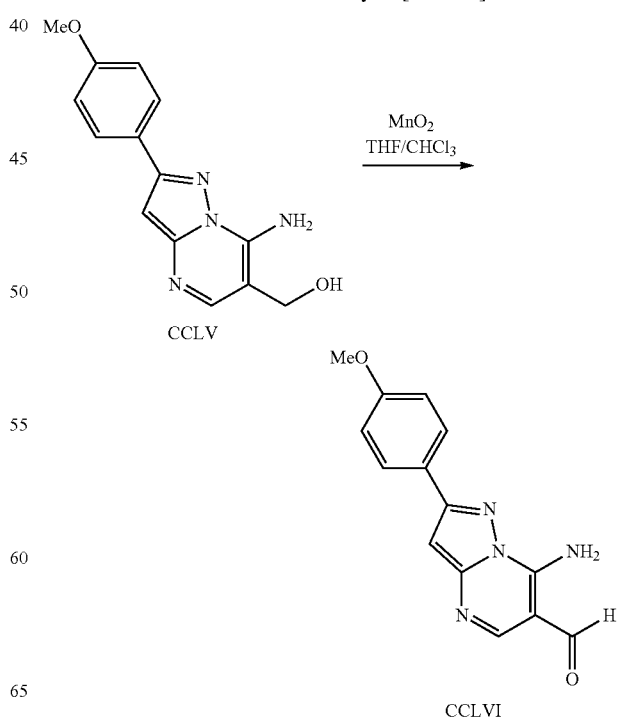

To a 100 mL round bottom flask containing Compound [CCLV] (0.67 g, 2.48 mmol, 1.00 eq.) was added CHCl₃ (30 mL) and THF (15 mL) followed by MnO₂ (2.2 g, 24.79 mmol, 10.00 eq.). The mixture was stirred at room temperature for 2 days. The mixture was filtered and the filtered material washed with MeOH (~100 mL) until no additional product was observed through analysis of the filtrates by TLC. The resulting mixture was concentrated under vacuum. The residue was purified by a silica gel column using dichloromethane/methanol as the eluant. Concentration by rotary evaporation provided Compound 4 as a yellowish solid. LCMS (m/e) 269 (M+H); NMR (300 MHz, DMSO-$d_6$) δ ppm 3.84 (s, 3H) 7.02 (s, 1H) 7.08 (d, J=8.7 Hz, 2H) 8.05 (d, J=9 Hz, 2H) 8.52 (s, 1H) 9.88 (s, 1H).

2-(4-Methoxyphenyl)-7-phenyl-9H-1,4,9,9b-tetraaza-cyclopenta[a]naphthalene-8-one [CCLVII]

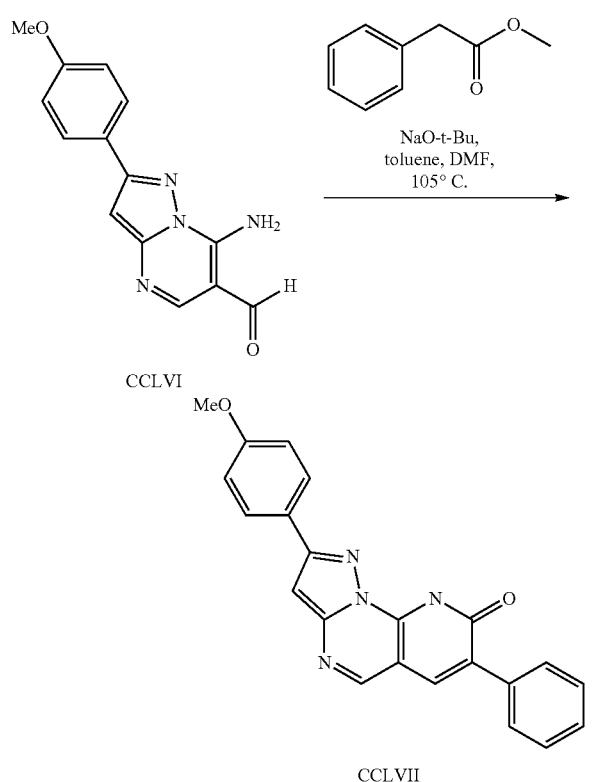

To a 100 mL round bottom flask was added Compound [CCLVI] (0.5 g, 1.86 mmol, 1.00 eq.), methyl phenylacetate (1.12 g, 7.45 mmol, 4.00 eq.), toluene (15 mL), and NaO-t-Bu (0.36 g, 3.73 mmol, 2.00 eq.). The mixture was heated at 105° C. for 30 min and the formation of large amounts of solid was noted. DMF (15 mL) was added and the solid was observed to go into solution. The mixture was heated for 3 days. After this time, the heat was removed and the mixture allowed to cool to room temperature. The reaction mixture was concentrated and the residue dissolved in CH₂Cl₂ 80 mL), followed by the addition of water (80 mL) to form a yellowish precipitate. The solid was filtered and washed with water (20 mL) and CH₂Cl₂ (30 mL). The collected solid was dried in an oven to furnish Compound [CCLVII] as a yellowish solid: ¹H NMR (300 MHz, DMSO-$d_6$) δ ppm 3.84 (s, 3H) 6.91 (s, 1H) 7.06 (d, J=8.7 Hz, 3H) 7.26-7.41 (m, 3H) 7.79 (d, J=7.2 Hz, 1H) 7.94 (s, 1H) 8.01 (d, J=8.7 Hz, 2H) 8.49 (s, 1H).

8-Chloro-2-(4-Methoxyphenyl)-7-phenyl-9H-1,4,9, 9b-tetraaza-cyclopenta[a]naphthalene-8-one [CCLVIII]

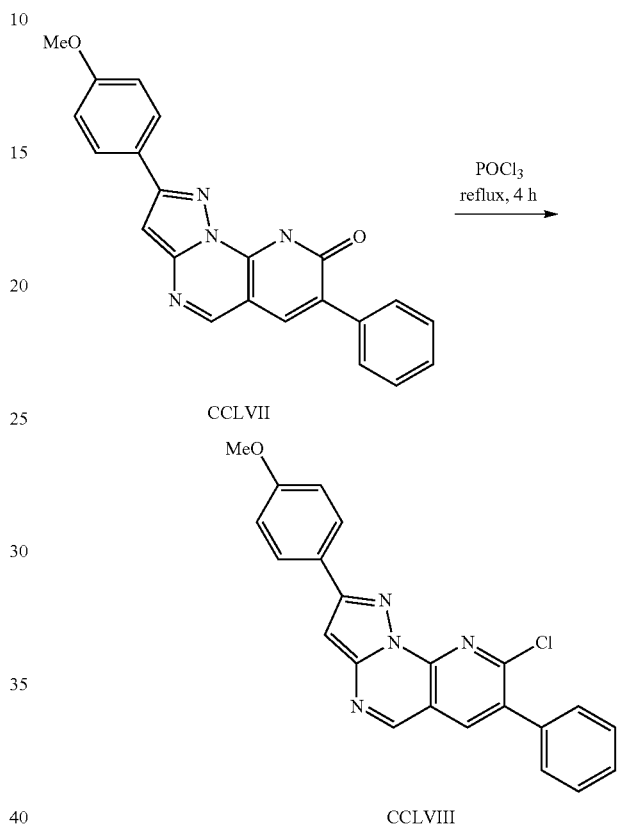

To a 50 mL round bottom flask was added Compound [CCLVII] (0.3 g, 0.81 mmol, 1.00 eq.), POCl₃ (15 mL). The mixture was heated to reflux in an oil bath for 4 h. The reaction was concentrated in vacuo and the residue was added to 10 mL of ice/water. Adjusted the pH value to 8 with Na₂CO₃. The aqueous phase was extracted with CH₂Cl₂ (3×30 mL). The combined organic phases were dried over anhydrous Na₂SO₄. After filtration and concentration, the residue was purified by a silica gel column using CH₂Cl₂/petroleum ether as the eluent. Concentration by rotary evaporation provided Compound [CCLVIII] as a light yellowish solid: LCMS in/e 387 (M+H); ¹H NMR (300 MHz, CHLOROFORM-d) δ ppm 3.91 (s, 3H) 7.04 (d, J=8.7 Hz, 2H) 7.19 (s, 1H) 7.55 (s, 5H) 8.12 (d, J=8.7 Hz, 2H) 8.24 (s, 1H) 8.88 (s, 1H).

Scheme: 2-isopropyl substituent

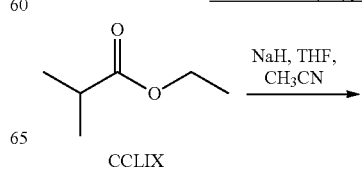

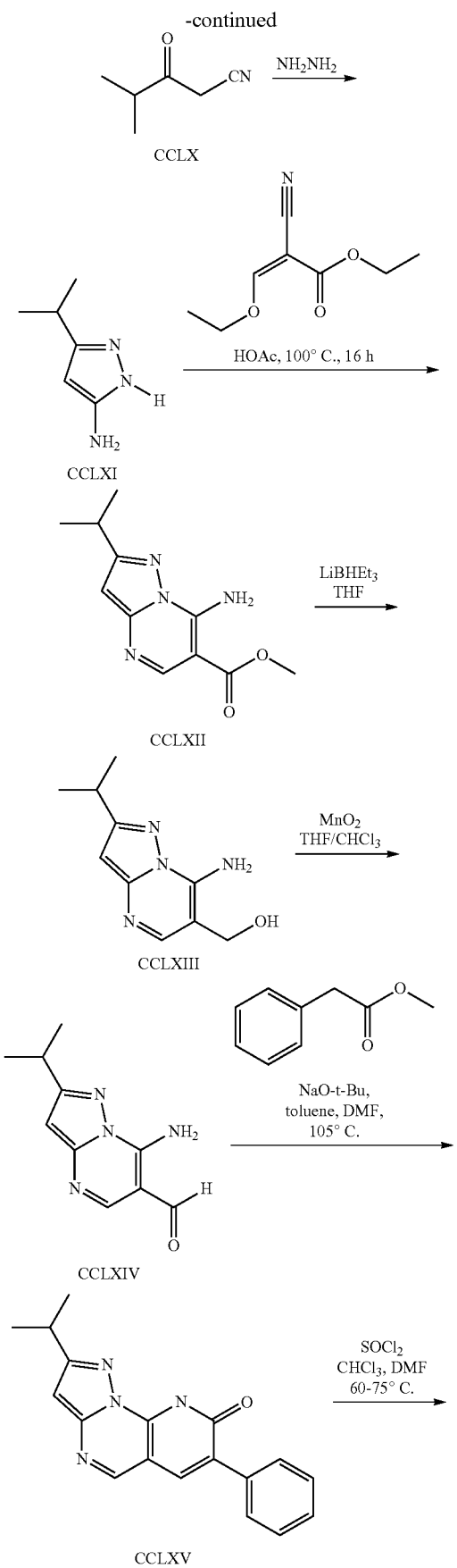

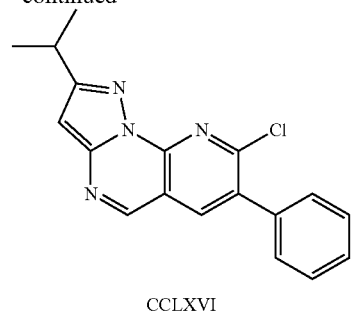

4-Methyl-3-oxopentanenitrile [CCLX]

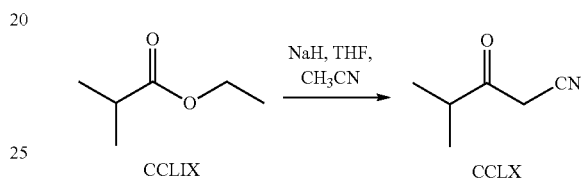

A 1 L three necked bottle containing NaH (70%, 23.2 g, 677 mmol, 1.60 equiv) and THF (300 mL) was maintained at reflux condition for about 1.5 hrs. Then a mixture of ethyl isobutyrate (Compound [CCLIX])(50 g, 430 mmol, 1.00 equiv) and acetonitrile (27.7 g, 675 mmol, 1.60 equiv) in THF (70 mL) was added dropwise with stirring in 2 hrs and heated to reflux for overnight. After cooling, the reaction mixture was then quenched with water and the pH value of the solution was adjusted to 4 with 2 N hydrogen chloride and extracted with ethyl acetate (3×100 mL). The organic layers were combined and washed with brine and dried. After concentration, the residue was loaded onto a silica gel column with ethyl acetate/petroleum ether as the eluent to afford Compound [CCLX] as a yellow oil: LC-MS m/e 112 (M+H)$^+$; $^1$H NMR (300 MHz, CDCl$_3$) δ ppm 3.55 (s, 2H), 2.81 (septet, J=6.9 Hz, 1H), 1.19 (d, J=6.9 Hz, 6H).

3-Isopropyl-1H-pyrazol-5-amine [CCLXI]

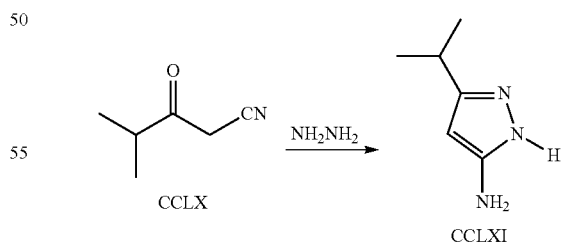

A solution of 4-methyl-3-oxopentanenitrile (Compound [CCLX]) (8.8 g, 79.2 mmol, 1.00 equiv) and NH$_2$NH$_2$.H$_2$O (80%, 7.5 g, 120 mmol, 1.50 equiv) in ethanol (300 mL) was heated to reflux for 1 h under nitrogen. After removed the solvent under vacuum, the residue was loaded onto a silica gel column with dichloromethane/methanol as an eluent to give Compound [CCLXI] as a yellowish oil: LC-MS m/e 126

(M+H)⁺; ¹H NMR (300 MHz, DMSO-d₆) δ ppm 5.17 (s, 1H), 2.75 (septet, J=6.9 Hz, 1H), 1.14 (d, J=6.9 Hz, 6H).

7-Amino-2-isopropyl-pyrazolo[1,5-a]pyrimidine-6-carboxylic acid ethyl ester [CCLXII]

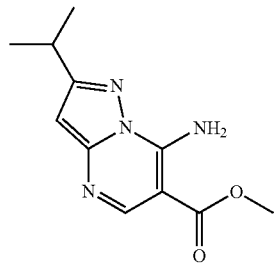

CCLXII

Compound [CCLXII] was prepared using a procedure similar to that of Compound [VII]. Data for Compound [CCLXII]: LCMS m/e 249 (M+H)⁺; ¹H NMR (300 MHz, DMSO-d₆) δ ppm 8.56 (s, 2H), 8.38 (s, 1H), 6.44 (s, 1H), 4.32 (q, J=6.9 Hz, 2H), 3.35 (s, 1H), 3.10 (septet, J=6.9 Hz, 1H), 1.36-1.30 (m, 9H).

(7-Amino-2-isopropyl-pyrazolo[1,5-a]pyrimidin-6-yl)-methanol [CCLXIII]

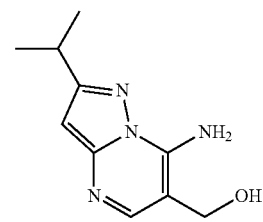

CCLXIII

Compound [CCLXIII] was prepared using a procedure similar to that of Compound [II]. Data for Compound [CCLXIII]: LCMS m/e 207 (M+H)⁺; ¹H NMR (300 MHz, DMSO-d₆) δ ppm 8.02 (s, 1H), 7.39 (s, 1H), 6.19 (s, 1H), 4.94 (t, J=4.2 Hz, 1H), 4.51 (d, J=4.2 Hz, 1H), 3.07 (septet, J=6.9 Hz, 1H), 1.32 (d, J=6.9 Hz, 6H).

7-Amino-2-isopropyl-pyrazolo[1,5-a]pyrimidin-6-carbaldehyde [CCLXIV]

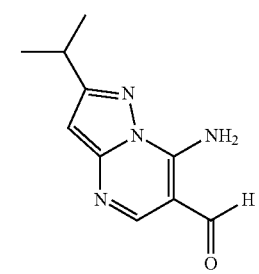

CCLXIV

Compound [CCLXIV] was prepared using a procedure similar to that of Compound [III]. Data for Compound [CCLXIV]: LCMS ink 205 (M+H)⁺; ¹H NMR (300 MHz, DMSO-d₆) δ ppm 9.87 (s, 1H), 8.99 (s, 1H), 8.49 (s, 1H), 6.47 (s, 1H), 3.10 (septet, J=6.9 Hz, 1H), 1.32 (d, J=6.9 Hz, 6H);

2-Isopropyl-7-phenyl-9H-1,4,9,9b-tetraaza-cyclopenta[a]naphthalen-8-one [CCLXV]

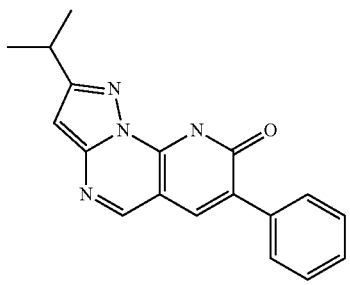

CCLXV

Compound [CCLXV] was prepared using a procedure similar to that of Compound [IV]. Data for Compound [CCLXV]: LCMS (m/e) 305 (M+H); ¹H NMR (300 MHz, DMSO-d₆) δ ppm 8.81 (s, 1H), 8.39 (s, 1H), 7.74-7.72 (m, 2H), 7.50-7.37 (m, 3H), 6.69 (s, 1H), 3.18 (septet, J=6.9 Hz, 1H), 1.36 (d, J=6.9 Hz, 6H).

8-Chloro-2-isopropyl-7-phenyl-1,4,9,9b-tetraaza-cyclopenta[a]naphthalene [CCLXVI]

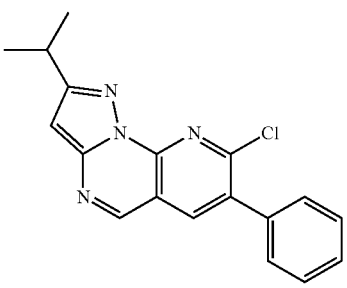

CCLXVI

Compound [CCLXVI] was prepared using a procedure similar to that of Compound [V], SOCl₂ procedure. Data for Compound [CCLXVI]: LCMS (m/e) 323 (M+H); ¹H NMR (300 MHz, DMSO-d₆) δ 9.10 (s, 1H), 8.74 (s, 1H), 7.63-7.50 (m, 5H), 6.91 (s, 1H), 3.21 (septet, J=6.9 Hz, 1H), 1.38 (d, J=6.9 Hz, 6H).

Scheme: 2-cyclobutyl substituent

CCLXVII

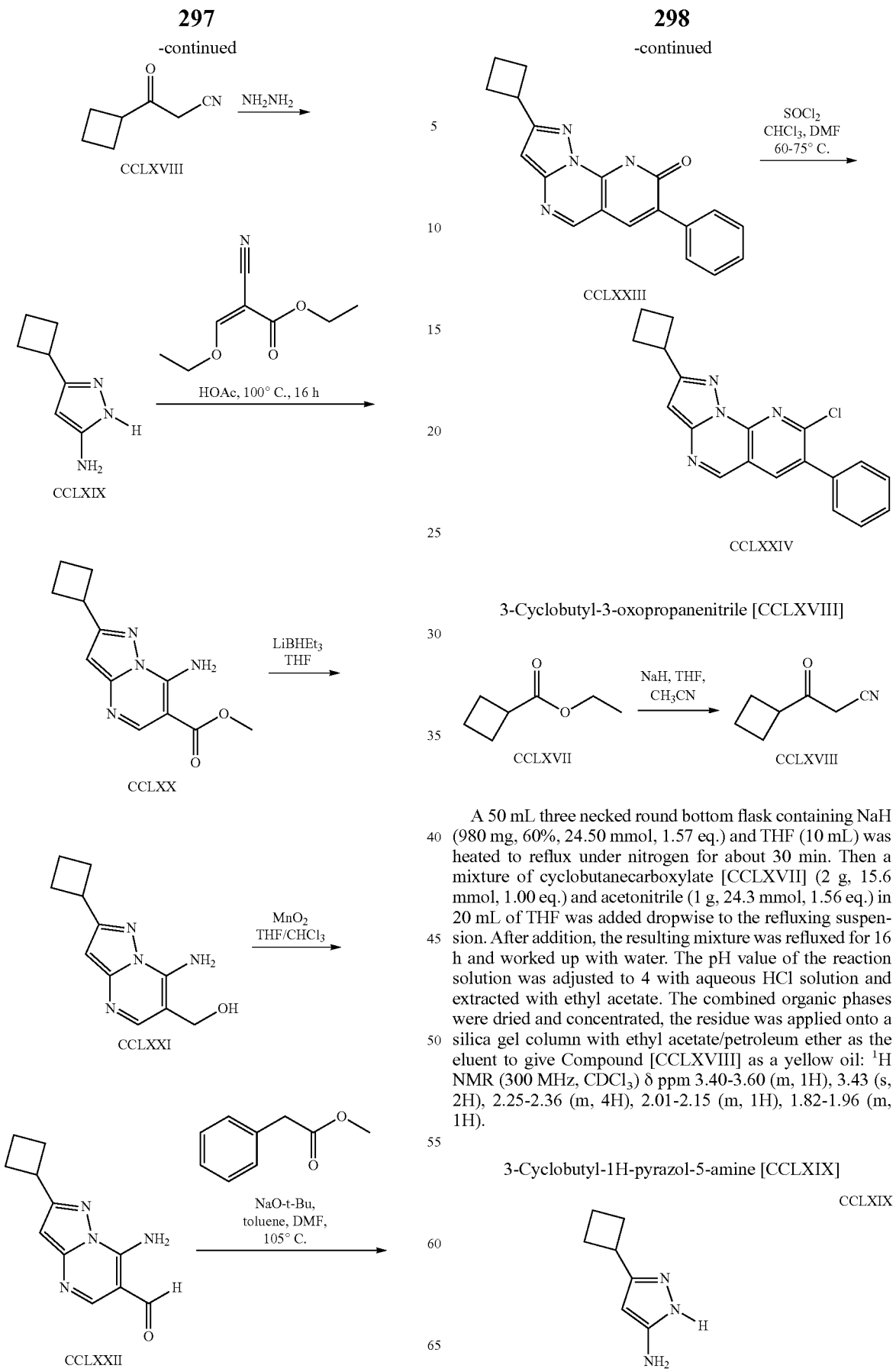

3-Cyclobutyl-3-oxopropanenitrile [CCLXVIII]

A 50 mL three necked round bottom flask containing NaH (980 mg, 60%, 24.50 mmol, 1.57 eq.) and THF (10 mL) was heated to reflux under nitrogen for about 30 min. Then a mixture of cyclobutanecarboxylate [CCLXVII] (2 g, 15.6 mmol, 1.00 eq.) and acetonitrile (1 g, 24.3 mmol, 1.56 eq.) in 20 mL of THF was added dropwise to the refluxing suspension. After addition, the resulting mixture was refluxed for 16 h and worked up with water. The pH value of the reaction solution was adjusted to 4 with aqueous HCl solution and extracted with ethyl acetate. The combined organic phases were dried and concentrated, the residue was applied onto a silica gel column with ethyl acetate/petroleum ether as the eluent to give Compound [CCLXVIII] as a yellow oil: $^1$H NMR (300 MHz, CDCl$_3$) δ ppm 3.40-3.60 (m, 1H), 3.43 (s, 2H), 2.25-2.36 (m, 4H), 2.01-2.15 (m, 1H), 1.82-1.96 (m, 1H).

3-Cyclobutyl-1H-pyrazol-5-amine [CCLXIX]

Compound [CCLXIX] was prepared using a procedure similar to that of Compound [CCLXI]. Data for Compound [CCLXIX]: LCMS (m/e) 138 (M+H); $^1$H NMR (300 MHz, DMSO-d$_6$) δ ppm 11.07 (s, 1H), 5.24 (s, 1H), 4.43 (s, 2H), 3.20-3.40 (m, 1H), 2.12-2.28 (m, 2H), 1.95-2.12 (m, 2H), 1.82-1.95 (m, 1H), 1.70-1.82 (m, 1H).

Ethyl 7-amino-2-cyclobutylpyrazolo[1,5-a]pyrimidine-6-carboxylate [CCLXX]

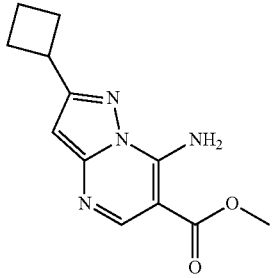

CCLXX

Compound [CCLXX] was prepared using a procedure similar to that of Compound [VII]. Data for Compound [CCLXX]: LCMS (m/e) 261 (M+H); $^1$H NMR (300 MHz, DMSO-d$_6$) cδ ppm 8.65 (s, 1H), 8.57 (s, 1H), 8.39 (s, 1H), 6.51 (s, 1H), 4.29-4.36 (m, 2H), 3.66-3.72 (m, 1H), 2.18-2.45 (m, 4H), 1.85-2.15 (m, 2H), 1.31-1.36 (t, J=7.2 Hz, 3H). Amount obtained: 1.3 g, 68% yield as a white solid.

(7-Amino-2-cyclobutylpyrazolo[1,5-a]pyrimidin-6-yl)methanol [CCLXXI]

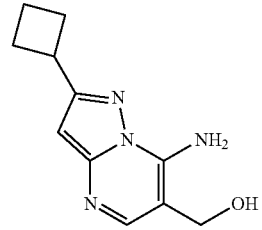

CCLXXI

Compound [CCLXXI] was prepared using a procedure similar to that of Compound [II]. Data for Compound [CCLXXI]: LCMS (m/e) 219 (M+H); $^1$H NMR (300 MHz, DMSO-d$_6$) δ ppm 8.03 (s, 1H), 7.43 (s, 2H), 6.27 (s, 1H), 4.90-5.00 (t, 4.8 Hz, 1H), 4.50-4.52 (d, f=4.8 Hz, 2H), 3.57-3.73 (m, 1H), 2.18-2.45 (m, 4H), 1.85-2.15 (m, 2H).

7-Amino-2-cyclobutylpyrazolo[1,5-a]pyrimidine-6-carbaldehyde [CCLXXIII]

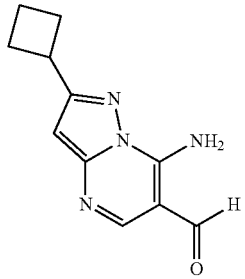

CCLXXII

Compound [CCLXXII] was prepared using a procedure similar to that of Compound [III]. Data for Compound [CCLXXII]: LCMS (m/e) 217 (M+H); $^1$H NMR (300 MHz, DMSO-d$_6$) δ ppm 9.87 (s, 1H), 9.02 (s, 2H), 8.50 (s, 1H), 6.54 (s, 1H), 3.60-3.78 (m, 1H), 2.20-2.40 (m, 4H), 1.98-2.12 (m, 1H), 1.82-1.98 (m, 1H).

2-Cyclobutyl-7-phenyl-9H-1,4,9,9b-tetraaza-cyclopenta[a]naphthalen-8-one [CCLXXIII]

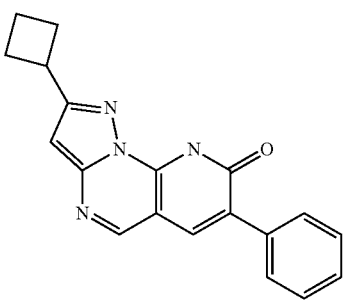

CCLXXIII

Compound [CCLXXIII] was prepared using a procedure similar to that of Compound [IV]. Data for Compound [CCLXXIII]: LCMS (m/e) 317 (M+H); $^1$H NMR (400 MHz, DMSO-d$_6$) δ ppm 13.36 (s, 1H), 8.79 (s, 1H), 8.37 (s, 1H), 7.35-7.73 (m, 5H), 6.72 (s, 1H), 3.70-3.80 (m, 1H), 2.22-2.42 (m, 4H), 1.85-2.15 (m, 2H).

8-Chloro-2-cyclobutyl-7-phenyl-1,4,9,9b-tetraaza-cyclopenta[a]naphthalene [CCLXXIV]

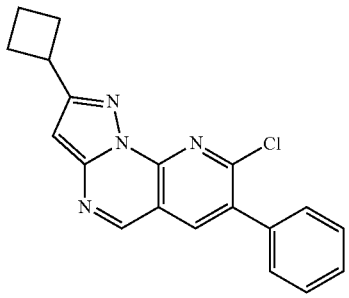

CCLXXIV

Compound [CCLXXIV] was prepared using a procedure similar to that of Compound [V], SOCl$_2$ procedure. Data for Compound [CCLXXIV]: LCMS (m/e) 335 (M+H); $^1$H NMR (300 MHz, CDCl$_3$) δ ppm 8.86 (s, 1H), 8.23 (s, 1H), 7.54 (s, 5H), 6.88 (s, 1H), 3.88-4.02 (m, 1H), 2.32-2.56 (m, 4H), 1.92-2.22 (m, 2H).

301 trans-2-{3-Methyl-3-hydroxy-1-[4-(2-(4-methoxyphenyl)-7-phenyl-1,4,9,9b-tetraaza-cyclopenta[a]naphthalen-8-yl)-phenyl]-cyclobutyl}-isoindole-1,3-dione [CCLXXV]

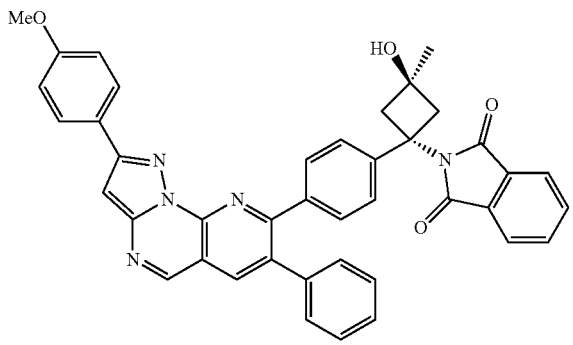

CCLXXV

Compound [CCLXXV] was prepared using a procedure similar to that of Compound [XL]. Data for Compound [CCLXXV]: LCMS (m/e) 658 (M+1)

This material was carried onto the next step without further purification or characterization.

trans-3-Amino-1-methyl-3-[4-(2-(4-methoxyphenyl)-7-phenyl-1,4,9,9b-tetraaza-cyclopenta[a]naphthalen-8-yl)-phenyl]-cyclobutanol [CCLXXVI]

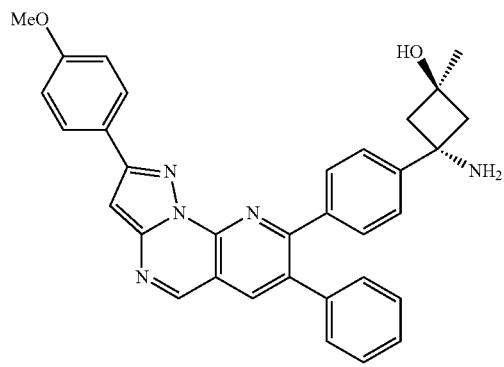

CCLXXVI

Compound [CCLXXVI] was prepared in a similar way to that of Compound [XLI]. Data for Compound [CCLXXVI]: LCMS (m/e) 530 (M+H); NMR (400 MHz, METHANOL-$d_4$) δ ppm 1.50 (s, 3H) 1.91 (s, 3H) 2.49-2.62 (m, 2H) 2.72-2.85 (m, 2H) 3.85 (s, 3H) 6.99-7.08 (m, 2H) 7.22 (s, 1H) 7.28-7.37 (m, 5H) 7.42-7.51 (m, 2H) 7.62-7.71 (m, 2H) 7.99-8.10 (m, 2H) 8.54 (s, 1H) 9.05 (s, 1H).

302 trans-2-{3-Methyl-3-hydroxy-1-[4-(2-isopropyl-7-phenyl-1,4,9,9b-tetraaza-cyclopenta[a]naphthalen-8-yl)-phenyl]-cyclobutyl}-isoindole-1,3-dione [CCLXXVII]

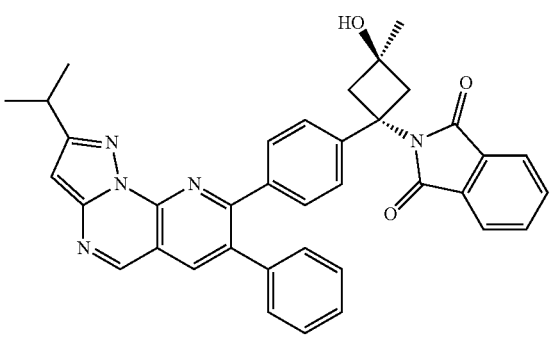

CCLXXVII

Compound [CCLXXVII] was prepared using a procedure similar to that of Compound [XL]. Data for Compound [CCLXXVII]: LCMS (m/e) 564 (M+1)

This material was carried onto the next step without further purification or characterization.

trans-3-Amino-1-methyl-3-[4-(2-isopropyl-7-phenyl-1,4,9,9b-tetraaza-cyclopenta[a]naphthalen-8-yl)-phenyl]-cyclobutanol [CCLXXVIII]

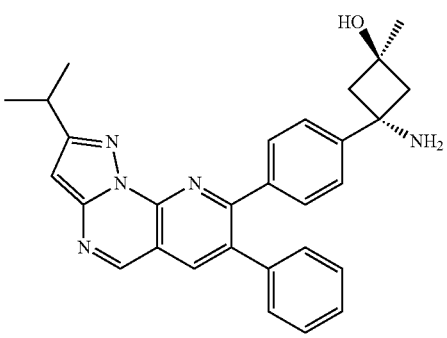

CCLXXVIII

Compound [CCLXXVIII] was prepared in a similar way to that of Compound [XLI]. Data for Compound [CCLXXVIII]: LCMS (m/e) 464 (M+H); $^1$H NMR (400 MHz, METHANOL-$d_4$) δ ppm 1.42 (d, J=6.96 Hz, 6H) 1.48 (s, 3H) 2.65-2.71 (m, 2H) 2.83-2.89 (m, 2H) 3.23-3.26 (m, 1H) 6.79 (s, 1H) 7.32 (br. s, 5H) 7.50 (d, J=8.40 Hz, 2H) 7.71 (d, J=8.37 Hz, 2H) 8.55 (s, 1H).

trans-2-{3-Methyl-3-hydroxy-1-[4-(2-cyclobutyl-7-phenyl-1,4,9,9b-tetraaza-cyclopenta[a]naphthalen-8-yl)-phenyl]-cyclobutyl}-isoindole-1,3-dione [CCLXXIX]

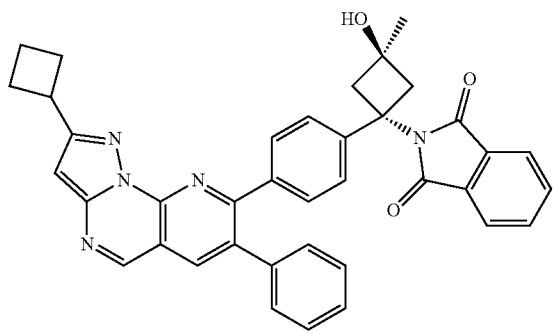

Compound [CCLXXIX] was prepared using a procedure similar to that of Compound [XL]. Data for Compound [CCLXXIX]: LCMS (m/e) 576 (M+1) This material was carried onto the next step without further purification or characterization.

trans-3-Amino-1-methyl-3-[4-(2-cyclobutyl-7-phenyl-1,4,9,9b-tetraaza-cyclopenta[a]naphthalen-8-yl)-phenyl]-cyclobutanol [CCLXXX]

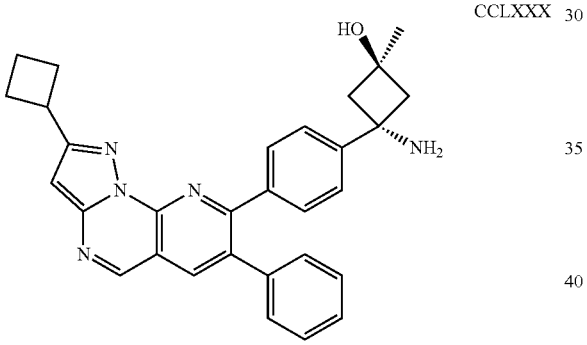

Compound [CCLXXX] was prepared in a similar way to that of Compound pout Data for Compound [CCLXXX]: LCMS (m/e) 476 (M+H); $^1$H NMR (400 MHz, METHANOL-$d_4$) δ ppm 1.48 (s, 3H) 2.10-2.18 (m, 1H) 2.37-2.49 (m, 3H) 2.68 (s, 2H) 2.82-2.89 (m, 2H) 3.85 (t, J=8.65 Hz, 1H) 6.86 (s, 1H) 7.30-7.35 (m, 5H) 7.49 (d, J=8.37 Hz, 2H) 7.71 (d, J=8.35 Hz, 2H) 8.55 (s, 1H) 9.04 (s, 1H).

2-tert-Butyl-7-(2'-fluoro-phenyl)-9H-1,4,9,9b-tetraaza-cyclopenta[a]naphthalen-8-one [CCLXXXI]

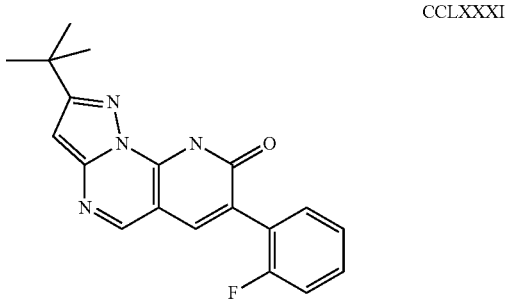 [SMILES: CC(C)(C)c1cc2ncc3cc(-c4ccccc4F)c(=O)[nH]c3n2n1]

Compound [CCLXXXI] was prepared in a similar way to that of Compound [IV]. Data for Compound [CCLXXXI]: LCMS (m/e) 337 (M+H); $^1$H NMR (300 MHz, DMSO-$d_6$) δ ppm 9.08 (s, 1H), 8.80 (s, 1H), 7.62-7.55 (m, 2H), 7.47-7.40 (m, 2H), 6.98 (s, 1H), 1.44 (s, 9H).

8-Chloro-2-tert-butyl-7-(2'-fluorophenyl)-1,4,9,9b-tetraaza-cyclopenta[a]naphthalene [CCLXXXII]

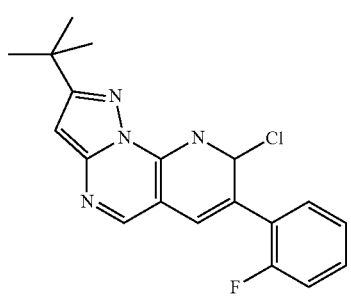

Compound [CCLXXXII] was prepared in a similar way to that of Compound [V], SOCl$_2$ method. Data for Compound [CCLXXXII]: LCMS (m/e) 355 (M+H); $^1$H NMR (300 MHz, DMSO-$d_6$) δ ppm 9.08 (s, 1H), 8.80 (s, 1H), 7.62-7.55 (m, 2H), 7.47-7.40 (m, 2H), 6.98 (s, 1H), 1.44 (s, 9H).

2-tert-Butyl-7-(2'-thienyl)-9H-1,4,9,9b-tetraaza-cyclopenta[a]naphthalen-8-one [CCLXXXII]

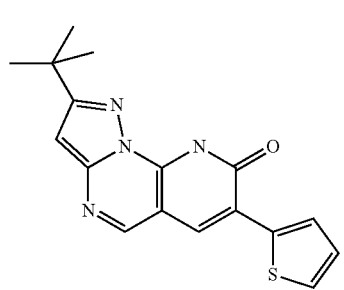

Compound [CCLXXXIII] was prepared in a similar way to that of Compound [IV]. Data for Compound [CCLXXXIII]: LCMS (m/e) 325 (M+H); $^1$H NMR (300 MHz, DMSO-$d_6$) δ ppm 8.79-8.75 (d, 2H), 7.84-7.82 (d, 1H), 7.64-7.62 (d, 1H), 7.21-7.18 (m, 1H), 6.73 (s, 1H), 1.42 (s, 9H).

8-Chloro-2-tert-butyl-7-(2'-thienyl)-1,4,9,9b-tetraaza-cyclopenta[a]naphthalene [CCLXXXIV]

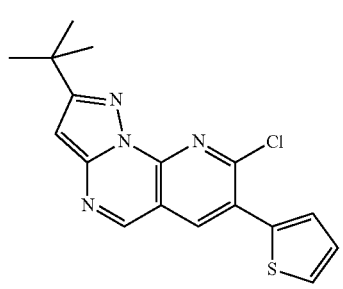

Compound [CCLXXXIV] was prepared in a similar way to that of Compound [V], SOCK method. Data for Compound [CCLXXXIV]: LCMS (m/e) 343 (M+H); $^1$H NMR (300 MHz, DMSO-$d_6$) (δ ppm 9.10 (s, 1H), 8.96 (s, 1H), 7.87-7.85 (d, 1H), 7.66-7.65 (d, 1H), 7.31-7.28 (m, 1H), 6.97 (s, 1H), 1.43 (s, 9H).

2-tert-Butyl-7-(3'-thienyl)-9H-1,4,9,9b-tetraaza-cyclopenta[a]naphthalen-8-one [CCLXXXV]

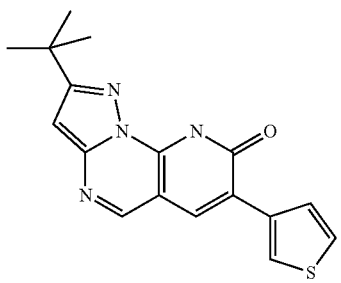

CCLXXXV

Compound [CCLXXXV] was prepared in a similar way to that of Compound [IV]. Data for Compound [CCLXXXV]: LCMS (m/e) 325 (M+H); $^1$H NMR (300 MHz, DMSO-d$_6$) δ ppm 8.78 (s, 1H), 8.65 (s, 1H), 8.23 (s, 1H), 7.72-7.65 (m, 2H), 6.71 (s, 1H), 1.41 (s, 9H).

8-Chloro-2-tert-butyl-7-(3'-thienyl)-1,4,9,9b-tetraaza-cyclopenta[a]naphthalene [CCLXXXVI]

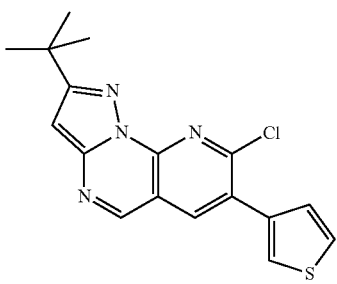

CCLXXXVI

Compound [CCLXXXVI] was prepared in a similar way to that of Compound [V], SOCl$_2$ method. Data for Compound [CCLXXXVI]: LCMS (m/e) 343 (M+H); $^1$H NMR (300 MHz, DMSO-d$_6$) δ ppm 9.08 (s, 1H), 8.82 (s, 1H), 7.98 (d, J=0.9 Hz, 1H), 7.77 (dd, J=3.0 Hz, 1H), 7.51 (dd, J=0.9 Hz, 1H), 6.96 (s, 1H), 1.43 (s, 9H).

trans-2-{3-Hydroxy-3-methyl-1-[4-(7-phenyl-1,4,9,9b-tetraaza-cyclopenta[a]naphthalen-8-yl)-phenyl]-cyclobutyl}-isoindole-1,3-dione [CCLXXXVII]

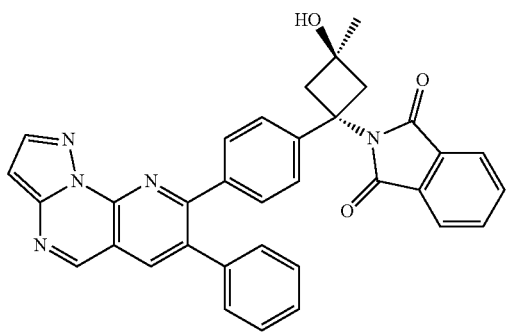

CCLXXXVII

Compound [CCLXXXVII] was prepared in a similar way to that of Compound [XL]. Data for Compound [CCLXXX-VII]: LCMS (m/e) 552 (M+H). This material was used in the next step without further characterization.

3-Amino-1-methyl-3-[4-(7-phenyl-1,4,9,9b-tetraaza-cyclopenta[a]naphthalen-8-yl)-phenyl]-cyclobutanol [CCLXXXVIII]

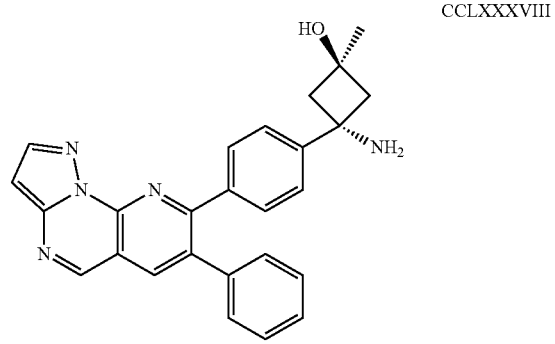 [SMILES: C[C@]1(O)C[C@@](N)(c2ccc(-c3nc4c(cnc5ccnn54)cc3-c3ccccc3)cc2)C1]

CCLXXXVIII

Compound [CCLXXXVIII] was prepared in a similar way to that of Compound [XLI]. Data for Compound [CCLXXX-VIII]: LCMS (m/e) 422 (M+H); $^1$H NMR (400 MHz, METHANOL-d$_4$) δ ppm 1.48 (s, 3H) 2.68 (d, J=14.64 Hz, 2H) 2.80-2.91 (m, 2H) 6.95 (d, J=2.15 Hz, 1H) 7.33 (s, 5H) 7.50 (d, J=8.40 Hz, 2H) 7.70 (d, J=8.40 Hz, 2H) 8.25 (d, J=1.95 Hz, 1H) 8.59 (s, 1H) 9.10 (s, 1H).

Scheme: 2-pyridyl substituent

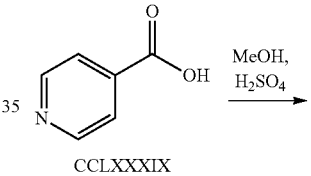

CCLXXXIX

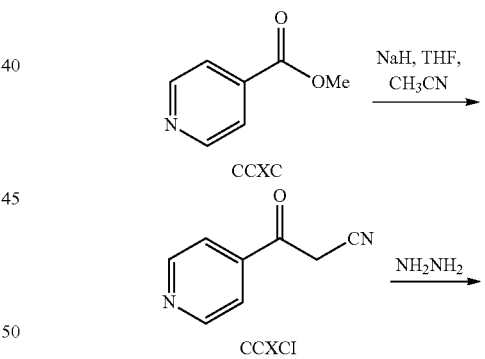

CCXC

CCXCI

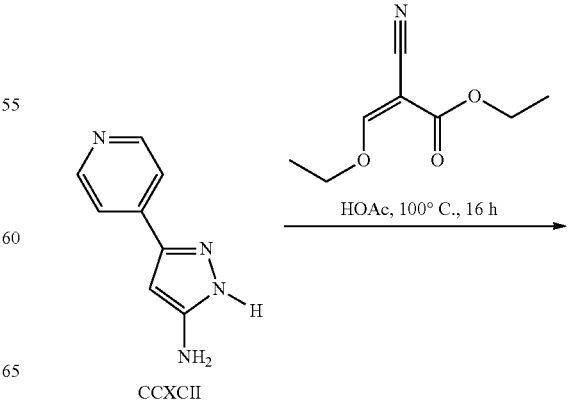

CCXCII

-continued

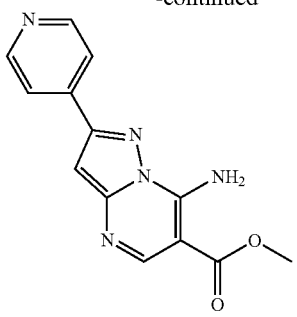

CCXCIII

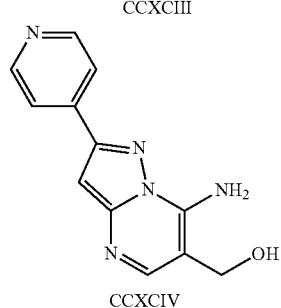

CCXCIV

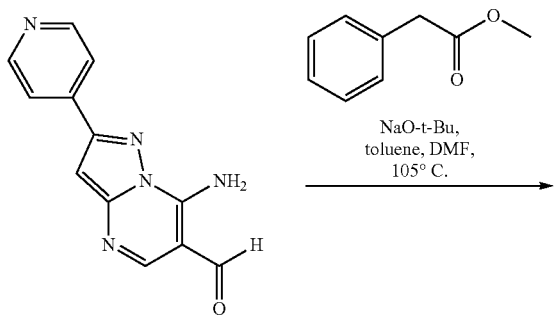

CCXCV

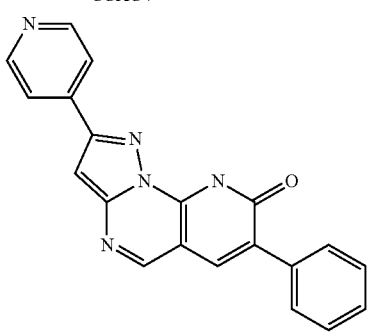

CCXCVI

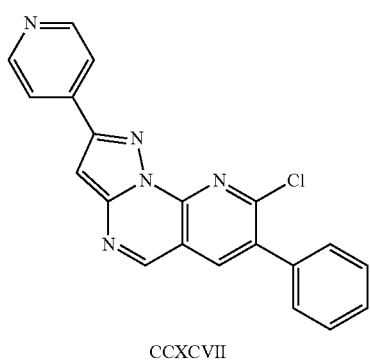

CCXCVII

Methyl Isonicontinate [CCXC]

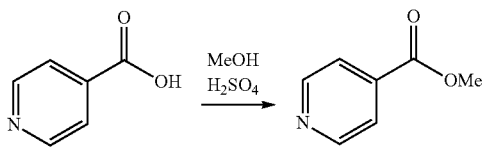

CCLXXXIX   CCXC

To a 250 mL 3-necked round-bottom flask was added a solution of Compound [CCLXXXIX] (10 g, 81.30 mmol, 1.00 eq.) in methanol (25 mL). To this, concentrated $H_2SO_4$ (12.5 mL) was added slowly at room temperature. The mixture was heated to reflux overnight in an oil bath. The resulting mixture was concentrated under vacuum. The resulting solution was extracted with 3×300 mL of ethyl acetate and the organic layers combined and dried over anhydrous sodium sulfate and concentrated under vacuum to provide Compound [CCXC] as colorless liquid: LCMS (m/e) 138 (M+H); $^1$H NMR (300 MHz, CHLOROFORM-d) δ ppm 3.93 (s, 3H) 7.80-7.82 (m, 2H) 8.74-8.76 (m, 2H).

3-Oxo-3-(pyridin-4-yl)propanenitrile [CCXCI]

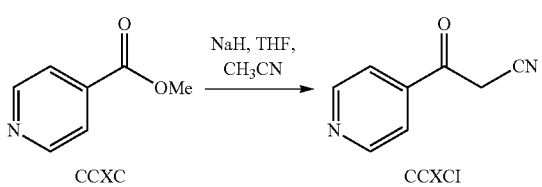 [SMILES: COC(=O)c1ccncc1 ; N#CCC(=O)c1ccncc1]

CCXC   CCXCI

To a 50 mL 3-necked round-bottom flask was added a solution of sodium hydride (520 mg, 13.00 mmol, 1.60 eq., 60% dispersion in mineral oil) in toluene (10 mL). The mixture was heated to reflux and Compound [CCXC] (1 g, 6.62 mmol, 1.00 eq.) in $CH_3CN$ (6.56 mL) was added dropwise. After addition, the mixture was stirred at reflux overnight in an oil bath. The reaction was then cooled to room temperature and quenched by addition of 200 mL of ice/water. The pH value was adjusted to 4 with aqueous hydrogen chloride (2 N). The mixture was extracted with 2×50 mL of dichloromethane and the organic layers combined and dried over anhydrous sodium sulfate and concentrated under vacuum to afford compound [CCXCI] as an orange solid: LCMS (m/e) 147 (M+H).

3-(Pyridin-4-yl)-1H-pyrazol-5-amine [CCXCII]

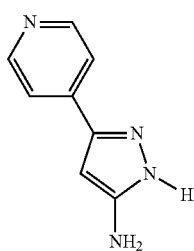

CCXCII

Compound [CCXCII] was prepared using a procedure similar to that of Compound [CCLXI]. Data for Compound [CCXCII]: LCMS (m/e) 161.

Ethyl 7-amino-2-(pyridin-4-yl)-pyrazolo[1,5-a]pyrimidine-6-carboxylate [CCXCIII]

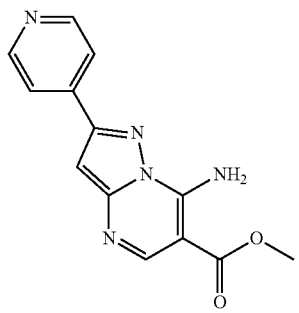

CCXCIII

Compound [CCXCIII] was prepared using a procedure similar to that of Compound [VII]. Data for Compound [CCXCIII]: LCMS (m/e) 284 (M+H); $^1$H NMR (300 MHz, DMSO-$d_6$) δ ppm 1.45 (t, J=6.9 Hz, 3H) 4.34 (q, J=6.9 Hz, 2H) 6.94 (s, 1H) 7.08 (s, 1H) 7.86~7.88 (m, 2H) 8.58 (s, 1H) 8.75 (m, 2H) 8.82 (s, 1H).

(7-Amino-2-(pyridin-4-yl)-pyrazolo[1,5-a]pyrimidin-6-yl)methanol [CCXCIV]

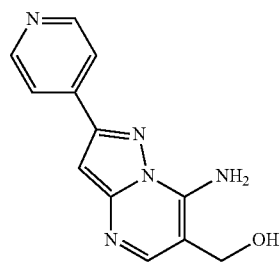

CCXCIV

Compound [CCXCIV] was prepared using a procedure similar to that of Compound [II]. Data for Compound [CCXCIV]: LCMS m/e 242 (M+H);

7-Amino-2-(pyridin-4-yl)-pyrazolo[1,5-a]pyrimidine-6-carbaldehyde [CCXCV]

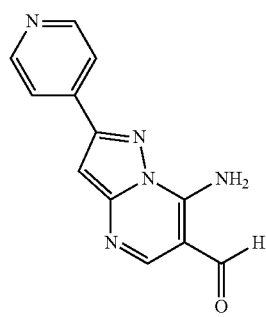

CCXCV

Compound [CCXCV] was prepared using a procedure similar to that of Compound [III]. Data for Compound [CCXCV]: LCMS (m/e) 240 (M+H); $^1$H NMR (300 MHz, DMSO-$d_6$) δ ppm 7.29 (s, 1H) 8.06 (m, 2H) 8.61 (s, 1H) 8.74 (s, 2H) 9.21 (s, 2H) 9.94 (s, 1H).

2-(Pyridin-4-yl)-7-phenyl-9H-1,4,9,9b-tetraaza-cyclopenta[a]naphthalen-8-one [CCXCVI]

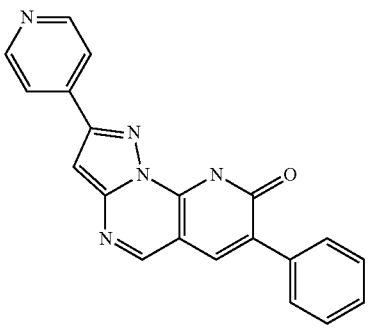

CCXCVI

Compound [CCXCVI] was prepared using a procedure similar to that of Compound [IV]. Data for Compound [CCXCVI]: LCMS (m/e): 340 (M+H); $^1$H NMR (300 MHz, DMSO-d) ppm 7.14 (s, 1H) 7.27-7.29 (m, 1H) 7.35-7.40 (m, 2H) 7.79-7.81 (m, 2H) 7.90 (s, 1H) 8.04 (s, 2H) 8.51 (s, 1H) 8.67 (s, 2H).

8-Chloro-2-(pyridin-4-yl)-7-phenyl-1,4,9,9b-tetraaza-cyclopenta[a]naphthalene [CCXCVII]

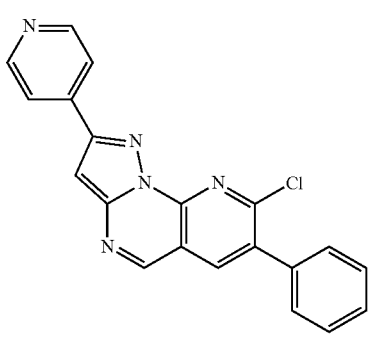

CCXCVII

To a 50 mL round bottom flask was added Compound [CCXCVI] ((450 mg, 1.33 mmol, 1.00 eq.), POCl$_3$ (40 mL). The mixture was heated to reflux in an oil bath for 9 h. The reaction was concentrated in vacuo and the residue was added to 50 mL of ice/water. After the pH value was adjusted to 8 with Na$_2$CO$_3$, the mixture was extracted three times with 120 ml CH$_2$Cl$_2$ and the organic layer was collected. The combined organic phases were dried over Na$_2$SO$_4$, filtered, concentrated and purified by silica gel chromatography using CH$_2$Cl$_2$/MeOH as the eluent to give Compound [CCXCVII]: LCMS (m/e) 358 (M+H); $^1$H NMR (300 MHz, CHLOROFORM-d) ppm 7.28 (s, 1H) 7.56 (s, 5H) 8.12 (m, 2H) 8.31 (s, 1H) 8.79 (s, 2H) 8.97 (s, 1H).

trans-2-{3-Methyl-3-hydroxy-1-[4-(2-(pyridin-4-yl)-7-phenyl-1,4,9,9b-tetraaza-cyclopenta[a]naphthalen-8-yl)-phenyl]-cyclobutyl}-isoindole-1,3-dione [CCXCVIII]

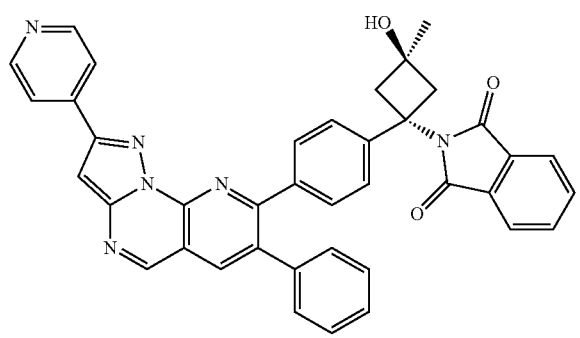

CCXCVIII

Compound [CCXCVIII] was prepared using a procedure similar to that of Compound [XL]. Data for Compound [CCXCVIII]: LCMS (m/e) 629 (M+1) This material was carried onto the next step without further purification or characterization.

trans-3-Amino-1-methyl-3-[4-(2-(pyridine-4-yl)-7-phenyl-1,4,9,9b-tetraaza-cyclopenta[a]naphthalen-8-yl)-phenyl]-cyclobutanol [CCXCIX]

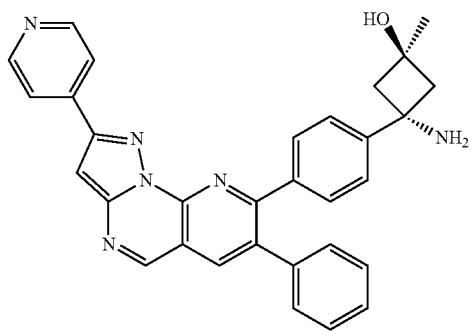

CCXCIX

Compound [CCXCIX] was prepared in a similar way to that of Compound [XLI]. Data for Compound [CCXCIX]: LCMS (m/e) 499 (M+H); $^1$H NMR (400 MHz, METHANOL-4) δ ppm 1.51 (s, 3H) 1.90 (s, 6H) 2.50-2.59 (m, 2H) 2.71-2.81 (m, 2H) 7.30-7.39 (m, 5H) 7.45-7.53 (m, 3H) 7.65 (d, J=8.35 Hz, 2H) 8.17 (d, J=5.76 Hz, 2H) 8.60 (s, 1H) 8.65 (d, J=5.56 Hz, 2H) 9.13 (s, 1H).

Scheme: 2-(thiophen-3-yl) substituent

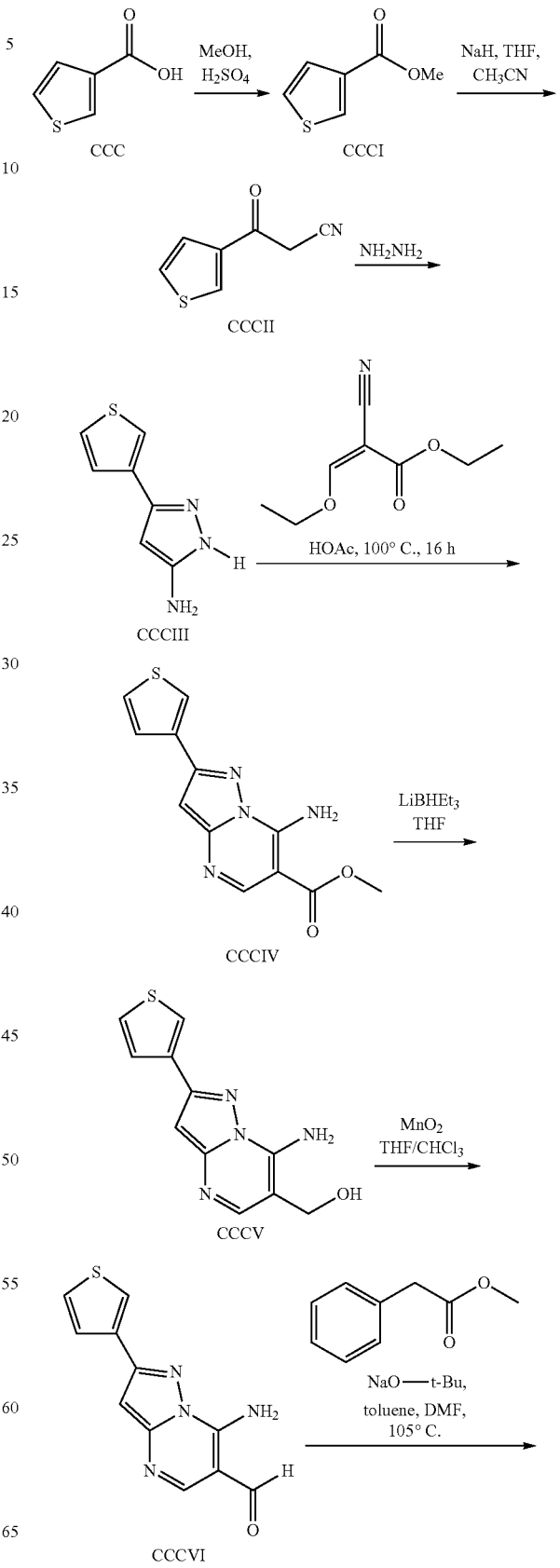

313

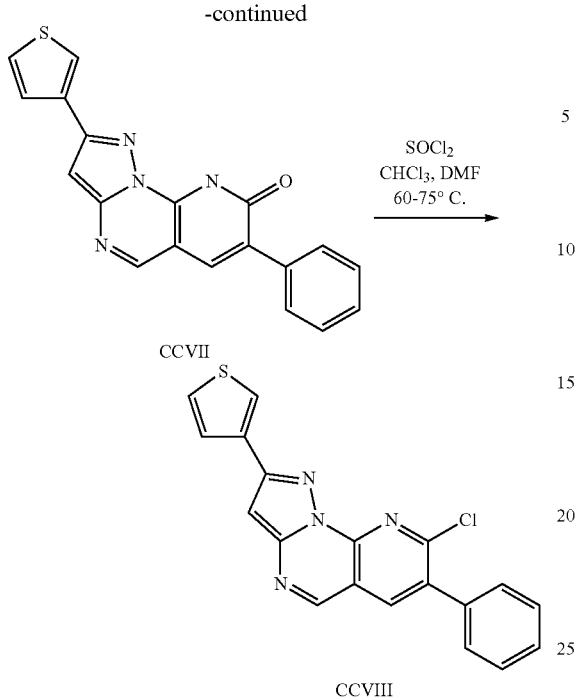

CCVII

CCVIII

Methyl thiophene-3-carboxylate [CCCI]

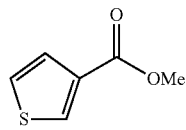

CCCI

Compound [CCCI] was prepared in a similar way to that of Compound [CCXC]. Data for Compound [CCCI]: LCMS (m/e) 143 (M+H); $^1$H NMR (300 MHz, CHLOROFORM-d) δ ppm 3.89 (s, 3H) 7.31-7.34 (m, 2H) 7.53 (m, 1H) 8.12 (m, 1H).

3-Oxo-3-(thiophen-3-yl)propanenitrile [CCCII]

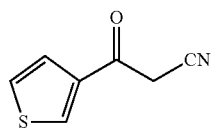

CCCII

Compound [CCCI] was prepared in a similar way to that of Compound [CCXCI]. Data for Compound [CCCI]: $^1$H NMR (300 MHz, DMSO-d$_6$) δ ppm 4.65 (s, 2H) 7.51 (m, 1H) 7.62 (m, 1H) 8.56 (m, 1H).

314

3-(thiophen-3-yl)-1/1-pyrazol-5-amine [CCCIII]

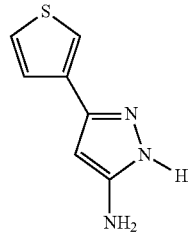

CCCIII

Compound [CCCIII] was prepared using a procedure similar to that of Compound [CCLXI]. Data for Compound [CCCIII]: LCMS (m/e) 166 (M+H); $^1$H NMR (300 MHz, DMSO-d$_6$) δ ppm 4.72 (br. s, 2H) 5.66 (s, 1H) 737 (s, 1H) 754 (s, 1H) 7.63 (s, 1H).

Ethyl 7-amino-2-(thiophen-3-yl)-pyrazolo[1,5-a]pyrimidine-6-carboxylate [CCCIV]

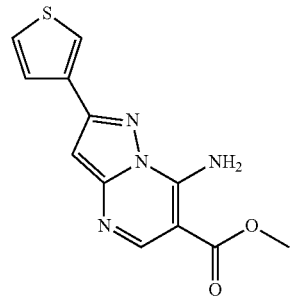

CCCIV

Compound [CCCIV] was prepared using a procedure similar to that of Compound [VII]. Data for Compound [CCCIV]: LCMS (m/e) 289 (M+H); $^1$H NMR (300 MHz, DMSO-d$_6$) δ ppm 132 (t, J=6.9 Hz, 3H) 4.31 (q, J=6.9 Hz, 2H) 6.97 (s, 1H) 7.70 (m, 2H) 8.16 (s, 1H) 8.51 (s, 1H) 8.61 (s, 2H).

(7-Amino-2-(thiophen-3-yl)-pyrazolo[1,5-a]pyrimidin-6-yl)methanol [CCCV]

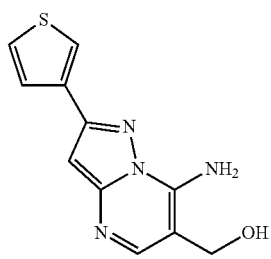

CCCV

Compound [CCCV] was prepared using a procedure similar to that of Compound [II]. Data for Compound [CCCV]: LCMS m/e 247 (M+H); NMR (300 MHz, DMSO-d$_6$) δ ppm 3.18 (s, 1H) 4.54 (s, 2H) 5.00 (s, 1H) 6.74 (s, 1H) 7.52 (s, 2H) 7.65 (m, 2H) 8.04 (s, 1H) 8.04 (m, 2H).

7-Amino-2-(thiophen-3-yl)-pyrazolo[1,5-a]pyrimidine-6-carbaldehyde [CCCVI]

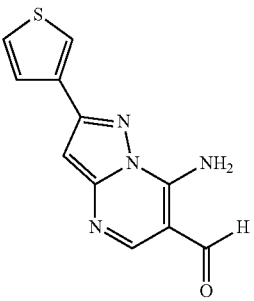

CCCVI

Compound [CCCVI] was prepared using a procedure similar to that of Compound [III]. Data for Compound [CCCVI]: LCMS m/e 245 (M+H); $^1$H NMR (300 MHz, DMSO-d$_6$) δ ppm 7.09 (s, 1H) 7.71 (m, 2H) 8.18 (s, 1H) 8.56 (s, 1H) 9.07 (s, 2H) 9.90 (s, 1H).

2-(Thiophen-3-yl)-7-phenyl-9H-1,4,9,9b-tetraaza-cyclopenta[a]naphthalen-8-one [CCCVII]

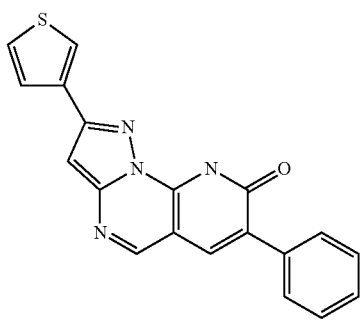

CCCVII

Compound [CCCVII] was prepared using a procedure similar to that of Compound [IV]. Data for Compound [CCCVII]: LCMS (m/e): 345 (M+H);

8-Chloro-2-(thiophen-3-yl)-7-phenyl-1,4,9,9b-tetraaza-cyclopenta[a]naphthalene [CCCVIII]

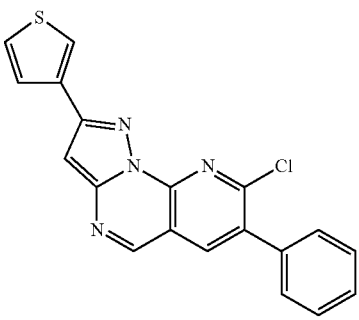

CCCVIII

To a 250 mL round bottom flask was added Compound [CCVII] (1 g, 2.91 mmol, 1.00 eq.), POCl$_3$ (40 mL). The mixture was heated to reflux in an oil bath for 4 h. The reaction was concentrated in vacuo and the residue was added to 50 mL of ice/water. Adjusted the pH value to 8 with Na$_2$CO$_3$. The mixture was extracted three times with 500 ml CH$_2$Cl$_2$ and the organic layers was collected. The combined organic phases were dried over Na$_2$SO$_4$, filtered, concentrated and purified by silica gel chromatography using CH$_2$Cl$_2$/petroleum ether as the eluent to give Compound [CCCVIII]: LCMS (mile) 363 (M+H); $^1$H NMR (300 MHz, CHLOROFORM-d) δ ppm 7.14 (s, 1H) 7.45 (dd, J$_1$=5.1 Hz, J$_2$=3 Hz, 1H) 7.55 (s, 5H) 7.80 (m, 1H) 8.02 (s, 1H) 8.26 (s, 1H) 8.90 (s, 1H).

trans-2-{3-Methyl-3-hydroxy-1-[4-(2-(thiophen-3-yl)-7-phenyl-1,4,9,9b-tetraaza-cyclopenta[a]naphthalen-8-yl)-phenyl]-cyclobutyl}-isoindole-4,3-dione [CCXCVIII]

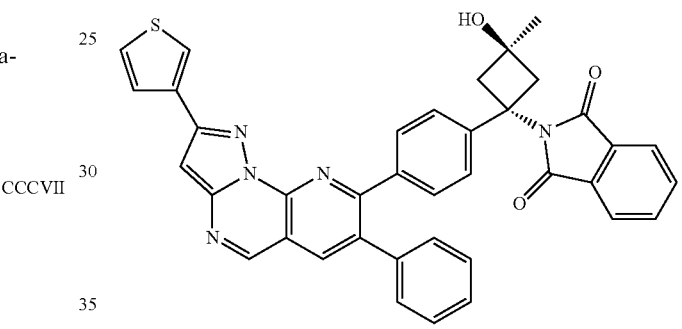

CCCIX

Compound [CCCIX] was prepared using a procedure similar to that of Compound [XL]. Data for Compound [CCCIX]: LCMS (m/e) (M+1)

This material was carried onto the next step without further purification or characterization.

trans-3-Amino-1-methyl-3-[4-(2-(thiophen-3-yl)-7-phenyl-1,4,9,9b-tetraaza-cyclopenta[a]naphthalen-8-yl)-phenyl]-cyclobutanol [CCCX]

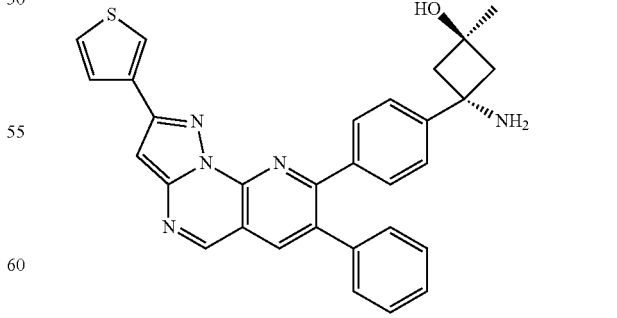

CCCX

Compound [CCCX] was prepared in a similar way to that of Compound [XLI]. Data for Compound [CCCX]: LCMS (m/e) 504 (M+H); $^1$H NMR (400 MHz, METHANOL-d$_4$) δ ppm 1.50 (s, 3H) 1.91 (s, 3H) 2.48-2.64 (m, 2H) 2.67-2.88 (m, 2H) 7.21 (s, 1H) 7.28-7.38 (m, 5H) 7.42-7.50 (m, 2H) 7.53 (dd, J=5.05, 2.95 Hz, 1H) 7.60-7.71 (m, 2H) 7.79 (dd, J=5.05, 1.20 Hz, 1H) 8.10 (dd, J=2.95, 1.20 Hz, 1H) 8.55 (s, 1H) 9.06 (s, 1H).

2-Methyl-7-phenyl-8-{4-[4-(5-pyridin-2-yl-4H-[1,2,4]triazol-3-yl)-piperidin-1-ylmethyl]-phenyl}-1,4,9,9b-tetraazacyclopenta[a]naphthalene

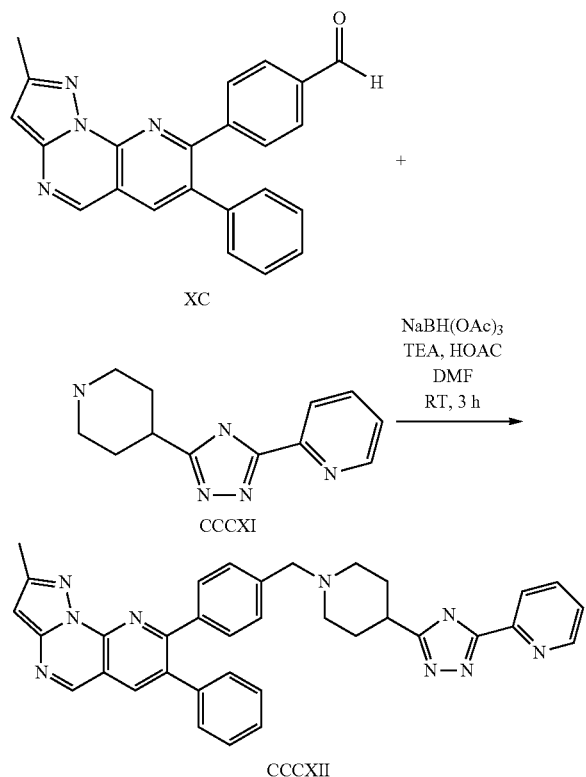

Compound [CCCXII] was prepared using a procedure similar to that of [XCII] using Compound [CCCXI] as starting material (known in WO 2009021992). Data for Compound [CCCXII]: LCMS ink 578 (M+H); $^1$H NMR (400 MHz, METHANOL-d$_4$) δ ppm 1.97 (s, 6H) 1.98-2.11 (m, 2H) 2.10-2.28 (m, 2H) 2.39-2.68 (m, 2H) 2.59 (s, 3H) 2.92-3.07 (m, 1H) 3.08-3.25 (m, 2H) 3.83 (br, s, 2H) 6.76 (s, 1H) 7.24-7.42 (m, 7H) 7.41-7.51 (m, 1H) 7.62 (d, J=8.20 Hz, 2H) 7.88-8.00 (m, 1H) 8.09 (d, J=7.86 Hz, 1H) 8.56 (s, 1H) 8.66 (d, J=4.39 Hz, 1H) 9.06 (s, 1H).

4-Methyl-3-(5-piperidin-4-yl-4H-[1,2,4]triazol-3-yl)-pyridine hydrochloride [CCCXV]

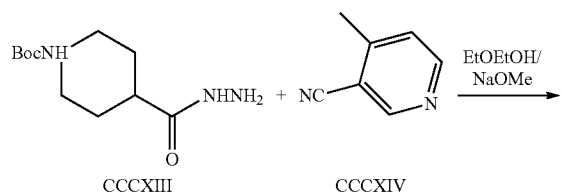

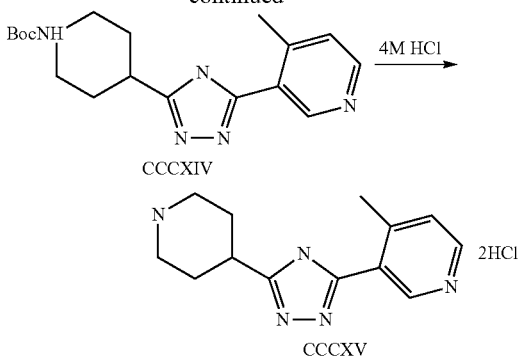

A mixture of Compound [CCCXIII] (600 mg, 2.47 mmol), Compound [CCCXIV] (291 mg, 2.47 mmol), and sodium methoxide (266 mg, 25 wt % solution in methanol) in 2-ethoxyethanol (6 mL) was heated at 125° C. for 16 h. The reaction mixture was partitioned between EtOAc and saturate aqueous ammonium chloride solution. The aqueous layer was extracted with additional EtOAc. The combined organic layer was dried over Na$_2$SO$_4$, filtered, and concentrated. The crude material was purified by ISCO to obtain Compound [CCCXV] as a colorless oil (73.3 mg, 9%). 1H NMR (400 MHz, CHLOROFORM-d) δ ppm 1.57 (s, 9H) 1.77-1.95 (m, 2H) 2.09 (d, J=2.44 Hz, 2H) 2.62 (s, 3H) 2.89-3.01 (m, 2H) 3.06 (br. s., 1H) 3.98-4.51 (m, 2H) 7.22 (d, J=4.59 Hz, 2H) 8.50 (d, J=4.93 Hz, 2H) 9.07 (br. s., 1H).

A solution of Compound [CCCXV] (73.3 mg) dissolved in 1 mL of 1,4-dioxane was treated with 4 M HCl in 1,4-dioxane (1.5 mL). The suspension was stirred at rt for 1 h. The volatiles was evaporated in vacuo. Compound [CCCXVI] was obtained as a while solid (015HXL012), which was used in the next step directly. 1H NMR (400 MHz, METHANOL-d$_4$) δ ppm 2.04-2.20 (m, 2H) 2.36 (d, J=11.08 Hz, 2H) 3.02 (s, 3H) 3.18-3.28 (m, 2H) 3.50-3.60 (m, 2H) 8.07 (d, J=6.10 Hz, 1H) 8.71 (d, J=5.37 Hz, 1H) 9.30 (s, 1H)

2-Methyl-8-(4-{4-[5-(4-methylpyridin-3-yl)-4H-[1,2,4]triazol-3-yl]-piperidin-1-ylmethyl}-phenyl)-7-phenyl-1,4,9,9b-tetraazacyclopenta[a]naphthalene [CCCXVII]

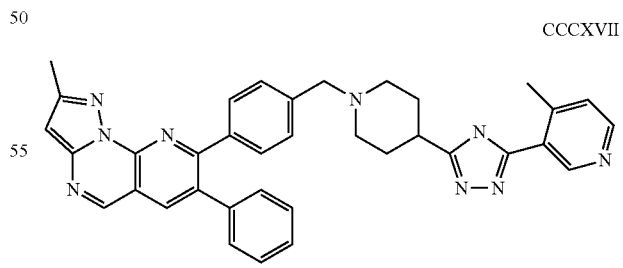

Compound [CCCXVII] was prepared using a procedure similar to that of [XCII]. Data for Compound [CCCXVII]: LCMS m/e 592 (M+H); $^1$H NMR (400 MHz, METHANOL-d$_4$) δ ppm 1.94 (br, s, 1H) 1.97 (s, 3H) 1.99-2.06 (m, 1H) 2.13 (d, J=2.88 Hz, 2H) 2.36-2.52 (m, 2H) 2.59 (s, 3H) 2.94-3.05 (m, 1H) 3.12 (d, J=9.23 Hz, 2H) 3.77 (br, s, 1H) 6.76 (s, 1H)

7.22-7.45 (m, 7H) 7.61 (d, J=8.20 Hz, 2H) 8.42 (d, J=5.08 Hz, 1H) 8.56 (s, 1H) 8.83 (s, 1H) 9.05 (s, 1H).

4-[5-(2-Trifluoromethyl-phenyl)-4H-[1,2,4]triazol-3-yl]-piperidine hydrochloride [CCCXVIII]

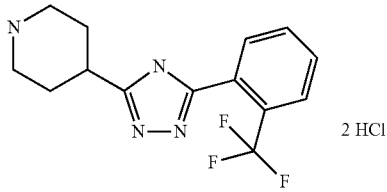

Compound [CCCXVIII] was prepared using a procedure similar to that of [CCCXV]. Data for Compound [CCCXVIII]: 1H NMR (400 MHz, METHANOL-d₄) δ ppm 2.02-2.18 (m, 2H) 2.27-2.40 (m, 2H) 3.15-3.27 (m, 2H) 3.46-3.59 (m, 2H) 7.73 (d, J=2.25 Hz, 1H) 7.76-7.87 (m, 2H) 7.92 (d, J=2.25 Hz, 1H)

2-Methyl-7-phenyl-8-(4-{4-[5-(2-trifluoromethyl-phenyl)-4H-[1,2,4]triazol-3-yl]-piperidin-1-ylmethyl}-phenyl)-1,4,9,9b-tetraaza-cyclopenta[a]naphthalene [CCCXIX]

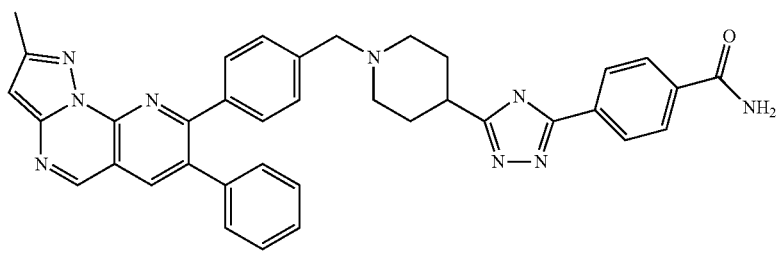

Compound [CCCXIX] was prepared using a procedure similar to that of [XCII]. Data for Compound [CCCXIX]: LCMS ink 645 (M+H); 1H NMR (400 MHz, METHANOL-d₄) δ ppm 1.88-2.05 (m, 2H) 1.96 (s, 3H) 2.07-2.17 (m, 2H) 2.37 (br, s, 2H) 2.59 (s, 3H) 2.90-3.01 (m, 1H) 3.07 (d, J=11.71 Hz, 2H) 3.71 (br, s, 2H) 6.76 (s, 1H) 7.27-7.39 (m, 7H) 7.54-7.78 (m, 6H) 7.85 (d, J=7.86 Hz, 1H) 8.55 (s, 1H) 9.05 (s, 1H).

4-(5-Piperidin-4-yl-4H-[1,2,4]triazol-3-yl)-benzamide hydrochloride [CCCXX]

Compound [CCCXX] was prepared using a procedure similar to that of [CCCXV]. Data for Compound [CCCXX]: 1H NMR (400 MHz, METHANOL-d₄) δ ppm 2.04-2.19 (m, 2H) 2.34 (d, J=13.96 Hz, 2H) 3.16-3.27 (m, 2H) 3.53 (d, J=13.13 Hz, 2H) 7.97-8.05 (m, 2H) 8.05-8.20 (m, 2H).

4-(5-{1-[4-(2-Methyl-7-phenyl-1,4,9,9b-tetraaza-cyclopenta[a]naphthalen-8-yl)-benzyl]-piperidin-4-yl}-4H-[1,2,4]triazol-3-yl)-benzamide [CCCXXI]

Compound [CCCXXI] was prepared using a procedure similar to that of [CCCXV]. Data for Compound [CCCXXI]: LCMS m/e 620 (M+H); 1H NMR, (400 MHz, METHANOL-d₄) δ ppm 1.90-2.06 (m, 2H) 1.96 (s, 3H) 2.06-2.18 (m, 2H) 2.27-2.48 (m, 2H) 2.59 (s, 3H) 2.88-3.03 (m, 1H) 3.04-3.18 (m, 2H) 3.73 (br, s, 2H) 6.76 (s, 1H) 7.21-7.41 (m, 7H) 7.60 (d, J=8.15 Hz, 2H) 7.96 (d, J=8.44 Hz, 2H) 8.09 (d, J=8.35 Hz, 2H) 8.55 (s, 1H) 9.05 (s, 1H).

4-[5-(3-Trifluoromethyl-phenyl)-4H-[1,2,4]triazol-3-yl]-piperidine hydrochloride [CCCXXII]

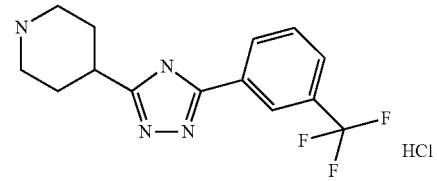

Compound [CCCXXII] was prepared using a procedure similar to that of [CCCXV]. Data for Compound [CCCXXIII]: 1H NMR (400 MHz, METHANOL-d₄) δ ppm 2.00-2.24 (m, 2H) 2.29-2.42 (m, 2H) 3.13-3.29 (m, 2H) 3.42-3.63 (m, 2H) 7.74 (d, J=7.81 Hz, 1H) 7.78-7.86 (m, 1H) 8.26 (d, J=7.86 Hz, 1H) 8.32 (s, 1H)

2-Methyl-7-phenyl-8-(4-{4-[5-(3-trifluoromethyl-phenyl)-4H-[1,2,4]triazol-3-yl]-piperidin-1-ylmethyl}-phenyl)-1,4,9,9b-tetraaza-cyclopenta[a]naphthalene [CCCXXIII]

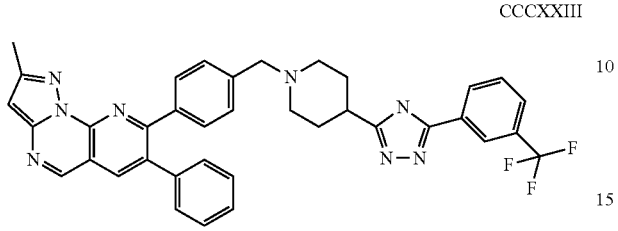

CCCXXIII

Compound [CCCXXIII] was prepared using a procedure similar to that of [XCII]. Data for Compound [CCCXXIII]: LCMS m/e 645 (M+H); ¹H NMR (400 MHz, METHANOL-d₄) δ ppm 1.91-2.05 (m, 2H) 1.96 (s, 3H) 2.07-2.17 (m, 2H) 2.29-2.45 (m, 1H) 2.59 (s, 3H) 2.96 (dd, J=15.62, 8.59 Hz, 1H) 3.09 (d, J=12.74 Hz, 2H) 3.71 (s, 2H) 6.76 (s, 1H) 7.26-7.41 (m, 7H) 7.60 (d, J=8.20 Hz, 2H) 7.68 (d, J=7.76 Hz, 1H) 7.71-7.77 (m, 1H) 8.26 (d, J=7.71 Hz, 1H) 8.31 (s, 1H) 8.55 (s, 1H) 9.05 (s, 1H)

4-(5-pyridin-3-yl-4H-[1,2,4]triazol-3-yl)-piperidine [CCCXXIV]

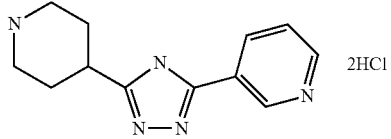 [SMILES: c1cncc(-c2nnc(C3CCNCC3)[nH]2)c1 ; "2HCl"]

2HCl was known in WO 2006135627.
Compound [CCCXXIV] was prepared as described in WO 2006135627.

2-Methyl-7-phenyl-8-{4-[4-(5-pyridin-3-yl-4H-[1,2,4]triazol-3-yl)-piperidin-1-ylmethyl]-phenyl}-1,4,9,9b-tetraaza-cyclopenta[a]naphthalene [CCCXXV]

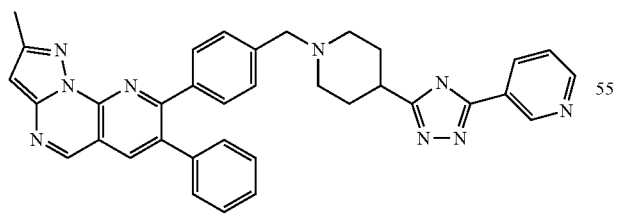

CCCXXV

Compound [CCCXXV] was prepared using a procedure similar to that of [XCII]. Data for Compound [CCCXXV]: LCMS m/e 578 (M+H); ¹H NMR (400 MHz, METHANOL-d₄) δ ppm 1.92-2.06 (m, 2H) 1.97 (s, 6H) 2.07-2.19 (m, 2H) 2.37-2.52 (m, 2H) 2.59 (s, 3H) 2.93-3.05 (m, 1H) 3.13 (d, J=11.81 Hz, 2H) 3.78 (s, 2H) 6.76 (s, 1H) 7.25-7.41 (m, 7H) 7.51-7.57 (m, 1H) 7.61 (d, J=8.20 Hz, 2H) 8.37-8.44 (m, 1H) 8.56 (s, 1H) 8.58 (dd, J=4.93, 1.51 Hz, 1H) 9.05 (s, 1H) 9.17 (d, J=1.71 Hz, 1H)

4-[5-(4-Trifluoromethyl-phenyl)-4H-[1,2,4]triazol-3-yl]-piperidine hydrochloride [CCCXXVI]

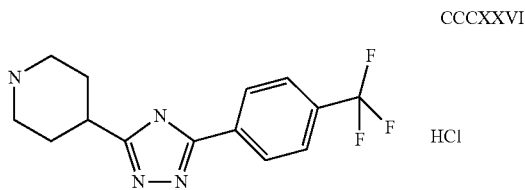 [SMILES: FC(F)(F)c1ccc(-c2nnc(C3CCNCC3)[nH]2)cc1 ; Cl]

HCl

Compound [CCCXXVI] was prepared using a procedure similar to that of [CCCXV]. Data for Compound [CCCXXVI]: ¹H NMR (400 MHz, METHANOL-d₄) δ ppm 1.99-2.21 (m, 2H) 2.27-2.48 (m, 2H) 3.16-3.27 (m, 2H) 3.49-3.59 (m, 2H) 7.84 (d, J=8.25 Hz, 2H) 8.19 (d, J=8.15 Hz, 2H).

2-Methyl-7-phenyl-8-(4-{4-[5-(4-trifluoromethyl-phenyl)-4H-[1,2,4]triazol-3-yl]-piperidin-1-ylmethyl}-phenyl)-1,4,9,9b-tetraaza-cyclopenta[a]naphthalene [CCCXXVII]

CCCXXVII

Compound [CCCXXVII] was prepared using a procedure similar to that of [XCII]. Data for Compound [CCCXXVII]: LCMS m/e 645 (M+H); ¹H NMR (400 MHz, METHANOL-d₄) δ ppm 1.96 (s, 3H) 1.89-2.04 (m, 2H) 2.05-2.19 (m, 2H) 2.27-2.45 (m, 2H) 2.59 (s, 3H) 2.89-3.02 (m, 1H) 3.08 (d, J=7.91 Hz, 2H) 3.70 (s, 2H) 6.76 (s, 1H) 7.23-7.42 (m, 7H) 7.60 (d, J=8.15 Hz, 2H) 7.76 (d, J=8.44 Hz, 2H) 8.19 (d, J=8.15 Hz, 2H) 8.56 (s, 1H) 9.05 (s, 1H)

4-(5-Phenoxymethyl-4H-[1,2,4]triazol-3-yl)-piperidine hydrochloride [CCCXXVIII]

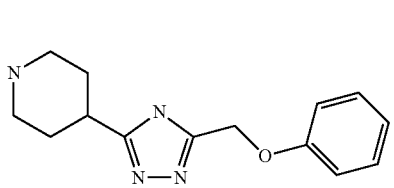

HCl

Compound [CCCXXVIII] was prepared using a procedure similar to that of [CCCXV]. Data for Compound [CCCXXVIII]: ¹H NMR (400 MHz, METHANOL-d₄) δ ppm 1.99-2.23 (m, 2H) 2.26 2.42 (m, 2H) 3.11-3.26 (m, 2H) 3.51 (d, J=12.45 Hz, 2H) 5.30 (s, 2H) 6.96-7.09 (m, 3H) 7.21-7.38 (m, 2H).

2-Methyl-8-{4-[4-(5-phenoxymethyl-4H-[1,2,4]triazol-3-yl)-piperidin-1-ylmethyl]-phenyl}-7-phenyl-1,4,9,9b-tetraaza-cyclopenta[a]naphthalene [CCCXXIX]

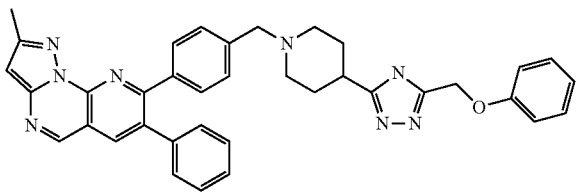

Compound [CCCXXIX] was prepared using a procedure similar to that of [XCII]. Data for Compound [CCCXXIX]: LCMS m/e 607 (M+H); $^1$H NMR (400 MHz, METHANOL-d$_4$) δ ppm 1.85 (2.04 (m, 2H) 1.95 (s, 3H) 2.09 (d, J=13.28 Hz, 2H) 2.45 (d, J=10.25 Hz, 2H) 2.59 (s, 3H) 2.83-3.05 (m, 1H) 3.12 (d, J=14.55 Hz, 2H) 3.78 (br, s, 2H) 5.12 (s, 2H) 6.76 (s, 1H) 6.86-7.07 (m, 3H) 7.18-7.42 (m, 9H) 7.61 (d, J=8.20 Hz, 2H) 8.56 (s, 1H) 9.05 (s, 1H).

3-Methyl-2-(5-piperidin-4-yl-4H-[1,2,4]triazol-3-yl)-pyridine hydrochloride [CCCXXX]

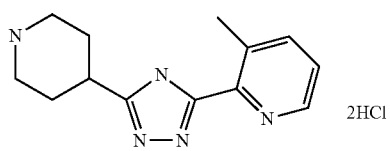

Compound [CCCXXX] was prepared using a procedure similar to that of [CCCXV]. Data for Compound [CCCXXX]: 1H NMR (400 MHz, METHANOL-d$_4$) δ ppm 2.10-2.25 (m, 2H) 2.26-2.45 (m, 2H) 2.93 (s, 3H) 3.21-3.31 (m, 2H) 3.49-3.65 (m, 2H) 7.97 (d, J=5.71 Hz, 1H) 8.55 (d, J=7.81 Hz, 1H) 8.69 (d, J=5.61 Hz, 1H).

2-Methyl-8-(4-{4-[5-(3-methyl-pyridin-2-yl)-4H-[1,2,4]triazol-3-yl]-piperidin-1-ylmethyl}-phenyl)-7-phenyl-1,4,9,9b-tetraaza-cyclopenta[a]naphthalene [CCCXXXI]

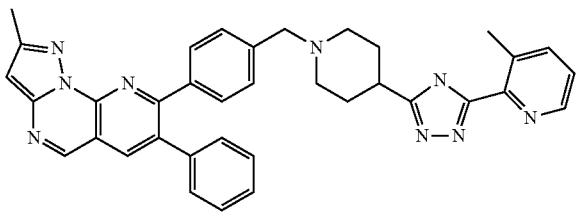

Compound [CCCXXXI] was prepared using a procedure similar to that of [XCII]. Data for Compound [CCCXXXI]: LCMS m/e 592 (M+H); $^1$H NMR (400 MHz, METHANOL-d$_4$) δ ppm 1.97 (s, 9H) 2.00-2.13 (m, 2H) 2.17 (d, J=6.05 Hz, 2H) 2.59 (s, 3H) 2.61 (br, s, 3H) 2.98-3.11 (m, 1H) 3.21 (d, J=6.74 Hz, 2H) 3.92 (br, s, 2H) 6.77 (s, 1H) 7.25-7.45 (m, 9H) 7.64 (d, J=8.10 Hz, 2H) 7.78 (d, J=7.32 Hz, 1H) 8.49 (d, J=5.12 Hz, 1H) 8.57 (s, 1H).

4-[5-(3-Methoxy-phenyl)-4H-[1,2,4]triazol-3-yl]-piperidine hydrochloride [CCCXXXII]

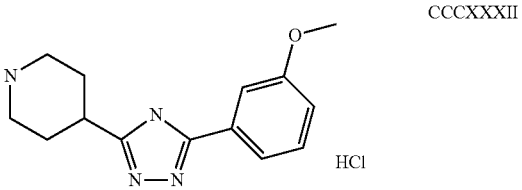 [SMILES: COc1cccc(-c2nnc(C3CCNCC3)[nH]2)c1 ; Cl]

Compound [CCCXXXII] was prepared using a procedure similar to that of [CCCXV]. Data for Compound [CCCXXXII]: $^1$H NMR (400 MHz, METHANOL-d$_4$) δ ppm 2.07-2.25 (m, 2H) 2.40 (d, J=14.74 Hz, 2H) 3.17-3.34 (m, 2H) 3.49-3.62 (m, 2H) 3.91 (s, 3 1.1) 7.11-7.35 (m, 1H) 7.42-7.64 (m, 3H).

8-(4-{4-[5-(3-Methoxy-phenyl)-4H-[1,2,4]triazol-3-yl]-piperidin-1-ylmethyl}-phenyl)-2-methyl-7-phenyl-1,4,9,9b-tetraaza-cyclopenta[a]naphthalene [CCCXXXIII]

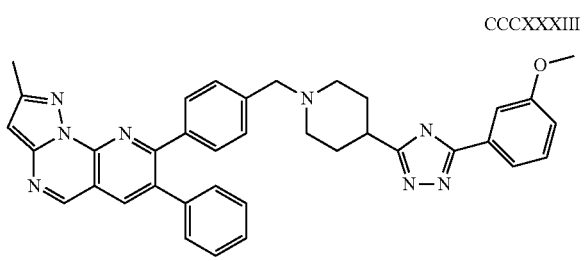 [SMILES: COc1cccc(-c2nnc(C3CCN(Cc4ccc(-c5nc6c(cnc7cc(C)nn76)cc5-c5ccccc5)cc4)CC3)[nH]2)c1]

Compound [CCCXXXIII] was prepared using a procedure similar to that of [XCII]. Data for Compound [CCCXXXIII]: LCMS m/e 607 (M+H); $^1$H NMR (400 MHz, METHANOL-4) δ ppm 1.97 (s, 6H) 1.98-2.11 (m, 2H) 2.10-2.26 (m, 2H) 2.59 (s, 3H) 2.90-3.04 (m, 1H) 3.09-3.25 (m, 3H) 3.86 (s, 3H) 6.76 (s, 1H) 6.92-7.13 (m, 1H) 7.24-7.45 (m, 8H) 7.49-7.59 (m, 2H) 7.62 (m, 2H) 8.56 (s, 1H) 9.05 (s, 1H).

4-[5-(4-Methoxy-phenyl)-4H-[1,2,4]triazol-3-yl]-piperidine hydrochloride [CCCXXXIV]

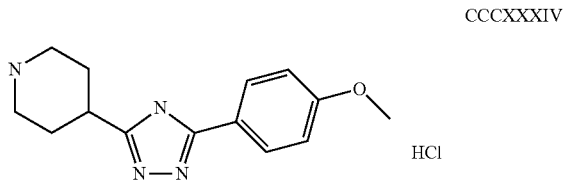 [SMILES: COc1ccc(-c2nnc(C3CCNCC3)[nH]2)cc1 ; Cl]

Compound [CCCXXXIV] was prepared using a procedure similar to that of [CCCXV]. Data for Compound [CCCXXXIV]: $^1$H NMR (400 MHz, METHANOL-$d_4$) δ ppm 2.07-2.23 (m, 2H) 2.31-2.43 (m, 2H) 3.16-3.28 (m, 2H) 3.47-3.57 (m, 2H) 3.91 (s, 3H) 7.17 (d, J=8.93 Hz, 2H) 7.74-8.11 (m, 2H).

8-(4-{4-[5-(4-Methoxy-phenyl)-4H-[1,2,4]triazol-3-yl]-piperidin-1-ylmethyl}-phenyl)-2-methyl-7-phenyl-1,4,9,9b-tetraaza-cyclopenta[a]naphthalene [CCCXXXV]

CCCXXXV

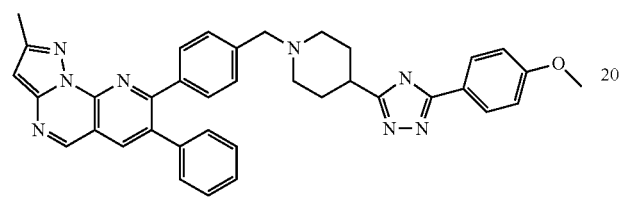

Compound [CCCXXXV] was prepared using a procedure similar to that of [XCII]. Data for Compound [CCCXXXV]: LCMS m/ee 607 (M+H); $^1$H NMR (400 MHz, METHANOL-$d_4$) δ ppm 1.97 (s, 3H) 1.98-2.08 (m, 2H) 2.09-2.23 (m, 2H) 2.59 (s, 3H) 2.89-3.04 (m, 1H) 3.08-3.26 (m, 2H) 185 (s, 3H) 6.76 (s, 1H) 7.02 (d, J=8.69 Hz, 2H) 7.20 (d, J=8.69 Hz, 2H) 7.20-7.47 (m, 71-1) 7.62 (d, J=8.15 hz, 2H) 7.88 (d, J=8.69 Hz, 2H) 8.56 (s, 1H) 9.05 (s, 1H).

2-Methyl-7-phenyl-8-{4-[4-(6,7,8,9-tetrahydro-5H-[1,2,4]triazolo[4,3-a]azepin-3-yl)-piperidin-1-ylmethyl]-phenyl}-1,4,9,9b-tetraaza-cyclopenta[a]naphthalene [CCCXXXVI]

CCCXXXVI

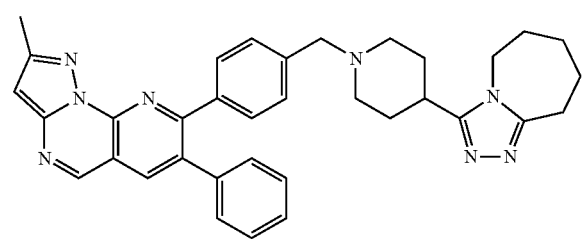

Compound [CCCXXXVI] was prepared using a procedure similar to that of [XCII]. Data for Compound [CCCXXX-VII]: LCMS m/e 569 (M+H); $^1$H NMR (400 MHz, METHANOL-$d_4$) δ ppm 1.66-1.84 (m, 4H) 1.98 (s, 6H) 1.87-2.03 (m, 4H) 2.38-2.54 (m, 2H) 2.59 (s, 3H) 2.86 3.02 (m, 3H) 3.16 (d, J=12.20 Hz, 2H) 3.80 (s, 2H) 4.06 (d, J=9.71 Hz, 2H) 6.76 (s, 1H) 7.23=7.42 (m, 7H) 7.61 (d, J=8.25 Hz, 2H) 8.56 (s, 1H) 9.05 (s, 1H).

4-(5-pyridin-2-yl-4H-[1,2,4]triazol-3-yl)-piperidine [CCCXXXVII]

CCCXXXVII

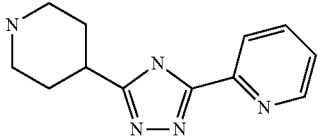

Compound [CCCXXXVII] was prepared as described in WO2009021992.

2-Methyl-7-phenyl-8-{4-[4-(5-pyridin-2-yl-4H-[1,2,4]triazol-3-yl)-piperidin-1-ylmethyl]-phenyl}-1,4,9,9b-tetraaza-cyclopenta[a]naphthalene [CCCXXX-VIII]

CCCXXXVIII

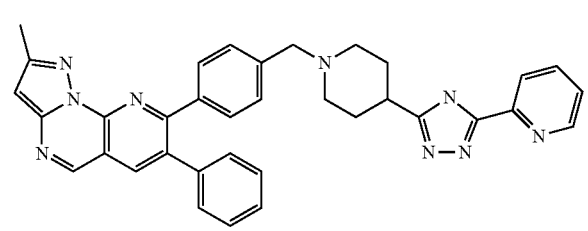

Compound [CCCXXXVI] was prepared using a procedure similar to that of [XCII]. Data for Compound [CCCXXX-VIII]: LCMS m/e 578 (M+H); $^1$H NMR (400 MHz, METHANOL-$d_4$) δ ppm 1.95-2.06 (m, 2H) 2.09-2.18 (m, 3H) 2.48 (t, J=9.76 Hz, 2H) 2.55 (s, 3H) 2.97 (s, 1H) 3.12 (d, J=11.91 Hz, 2H) 3.79 (s, 2H) 6.73 (s, 1H) 7.26-7.36 (m, 7H) 7.39-7.45 (m, 1H) 7.58 (d, J=8.20 Hz, 2H) 7.86-7.95 (m, 1H) 8.06 (d, J=7.81 Hz, 1H) 8.52 (s, 1H) 8.63 (d, J=4.49 Hz, 1H) 9.01 (s, 1H)

4-[4-(5-pyridin-4-yl-4H-[1,2,4]triazol-3-yl)-piperidine [CCCXXXIX]

CCCXXXIX

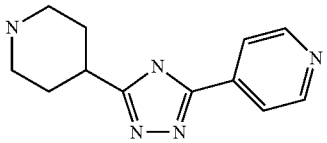

Compound [CCCXXXIX] was prepared as described in WO2009021992.

2-Methyl-7-phenyl-8-{4-[4-(5-pyridin-4-yl-4H-[1,2,4]triazol-3-yl)-piperidin-1-ylmethyl]-phenyl}-1,4,9,9b-tetraaza-cyclopenta[a]naphthalene [CCCXL]

CCCXL

Compound [CCCXL] was prepared using a procedure similar to that of [XCII]. Data for Compound [CCCXL] LCMS m/e 578 (M+H); $^1$H NMR (400 MHz, METHANOL-d$_4$) δ ppm 2.02-2.20 (m, 1H) 2.32-2.46 (m, 2H) 2.57 (s, 3H) 3.07-3.24 (m, 2H) 3.62 (d, J=12.30 Hz, 2H) 4.38 (s, 2H) 6.76 (s, 1H) 7.33 (br, s, 5H) 7.48 (d, J=8.00 Hz, 2H) 7.71 (d, J=8.00 Hz, 2H) 8.53 (d, J=5.86 Hz, 2H) 8.57 (s, 1H) 8.85 (d, J=6.05 Hz, 2H) 9.05 (s, 1H)

4-{4-[5-(4-methyl-pyridin-2-yl)-4H-[1,2,4]triazol-3-yl]-piperidine [CCCXLI]

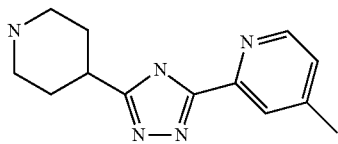

CCCXLI

Compound [CCCXLI] was prepared as described in WO2009021992.

2-Methyl-8-(4-{4-[5-(4-methyl-pyridin-2-yl)-4H-[1,2,4]triazol-3-yl]-piperidin-1-ylmethyl}-phenyl)-7-phenyl-1,4,9,9b-tetraaza-cyclopenta[a]naphthalene [CCCXLII]

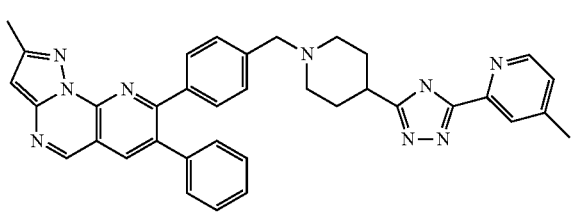

CCCXLII

Compound [CCCXLII] was prepared using a procedure similar to that of MOII. Data for Compound [CCCXLII]: LCMS m/e 592 (M+H); $^1$H NMR (400 MHz, METHANOL-d$_4$) δ ppm 2.05-2.45 (m, 2H) 2.56 (s, 3H) 2.62 (br, s, 3H) 2.99-3.22 (m, 2H) 3.40-3.67 (m, 3H) 4.38 (s, 2H) 6.75 (s, 1H) 7.41-7.51 (m, 2H) 7.70 (d, J=7.42 Hz, 3H) 8.57 (s, 2H) 9.04 (s, 1H).

2-(5-Piperidin-4-yl-4H-[1,2,4]triazol-3-yl)-pyrimidine hydrochloride [CCCXLIII]

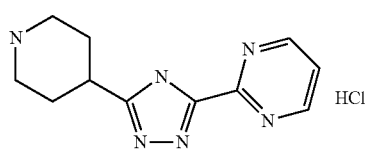

CCCXLIII

Compound [CCCXXXIV] was prepared using a procedure similar to that of [CCCXV]. Data for Compound [CCCXLIII]: 1H NMR (400 MHz, METHANOL-d$_4$) δ ppm 2.19 (br. s., 2H) 2.38 (hr. s., 2H) 3.19-3.30 (m, 2H) 3.45-3.62 (m, 2H) 7.70 (d, J=9.91 Hz, 1H) 9.05 (d, J=4.93 Hz, 2H).

2-Methyl-7-phenyl-8-{4-[4-(5-pyrimidin-2-yl-4H-[1,2,4]triazol-3-yl)-piperidin-1-ylmethyl]-phenyl}-1,4,9,9b-tetraaza-cyclopenta[a]naphthalene [CCCXLIV]

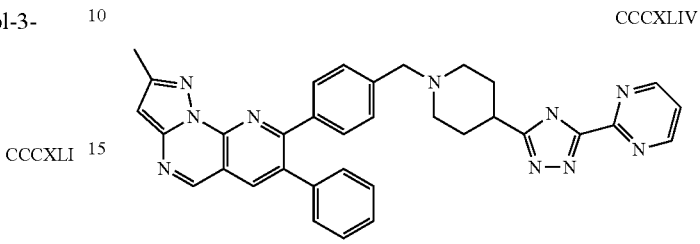

CCCXLIV

Compound [CCCXLIV] was prepared using a procedure similar to that of [XCII]. Data for Compound [CCCXLIV]: LCMS m/e 579 (M+H); $^1$H NMR (400 MHz, METHANOL-d$_4$) δ ppm 2.08 (d, J=13.67 Hz, 2H) 2.35 (d, J=12.89 Hz, 1H) 2.57 (s, 3H) 3.19 (t, J=12.40 Hz, 3H) 3.60 (d, J=13.28 Hz, 2H) 4.37 (s, 2H) 6.76 (s, 1H) 7.33 (d, J=4.49 Hz, 6H) 7.43-7.56 (m, 3H) 7.72 (d, J=8.20 Hz, 2H) 8.58 (s, 1H) 8.92 (d, J=4.88 Hz, 2H) 9.05 (s, 1H)

5-(5-Piperidin-4-yl-4H-[1,2,4]triazol-3-yl)-2-trifluoromethyl-pyridine hydrochloride [CCCXLV]

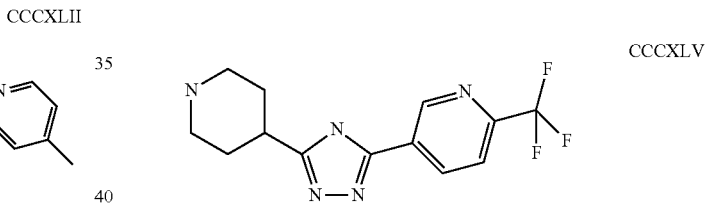

CCCXLV

Compound [CCCXLV] was prepared using a procedure similar to that of [CCCXV]. Data for Compound [CCCXLV]: $^1$H NMR (400 MHz, METHANOL-d$_4$) δ ppm 2.12-2.29 (m, 2H) 2.27-2.47 (m, 2H) 3.18-3.31 (m, 2H) 3.52-3.62 (m, 2H) 7.99 (d, J=8.25 Hz, 1H) 8.55-8.76 (m, 1H) 9.35 (d, J=1.81 Hz, 1H).

2-Methyl-7-phenyl-8-(4-{4-[5-(6-trifluoromethyl-pyridin-3-yl)-4H-[1,2,4]triazol-3-yl]-piperidin-1-ylmethyl}-phenyl)-1,4,9,9b-tetraaza-cyclopenta[a]naphthalene [CCCXLVI]

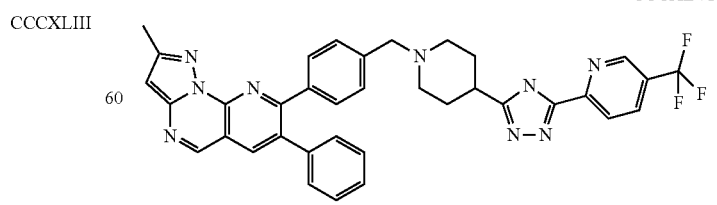

CCCXLVI

Compound [CCCXLVI] was prepared using a procedure similar to that of [XCII]. Data for Compound [CCCXLVI]:

LCMS m/e 646 (M+H); ¹H NMR (400 MHz, METHANOL-d₄) δ ppm 1.99-2.16 (m, 2H) 2.38 (d, J=13.86 Hz, 2H) 2.57 (s, 3H) 3.05-3.24 (m, 3H) 3.61 (d, J=12.30 Hz, 2H) 4.38 (s, 2H) 6.76 (s, 1H) 7.33 (m, 4H) 7.48 (d, J=8.20 Hz, 2H) 7.63-7.78 (m, 4H) 8.21 (d, J=7.61 Hz, 1H) 8.27 (s, 1H) 8.58 (s, 1H) 9.05 (s, 1H).

4-{4-[5-(6-methyl-pyridin-2-yl)-4H-1,2,4]triazol-3-yl)-piperidine [CCCXLVII]

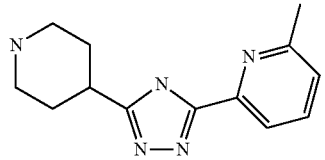

CCCXLVII

Compound [CCCXLVII] was known WO 2009021992.

2-Methyl-8-(4-{4-[5-(6-methyl-pyridin-2-yl)-4H-[1,2,4]triazol-3-yl]-piperidin-1-ylmethyl}-phenyl)-7-phenyl-1,4,9,9b-tetraaza-cyclopenta[a]naphthalene [CCCXLVIII]

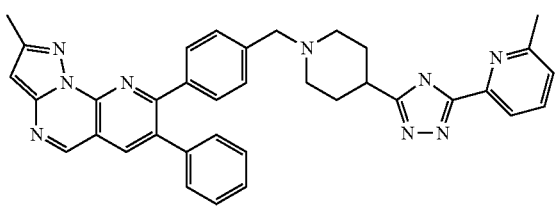

CCCXLVIII

Compound [CCCXLVIII] was prepared using a procedure similar to that of [XCII]. Data for Compound [CCCXLVIII]: LCMS m/e 592 (M+H); ¹H NMR (400 MHz, METHANOL-d₄) δ ppm 2.01-2.19 (m, 1H) 2.39 (d, J=14.25 Hz, 1H) 2.57 (s, 3H) 2.68 (s, 3H) 2.93-3.24 (m, 2H) 3.39-3.69 (m, 2H) 4.38 (s, 2H) 6.76 (s, 1H) 7.33 (br, s, 5H) 7.43-7.55 (m, 3H) 7.71 (d, J=7.81 Hz, 2H) 8.04 (d, J=4.10 Hz, 2H) 8.57 (s, 1H) 9.05 (s, 1H).

(Piperidin-4-yl)-1,3-dihydro-benzoimidazol-2-one [CCCXLIX]

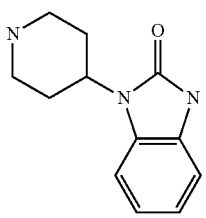

CCCXLIX

Compound [CCCXLIX] was prepared using the procedure described in *J. Med. Chem.* 2007, 50(23), 5564-5567.

1-{1-[4-(2-Methyl-7-phenyl-1,4,9,9b-tetraaza-cyclopenta[a]naphthalen-8-yl)-benzyl]-piperidin-4-yl}-1,3-dihydro-benzoimidazol-2-one [CCCL]

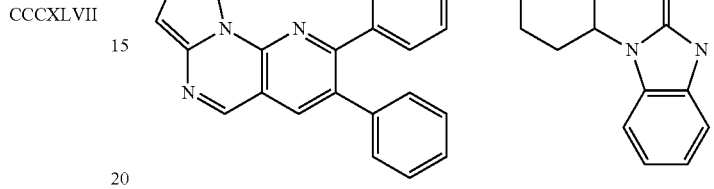

CCCL

Compound [CCCL] was prepared using a procedure similar to that of [XCII]. Data for Compound [CCCL]: LCMS m/e 566 (M+H); ¹H NMR (400 MHz, METHANOL-d₄) δ ppm 2.08 (d, J=14.15 Hz, 2H) 2.59 (s, 3H) 2.70-2.90 (m, 2H) 3.16-3.29 (m, 2H) 3.54-3.68 (m, 2H) 4.37 (br, s, 2H) 4.54 (tt, J=12.15, 4.13 Hz, 1H) 6.75 (s, 1H) 7.03-7.10 (m, 3H) 7.20-7.27 (m, 1H) 7.27-7.32 (m, 2H) 7.32-7.38 (m, 3H) 7.48 (d, J=8.25 Hz, 2H) 7.72 (d, J=8.30 Hz, 2H) 7.74 (s, 1H) 8.54 (s, 1H) 9.03 (s, 1H).

4-(4-methyl-4H-[1,2,4]triazol-3-yl)-piperidine [CCCLI]

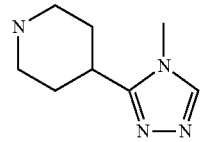

CCCLI

Compound [CCCLI] was prepared using the procedure described in WO 2000056727.

2-Methyl-8-{4-[4-(4-methyl-4H-[1,2,4]triazol-3-yl)-piperidin-1-ylmethyl]-phenyl}-7-phenyl-1,4,9,9b-tetraaza-cyclopenta[a]naphthalene [CCCLII]

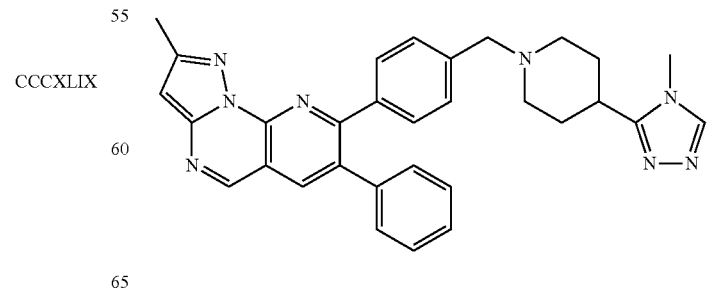

CCCLII

Compound [CCCLII] was prepared using a procedure similar to that of [XCII]. Data for Compound [CCCLII]:

LCMS ink 515 (M+H); $^1$H NMR (400 MHz, METHANOL-$d_4$) δ ppm 2.01-2.15 (m, 2H) 2.24-2.34 (m, 2H) 2.57 (s, 3H) 3.13-3.24 (m, 2H) 3.29-3.32 (m, 1H) 3.56 3.66 (m, 2H) 3.79 (s, 3H) 4.38 (br, s, 2H) 6.76 (s, 1H) 7.26 7.36 (m, 5H) 7.47 (d, J=8.22 Hz, 2H) 7.71 (d, J=8.08 Hz, 2H) 8.57 (s, 1H) 8.83 (s, 1H).

1,3,8-triaza-spiro[4.5]decane-2,4-dione [CCCLIII]

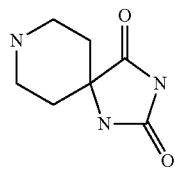

CCCLIII

Compound [CCCLIII] was prepared as according to WO 9700872.

8-[4-(2-Methyl-7-phenyl-1,4,9,9b-tetraaza-cyclopenta[a]naphthalen-8-yl)-benzyl]-1,3,8-triaza-spiro[4.5]decane-2,4-dione [CCCLIV]

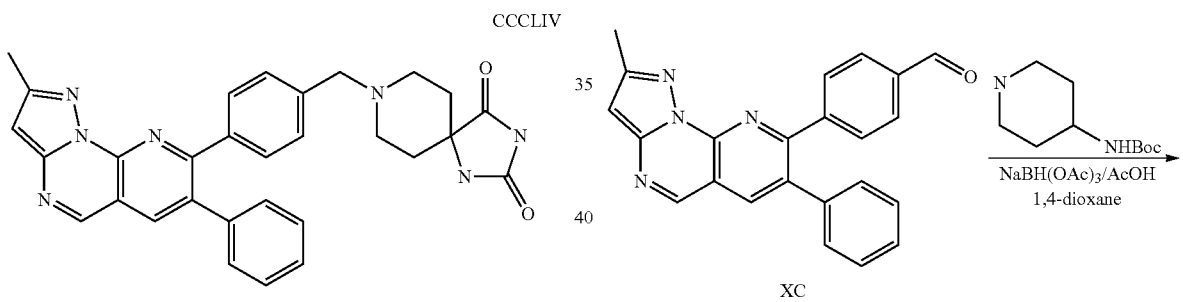

CCCLIV

Compound [CCCLIV] was prepared using a procedure similar to that of [XCII]. Data for Compound [CCCLIV]: LCMS ink 518 (M+H); $^1$H NMR (400 MHz, METHANOL-$d_4$) δ ppm 1.95-2.11 (m, 2H) 2.20-2.31 (m, 32H) 2.57 (s, 3H) 3.07-3.22 (m, 1H) 3.40-3.53 (m, 1H) 3.54-3.72 (m, 2H) 4.29-4.46 (m, 2H) 6.75 (s, 1H) 7.27-7.37 (m, 5H) 7.46 (d, J=8.00 Hz, 2H) 7.70 (d, J=8.00 Hz, 2H) 8.57 (s, 1H) 9.04 (s, 1H).

5-(4-Chloro-phenyl)-1H-pyrazol-3-yl]-piperidine [CCCLV]

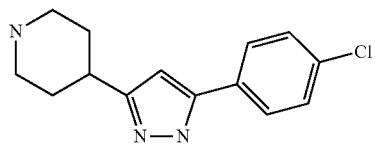

CCCLV

Compound [CCCLV] was prepared as according to CAN 149:489055.

8-(4-{4-[5-(4-Chloro-phenyl)-1H-pyrazol-3-yl]-piperidin-1-ylmethyl}-phenyl)-2-methyl-7-phenyl-1,4,9,9b-tetraaza-cyclopenta[a]naphthalene [CCCLVI]

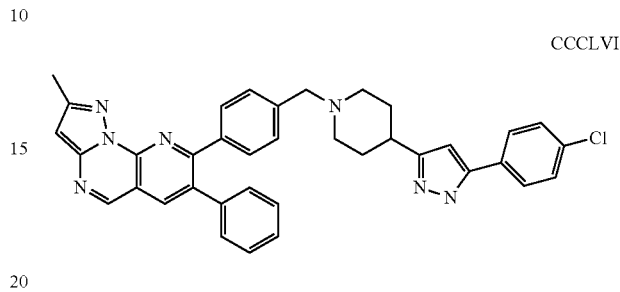

CCCLVI

Compound [CCCLVI] was prepared using a procedure similar to that of [XCII]. Data for Compound [CCCLVI]: LCMS m/e 610 (M+H); $^1$H NMR (400 MHz, METHANOL-$d_4$) δ ppm 1.79-2.03 (m, 2H) 2.30 (d, J=14.42 Hz, 2H) 2.57 (s, 3H) 2.95-3.24 (m, 3H) 3.57 (d, J=12.25 Hz, 2H) 4.36 (s, 2H) 6.51 (s, 1H) 6.76 (s, 1H) 7.26-7.36 (m, 5H) 7.40 (d, J=8.49 Hz, 2H) 7.47 (d, J=8.20 Hz, 2H) 7.69 (dd, J=21.52, 8.37 Hz, 4H) 8.57 (s, 1H) 9.05 (s, 1H).

Tricyclic Compounds Via Acylation

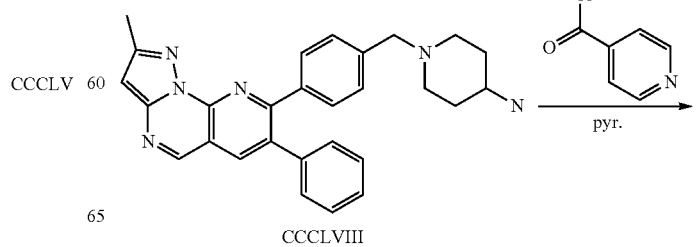

XC

CCCLVII

CCCLVIII

-continued

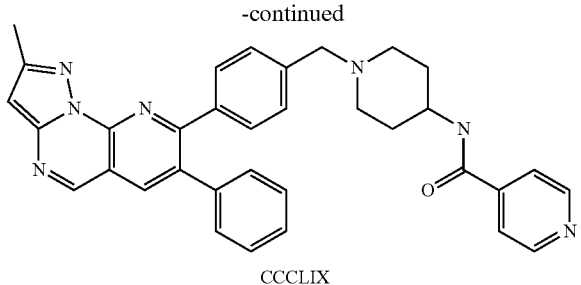

{1-[4-(2-Methyl-7-phenyl-1,4,9,9b-tetraaza-cyclopenta[a]naphthalen-8-yl)-benzyl]-piperidin-4-yl}-carbamic acid tert-butyl ester [CCCLVII]

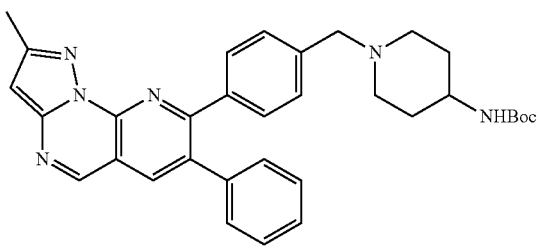

Compound [CCCLVII] was prepared in the similar fashion as that of [XCII]. This material was taken on to the next step without father characterization.

1-[4-(2-Methyl-7-phenyl-1,4,9,9b-tetraaza-cyclopenta[a]naphthalen-8-yl)-benzyl]-piperidin-4-ylamine [CCCLVIII]

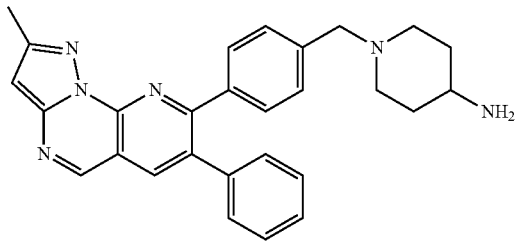

Compound [CCCLVII] (510 mg, 0.93 mmol) was dissolved in 10 mL of dichloromethane, to which solution was added TFA (5 mL). The reaction mixture was stirred at rt overnight. The volatiles were evaporated in vacuo. The product (311 mg, 75%) was used in the next step without any purification. Data for Compound [CCCLVIII]: NMR (400 MHz, METHANOL-$d_4$) δ ppm 1.79-2.10 (m, 2H) 2.28 (d, J=13.86 Hz, 2H) 2.59 (s, 3H) 3.02-3.23 (m, 2H) 3.38-3.53 (m, 1H) 3.58 (d, J=11.57 Hz, 2H) 4.35 (s, 2H) 6.78 (s, 1H) 7.27-7.39 (m, 5H) 7.47 (d, J=8.30 Hz, 2H) 7.71 (d, J=8.30 Hz, 2H) 8.59 (s, 1H) 9.07 (s, 1H).

N-{1-[4-(2-Methyl-7-phenyl-1,4,9,9b-tetraaza-cyclopenta[a]naphthalen-8-yl)-benzyl]-piperidin-4-yl}-isonicotinamide [CCCLIX]

To a solution of Compound [CCCLVIII] (17.4 mg, 0.039 mmol) in anhydrous pyridine was added the acid chloride (10.9 mg, 0.058 mmol). The mixture was stirred at room temperature for 2 h. The volatiles were evaporated in vacuo and the crude product was purified by HPLC to obtain as a yellow solid (16.9 mg, 78%). Data for Compound [CCCLIX]: LCMS m/e 554 (M+H); $^1$H NMR (400 MHz, METHANOL-$d_4$) δ ppm 1.90 (d, J=12.50 Hz, 2H) 2.28 (d, J=12.89 Hz, 2H) 2.58 (s, 3H) 3.14 (d, J=16.60 Hz, 2H) 3.56 (d, J=11.91 Hz, 2H) 4.17 (t, J=11.71 Hz, 1H) 4.35 (s, 2H) 6.78 (s, 1H) 7.26-7.40 (m, 5H) 7.47 (d, J=8.00 Hz, 2H) 7.72 (d, J=7.81 Hz, 2H) 7.99 (d, J=5.08 Hz, 2H) 8.59 (s, 1H) 8.80 (d, J=5.27 Hz, 2H) 9.06 (1H).

N-{1-[4-(2-Methyl-7-phenyl-1,4,9,9b-tetraaza-cyclopenta[a]naphthalen-8-yl)-benzyl]-piperidin-4-yl}-phthalamic acid [CCCLX]

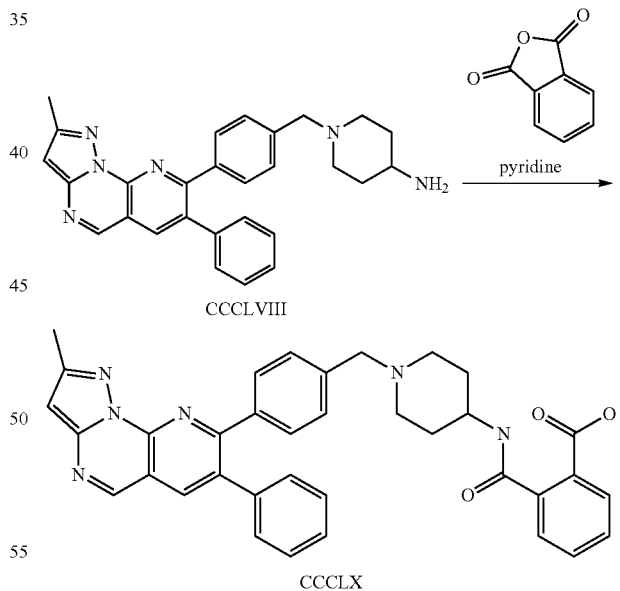

Compound [CCCLVIII] (16.0 mg, 0.036 mmol) and the anhydride (7.92 mg, 0.053 mmol) were taken in pyridine and the reaction mixture was stirred at rt for 2 h. The volatiles were evaporated in vacuo and the crude product was purified by HPLC to obtain Compound [CCCLX] (yellow solid, 22.1 mg, 98%): LCMS m/e 597 (M+H); $^1$H NMR (400 MHz, METHANOL-$d_4$) δ ppm 1.72-2.11 (m, 2H) 2.27 (t, J=15.72 Hz, 2H) 2.56 (s, 3H) 3.09-3.21 (m, 2H) 3.47-3.56 (m, 2H) 4.03-4.13 (m, 1H) 4.32 (s, 2H) 6.75 (s, 1H) 7.27-7.35 (m, 5H)

7.36-7.40 (m, 1H) 7.44 (d, J=7.81 Hz, 2H) 7.48-7.63 (m, 2H) 7.68 (d, J=8.00 Hz, 2H) 7.93-7.99 (m, 1H) 8.56 (s, 1H) 9.03 (s, 1H).

1-{1-[4-(2-Methyl-7-phenyl-1,4,9,9b-tetraaza-cyclopenta[a]naphthalen-8-yl)-benzyl]-piperidin-4-yl}-3-pyridin-4-yl-urea [CCCLXI]

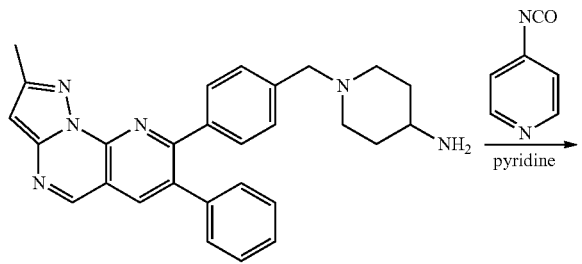

CCCLVIII

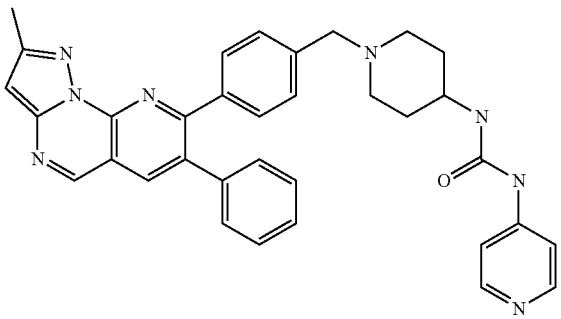

CCCLXI

Compound [CCCLVIII] (16.0 mg, 0.036 mmol) and the isocyanate (12.8 mg, 0.11 mmol) were dissolved in anhydrous pyridine. The mixture was stirred at 100° C. for 1 h. The volatiles were evaporated in vacuo. The crude product was purified by HPLC to obtain Compound [CCCLXI] as a yellow solid (21.0 mg, 97%): LCMS m/e 570 (M+H); $^1$H NMR (400 MHz, METHANOL-$d_4$) δ ppm 1.77 (d, J=12.10 Hz, 2H) 2.22 (d, J=12.69 Hz, 2H) 2.56 (s, 3H) 3.12 (d, J=9.37 Hz, 2H) 3.51 (d, J=11.71 Hz, 2H) 3.82-3.95 (m, 1H) 4.32 (s, 2H) 6.75 (s, 1H) 7.24-7.37 (m, 5H) 7.69 (d, J=8.00 Hz, 2H) 7.87-8.02 (m, 2H) 8.42 (d, J=7.03 Hz, 2H) 8.56 (s, 1H) 9.04 (s, 1H)

1-{1-[4-(2-Methyl-7-phenyl-1,4,9,9b-tetraaza-cyclopenta[a]naphthalen-8-yl)-benzyl]-piperidin-4-yl}-N-morpholinyl-urea [CCCLXII]

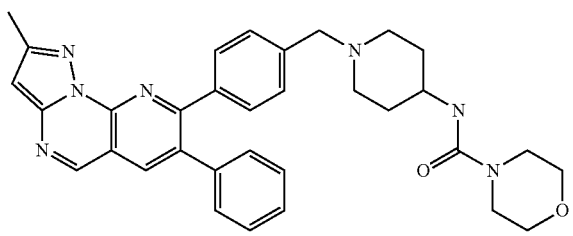

CCCLXII

Compound [CCCLXII] was prepared in a similar way to that of Compound [CCCLXI]. Data for Compound [CCCLXII]: LCMS m/e 562 (M+H); $^1$H NMR (400 MHz, METHANOL-$d_4$) δ ppm 1.70 (d, J=13.08 Hz, 2H) 2.13 (d, J=13.67 Hz, 2H) 2.57 (s, 3H) 3.05-3.12 (m, 2H) 3.31-3.35 (m, 4H) 3.43-3.50 (m, 2H) 3.58 3.63 (m, 4H) 3.74 3.86 (m, 1H) 4.30 (s, 2H) 6.76 (s, 1H) 7.28-7.35 (m, 5H) 7.43 (d, J=8.00 Hz, 2H) 7.69 (d, J=8.00 Hz, 2H) 8.57 (s, 1H) 9.05 (s, 1H 1-[4-(2-Methyl-7-phenyl-1,4,9,9b-tetraaza-cyclopenta[a]naphthalen-8-yl)-benzyl]-piperidine-4-carboxylic acid pyridin-4-ylamide [CCCLXIII]

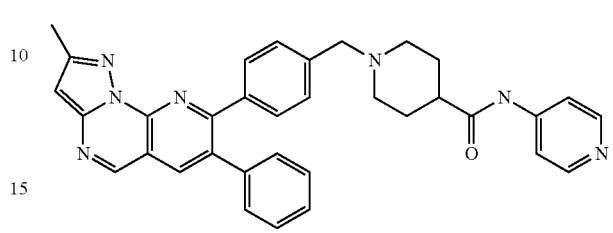

CCCLXIII

Compound [CCCLXIII] was obtained in a similar way as that for Compound [CLXII]. Data for Compound [CCCLXIII]: LCMS m/e 554 (M+H); $^1$H NMR (400 MHz, METHANOL-$d_4$) δ ppm 1.93-2.07 (m, 2H) 2.21 (d, J=-10.35 Hz, 2H) 2.57 (s, 3H) 2.80-2.89 (m, 1H) 3.07-3.15 (m, 2H) 3.18-3.22 (m, 1H) 3.51-3.61 (m, 1H) 4.35 (s, 2H) 6.76 (s, 1H) 7.28-7.35 (m, 5H) 7.46 (d, J=8.00 Hz, 2H) 7.70 (d, J=7.1 Hz, 2H) 8.13 (d, J=6.64 Hz, 2H) 8.55-8.61 (m, 3H) 9.05 (s, 1H).

1-[4-(2-Methyl-7-phenyl-1,4,9,9b-tetraaza-cyclopenta[a]naphthalen-8-yl)-benzyl]-piperidine-4-carboxylic acid (2-methoxy-phenyl)-amide [CCCLXIV]

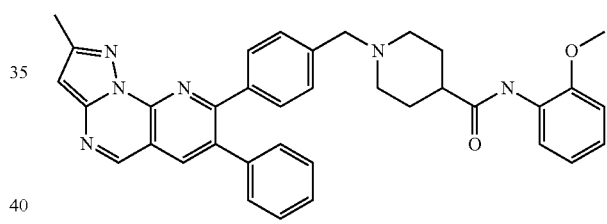

CCCLXIV

Compound [CCCLXIV] was obtained in a similar way as that for Compound [CLXII]. Data for Compound [CCCLXIV]: LCMS m/e 583 (M+H); $^1$H NMR (400 MHz, METHANOL-$d_4$) δ ppm 1.93-2.01 (m, 2H) 2.11-2.19 (m, 2H) 2.57 (s, 3H) 2.80 (t, J=11.52 Hz, 1H) 3.01-3.08 (m, 2H) 3.50-3.60 (m, 2H), 3.86 (s, 3H) 4.33 (s, 2H) 6.76 (s, 1H) 6.89 (t, J=7.61 Hz, 1H) 6.96-7.21 (m, 2H) 7.27-7.37 (m, 5H) 7.45 (d, J=8.00 Hz, 2H) 7.71 (d, J=7.81 Hz, 2H) 7.87 (d, J=7.81 Hz, 1H) 8.57 (s, 1H) 9.05 (s, 1H)

1-[4-(2-Methyl-7-phenyl-1,4,9,9b-tetraaza-cyclopenta[a]naphthalen-8-yl)-benzyl]-piperidine-4-carboxylic acid (4-carbamoyl-2-methoxy-phenyl)-amide [CCCLXV]

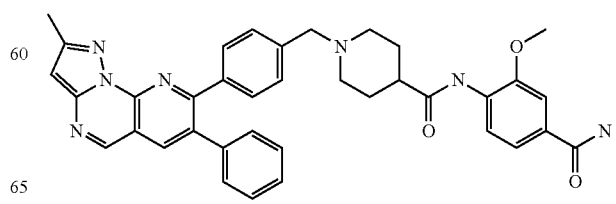

CCCLXV

Compound [CCCLXV] was obtained in a similar way as that for Compound [CLXII]. Data for Compound [CCCLXV]: LCMS m/e 626 (M+H); $^1$H NMR (400 MHz, METHANOL-$d_4$) δ ppm 1.89-2.22 (m, 1H) 2.57 (s, 3H) 2.84-3.14 (m, 2H) 3.39-3.72 (m, 2H) 3.93 (s, 2H) 4.32 (d, J=14.45 Hz, 2H) 6.76 (s, 1H) 7.08 (d, J=8.59 Hz, 1H) 7.32 (dd, J=6.15, 2.64 Hz, 5H) 7.40-7.50 (m, 2H) 7.61-7.76 (m, 3H) 8.57 (s, 1H) 9.05 (s, 1H).

1-[4-(2-Methyl-7-phenyl-1,4,9,9b-tetraaza-cyclopenta[a]naphthalen-8-yl)-benzyl]-piperidine-4-carboxylic acid hydrazide [CCCLXVI]

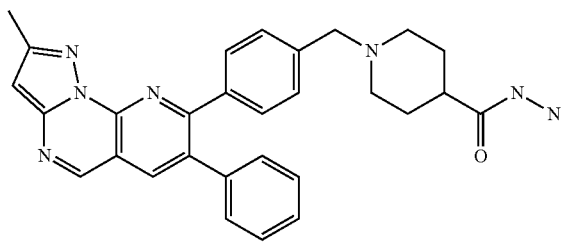

CCCLXVI

Compound [CCCLXVI] was obtained in a similar way as that for Compound [CLXII]. Data for Compound [CCCLXVI] LCMS m/e 492 (M+H); $^1$H NMR (400 MHz, METHANOL-$d_4$) δ ppm 1.77 (q, J=10.82 Hz, 4H) 2.13-2.29 (m, 3H) 2.56 (s, 3H) 3.00 (d, J=11.79 Hz, 2H) 6.73 (s, 1H) 7.23-7.36 (m, 7H) 7.55 (d, J=8.13 Hz, 2H) 8.52 (s, 1H) 9.02 (s, 1H).

trans-1-{3-Methyl-3-hydroxy-1-[4-(2-tert-butyl-7-(thiophen-2-yl)-1,4,9,9b-tetraaza-cyclopenta[a]naphthalen-8-yl)-phenyl]-cyclobutyl}-carbamic acid tert-butyl ester [CCCLXVII]

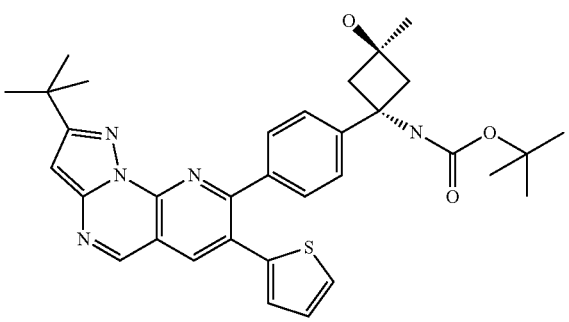

CCCLXVII

Compound [CCCLXVII] was prepared in a similar as for Compound [XL] using Compound [CCLXXXIV] as the starting material. This material was used in the next step without further purification or characterization.

trans-3-Amino-3-[4-(2-tert-butyl-7-(thiophen-2-yl)-1,4,9,9b-tetraaza-cyclopenta[a]naphthalen-8-yl)-phenyl]-1-methyl-cyclobutanol [CCCLXVIII]

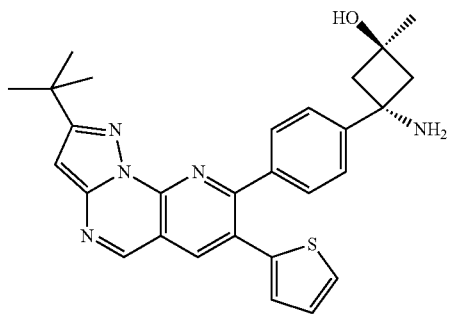

CCCLXVIII

Compound [CCCLXVIII] was prepared in a similar was as Compound [XLIV]. Data for Compound [CCCLXVIII] LCMS trite 484 (M+H); $^1$H NMR (400 MHz, METHANOL-$d_4$) 3 ppm 1.49 (s, 9H) 1.52 (s, 3H) 2.74 (d, J=14.64 Hz, 2H) 2.93 (d, J=14.64 Hz, 2H) 6.85 (s, 1H) 6.93-7.10 (m, 2H) 7.48 (dd, J=4.78, 1.51 Hz, 1H) 7.60 (d, J=8.54 hz, 2H) 7.78 (d, J=8.54 Hz, 2H) 8.68 (s, 1H) 9.04 (s, 1H).

trans-1-{3-Methyl-3-hydroxy-1-[4-tert-butyl-7-(2'-fluorophenyl)-1,4,9,9b-tetraaza-cyclopenta[a]naphthalen-8-yl)-phenyl]-cyclobutyl}-carbamic acid text-butyl ester [CCCLXIX]

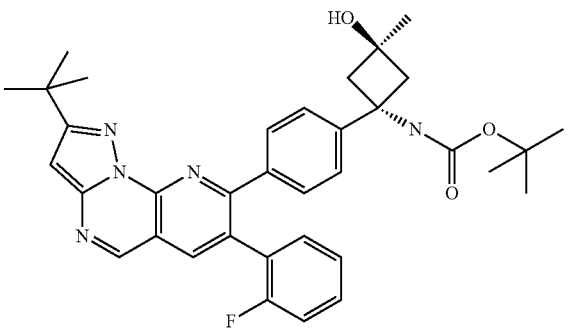

CCCLXIX

Compound [CCCLXIX] was prepared in a similar as for Compound [XL] using Compound [CCLXXXII] as the starting material. This material was used in the next step without further purification or characterization.

trans-3-Amino-3-{4-[2-tert-butyl-7-(2-fluoro-phenyl)-1,4,9,9b-tetraaza-cyclopenta[a]naphthalen-8-yl]-phenyl}-1-methyl-cyclobutanol [CCCLXX]

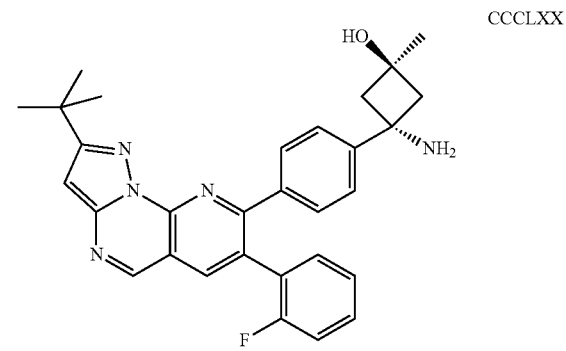 [SMILES: CC(C)(C)c1cc2ncc3cc(-c4ccccc4F)c(-c4ccc([C@]5(N)C[C@](C)(O)C5)cc4)nc3n2n1]

CCCLXX

Compound [CCCLXX] was prepared in a similar was as Compound [XLIV]. Data for Compound [CCCLXX]: LCMS m/e 496 (M+H); $^1$H NMR (400 MHz, METHANOL-d$_4$) δ ppm 1.47 (s, 3H) 1.48 (s, 9H) 2.62-2.73 (m, 2H) 2.80-2.90 (m, 2H) 6.84 (s, 1H) 6.98-7.06 (m, 1H) 7.23 (td, J=7.54, 1.02 Hz, 1H) 7.35-7.48 (m, 2H) 7.48-7.54 (m, 2H) 7.68-7.74 (m, 2H) 8.58 (s, 1H) 9.02 (s, 1H).

trans-1-{3-Methyl-3-hydroxy-1-[4-tert-butyl-7-(thiophen-3-yl)-1,4,9,9b-tetraaza-cyclopenta[a]naphthalen-8-yl)-phenyl]-cyclobutyl}-carbamic acid tert-butyl ester [CCCLXIX]

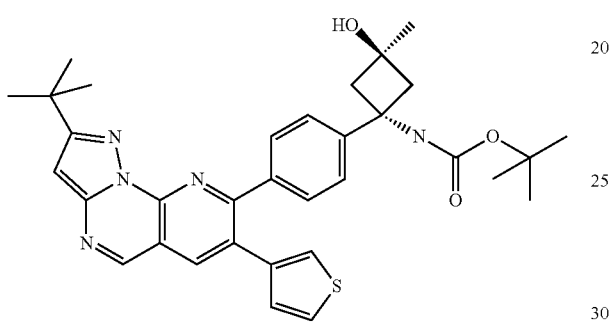

CCCLXXI

Compound [CCCLXXI] was prepared in a similar as for Compound [XL] using Compound [CCLXXXV] as the starting material. This material was used in the next step without further purification or characterization.

trans-3-Amino-3-[4-(2-tert-butyl-7-(thiophen-3-yl)-1,4,9,9b-tetraaza-cyclopenta[a]naphthalen-8-yl)-phenyl]-1-methyl-cyclobutanol [CCCLXXII]

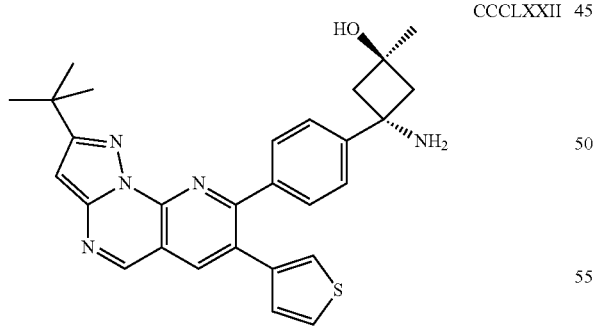

CCCLXXII

Compound [CCCLXXII] was prepared in a similar was as Compound [XLIV]. Data for Compound [CCCLXXII]: LCMS m/e 484 (M+H); $^1$H NMR (400 MHz, METHANOL-d$_4$) δ ppm 1.49 (s, 9H) 1.52 (s, 3H) 2.73 (d, J=14.64 Hz, 2H) 2.92 (d, J=14.74 Hz, 2H) 6.84 (s, 1H) 6.90 (dd, J=4.98, 1.27 Hz, 1H) 7.39 (dd, J=4.98, 2.98 Hz, 1H) 7.41-7.49 (m, 1H) 7.58 (d, J=8.49 Hz, 2H) 7.76 (d, J=8.49 Hz, 2H) 8.64 (s, 1H) 9.04 (s, 1H).

7-Amino-2-methyl-pyrazolo[1,5-a]pyrimidine-6-carboxylic acid hydrazide [CCCLXXIII]

CCCLXXIII

Compound [CCCLXXIII] was prepared in a similar was as Compound [CCXXVII]. Data for Compound [CCCLXXIII]: LCMS (m/e) 193 (M+H); $^1$H NMR (300 MHz, DMSO-d$_6$) δ 4.46 (s, 2H) 6.50 (s, 1H) 8.17 (s, 1H) 8.62 (s, 1H) 935 (s, 1H).

1,3-Dihydro-pyrazolo[5,1-b]purin-2-one [CCCLXXIV]

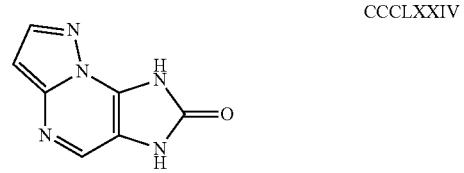 [SMILES: O=c1[nH]c2cnc3ccnn3c2[nH]1]

CCCLXXIV

Compound [CCCLXXIV] was prepared in a similar was as Compound [CCXXVIII]. Data for Compound [CCCLXXIV]: LCMS (m/e) 176 (M+H); $^1$H NMR (300 MHz, DMSO-d$_6$) δ 6.61 (s, 1H) 8.18 (s, 1H) 8.31 (s, 1H) 11.22 (s, 1H).

Pyrazolo[1,5-a]pyrimidine-6,7-diamine [CCLXXV]

CCCLXXV

Compound [CCCLXXV] was prepared in a similar was as Compound [CCXXIX]. Data for Compound [CCCLXXV]: LCMS (m/e) 150 (M+H).

7-Phenyl-1,4,6,9,9b-pentaaza-cyclopenta[a]naphthalen-8-ol [CCCLXXVI]

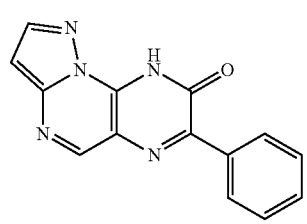

CCCLXXVI

Compound [CCCLXXVI] was prepared in a similar was as Compound [CCXXX]. Data for Compound [CCCLXXVI] (yellowish solid): LCMS (m/e) 264 (M+H).

8-Chloro-7-phenyl-1,4,6,9,9b-pentaaza-cyclopenta[a]naphthalene [CCCLXXVII]

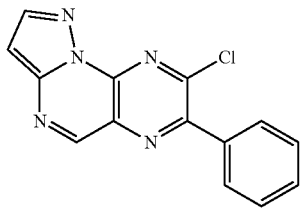

CCCLXXVII

Compound [CCCLXXVII] was prepared in a similar was as Compound [CCXXXI]. Data for Compound [CCCLXXVII] (yellowish solid): LCMS (m/e) 282 (M+H); $^1$H NMR (300 MHz, CHLOROFORM-d) δ 7.01 (s, 1H) 7.56-7.61 (m, 3H) 7.87-7.91 (m, 2H) 8.32 (s, 1H) 9.17 (s, 1H).

trans-2-{3-Hydroxy-3-methyl-1-[4-(7-phenyl-1,4,6,9,9b-pentaaza-cyclopenta[a]naphthalen-8-yl)-phenyl]-cyclobutyl}-isoindole-1,3-dione [CCCLXXVIII]

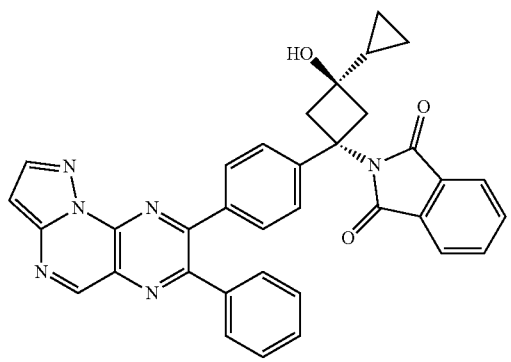

CCCLXXVIII

Compound [CCCLXXVIII] was prepared in a similar as for Compound [XL] using Compound [CCCLXXVII] as the starting material. This material was used in the next step without further purification or characterization.

trans-3-Amino-1-cyclopropyl-3-[4-(7-phenyl-4,5-dihydro-1,4,6,9,9b-pentaaza-cyclopenta[a]naphthalen-8-yl)-phenyl]-cyclobutanol [CCCLXXIX]

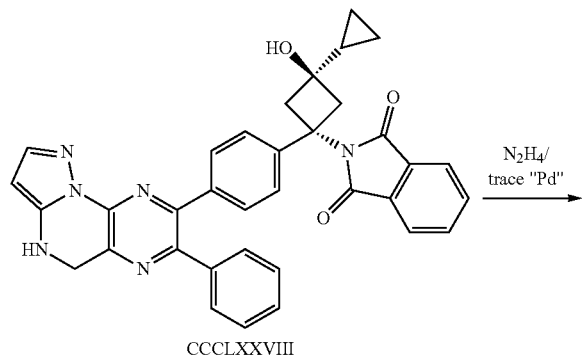

N$_2$H$_4$/ trace "Pd"

CCCLXXVIII

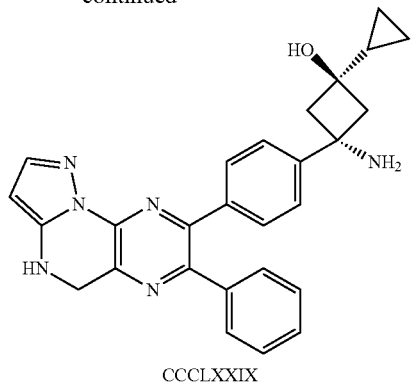

CCCLXXIX

Treatment of Compound [CCCLXXVIII] was under the same conditions as for the preparation of Compound [XLI] furnished Compound [CCCLXXIX]. Data for Compound [CCCLXXIX]: LCMS m/e 451 (M+H); $^1$H NMR. (400 MHz, METHANOL-d$_4$) δ ppm 0.27-0.60 (m, 4H) 1.07-1.38 (m, 1H) 2.54-2.70 (m, 2H) 2.70-2.86 (m, 2H) 4.72 (s, 2H) 7.14-7.98 (m, 11H).

trans-3-Amino-1-cyclopropyl-3-[4-(7-phenyl-1,4,6,9,9b-pentaaza-cyclopenta[a]naphthalen-8-yl)-phenyl]-cyclobutanol [CCCLXXX]

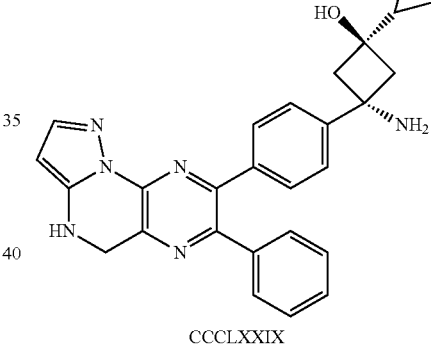

CCCLXXIX

MnO$_2$/THF →

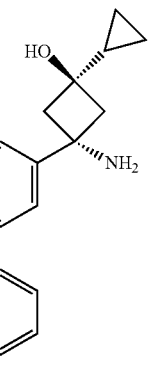

CCCLXXX

Compound [CCCLXXIX] was dissolved in anhydrous THF (15 mL), to which solution was added manganese dioxide (60 mg). The mixture was stirred for 1 h and the precipitation was filtered. The solvent was removed by rotary evaporation and the crude product was purified by HPLC to obtain Compound [CCCLXXX] as a yellow solid: LCMS m/e 449 (M+H); $^1$H NMR (400 MHz, METHANOL-d$_4$) δ ppm 0.27-0.73 (m, 4H) 1.07-1.35 (m, 1H) 2.63 (d, J=14.25 Hz, 2H) 2.81

(d, J=14.25 Hz, 2H) 7.05 (d, J=2.15 Hz, 1H) 7.27-7.45 (m, 3H) 7.52-7.67 (m, 4H) 7.82 (d, J=8.49 Hz, 2H) 8.34 (d, J=2.15 Hz, 1H) 9.22 (s, 1H).

trans-1-{3-Methyl-3-hydroxy-1-[4-(7-phenyl-1,4,6,9,9b-pentaaza-cyclopenta[a]naphthalen-8-yl)-phenyl]-cyclobutyl}-carbamic acid text-butyl ester [CCCLXXXI]

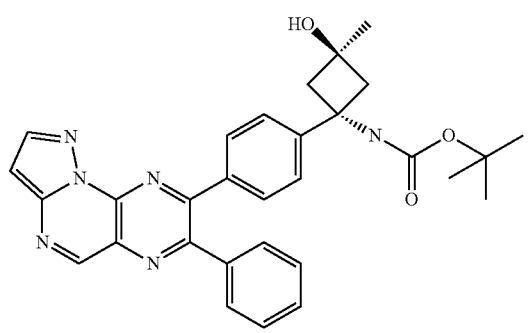

CCCLXXXI

Compound [CCCLXXXI] was prepared in a similar as for Compound [XL] using Compound [CCCLXXVII] as the starting material. This material was used in the next step without further purification or characterization.

trans-3-Amino-1-methyl-3-[4-(7-phenyl-1,4,6,9,9b-pentaaza-cyclopenta[a]naphthalen-8-yl)-phenyl]-cyclobutanol [CCCLXXXII]

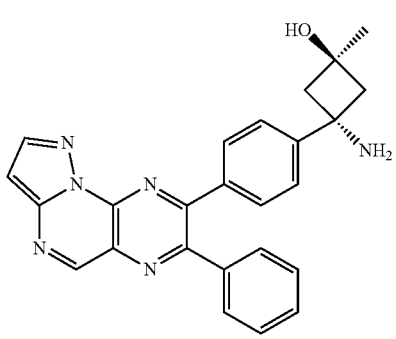

CCCXXXII

Compound [CCCLXXXII] was prepared in a similar as for Compound [XLIV]. Data for Compound [CCCLXXXII] LCMS m/e 423 (M+H); $^1$H NMR (400 MHz, METHANOL-$d_4$) δ ppm 1.51 (s, 3H) 2.72 (d, J=14.55 Hz, 2H) 2.90 (d, J=14.55 Hz, 2H) 7.05 (d, J=2.10 Hz, 1H) 7.30-7.49 (m, 3H) 7.51-7.68 (m, 4H) 7.83 (d, J=8.40 Hz, 2H) 8.34 (d, J=2.10 Hz, 1H) 9.22 (s, 1H).

Ethyl 7-amino-5-methylpyrazolo[1,5-a]pyrimidine-6-carboxylate [CCCLXXXIII]

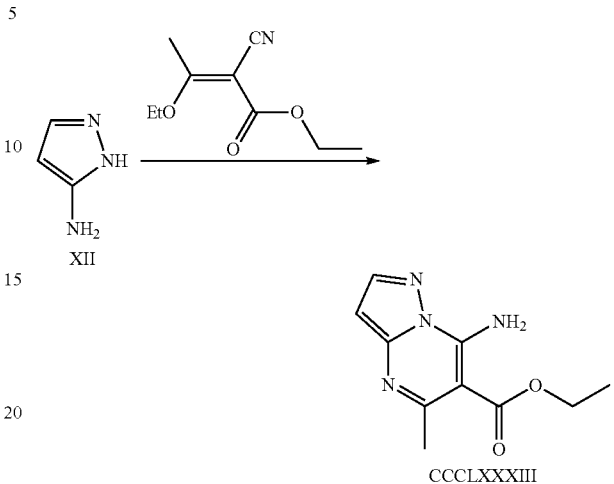

To a 1000 mL 3-necked round-bottom flask was added Compound [XII] (10 g, 120 mmol, 1.00 eq.), ethyl 2-cyano-3-ethoxybut-2-enoate (23 g, 126 mmol, 1.05 eq.), and HOAc (400 mL). The mixture was heated at 100° C. for 16 h. The solid was filtered out. The reaction was concentrated and the residue was treated with H$_2$O (200 mL). The resulting precipitate was filtered, and the precipitate washed with H$_2$O (200 mL). The crude product was dried in an oven to afford Compound [CCCLXXXIII]: LCMS (m/e) 221 (M+H); $^1$H NMR (300 MHz, DMSO-$d_6$) δ 1.32 (t, J=7.20 Hz, 3H) 2.62 (s, 3H) 4.29 (q, J=7.20 Hz, 2H) 6.39 (s, 1H) 8.15 (s, 1H) 8.50 (br.s, 2H).

(7-Amino-5-methylpyrazolo[1,5-a]pyrimidin-6-yl)methanol [CCCLXXXIV]

To a 250 mL three-necked round bottom flask was added Compound [CCCLXXXIII] (3.3 g, 15.0 mmol, 1.00 eq.) and THF (60 mL). The mixture was cooled to 0° C. and LiBHEt$_3$ (48 mL of a 1.0 M solution in THF, 48 mmol, 3.3 eq.) was added slowly through an addition funnel under nitrogen. After addition, the mixture was stirred at room temperature overnight. The mixture was slowly treated with EtOAc (60 mL) and then water (30 mL). The layers were separated and the aqueous phase was extracted with EtOAc (2×30 mL). The combined organic phases were dried over anhydrous Na$_2$SO$_4$. After filtration and concentration, the residue was purified by a silica gel column with dichloromethane/methanol (15:1). Concentration by rotary evaporation provided Compound [CCCLXXXIV] as a light yellowish solid. This material was used in the next step without father characterization.

7-Amino-5-methylpyrazolo[1,5-a]pyrimidine-6-carbaldehyde [CCCLXXXV]

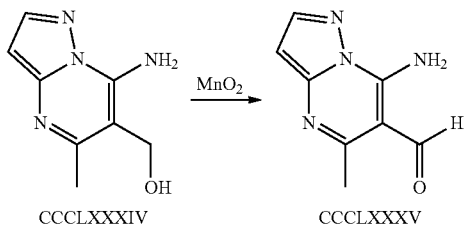

To a 1 L round bottom flask containing Compound [CCCLXXXIV] (2.33 g, 13.1 mmol, 1.00 eq.) was added CHCl$_3$ (200 mL) and THF (100 mL) followed by MnO$_2$ (9.2 g, 106 mmol, 10.00 eq.). The mixture was stirred at room temperature for 2 days. The mixture was filtered and the filtered material washed with CH$_2$Cl$_2$: MeOH until no additional product was observed through analysis of the filtrates by TLC. The resulting mixture was concentrated under vacuum and provided Compound [CCCLXXXV] as a yellowish solid. LCMS m/e 177 (M+H); $^1$H NMR (300 MHz, DMSO-d$_6$) δ 2.67 (s, 3H) 6.44 (s, 1H) 8.19 (s, 1H) 9.08 (br.s, 1H) 9.47 (br.s, 1H) 10.15 (s, 1H).

5-Methyl-7-phenyl-9H-1,4,9,9b-tetraaza-cyclopenta[a]naphthalen-8-one [CCCLXXXVI](DBU Procedure)

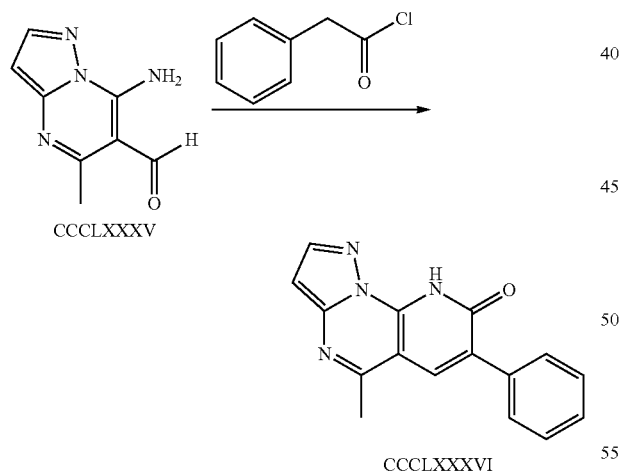

To a 50 id, round-bottom flask was added Compound [CCCLXXXV] (500 mg, 2.84 mmol, 1.00 eq.), DBU (1.72 g, 11.3 mmol, 4.00 eq.) and DMF (10 mL), then 2-phenylacetyl chloride (880 mg in 10 mL of DMF, 5.68 mmol, 2.00 eq.) was added dropwise at room temperature. The reaction was stirred at room temperature overnight. The solvent and reagent were removed in vacuo. The residue was dissolved in 50 mL of CH$_2$Cl$_2$ and purified on a silica gel column with dichloromethane/methanol (50:1) to afford Compound [CCCLXXXVI] as a yellowish solid: LCMS (m/e): 277 (M+H); $^1$H NMR (300 MHz, DMSO-d6) δ 2.80 (s, 3H) 6.66 (s, 1H) 7.41 (m, 3H) 7.77 (d, J=6.9 Hz, 2H) 8.23 (s, 1H) 8.30 (s, 1H).

8-Chloro-5-methyl-7-phenyl-1,4,9,9b-tetraaza-cyclopenta[a]naphthalene [CCCLXXXVII]

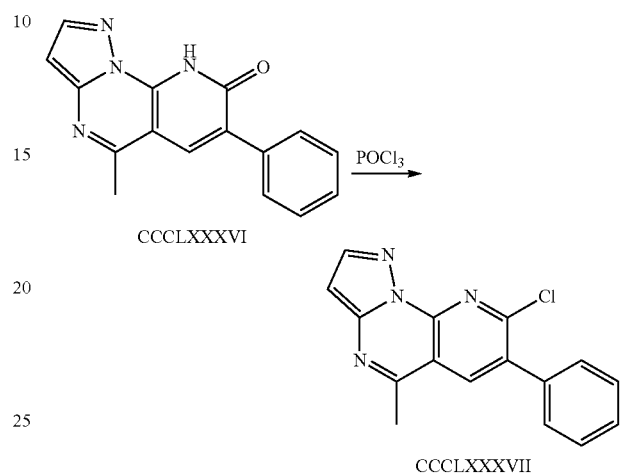

To a 50 mL round bottom flask was added Compound [CCCLXXXVI] (500 mg, 1.81 mmol, 1.00 eq.), POCl$_3$ (10 mL). The mixture was heated to reflux in an oil bath for 4 h. The reaction was concentrated in vacuo and adjusted the pH value to 8 with 100 mL sat. NaHCO$_3$. The mixture was extracted three times with 100 ml CH$_2$Cl$_2$ and the organic layers were collected. The combined organic phases were dried over Na$_2$SO$_4$, filtered, concentrated and purified by silica gel chromatography using EtOAc:petroleum ether (1:2) as the eluent to give Compound [CCCLXXXVII]: LCMS (m/e) 295 (M+H); $^1$H NMR (300 MHz, CHLOROFORM-d) δ 2.89 (s, 3H) 6.79 (s, 1H) 7.53 (s, 5H) 8.18 (s, 1H) 8.27 (s, 1H).

trans-1-{3-Methyl-3-hydroxy-1-[4-(5-methyl-7-phenyl-1,4,9,9b-tetraaza-cyclopenta[a]naphthalen-8-yl)-phenyl]-cyclobutyl}-carbamic acid tert-butyl ester [CCCLXXXVIII]

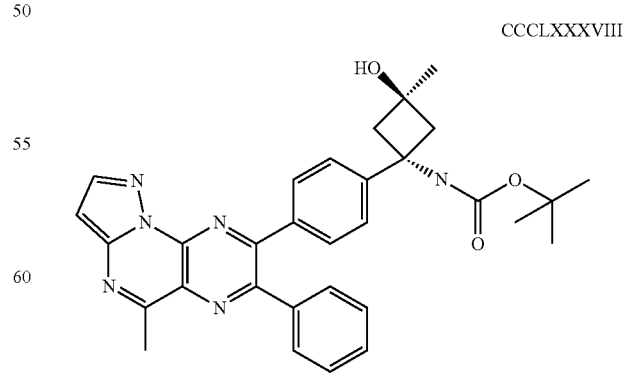

Compound [CCCLXXXVIII] was prepared in a similar as for Compound [XL] using Compound [CCCLXXXVII] as trans-3-Amino-1-methyl-3-[4-(5-methyl-7-phenyl-1,4,9,9b-tetraaza-cyclopenta[a]naphthalen-8-yl)-phenyl]-cyclobutanol [CCCLXXXIX]

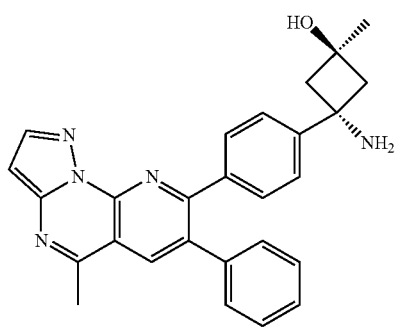

CCCLXXXIX

Compound [CCCLXXXIX] was prepared in a similar as for Compound [XLIV]. Data for Compound [CCCLXXXIX]: LCMS m/e 436 (M+H); $^1$H NMR (400 MHz, METHANOL-$d_4$) δ ppm 1.50 (s, 3H) 2.71 (d, J=14.64 Hz, 2H) 2.88 (d, J=14.64 Hz, 2H) 2.95 (s, 3H) 6.82 (d, J=2.15 Hz, 1H) 7.37 (s, 5H) 7.45-7.56 (m, 2H) 7.65-7.78) m, 2H) 8.20 (d, J=2.10 Hz, 1H) 8.60 (s, 1H).

7-Thiophene-1,4,6,9b-pentaaza-cyclopenta[a]naphthalen-8-ol [CCCXC]

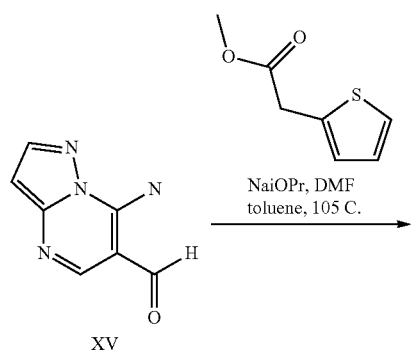

To a 100 mL round-bottom flask was added Compound [XV] (1.12 g, 6.91 mmol, 1.00 eq), Toluene (18 mL), methyl 2-(thiophen-2-yl)acetate (4.31 g, 27.6 mmol, 4.00 eq.), sodium 2-methylpropan-2-olate (870 mg, 9.06 mmol, 2.00 eq.). The resulting solution was stirred for 30 min at 105° C., DMF (18 mL) was added. The mixture was stirred at 105° C. for 3 days, then cooled to room temperature, concentrated and was purified by a silica gel column with $CH_2Cl_2$:MeOH (25:1) to afford Compound [CCCXC] as a yellow solid: LCMS (m/e) 269 (M+H).

8-Chloro-7-phenyl-1,4,6,9b-pentaaza-cyclopenta[a]naphthalene [CCCXCI]

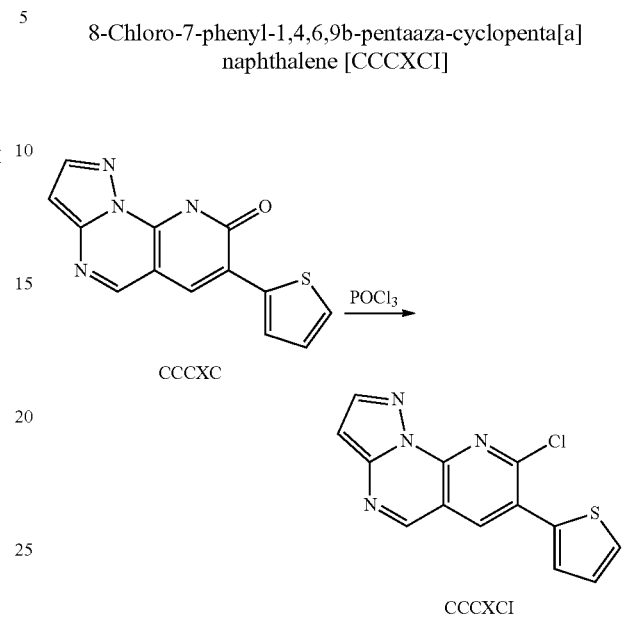

To a 50-mL round-bottom flask was added Compound [CCCXC] (1.5 g, 5.60 mmol, 1.00 eq.), $POCl_3$ (20 mL). The resulting solution was stirred for 1.5 h at 100° C. then the mixture was cooled. The pH value of the solution was adjusted to 8 with sodium bicarbonate and the resulting mixture extracted with of ethyl acetate (3×50 mL) and the organic layers combined and dried over $Na_2SO_4$, concentrated, and then purified by a silica gel column with $CH_2Cl_2$/MeOH (60:1) to afford Compound [CCXCI] as a yellow solid: LCMS (m/e): 287 (M+H); $^1$HNMR (300 MHz, CHLOROFORM-d) δ: 6.94 (s, 1H) 7.1-7.22 (m, 1H) 7.51-7.51 (m, 2H) 8.25 (s, 1H) 8.39 (s, 1H) 8.89 (s, 1H).

trans-1-{3-Methyl-3-hydroxy-1-[4-(5-methyl-7-(thiophen-2-yl)-1,4,9,9b-tetraaza-cyclopenta[a]naphthalen-8-yl)-phenyl]-cyclobutyl}-carbamic acid tert-butyl ester [CCCXCII]

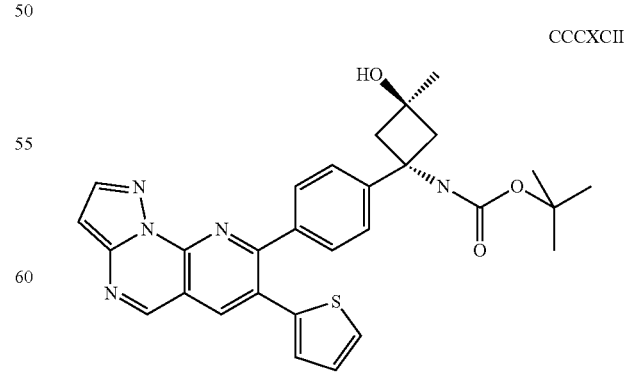

CCCXCII

Compound [CCCXCII] was prepared in a similar as for Compound [XL] using Compound [CCCXCI] as the starting trans-3-Amino-1-methyl-3-[4-(7-thiophen-2-yl-1,4,9,9b-tetraaza-cyclopenta[a]naphthalen-8-yl)-phenyl]-cyclobutanol [CCCXCIII]

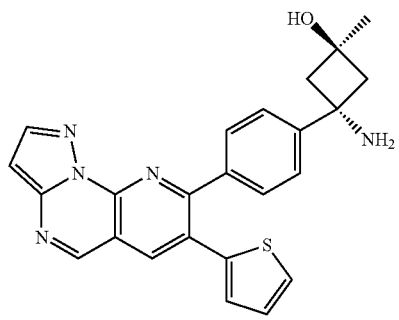

Compound [CCCXCIII] was prepared in a similar as for Compound [XLIV]. Data for Compound [CCCXCIII]: LCMS m/e 428 (M+H); $^1$H NMR (400 MHz, METHANOL-d$_4$) δ ppm 1.54 (s, 3H) 1.94 (s, 3H) 2.62 (d, J=14.06 Hz, 2H) 2.84 (d, J=14.01 Hz, 2H) 6.97 (d, J=2.15 Hz, 1H) 6.99-7.13 (m, 2H) 7.55 (d, J=8.49 Hz, 2H) 7.75 (d, J=8.44 Hz, 2H) 8.26 (d, J=2.20 Hz, 1H) 8.71 (s, 1H) 9.11 (s, 1H).

trans-3-Amino-1-cyclopropyl-3-[4-(2-methyl-3,7-diphenyl-1,4,9,9b-tetraaza-cyclopenta[a]naphthalen-8-yl)-phenyl]-cyclobutanol [CCCXCIV]

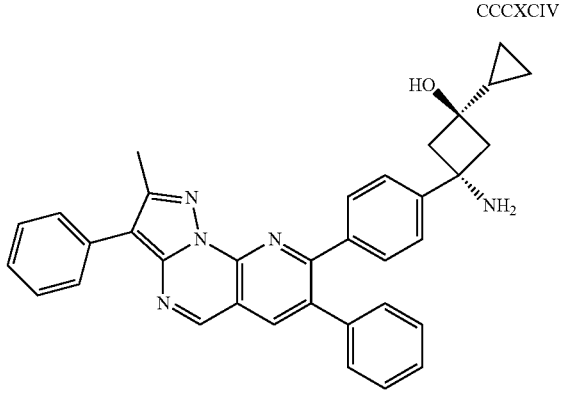 [SMILES: Cc1nn2c(ncc3cc(-c4ccccc4)c(-c4ccc([C@]5(N)C[C@@](O)(C6CC6)C5)cc4)nc32)c1-c1ccccc1]

Compound [CCCXCIV] was prepared using a procedure similar to that of [CCXLII]. Data for Compound [CCCXCIV]: LCMS (m/e) 538 (M+H); NMR (400 MHz, METHANOL-d4) δ ppm 0.38-0.54 (m, 4H) 1.12-1.23 (m, 1H) 2.59-2.65 (m, 2H) 2.68 (s, 3H) 2.74-2.83 (m, 1H) 7.31-7.42 (m, 6H) 7.47-7.58 (m, 4H) 7.71-7.78 (m, 4H) 8.56 (s, 1H) 9.06 (s, 1H).

trans-3-Amino-1-cyclopropyl-3-{4-[3-(4-methoxyphenyl)-2-methyl-7-phenyl-1,4,9,9b-tetraaza-cyclopenta[a]naphthalen-8-yl]-phenyl}-cyclobutanol [CCCXCV]

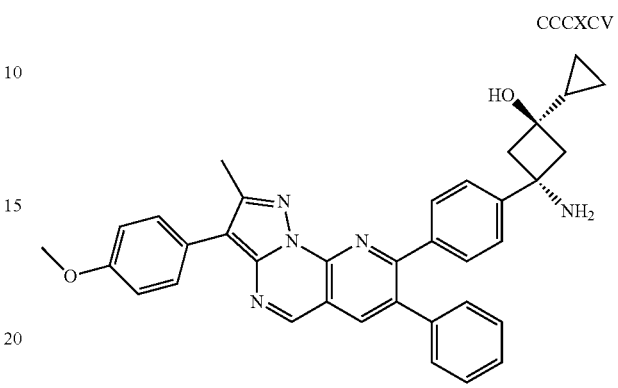

Compound [CCCXCV] was prepared using a procedure similar to that of [CCXLII]. Data for Compound [CCCXCV]: LCMS (m/e) 568 (M+H); $^1$H NMR (400 MHz, METHANOL-d4) δ ppm 0.33-0.56 (m, 4H) 1.13-1.24 (m, 1H) 2.57-2.64 (m, 2H) 2.66 (s, 3H) 2.75-2.83 (m, 2H) 3.86 (s, 3H) 7.02-7.10 (m, 2H) 7.27-7.39 (m, 5H) 7.51-7.56 (m, 2H) 7.62-7.69 (m, 2H) 7.74 (d, J=8.42 Hz, 2H) 8.54 (s, 1H) 9.02 (s, 1H).

trans-3-Amino-1-cyclopropyl-3-[4-(2-methyl-7-phenyl-3-pyridin-4-yl-1,4,9,9b-tetraaza-cyclopenta[a]naphthalen-8-yl)-phenyl]-cyclobutanol [CCCXCVI]

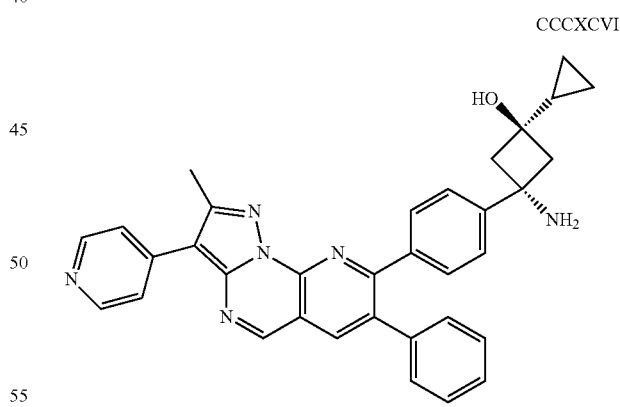

Compound [CCCXCVI] was prepared using a procedure similar to that of [CCXLII]. Data for Compound [CCCXCVI]: LCMS (m/e) 539 (M+H); $^1$H NMR (400 MHz, METHANOL-d4) δ ppm 0.41 (d, J=4.49 Hz, 2H) 0.48 (d, J=8.00 Hz, 2H) 1.18 (t, J=8.10 Hz, 1H) 2.62 (d, J=14.25 Hz, 2H) 2.79 (d, J=14.06 Hz, 2H) 2.92 (s, 3H) 7.36 (s, 5H) 7.57 (d, J=8.20 Hz, 2H) 7.75 (d, J=8.20 Hz, 2H) 8.69 (d, J=6.25 Hz, 2H) 8.71 (s, 1H) 8.79 (d, J=6.44 Hz, 2H) 9.38 (s, 1H).

351 trans-2-[1-(4-Bromo-phenyl)-3-ethyl-3-hydroxy-cyclobutyl]-isoindole-1,3-dione [CCCXCVII]

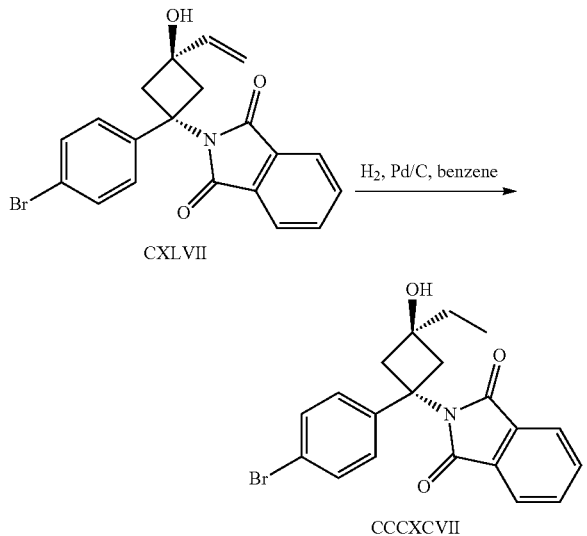

A 50-mL round-bottom flask was added a solution of Compound [CXLVII] (700 mg, 1.76 mmol, 1.00 eq.) in benzene (50 mL), Pd/C (300 mg). Then hydrogen was bubbled by a balloon. The mixture was stirred for 4 h at room temperature. The solid was filtered out. The resulting mixture was concentrated in vacuum and purified by flash-HPLC to give Compound [CCCXCVII] as a white solid: LCMS (m/e) 400 (M+H); $^1$H NMR (300 MHz, CHLOROFORM-d) δ ppm 1.15 (t, 3H) 1.64 (q, 2H) 3.17-3.20 (m, 2H) 3.29-3.32 (m, 2H) 7.47-7.87 (m, 8H).

trans-{3-Ethyl-3-hydroxy-1-[4-(4,4,5,5-tetramethyl-[1,3,2]dioxaborolan-2-yl)-phenyl]-cyclobutyl}-isoindole-1,3-dione [CCCXCVIII]

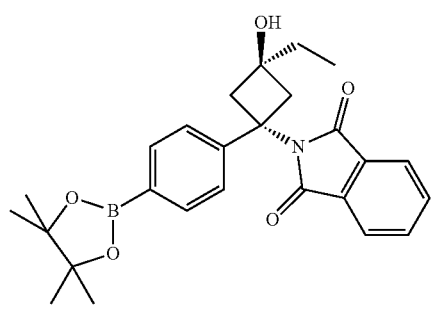

Compound [CCCXCVIII] was prepared using a procedure similar to that of [XXXIX]. Data for Compound [CCCXCVIII]: LCMS (m/e) 430 (M–H$_2$O); $^1$H NMR (300 MHz, CHLOROFORM-d) δ ppm 0.92-0.97 (t, J=7.2 Hz, 3H) 1.32 (s, 12H) 1.64 (q, J=7.2 Hz) 3.12-3.17 (m, 2H) 3.27-3.32 (m, 2H) 7.66-7.83 (m, 8H).

352 trans-2-{3-Ethyl-3-hydroxy-1-[4-(2-methyl-7-phenyl-1,4,9,9b-tetraaza-cyclopenta[a]naphthalen-8-yl)-phenyl]-cyclobutyl}-isoindole-1,3-dione [CCCXCIX]

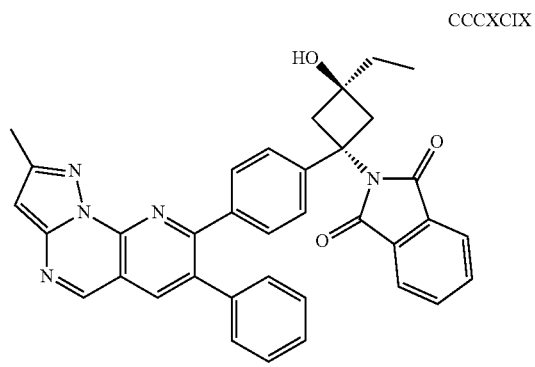 [SMILES: CC[C@]1(O)C[C@](c2ccc(-c3nc4c(cnc5cc(C)nn54)cc3-c3ccccc3)cc2)(N2C(=O)c3ccccc3C2=O)C1]

Compound [CCCXCIX] was prepared using a procedure similar to that of [XL]. Data for Compound [CCCXCIX]: LCMS (m/e) 580 (M+H).

trans-3-Amino-1-ethyl-3-[4-(2-methyl-7-phenyl-1,4,9,9b-tetraaza-cyclopenta[a]naphthalen-8-yl)-phenyl]-cyclobutanol [CD]

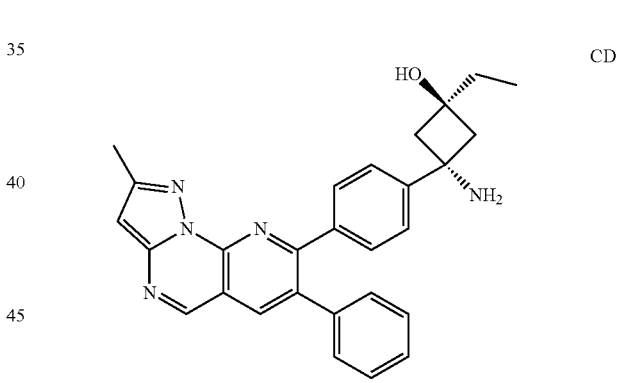

Compound [CD] was prepared using a procedure similar to that of [XLI]. Data for Compound [CD]: LCMS (m/e) 450 (M+H); $^1$H NMR (400 MHz, METHANOL-d4) δ ppm 0.92 (t, J=7.35 Hz, 3H) 1.76 (q, J=7.24 Hz, 2H) 1.91 (s, 3H) 2.50-2.56 (m, 2H) 2.56 (s, 3H) 2.67-2.78 (m, 2H) 6.74 (s, 1H) 7.24-7.37 (m, 5H) 7.40-7.53 (m, 2H) 7.61-7.74 (m, 2H) 8.52 (s, 1H) 9.02 (s, 1H).

Scheme-Synthesis of [XI]

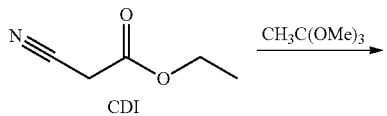

353
-continued

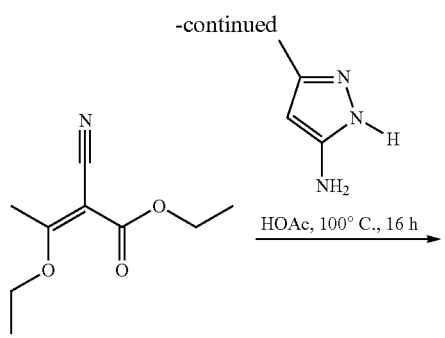

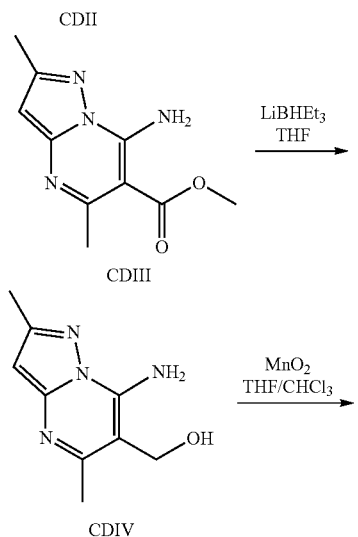

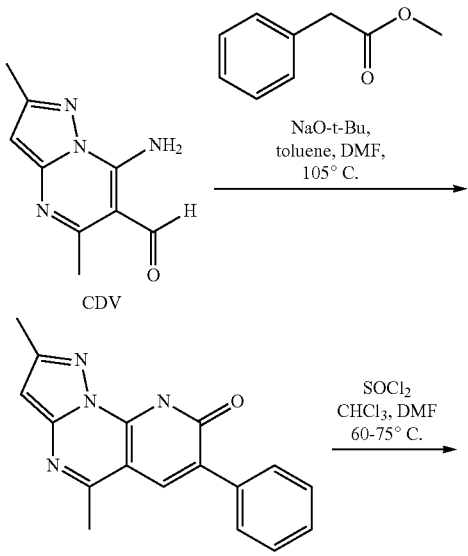

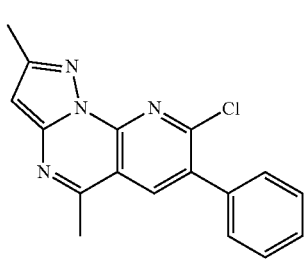

354

(Z)-2-Cyano-3-ethoxy-but-2-enoic acid ethyl ester [CDII]

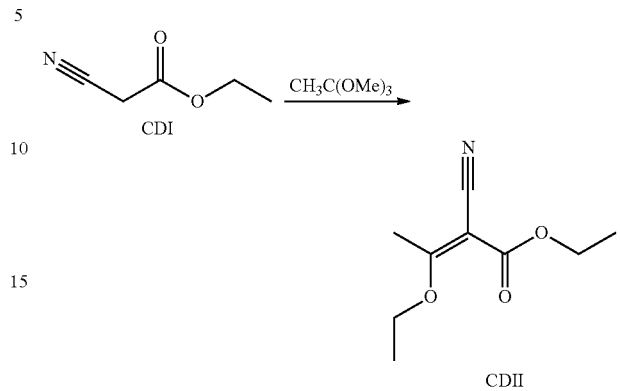

To a 2000 mL round-bottom flask was added $CH_3C(OEt)_3$ (583.2 g, 3.6 mol, 1.00 eq.) and Compound [CDI] (407.2 g, 3.6 mol, 1.00 eq.) in $Ac_2O$ (1000 mL). The mixture was heated to reflux at 130-150° C. for 3 hours. The reaction mixture was concentrated to a small volume and then allowed to cool to room temperature. The mixture was allowed to sit in refrigerate overnight. The precipitated solid was filtered and dried in vacuo to give Compound [CDII] as yellow solid: LCMS (m/e) 184 (M+H).

7-Amino-2,5-dimethylpyrazolo[1,5-a]pyrimidine-6-carboxylic acid ethyl ester [CDIII]

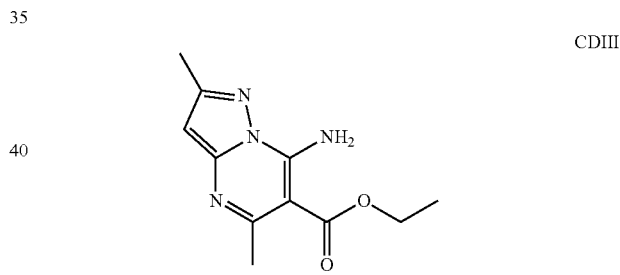

Compound was prepared using a procedure similar to that of Compound [VII]. Data for Compound [CDIII]: LCMS (m/e) 235 (M+H).

(7-Amino-2,5-dimethylpyrazolo[1,5-a]pyrimidine-6-yl)-methanol [CDIV]

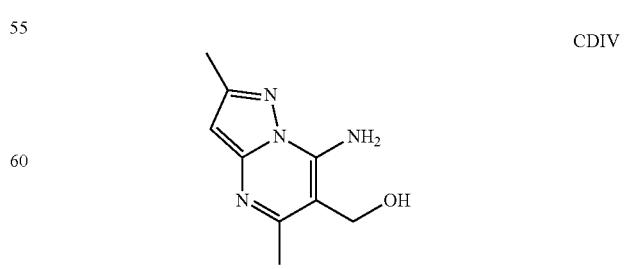

Compound [CDIV] was prepared using a procedure similar to that of Compound [II]. Data for Compound [CDIV]:

LCMS (m/e) 193 (M+H); ¹H NMR (300 MHz, DMSO-d₆) δ ppm 7.27 (s, 2H) 6.02 (s, 1H) 4.73 (t, 1H) 4.53-4.55 (d, 2H) 2.42 (s, 3H) 2.36 (s, 3H).

7-Amino-2,5-dimethylpyrazolo[1,5-a]pyrimidine-6-carbaldehyde [CDV]

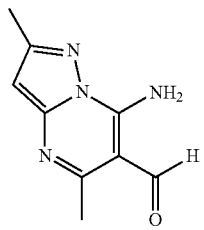
CDV

Compound [CDV] was prepared using a procedure similar to that of Compound [III]. Data for Compound [CDV]: LCMS (m/e) 191 (M+H); ¹H NMR (300 MHz, CHLOROFORM-d) δ ppm 10.21 (s, 1H) 9.59 (s, 1H) 6.93 (s, 1H) 6.28 (s, 1H) 2.76 (s, 3H) 2.47 (s, 3H).

2,5-Dimethyl-7-phenyl-1,4,9,9b-tetraaza-cyclopenta[a]naphthalene-8-ol [CIX] (from CDV)

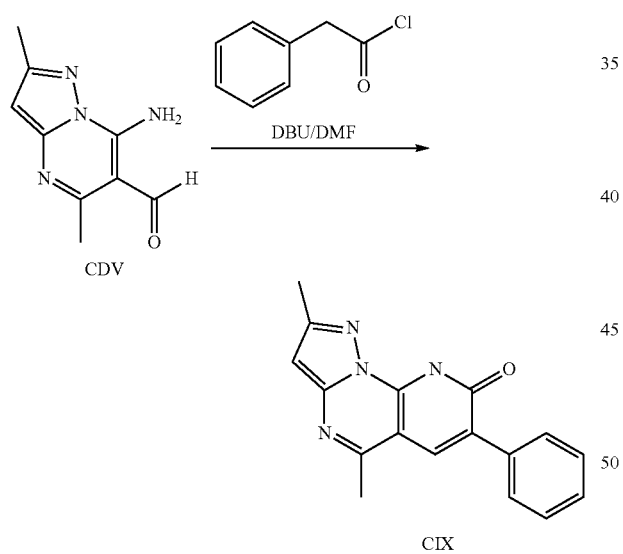

To a 250 mL round-bottom flask was added Compound [CDV] (6.7 g, 35.3 mmol, 1.00 eq.), DBU (7.6 g, 50.00 mmol, 1.40 eq.), and DMF (170 mL). Then 2-phenylacetyl chloride (21.44 g in DMF of 20 mL, 139 mmol, 4.00 eq.) was added dropwise at room temperature. The reaction was stirred at room temperature overnight. The solvent and reagent were removed in vacuo. The residue was dissolved in 10 mL of CH₂Cl₂ and purified by silica gel chromatography using MeOH/DCM as the eluant to give Compound [CIX] as a light yellowish solid: LCMS (m/e) 291 (M+H); ¹H NMR (400 MHz, CHLOROFORM-d) δ ppm 2.50 (s, 3H) 2.75 (s, 3H) 7.37-7.70 (m, 5H) 7.96 (s, 1H).

trans-3-Amino-1-cyclopropyl-3-[4-(3-bromo-2-methyl-7-phenyl-1,4,6,9,9b-pentaaza-cyclopenta[a]naphthalen-8-yl)-phenyl]-cyclobutanol [CDVI]

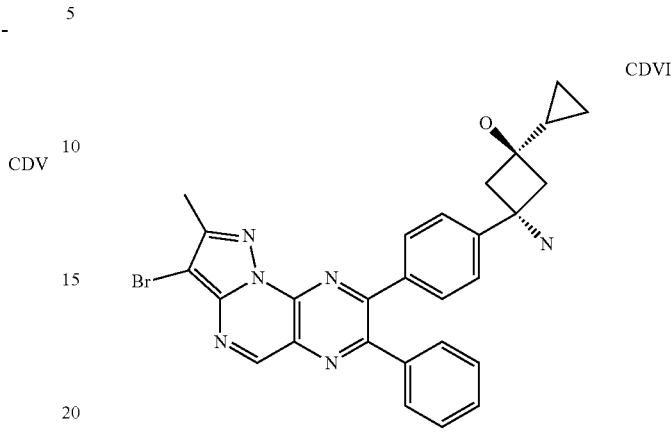

Compound [CDVI] was prepared in a similar way as that for Compound [CV]. This material was used in the next step without further characterization.

trans-3-Amino-1-cyclopropyl-3-[4-(2,3-dimethyl-7-phenyl-1,4,6,9,9b-pentaaza-cyclopenta[a]naphthalen-8-yl)-phenyl]-cyclobutanol [CDVII]

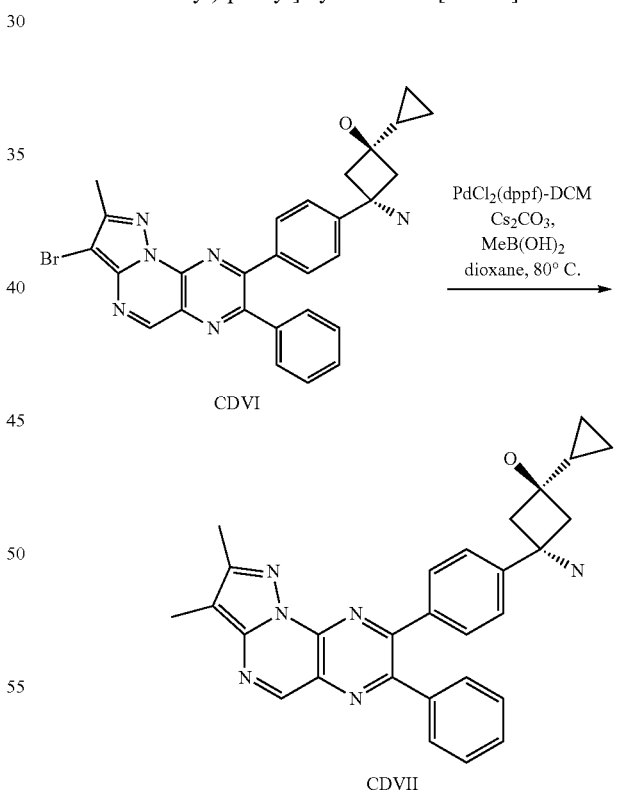

A 20 ml scintillation vial containing Compound [CDVI] (96 mg, 0.17 mmol), MeB(OH)₂ (306 mg, 5.1 mmol), Cs₂CO₃ (662 mg, 1.7 mmol), and dioxane (10 ml) was evacuated and flushed three times with nitrogen. Then PdCl₂(dppf)-DCM (21 mg, 0.026 mmol) was added and the resulting solution was evacuated and flushed three times with nitrogen. The mixture was heated at 80° C. for 2.5 h. LCMS indicated the product was formed as a major product. Then it was allowed to cool and concentrated. The residue was dissolved with MeOH (5 mL). After filtration, the filtrate was purified by reverse-phase preparative HPLC using water-acetonitrile-TFA [95:5:0.05] and acetonitrile-water-TFA [95:5:0.05] as the mobile phases to provide Compound [CDVII] as a yellow solid:

LCMS (m/e) 476 (M+1); $^1$H NMR (400 MHz, METHANOL-d4) δ ppm 0.35-0.51 (m, 4H) 1.11-1.22 (m, 1H) 2.34 (s, 3H) 2.50 (s, 3H) 2.56-2.64 (m, 2H) 2.72-2.81 (m, 2H) 7.26-7.36 (m, 5H) 7.51 (d, J=8.49 Hz, 2H) 7.70 (d, J=8.40 Hz, 2H) 8.49 (s, 1H) 8.94 (s, 1H).

trans-{3-Hydroxy-3-methyl-1-[4-(2-methyl-6,7-diphenyl-1,4,9,9b-tetraaza-cyclopenta[a]naphthalen-8-yl)-phenyl]-cyclobutyl}-carbamic acid tert-butyl ester [CDVIII]

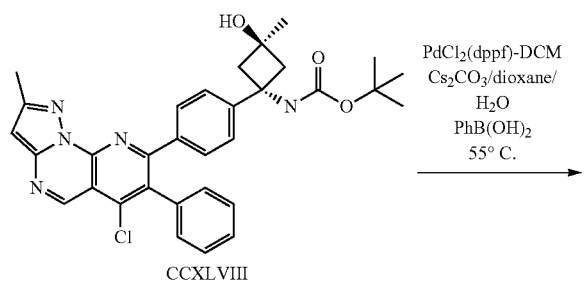

A 20 ml scintillation vial containing Compound [CCXLVIII] (90 mg, 0.16 mmol, 1 eq.), the borate (98 mg, 0.8 mmol, 5 eq.), Cs$_2$CO$_3$ (260 mg, 0.8 mmol, 5 eq.), dioxane (5.0 ml), and water (0.8 ml) was evacuated and flushed three times with nitrogen. Then PdCl$_2$(dppf)-CH$_2$Cl$_2$ (13 mg, 0.016 mmol, 0.15 eq.) was added and the resulting solution was evacuated and flushed three times with nitrogen. The mixture was heated at 55° C. for 3 h. Then it was allowed to cool. The solvent was removed in vacuo. The residue was dissolved in CH$_2$Cl$_2$ (10 mL). After filtration and concentration, it was purified by silica gel chromatography by using MeOH and CH$_2$Cl$_2$ as the mobile phases to furnish Compound [CDVIII] as a yellowish solid (97 mg, 99%): LCMS (m/e) 612 (M+H).

trans-3-Amino-1-methyl-3-[4-(2-methyl-6,7-diphenyl-1,4,9,9b-tetraaza-cyclopenta[a]naphthalen-8-yl)-phenyl]-cyclobutanol [CDIX]

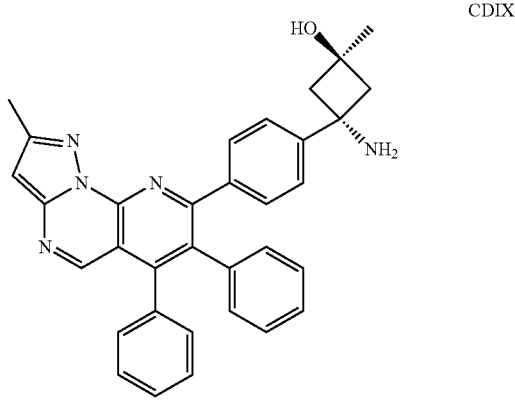 [SMILES: Cc1cc2ncc3c(-c4ccccc4)c(-c4ccccc4)c(-c4ccc([C@]5(N)C[C@](C)(O)C5)cc4)nc3n2n1]

Compound [CDIX] was prepared using a procedure similar to that of Compound [XLIV]. Data for Compound [CDIX]: LCMS (m/e) 512 (M+H); $^1$H NMR (400 MHz, METHANOL-d4) δ ppm 1.46 (s, 3H) 2.57 (s, 3H) 2.60-2.71 (m, 7H) 2.78-2.88 (m, 2H) 6.73 (s, 1H) 6.92-7.12 (m, 5H) 7.14-7.29 (m, 3H) 7.29 7.39 (m, 4H) 7.39-7.53 (m, 2H) 7.60-7.78 (m, 2H) 8.48 (s, 1H).

trans-{3-Hydroxy-1-[4-(6-hydroxy-2-methyl-7-phenyl-1,4,9,9b-tetraaza-cyclopenta[a]naphthalen-8-yl)-phenyl]-3-methyl-cyclobutyl}-carbamic acid tert-butyl ester [CDX]

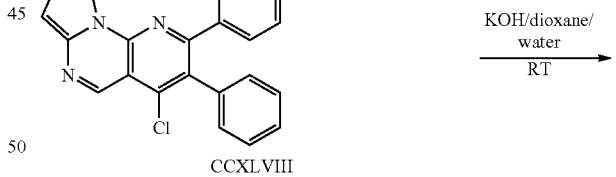

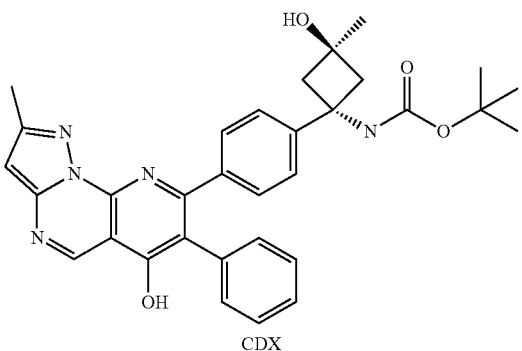

A 20 ml scintillation vial containing Compound [CCX-LVIII] (100 mg, 0.18 mmol), dioxane (2 ml), water (2 ml), and KOH (400 mg) was stirred at RT for 36 h. Then it was dissolved in DCM (10 mL) and water (2 mL). The water solution was extracted with DCM. The combined organic solution was concentrated. The residue was dissolved in $CH_2Cl_2$ (1.5 mL) and purified by silica gel chromatography by using MeOH and $CH_2Cl_2$ as the mobile phases to furnish Compound [CDX] as a yellowish solid (79 mg, 78%): LCMS (m/e) 552 (M+H).

trans-8-[4-(1-Amino-3-hydroxy-3-methyl-cyclobutyl)-phenyl]-2-methyl-7-phenyl-1,4,9,9b-tetraaza-cyclopenta[a]naphthalen-6-ol [CDXI]

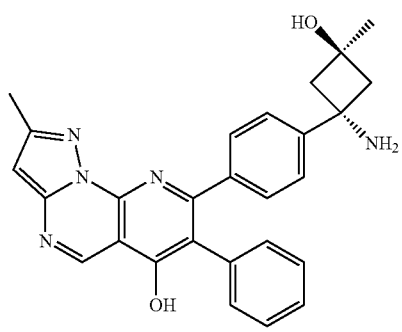

Compound [CDXI] was prepared using a procedure similar to that of Compound Data for Compound [CDXI]: LCMS (m/e) 452 (M+H); $^1$H NMR (400 MHz, METHANOL-d4) δ ppm 1.45 (s, 3H) 2.52 (s, 3H) 2.60-2.71 (m, 2H) 2.76-2.87 (m, 2H) 6.63 (s, 1H) 7.11-7.17 (m, 2H) 7.17-7.26 (m, 3H) 7.51 (s, 4H) 9.07 (s, 1H).

trans-2-{1-[4-(6-Cyclopropyl-2-methyl-7-phenyl-1,4,9,9b-tetraaza-cyclopenta[a]naphthalen-8-yl)-phenyl]-3-hydroxy-3-methyl-cyclobutyl}-isoindole-1,3-dione [CDXII]

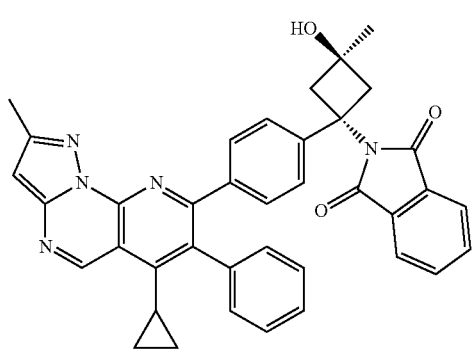

Compound [CDXII] was prepared using a procedure similar to that of Compound [CCL]. Data for Compound [CDXII]: LCMS (m/e) 606 (M+H).

trans-3-Amino-3-[4-(6-cyclopropyl-2-methyl-7-phenyl-1,4,9,9b-tetraaza-cyclopenta[a]naphthalen-8-yl)-phenyl]-1-methyl-cyclobutanol [CDXIII]

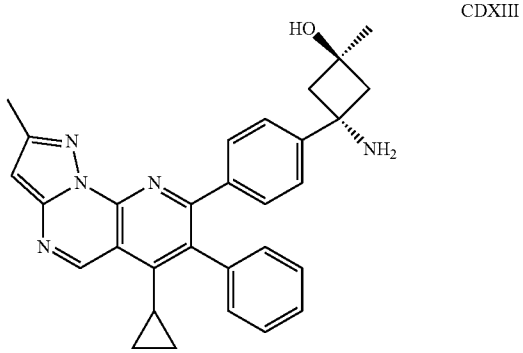 [SMILES: Cc1cc2ncc3c(C4CC4)c(-c4ccccc4)c(-c4ccc([C@]5(N)C[C@](C)(O)C5)cc4)nc3n2n1]

Compound [CDXIII] was prepared using a procedure similar to that of Compound [XLI]. Data for Compound [CDXIII]: LCMS (m/e) 476 (M+H); $^1$H NMR (400 MHz, METHANOL-d4) δ ppm 0.33-0.44 (m, 2H) 0.85-0.98 (m, 2H) 1.49 (s, 3H) 2.30-2.43 (m, 1H) 2.57 (s, 3H) 2.65-2.75 (m, 2H) 2.80-2.90 (m, 2H) 6.74 (s, 1H) 7.21-7.27 (m, 2H) 7.30-7.35 (m, 3H) 7.44 (d, J=8.44 Hz, 2H) 7.55 (d, J=8.44 Hz, 2H) 9.66 (s, 1H).

2-Isopropyl-7-thiophen-3-yl-9H-1,4,9,9b-tetraaza-cyclopenta[a]naphthalen-8-one [CDXIV]

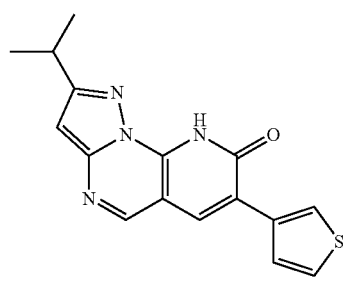

Compound [CDXIV] was prepared using a procedure similar to that of Compound [IV]. Data for Compound [CDXIV]: LCMS (m/e) 311 (M+H); $^1$H NMR (300 MHz, DMSO-d$_6$) δ ppm 1.31 (d, J=6.9 Hz, 6H) 3.10 (m, 1H) 6.25 (s, 1H) 7.49 (m, 1H) 7.70 (m, 1H) 8.09 (s, 1H) 8.36 (s, 1H) 8.41 (m, 1H).

8-Chloro-2-isopropyl-7-thiophen-3-yl-1,4,9,9b-tetraaza-cyclopenta[a]naphthalene [CDXV]

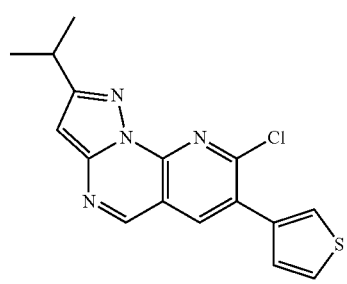

Compound [CDXV] was prepared using a procedure similar to that of Compound [V] (SOCl₂ procedure). Data for Compound [CDXV]: LCMS (m/e) 329 (M+H); ¹H NMR (300 MHz, DMSO-d₆) δ ppm 1.39 (d, J=7.2 Hz, 6H) 3.23 (m, 1H) 6.90 (s, 1H) 7.52 (m, 1H) 7.77 (m, 1H) 7.98 (m, 1H) 8.82 (s, 1H) 9.08 (s, 1H).

2-{3-Hydroxy-1-[4-(2-isopropyl-7-thiophen-3-yl-1, 4,9,9b-tetraaza-cyclopenta[a]naphthalen-8-yl)-phenyl]-3-methyl-cyclobutyl}-isoindole-1,3-dione [CDXVI]

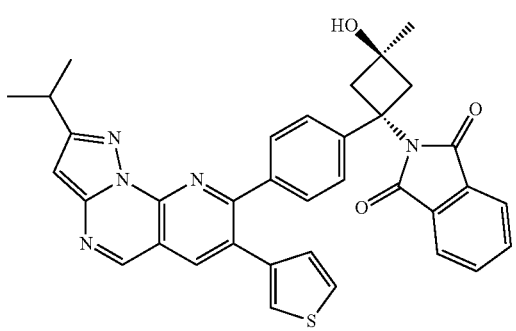

CDXVI

Compound [CDXVI] was prepared using a procedure similar to that of Compound [XL]. Data for Compound [CDXVI]: LCMS (m/e) 600 (M+H).

trans-3-Amino-3-[4-(2-isopropyl-7-thiophen-3-yl-1, 4,9,9b-tetraaza-cyclopenta[a]naphthalen-8-yl)-phenyl]-1-methyl-cyclobutanol [CDXVII]

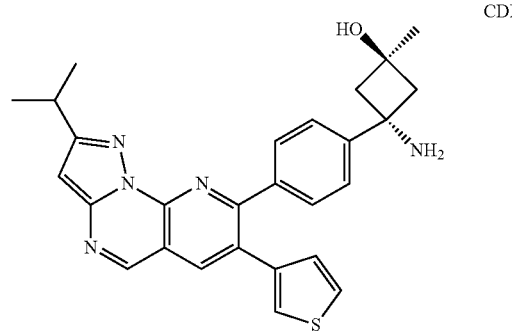

CDXVII

Compound [CDXVII] was prepared using a procedure similar to that of Compound [XLI]. Data for Compound [CDXVII]: LCMS (m/e) 470 (M+H); NMR (400 MHz, METHANOL-d4) δ ppm 1.41 (4, J=6.98 Hz, 6H) 1.50 (s, 3H) 1.93 (s, 2H) 2.57-2.69 (m, 2H) 2.79-2.89 (m, 2H) 3.22-3.26 (m, 1H) 6.78 (s, 1H) 6.87 (dd, J=5.00, 1.29 Hz, 1H) 7.36 (dd, J=4.98, 2.98 Hz, 1H) 7.42 (dd, J=2.95, 1.29 Hz, 1H) 7.50-7.56 (m, 2H) 7.68-7.75 (m, 2H) 8.60 (s, 1H) 9.02 (s, 1H).

2-Isopropyl-7-thiophen-2-yl-9H-1,4,9,9b-tetraazacyclopenta[a]naphthalen-8-one [CDXVIII]

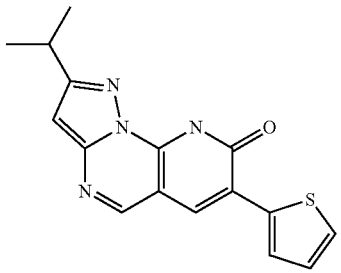

CDXVIII

Compound [CDXVIII] was prepared using a procedure similar to that of Compound [IV] (NaO-t-Bu procedure). Data for Compound [CXVIII]: LCMS (m/e) 311 (M+H); ¹H NMR (300 MHz, DMSO-d₆) δ ppm 1.31 (d, J=6.9 Hz, 6H) 3.09 (m, 1H) 6.27 (s, 1H) 7.06 (t, J=4.5 Hz, 1H) 7.34 (d, J=5.1 Hz, 1H) 7.66 (d, J=3.6 Hz, 1H) 8.25 (s, 1H) 8.39 (s, 1H).

8-Chloro-2-isopropyl-7-thiophen-2-yl-1,4,9,9b-tetraazacyclopenta[a]naphthalene [CDXIX]

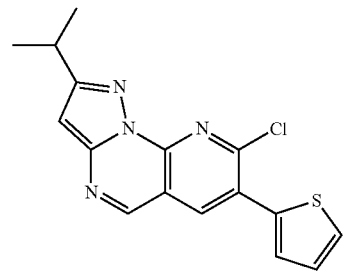

CDXIX

Compound [CDXIX] was prepared using a procedure similar to that of Compound [V] (SOCl₂ procedure). Data for Compound [CDXIX]: LCMS (m/e) 329 (M+H); ¹H NMR (300 MHz, DMSO-d₆ ppm □) 1.36 (d, J=6.9 Hz, 6H) 3.21 (m, 1H) 6.90 (s, 1H) 7.28 (m, 1H) 7.64 (m, 1H) 7.84 (m, 1H) 8.94 (s, 1H) 9.10 (s, 1H).

trans-2-{3-Hydroxy-1-[4-(2-isopropyl-7-thiophen-2-yl-4,4,9,9b-tetraaza-cyclopenta[a]naphthalen-8-yl)-phenyl]-3-methyl-cyclobutyl}-isoindole-1,3-dione [CDXX]

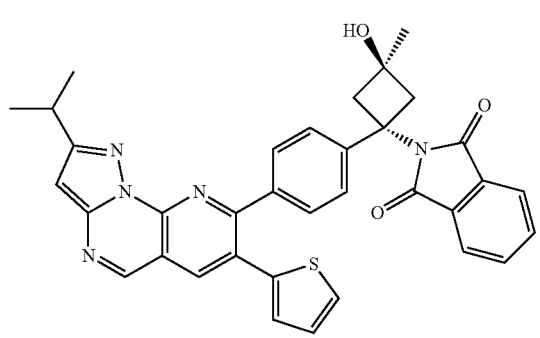

CDXX

Compound [CDXX] was prepared using a procedure similar to that of Compound [XL]. Data for Compound [CDXX]: LCMS m/e 600 (M+H).

trans-3-Amino-3-[4-(2-isopropyl-7-thiophen-2-yl-4,4,9,9b-tetraaza-cyclopenta[a]naphthalen-8-yl)-phenyl]-1-methyl-cyclobutanol [CDXXI]

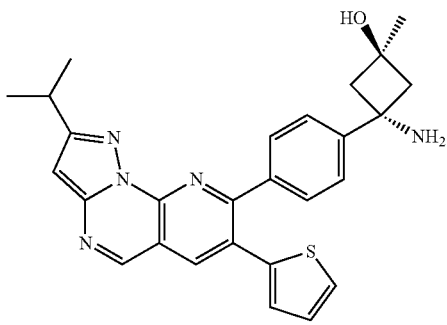

Compound [CDXXI] was prepared using a procedure similar to that of Compound [XLI]. Data for Compound [017WMF082_5]: LCMS m/e 470 (M+H); $^1$H NMR (400 MHz, METHANOL-d4) δ ppm 1.40 (d, J=6.98 Hz, 6H) 1.51 (s, 3H) 1.91 (s, 3H) 2.53-2.61 (m, 2H) 2.75-2.85 (m, 2H) 3.20-3.26 (m, 1H) 6.78 (s, 1H) 6.96-7.03 (m, 2H) 7.45 (dd, J=4.10, 2.25 Hz, 1H) 7.49-7.55 (m, 2H) 7.68-7.75 (m, 2H) 8.63 (s, 1H) 9.01 (s, 1H).

7-(2-Fluoro-phenyl)-2-isopropyl-9H-1,4,9,9b-tetraaza-cyclopenta[a]naphthalen-8-one [CDXXII]

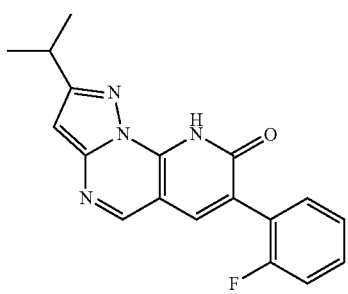

Compound [CDXXIII] was prepared using a procedure similar to that of Compound [IV] (NaO-t-Bu procedure). Data for Compound [CDXXII]: LCMS (m/e) N/A.

8-Chloro-7-(2-fluoro-phenyl)-2-isopropyl-1,4,9,9b-tetraaza-cyclopenta[a]naphthalene [CDXXIII]

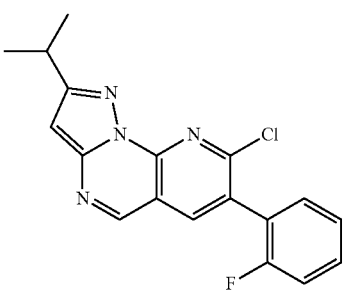

Compound [CDXXIII] was prepared using a procedure similar to that of Compound [IV] (SOCl$_2$ procedure). Data for Compound [CDXXIII]: LCMS m/e 341 (M+H); $^1$H NMR (300 MHz, DMSO-d$_6$) δ ppm 1.37 (d, J=6.9 Hz, 6H) 3.21 (m, 1H) 6.92 (s, 1H) 7.44 (m, 2H) 7.60 (m, 2H) 8.79 (s, 1H) 9.08 (s, 1H).

trans-2-(1-{4-[7-(2-Fluoro-phenyl)-2-isopropyl-1,4,9,9b-tetraaza-cyclopenta[a]naphthalen-8-yl]-phenyl}-3,3-dimethyl-cyclobutyl)-isoindole-1,3-dione [CDXXIV]

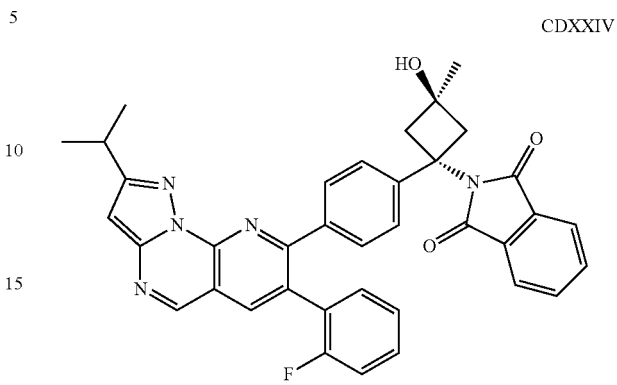

Compound [CDXXIV] was prepared using a procedure similar to that of Compound [XL]. Data for Compound [CDXXIV]: LCMS (m/e) 612 (M+H).

trans-3-Amino-3-{4-[7-(2-fluoro-phenyl)-2-isopropyl-1,4,9,9b-tetraaza-cyclopenta[a]naphthalen-8-yl]-phenyl}-1-methyl-cyclobutanol [CDXXV]

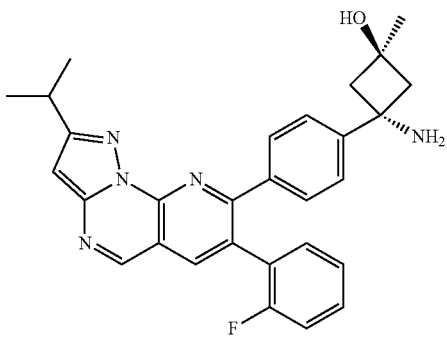

Compound [CDXXV] was prepared using a procedure similar to that of Compound [XLI]. Data for Compound [CDXXV]: LCMS (m/e) 481 (M+H); $^1$H NMR (400 MHz, METHANOL-d4) δ ppm 1.42 01, J=6.98 Hz, 6H) 1.49 (s, 3H) 1.91 (s, 4H) 2.51-2.60 (m, 2H) 2.72-2.81 (m, 1H) 3.23-3.26 (m, 1H) 6.79 (s, 1H) 7.03 (dd, J=9.76, 8.59 Hz, 1H) 7.19-7.27 (m, 1H) 7.35-7.49 (m, 4H) 7.65-7.70 (m, 2H) 8.56 (s, 1H).

trans-2-[1-(4-Bromo-phenyl)-3-hydroxy-3-isopropenyl-cyclobutyl]-isoindole-1,3-dione [CDXXVI]

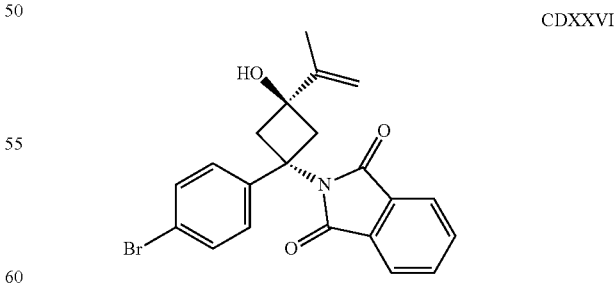

Compound [CDXXVI] was prepared using a procedure similar to that of Compound [XXXVIII]. Data for Compound [CDXXVI]: LCMS (m/e) 412 (M+H); $^1$H NMR (300 MHz, CHLOROFORM-d) δ ppm 1.80 (s, 3H) 3.19 (m, 2H) 3.43 (m, 2H) 4.87 (s, 1H) 4.98 (s, 1H) 7.47 (m, 2H) 7.63 (m, 4H) 7.73 (m, 2H).

trans-2-[1-(4-Bromo-phenyl)-3-hydroxy-3-isopropyl-cyclobutyl]-isoindole-4,3-dione [CDXXVII]

CDXXVII

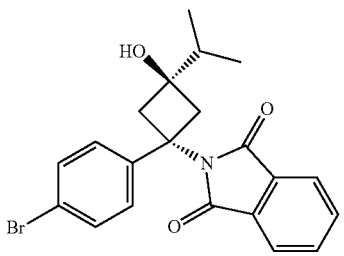

Compound [CDXXVII] was prepared using a procedure similar to that of Compound [CCCXCVII]. Data for Compound: LCMS (m/e) 413 (M); $^1$H NMR (300 MHz, CHLOROFORM-d) δ ppm 0.89 (d, J=6.9 Hz) 1.68 (m, 1H) 3.07 (m, 4H) 7.45 (m, 2H) 7.61 (m, 4H) 7.75 (m, 2H).

trans-2-{3-Hydroxy-3-isopropyl-1-[4-(4,4,5,5-tetramethyl-[1,3,2]dioxaborolan-2-yl)-phenyl]-cyclobutyl}-isoindole-1,3-dione [CDXXVIII]

CDXXVIII

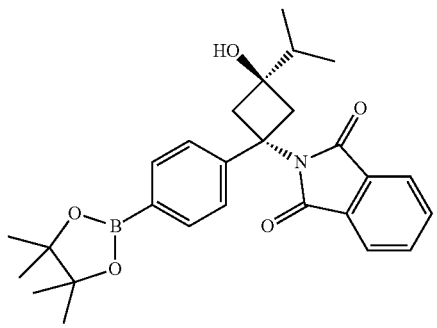

Compound [CDXXVIII] was prepared using a procedure similar to that of Compound [XXXIX]. Data for Compound [CDXXVIII]: LCMS (m/e) 484 (M+Na); $^1$H NMR (300 MHz, CHLOROFORM-d) δ ppm 0.90 (d, J=6.6 Hz, 6H) 1.33 (s, 12H) 1.70 (m, 1H) 3.18 (m, 4H) 7.65 (m, 2H) 7.75 (m, 6H).

trans-2-{1-[4-(2-Cyclopropyl-7-phenyl-1,4,9,9b-tetraaza-cyclopenta[a]naphthalen-8-yl)-phenyl]-3-hydroxy-3-isopropyl-cyclobutyl}-isoindole-1,3-dione [CDXXIX]

CDXXIX

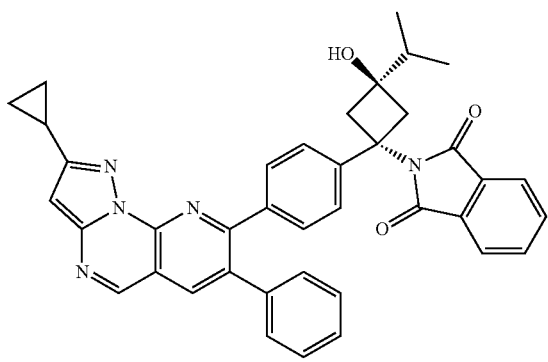

Compound [CDXXIX] was prepared using a procedure similar to that of Compound [XL]. Data for Compound [CDXXIX]: LCMS m/e 620 (M+H).

trans-3-Amino-3-[4-(2-cyclopropyl-7-phenyl-1,4,9,9b-tetraaza-cyclopenta[a]naphthalen-8-yl)-phenyl]-1-isopropyl-cyclobutanol [CDXXX]

CDXXX

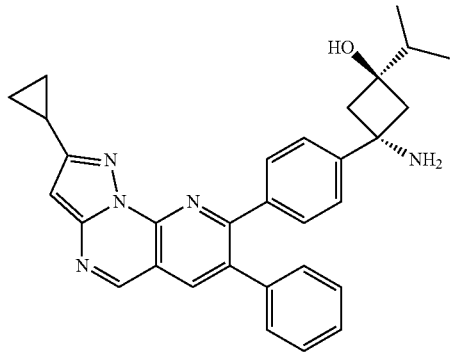

Compound [CDXXX] was prepared using a procedure similar to that of Compound [XLI]. Data for Compound [CDXXX]: LCMS (m/e) 490 (M+H); $^1$H NMR (400 MHz, METHANOL-d4) δ ppm 0.88 (4, J=6.83 Hz, 6H) 0.93-1.02 (m, 2H) 1.06-1.17 (m, 2H) 1.77-1.90 (m, 1H) 1.94 (s, 1H) 2.16-2.27 (m, 1H) 2.51-2.61 (m, 2H) 2.73-2.83 (m, 2H) 6.59 (s, 1H) 7.27-7.37 (m, 5H) 7.48-7.57 (m, 2H) 7.66-7.74 (m, 2H) 8.52 (s, 1H) 9.01 (s, 1H).

trans-2-{3-Hydroxy-3-isopropyl-1-[4-(2-methyl-7-phenyl-1,4,9,9b-tetraaza-cyclopenta[a]naphthalen-8-yl)-phenyl]-cyclobutyl}-isoindole-1,3-dione [CDXXXI]

CDXXXI

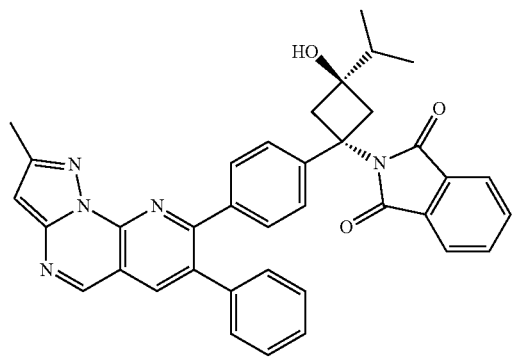

Compound [CDXXXI] was prepared using a procedure similar to that of Compound [XL]. Data for Compound [CDXXXI]: LCMS m/e 594 (M+H).

367 trans-3-Amino-1-isopropyl-3-[4-(2-methyl-7-phenyl-1,4,9,9b-tetraaza-cyclopenta[a]naphthalen-8-yl)-phenyl]-cyclobutanol [CDXXXII]

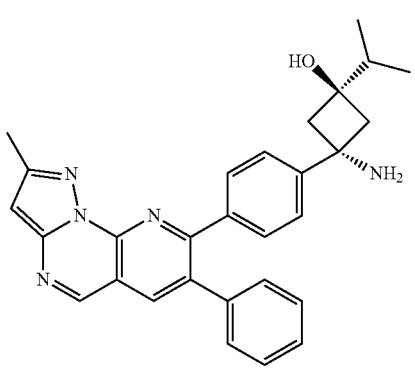

CDXXXII

Compound [CDXXXII] was prepared using a procedure similar to that of Compound [XLI]. Data for Compound [CDXXXII]: LCMS (m/e) 463 (M+H); $^1$H NMR (400 MHz, METHANOL-d4) δ ppm 0.88 (4, J=6.83 Hz, 6H) 1.68-1.90 (m, 1H) 1.96 (s, 1H) 2.57 (s, 3H) 2.58-2.69 (m, 2H) 2.70-2.87 (m, 2H) 6.75 (s, 1H) 7.24-7.41 (m, 5H) 7.46-7.60 (m, 2H) 7.65-7.83 (m, 2H) 8.54 (s, 1H) 9.04 (s, 1H).

cis-2-[1-(4-Bromo-phenyl)-3-hydroxy-3-isopropenyl-cyclobutyl]-isoindole-1,3-dione [CDXXXIII]

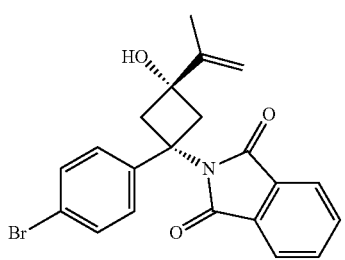

CDXXXIII

Compound [CDXXXIII] was prepared using a procedure similar to that of Compound [XXXVIII]. Data for Compound [CDXXXIII]: LCMS m/e 412 (M+H); $^1$H NMR (300 MHz, CHLOROFORM-d) δ ppm 1.73 (s, 3H) 3.27 (m, 2H) 3.52 (m, 2H) 4.78 (s, 1H) 4.83 (s, 1H) 7.41 (m, 2H) 7.50 (m, 2H) 7.67 (m, 2H) 7.75 (m, 2H).

cis-2-[1-(4-Bromo-phenyl)-3-hydroxy-3-isopropyl-cyclobutyl]-isoindole-1,3-dione [CDXXXIV]

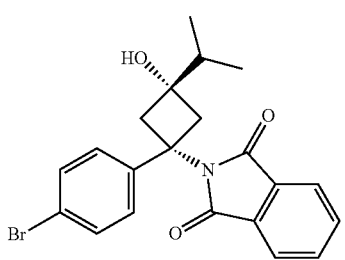

CDXXXIV

Compound [CDXXXIV] was prepared using a procedure similar to that of Compound [CCCXCCVII]. Data for Compound [CDXXXIV]: LCMS (m/e) 413 (M); $^1$H NMR (300 MHz, CHLOROFORM-d) δ ppm 0.84 (d, J=6.6 Hz) 1.35 (m, 1H) 3.11 (m, 2H) 3.30 (m, 2H) 7.46 (m, 2H) 7.57 (m, 2H) 7.66 (m, 2H) 7.75 (m, 2H).

368 cis-2-{3-Hydroxy-3-isopropyl-1-[4-(4,4,5,5-tetramethyl-[1,3,2]dioxaborolan-2-yl)-phenyl]-cyclobutyl}-isoindole-1,3-dione [CDXXXV]

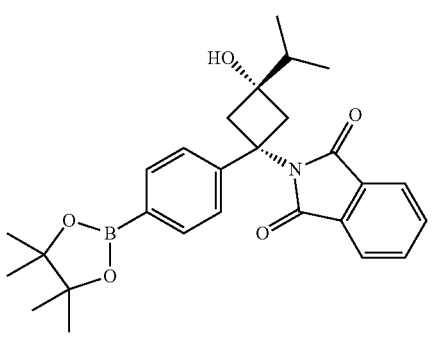

CDXXXV

Compound [CDXXXV] was prepared using a procedure similar to that of Compound [XXXIX]. Data for Compound: LCMS (m/e) 484 (M+Na); $^1$H NMR (300 MHz, CHLOROFORM-d ppm □) 0.82 (d, J=6.6 Hz, 6H) 1.25 (m, 1H) 1.36 (s, 12H) 3.11 (m, 2H) 3.38 (m, 2H) 7.63 (m, 8H).

cis-2-{1-[4-(2-Cyclopropyl-7-phenyl-1,4,9,9b-tetraaza-cyclopenta[a]naphthalen-8-yl)-phenyl]-3-hydroxy-3-isopropyl-cyclobutyl}-isoindole-1,3-dione [CDXXXVI]

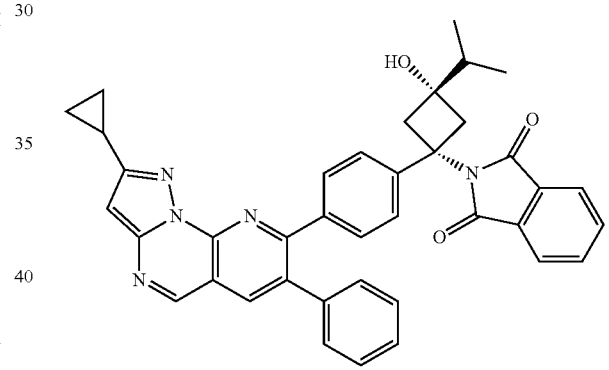

CDXXXVI

Compound [CDXXXVI] was prepared using a procedure similar to that of [XL]. Data for Compound [CDXXXVI]: LCMS m/e 620 (M+H).

cis-3-Amino-3-[4-(2-cyclopropyl-7-phenyl-1,4,9,9b-tetraaza-cyclopenta[a]naphthalen-8-yl)-phenyl]-1-isopropyl-cyclobutanol [CDXXXVII]

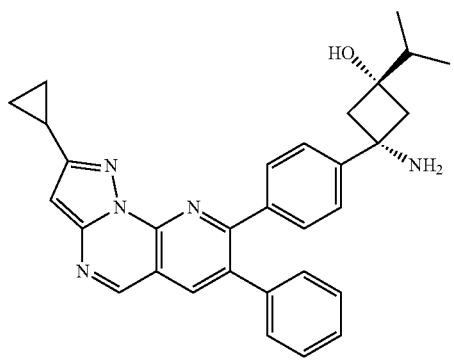

CDXXXVI

Compound [CDXXXVII] was prepared using a procedure similar to that of Compound [XLI]. Data for Compound [CDXXXVII]: LCMS (m/e) 490 (M+H); $^1$H NMR (400 MHz, METHANOL-d4) δ ppm 0.83 (d, J=6.83 Hz, 6H) 0.92-1.04 (m, 2H) 1.07-1.17 (m, 2H) 1.45-1.59 (m, 1H) 1.96 (s, 1H) 2.15-2.30 (m, 1H) 2.43-2.54 (m, 2H) 2.70-2.86 (m, 2H) 6.60 (s, 1H) 7.26-7.35 (m, 5H) 7.36-7.44 (m, 2H) 7.60-7.75 (m, 2H) 8.54 (s, 1H) 9.02 (s, 1H).

Ethyl 7-amino-2-cyclopropyl-5-methylpyrazolo[1,5-a]pyrimidine-6-carboxylate [CDXXXVIII]

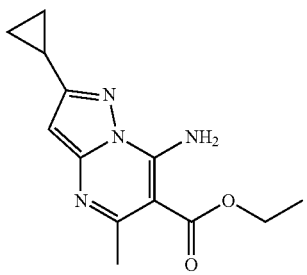

Compound [CDXXXVIII] was prepared using a procedure similar to that of Compound [CDIII]. This material was taken on to the next step without further purification or characterization.

(7-Amino-2-cyclopropyl-5-methyl-pyrazolo[1,5-a]pyrimidin-6-yl)-methanol [CDXXXIX]

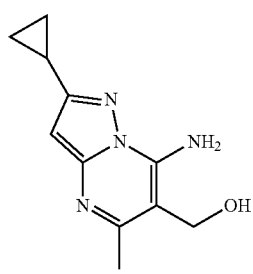

Compound [CDXXXIX] was prepared using a procedure similar to that of Compound [II]. Data for Compound [CDXXXIX]: LCMS (m/e) 219 (M+H); $^1$H NMR (300 MHz, DMSO-d$_6$) δ ppm 0.79 (m, 2H) 0.93 (m, 2H) 1.98 (m, 1H) 2.46 (s, 3H) 4.53 (d, J=5.4 Hz, 2H) 4.70 (t, J=5.1 Hz, 1H) 5.91 (s, 1H) 7.21 (s, 2H).

7-Amino-2-cyclopropyl-5-methyl-pyrazolo[1,5-a]pyrimidine-6-carbaldehyde [CDXL]

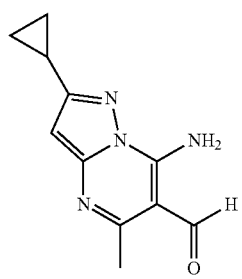

Compound [CDXL] was prepared using a procedure similar to that of Compound [III]

Data for Compound [CDXL]: LCMS (m/e) 217 (M+H); NMR (300 MHz, CHLOROFORM-d) δ ppm 0.94 (m, 2H) 1.01 (m, 2H) 2.03 (m, 1H) 2.73 (s, 3H) 6.13 (s, 1H) 6.95 (br.s, 1H) 9.55 (br.s, 1H) 10.20 (s, 1H).

2-Cyclopropyl-5-methyl-7-phenyl-9H-1,4,9,9b-tetraaza-cyclopenta[a]naphthalen-8-one [CDXLI]

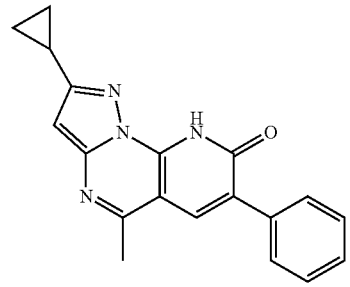

Compound [CDXLI] was prepared using a procedure similar to that of Compound [CCCLXXXVI] (DBU procedure). This compound was taken on to the next step.

8-Chloro-2-cyclopropyl-5-methyl-7-phenyl-1,4,9,9b-tetraaza-cyclopenta[a]naphthalene [CDXLII]

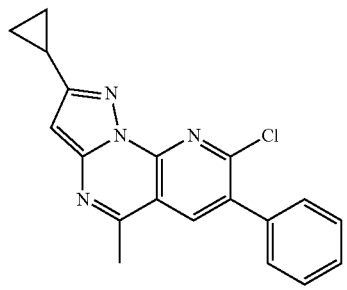

Compound [CDXLII] was prepared using a procedure similar to that of Compound [V] (POCl$_3$ procedure). Data for Compound [CDXLII]: LCMS (m/e) 335 (M+H); $^1$H NMR (300 MHz, CHLOROFORM-d) δ ppm 0.95 (m, 2H) 1.00 (m, 2H) 2.28 (m, 1H) 2.86 (s, 3H) 6.38 (s, 1H) 7.53 (s, 5H) 8.24 (s, 1H).

trans-2-{1-[4-(2-Cyclopropyl-5-methyl-7-phenyl-1,4,9,9b-tetraaza-cyclopenta[a]naphthalen-8-yl)-phenyl]-3-hydroxy-3-methyl-cyclobutyl}-isoindole-1,3-dione [CDXLIII]

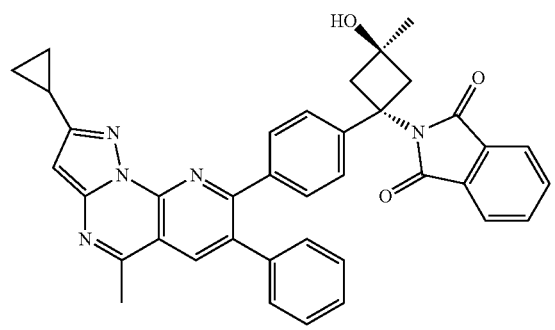

Compound [CDXLIII] was prepared using a procedure similar to that of Compound [XL]. Data for Compound [CDXLIII]: LCMS m/e 606 (M+H).

trans-2-{1-[4-(2-Cyclopropyl-5-methyl-7-phenyl-1,4,9,9b-tetraaza-cyclopenta[a]naphthalen-8-yl)-phenyl]-3-hydroxy-3-methyl-cyclobutyl}-isoindole-1,3-dione [CDXLIV]

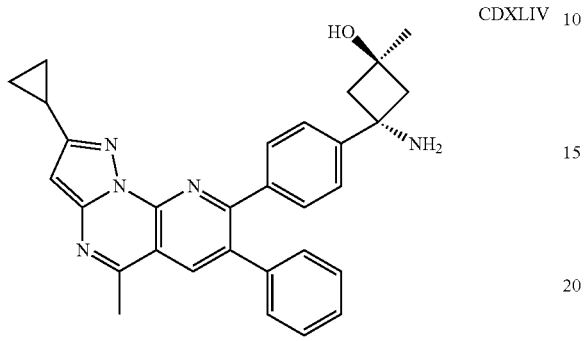

CDXLIV

Compound [CDXLIV] was prepared using a procedure similar to that of Compound [XLI]. Data for Compound [CDXLIV]: LCMS (m/e) 476 (M+H); $^1$H NMR (400 MHz, METHANOL-d4) δ ppm 0.89-1.01 (m, 2H) 1.03-1.15 (m, 2H) 1.50 (s, 3H) 1.91 (s, 3H) 2.19 (tt, J=8.49, 4.83 Hz, 1H) 2.48-2.61 (m, 2H) 2.70-2.81 (m, 2H) 2.88 (s, 3H) 6.42 (s, 1H) 7.28-7.38 (m, 5H) 7.41-7.49 (m, 2H) 7.60-7.69 (m, 2H) 8.50 (s, 1H).

7-Amino-2-isopropyl-5-methyl-pyrazolo[1,5-a]pyrimidine-6-carboxylic acid ethyl ester [CDXLV]

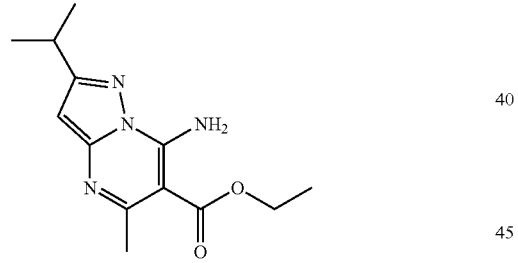

CDXLV

Compound [CDXLV] was prepared using a procedure similar to that of Compound [VII] using Compound [CLXI] as the starting material. Data for Compound [CDXLV]: LCMS (m/e) 263 (M+H).

(7-Amino-2-isopropyl-5-methyl-pyrazolo[1,5-a]pyrimidin-6-yl)-methanol [CDXLVI]

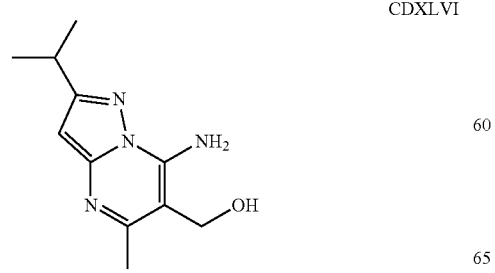

CDXLVI

Compound [CDXLVI] was prepared using a procedure similar to that of Compound [II]. Data for Compound [CDXLVI]: LCMS (m/e) 221 (M+H); $^1$H NMR (300 MHz, CHLOROFORM-d) δ ppm 1.36 (d, J=6.9 Hz, 6H) 2.44 (s, 3H) 3.07-3.17 (m, 1H) 4.82 (s, 2H) 6.18 (s, 1H) 6.22 (br, 2H).

7-Amino-2-isopropyl-5-methyl-pyrazolo[1,5-a]pyrimidine-6-carbaldehyde [CDXLVII]

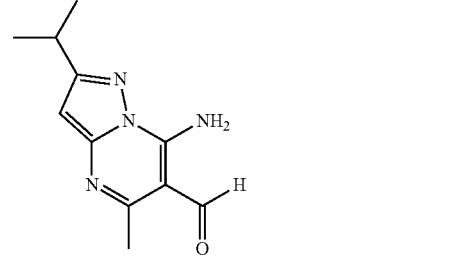

CDXLVII

Compound [CDXLVII] was prepared using a procedure similar to that of Compound [III]. Data for Compound [CDXLVII]: LCMS (m/e) (219) (M+H); $^1$H NMR (300 MHz, DMSO-d$_6$) δ ppm 1.30 (d, J=6.9 Hz, 6H) 2.64 (s, 3H) 3.03-3.12 (m, 1H) 6.33 (s, 1H) 8.34 (s, 1H) 9.42 (s, 1H) 10.11 (s, 1H).

2-Isopropyl-5-methyl-7-phenyl-9H-1,4,9,9b-tetraaza-cyclopenta[a]naphthalen-8-one [CDXLVIII]

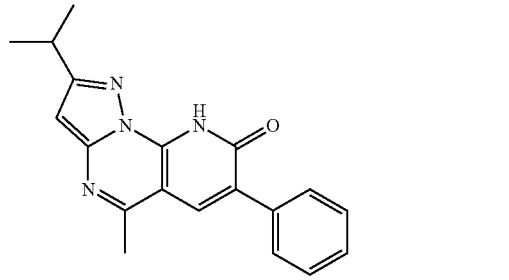

CDXLVIII

Compound [CDXLVIII] was prepared using a procedure similar to that of Compound [CCCLXXXVI] (DBU procedure). This compound was taken on directly to the next step without further characterization.

8-Chloro-2-isopropyl-5-methyl-7-phenyl-1,4,9,9b-tetraaza-cyclopenta[a]naphthalene [CDXLIX]

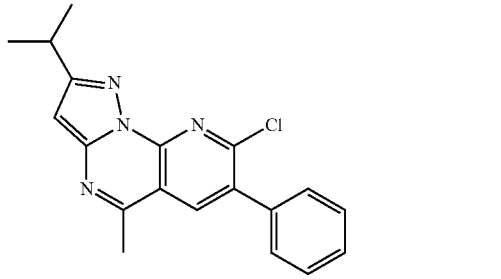

CDXLIX

Compound [CDXLIX] was prepared using a procedure similar to that of Compound [V] (POCl₃ procedure). Data for Compound [CDXLIX]: LCMS m/e (337) (M+H); $^1$H NMR (300 MHz, CHLOROFORM-d) δ ppm 1.43 (d, J=6.9 Hz, 6H) 2.89 (s, 3H) 3.40-3.43 (m, 1H) 6.66 (s, 1H) 7.54 (s, 5H) 8.26 (s, 1H).

trans-2-{3-Hydroxy-1-[4-(2-isopropyl-5-methyl-7-phenyl-1,4,9,9b-tetraaza-cyclopenta[a]naphthalen-8-yl)-phenyl]-3-methyl-cyclobutyl}-isoindole-1,3-dione [CDL]

CDL

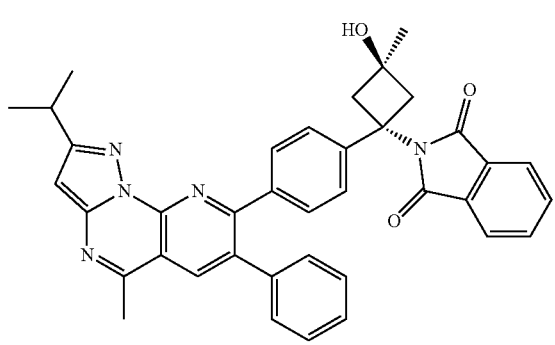

Compound [CDL] was prepared using a procedure similar to that of Compound [XL]. Data for Compound [CDL]: LCMS (m/e) 608 (M+H).

trans-3-Amino-3-[4-(2-isopropyl-5-methyl-7-phenyl-1,4,9,9b-tetraaza-cyclopenta[a]naphthalen-8-yl)-phenyl]-1-methyl-cyclobutanol [CDLI]

CDLI

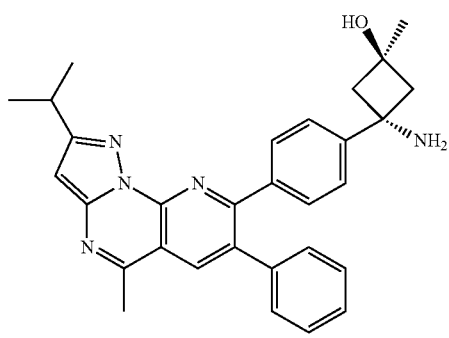

Compound [CDLI] was prepared using a procedure similar to that of Compound [XLI]. Data for Compound [CLDI]: LCMS (m/e) 478 (M+H); $^1$H NMR (400 MHz, METHANOL-d4) δ ppm 1.40 (4, J=6.93 Hz, 6H) 1.50 (s, 3H) 1.90 (s, 3H) 2.48-2.59 (m, 2H) 2.69-2.80 (m, 2H) 2.89 (s, 3H) 3.18-3.26 (m, 1H) 6.62 (s, 1H) 7.26-7.37 (m, 5H) 7.40-7.48 (m, 2H) 7.61-7.70 (m, 2H) 8.51 (s, 1H).

7-(3-Fluoro-phenyl)-2-methyl-9H-1,4,9,9b-tetraaza-cyclopenta[a]naphthalen-8-one [CDLII]

CDLII

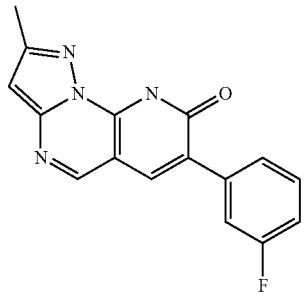

Compound [CDLII] was prepared using a procedure similar to that of Compound [CCCLXXXVI] (DBU procedure). This compound was used in the next step without further purification.

8-Chloro-7-(3-fluoro-phenyl)-2-methyl-1,4,9,9b-tetraaza-cyclopenta[a]naphthalene [CDLIII]

CDLIII

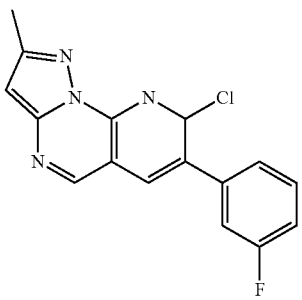

Compound [CDLIII] was prepared using a procedure similar to that of Compound [V] (POCl₃ procedure). Data for Compound LCMS (m/e) 313 (M+H); $^1$H NMR (300 MHz, CD₃OD-d₄) δ ppm 9.03 (s, 1H) 7.54-7.61 (q, 1H) 7.37-7.43 (t, 2H) 7.24-7.30 (t, 1H) 6.79 (s, 1H) 2.59 (s, 1H).

trans-2-(1-{4-[7-(3-Fluoro-phenyl)-2-methyl-1,4,9,9b-tetraaza-cyclopenta[a]naphthalen-8-yl]-phenyl}-3-hydroxy-3-methyl-cyclobutyl)-isoindole-1,3-dione [CDLIV]

CDLIV

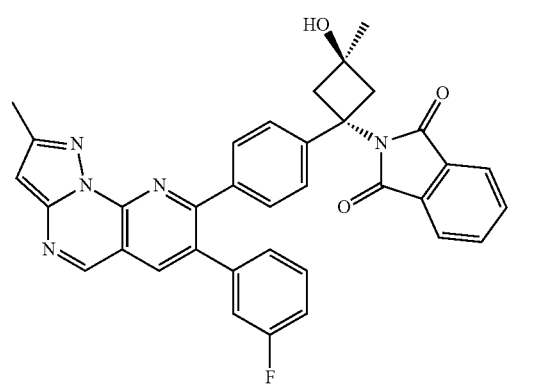

Compound [CDLIV] was prepared using a procedure similar to that of Compound [XL]. Data for Compound [CDLIV]: LCMS (m/e) 584 (M+H).

trans-3-Amino-3-{4-[7-(3-fluoro-phenyl)-2-methyl-1,4,9,9b-tetraaza-cyclopenta[a]naphthalen-8-yl]-phenyl}-1-methyl-cyclobutanol [CDLV]

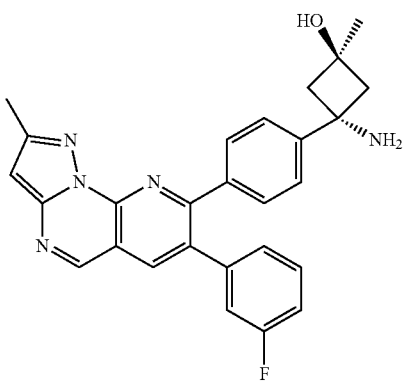

Compound [CDLV] was prepared using a procedure similar to that of Compound [XLI]. Data for Compound [CDLV]: LCMS (m/e) 454 (M+H); $^1$H NMR (400 MHz, METHANOL-d)ppm 1.50 (s, □4) 3H) 1.91 (s, 3H) 2.51-2.62 (m, 5H) 2.71-2.84 (m, 2H) 6.75 (s, 1H) 6.97-7.11 (m, 2H) 7.14 (dd, J=7.76, 1.12 Hz, 1H) 7.29-7.41 (m, 1H) 7.45-7.53 (m, 2H) 7.62-7.72 (m, 2H) 8.55 (s, 1H) 9.03 (s, 1H).

7-(4-Fluoro-phenyl)-2-methyl-9H-1,4,9,9b-tetraaza-cyclopenta[a]naphthalen-8-one [CDLVI]

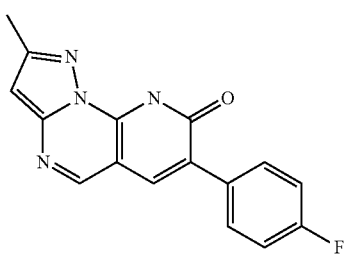

Compound [CDLVI] was prepared using a procedure similar to that of Compound [CCCLXXXVI] (DBU procedure). This material was carried on to the next step without further purification.

8-Chloro-7-(4-fluoro-phenyl)-2-methyl-1,4,9,9b-tetraaza-cyclopenta[a]naphthalene [CDLVII]

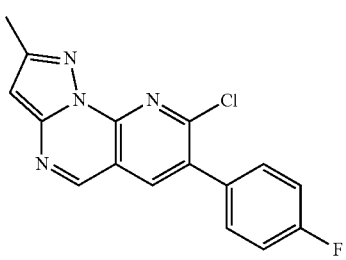

Compound [CDLVII] was prepared using a procedure similar to that of Compound [V] (POCl$_3$ procedure). Data for Compound [CDLVII]: LCMS (m/e) 313 (M+H); $^1$H NMR (300 MHz, CHLOROFORM-d) δ ppm 2.66 (s, 3H) 6.76 (s, 1H) 7.20 (m, 2H) 7.50 (m, 2H) 8.20 (s, 1H) 8.84 (s, 1H).

trans-2-(1-{4-[7-(4-Fluoro-phenyl)-2-methyl-1,4,9,9b-tetraaza-cyclopenta[a]naphthalen-8-yl]-phenyl}-3-hydroxy-3-methyl-cyclobutyl)-isoindole-1,3-dione [CDLVIII]

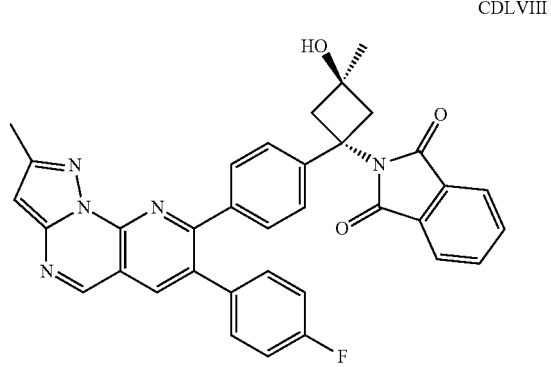 [SMILES: Cc1cc2ncc3cc(-c4ccc(F)cc4)c(-c4ccc([C@]5(N6C(=O)c7ccccc7C6=O)C[C@](C)(O)C5)cc4)nc3n2n1]

Compound [CDLVIII] was prepared using a procedure similar to that of Compound [XL]. Data for Compound [CDLVIII]: LCMS (m/e) 584 (M+H).

trans-3-Amino-3-{4-[7-(4-fluoro-phenyl)-2-methyl-1,4,9,9b-tetraaza-cyclopenta[a]naphthalen-8-yl]-phenyl}-1-methyl-cyclobutanol [CDLIX]

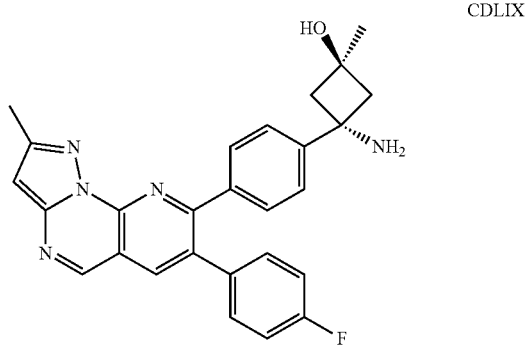 [SMILES: Cc1cc2ncc3cc(-c4ccc(F)cc4)c(-c4ccc([C@]5(N)C[C@](C)(O)C5)cc4)nc3n2n1]

Compound [CDLIX] was prepared using a procedure similar to that of Compound [XLI]. Data for Compound [CDLIX]: LCMS (m/e) 454 (M+H); $^1$H NMR (400 MHz, METHANOL-d4) δ ppm 1.50 (s, 3H) 1.91 (s, 3H) 2.50-2.62 (m, 5H) 2.74-2.83 (m, 2H) 6.74 (s, 1H) 7.00-7.13 (m, 2H) 7.27-7.36 (m, 2H) 7.43-7.51 (m, 2H) 7.60-7.69 (m, 2H) 8.53 (s, 1H) 9.02 (s, 1H).

7-(4-Chloro-phenyl)-2-methyl-9H-1,4,9,9b-tetraaza-cyclopenta[a]naphthalen-8-one [CDLX]

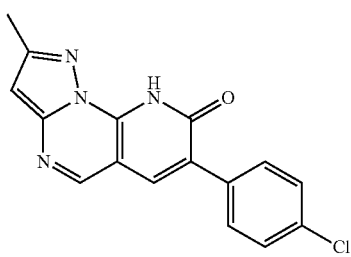

Compound [CDLX] was prepared using a procedure similar to that of Compound [CCCLXXXVI] (DBU procedure). The material was taken on to the next step without further characterization.

8-Chloro-7-(4-chloro-phenyl)-2-methyl-1,4,9,9b-tetraaza-cyclopenta[a]naphthalene [CDLXI]

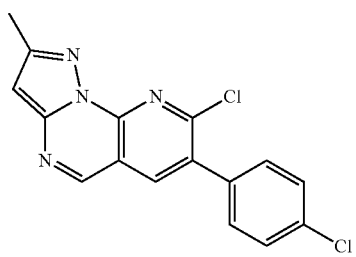

Compound [CDLXI] was prepared using a procedure similar to that of Compound [V] (POCl$_3$ procedure). Data for Compound [CDLXI]: LCMS (m/e) 329 (M+H); $^1$H NMR (300 MHz, CHLOROFORM-d) δ ppm 2.66 (s, 3H) 6.76 (s, 1H) 7.38 (m, 4H) 8.20 (s, 1H) 8.85 (s, 1H).

trans-2-(1-{4-[7-(4-Chloro-phenyl)-2-methyl-1,4,9,9b-tetraaza-cyclopenta[a]naphthalen-8-yl]-phenyl}-3-hydroxy-3-methyl-cyclobutyl)-isoindole-1,3-dione [CDLXII]

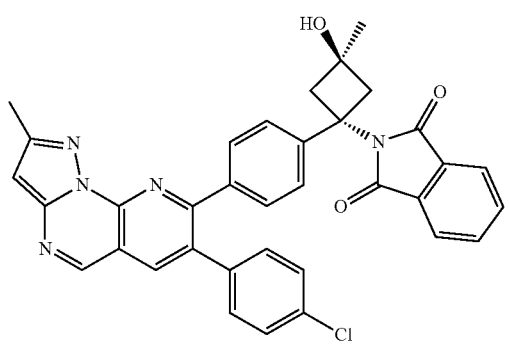

Compound [CDLXII] was prepared using a procedure similar to that of Compound [XL]. Data for Compound [CDLXII]: LCMS m/e 600 (M+H).

trans-3-Amino-3-{4-[7-(4-chloro-phenyl)-2-methyl-1,4,9,9b-tetraaza-cyclopenta[a]naphthalen-8-yl]-phenyl}-1-methyl-cyclobutanol [CDLXIII]

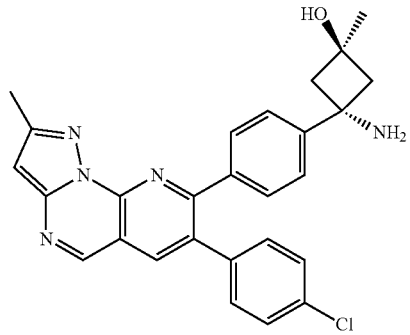

Compound [CDLXIII] was prepared using a procedure similar to that of Compound [XLI]. Data for Compound [CDLXIII]: LCMS (m/e) 470 (M+H).

7-(3-Chloro-phenyl)-2-methyl-9H-1,4,9,9b-tetraaza-cyclopenta[a]naphthalen-8-one [CDLXIV]

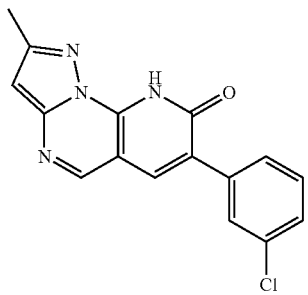

Compound [CDLXIV] was prepared using a procedure similar to that of Compound [CCCLXXXVI] (DBU procedure). This compound was taken on to the next step without further characterization.

8-Chloro-7-(3-chloro-phenyl)-2-methyl-1,4,9,9b-tetraaza-cyclopenta[a]naphthalene [CDLXV]

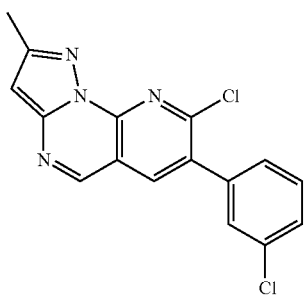

Compound [CDLXV] was prepared using a procedure similar to that of Compound [V] (POCl$_3$ procedure). Data for Compound [CDLXV]: LCMS (m/e) 329 (M+H); $^1$H NMR (300 MHz, CHLOROFORM-d) δ ppm, 2.66 (s, 3H) 6.76 (s, 1H) 7.28-7.53 (m, 4H) 8.21 (s, 1H) 8.8 (s, 1H).
Amount obtained: 200 mg, 9% yield.

2-(1-{4-[7-(3-Chloro-phenyl)-2-methyl-1,4,9,9b-tetraaza-cyclopenta[a]naphthalen-8-yl]-phenyl}-3-hydroxy-3-methyl-cyclobutyl)-isoindole-1,3-dione [CDLXVI]

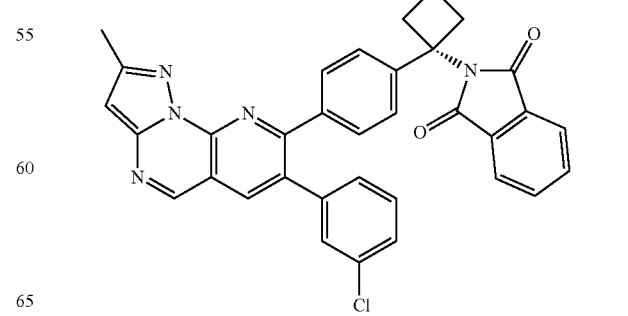

Compound [CDLXVI] was prepared using a procedure similar to that of Compound [XL]. Data for Compound [CDLXVI]: LCMS (m/e) 600 (M+H).

trans-3-Amino-3-{4-[7-(3-chloro-phenyl)-2-methyl-1,4,9,9b-tetraaza-cyclopenta[a]naphthalen-8-yl]-phenyl}-1-methyl-cyclobutanol [CDLXVII]

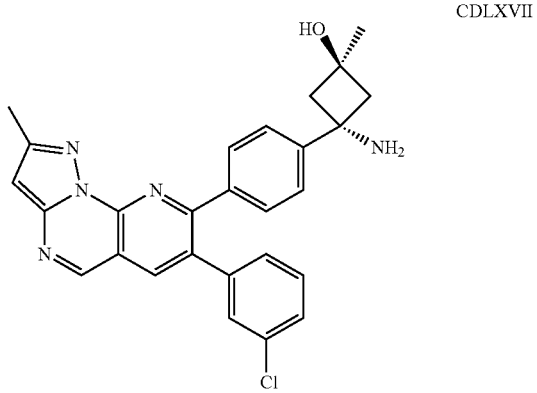 [SMILES: Cc1cc2ncc3cc(-c4cccc(Cl)c4)c(-c4ccc([C@]5(N)C[C@](C)(O)C5)cc4)nc3n2n1]

CDLXVII

Compound [CDLXVII] was prepared using a procedure similar to that of Compound [XLI]. Data for Compound [CDLXVII]: LCMS (m/e) 470 (M+H); $^1$H NMR (400 MHz, METHANOL-d4) δ ppm 1.50 (s, 3H) 1.91 (s, 3H) 2.53-2.62 (m, 5H) 2.75-2.83 (m, 2H) 6.75 (s, 1H) 7.21 (d, J=7.37 Hz, 1H) 7.27-7.41 (m, 3H) 7.46-7.53 (m, 2H) 7.63-7.70 (m, 2H) 8.55 (s, 1H) 9.02 (s, 1H).

2-Methyl-7-o-tolyl-9H-1,4,9,9b-tetraaza-cyclopenta[a]naphthalen-8-one [CDLXVIII]

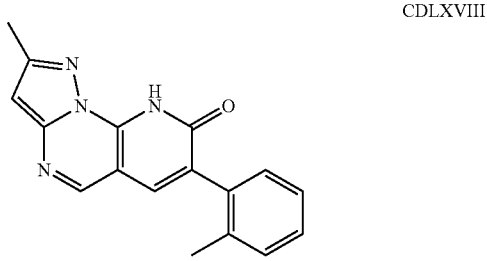 [SMILES: Cc1cc2ncc3cc(-c4ccccc4C)c(=O)[nH]c3n2n1]

CDLXVIII

Compound [CDLXVIII] was prepared using a procedure similar to that of Compound [CCCLXXXVI] (DBU procedure). This material was taken on to the next step without further characterization.

8-Chloro-2-methyl-7-o-tolyl-1,4,9,9b-tetraaza-cyclopenta[a]naphthalene [CDLXIX]

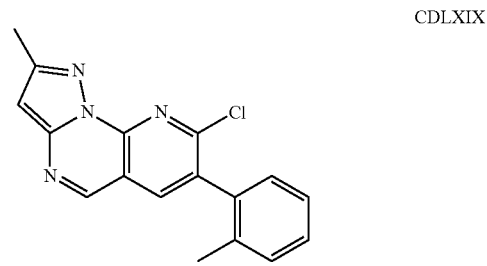 [SMILES: Cc1cc2ncc3cc(-c4ccccc4C)c(Cl)nc3n2n1]

CDLXIX

Compound [CDLXIX] was prepared using a procedure similar to that of Compound [V] (POCl$_3$ procedure). Data for Compound [CDLXIX]: LCMS (m/e) 309 (M+H); $^1$H NMR (300 MHz, CHLOROFORM-d) δ ppm 2.19 (s, 3H) 2.66 (s, 3H) 6.76 (s, 1H) 7.22 (m, 1H) 7.32 (m, 3H) 8.14 (s, 1H) 8.83 (s, 1H).

trans-2-{3-Hydroxy-3-methyl-1-[4-(2-methyl-7-o-tolyl-1,4,9,9b-tetraaza-cyclopenta[a]naphthalen-8-yl)-phenyl]-cyclobutyl}-isoindole-1,3-dione [CDLXX]

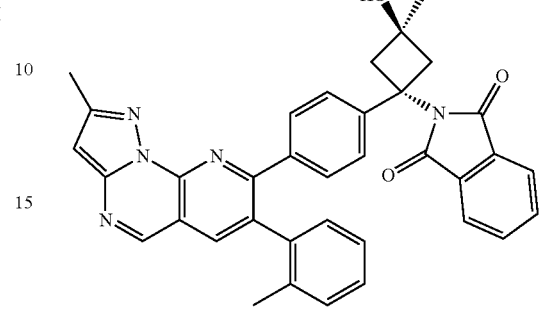

CDLXX

Compound [CDLXX] was prepared using a procedure similar to that of Compound [XL]. Data for Compound [CDLXX]: LCMS (m/e) 580 (M+H).

trans-3-Amino-1-methyl-3-[4-(2-methyl-7-o-tolyl-1,4,9,9b-tetraaza-cyclopenta[a]naphthalen-8-yl)-phenyl]-cyclobutanol [CDLXXI]

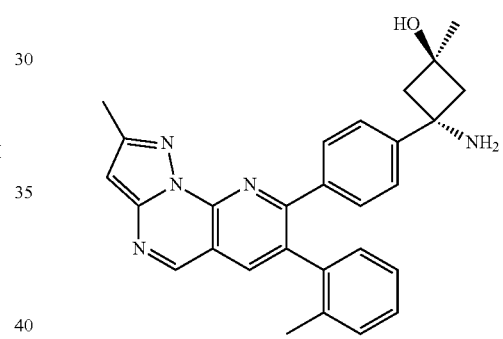

CDLXXI

Compound [CDLXXI] was prepared using a procedure similar to that of [XLI]. Data for Compound [CDLXXI]: LCMS (m/e) 450 (M+H); $^1$H NMR. (400 MHz, METHANOL-d4) δ ppm 1.48 (s, 3H) 1.90 (s, 3H) 1.91 (s, 3H) 2.51-2.57 (m, 2H) 2.58 (s, 3H) 2.71-2.82 (m, 2H) 6.75 (s, 1H) 7.16 (dd, J=7.22, 1.27 Hz, 1H) 7.21-7.34 (m, 3H) 7.37-7.48 (m, 2H) 7.63-7.75 (m, 2H) 7.68-7.68 (m, 0H) 8.42 (s, 1H) 9.01 (s, 1H).

7-(2-Methoxy-phenyl)-2-methyl-9H-1,4,9,9b-tetraaza-cyclopenta[a]naphthalen-8-one [CDLXXII]

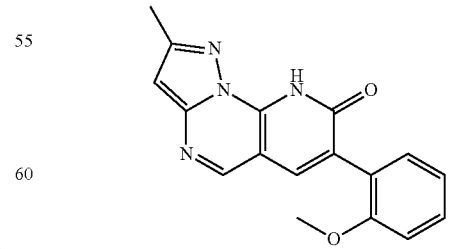

CDLXXII

Compound [CDLXXII] was prepared using a procedure similar to that of Compound [CCCLXXXVI] (DBU procedure). This material was taken on to the next step without further characterization.

8-Chloro-7-(2-methoxy-phenyl)-2-methyl-1,4,9,9b-tetraaza-cyclopenta[a]naphthalene [CDLXXIII]

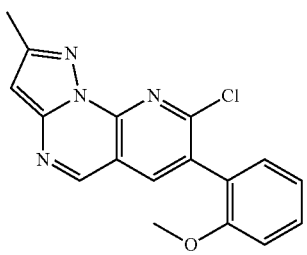

CDLXXIII

Compound [CDLXXIII] was prepared using a procedure similar to that of Compound [V] (POCl₃ procedure). Data for Compound [CDLXXIII]: LCMS m/e 325 (M+H); ¹H NMR (300 MHz, CHLOROFORM-d) δ ppm 2.63 (s, 3H) 3.80 (s, 3H) 6.71 (s, 1H) 7.02 (m, 2H) 7.29 (s, 1H) 7.44 (m, 1H) 8.16 (s, 1H) 8.80 (s, 1H).

trans-2-(3-Hydroxy-1-{4-[7-(2-methoxy-phenyl)-2-methyl-1,4,9,9b-tetraaza-cyclopenta[a]naphthalen-8-yl]-phenyl}-3-methyl-cyclobutyl)-isoindole-1,3-dione [CDLXXIV]

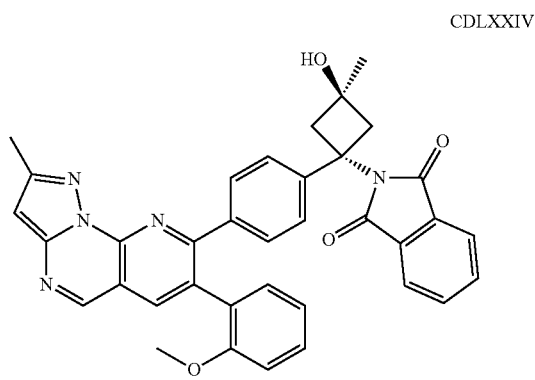 [SMILES: COc1ccccc1-c1cc2cnc3cc(C)nn3c2nc1-c1ccc([C@]2(N3C(=O)c4ccccc4C3=O)C[C@](C)(O)C2)cc1]

CDLXXIV

Compound [CDLXXIV] was prepared using a procedure similar to that of Compound [XL]. Data for Compound [CDLXXIV]: LCMS (m/e) 596 (M+H).

trans-3-Amino-3-{4-[7-(2-methoxy-phenyl)-2-methyl-1,4,9,9b-tetraaza-cyclopenta[a]naphthalen-8-yl]-phenyl}-1-methyl-cyclobutanol [CDLXXV]

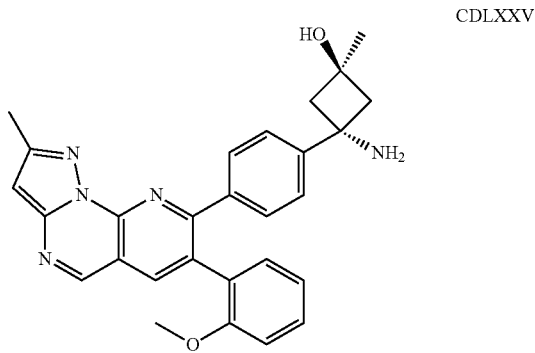 [SMILES: COc1ccccc1-c1cc2cnc3cc(C)nn3c2nc1-c1ccc([C@]2(N)C[C@](C)(O)C2)cc1]

CDLXXV

Compound [CDLXXV] was prepared using a procedure similar to that of Compound [XII]. Data for Compound [CDLXXV]: LCMS (m/e) 466 (M+H); ¹H NMR (400 MHz, METHANOL-d4) δ ppm 1.48 (s, 3H) 1.91 (s, 3H) 2.52-2.62 (m, 5H) 2.73-2.81 (m, 2H) 6.73 (s, 1H) 6.88 (d, J=8.30 Hz, 1H) 6.98-7.06 (m, 1H) 7.29-7.38 (m, 2H) 7.38-7.47 (m, 2H) 7.60-7.69 (m, 2H) 8.45 (s, 1H) 9.00 (s, 1H).

7-(3-Methoxy-phenyl)-2-methyl-9H-1,4,9,9b-tetraaza-cyclopenta[a]naphthalen-8-one [CDLXXVI]

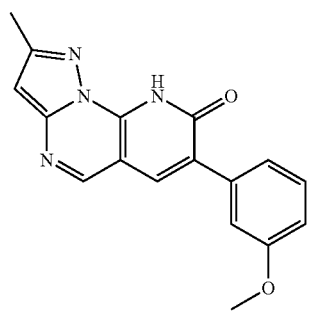

CDLXXVI

Compound [CDLXXVI] was prepared using a procedure similar to that of Compound [CCCLXXXVI] (DBU procedure). This material was taken on to the next step without further characterization.

8-Chloro-7-(3-methoxy-phenyl)-2-methyl-1,4,9,9b-tetraaza-cyclopenta[a]naphthalene [CDLXXVII]

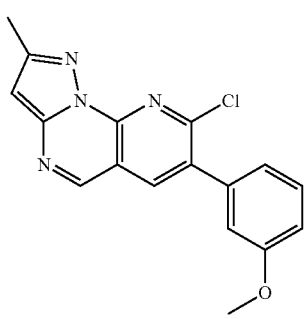

CDLXXVII

Compound [CDLXXVII] was prepared using a procedure similar to that of Compound [V] (POCl₃ procedure). Data for Compound [CDLXXVII]: LCMS (m/e) 325 (M+H); ¹H NMR (300 MHz, CHLOROFORM-d) δ ppm 2.66 (s, 3H) 3.90 (s, 3H) 6.75 (s, 1H) 7.03-7.11 (m, 3H) 7.42-7.47 (m, 3H) 8.22 (s, 1H) 8.84 (s, 1H).

trans-2-(3-Hydroxy-1-{4-[7-(3-methoxy-phenyl)-2-methyl-1,4,9,9b-tetraaza-cyclopenta[a]naphthalen-8-yl]-phenyl}-3-methyl-cyclobutyl)-isoindole-1,3-dione [CDLXXVIII]

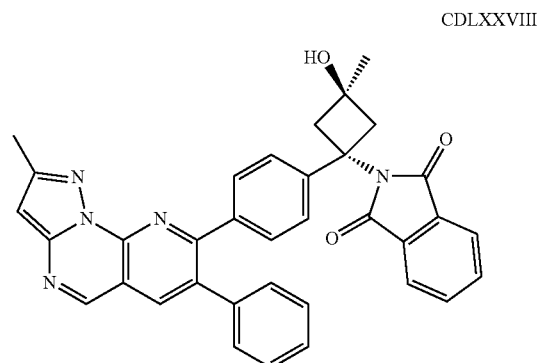

CDLXXVIII

Compound [CDLXXVIII] was prepared using a procedure similar to that of Compound [XLI]. Data for Compound [CDLXXVIII]: LCMS (m/e) 596 (M+H).

trans-3-Amino-3-{4-[7-(3-methoxy-phenyl)-2-methyl-1,4,9,9b-tetraaza-cyclopenta[a]naphthalen-8-yl]-phenyl}-1-methyl-cyclobutanol [CDLXXIX]

CDLXXIX

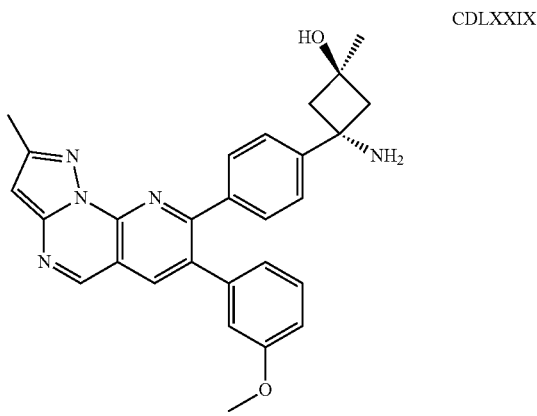 [SMILES: COc1cccc(-c2cc3cnc4cc(C)nn4c3nc2-c2ccc([C@]3(N)C[C@](C)(O)C3)cc2)c1]

Compound [CDLXXIX] was prepared using a procedure similar to that of Compound [XLI]. Data for Compound [CDLXXIX]: LCMS (m/e) 466 (M+H); $^1$H NMR (400 MHz, METHANOL-d4) δ ppm 1.49 (s, 3H) 1.91 (s, 3H) 2.53-2.61 (m, 5H) 2.74-2.83 (m, 2H) 3.66 (s, 3H) 6.74 (s, 1H) 6.81-6.85 (m, 1H) 6.85-6.92 (m, 2H) 7.24 (t, J=7.91 Hz, 1H) 7.43-7.50 (m, 2H) 7.65-7.72 (m, 2H) 8.53 (s, 1H) 9.02 (s, 1H).

7-(2-Chloro-phenyl)-2-methyl-9H-1,4,9,9b-tetraaza-cyclopenta[a]naphthalen-8-one [CDLXXX]

CDLXXX

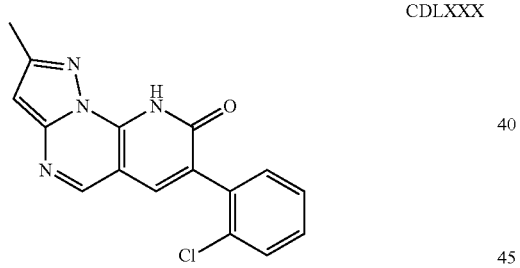

Compound [CDLXXX] was prepared using a procedure similar to that of Compound [CCCLXXXVI] (DBU procedure). This material was taken on to the next step without further characterization.

8-Chloro-7-(2-chloro-phenyl)-2-methyl-1,4,9,9b-tetraaza-cyclopenta[a]naphthalene [CDLXXXI]

CDLXXXI

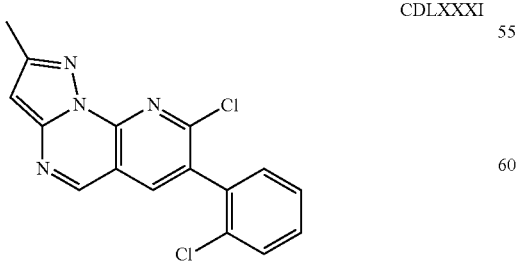

Compound [CDLXXXI] was prepared using a procedure similar to that of Compound [V] (POCl$_3$ procedure). Data for Compound [CDLXXXI]: LCMS (m/e) 325 (M+H); $^1$H NMR (300 MHz, CHLOROFORM-d) δ ppm 2.66 (s, 3H) 5.32 (s, 1H) 6.70 (s, 1H) 7.20-7.60 (m, 4H) 8.19 (s, 1H) 8.84 (s, 1H).

trans-2-(1-{4-[7-(2-Chloro-phenyl)-2-methyl-1,4,9,9b-tetraaza-cyclopenta[a]naphthalen-8-yl]-phenyl}-3-hydroxy-3-methyl-cyclobutyl)-isoindole-1,3-dione [CDLXXXII]

CDLXXXII

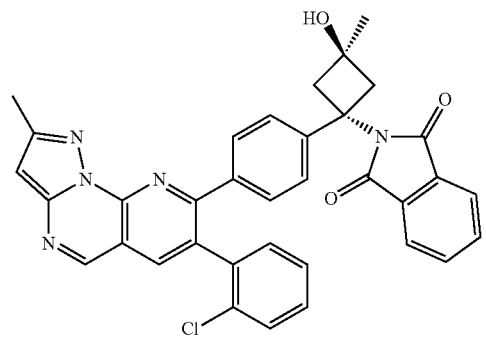

Compound [CDLXXXII] was prepared using a procedure similar to that of Compound [XL]. Data for Compound [CDLXXXII]: LCMS m/e 600 (M+H).

trans-3-Amino-3-{4-[7-(2-chloro-phenyl)-2-methyl-1,4,9,9b-tetraaza-cyclopenta[a]naphthalen-8-yl]-phenyl}-1-methyl-cyclobutanol [CDLXXXIII]

CDLXXXIII

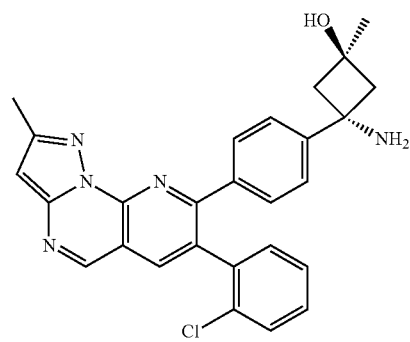

Compound [CDLXXXIII] was prepared using a procedure similar to that of Compound [XLI]. Data for Compound [CDLXXXIII]: LCMS (m/e) 470 (M+H); $^1$H NMR (400 MHz, METHANOL-d4) δ ppm 1.50 (s, 3H) 2.61 (s, 3H) 2.63-2.82 (m, 2H) 2.82-2.96 (m, 2H) 6.80 (s, 1H) 7.26-7.63 (m, 6H) 7.76 (d, J=8.54 Hz, 2H) 8.54 (s, 1H) 9.06 (s, 1H).

2-Methyl-7-m-tolyl-9H-1,4,9,9b-tetraaza-cyclopenta[a]naphthalen-8-one [CDLXXXIV]

CDLXXXIV

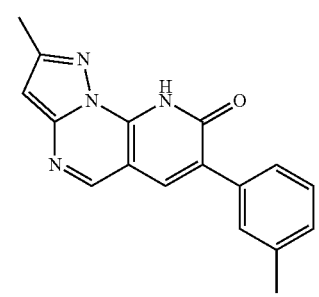

Compound [CDLXXXIV] was prepared using a procedure similar to that of Compound [CCCLXXXVI] (DBU procedure). This material was taken on to the next step without further characterization.

8-Chloro-2-methyl-7-m-tolyl-1,4,9,9b-tetraaza-cyclopenta[a]naphthalene [CDLXXXV]

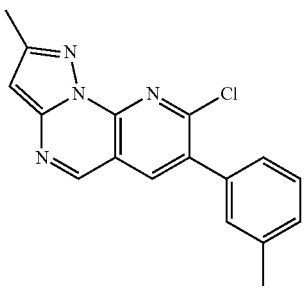

CDLXXXV

Compound [CDLXXXV] was prepared using a procedure similar to that of Compound [V] (POCl₃ procedure). Data for Compound [CDLXXXV]: LCMS (m/e) 309 (M+H); $^1$H NMR (300 MHz, CHLOROFORM-d) δ ppm 2.48 (s, 3H) 2.66 (s, 3H) 6.76 (s, 1H) 7.33 (s, 3H) 7.40-7.45 (m, 1H) 8.85 (s, 1H).

trans-2-{3-Hydroxy-3-methyl-1-[4-(2-methyl-7-m-tolyl-1,4,9,9b-tetraaza-cyclopenta[a]naphthalen-8-yl)-phenyl]-cyclobutyl}-isoindole-1,3-dione [CDLXXXVI]

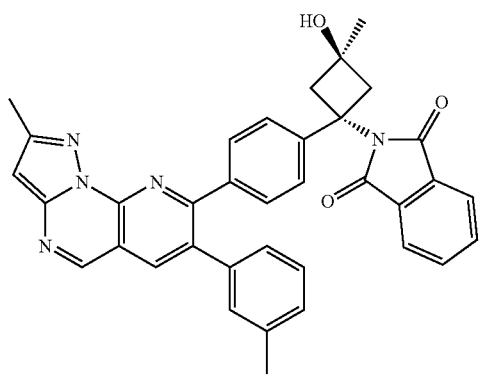

CDLXXXVI

Compound [CDLXXXVI] was prepared using a procedure similar to that of Compound [XL]. Data for Compound [CDLXXXVI]: LCMS (m/e) 580 (M+H).

trans-3-Amino-1-methyl-3-[4-(2-methyl-7-m-tolyl-1,4,9,9b-tetraaza-cyclopenta[a]naphthalen-8-yl)-phenyl]-cyclobutanol [CDLXXXVII]

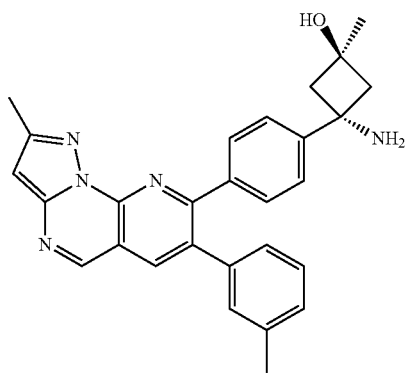

CDLXXXVII

Compound [CDLXXXVII] was prepared using a procedure similar to that of Compound [XLI]. Data for Compound [CDLXXXVII]: LCMS (m/e) 450 (M+H); $^1$H NMR (400 MHz, METHANOL-d4) δ ppm 1.50 (s, 3H) 2.32 (s, 3H) 2.60 (s, 3H) 2.71 (d, J=14.59 Hz, 2H) 2.89 (d, J=14.64 Hz, 2H) 6.78 (s, 1H) 7.08 (d, J=5.42 Hz, 1H) 7.13-7.35 (m, 3H) 7.44-7.60 (m, 2H) 7.75 (d, J=8.59 Hz, 2H) 8.55 (s, 1H) 9.06 (s, 1H).

7-(4-Methoxy-phenyl)-2-methyl-9H-1,4,9,9b-tetraaza-cyclopenta[a]naphthalen-8-one [CDLXXXVIII]

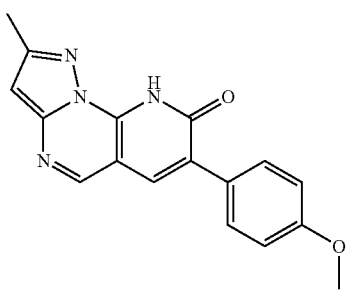

CDLXXXVIII

Compound [CDLXXXVIII] was prepared using a procedure similar to that of Compound [CCCLXXXVIII] (DBU procedure). Data for Compound: LCMS (m/e) 307 (M+H).

8-Chloro-7-(4-methoxy-phenyl)-2-methyl-1,4,9,9b-tetraaza-cyclopenta[a]naphthalene [CDLXXXIX]

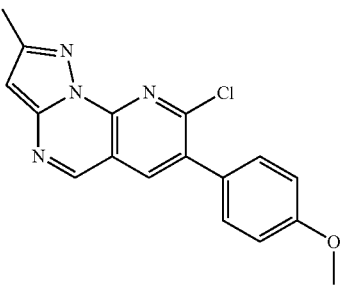

CDLXXXIX

Compound [CDLXXXIX] was prepared using a procedure similar to that of Compound [V] (POCl₃ procedure). Data for Compound [CDLXXXIX]: LCMS (m/e) 325 (M+H); $^1$H NMR (300 MHz, CHLOROFORM-d) δ ppm 2.63 (s, 3H) 3.89 (s, 3H) 6.72 (s, 1H) 7.02 (d, J=8.4 Hz, 2H) 7.44-7.47 (d, J=8.7 Hz, 2H) 8.17 (s, 1H) 8.82 (s, 1H).

trans-2-(3-Hydroxy-1-{4-[7-(4-methoxy-phenyl)-2-methyl-1,4,9,9b-tetraaza-cyclopenta[a]naphthalen-8-yl]-phenyl}-3-methyl-cyclobutyl)-isoindole-1,3-dione [CDXC]

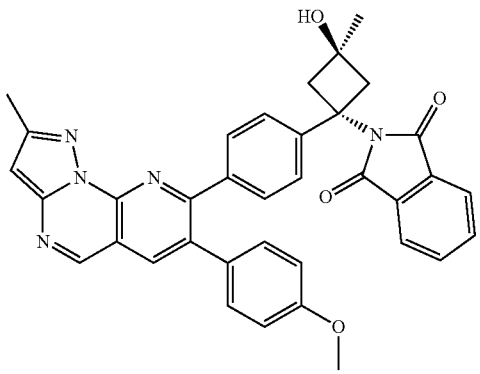

CDXC

Compound [CDXC] was prepared using a procedure similar to that of Compound [XL]. Data for Compound [CDXC]: LCMS (rife) 596 (M+H).

trans-3-Amino-3-{4-[7-(4-methoxy-phenyl)-2-methyl-1,4,9,9b-tetraaza-cyclopenta[a]naphthalen-8-yl]-phenyl}-1-methyl-cyclobutanol [CDXCI]

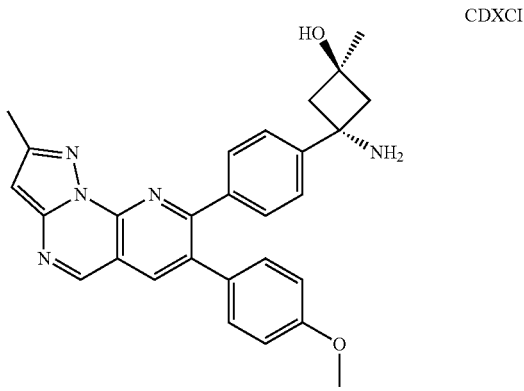 [SMILES: COc1ccc(-c2cc3cnc4cc(C)nn4c3nc2-c2ccc([C@]3(N)C[C@](C)(O)C3)cc2)cc1]

CDXCI

Compound [CDXCI] was prepared using a procedure similar to that of Compound [XLI], Data for Compound [CDXCI]: LCMS (m/e) 466 (M+H); ¹H NMR (400 MHz, METHANOL-d4) δ ppm 1.51 (s, 3H) 2.59 (s, 3H) 2.71 (4, J=14.64 Hz, 2H) 2.80-3.01 (m, 2H) 6.77 (s, 1H) 6.91 (d, J=8.79 Hz, 2H) 7.18-7.31 (m, 2H) 7.53 (d, J=8.54 Hz, 2H) 7.75 (d, J=8.49 Hz, 2H) 8.54 (s, 1H) 9.05 (s, 1H).

2-Methyl-7-(2-trifluoromethyl-phenyl)-9H-1,4,9,9b-tetraaza-cyclopenta[a]naphthalen-8-one [CDXCII]

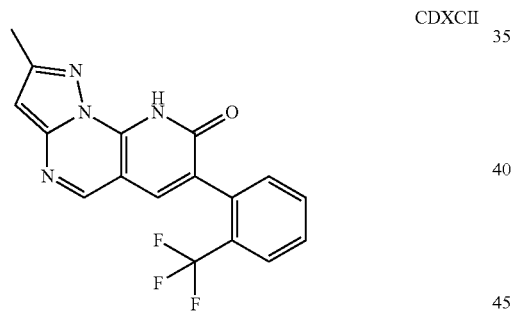

CDXCII

Compound [CDXCII] was prepared using a procedure similar to that of Compound [CCCLXXXVIII] (DBU procedure). Data for Compound: LCMS (m/e) 363 (M+H).

8-Chloro-2-methyl-7-(2-trifluoromethyl-phenyl)-1,4,9,9b-tetraaza-cyclopenta[a]naphthalene [CDXCIII]

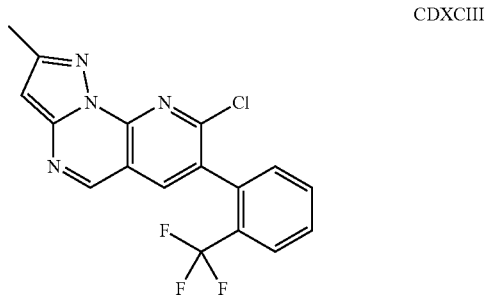 [SMILES: Cc1cc2ncc3cc(-c4ccccc4C(F)(F)F)c(Cl)nc3n2n1]

CDXCIII

Compound [CDXCIII] was prepared using a procedure similar to that of Compound [V] (POCl₃ procedure). Data for Compound [CDXCIII]: LCMS (m/e) 363 (M+H); ¹H NMR (300 MHz, CHLOROFORM-d) δ ppm 2.66 (s, 3H) 6.77 (s, 1H) 7.41 (d, J=7.2 Hz 1H) 7.63-7.74 (m, 2H) 7.88 (d, J=7.2 Hz, 1H) 8.17 (s, 1H) 8.83 (s, 1H).

trans-2-(3-Hydroxy-3-methyl-1-{4-[2-methyl-7-(2-trifluoromethyl-phenyl)-1,4,9,9b-tetraaza-cyclopenta[a]naphthalen-8-yl]-phenyl}-cyclobutyl)-isoindole-1,3-dione [CDXCIV]

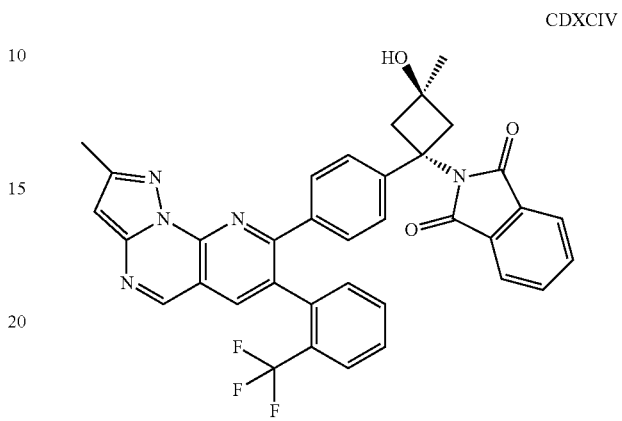

CDXCIV

Compound [CDXCIV] was prepared using a procedure similar to that of Compound [XL]. Data for Compound [CDXCIV]: LCMS m/e 634 (M+H).

trans-3-Amino-1-methyl-3-{4-[2-methyl-7-(2-trifluoromethyl-phenyl)-1,4,9,9b-tetraaza-cyclopenta[a]naphthalen-8-yl]-phenyl}-cyclobutanol [CDXCV]

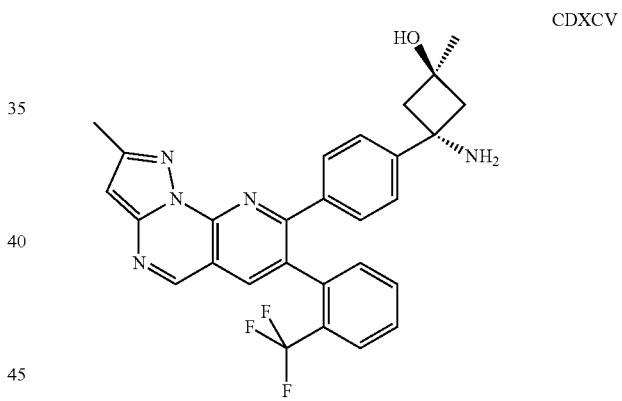

CDXCV

Compound [CDXCV] was prepared using a procedure similar to that of Compound [XLI]. Data for Compound [CDXCV]: LCMS (m/e) 504 (M+H); ¹H NMR (400 MHz, METHANOL-d4) δ ppm 1.49 (s, 3H) 2.61 (s, 3H) 2.64-2.74 (m, 2H) 2.80-2.93 (m, 2H) 6.81 (s, 1H) 7.44 (d, J=4.54 Hz, 1H) 7.47-7.54 (m, 2H) 7.62 (d, J=9.13 Hz, 2H) 7.72 (d, J=8.54 Hz, 2H) 7.78-7.97 (m, 1H) 8.52 (s, 1H) 9.05 (s, 1H)

2-Methyl-7-pyridin-3-yl-9H-1,4,9,9b-tetraaza-cyclopenta[a]naphthalen-8-one [CDXCVI]

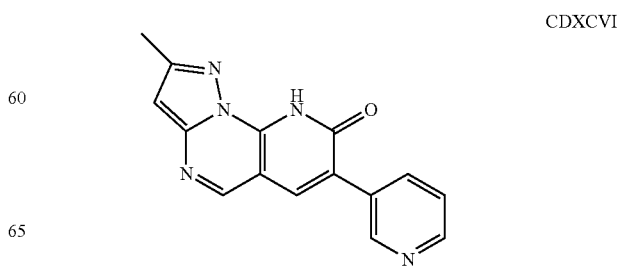

CDXCVI

Compound [CDXCVI] was prepared using a procedure similar to that of Compound [IV] (NaO-t-Bu procedure). Data for Compound [CDXCVI]: LCMS (m/e) 278 (M+H).

8-Chloro-2-methyl-7-pyridin-3-yl-1,4,9,9b-tetraaza-cyclopenta[a]naphthalene [CDXCVII]

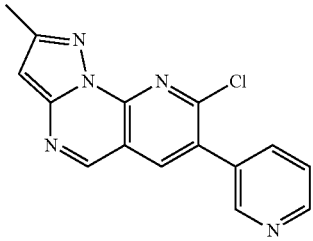

CDXCVII

Compound [CDXCVII] was prepared using a procedure similar to that of Compound [V] (POCl$_3$ procedure). Data for Compound [CDXCVII]: LCMS (m/e) 296 (M+H); $^1$H NMR (300 MHz, CHLOROFORM-d) δ ppm 2.59 (s, 3H) 6.80 (s, 1H) 7.62-7.67 (m, 2H) 8.12-8.16 (m, 1H) 8.79 (d, J=3.0 Hz, 2H) 9.04 (s, 1H).

trans-2-{3-Hydroxy-3-methyl-1-[4-(2-methyl-7-pyridin-3-yl-1,4,9,9b-tetraaza-cyclopenta[a]naphthalen-8-yl)-phenyl]-cyclobutyl}-isoindole-1,3-dione [CDXCVIII]

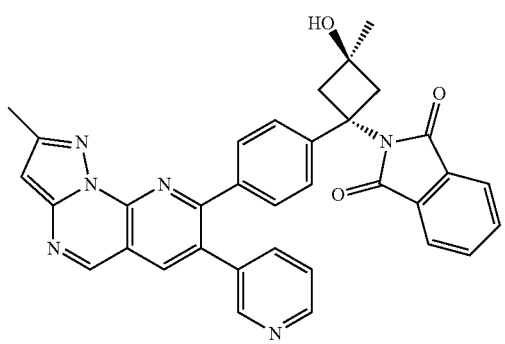

CDXCVIII

Compound [CDXCVIII] was prepared using a procedure similar to that of Compound [XL]. Data for Compound [CDXCVIII]: LCMS (m/e) 567 (M+H).

trans-3-Amino-1-methyl-3-[4-(2-methyl-7-pyridin-3-yl-1,4,9,9b-tetraaza-cyclopenta[a]naphthalen-8-yl)-phenyl]-cyclobutanol [CDXCIX]

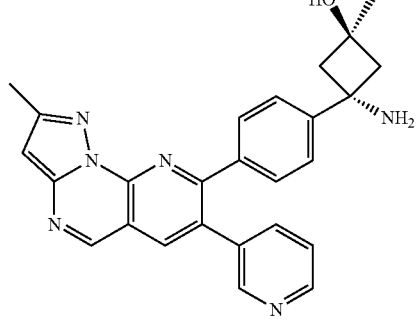

CDXCIX

Compound [CDXCIX] was prepared using a procedure similar to that of Compound [XLI]. Data for Compound [CDXCIX]: LCMS (m/e) 437 (M+H); $^1$H NMR (400 MHz, METHANOL-d4) δ ppm 1.51 (s, 3H) 2.60 (s, 3H) 2.72 (4, J=14.59 Hz, 2H) 2.82-2.93 (m, 2H) 6.81 (s, 1H) 7.51-7.56 (m, 1H) 7.58 (d, J=8.54 Hz, 2H) 7.67-7.75 (m, 2H) 7.96 (dd, J=7.96, 3.76 Hz, 1H) 8.52 (d, J=1.85 Hz, 1H) 8.57 (dd, J=5.08, 1.46 Hz, 1H) 8.69 (s, 1H) 9.08 (s, 1H).

3-(2-Methyl-8-oxo-8,9-dihydro-1,4,9,9b-tetraaza-cyclopenta[a]naphthalen-7-yl)-benzonitrile [D]

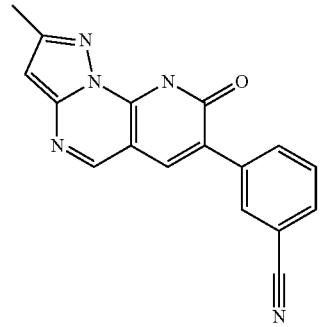

D

Compound [D] was prepared using a procedure similar to that of Compound [IV] (NaO-t-Bu procedure). Data for Compound: LCMS (m/e) 302 (M+H).

3-(8-Chloro-2-methyl-1,4,9,9b-tetraaza-cyclopenta[a]naphthalen-7-yl)-benzonitrile [DI]

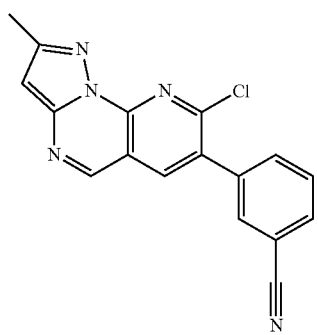

DI

Compound [DI] was prepared using a procedure similar to that of Compound [V] (POCl$_3$ procedure). Data for Compound [DI]: LCMS (m/e) 320 (M+H); $^1$H NMR (300 MHz, CHLOROFORM-d) δ ppm 2.66 (s, 3H) 6.77 (s, 1H) 7.64-7.70 (m, 1H) 7.79-7.84 (t, J=9.0 Hz, 3H) 8.22 (s, 1H) 8.85 (s, 1H).

trans-(1-{4-[7-(3-Cyano-phenyl)-2-methyl-1,4,9,9b-tetraaza-cyclopenta[a]naphthalen-8-yl]-phenyl}-3-hydroxy-3-methyl-cyclobutyl)-carbamic acid tert-butyl ester [DII]

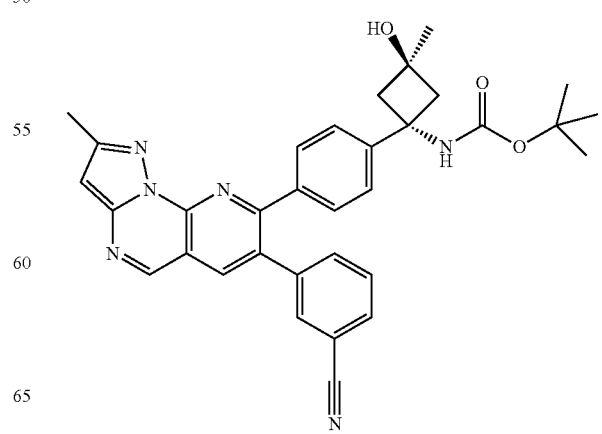

DII

Compound [DII] was prepared using a procedure similar to that of Compound [XL]. Data for Compound [DII]: LCMS (m/e) 561 (M+H).

trans-3-{8-[4-(1-Amino-3-hydroxy-3-methyl-cyclobutyl)-phenyl]-2-methyl-1,4,9,9b-tetraaza-cyclopenta[a]naphthalen-7-yl}-benzonitrile [DIII]

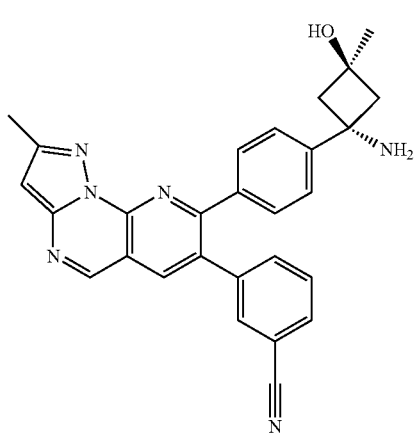

Compound [DIII] was prepared using a procedure similar to that of Compound [XLIV]. Data for Compound [DIII]: LCMS (m/e) 461 (M+H); $^1$H NMR (400 MHz, METHANOL-d4) δ ppm 1.51 (s, 3H) 2.60 (s, 3H) 2.31 (d, J=14.64 Hz, 2H) 2.89 (d, J=14.64 Hz, 2H) 6.80 (s, 1H) 7.48-7.60 (m, 3H) 7.62-7.68 (m, 1H) 7.68-7.79 (m, 4H) 8.64 (s, 1H) 9.07 (s, 1H).

2-(2-Methyl-8-oxo-8,9-dihydro-1,4,9,9b-tetraaza-cyclopenta[a]naphthalen-7-yl)-benzonitrile [DIV]

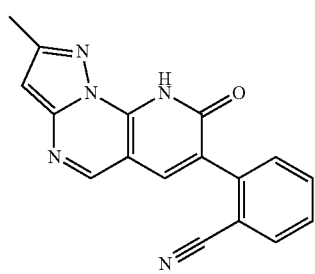

Compound [DIV] was prepared using a procedure similar to that of Compound [IV] (NaO-t-Bu procedure). This compound was taken on to the next step without further characterization.

2-(8-Chloro-2-methyl-1,4,9,9b-tetraaza-cyclopenta[a]naphthalen-7-yl)-benzonitrile [DV]

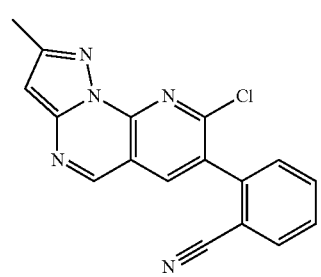

Compound [DV] was prepared using a procedure similar to that of Compound [V] (POCl$_3$ procedure). Data for Compound [DV]: LCMS (m/e) 320 (M+H); $^1$H NMR (300 MHz, CHLOROFORM-d) δ ppm 2.67 (s, 3H) 6.79 (s, 1H) 7.59-7.67 (m, 2H) 7.76-7.81 (t, J=6.6 Hz, 1H) 7.89 (d, J=7.8 Hz, 1H) 8.29 (s, 1H) 8.87 (s, 1H).

trans-(1-{4-[7-(2-Cyano-phenyl)-2-methyl-1,4,9,9b-tetraaza-cyclopenta[a]naphthalen-8-yl]-phenyl}-3-hydroxy-3-methyl-cyclobutyl)-carbamic acid tert-butyl ester [DVI]

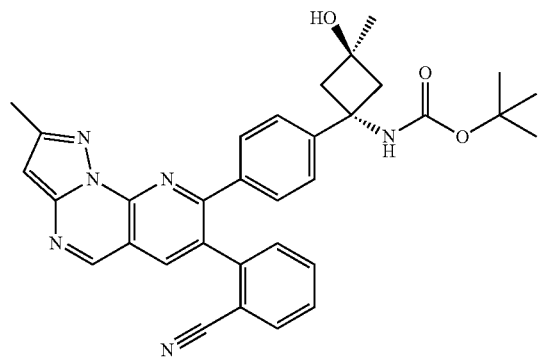

Compound [DVI] was prepared using a procedure similar to that of Compound [X]. Data for Compound [DVI]: LCMS (m/e) 561 (M+H).

trans-2-{8-[4-(1-Amino-3-hydroxy-3-methyl-cyclobutyl)-phenyl]-2-methyl-1,4,9,9b-tetraaza-cyclopenta[a]naphthalen-7-yl}-benzonitrile [DVII]

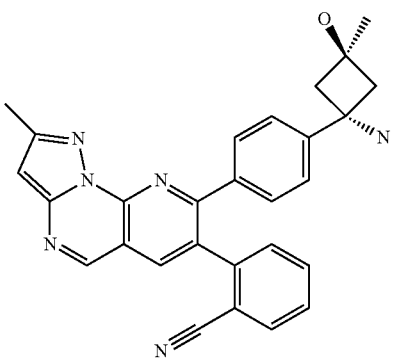

Compound [DVII] was prepared using a procedure similar to that of Compound [XLIV]. Data for Compound [DVII]: LCMS (m/e) 461 (M+H); $^1$H NMR (400 MHz, METHANOL-d4) δ ppm 1.47 (s, 3H) 2.58 (s, 3H) 2.64-2.72 (m, 2H) 2.80-2.90 (m, 2H) 6.79 (s, 1H) 7.47-7.59 (m, 3H) 7.63-7.78 (m, 5H) 8.64 (s, 1H) 9.05 (s, 1H)

4-(2-Methyl-8-oxo-8,9-dihydro-1,4,9,9b-tetraaza-cyclopenta[a]naphthalen-7-yl)-benzonitrile [DVIII]

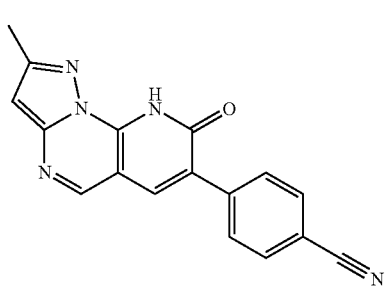

Compound [DVIII] was prepared using a procedure similar to that of Compound [CCCLXXXVIII] (DBU procedure). Data for Compound [DVIII]: LCMS (m/e) 302 (M+H).

4-(8-Chloro-2-methyl-1,4,9,9b-tetraaza-cyclopenta[a]naphthalen-7-yl)-benzonitrile [DIX]

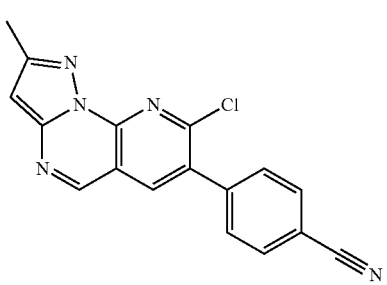

Compound [DIX] was prepared using a procedure similar to that of Compound [V] (POCl₃ procedure). Data for Compound [DIX]: LCMS (m/e) 320 (M+H); ¹H NMR (300 MHz, CHLOROFORM-d) δ ppm 2.64 (s, 3H) 636 (s, 1H) 7.64 (d, J=8.1 Hz, 2H) 7.81 (d, J=8.1 Hz, 4H) 8.20 (s, 1H) 8.83 (s, 1H).

trans-(1-{4-[7-(4-Cyano-phenyl)-2-methyl-1,4,9,9b-tetraaza-cyclopenta[a]naphthalen-8-yl]-phenyl}-3-hydroxy-3-methyl-cyclobutyl)-carbamic acid tert-butyl ester [DX]

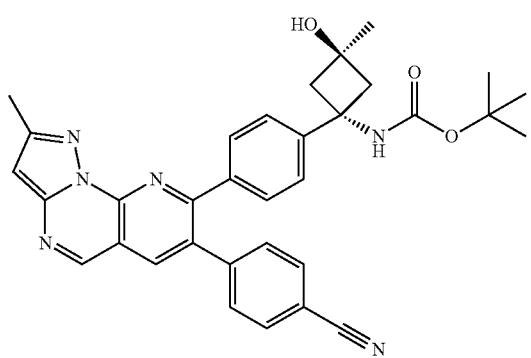

Compound [DX] was prepared using a procedure similar to that of Compound [XL].
Data for Compound [DX]: LCMS (m/e) 561 (M+H).

trans-4-{8-[4-(1-Amino-3-hydroxy-3-methyl-cyclobutyl)-phenyl]-2-methyl-1,4,9,9b-tetraaza-cyclopenta[a]naphthalen-7-yl}-benzonitrile [DXI]

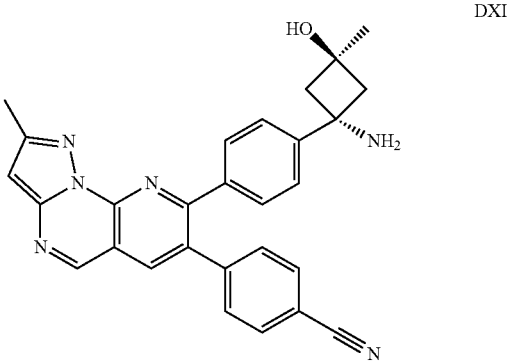 [SMILES: Cc1cc2ncc3cc(-c4ccc(C#N)cc4)c(-c4ccc([C@]5(N)C[C@](C)(O)C5)cc4)nc3n2n1]

Compound [DXI] was prepared using a procedure similar to that of [XLIV]. Data for Compound [DXI]: LCMS (m/e) 461 (M+H); ¹H NMR (400 MHz, METHANOL-d4) δ ppm 1.48 (s, 3H) 2.57 (s, 3H) 2.63-2.74 (m, 2H) 2.86 (d, J=14.69 Hz, 2H) 6.77 (s, 1H) 7.47-7.57 (m, 4H) 7.63-7.73 (m, 4H) 8.62 (s, 1H) 9.04 (s, 1H).

4-(8-Chloro-2-methyl-1,4,9,9b-tetraaza-cyclopenta[a]naphthalen-7-yl)-phenol [DXII]

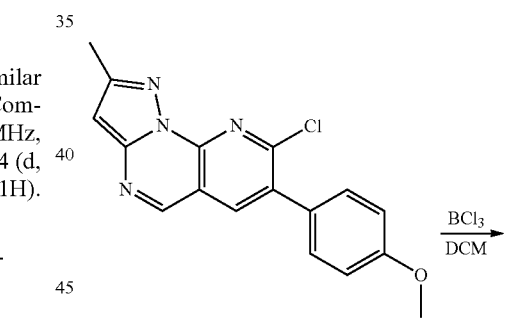

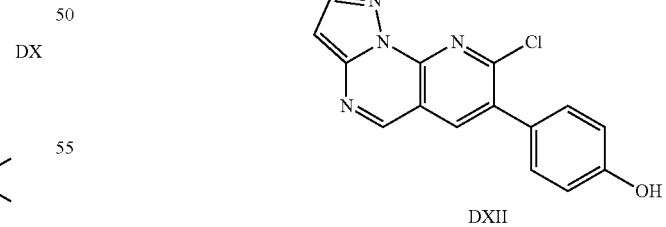

To a 50 mL round-bottom flask was added Compound [CDLXXXIX] (0.75 g, 2.31 mmol, 1.00 eq.) in BCl₃/CH₂Cl₂ (8 mL). The mixture was stirred for 4 days at room temperature and then was quenched with water (20 mL). The mixture was extracted three times with 60 mL of ethyl acetate and the organic layers were collected. The combined organic phases were dried over Na₂SO₄, filtered, concentrated and purified by silica gel chromatography using CH₂Cl₂/MeOH (100:1)

as the eluent to give Compound [DXII] as a yellow solid: LCMS (m/e) 325 (M+H); ¹H NMR (300 MHz, CHLOROFORM-d) δ ppm 8.84 (s, 1H) 8.19 (s, 1H) 7.42 (d, J=9 Hz, 2H) 7.00 (d, J=9 Hz, 2H) 6.75 (s, 1H) 2.65 (s, 3H).

Acetic acid, 4-(8-chloro-2-methyl-1,4,9,9b-tetraaza-cyclopenta[a]naphthalen-7-yl)-phenyl ester [DXIII]

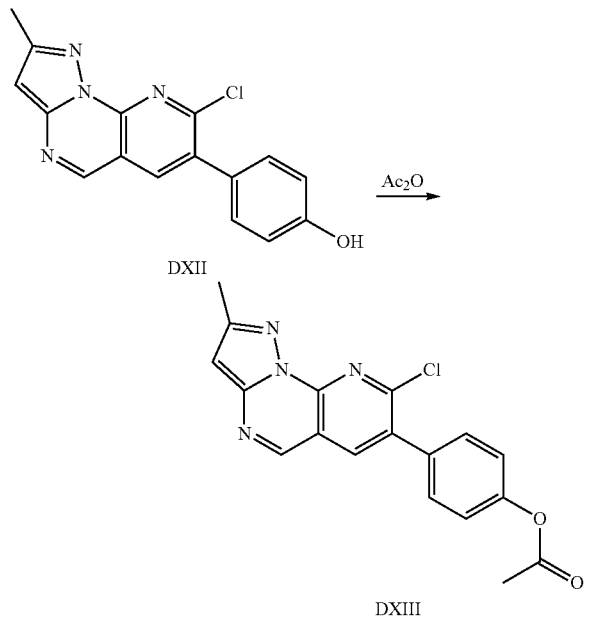

To a 50 mL round-bottom flask was added Compound [DXII] (0.29 g, 0.94 mmol, 1.00 eq.) in Ac$_2$O (20 mL). The mixture was stirred for 3 h at 40° C. and then quenched with water (60 mL). The mixture was extracted three times with 150 mL of ethyl acetate and the organic layers were collected. The combined organic phases were dried over Na$_2$SO$_4$, filtered, concentrated and purified by silica gel chromatography using acetate/petroleum ether (1:5) as the eluent to give Compound [DXIII] as a yellow solid: LCMS (m/e) 352 (M+H); ¹H NMR (300 MHz, CHLOROFORM-d) δ ppm 8.84 (s, 1H) 8.19 (s, 1H) 7.55 (d, J=9 Hz, 2H) 7.26 (d, J=9 Hz, 2H) 6.75 (s, 1H) 2.65 (s, 3H) 2.41 (s, 3H).

trans-Acetic acid 4-{8-[4-(1-tert-butoxycarbonylamino-3-hydroxy-3-methyl-cyclobutyl)-phenyl]-2-methyl-1,4,9,9b-tetraaza-cyclopenta[a]naphthalen-7-yl}-phenyl ester [DXIV]

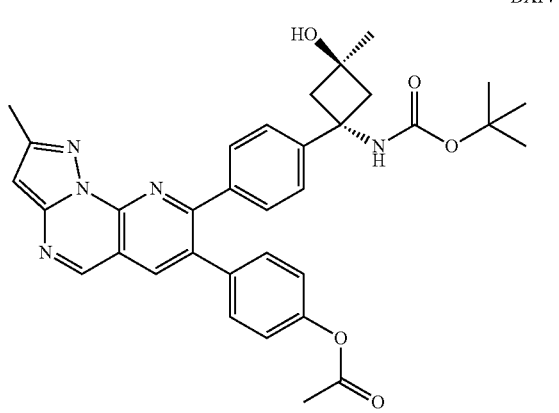

Compound [DXIV] was prepared using a procedure similar to that of Compound [XL]. Data for Compound [DXIV]: LCMS (m/e) 594 (M+H).

trans-Acetic acid 4-{8-[4-(1-amino-3-hydroxy-3-methyl-cyclobutyl)-phenyl]-2-methyl-1,4,9,9b-tetraaza-cyclopenta[a]naphthalen-7-yl}-phenyl ester [DXV]

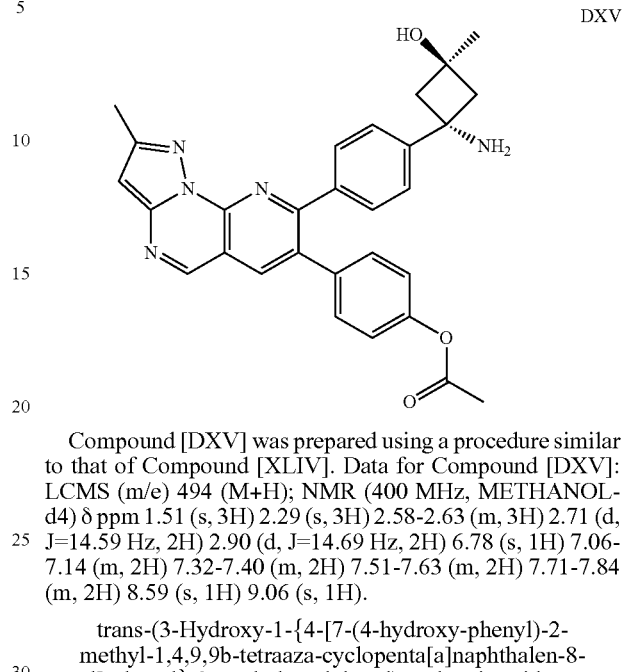

Compound [DXV] was prepared using a procedure similar to that of Compound [XLIV]. Data for Compound [DXV]: LCMS (m/e) 494 (M+H); NMR (400 MHz, METHANOL-d4) δ ppm 1.51 (s, 3H) 2.29 (s, 3H) 2.58-2.63 (m, 3H) 2.71 (d, J=14.59 Hz, 2H) 2.90 (d, J=14.69 Hz, 2H) 6.78 (s, 1H) 7.06-7.14 (m, 2H) 7.32-7.40 (m, 2H) 7.51-7.63 (m, 2H) 7.71-7.84 (m, 2H) 8.59 (s, 1H) 9.06 (s, 1H).

trans-(3-Hydroxy-1-{4-[7-(4-hydroxy-phenyl)-2-methyl-1,4,9,9b-tetraaza-cyclopenta[a]naphthalen-8-yl]-phenyl}-3-methyl-cyclobutyl)-carbamic acid tert-butyl ester [DXVI]

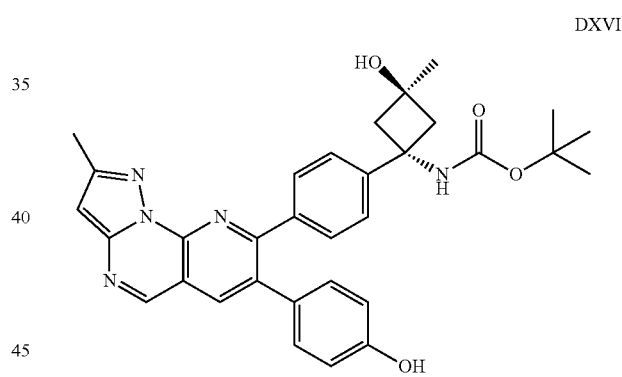

Compound [DXVI] was prepared using a procedure similar to that of [XL]. Data for Compound [DXVI]: LCMS (m/e) 552 (M+H).

trans-4-{8-[4-(1-Amino-3-hydroxy-3-methyl-cyclobutyl)-phenyl]-2-methyl-1,4,9,9b-tetraaza-cyclopenta[a]naphthalen-7-yl}-phenol [DXVII]

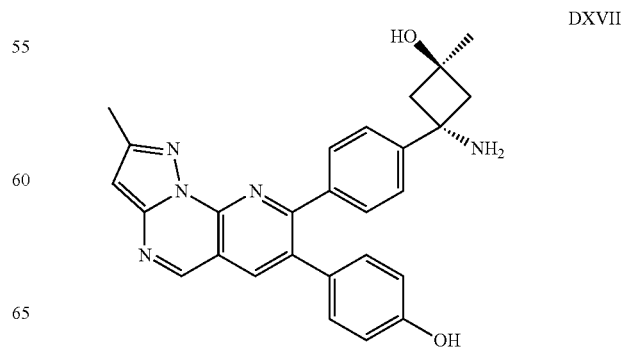

Compound [DXVII] was prepared using a procedure similar to that of Compound [XLIV]. Data for Compound [DXVII]: LCMS (m/e) 452 (M+H); $^1$H NMR (400 MHz, METHANOL-d4) δ ppm 1.51 (s, 3H) 2.59 (s, 3H) 2.71 (d, J=14.69 Hz, 2H) 2.90 (d, J=14.64 Hz, 2H) 6.73-6.78 (m, 3H) 7.14 (d, J=8.59 Hz, 2H) 7.54 (d, J=8.54 Hz, 2H) 7.76 (d, J=8.54 Hz, 2H) 8.52 (s, 1H) 9.04 (s, 1H).

3-(8-Chloro-2-methyl-1,4,9,9b-tetraaza-cyclopenta[a]naphthalen-7-yl)-phenol [DXVIII] and 3-(8-Bromo-2-methyl-1,4,9,9b-tetraaza-cyclopenta[a]naphthalen-7-yl)-phenol [DXIX]

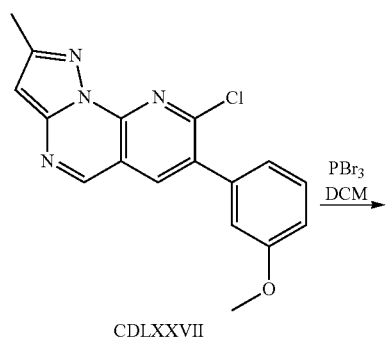

CDLXXVII

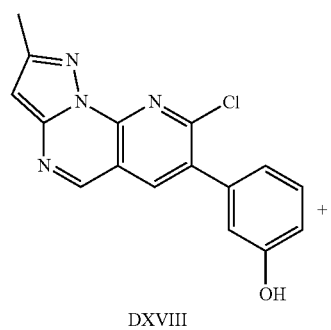

DXVIII

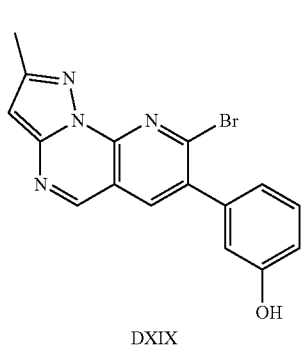

DXIX

To a 50 mL round-bottom flask was added Compound [CDLXXVII] (0.75 g, 2.31 mmol, 1.00 eq.) in BBr$_3$/CH$_2$Cl$_2$ (6 mL). The mixture was stirred for overnight at room temperature and then was quenched with water (30 mL). The mixture was extracted three times with 60 mL ethyl acetate and the organic layer was collected. The combined organic phases were dried over Na$_2$SO$_4$, filtered, concentrated and purified by silica gel chromatography using CH$_2$Cl$_2$/MeOH (100:1) as the eluent to give a mixture of Compound [DXVIII] and [DXIX] as a yellow solid which was characterized as a mixture LCMS (m/e) 311 and 355 (M+H); $^1$H NMR (300 MHz, CHLOROFORM-d) δ ppm 8.71 (s, 1H) 8.16 (s, 1H) 7.40 (d, J=9 Hz, 1H) 7.07 (d, J=9 Hz, 1H) 6.75 (s, 1H) 2.66 (s, 3H).

trans-(3-Hydroxy-1-{4-[7-(3-hydroxy-phenyl)-2-methyl-1,4,9,9b-tetraaza-cyclopenta[a]naphthalen-8-yl]-phenyl}-3-methyl-cyclobutyl)-carbamic acid tert-butyl ester [DXX]

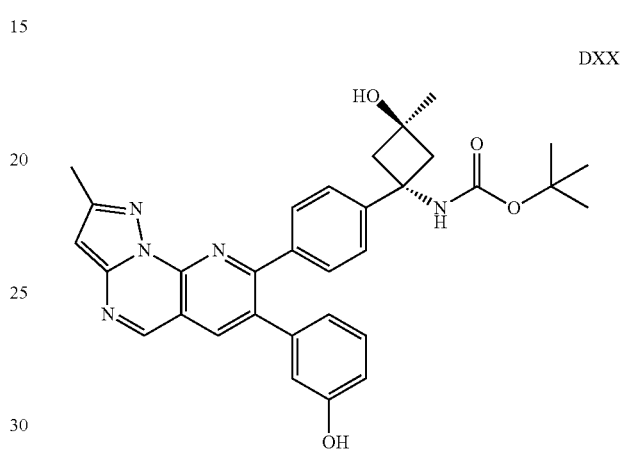

Compound [DXX] was prepared using a procedure similar to that of Compound [XL]. Data for Compound [DXX]: LCMS (m/e) 552 (M+H).

trans-3-{8-[4-(1-Amino-3-hydroxy-3-methyl-cyclobutyl)-phenyl]-2-methyl-1,4,9,9b-tetraaza-cyclopenta[a]naphthalen-7-yl}-phenol [DXXI]

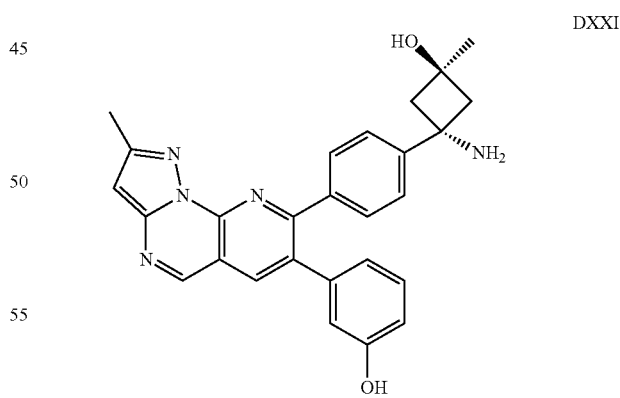

Compound [DXXI] was prepared using a procedure similar to that of Compound [XLIV]. Data for Compound [DXXI]: LCMS (m/e) 452 (M+H); $^1$H NMR. (400 MHz, METHANOL-d4) δ ppm 1.51 (s, 3H) 2.60 (s, 3H) 2.71 (4, J=14.64 Hz, 2H) 2.90 (d, J=14.74 Hz, 2H) 6.65-6.92 (m, 4H) 7.18 (t, J=7.81 Hz, 1H) 7.54 (d, J=8.54 Hz, 2H) 7.80 (d, J=8.54 Hz, 2H) 8.54 (s, 1H) 9.05 (s, 1H).

Acetic acid 3-(8-chloro-2-methyl-1,4,9,9b-tetraaza-cyclopenta[a]naphthalen-7-yl)-phenyl ester [DXXII] and Acetic acid 3-(8-bromo-2-methyl-1,4,9,9b-tetraaza-cyclopenta[a]naphthalen-7-yl)-phenyl ester [DXXIII]

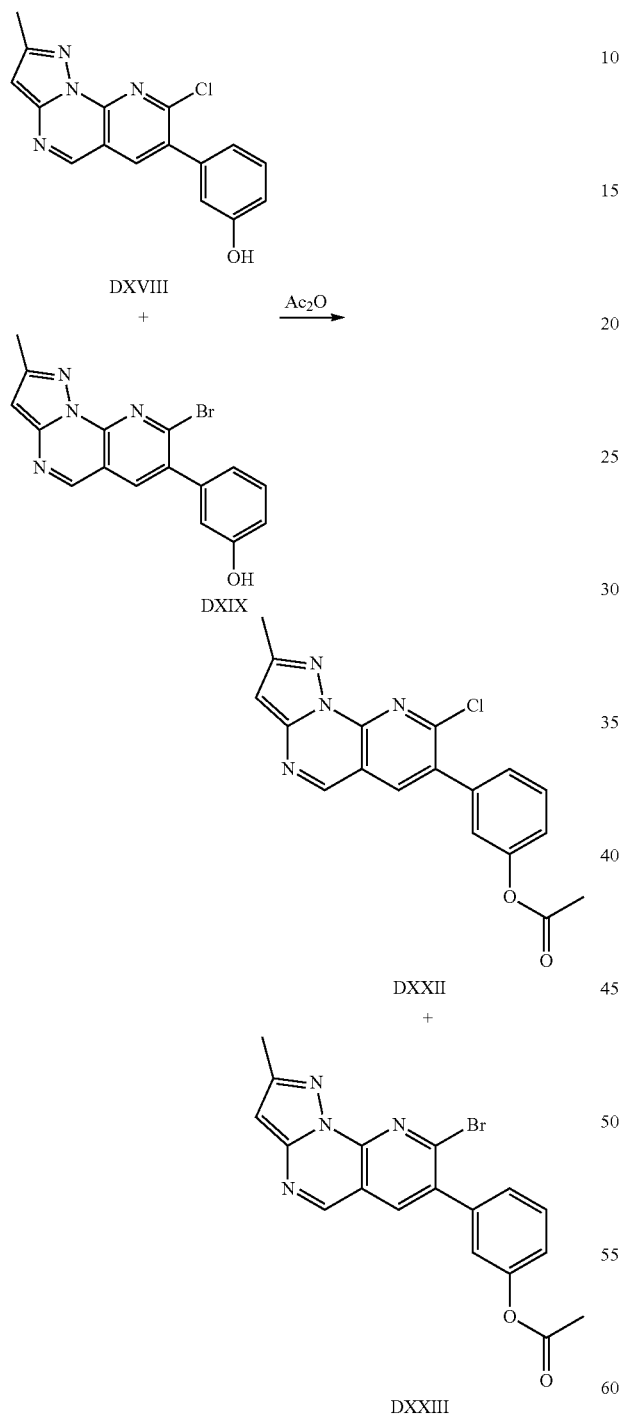

To a 50 mL round-bottom flask was added a mixture of Compound [DXVIII] and Compound [DXIX] (0.25 g, 1.00 eq.) in Ac$_2$O (15 mL) and one drop pyridine. The mixture was stirred for 3 h at 40° C. and then quenched with water (25 mL). The mixture was extracted three times with 90 ml of ethyl acetate and the organic layers were collected. The combined organic phases were dried over Na$_2$SO$_4$, filtered, concentrated and purified by silica gel chromatography using acetate/petroleum ether (1:4) as the eluent to give Compound [DXXII] and Compound [DXXIII] as a yellow solid: LCMS (m/e) 353 and 397 (M+H); $^1$H NMR (300 MHz, CHLOROFORM-d) δ ppm 8.84 (s, 1H) 8.24 (s, 1H) 7.56 (d, J=9 Hz, 2H) 7.39 (d, J=9 Hz, 2H) 6.76 (s, 1H) 2.66 (s, 3H) 2.34 (s, 3H).

trans-Acetic acid 3-{8-[4-(1-tert-butoxycarbonylamino-3-hydroxy-3-methyl-cyclobutyl)-phenyl]-2-methyl-1,4,9,9b-tetraaza-cyclopenta[a]naphthalen-7-yl}-phenyl ester [DXXIV]

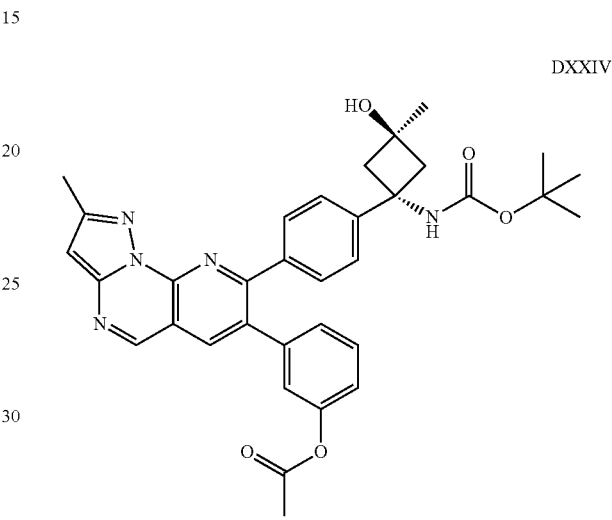

Compound [DXXIV] was prepared using a procedure similar to that of Compound [XL]. Data for Compound [DXXIV]: LCMS (m/e) 594 (M+H).

trans-Acetic acid 3-{8-[4-(1-amino-3-hydroxy-3-methyl-cyclobutyl)-phenyl]-2-methyl-1,4,9,9b-tetraaza-cyclopenta[a]naphthalen-7-yl}-phenyl ester [DXXV]

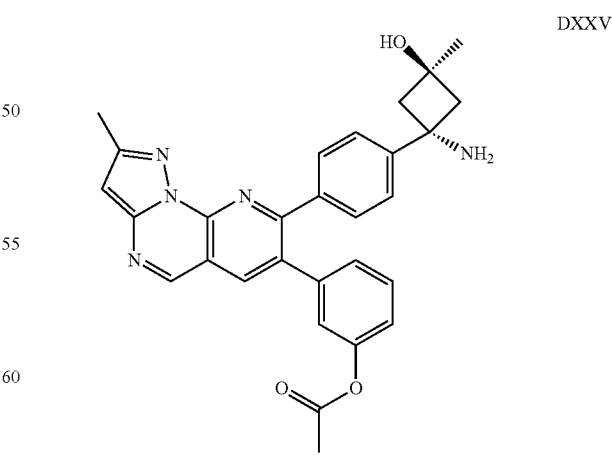

Compound [DXXV] was prepared using a procedure similar to that of [XLIV]. Data for Compound [DXXV]: LCMS (m/e) 494 (M+H); $^1$H NMR (400 MHz, METHANOL-d4)

ppm 1.51 (s, 3H) 2.24 (s, 3H) 2.60 (s, 3H) 2.72 (d, J=14.55 Hz, 2H) 2.91 (d, J=14.64 Hz, 2H) 6.78 (s, 1H) 7.11 (d, J=1.85 Hz, 2H) 7.23 (d, J=7.76 Hz, 1H) 7.38 (d, J=7.81 Hz, 1H) 7.54 (d, J=8.49 Hz, 2H) 7.74 (d, J=8.49 Hz, 2H) 8.60 (s, 1H) 9.06 (s, 1H).

2-(8-Chloro-2-methyl-1,4,9,9b-tetraaza-cyclopenta[a]naphthalen-7-yl)-phenol [DXXVI] and 2-(8-bromo-2-methyl-1,4,9,9b-tetraaza-cyclopenta[a]naphthalen-7-yl)-phenol [DXXVII]

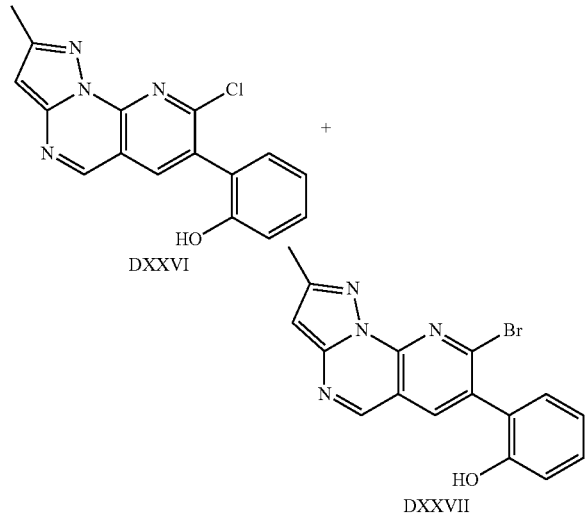

DXXVI

DXXVII

A mixture of Compound [DXXVI] and Compound [DXXVI] was prepared using a procedure similar to that of the mixture of Compound [DXXI] and Compound [DXXII]. Data for the mixture of Compound [DXXVI] and [DXXVII]: CMS (m/e) 311 and 355 (M+H); $^1$H NMR (300 MHz, CHLOROFORM-d) δ ppm 8.71 (s, 1H) 8.16 (s, 1H) 7.36 (d, J=9 Hz, 1H) 7.24 (d, J=9 Hz, 1H) 6.69 (s, 1H) 3.44 (s, 2H) 2.57 (s, 3H).

Acetic acid 2-(8-chloro-2-methyl-1,4,9,9b-tetraaza-cyclopenta[a]naphthalen-7-yl)-phenyl ester [DXXVIII] and Acetic acid 2-(8-bromo-2-methyl-1,4,9,9b-tetraaza-cyclopenta[a]naphthalen-7-yl)-phenyl ester [DXXIX]

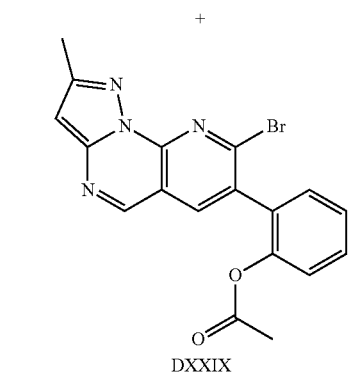

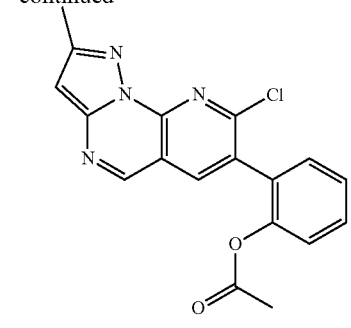

DXXVIII

DXXIX

To a 50 mL round-bottom flask was added a mixture of Compound [DXXVI] and Compound [DXXVI] (0.22 g, 1.00 eq.) in Ac$_2$O (10 mL) and one drop pyridine. The mixture was stirred for 3 h at 40° C. and then quenched with water (30 mL). The mixture was extracted three times with 60 mL of ethyl acetate and the organic layers were collected. The combined organic phases were dried over Na$_2$SO$_4$, filtered, concentrated and purified by silica gel chromatography using acetate/petroleum ether (1:5) as the eluent to give Compound [DXXVIII] and Compound [DXXIX] as a yellow solid: LCMS (m/e) 353 and 397 (M+H); $^1$H NMR (300 MHz, CHLOROFORM-d) δ ppm 8.83 (s, 1H) 8.10 (s, 1H) 7.57 (d, J=9 Hz, 2H) 7.44 (d, 2H) 6.76 (s, 1H) 2.66 (s, 3H) 2.03 (s, 3H).

trans-Acetic acid 2-{8-[4-(1-tert-butoxycarbonylamino-3-hydroxy-3-methyl-cyclobutyl)-phenyl]-2-methyl-1,4,9,9b-tetraaza-cyclopenta[a]naphthalen-7-yl}-phenyl ester [DXXX]

DXXX

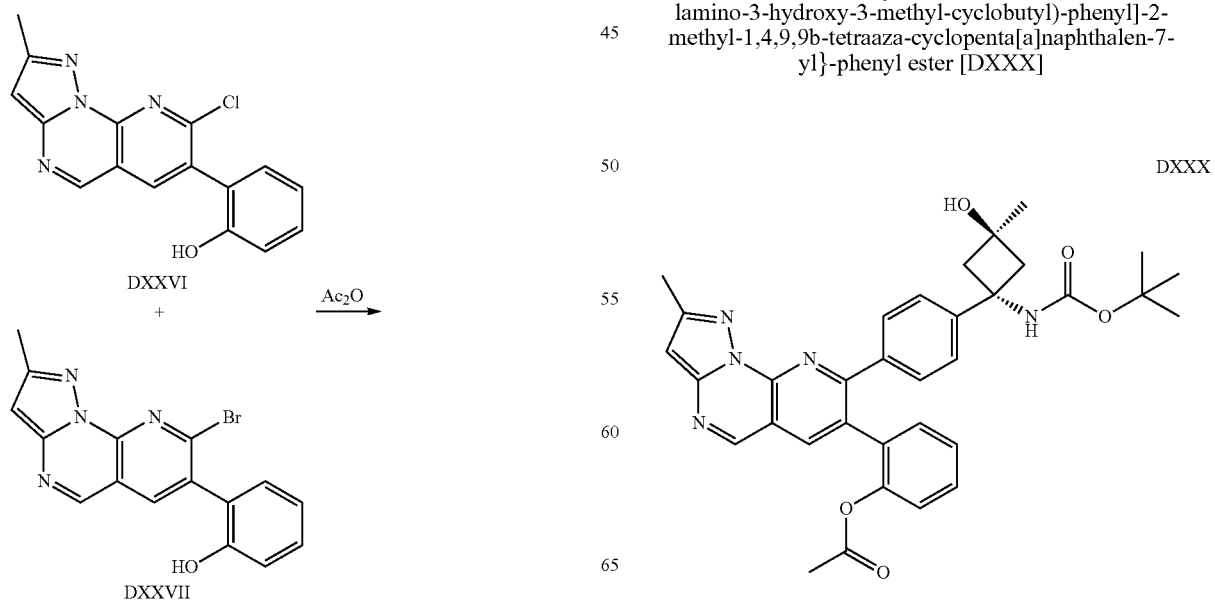

Compound [DXXX] was prepared using a procedure similar to that of Compound [XL]. Data for Compound [DXXX]: LCMS (m/e) 594 (M+H).

trans-Acetic acid 2-{8-[4-(1-amino-3-hydroxy-3-methyl-cyclobutyl)-phenyl]-2-methyl-1,4,9,9b-tetraaza-cyclopenta[a]naphthalen-7-yl}-phenyl ester [DXXXI]

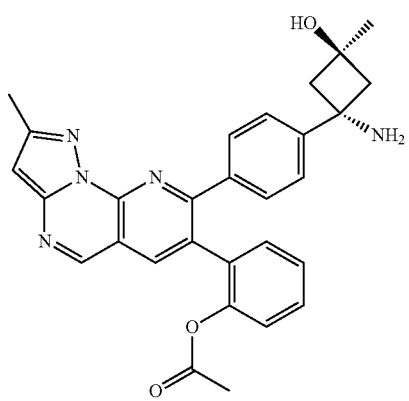

Compound [DXXXI] was prepared using a procedure similar to that of Compound [XLIV]. Data for Compound [DXXXI]: LCMS (m/e) 494 (M+H); $^1$H NMR (400 MHz, METHANOL-d4) δ ppm 1.50 (s, 3H) 1.94 (s, 3H) 2.60 (s, 3H) 2.70 (d, J=14.69 Hz, 2H) 2.89 (d, J=14.50 Hz, 2H) 6.79 (s, 1H) 7.14 (d, J=8.10 Hz, 1H) 7.26-7.38 (m, 1H) 7.37-7.62 (m, 4H) 7.82 (d, J=8.54 Hz, 2H) 8.53 (s, 1H) 9.06 (s, 1H).

Methyl 2-(Pyridin-4-yl)acetate [DXXXIII]

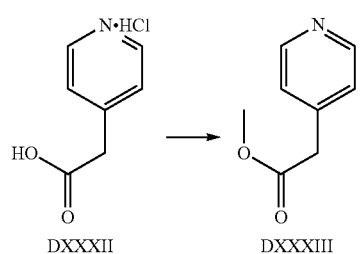

To a 250 mL round-bottom flask was added a solution of Compound [DXXXII] (2 g, 11.6 mmol, 1.00 eq.) in methanol (30 mL). To the above reaction mixture, concentrated $H_2SO_4$ (20 mL) was added drop wise. The mixture was stirred for 2 h at 64° C. in an oil bath. The resulting mixture was cooled and the PH value of the solution was adjusted to 8 with sodium bicarbonate. Then it was extracted with ethyl acetate (3×25 mL) and concentrated under vacuum. It was purified by a silica gel column with EtOAc:petroleum (1:1) to afford Compound [DXXXIII] as a yellow liquid: LCMS (m/e) 152 (M+H); $^1$H NMR (300 MHz, CHLOROFORM-d) δ ppm 3.62 (s, 2H) 3.70 (s, 3H) 7.23 (d, J=3.0 Hz, 2H) 8.35 (s, 2H).

2-Methyl-7-pyridin-4-yl-9H-1,4,9,9b-tetraaza-cyclopenta[a]naphthalen-8-one [DXXXIV]

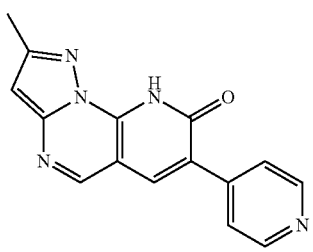

Compound [DXXXIV] was prepared using a procedure similar to that of Compound [IV] (NaO-t-Bu procedure). Data for Compound: LCMS (m/e) 278 (M+H).

8-Chloro-2-methyl-7-pyridin-4-yl-1,4,9,9b-tetraaza-cyclopenta[a]naphthalene [DXXXV]

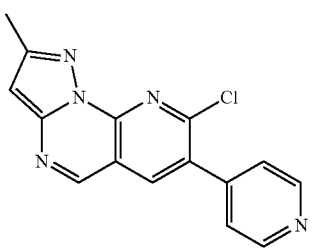 [SMILES: Cc1cc2ncc3cc(-c4ccncc4)c(Cl)nc3n2n1]

Compound [DXXXV] was prepared using a procedure similar to that of Compound [V] (POCl$_3$ procedure). Data for Compound [DXXXV]: LCMS (m/e) 296 (M+H); $^1$H NMR (300 MHz, CHLOROFORM-d) δ ppm 2.64 (s, 3H) 6.77 (s, 1H) 7.56 (s, 2H) 8.23 (s, 1H) 8.81 (s, 2H) 8.84 (s, 1H).

trans-2-{3-Hydroxy-3-methyl-1-[4-(2-methyl-7-pyridin-4-yl-1,4,9,9b-tetraaza-cyclopenta[a]naphthalen-8-yl)-phenyl]-cyclobutyl}-isoindole-4,3-dione [DXXXVI]

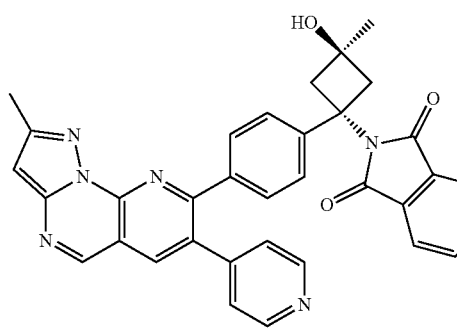

Compound [DXXXVI] was prepared using a procedure similar to that of Compound [XL]. Data for Compound [DXXXVI]: LCMS (m/e) 643 (M+H).

trans-3-Amino-1-methyl-3-[4-(2-methyl-7-pyridin-4-yl-1,4,9,9b-tetraaza-cyclopenta[a]naphthalen-8-yl)-phenyl]-cyclobutanol [DXXXVII]

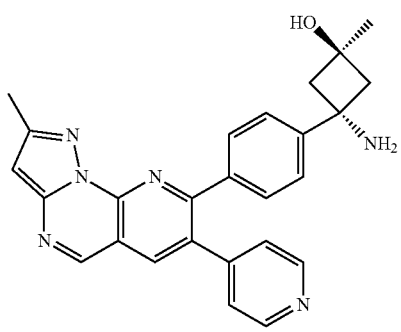

Compound [DXXXVII] was prepared using a procedure similar to that of Compound [XII]. Data for Compound [DXXXVII]: LCMS (m/e) 437 (M+H); $^1$H NMR (400 MHz, METHANOL-d4) δ ppm 1.49 (s, 3H) 2.57 (s, 3H) 2.65-2.76 (m, 7H) 2.80-2.91 (m, 2H) 6.79 (s, 1H) 7.52-7.61 (m, 2H) 7.61-7.67 (m, 2H) 7.67-7.75 (m, 2H) 8.61 (d, J=6.00 Hz, 2H) 8.72 (s, 1H).

trans-2-{3-hydroxy-3-methyl-1-[4-(2-methyl-7-phenyl-6-pyridin-3-yl-1,4,9,9b-tetraaza-cyclopenta[a]naphthalen-8-yl)-phenyl]-cyclobutyl}-isoindole-1,3-dione [DXXXVIII]

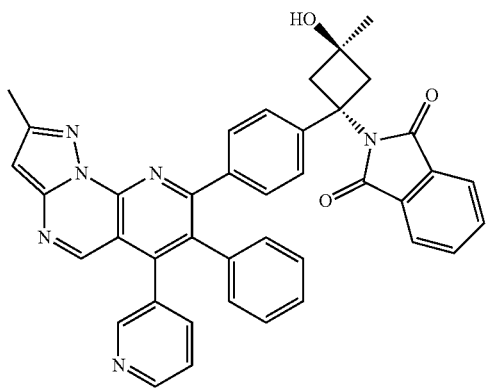

Compound [DXXXVIII] was prepared using a procedure similar to that of Compound [CDVIII]. Data for Compound [DXXXVIII]: LCMS (mile) 643 (M+H).

trans-3-Amino-1-methyl-3-[4-(2-methyl-7-phenyl-6-pyridin-3-yl-1,4,9,9b-tetraaza-cyclopenta[a]naphthalen-8-yl)-phenyl]-cyclobutanol [DXXXIX]

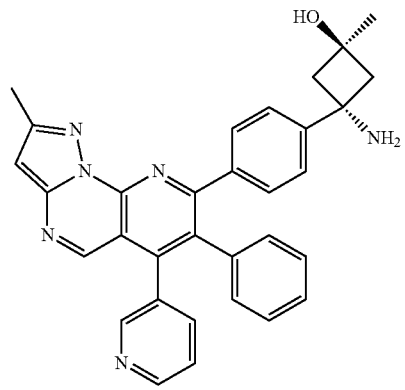

Compound [DXXXIX] was prepared using a procedure similar to that of Compound [XLI]. Data for Compound [DXXXIX]: LCMS (m/e) 513 (M+H); $^1$H NMR (400 MHz, METHANOL-d4) δ ppm 1.46 (s, 3H) 2.59 (s, 3H) 2.62-2.71 (m, 2H) 2.77-2.89 (m, 2H) 6.77 (s, 1H) 6.94-7.16 (m, 5H) 7.43-7.48 (m, 2H) 7.48-7.55 (m, 1H) 7.64-7.71 (m, 2H) 7.89 (dt, J=7.87, 1.85 Hz, 1H) 8.43-8.46 (m, 1H) 8.50 (s, 1H) 8.54 (dd, J=5.08, 1.56 Hz, 1H).

trans-2-{3-Hydroxy-3-methyl-1-[4-(2-methyl-7-phenyl-6-pyridin-4-yl-1,4,9,9b-tetraaza-cyclopenta[a]naphthalen-8-yl)-phenyl]-cyclobutyl}-isoindole-1,3-dione [DXL]

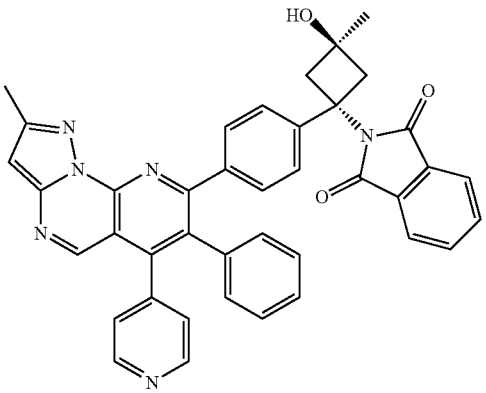

Compound [DXL] was prepared using a procedure similar to that of Compound [CDVIII]. Data for Compound [DXL]: LCMS (m/e) 643 (M+H).

trans-3-Amino-1-methyl-3-[4-(2-methyl-7-phenyl-6-pyridin-4-yl-1,4,9,9b-tetraaza-cyclopenta[a]naphthalen-8-yl)-phenyl]-cyclobutanol [DXLI]

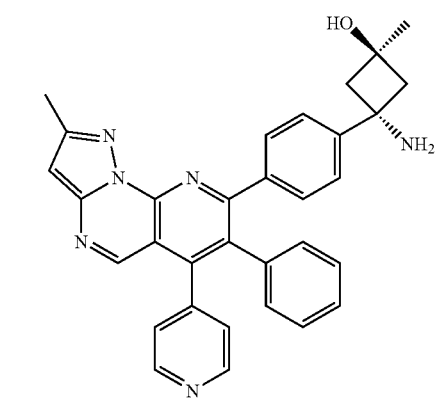

Compound [DXLI] was prepared using a procedure similar to that of Compound [XLI]. Data for Compound [DXLI]: LCMS (m/e) 513 (M+H); $^1$H NMR (400 MHz, METHANOL-d4) δ ppm 1.46 (s, 3H) 2.59 (s, 3H) 2.62-2.69 (m, 2H) 2.78-2.87 (m, 2H) 6.77 (s, 1H) 7.01-7.19 (m, 5H) 7.42-7.48 (m, 2H) 7.48-7.52 (m, 2H) 7.64-7.72 (m, 2H) 8.46 (s, 1H) 8.56-8.58 (m, 2H).

407 trans-2-{3-Hydroxy-3-methyl-1-[4-(2-methyl-7-phenyl-6-pyrimidin-5-yl-1,4,9,9b-tetraaza-cyclopenta[a]naphthalen-8-0)-phenyl]-cyclobutyl}-isoindole-1,3-dione [DXLII]

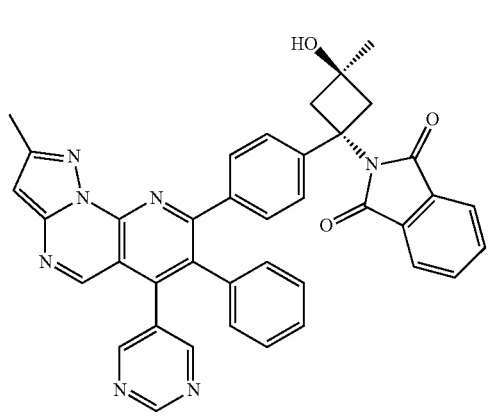

Compound [DXLII] was prepared using a procedure similar to that of Compound [CDVIII]. Data for Compound [DXLIII]: LCMS (m/e) 644 (M+H).

trans-3-Amino-1-methyl-3-[4-(2-methyl-7-phenyl-6-pyrimidin-5-yl-1,4,9,9b-tetraaza-cyclopenta[a]naphthalen-8-yl)-phenyl]-cyclobutanol [DXLIII]

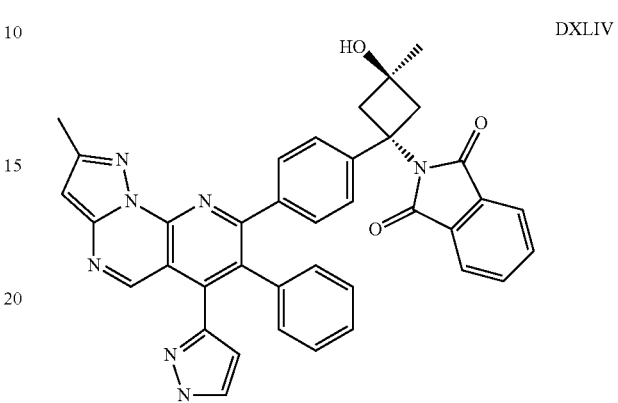

Compound [DXLIII] was prepared using a procedure similar to that of Compound [XLI]. Data for Compound [DXLIII]: LCMS (m/e) 514 (M+H); $^1$H NMR (400 MHz, METHANOL-d4) δ ppm 1.46 (s, 3H) 2.59 (s, 3H) 2.62-2.70 (m, 2H) 2.78-2.88 (m, 2H) 6.78 (s, 1H) 7.00-7.10 (m, 2H) 7.10-7.19 (m, 3H) 7.41-7.50 (m, 2H) 7.65-7.71 (m, 2H) 8.56 (s, 1H) 8.69 (s, 2H) 9.08 (s, 1H).

408 trans-2-(3-Hydroxy-3-methyl-1-{4-[2-methyl-7-phenyl-6-(1H-pyrazol-3-yl)-1,4,9,9b-tetraaza-cyclopenta[a]naphthalen-8-yl]-phenyl}-cyclobutyl)-isoindole-1,3-dione Compound [DXLIV] was prepared using a procedure similar to that of Compound [CDVIII]. Data for Compound [DXLIV]: LCMS (m/e) 632 (M+H).

trans-3-Amino-1-methyl-3-{4-[2-methyl-7-phenyl-6-(1H-pyrazol-3-yl)-1,4,9,9b-tetraaza-cyclopenta[a]naphthalen-8-yl]-phenyl}-cyclobutanol [DXLV]

Compound [DXLV] was prepared using a procedure similar to that of Compound [XLI]. Data for Compound [DXLV]: LCMS (m/e) 502 (M+H); $^1$H NMR. (400 MHz, METHANOL-dppm 1.46 (s, □4) 3H) 2.57 (s, 3H) 2.61-2.70 (m, 2H) 2.78-2.88 (m, 2H) 5.96 (d, J=2.34 Hz, 1H) 6.73 (s, 1H) 7.00-7.08 (m, 2H) 7.09-7.20 (m, 4H) 7.41-7.47 (m, 2H) 7.59 (d, J=2.34 Hz, 1H) 7.61-7.66 (m, 2H) 8.81 (s, 1H).

trans-{1-[4-(6-Cyano-2-methyl-7-phenyl-1,4,9,9b-tetraaza-cyclopenta[a]naphthalen-8-yl)-phenyl]-3-hydroxy-3-methyl-cyclobutyl}-carbamic acid tert-butyl ester [DXLVI]

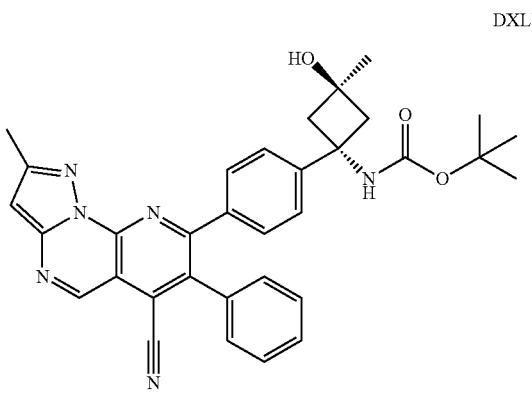

A 20 ml scintillation vial containing [CCXLIX] (113 mg, 0.20 mmol), $ZnCN_2$ (56 mg, 0.48 mmol), Zn dust (13 mg, 0.20 mmol), and DMA (4 ml) was evacuated and flushed three times with nitrogen. Then Pd (P-t-$Bu_3$)$_2$ (15.4 mg, 0.030 mmol) was added and the resulting solution was evacuated and flushed three times with nitrogen. The mixture was heated at 110-120° C. for 3 h. LCMS indicated the reaction was complete. Then it was allowed to cool and concentrated. The residue was dissolved with DCM (1.5 mL). After filtration, the filtrate was purified by silica gel chromatography by using MeOH and $CH_2Cl_2$ as the mobile phases to furnish Compound [DXLVI] as a yellowish solid: LCMS (m/e) 561 (M+H).

trans-8-[4-(1-Amino-3-hydroxy-3-methyl-cyclobutyl)-phenyl]-2-methyl-7-phenyl-1,4,9,9b-tetraaza-cyclopenta[a]naphthalene-6-carbonitrile [DXLVII]

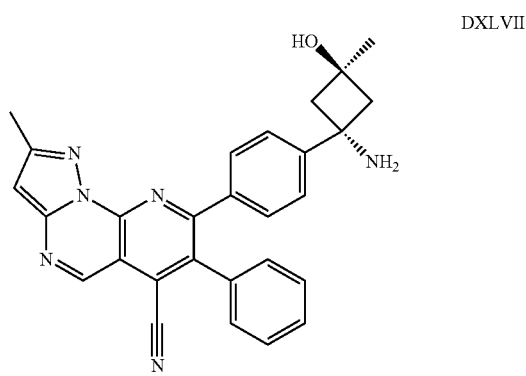

Compound [DXLVII] was prepared using a procedure similar to that of Compound [XLIV]. Data for Compound [DXLVII]: LCMS (m/e) 461 (M+H); $^1$H NMR (400 MHz, METHANOL-d4) δ ppm 1.47 (s, 3H) 2.59 (s, 3H) 2.62-2.73 (m, 2H) 2.77-2.90 (m, 2H) 6.87 (s, 1H) 7.36-7.45 (m, 5H) 7.46-7.53 (m, 2H) 7.63-7.73 (m, 2H) 9.18 (s, 1H).

trans-{3-Hydroxy-1-[4-(6-methoxy-2-methyl-7-phenyl-1,4,9,9b-tetraaza-cyclopenta[a]naphthalen-8-yl)-phenyl]-3-methyl-cyclobutyl}-carbamic acid tert-butyl ester [DXLVIII]

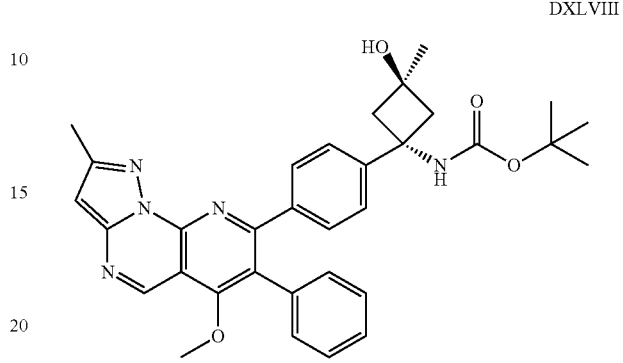

A 20 ml scintillation vial containing [CCXLIX] (100 mg, 0.18 mmol), dioxanet (2 mL), water (2 mL), MeOH (2 mL), and KOH (~400 mg, large excess) was stirred at room temperature for 24 h. LCMS indicated the reaction was complete. It gave 6-methoxy analog as a major product along with 6-hydroxy as a minor one. The reaction mixture was concentrated and the residue was dissolved in DCM (10 mL) and water (5 mL). The water solution was extracted with DCM (5 mL×2). The combined organic solution was concentrated and the residue was dissolved with DCM (1.5 mL). After filtration, the filtrate was purified by silica gel chromatography by using MeOH and $CH_2Cl_2$ as the mobile phases to furnish Compound [DXLVIII] as a yellowish solid (79 mg, 78.2%): LCMS (m/e) 566 (M+H).

trans-3-Amino-3-[4-(6-methoxy-2-methyl-7-phenyl-1,4,9,9b-tetraaza-cyclopenta[a]naphthalen-8-yl)-phenyl]-1-methyl-cyclobutanol [DXLIX]

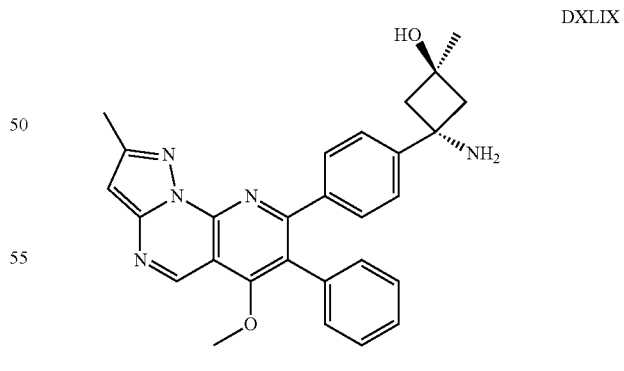

Compound [DXLIX] was prepared using a procedure similar to that of Compound [XLIV]. Data for Compound [DXLIX]: LCMS (m/e) 465 (M+H); $^1$H NMR (400 MHz, METHANOL-d4) δ ppm 1.46 (s, 3H) 2.55 (s, 3H) 2.61-2.71 (m, 7H) 2.77-2.88 (m, 2H) 3.60 (s, 3H) 6.74 (s, 1H) 7.27-7.32 (m, 2H) 7.32-7.37 (m, 3H) 7.39-7.46 (m, 2H) 7.51-7.60 (m, 2H) 9.20 (s, 1H).

trans-{1-[4-(6-Amino-2-methyl-7-phenyl-1,4,9,9b-tetraaza-cyclopenta[a]naphthalen-8-yl)-phenyl]-3-hydroxy-3-methyl-cyclobutyl}-carbamic acid tert-butyl ester [DL]

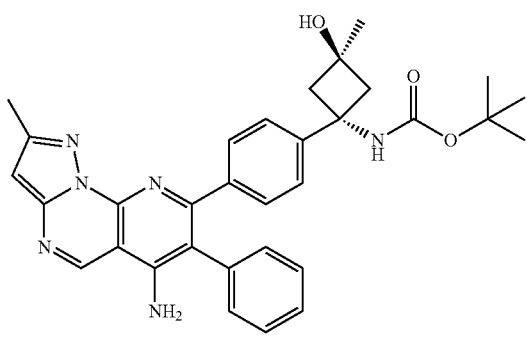

A 40 ml bomb containing [CCXLIX] (57 mg, 0.10 mmol), dioxane (8 mL), and concentrated $NH_4OH$ (8 mL) was heated at 120° C. for 15 h. The reaction was allowed to cool to RT. The solvent was removed in vacuo and the residue was dissolved with MeOH (2 mL). After filtration and concentration, the residue was purified by silica gel chromatography by using MeOH and $CH_2Cl_2$ as the mobile phases to furnish Compound [DL] as a yellowish solid (~50 mg, 91%, crude): LCMS (m/e) 551 (M+H).

trans-3-Amino-3-[4-(6-amino-2-methyl-7-phenyl-1,4,9,9b-tetraaza-cyclopenta[a]naphthalen-8-yl)-phenyl]-1-methyl-cyclobutanol [DLI]

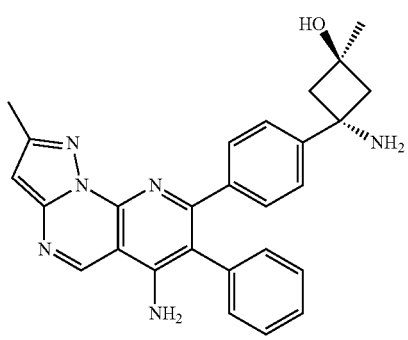

Compound [DLI] was prepared using a procedure similar to that of Compound [XLIV]. Data for Compound [DLI]: LCMS (m/e) 451 (M+H); $^1$H NMR (400 MHz, METHANOL-d4) δ ppm 1.46 (s, 3H) 2.52 (s, 3H) 2.59-2.68 (m, 2H) 2.77-2.85 (m, 2H) 6.61 (s, 1H) 7.13-7.30 (m, 3H) 7.34-7.42 (m, 4H) 7.51-7.58 (m, 2H) 9.20 (s, 1H).

trans-2-{1-[4-(3-Bromo-7-phenyl-1,4,9,9b-tetraaza-cyclopenta[a]naphthalen-8-yl)-phenyl]-3-hydroxy-3-methyl-cyclobutyl}-isoindole-1,3-dione [DLII]

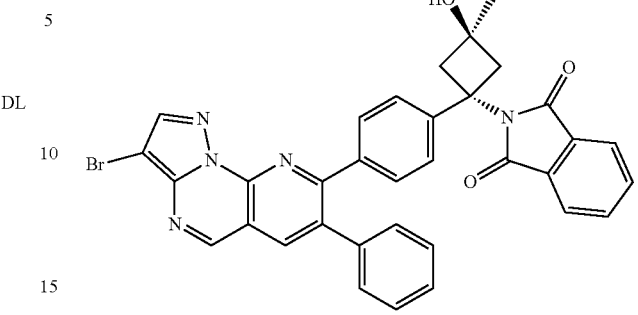

Compound [DLII] was prepared using a procedure similar to that of Compound [CV]. Data for Compound [DLII]: LCMS (m/e) 631 (M+H).

trans-3-Amino-3-[4-(3-bromo-7-phenyl-1,4,9,9b-tetraaza-cyclopenta[a]naphthalen-8-yl)-phenyl]-1-methyl-cyclobutanol [DLIII]

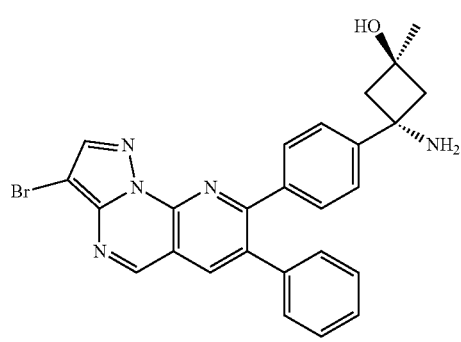

Compound [DLIII] was prepared using a procedure similar to that of Compound [XLI].
Data for Compound [DLIII] LCMS (m/e) 501 (M+H); $^1$H NMR (400 MHz, METHANOL-d4) δ ppm 1.47 (s, 3H) 2.64-2.73 (m, 2H) 2.81-2.90 (m, 2H) 7.28-7.38 (m, 5H) 7.45-7.54 (m, 2H) 7.65-7.72 (m, 2H) 8.30 (s, 1H) 8.63 (s, 1H) 9.15 (s, 1H).

trans-2-{1-[4-(3-Bromo-2-methyl-7-phenyl-1,4,9,9b-tetraaza-cyclopenta[a]naphthalen-8-yl)-phenyl]-3-hydroxy-3-methyl-cyclobutyl}-isoindole-1,3-dione [DLIV]

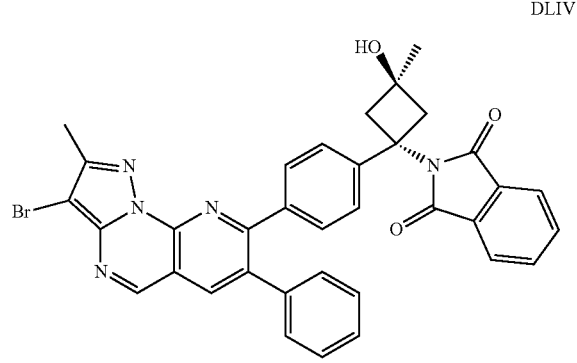 [SMILES: Cc1nn2c(ncc3cc(-c4ccccc4)c(-c4ccc([C@]5(N6C(=O)c7ccccc7C6=O)C[C@](C)(O)C5)cc4)nc32)c1Br]

Compound [DLIV] was prepared using a procedure similar to that of Compound [CV]. Data for Compound [DLIV]: LCMS (m/e) 645 (M+H).

trans-8-{4-[1-(1,3-Dioxo-1,3-dihydro-isoindol-2-yl)-
3-hydroxy-3-methyl-cyclobutyl]-phenyl}-2-methyl-
7-phenyl-1,4,9,9b-tetraaza-cyclopenta[a]
naphthalene-3-carbonitrile [DLV]

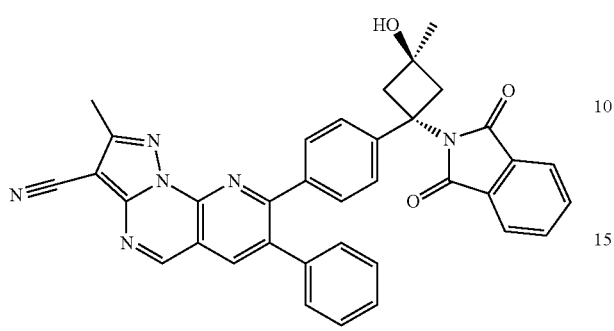

Compound [DLV] was prepared using a procedure similar to that of Compound [DXLVI]. Data for Compound [DLV]: LCMS (m/e) 591 (M+H).

trans-8-[4-(1-Amino-3-hydroxy-3-methyl-cyclobu-
tyl)-phenyl]-2-methyl-7-phenyl-1,4,9,9b-tetraaza-
cyclopenta[a]naphthalene-3-carbonitrile [DLVI]

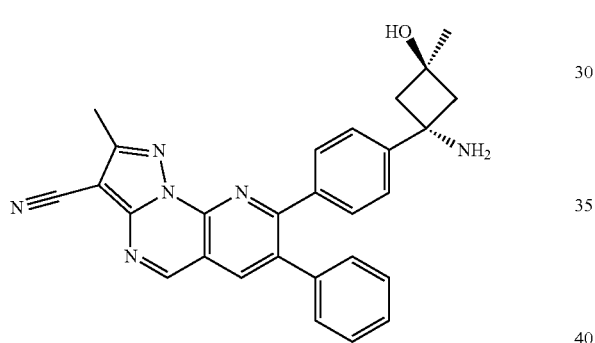

Compound [DLVI] was prepared using a procedure similar to that of Compound [XLI]. Data for Compound [DLVI]: LCMS (m/e) 461 (M+H); $^1$H NMR (400 MHz, METHANOL-d4) δ ppm 0.90 (s, 1H) 1.29 (br. s., 2H) 1.53 (s, 3H) 1.93 (s, 3H) 2.53 (d, J=13.81 Hz, 2H) 2.70 (s, 3H) 2.76 (d, J=13.52 Hz, 2H) 7.23-7.43 (m, 5H) 7.47 (d, J=8.49 Hz, 2H) 7.66 (d, J=8.44 Hz, 2H) 8.69 (s, 1H) 9.33 (s, 1H).

trans-8-{4-[1-(1,3-Dioxo-1,3-dihydro-isoindol-2-yl)-
3-hydroxy-3-methyl-cyclobutyl]-phenyl}-7-phenyl-
1,4,9,9b-tetraaza-cyclopenta[a]naphthalene-3-carbo-
nitrile [DLVII]

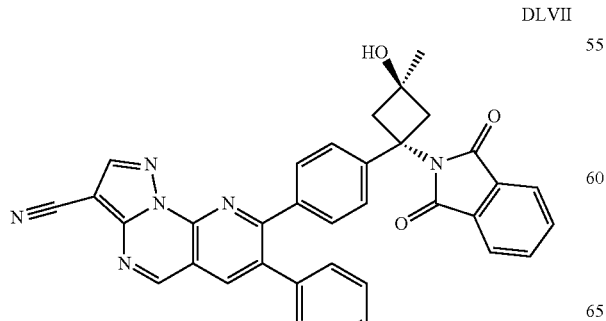

Compound [DLVII] was prepared using a procedure similar to that of Compound [DXLVI]. Data for Compound [DLVII]: LCMS (m/e) 577 (M+H).

trans-8-[4-(1-Amino-3-hydroxy-3-methyl-cyclobu-
tyl)-phenyl]-7-phenyl-1,4,9,9b-tetraaza-cyclopenta
[a]naphthalene-3-carbonitrile [DLVIII]

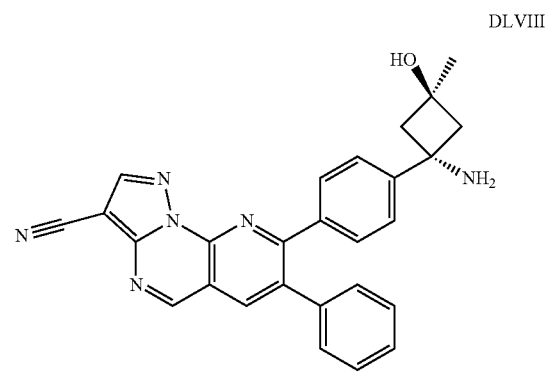 [SMILES: C[C@]1(O)C[C@@](N)(c2ccc(-c3nc4c(cnc5c(C#N)cnn54)cc3-c3ccccc3)cc2)C1]

Compound [DLVIII] was prepared using a procedure similar to that of Compound [XII]. Data for Compound [DLVIII]: LCMS (rule) 447 (M+H); $^1$H NMR (400 MHz, METHANOL-d4) δ ppm 1.47 (s, 3H) 2.64-2.76 (m, 2H) 2.79-2.94 (m, 2H) 7.28-7.42 (m, 5H) 7.47-7.57 (m, 2H) 7.65-7.74 (m, 2H) 8.64 (s, 1H) 8.73 (s, 1H) 9.37 (s, 1H).

trans-3-Amino-1-methyl-3-[4-(3-methyl-7-phenyl-1,
4,9,9b-tetraaza-cyclopenta[a]naphthalen-8-yl)-phe-
nyl]-cyclobutanol [DLIX]

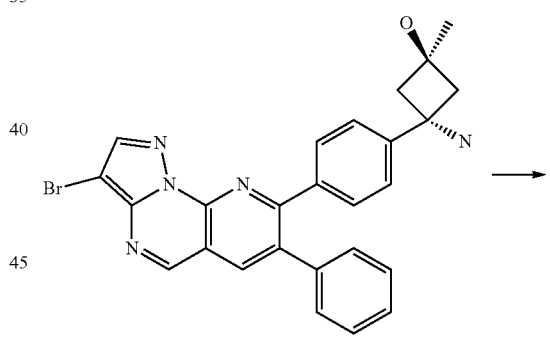

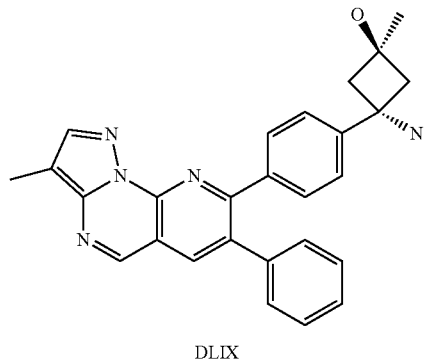

Compound [DLIII] was prepared using a procedure similar to that of Compound [CCL]. Data for Compound [DLIX]: LCMS (m/e) 436 (M+H); $^1$H NMR (400 MHz, METHA- NOL-d4) δ ppm 1.49 (s, 3H) 1.91 (s, 4H) 2.43 (s, 3H) 2.50-2.62 (m, 2H) 2.71-2.83 (m, 2H) 7.25-7.37 (m, 5H) 7.39-7.49 (m, 2H) 7.60-7.69 (m, 2H) 8.09 (s, 1H) 8.53 (s, 1H) 9.00 (s, 1H).

7-Amino-2-cyclopropyl-pyrazolo[1,5-a]pyrimidine-6-carboxylic acid hydrazide [DLX]

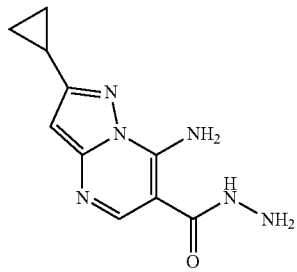

Compound [DLX] was prepared using a procedure similar to that of [CCXXVII]. Data for Compound [DLX]: LCMS (m/e) 233 (M+H).

7-Amino-2-cyclopropyl-pyrazolo[1,5-a]pyrimidine-6-carboxylic acid hydrazide [DLXI]

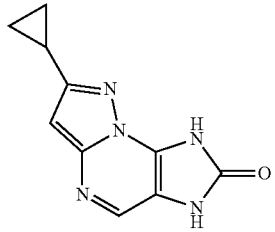

Compound [DLXI] was prepared using a procedure similar to that of Compound [CCXXVIII]. Data for Compound [DLXI]: LCMS (m/e) 216 (M+H).

2-Cyclopropyl-pyrazolo[1,5-a]pyrimidine-6,7-diamine

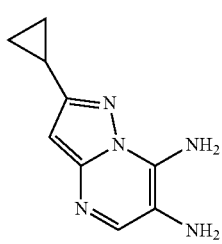

Compound [DLXII] was prepared using a procedure similar to that of Compound [CCXXIX]. Data for Compound [DLXII]: LCMS (m/e) 190 (M+H).

2-Cyclopropyl-7-phenyl-9H-1,4,6,9,9b-pentaaza-cyclopenta[a]naphthalen-8-one [DLXIII]

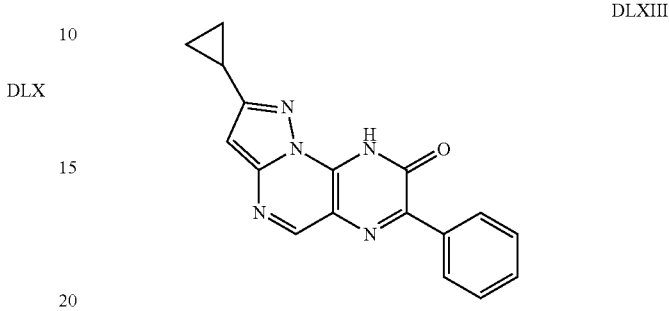

[DLXIII] was prepared using a procedure similar to that of Compound [CCXXX]. Data for Compound [DLXIII]: LCMS (m/e) 304 (M+H).

8-Chloro-2-isopropenyl-7-phenyl-1,4,6,9,9b-pentaaza-cyclopenta[a]naphthalene [DLXIV]

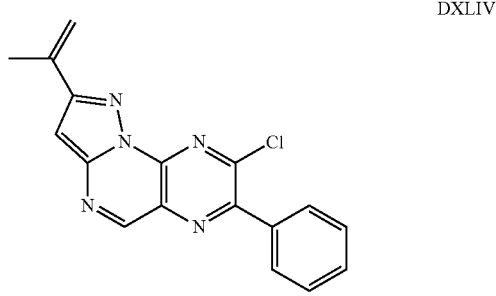 [SMILES: C=C(C)c1cc2ncc3nc(-c4ccccc4)c(Cl)nc3n2n1]

Compound [DXLIV] was prepared using a procedure similar to that of Compound [V] (POCl₃ procedure). Data for Compound [DXLIV]: LCMS (Ink) 322 (M+H).

trans-2-{3-Hydroxy-1-[4-(2-isopropenyl-7-phenyl-1,4,6,9,9b-pentaaza-cyclopenta[a]naphthalen-8-yl)-phenyl]-3-methyl-cyclobutyl}-isoindole-1,3-dione [DLXV]

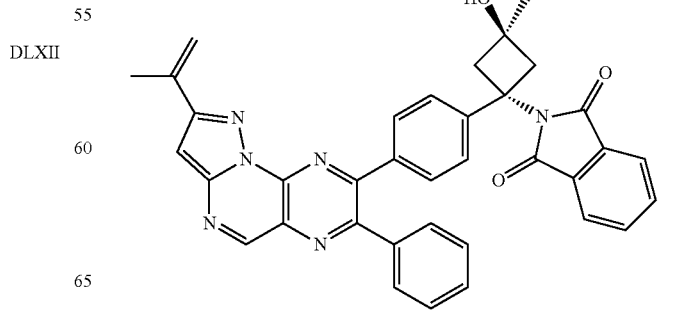

Compound [DLXV] was prepared using a procedure similar to that of Compound [XL]. Data for Compound [DLXV]: LCMS (m/e) 593 (M+H); ¹H NMR (400 MHz, CHLOROFORM-d) δ ppm 6.64-9.20 (m, 15H), 3.40 (d, 2H), 3.15 (d, 2H), 1.98 (m, 2H), 1.63 (m, 3H), 1.46 (s, 2H).

trans-3-Amino-3-[4-(2-isopropenyl-7-phenyl-1,4,6,9, 9b-pentaaza-cyclopenta[a]naphthalen-8-yl)-phenyl]-1-methyl-cyclobutanol [DLXVI]

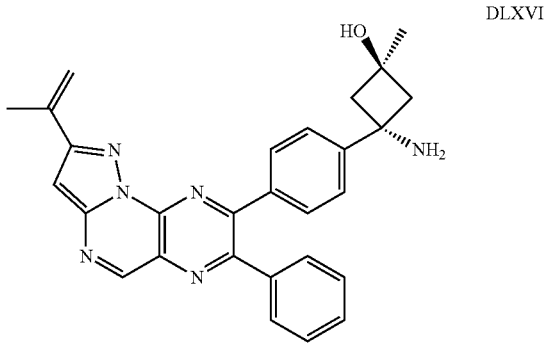 [SMILES: C=C(C)c1cc2ncc3nc(-c4ccccc4)c(-c4ccc([C@]5(N)C[C@](C)(O)C5)cc4)nc3n2n1]

DLXVI

Compound [DLXVI] was prepared using a procedure similar to that of [CLXI] (MeNHNH₂ procedure). Data for Compound [DXLVI]: LCMS (m/e) 463 (M+H); ¹H NMR (400 MHz, METHANOL-d4) δ ppm 1.49 (s, 3H) 1.92-2.02 (m, 3H) 2.65-2.74 (m, 2H) 2.82-2.92 (m, 2H) 6.57-6.79 (m, 2H) 7.06 (s, 1H) 7.29-7.44 (m, 3H) 7.49-7.60 (m, 4H) 7.75-7.83 (m, 2H) 9.11 (s, 1H).

2-Cyclopropyl-7-thiophen-2-yl-9H-1,4,9,9b-tetraaza-cyclopenta[a]naphthalen-8-one [DLXVII]

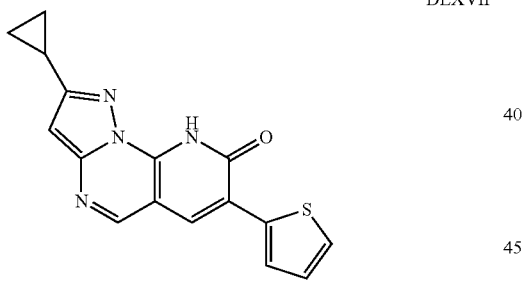

DLXVII

Compound [DLXVII] was prepared using a procedure similar to that of Compound [IV] (NaO-t-Bu procedure). This compound was taken on to the next step without further characterization.

8-Chloro-2-cyclopropyl-7-thiophen-2-yl-1,4,9,9b-tetraaza-cyclopenta[a]naphthalene [DLXVIII]

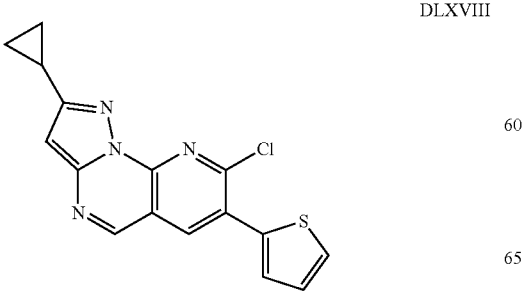

DLXVIII

Compound [DLXVIII] was prepared using a procedure similar to that of Compound [V] (POCl₃ procedure). Data for Compound [DLXVIII]: LCMS (m/e) 327 (M+H).

trans-2-{1-[4-(2-Cyclopropyl-7-thiophen-2-yl-1,4,9, 9b-tetraaza-cyclopenta[a]naphthalen-8-yl)-phenyl]-3-hydroxy-3-methyl-cyclobutyl}-isoindole-1,3-dione [DLXIX]

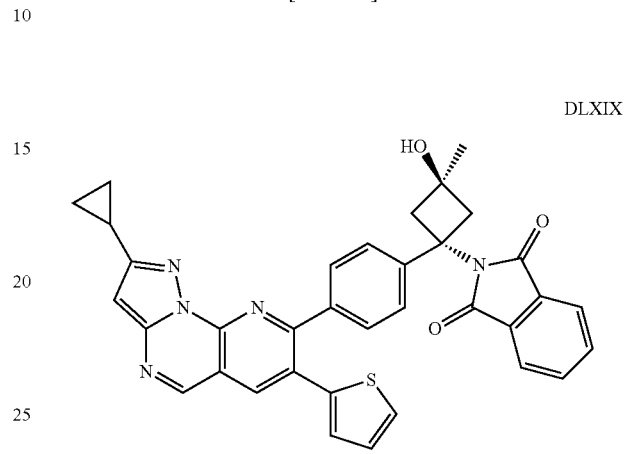

DLXIX

Compound [DLXIX] was prepared using a procedure similar to that of Compound [XL]. Data for Compound [DLXIX]: LCMS (m/e) 598 (M+H); ¹H NMR (300 MHz, CHLOROFORM-d) δ ppm 0.98 (m, 2H), 1.07 (m, 2H), 1.26 (s, 1H), 1.46 (s, 3H), 1.81 (s, 1H), 2.29 (m, 1H), 3.15 (d, 2H), 3.38 (d, 2H), 6.47 (s, 1H), 6.87 (m, 1H), 6.95 (m, 1H), 7.25 (m, 1H), 7.31 (m, 1H), 7.59-7.81 (m, 8H), 8.30 (s, 1H), 8.82 (m, 1H).

trans-3-Amino-3-[4-(2-cyclopropyl-7-thiophen-2-yl-1,4,9,9b-tetraaza-cyclopenta[a]naphthalen-8-yl)-phenyl]-1-methyl-cyclobutanol [DLXX]

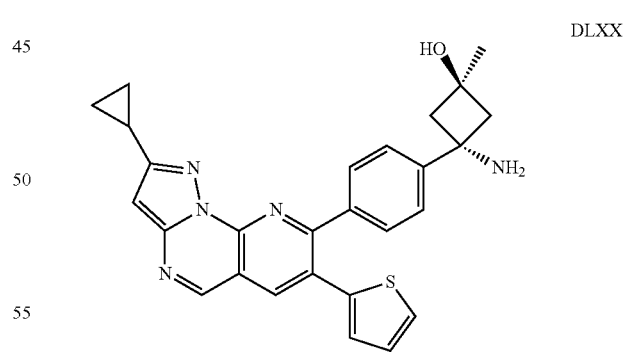

DLXX

Compound [DLXX] was prepared using a procedure similar to that of Compound [XLI]. Data for Compound [DLXX]: LCMS (m/e) 468 (M+H); ¹H NMR (400 MHz, METHANOL-d4) δ ppm 0.88-1.17 (m, 4H) 1.51 (s, 3H) 1.92 (s, 4H) 2.21 (tt, J=8.44, 5.00 Hz, 1H) 2.55-2.66 (m, 2H) 2.76-2.88 (m, 2H) 6.59 (s, 1H) 6.99 (d, J=1.03 Hz, 1H) 7.00 (s, 1H) 7.45 (dd, J=3.59, 2.81 Hz, 1H) 7.50-7.57 (m, 2H) 7.66-7.78 (m, 2H) 8.61 (s, 1H) 8.99 (s, 1H).

2-Cyclopropyl-7-thiophen-2-yl-9H-1,4,6,9,9b-pentaaza-cyclopenta[a]naphthalen-8-one [DLXXI]

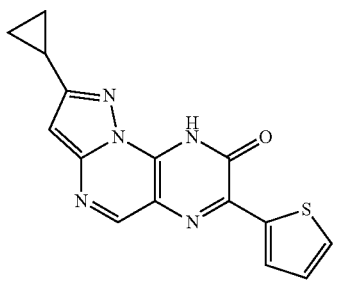

Compound [DLXXI] was prepared using a procedure similar to that of Compound [CCXXX]. Data for Compound [DLXXI]: LCMS (m/e) 310 (M+H).

8-Chloro-2-isopropenyl-7-thiophen-2-yl-1,4,6,9,9b-pentaaza-cyclopenta[a]naphthalene [DLXXII]

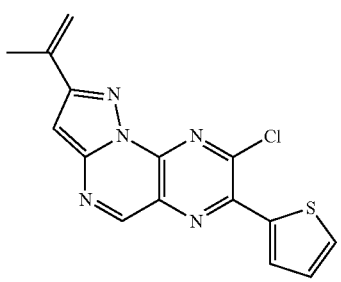

Compound [DLXXII] was prepared using a procedure similar to that of Compound [V] (POCl₃ procedure). Data for Compound [DLXXII]: This compound was taken on to the next step without further characterization.

trans-2-{3-Hydroxy-1-[4-(2-isopropenyl-7-thiophen-2-yl-1,4,6,9,9b-pentaaza-cyclopenta[a]naphthalen-8-yl)-phenyl]-3-methyl-cyclobutyl}-isoindole-1,3-dione [DLXXIII]

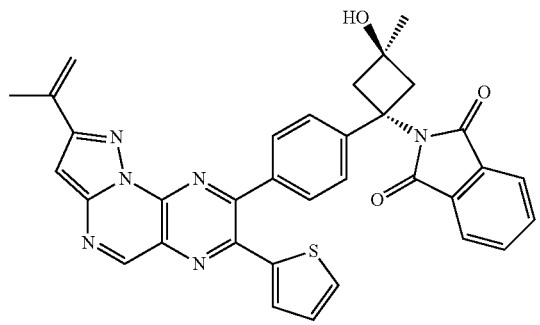

Compound [DLXXIII] was prepared using a procedure similar to that of Compound [XL]. Data for Compound [DLXXIII]: LCMS (m/e) 599 (M+H); ¹H NMR (400 MHz, CHLOROFORM-d) δppm 6.57-9.13 (m, 13H), 3.46 (d, 2H), 3.36 (m, 0.6H), 3.22 (d, 2H), 1.96 (m, 1.4H), 1.60 (m, 3H), 1.50 (s, 3H).

trans-3-Amino-3-[4-(2-isopropenyl-7-thiophen-2-yl-1,4,6,9,9b-pentaaza-cyclopenta[a]naphthalen-8-yl)-phenyl]-1-methyl-cyclobutanol [DLXXIV]

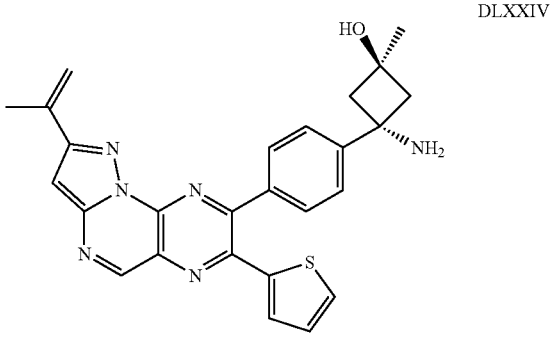 [SMILES: C=C(C)c1cc2ncc3nc(-c4cccs4)c(-c4ccc([C@]5(N)C[C@](C)(O)C5)cc4)nc3n2n1]

Compound [DLXXIV] was prepared using a procedure similar to that of Compound [CLIX] (MeNHNH₂ procedure). Data for Compound [DLXXIV]: LCMS (m/e) 469 (M+H); ¹H NMR (400 MHz, METHANOL-d4) δ ppm 1.52 (s, 3H) 1.92 (dd, J=6.44, 1.37 Hz, 3H) 2.71-2.99 (m, 4H) 6.47-6.71 (m, 2H) 6.82-6.91 (m, 2H) 6.96 (s, 1H) 7.54 (dd, J=4.56, 1.64 Hz, 1H) 7.68-7.74 (m, 2H) 7.80-7.89 (m, 2H) 9.00 (s, 1H).

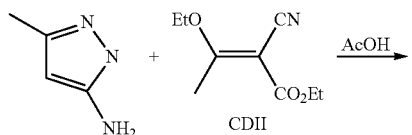

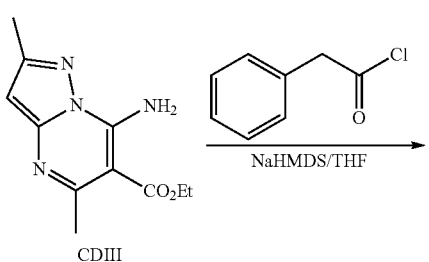

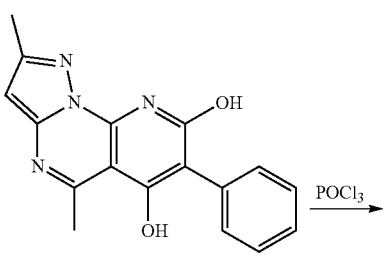

-continued

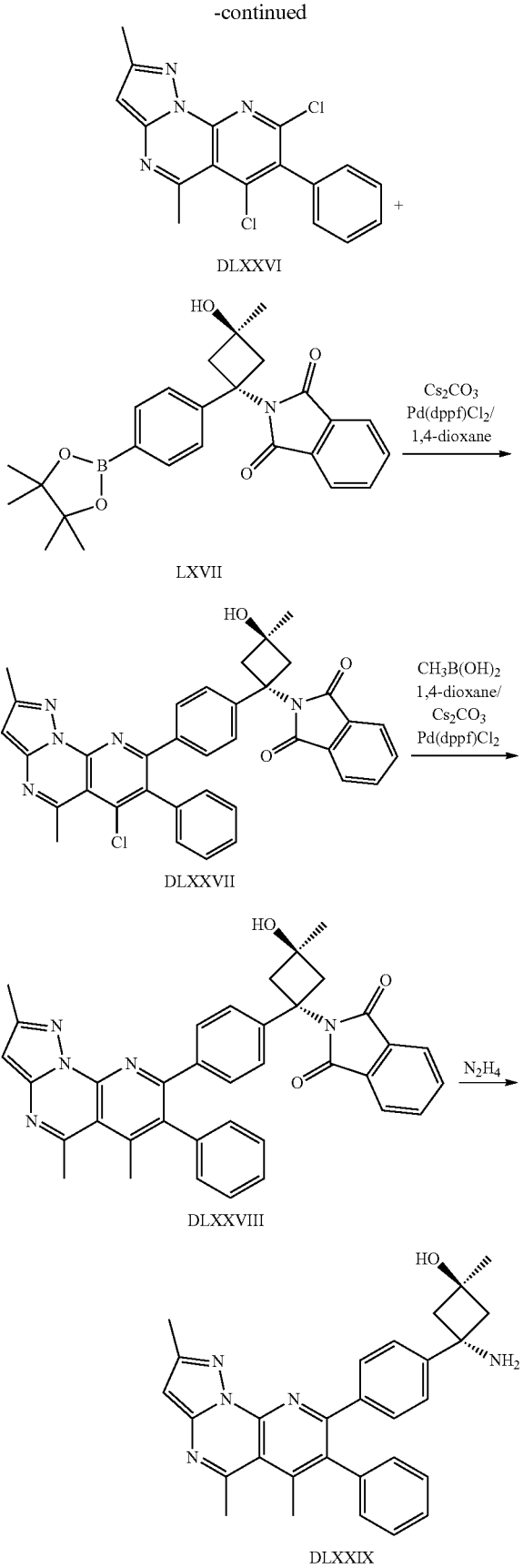

422

Synthesis of PH-MC-079-3: 2,5-Dimethyl-7-phenyl-1,4,9,9b-tetraaza-cyclopenta[a]naphthalene-6,8-diol [DLXXV]

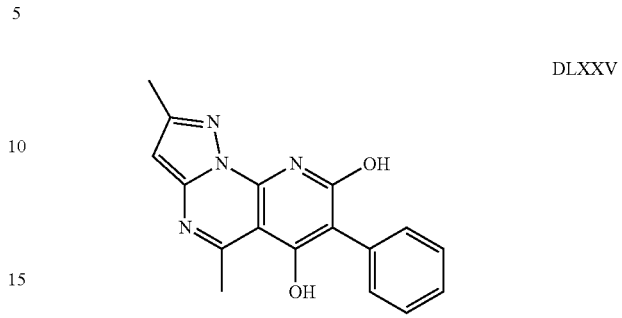

Into a 250-mL 3-necked round-bottom flask purged and maintained with an inert atmosphere of nitrogen, was placed a solution of Compound [CCCLXXXIII] (2 g, 8.54 mmol, 1.00 equiv) in tetrahydrofuran (50 mL). This was followed by the addition of 2-phenylacetyl chloride (3 g, 19.40 mmol, 2.27 equiv) dropwise with stirring at 0-10° C. To this was added NaN[Si(CH$_3$)$_3$]$_2$/tetrahydrofuran (1N) (40 mL) dropwise with stirring at 0-10° C. The resulting solution was stirred overnight at room temperature. The resulting mixture was concentrated under vacuum and the residue was dissolved in 100 mL of H$_2$O. The resulting solution was extracted with 3×50 mL of dichloromethane and the aqueous layers combined. The pH value of the solution was adjusted to 3-4 with aqueous 5 N HCl solution. The solids were collected by filtration and dried in an oven under reduced pressure to give Compound [DLXXV]. This material was taken onto the next step without further characterization.

Synthesis of PH-MC-979-4: 6,8-Dichloro-2,5-dimethyl-7-phenyl-1,4,9,9b-tetraaza-cyclopenta[a]naphthalene [DLXXVI]

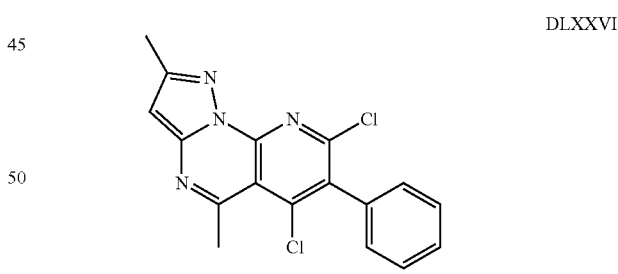

Into a 250-mL round-bottom flask, was placed Compound [DLXXV] (4 g, 10.45 mmol, 1.00 equiv, 80%), phosphoryl trichloride (177 g, 1.15 mol, 110.52 equiv). The resulting solution was stirred for 2 h at 100° C. The resulting mixture was concentrated under vacuum. The resulting solution was diluted with 100 mL of dichloromethane. The reaction was then quenched by the addition of 200 mL of water/ice. The resulting solution was extracted with 2×50 mL of dichloromethane and the organic layers combined and dried over anhydrous sodium sulfate and concentrated under vacuum to provide [DLXXVI]. This material was taken onto the next step without further characterization.

2-{1-[4-(6-Chloro-2,5-dimethyl-7-phenyl-1,4,9,9b-tetraaza-cyclopenta[a]naphthalen-8-yl)-phenyl]-3-hydroxy-3-methyl-cyclobutyl}-isoindole-1,3-dione [DLXXVII]

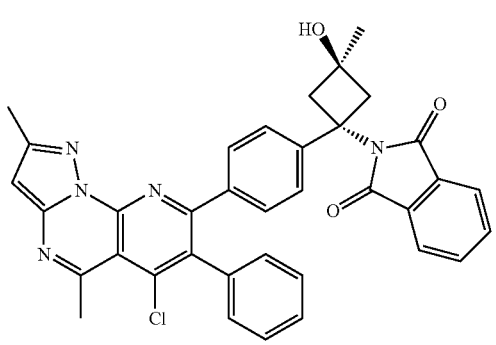

DLXXVII

Into a 500-mL 3-necked round-bottom flask purged and maintained with an inert atmosphere of nitrogen, was placed Compound [DLXXVI] (4 g, 9.32 mmol, 1.15 equiv, 80%), Compound [LXVII] (3.5 g, 8.08 mmol, 1.00 equiv), Cs$_2$CO$_3$ (15 g, 46.04 mmol, 5.70 equiv), 1,4-dioxane (200 mL), and Pd(dppf)Cl$_2$ (1 g, 1.37 mmol, 0.17 equiv). The resulting solution was stirred for 2 h at 40° C. The resulting solution was diluted with 500 mL of dichloromethane and the resulting mixture washed with 2×200 mL of brine. The mixture was dried over anhydrous sodium sulfate, concentrated, and the residue was applied onto a silica gel column with dichloromethane/ethyl acetate (10:1) to furnish Compound [DLXXVII].

Synthesis of PH-MC-079-0: 2-{3-Hydroxy-3-methyl-1-[4-(2,5,6-trimethyl-7-phenyl-1,4,9,9b-tetraaza-cyclopenta[a]naphthalen-8-yl)-phenyl]-cyclobutyl}-isoindole-1,3-dione [DLXXVIII]

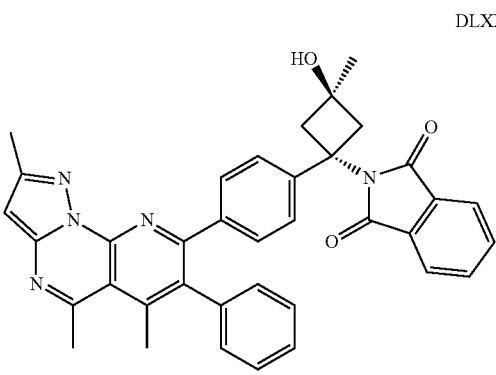

DLXXVIII

Into a 250-mL 3-necked round-bottom flask purged and maintained with an inert atmosphere of nitrogen, was placed Compound [DLXXVII] (1.1 g, 1.79 mmol, 1.00 equiv), methylboronic acid (1.1 g, 18.36 mmol, 10.25 equiv), Cs$_2$CO$_3$ (2.9 g, 8.90 mmol, 4.97 equiv), 1,4-dioxane (100 mL), and Pd(dppf)Cl$_2$ (260 mg, 0.36 mmol, 0.20 equiv). The resulting solution was stirred for 2 h at 40° C. The resulting solution was diluted with 300 mL of dichloromethane. The resulting mixture was washed with 2×150 mL of brine. The mixture was dried over anhydrous sodium sulfate, concentrated, and the residue purified by silica gel chromatography using dichloromethane/ethyl acetate (10:1) as the eluant to provide Compound [DLXXVIII] as a yellow solid. LCMS (m/e) 594 [M+H], $^1$H NMR (400 MHz, CDCl$_3$) δ ppm 6.65-7.77 (m, 14H), 3.33 (m, 2H), 3.16 (s, 3H), 3.08 (m, 2H), 2.65 (s, 3H), 2.56 (s, 3H), 1.41 (s, 3H).

3-Amino-1-methyl-3-[4-(2,5,6-trimethyl-7-phenyl-1,4,9,9b-tetraaza-cyclopenta[a]naphthalen-8-yl)-phenyl]-cyclobutanol [DLXXIX]

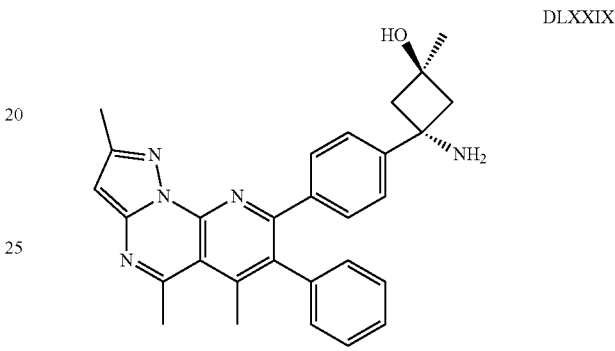

Compound [DLXXIX] was prepared using a procedure similar to that of Compound [XLI]. Data for Compound [DLXXIX]: LCMS 464 [M+H]$^+$; $^1$H NMR (400 MHz, MeOH-d$_4$) δ ppm 1.50 (s, 3H) 1.93 (s, 3H) 2.51-2.60 (m, 5H) 2.69 (s, 3H) 2.75 (d, J=13.96 Hz, 2H) 3.08 (s, 3H) 6.55 (s, 1H) 7.11-7.27 (m, 2H) 7.27 7.43 (m, 5H) 7.55 (d, =8.49 Hz, 2H).

Synthesis of CCXXXII Alternate Method trans-2-[3-Hydroxy-3-methyl-1-(4-phenylethynyl-phenyl)-cyclobutyl]-isoindole-1,3-dione [DLXXX]

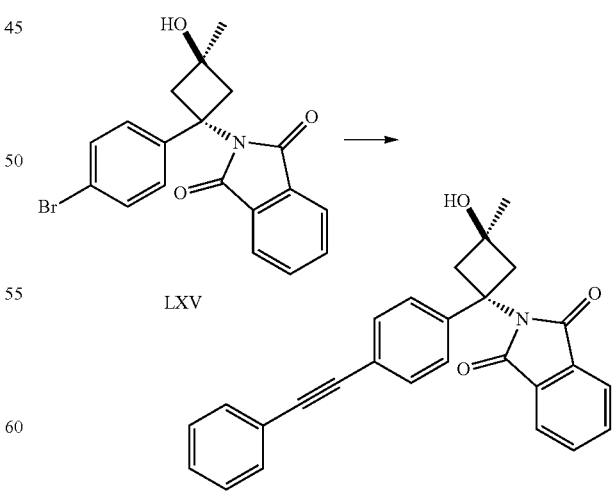

To a 100 mL round bottom flask was added Compound [LXV] (2 g, 51.8 mmol, 1.0 eq.), 1-ethynylbenzene (1.58 g, 154.7 mmol, 3.0 eq), Pd(PPh$_3$)Cl$_2$ (0.36 g, 5.1 mmol, 0.1 eq.), PPh$_3$ (0.27 g, 10.3 mmol, 0.2 eq.), CuI (0.197 g, 10.4 mmol, 0.2 eq.) and Et$_3$N (30 mL). The mixture was evacuated and refilled with a nitrogen atmosphere three times. The reaction mixture was stirred at 90° C. overnight. EtOAc was added and then the mixture was filtered through silica gel, rinsing with EtOAc. The filtrate was concentrated in vacuo and the residue was purified by a silica gel column with ethyl acetate/petroleum ether (1:10) and provided Compound [DLXXX] as a yellow solid: LCMS (m/e) 390 (M−H$_2$O+H); $^1$H NMR (300 MHz, CHLOROFORM-d) δ ppm 1.46 (s, 3H) 3.17 (d, J=14.4 Hz, 2H) 3.37 (d, J=14.4 Hz, 2H) 7.33-7.82 (m, 13H).

trans-2-{3-Hydroxy-3-methyl-1-[4-(2-oxo-2-phenyl-acetyl)-phenyl]-cyclobutyl}-isoindole-1,3-dione [DLXXXI]

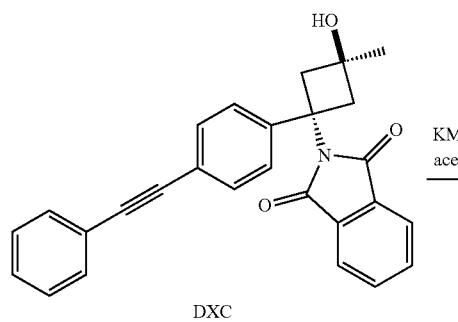

To a solution of Compound [DXC] (1.5 g, 36.8 mmol, 1.00 eq.) in anhydrous acetone (100 mL) was added KMnO$_4$ (2.33 g, 147.4 mmol, 4.00 eq.). The reaction mixture was heated to 35° C. for 2 h. The reaction mixture was cooled to room temperature and EtOAc and water were added to the mixture. The organic layer was washed with water and brine. The organic solution was dried over Na$_2$SO$_4$. The residue was purified by a silica gel column with ethyl acetate/petroleum ether (1:10) and provided Compound [DLXXXI] as a light yellow solid: LCMS (m/e) 422 (M−H$_2$O+H); $^1$H NMR (300 MHz, CHLOROFORM-d) δ ppm 1.47 (s, 3H) 3.17 (d, J=14.4 Hz, 2H) 3.38 (d, J=14.4 Hz, 2H) 7.50 (t, J=7.8 Hz, 2H) 7.63-7.98 (m, 11H).

trans-3-Amino-1-methyl-3-[4-(8-phenyl-1,4,6,9,9b-pentaaza-cyclopenta[a]naphthalen-7-yl)-phenyl]-cyclobutanol [DLXXXII]

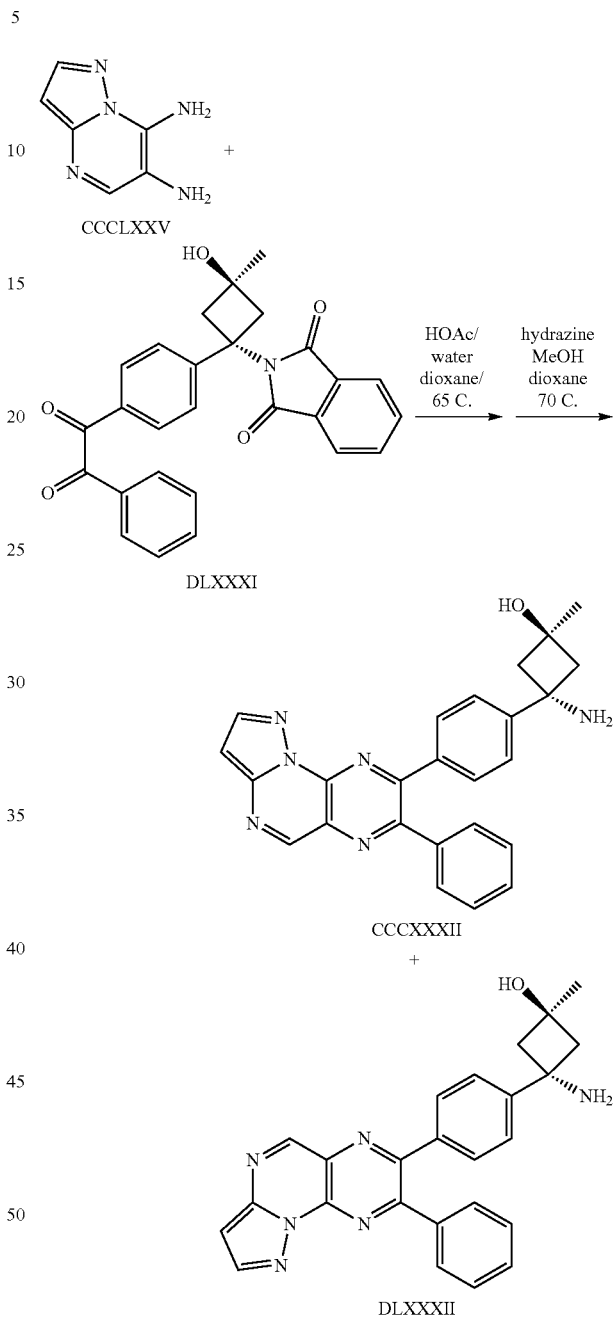

A 40 ml scintillation vial containing [CCCLXXV] (78 mg, 0.3 mmol), [DLXXI] (132 mg, 0.3 mmol), HOAc (1.5 mL), dioxane (3 mL), and water (3 mL) was heated at 65° C. for 3 days. The reaction was allowed to cool to RT and the solvent was removed in vacuo. The residue was dissolved in MeOH (3 mL), dioxane (3 mL), and hydrazine hydrate (1.5 mL). The mixture was heated at 70° C. for 3 h. The solvent was removed in vacuo. The residue was dissolved in MeOH (4 mL), water (1 mL), and TFA (0.5 mL). After filtration, the filtrate was purified by reverse-phase preparative HPLC using water-methanol-TFA [95:5:0.05] and methanol-water-TFA [95:5:0.05] as the mobile phases to provide Compound [DLXXXII]

as a yellowish solid (~14 mg, 6.1%, 3 TFA salt): LCMS (m/e) 423 (M+H) (m/e); $^1$H NMR (400 MHz, METHANOL-d4) ppm 1.49 (s, 3H) 2.70 (d, ☐ J=14.59 Hz, 2H) 2.83-2.92 (m, 2H) 7.02 (s, 1H) 7.30-7.39 (m, 1H) 7.37 (d, J=7.76 Hz, 2H) 7.40-7.47 (m, 1H) 7.57 (d, J=8.54 Hz, 2H) 7.64-7.72 (m, 4H) 8.31 (s, 1H) 9.17 (s, 1H).

Also isolated was Compound [CCCXXXII]: LCMS (m/e) 423 (M+H); $^1$H NMR is same previous. 3 TFA salt.

Example 1

Cloning of the Human Akt Isoforms and Delta-PH-Akt1 (PH Domain Deleted AKT1)

The pS2neo vector (deposited in the ATCC on Apr. 3, 2001 as ATCC PTA-3253) was prepared as follows: The pRmHA3 vector (prepared as described in *Nucl. Acid Res.* 16:1043-1061 (1988)) was cut with BglII and a 2734 bp fragment was isolated. The pUChsneo vector (prepared as described in *EMBO J.* 4:167-171 (1985)) was also cut with BglII and a 4029 bp band was isolated. These two isolated fragments were ligated together to generate a vector termed pS2neo-1. This plasmid contains a polylinker between a metallothionine promoter and an alcohol dehydrogenase poly A addition site. It also has a neo resistance gene driven by a heat shock promoter. The pS2neo-1 vector was cut with Psp5II and BsiWI. Two complementary oligonucleotides were synthesized and then annealed (CTGCGGCCGC (SEQ. ID. NO. 1) and GTACGCGGCCGCAG (SEQ. ID. NO. 2)). The cut pS2neo-1 and the annealed oligonucleotides were ligated together to generate a second vector, pS2neo. Added in this conversion was a NotI site to aid in the linearization prior to transfection into S2 cells.

Human Akt1 gene was amplified by PCR (Clontech) out of a human spleen cDNA (Clontech) using the 5' primer: 5'CGC-GAATTCAGATCTACCATGAGCGACGTGGCTATTGTG 3' (SEQ. ID. NO. 3), and the 3' primer: 5'CGCTCTAGAG-GATCCTCAGGCCGTGCTGCTGGC3' (SEQ. ID. NO. 4). The 5' primer included an EcoRI and BglII site. The 3' primer included an XbaI and BamHI site for cloning purposes. The resultant PCR product was subcloned into pGEM3Z (Promega) as an EcoRI/Xba I fragment. For expression/purification purposes, a middle T tag was added to the 5' end of the full length Akt1 gene using the PCR primer: 5'GTACGAT-GCTGAACGATATCTTCG 3' (SEQ. ID. NO. 5). The resulting PCR product encompassed a 5' KpnI site and a 3' BamHI site which were used to subclone the fragment in frame with a biotin tag containing insect cell expression vector, pS2neo.

For the expression of a pleckstrin homology domain (PH) deleted (Δaa 4-129, which includes deletion of a portion of the Akt1 hinge region) version of Akt1, PCR deletion mutagenesis was done using the full length Akt1 gene in the pS2neo vector as template. The PCR was carried out in 2 steps using overlapping internal primers (5'GAATACATGC-CGATGGAAAGCGACGGGGCTGAA-GAGATGGAGGTG 3' (SEQ. ID. NO. 6), and 5'CCCCTC-CATCTCTTCAGCCCCGTCGCTTTCCATCGGCATG TATTC 3' (SEQ. ID. NO. 7)) which encompassed the deletion and 5' and 3' flanking primers which encompassed the KpnI site and middle T tag on the 5' end. The final PCR product was digested with KpnI and SmaI and ligated into the pS2neo full length Akt1 KpnI/SmaI cut vector, effectively replacing the 5' end of the clone with the deleted version.

Human Akt3 gene was amplified by PCR of adult brain cDNA (Clontech) using the amino terminal oligo primer: 5' GAATTCAGATCTACCATGAGCGATGTTACCATTGTG 3' (SEQ. ID. NO. 8); and the carboxy terminal oligo primer: 5' TCTAGATCTTATTCTCGTCCACTTGCAGAG 9).

These primers included a 5' EcoRI/BglII site and a 3' XbaI/BglII site for cloning purposes. The resultant PCR product was cloned into the EcoRI and XbaI sites of pGEM4Z (Promega). For expression/purification purposes, a middle T tag was added to the 5' end of the full length Akt3 clone using the PCR primer: 5'GGTACCATGGAATACATGCCGATG-GAAAGCGATGTTACCATTGTGAAG 3'(SEQ. ID. NO. 10). The resultant PCR product encompassed a 5' KpnI site which allowed in frame cloning with the biotin tag containing insect cell expression vector, pS2neo.

Human Akt2 gene was amplified by PCR from human thymus cDNA (Clontech) using the amino terminal oligo primer: 5' AAGCTTAGATCTACCATGAATGAGGT-GTCTGTC 3' (SEQ. ID. NO. 11); and the carboxy terminal oligo primer: 5'GAATTCGGATCCTCACTCGCGGAT-GCTGGC 3' (SEQ. ID. NO. 12). These primers included a 5' HindIII/BglII site and a 3' EcoRI/BamHI site for cloning purposes. The resultant PCR product was subcloned into the HindIII/EcoRI sites of pGem3Z (Promega). For expression/purification purposes, a middle T tag was added to the 5' end of the full length Akt2 using the PCR primer: 5'GGTAC-CATGGAATACATGCCGATGGAAAATGAG-GTGTCTGTCATCAAAG 3' (SEQ. ID. NO. 13). The resultant PCR product was subcloned into the pS2neo vector as described above.

Example 2

Expression of Human Akt Isoforms and Delta-PH-Akt1

The DNA containing the cloned Akt1, Akt2, Akt3 and delta-PH-Akt1 genes in the pS2neo expression vector was purified and used to transfect *Drosophila* S2 cells (ATCC) by the calcium phosphate method. Pools of antibiotic (G418, 500 μg/mL) resistant cells were selected. Cell were expanded to a 1.0 L volume (~7.0×10$^6$/mL), biotin and CuSO$_4$ were added to a final concentration of 50 μM and 50 mM respectively. Cells were grown for 72 h at 27° C. and harvested by centrifugation. The cell paste was frozen at −70° C. until needed.

Example 3

Purification of Human Akt Isoforms and Delta-PH-Akt1

Cell paste from one liter of S2 cells, described in Example 2, was lysed by sonication with 50 mL 1% CHAPS in buffer A: (50 mM Tris pH 7.4, 1 mM EDTA, 1 mM EGTA, 0.2 mM AEBSF, 10 μg/mL benzamidine, 5 μg/mL of leupeptin, aprotinin and pepstatin each, 10% glycerol and 1 mM DTT). The soluble fraction was purified on a Protein G Sepharose fast flow (Pharmacia) column loaded with 9 mg/mL anti-middle T monoclonal antibody and eluted with 75 μM EYMPME (SEQ ID. NO. 14) peptide in buffer A containing 25% glycerol. Akt/PKB containing fractions were pooled and the protein purity evaluated by SDS-PAGE. The purified protein was quantitated using a standard Bradford protocol. Purified protein was flash frozen on liquid nitrogen and stored at −70° C.

Akt and Akt pleckstrin homology domain deletions purified from S2 cells required activation. Akt and Akt pleckstrin homology domain deletions were activated (Alessi et al. *Current Biology* 7:261-269) in a reaction containing 10 nM PDK1 (Upstate Biotechnology, Inc.), lipid vesicles (10 μM phosphatidylinositol-3,4,5-trisphosphate—Metreya, Inc, 100 μM phosphatidylcholine and 100 μM phosphatidylserine—Avanti Polar lipids, Inc.) and activation buffer (50 mM Tris pH7.4, 1.0 mM DTT, 0.1 mM EGTA, 1.0 μM Microcystin-LR, 0.1 mM ATP, 10 mM MgCl$_2$, 333 μg/mL BSA and 0.1 mM EDTA). The reaction was incubated at 22° C. for 4 hours. Aliquots were flash frozen in liquid nitrogen.

Example 4

Akt Kinase Assays

Activated Akt isoforms and pleckstrin homology domain deletion constructs were assayed utilizing a GSK-derived biotinylated peptide substrate. The extent of peptide phosphorylation was determined by Homogeneous Time Resolved Fluorescence (HTRF) using a lanthanide chelate (Lance)-coupled monoclonal antibody specific for the phosphopeptide in combination with a streptavidin-linked allophycocyanin (SA-APC) fluorophore which will bind to the biotin moiety on the peptide. When the Lance and APC are in proximity (i.e. bound to the same phosphopeptide molecule), a non-radiative energy transfer takes place from the Lance to the APC, followed by emission of light from APC at 665 nm. Materials required for the assay:
A. Activated Akt isozyme or pleckstrin homology domain deleted construct
B. Akt peptide substrate: GSK3α (S21) Peptide #3928 biotin-GGRARTSSFAEPG (SEQ. ID. NO. 15), Macromolecular Resources.
C. Lance labeled anti-phospho GSK3α monoclonal antibody (Cell Signaling Technology, clone #27).
D. SA-APC (Prozyme catalog no. MSS lot #896067).
E. Microfluor®B U Bottom Microtiter Plates (Dynex Technologies, Catalog no. 7205).
F. Discovery® HTRF Microplate Analyzer, Packard Instrument Company.
G. 100× Protease Inhibitor Cocktail (PIC): 1 mg/mL benzamidine, 0.5 mg/mL pepstatin, 0.5 mg/mL leupeptin, 0.5 mg/mL aprotinin.
H. 10× Assay Buffer: 500 mM HEPES, pH 7.5, 1% PEG, mM EDTA, 1 mM EGTA, 1% BSA, 20 mM θ-Glycerol phosphate.
I. Quench Buffer: 50 mM HEPES pH 7.3, 16.6 mM EDTA, 0.1% BSA, 0.1% Triton X-100, 0.17 nM Lance labeled monoclonal antibody clone #27, 0.0067 mg/mL SA-APC
J. ATP/MgCl$_2$ working solution: 1× Assay buffer, 1 mM DTT, 1×PIC, 125 mM KCl, 5% Glycerol, 25 mM MgCl$_2$, 375 μM ATP
K. Enzyme working solution: 1× Assay buffer, 1 mM DTT, 1×PIC, 5% Glycerol, active Akt. The final enzyme concentrations were selected so that the assay was in a linear response range.
L. Peptide working solution: 1× Assay buffer, 1 mM DTT, 1×PIC, 5% Glycerol, 2 μM GSK3 biotinylated peptide #3928

The reaction is assembled by adding 16 μL of the ATP/MgCl$_2$ working solution to the appropriate wells of a 96-well microliter plate. Inhibitor or vehicle (1.0 μL) is added followed by 10 μL of peptide working solution. The reaction is started by adding 13 μL of the enzyme working solution and mixing. The reaction is allowed to proceed for 50 min and then stopped by the addition of 60 μL HTRF quench buffer. The stopped reactions were incubated at room temperature for at least 30 min and then read on the Discovery instrument.

IC$_{50}$ of example compounds to Akt1 kinase and Akt2 kinase are shown in the table below.

| Compound | IC$_{50}$ (nM) Akt1 | Akt2 |
|---|---|---|
| EXAMPLE 1-9 | 4.0 | 29.0 |
| EXAMPLE 9-2 | 32.7 | 33.8 |
| EXAMPLE 12-3 | 4.6 | 33.8 |
| EXAMPLE 15-3 | 37.2 | 578 |

Procedure for Streptavidin Flash Plate Assay:
Step 1:
A 1 μL solution of the test compound in 100% DMSO was added to 20 μL of 2× substrate solution (20 uM GSK3 Peptide, 300 μM ATP, 20 mM MgCl$_2$, 20 μCi/mL [γ$^{33}$P] ATP, 1× Assay Buffer, 5% glycerol, 1 mM DTT, 1×PIC, 0.1% BSA and 100 mM KCl). Phosphorylation reactions were initiated by adding 19 μL of 2× Enzyme solution (6.4 nM active Akt/PKB, 1× Assay Buffer, 5% glycerol, 1 mM DTT, 1×PIC and 0.1% BSA). The reactions were then incubated at room temperature for 45 minutes.
Step 2:
The reaction was stopped by adding 170 μL, of 125 mM EDTA. 2004 of stopped reaction was transferred to a Streptavidin Flashplate® PLUS (NEN Life Sciences, catalog no. SMP103). The plate was incubated for ≥10 minutes at room temperature on a plate shaker. The contents of each well was aspirated, and the wells rinsed 2 times with 200 μL TBS per well. The wells were then washed 3 times for 5 minutes with 200 μL TBS per well with the plates incubated at room temperature on a platform shaker during wash steps.

The plates were covered with sealing tape and counted using the Packard TopCount with the appropriate settings for counting [$^{33}$P] in Flashplates.
Procedure for Streptavidin Filter Plate Assay:
Step 1:
The enzymatic reactions as described in Step 1 of the Streptavidin Flash Plate Assay above were performed.
Step 2:
The reaction was stopped by adding 20 μL of 7.5M Guanidine Hydrochloride. 50 μL of the stopped reaction was transferred to the Streptavidin filter plate (SAM$^{2™}$ Biotin Capture Plate, Promega, catalog no. V7542) and the reaction was incubated on the filter for 1-2 minutes before applying vacuum.

The plate was then washed using a vacuum manifold as follows: 1) 4×200 μL/well of 2M NaCl; 2) 6×200 μL/well of 2M NaCl with 1% H$_3$PO$_4$; 3) 2×200 μL/well of diH$_2$O; and 4) 2×100 μL/well of 95% Ethanol. The membranes were then allowed to air dry completely before adding scintillant.

The bottom of the plate was sealed with white backing tape, 30 μL/well of Microscint 20 (Packard Instruments, catalog no. 6013621) was added. The top of the plate was sealed with clear sealing tape, and the plate then counted using the Packard TopCount with the appropriate settings for [$^{33}$P] with liquid scintillant.
Procedure for Phosphocellulose Filter Plate Assay:
Step 1:
The enzymatic reactions were performed as described in Step 1 of the Streptavidin Flash Plate Assay (above) utilizing KKGGRARTSSFAEPG (SEQ. ID. NO. 16) as the substrate in place of biotin-GGRARTSSFAEPG.
Step 2:
The reaction was stopped by adding 20 μl, of 0.75% H$_3$PO$_4$. 50 μL of stopped reaction was transferred to the filter plate (UNIFILTER™, Whatman P81 Strong Cation Exchanger, White Polystyrene 96 Well Plates, Polyfiltronics, catalog no. 7700-3312) and the reaction incubated on the filter for 1-2 minutes before applying vacuum.

The plate was then washed using a vacuum manifold as follows: 1) 9×200 µL/well of 0.75% $H_3PO_4$; and 2) 2×200 µL/well of $diH_2O$. The bottom of the plate was sealed with white backing tape, then 30 µL/well of Microscint 20 was added. The top of the plate was sealed with clear sealing tape, and the plate counted using the Packard TopCount with the appropriate settings for [$^{33}P$] and liquid scintillant.

PKA Assay:
Each individual PKA assay consists of the following components:
A. 5×PKA assay buffer (200 mM Tris pH7.5, 100 mM $MgCl_2$, 5 mM θ-mercaptoethanol, 0.5 mM EDTA)
B. 50 µM stock of Kemptide (Sigma) diluted in water
C. $^{33}P$-ATP prepared by diluting 1.0 µL $^{33}P$-ATP [10 mCi/mL] into 200 µL of a 50 µM stock of unlabeled ATP
D. 10 µL of a 70 nM stock of PKA catalytic subunit (UBI catalog #14-114) diluted in 0.5 mg/mL BSA
E. PKA/Kemptide working solution: equal volumes of 5×PKA assay buffer, Kemptide solution and PKA catalytic subunit.

The reaction is assembled in a 96 deep-well assay plate. The inhibitor or vehicle (10 µL) is added to 10 µL of the $^{33}P$-ATP solution. The reaction is initiated by adding 30 µL of the PKA/Kemptide working solution to each well. The reactions were mixed and incubated at room temperature for 20 min. The reactions were stopped by adding 50 µL of 100 mM EDTA and 100 mM sodium pyrophosphate and mixing.

The enzyme reaction product (phosphorylated Kemptide) was collected on p81 phosphocellulose 96 well filter plates (Millipore). To prepare the plate, each well of a p81 filter plate was filled with 75 mM phosphoric acid. The wells were emptied through the filter by applying a vacuum to the bottom of the plate. Phosphoric acid (75 mM, 170 µL) was added to each well. A 30 µL aliquot from each stopped PKA reaction was added to corresponding wells on the filter plate containing the phosphoric acid. The peptide was trapped on the filter following the application of a vacuum and the filters were washed 5 times with 75 mM phosphoric acid. After the final wash, the filters were allowed to air dry. Scintillation fluid (30 µL) was added to each well and the filters counted on a TopCount (Packard).

PKC Assay:
Each PKC assay consists of the following components:
A. 10×PKC co-activation buffer: 2.5 mM EGTA, 4 mM $CaCl_2$
B. 5×PKC activation buffer: 1.6 mg/mL phosphatidylserine, 0.16 mg/mL diacylglycerol, 100 mM Tris pH 7.5, 50 mM $MgCl_2$, 5 mM θ-mercaptoethanol
C. $^{33}P$-ATP prepared by diluting 1.0 µL $^{33}P$-ATP [10 mCi/mL] into 100 µL of a 100 µM stock of unlabeled ATP
D. Myelin basic protein (350 µg/mL, UBI) diluted in water
E. PKC (50 ng/mL, UBI catalog #14-115) diluted into 0.5 mg/mL BSA
F. PKC/Myelin Basic Protein working solution: Prepared by mixing 5 volumes each of PKC co-activation buffer and Myelin Basic protein with 10 volumes each of PKC activation buffer and PKC.

The assays were assembled in 96 deep-well assay plates. Inhibitor or vehicle (10 µL) was added to 5.0 µL, of $^{33}P$-ATP. Reactions were initiated with the addition of the PKC/Myelin Basic Protein working solution and mixing. Reactions were incubated at 30° C. for 20 min. The reactions were stopped by adding 50 µL of 100 mM EDTA and 100 mM sodium pyrophosphate and mixing. Phosphorylated Mylein Basic Protein was collected on PVDF membranes in 96 well filter plates and quantitated by scintillation counting.

Compounds of the instant invention described in the Schemes and Tables were tested in the assay described above and were found to have $IC_{50}$ of ≤50 µM against one or more of Akt1, Akt2 and Akt3.

Example 5

Cell based Assays to Determine Inhibition of Akt/PKB

Cells (for example LnCaP or a PTEN$^{(-/-)}$ tumor cell line with activated Akt/PKB) were plated in 100 mm dishes. When the cells were approximately 70 to 80% confluent, the cells were refed with 5 mls of fresh media and the test compound added in solution. Controls included untreated cells, vehicle treated cells and cells treated with either LY294002 (Sigma) or wortmanin (Sigma) at 20 µM or 200 nM, respectively. The cells were incubated for 2, 4 or 6 hrs, and the media removed, the cells were washed with PBS, scraped and transferred to a centrifuge tube. They were pelleted and washed again with PBS. Finally, the cell pellet was resuspended in lysis buffer (20 mM Tris pBS, 140 mM NaCl, 2 mM EDTA, 1% Triton X-100, 1 mM Na Pyrophosphate, 10 mM beta-Glycerol Phosphate, 10 mM NaF, 0.5 mm $NaVO_4$, 1 µM Microsystine, and 1× Protease Inhibitor Cocktail), placed on ice for 15 minutes and gently vortexed to lyse the cells. The lysate was spun in a Beckman tabletop ultra centrifuge at 100,000×g at 4° C. for 20 min. The supernatant protein was quantitated by a standard Bradford protocol (BioRad) and stored at −70° C. until needed.

Proteins were immunoprecipitated (IP) from cleared lysates as follows: For Akt1/PKBI, lysates are mixed with Santa Cruz sc-7126 (D-17) in NETN (100 mM NaCl, 20 mM Tris pH 8.0, 1 mM EDTA, 0.5% NP-40) and Protein A/G Agarose (Santa Cruz se-2003) was added. For Akt2/PKBθ, lysates were mixed in NETN with anti-Akt2 agarose (Upstate Biotechnology #16-174) and for Akt3/PKBK, lysates were mixed in NETN with anti-Akt3 agarose (Upstate Biotechnology #16-175). The IPs were incubated overnight at 4° C., washed and separated by SDS-PAGE.

Western blots were used to analyze total Akt, pThr308 Akt1, pSer473 Akt1, and corresponding phosphorylation sites on Akt2 and Akt3, and downstream targets of Akt using specific antibodies (Cell Signaling Technology): Anti-Total Akt (cat. no. 9272), Anti-Phopho Akt Serine 473 (cat. no. 9271), and Anti-Phospho Akt Threonine 308 (cat. no. 9275). After incubating with the appropriate primary antibody diluted in PBS+0.5% non-fat dry milk (NFDM) at 4° C. overnight, blots were washed, incubated with Horseradish peroxidase (HRP)-tagged secondary antibody in PBS+0.5% NFDM for 1 hour at room temperature. Proteins were detected with ECL Reagents (Amersham/Pharmacia Biotech RPN2134).

Example 6

Heregulin Stimulated Akt Activation

MCF7 cells (a human breast cancer line that is PTEN$^{+/+}$) were plated at 1×10$^6$ cells per 100 mM plate. When the cells were 70-80% confluent, they were refed with 5 mL of serum free media and incubated overnight. The following morning, compound was added and the cells were incubated for 1-2 hrs, after which time heregulin was added (to induce the activation of Akt) for 30 minutes and the cells were analyzed as described above.

Example 7

Inhibition of Tumor Growth

In vitro/in vivo efficacy of an inhibitor of the growth of cancer cells may be confirmed by several protocols well known in the art.

In vitro, 2000-6000 cells/well are seeded into triplicate wells in 96 well plate in complete medium (RPMI-1640 supplemented with 10% heat-inactivated fetal bovine serum (FBS)) and incubated at 37° C./5% $CO_2$ overnight. The next day, inhibitors are added as a dilution series in complete medium (final DMSO concentration in the assay is 0.1%). The plates are incubated at 37° C./5% $CO_2$ for 72-96 hours. The number of viable cells is then measured using the Cell-Titer-Glo kit (Promega). The luminescence signals are measured using ARVO/Victor 3 plate reader (Perkin-Elmer). The data are fitted with a four parameter dose-response equation and the inflection point of the least square fit curve or concentration at 50% inhibition is determined as an $IC_{50}$ value.

In vivo, human tumor cell lines which exhibit a deregulation of the PI3K pathway (such as LNCaP, PC3, C33a, OVCAR-3, MDA-MB-468, A2780 or the like) are injected subcutaneously into the left flank of 6-10 week old female nude (also male mice [age 10-14 weeks] are used for prostate tumor xenografts [LnCaP and PC3]) mice (Harlan), or female nude rats (F344/N Jcl-rnu) (CLEA Japan) on day 0. The mice or rats are randomly assigned to a vehicle, compound or combination treatment group. Daily or every other day subcutaneous or oral administration begins on day 1 and continues for the duration of the experiment. Alternatively, the inhibitor test compound may be administered by a continuous infusion pump. Compound, compound combination or vehicle is delivered in a total volume of 0.2 mL. Tumors are excised and weighed when all of the vehicle-treated animals exhibited lesions of 0.5-1.0 cm in diameter, typically 4 to 5.5 weeks after the cells were injected. The average weight of the tumors in each treatment group for each cell line is calculated.

Example 8

Spot Multiplex Assay

This procedure describes a sandwich immunoassay used to detect multiple phosphorylated proteins in the same well of a 96 well format plate. Cell lysates are incubated in 96-well plates on which different capture antibodies are placed on spatially distinct spots in the same well. Phosphorylation-specific rabbit polyclonal antibodies are added and the complex is detected by an anti-rabbit antibody labeled with an electrochemiluminescent tag.

96-Well LNCaP Plates+/−Compounds:

Spin in Beckman J6 1200 rpm 10 min, aspirate media. Add 50 µl/well: TBS (Pierce #28376-20 mM Tris pH 7.5, 150 mM NaCl)+1% Triton X-100+Protease and Phosphatase Inhibitors. Wrap in plastic wrap, place in −70° C. freezer until completely frozen. Block Multiplex Plates (Meso Scale Discovery, Gaithersburg, Md.) with 3% Blocker A in 1× Tris Wash Buffer, 150 µl/well. Cover with plate sealer, incubate on Micromix shaker RT 2 h (minimum). Wash with 1×RCM 51 (TTBS). Thaw cell lysate plates on ice, add 4° C. O/N lysate/well into blocked plates. Cover with plate sealer, incubate on Micromix shaker 4° C., O/N, Wash with 1×RCM 51. Dilute Secondary Antibodies in 1% Blocker A in 1× Tris Wash Buffer: Anti phospho AKT (T308), Anti phospho Tuberin (T1462), alone or in combination. Add 25 µl/well, cover with plate sealer, incubate on Micromix shaker RT 3 h. Wash with 1×RCM 51. Dilute Ru-GAR in 1% Blocker A in 1× Tris Wash Buffer. Add 25 µl/well, cover with plate sealer, incubate on Micromix shaker RT 1 h. Wash with 1×RCM 51. Dilute 4× Read Buffer T to 1× with Water, add 200 µl diluted Read Buffer/well. Read on Sector 6000 Imager.

Protease and Phosphatase Inhibitors:
Microcystin-LR, Calbiochem #475815 to 1 µM final concentration (stock=500 µM)
Calbiochem #524624, 100× Set I
Calbiochem #524625, 100× Set II
Calbiochem #539134, 100× Set III
Anti Phospho AKT (T308):
Cell Signaling Technologies #9275
Anti Phospho Tuberin (T1462):
Covance Affinity Purified (Rabbits MS 2731/2732)
Ru-GAR=Ruthenylated Goat anti Rabbit
10× Tris Wash Buffer, Blocker A and 4× Read Buffer T
10×RCM 51 (10×TTBS, RCM 51)
1×=20 mM Tris pH 7.5, 140 mM NaCl, 0.1% Tween-20

Example 9

Cell-Based (In-Vivo) Assay

This procedure describes a cell-based (in vivo) activity assay for the Akt serine/threonine kinase. Activated endogenous Akt is capable of phosphorylating specific Akt substrate (GSK3β) peptide which is biotinylated. Detection is performed by Homogeneous Time Resolved Fluorescence (HTRF) using a Europium Kryptate [Eu(K)] coupled antibody specific for the phosphopeptide and streptavidin linked XL665 fluorophore which will bind to the biotin moiety on the peptide. When the [Eu(K)] and XL665 are in proximity (i.e. bound to the same phosphopeptide molecule) a non-radiative energy transfer takes place from the Eu(K) to the XL665, followed by emission of light from XL665 at 665 nm.

The assay can be used to detect inhibitors of all three Akt isozymes (Akt1, Akt2, and Akt3) from multiple different species if specific antibodies to each exist.

Materials and Reagents
A. Cell Culture Microtiter Flat Bottom 96 well plates, Corning Costar, Catalog no. 3598
B. Reacti-Bind Protein A Coated 96-well plates, Pierce, Catalog no 15130.
C. Reacti-Bind Protein G Coated 96-well plates, Pierce, Catalog no 15131.
D. Micromix 5 Shaker.
E. Microfluor®B U Bottom Microtiter Plates, Dynex Technologies, Catalog no. 7205.
F. 96 Well Plate Washer, Bio-Tek Instruments, Catalog no. EL 404.
G. Discovery® HTRF Microplate Analyzer, Packard Instrument Company.
Buffer Solutions
A. IP Kinase Cell Lysis Buffer: 1×TBS; 0.2% Tween 20; 1× Protease Inhibitor Cocktail III (Stock is 100×, Calbiochem, 539134); 1× Phosphatase Inhibitor Cocktail I (Stock is 100×, Calbiochem, 524624); and 1× Phosphatase Inhibitor Cocktail II (Stock is 100×, Calbiochem, 524625).
B. 10× Assay Buffer: 500 mM Hepes pH 7.5; 1% PEG; 1 mM EDTA; 1 mM EGTA; and 20 mM β-glycerophosphate.

C. IP Kinase Assay Buffer: 1×Assay Buffer; 50 mM KCl; 150 µM ATP; 10 mM MgCl$_2$; 5% Glycerol; 1 mM DTT; 1 Tablet Protease Inhibitor Cocktail per 50 mL Assay Buffer; and 0.1% BSA D. GSK3β Substrate Solution: IP Kinase Assay Buffer; and 500 nM Biotinylated GSK3β peptide.

E. Lance Buffer: 50 mM Hepes pH 7.5; 0.1% BSA; and 0.1% Triton X-100.

F. Lance Stop Buffer: Lance Buffer; and 33.3 mM EDTA.

G. Lance Detection Buffer: Lance Buffer; 13.3 µg/mL SA-APC; and 0.665 nM EuK Ab a-phospho (Ser-21) GSK3β

Multi-Step Immunoprecipitation Aid Kinase Assay

Day 1

A. Seed C33a cells Step: Plate 60,000 C33a cells/well in 96 well microtiter plate.

B. Incubate cells overnight at 37° C.

Day 2

D. Compound Addition Step: Add compounds in fresh media (alpha-MEM/10% FBS, room temp) to 96 well plate from above and incubate for 5 hrs in tissue culture incubator.

E. Cell Lysis Step: Aspirate media and add 100 µl of IP Kinase Cell Lysis Buffer.

F. Freeze 96 well microtiter plate at −70° C. (NOTE: This step can be done for a minimum of 1 hour or overnight.)

Day 3

G. Coat Protein A/G 96 well plate Step: Add appropriate concentration of α-Akt antibody (Akt1, Akt2, or Akt3) in a 100 µl of PBS to the following wells:

| | |
|---|---|
| α-Akt 1 (20 ng/well) | B2 thru B10 |
| α-Akt 2 (rabbit-human, dog) (50 ng/well) | B2 thru B10 |
| α-Akt 2 (sheep-mouse, rat) (100 ng/well) | B2 thru B10 |
| α-Akt 3 (20 ng/well/100 µL) | B2 thru B10 |
| Control-IgG: | B11-G11 on every plate |

AKT1: rabbit IgG 20 ng/well in 100 µl, PBS, Santa Cruz sc-2027

AKT2 (for human tumor and dog tissues) rabbit IgG 50 ng/well in 100 µL PBS

AKT2 (for rats and mice) sheep IgG 100 ng/well in 100 µl, PBS, Santa Cruz se-2717

AKT3 rabbit IgG 20 ng/well in 100 µL PBS

H. Incubate in the cold room (+4° C.) for 4 hours on the Micromix 5 (Form 20; Attitude 2) (NOTE: Attitude depends on which Micromix 5 machine).

I. Aspirate off α-Akt antibody solution and add 100 µl of PBS to each well.

J. Akt Immunoprecipitation Step: To the 100 µl of PBS from Step (I) add 5 µl of thawed cell lysate for Akt1 plates and 10 µl of thawed cell lysate for Akt2 plates. NOTE: Thaw cell lysate on ice. Mix thawed lysate by pipetting up & down 10× before transferring to antibody plates. Keep the cell lysate plates on ice. After transfer of cell lysate to the antibody plates refreeze the cell lysate plates at −70° C.

K. Incubate in the cold room (+4° C.) overnight on Micromix 5 shaker (form 20, attitude 3).

Day 4

L. Immunoprecipitation Plate Wash Step: Wash 96 well plates 1× with TTBS (RCM 51, 1×=2 cycles) using the 96-Well Plate Washer. Fill wells with TTBS and incubate for 10 minutes. Wash 96 well plates 2× with TTBS. (NOTE: Prime plate washer before use: 1. Check buffer reservoirs, making sure they are full and 2. empty waste containers.

M. Manual Plate Wash Step: Add 180 µl of IP Kinase Assay buffer.

N. Start Akt Enzyme Reaction: Aspirate supernatant. Add 60 µl of GSK3β Substrate Solution.

O. Incubate for 2.5 hours on Micromix 5 shaker @ RT. NOTE: Time of incubation should be adjusted so that the ratio of Column 10/Column 11 is not >10.

P. Combine 30 µl of Lance Detection Buffer with 30 µl of Lance Stop Buffer (60 µl total/well) and add to Microfluor U bottom 96 well black plates.

Q. Stop Akt Enzyme Reaction: Transfer 40 µl of Akt Enzyme Reaction Mix from Protein A/G 96 well plate from Step (O) to Microfluor U bottom 96 well black plates from Step (P).

U. Incubate at room temperature for 1-2 hrs on Micromix 5 shaker (form 20, attitude 3), then read with the Discovery HTRF Microplate Analyzer using Akt program.

IP Kinase Cell Lysis Buffer

1×TBS 0.25% Tween 20 (Fisher BP337-500)

1× Protease Inhibitor Cocktail III (Stock is 100×, Calbiochem, 539134)

1× Phosphatase Inhibitor Cocktail I (Stock is 100×, Calbiochem, 524624)

1× Phosphatase Inhibitor Cocktail II (Stock is 100×, Calbiochem, 524625)

1 uM Microcystin LR (Calbiochem 475815)

IP Kinase Assay Buffer 50 mM Hepes pH 7.5

0.1% PEG (Sigma P-3265)

0.1 mM EDTA (USB 15694)

0.1 mM EGTA (Sigma E8145-50G)

2 mM β-glycerophosphate (Sigma G-6376)

50 mM KCl (Fisher P-217) (1M stock, RT)

150 uM ATP (Sigma)

10 mM MgCl$_2$ (Sigma M-1028)

5% Glycerol (Fisher G33-500)

1 mM DTT (Sigma D0632-25G)

1 Tablet Protease Inhibitor Cocktail per 50 mL (Roche 11 836 145 001)

0.1% BSA (Roche 03 117 405 001)

GSK3β Substrate Solution

IP Kinase Assay Buffer 500 nM Biotinylated GSK3β peptide (Biotin-GGRARTSS-FAEPG-COOH)

Lance Stop Buffer 25 mM Hepes pH 7.5

0.05% BSA 0.05% Triton X-100

16.7 mM EDTA

Lance Detection Buffer 6.65 ug/mL SA-APC (Perkin Elmer CR130-100)

0.665 nM EuK Ab a-phospho (Ser-21) GSK3β monoclonal antibody in Lance Stop Buffer

What is claimed is:

1. A compound according to Formula A:

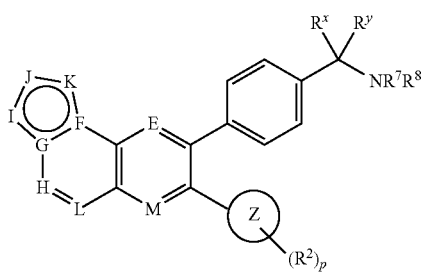

wherein:

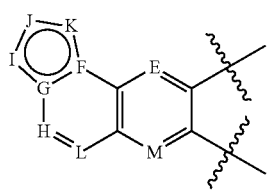

is

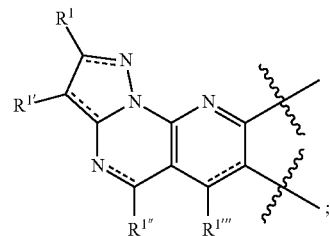

each $R^1$, $R^{1'}$, $R^{1''}$ and $R^{1'''}$ is independently selected from: H, oxo, $(C=O)_aO_b(C_1-C_{10})$alkyl, $(C=O)_aO_b$-aryl, $(C=O)_aO_b(C_2-C_{10})$alkenyl, $(C=O)_aO_b(C_2-C_{10})$alkynyl, $CO_2H$, halo, OH, $O_b(C_1-C_6)$perfluoroalkyl, $(C=O)_aNR^7R^8$, CN, $(C=O)_aO_b(C_3-C_8)$cycloalkyl, $S(O)_mNR^7R^8$, SH, $S(O)_m-(C_1-C_{10})$alkyl and $(C=O)_aO_b$-heterocyclyl, said alkyl, aryl, alkenyl, alkenyl, cycloalkyl, and heterocyclyl is optionally substituted with one or more substituents selected from $R^6$;

Bond: ------ is a single or double bond, provided that when each $R^1$, $R^{1'}$, $R^{1''}$ and $R^{1'''}$ is oxo, then said bond adjacent to the oxo is a single bond and C or N which is attached to the resulting carbonyl with said single bond bears H;

a is 0 or 1; b is 0 or 1; m is 0, 1 or 2; p is independently 0, 1, 2, 3, 4 or 5;

Ring Z is selected from: $(C_3-C_8)$cycloalkyl, aryl, and heterocyclyl;

$R^2$ is independently selected from: oxo, $(C=O)_aO_b(C_1-C_{10})$alkyl, $(C=O)_aO_b$-aryl, $(C=O)_aO_b(C_2-C_{10})$alkenyl, $(C=O)_aO_b(C_2-C_{10})$alkynyl, $CO_2H$, halo, OH, $O_b(C_1-C_6)$perfluoroalkyl, $(C=O)_aNR^7R^8$, CN, $(C=O)_aO_b(C_3-C_8)$cycloalkyl, $S(O)_mNR^7R^8$, SH, $S(O)_m-(C_1-C_{10})$alkyl and $(C=O)_aO_b$-heterocyclyl, said alkyl, aryl, alkenyl, alkynyl, cycloalkyl, and heterocyclyl is optionally substituted with one or more substituents selected from $R^6$;

$R^6$ is: $(C=O)_aO_b(C_1-C_{10})$alkyl, $(C=O)_aO_b$aryl, $(C_2-C_{10})$alkenyl, $(C_2-C_{10})$alkynyl, $(C=O)_aO_b$ heterocyclyl, $CO_2H$, halo, CN, OH, $O_b(C_1-C_6)$perfluoroalkyl, $O_a(C=O)_bNR^7R^8$, oxo, CHO, $(N=O)R^7R^8$, $S(O)_mNR^7R^8$, SH, $S(O)_m-(C_1-C_{10})$alkyl or $(C=O)_aO_b(C_3-C_8)$cycloalkyl, said alkyl, aryl, alkenyl, alkynyl, heterocyclyl, and cycloalkyl optionally substituted with one or more substituents selected from $R^{6a}$;

$R^{6a}$ is selected from: $(C=O)_aO_b(C_1-C_{10})$alkyl, $O_a(C_1-C_3)$perfluoroalkyl, $(C_0-C_6)$alkylene-$S(O)_mR^a$, SH, oxo, OH, halo, CN, $(C_2-C_{10})$alkenyl, $(C_2-C_{10})$alkynyl, $(C_3-C_6)$cycloalkyl, $(C_0-C_6)$alkylene-aryl, $(C_0-C_6)$alkylene-heterocyclyl, $(C_0-C_6)$alkylene-$N(Rb)_2$, $C(O)R^a$, $(C_0-C_6)$alkylene-$CO_2R^a$, C(O)H, $(C=O)_aNR^b_2$, and $(C_0-C_6)$alkylene-$CO_2H$, said alkyl, alkenyl, alkynyl, cycloalkyl, aryl, and heterocyclyl is optionally substituted with up to three substituents selected from $R^b$, OH, halogen, $CO_2H$, CN, $O_a(C=O)_b(C_1-C_6)$alkyl, oxo, and $N(Rb)_2$;

$R^7$ and $R^8$ are independently selected from: H, $(C=O)_aO_b(C_1-C_{10})$alkyl, $(C=O)_aO_b(C_3-C_8)$cycloalkyl, $(C=O)_aO_b$-aryl, $(C=O)_aO_b$-heterocyclyl, $(C_2-C_{10})$alkenyl, $(C_2-C_{10})$alkynyl, SH, $SO_2R^a$, and $(C=O)_aNR^b_2$, said alkyl, cycloalkyl, aryl, heterocyclyl, alkenyl, and alkynyl is optionally substituted with one or more substituents selected from $R^{6a}$, or $R^7$ and $R^8$ can be taken together with the nitrogen to which they are attached to form a monocyclic, bicyclic or tricyclic heterocycle with 3-7 members in each ring and optionally containing, in addition to the nitrogen, one or two additional heteroatoms selected from N, O and S, said monocyclic, bicyclic or tricyclic heterocycle is optionally substituted with one or more substituents selected from $R^{6a}$;

$R^a$ is $(C_1-C_6)$alkyl, $(C_3-C_6)$cycloalkyl, aryl, or heterocyclyl, said alkyl, cycloalkyl, aryl, and heterocyclyl is optionally substituted with one or more substituents selected from $R^c$;

$R^b$ is independently: H, $(C=O)_aO_b(C_1-C_6)$alkyl, $(C_2-C_{10})$alkenyl, $S(O)_mR^a$, $(C=O)_aNR^d_2$, $(C=O)_aR^a$, or $S(O)_mNR^e_2$, said alkyl and alkenyl is optionally substituted with one or more substituents selected from $R^a$, $(C=O)_aO_b(C_1-C_6)$alkyl, OH, halo, CN, $CO_2H$, and $(C=O)_aNR^d_2$;

$R^c$ is independently: $(C=O)_aO_b(C_1-C_6)$alkyl, aryl, heterocyclyl, $(C_3-C_6)$cycloalkyl, oxo, OH, halo, CN, $(C=O)_aNR^d_2$, or $S(O)_mR^d$, said alkyl, aryl, heterocyclyl, and cycloalkyl is optionally substituted with one or more substituents selected from $(C=O)_aO_b(C_1-C_6)$alkyl, $O_a(C_1-C_3)$perfluoroalkyl, OH, halo, and CN;

$R^d$ is independently: H, $(C=O)_aO_b(C_1-C_6)$alkyl, aryl, or $S(O)_mR^e$, said alkyl and aryl is optionally substituted with one or more substituents selected from $(C=O)_aO_b(C_1-C_6)$alkyl, OH, halo, and CN;

$R^e$ is independently: H, or $(C_1-C_6)$alkyl; and $R^x$ and $R^y$ are independently selected from: H, $(C_1-C_6)$alkyl, $(C_2-C_6)$alkenyl, and $(C_2-C_6)$alkynyl, wherein said alkyl is optionally substituted with up to three substituents selected from: OH and halo, or $R^x$ and $R^y$ can be taken together to form a monocyclic or bicyclic carbo- or heterocycle with 3-7 members in each ring, said heterocycle is containing one or more heteroatoms selected from N, O and S, and said carbo- or heterocycle is optionally substituted with one or more substituents selected from: $(C_1-C_6)$alkyl, $(C_2-C_6)$alkenyl, $(C_3-C_6)$cycloalkyl, $(C_1-C_6)$alkylidene, $(C_1-C_6)$alkoxy, $CO_2H$, halo, OH, oxo, CN and $NR^7R^8$, said alkyl, cycloalkyl and alkoxy is optionally substituted with one or more substituents selected from halo, CN, OH and $NR^7R^8$;

or a pharmaceutically acceptable salt, stereoisomer or N-oxide derivative thereof.

2. A compound according to claim 1 of Formula C:

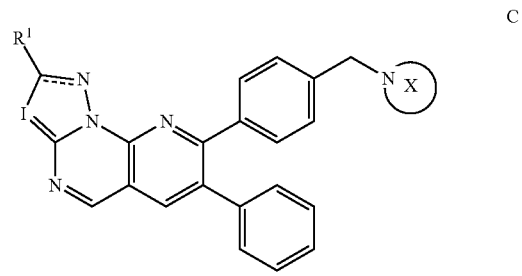

wherein:

I is CH;

a is 0 or 1; b is 0 or 1;

Ring X is selected from:

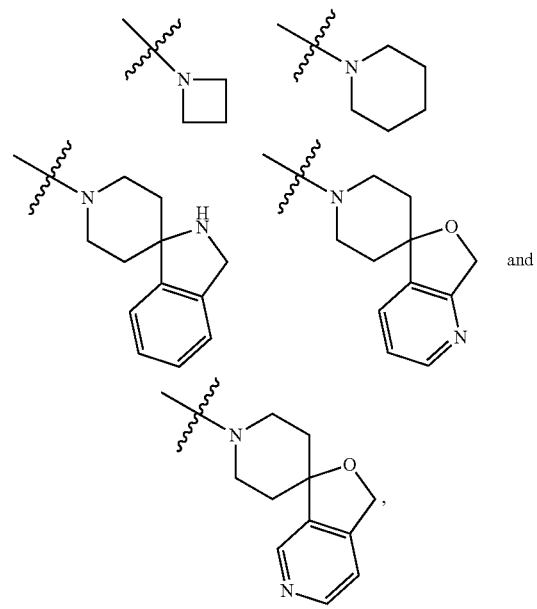

each of which is optionally substituted with one or more substituents selected from $R^{6a}$;

$R^1$ is selected from: H, oxo, $(C=O)_aO_b(C_1-C_{10})$alkyl, OH, and $(C=O)_aO_b$-heterocyclyl;

$R^{6a}$ is selected from: $(C=O)_aO_b(C_1-C_{10})$alkyl, oxo, OH, halo, $(C_0-C_6)$alkylene-heterocyclyl, and $(C=O)_aNR^b_2$, said alkyl, and heterocyclyl is optionally substituted with up to three substituents selected from $R^b$;

$R^a$ is $(C_1-C_6)$alkyl, $(C_3-C_6)$cycloalkyl, aryl, or heterocyclyl, said alkyl, cycloalkyl, aryl, and heterocyclyl is optionally substituted with one or more substituents selected from $R^c$;

$R^b$ is independently: H, $(C=O)_aO_b(C_1-C_6)$alkyl, or $(C=O)_aR^a$, said alkyl is optionally substituted with one or more substituents selected from $(C=O)_aO_b(C_1-C_6)$alkyl, OH, halo, CN, and $(C=O)_aNR^d_2$;

$R^c$ is independently: $(C=O)_aO_b(C_1-C_6)$alkyl, oxo, OH, halo, CN, or $(C=O)_aNR^d_2$, said alkyl is optionally substituted with one or more substituents selected from $(C_1-C_6)$alkyl, OH, halo, and CN;

$R^d$ is independently: H, or $(C_1-C_6)$alkyl; and

Bond: ------ is a single or double bond, provided that when $R^1$ is oxo, then said bond is a single bond and adjacent N bears H;

or a pharmaceutically acceptable salt, stereoisomer or N-oxide derivative thereof.

3. A compound according to claim 1 of Formula D:

wherein:
a is 0 or 1; b is 0 or 1;
Ring Y is a group of formula:

$R^1$ is selected from: H, oxo, $(C=O)_aO_b(C_1-C_{10})$alkyl, $(C=O)_aO_b$-aryl, OH, $(C=O)_aO_b(C_3-C_8)$cycloalkyl, and $(C=O)_aO_b$-heterocyclyl, said alkyl, aryl, cycloalkyl, and heterocyclyl is optionally substituted with one or more substituents selected from $R^6$;

$R^{1'}$ is selected from: H, $(C=O)_aO_b(C_1-C_{10})$alkyl, $(C=O)_aO_b$-aryl, halo, CN and $(C=O)_aO_b$-heterocyclyl, said alkyl, aryl, and heterocyclyl is optionally substituted with one or more substituents selected from $R^6$;

$R^6$ is: $(C=O)_aO_b(C_1-C_{10})$alkyl, halo or OH;

$R^7$ and $R^8$ are independently selected from: H, and $(C_1-C_6)$alkyl;

$R^{11}$ and $R^{12}$ are independently selected from: H, $(C_1-C_6)$alkyl, $(C_2-C_6)$alkenyl, $(C_3-C_6)$cycloalkyl, $(C_1-C_6)$alkoxy, $CO_2H$, halo, OH, CN and $NR^7R^8$, said alkyl, cycloalkyl and alkoxy is optionally substituted with one or more substituents selected from halo, CN, OH and $NR^7R^8$, or $R^{11}$ and $R^{12}$ can be taken together to form oxo, $(C_1-C_6)$alkylidene, or a monocyclic carbo- or heterocycle with 3-7 members, said heterocycle is containing one or more heteroatoms selected from N, O and S; and Bond: ------ is a single or double bond, provided that when $R^1$ is oxo, then said bond is a single bond and adjacent N bears H;

or a pharmaceutically acceptable salt, stereoisomer or N-oxide derivative thereof.

4. A compound of claim 1 selected from:

trans-3-amino-1-methyl-3-[4-(2-methyl-7-phenylpyrazolo[1,5-a]pyrido[3,2-e]pyrimidin-8-yl)phenyl]cyclobutanol;

cis-3-amino-1-methyl-3-[4-(2-methyl-7-phenylpyrazolo[1,5-a]pyrido[3,2-e]pyrimidin-8-yl)phenyl]cyclobutanol;

trans-3-amino-1-cyclopropyl-3-[4-(2-methyl-7-phenylpyrazolo[1,5-a]pyrido[3,2-e]pyrimidin-8-yl)phenyl]cyclobutanol;

trans-3-amino-3-[4-(2-methyl-7-phenylpyrazolo[1,5-a]pyrido[3,2-e]pyrimidin-8-yl)phenyl]cyclobutanol;

trans-3-methoxy-1-[4-(2-methyl-7-phenylpyrazolo[1,5-a]pyrido[3,2-e]pyrimidin-8-yl)phenyl]cyclobutanamine;

methyl {1-[4-(2-methyl-7-phenylpyrazolo[1,5-a]pyrido[3,2-e]pyrimidin-8-yl)phenyl]-3-oxocyclobutyl}carbamate;

1-[4-(2-methyl-7-phenylpyrazolo[1,5-a]pyrido[3,2-e]pyrimidin-8-yl)phenyl]methanamine;

2-methyl-7-phenyl-8-[4-(1H-pyrazol-1-ylmethyl)phenyl]pyrazolo[1,5-a]pyrido[3,2-e]pyrimidine;

(1R)-1-[4-(2-methyl-7-phenylpyrazolo[1,5-a]pyrido[3,2-e]pyrimidin-8-yl)phenyl]ethanamine;

trans-3-amino-1-ethyl-3-[4-(2-methyl-7-phenylpyrazolo[1,5-a]pyrido[3,2-e]pyrimidin-8-yl)phenyl]cyclobutanol;

cis-3-amino-1-ethyl-3-[4-(2-methyl-7-phenylpyrazolo[1,5-a]pyrido[3,2-e]pyrimidin-8-yl)phenyl]cyclobutanol;

trans-3-amino-1-ethenyl-3-[4-(2-methyl-7-phenylpyrazolo[1,5-a]pyrido[3,2-e]pyrimidin-8-yl)phenyl]cyclobutanol;

3-methylidene-1-[4-(2-methyl-7-phenylpyrazolo[1,5-a]pyrido[3,2-e]pyrimidin-8-yl)phenyl]cyclobutanamine;

3,3-difluoro-1-[4-(2-methyl-7-phenylpyrazolo[1,5-a]pyrido[3,2-e]pyrimidin-8-yl)phenyl]cyclobutanamine;

8-{4-[trans-1-amino-3-(1,2-dihydroxyethyl)-3-hydroxycyclobutyl]phenyl}-2-methyl-7-phenylpyrazolo[1,5-a]pyrido[3,2-e]pyrimidine;

8-{4-[1-amino-3-hydroxy-3-(hydroxymethyl)cyclobutyl]phenyl}-2-methyl-7-phenylpyrazolo[1,5-a]pyrido[3,2-e]pyrimidine;

2-[4-(2-methyl-7-phenylpyrazolo[1,5-a]pyrido[3,2-e]pyrimidin-8-yl)phenyl]-5,8-dioxaspiro[3.4]octan-2-amine;

cis-3-amino-1-cyclopropyl-3-[4-(2-cyclopropyl-7-phenylpyrazolo[1,5-a]pyrido[3,2-e]pyrimidin-8-yl)phenyl]cyclobutanol;

trans-3-amino-1-cyclopropyl-3-[4-(7-phenylpyrazolo[1,5-a]pyrido[3,2-e]pyrimidin-8-yl)phenyl]cyclobutanol;

8-[4-(trans-1-amino-3-cyclopropyl-3-hydroxycyclobutyl)phenyl]-7-phenyl-2-(trifluoromethyl)pyrazolo[1,5-a]pyrido[3,2-e]pyrimidine;

trans-3-cyclopropyl-1-{4-[2-(4-fluorophenyl)-7-phenylpyrazolo[1,5-a]pyrido[3,2-e]pyrimidin-8-yl]phenyl}-3-hydroxycyclobutanamine;

trans-1-[4-(2-cyclopropyl-7-phenylpyrazolo[1,5-a]pyrido
[3,2-e]pyrimidin-8-yl)phenyl]-3-hydroxy-3-methylcy-
clobutanamine;
trans-3-amino-3-[4-[2-(1,1-dimethylethyl)-7-phenylpyra-
zolo[1,5-a]pyrido[3,2-e]pyrimidin-8-yl]phenyl]-1-me-
thyl-cyclobutanol;
trans-3-amino-1-methyl-3-{4-[2-methyl-7-(thiophen-2-
yl)pyrazolo[1,5-a]pyrido[3,2-e]pyrimidin-8-yl]
phenyl}cyclobutanol;
trans-3-amino-3-{4-[7-(2-fluorophenyl)-2-methylpyra-
zolo[1,5-a]pyrido[3,2-e]pyrimidin-8-yl]phenyl}-1-me-
thylcyclobutanol;
trans-3-amino-1-methyl-3-{4-[2-methyl-7-(thiophen-3-
yl)pyrazolo[1,5-a]pyrido[3,2-e]pyrimidin-8-yl]
phenyl}cyclobutanol;
1-[4-(2-methyl-7-phenylpyrazolo[1,5-a]pyrido[3,2-e]py-
rimidin-8-yl)phenyl]cyclobutanamine;
2-methyl-7-phenyl-8-(4-{[4-(5-pyridin-2-yl-4H-1,2,4-
triazol-3-yl)piperidin-1-yl]methyl}phenyl)pyrazolo[1,
5-a]pyrido[3,2-e]pyrimidine;
1'-[4-(2-methyl-7-phenylpyrazolo[1,5-a]pyrido[3,2-e]py-
rimidin-8-yl)benzyl]-1H-spiro[furo[3,4-c]pyridine-3,
4'-piperidin]-1-one;
2-methyl-1'-[4-(2-methyl-7-phenylpyrazolo[1,5-a]pyrido
[3,2-e]pyrimidin-8-yl)benzyl]spiro[isoindole-1,4'-pip-
eridin]-3(2H)-one;
1'-[4-(2-methyl-7-phenylpyrazolo[1,5-a]pyrido[3,2-e]py-
rimidin-8-yl)benzyl]-7H-spiro[furo[3,4-b]pyridine-5,
4'-piperidin]-7-one;
1-[4-(2-methyl-7-phenylpyrazolo[1,5-a]pyrido[3,2-e]py-
rimidin-8-yl)benzyl]piperidine-4-carboxamide;
2-methyl-8-(4-{[4-(2-oxo-2,3-dihydro-1H-benzimidazol-
1-yl)piperidin-1-yl]methyl}phenyl)-7-phenylpyrazolo
[1,5-a]pyrido[3,2-e]pyrimidine;
8-(4-{[4-(1,3-benzodioxol-5-ylmethyl)piperazin-1-yl]
methyl}phenyl)-2-methyl-7-phenylpyrazolo[1,5-a]py-
rido[3,2-e]pyrimidine;
2-methyl-7-phenyl-8-[4-(piperazin-1-ylmethyl)phenyl]
pyrazolo[1,5-a]pyrido[3,2-e]pyrimidine;
2-methyl-8-{4-[(4-methylpiperazin-1-yl)methyl]phenyl}-
7-phenylpyrazolo[1,5-a]pyrido[3,2-e]pyrimidine;
N-[4-(2-methyl-7-phenylpyrazolo[1,5-a]pyrido[3,2-e]py-
rimidin-8-yl)benzyl]-2-(1-methylpyrrolidin-2-yl)etha-
namine;
2-methyl-8-[4-(morpholin-4-ylmethyl)phenyl]-7-phe-
nylpyrazolo[1,5-a]pyrido[3,2-e]pyrimidine;
3-{1-[4-(2-methyl-7-phenylpyrazolo[1,5-a]pyrido[3,2-e]
pyrimidin-8-yl)benzyl]piperidin-4-yl}phenol;
1-[4-(2-methyl-7-phenylpyrazolo[1,5-a]pyrido[3,2-e]py-
rimidin-8-yl)benzyl]piperidin-4-ol;
2-methyl-7-phenyl-8-[4-(piperidin-1-ylmethyl)phenyl]
pyrazolo[1,5-a]pyrido[3,2-e]pyrimidine;
1-{4-[4-(2-methyl-7-phenylpyrazolo[1,5-a]pyrido[3,2-e]
pyrimidin-8-yl)benzyl]piperazin-1-yl}ethanone;
1-[4-(2-methyl-7-phenylpyrazolo[1,5-a]pyrido[3,2-e]py-
rimidin-8-yl)benzyl]piperidin-4-amine;
1-{1-[4-(2-methyl-7-phenylpyrazolo[1,5-a]pyrido[3,2-e]
pyrimidin-8-yl)benzyl]piperidin-4-yl}-1,3-dihydro-
2H-benzimidazol-2-one;
4-hydroxy-N-{1-[4-(2-methyl-7-phenylpyrazolo[1,5-a]
pyrido[3,2-e]pyrimidin-8-yl)benzyl]piperidin-4-
yl}benzamide;
ethyl 1-[4-(2-methyl-7-phenylpyrazolo[1,5-a]pyrido[3,2-
e]pyrimidin-8-yl)benzyl]piperidine-4-carboxylate;
methyl 1-[4-(2-methyl-7-phenylpyrazolo[1,5-a]pyrido[3,
2-e]pyrimidin-8-yl)benzyl]piperidine-4-carboxylate;

1-[4-(2-methyl-7-phenylpyrazolo[1,5-a]pyrido[3,2-e]py-
rimidin-8-yl)benzyl]piperidine-4-carboxylic acid;
2-methyl-7-phenyl-8-(4-{[4-(phenylcarbamoyl)piperidin-
1-yl]methyl}phenyl)pyrazolo[1,5-a]pyrido[3,2-e]pyri-
midine;
8-[4-({4-[(2-methoxyethyl)carbamoyl]piperidin-1-
yl}methyl)phenyl]-2-methyl-7-phenylpyrazolo[1,5-a]
pyrido[3,2-e]pyrimidine;
2-methyl-7-phenyl-8-(4-{[4-(prop-2-en-1-ylcarbamoyl)
piperidin-1-yl]methyl}phenyl)pyrazolo[1,5-a]pyrido
[3,2-e]pyrimidine;
8-{4-[(4-{[2-(dimethylamino)ethyl]carbamoyl}piperidin-
1-yl)methyl]phenyl}-2-methyl-7-phenylpyrazolo[1,5-
a]pyrido[3,2-e]pyrimidine;
8-{4-[(4-{[3-(1H-imidazol-1-yl)propyl]
carbamoyl}piperidin-1-yl)methyl]phenyl}-2-methyl-7-
phenylpyrazolo[1,5-a]pyrido[3,2-e]pyrimidine;
8-[4-({4-[(3,4-dimethoxybenzyl)carbamoyl]piperidin-1-
yl}methyl)phenyl]-2-methyl-7-phenylpyrazolo[1,5-a]
pyrido[3,2-e]pyrimidine;
2-methyl-8-[4-({4-{[2-(1-methylpyrrolidin-2-yl)ethyl]
carbamoyl}piperidin-1-yl)methyl]phenyl}-7-phe-
nylpyrazolo[1,5-a]pyrido[3,2-e]pyrimidine;
{1-[4-(2-methyl-7-phenylpyrazolo[1,5-a]pyrido[3,2-e]
pyrimidin-8-yl)benzyl]piperidin-4-yl}(morpholin-4-
yl)methanone;
8-[4-({4-[(1H-benzimidazol-2-ylmethyl)carbamoyl]pip-
eridin-1-yl}methyl)phenyl]-2-methyl-7-phenylpyra-
zolo[1,5-a]pyrido[3,2-e]pyrimidine;
N-[2-(1H-imidazol-5-yl)ethyl]-1-[4-(2-methyl-7-phe-
nylpyrazolo[1,5-a]pyrido[3,2-e]pyrimidin-8-yl)benzyl]
piperidine-4-carboxamide;
2-methyl-7-phenyl-8-{4-[(4-{[4-(pyrimidin-2-yl)piper-
azin-1-yl]carbonyl}piperidin-1-yl)methyl]
phenyl}pyrazolo[1,5-a]pyrido[3,2-e]pyrimidine;
2-methyl-7-phenyl-8-(4-{[4-({4-[5-(trifluoromethyl)pyri-
din-2-yl]piperazin-1-yl}carbonyl)piperidin-1-yl]
methyl}phenyl)pyrazolo[1,5-a]pyrido[3,2-e]pyrimi-
dine;
2-methyl-7-phenyl-8-{4-[(4-{[4-(pyridin-2-yl)piperazin-
1-yl]carbonyl}piperidin-1-yl)methyl]phenyl}pyrazolo
[1,5-a]pyrido[3,2-e]pyrimidine;
2-methyl-7-phenyl-8-{4-[(4-{[2-(pyridin-3-yl)ethyl]
carbamoyl}piperidin-1-yl)methyl]phenyl}pyrazolo[1,
5-a]pyrido[3,2-e]pyrimidine;
2-methyl-7-phenyl-8-[4-({4-[(pyridin-2-ylmethyl)car-
bamoyl]piperidin-1-yl}methyl)phenyl]pyrazolo[1,5-a]
pyrido[3,2-e]pyrimidine;
2-methyl-7-phenyl-8-[4-({4-[(pyridin-4-ylmethyl)car-
bamoyl]piperidin-1-yl}methyl)phenyl]pyrazolo[1,5-a]
pyrido[3,2-e]pyrimidine;
8-[4-({4-[(3-hydroxyphenyl)carbamoyl]piperidin-1-
yl}methyl)phenyl]-2-methyl-7-phenylpyrazolo[1,5-a]
pyrido[3,2-e]pyrimidine;
8-[4-({4-[(trans-4-hydroxycyclohexyl)carbamoyl]piperi-
din-1-yl}methyl)phenyl]-2-methyl-7-phenylpyrazolo
[1,5-a]pyrido[3,2-e]pyrimidine;
8-{4-[(4-{[2-hydroxy-2-(3-hydroxyphenyl)ethyl]
carbamoyl}piperidin-1-yl)methyl]phenyl}-2-methyl-7-
phenylpyrazolo[1,5-a]pyrido[3,2-e]pyrimidine;
8-{4-[(4-{[2-(4-hydroxyphenyl)ethyl]
carbamoyl}piperidin-1-yl)methyl]phenyl}-2-methyl-7-
phenylpyrazolo[1,5-a]pyrido[3,2-e]pyrimidine;
8-[4-({4-[(3-hydroxy-4-methoxyphenyl)carbamoyl]pip-
eridin-1-yl}methyl)phenyl]-2-methyl-7-phenylpyra-
zolo[1,5-a]pyrido[3,2-e]pyrimidine;

8-{4-[(4-{[2-(3,4-dihydroxyphenyl)ethyl]carbamoyl}piperidin-1-yl)methyl]phenyl}-2-methyl-7-phenylpyrazolo[1,5-a]pyrido[3,2-e]pyrimidine;

8-[4-({4-[(4-hydroxy-3-methoxybenzyl)carbamoyl]piperidin-1-yl}methyl)phenyl]-2-methyl-7-phenylpyrazolo[1,5-a]pyrido[3,2-e]pyrimidine;

8-[4-({4-[(3,4-dihydroxybenzyl)carbamoyl]piperidin-1-yl}methyl)phenyl]-2-methyl-7-phenylpyrazolo[1,5-a]pyrido[3,2-e]pyrimidine;

8-(4-{[4-(benzylcarbamoyl)piperidin-1-yl]methyl}phenyl)-2-methyl-7-phenylpyrazolo[1,5-a]pyrido[3,2-e]pyrimidine;

8-[4-({4-[benzyl(methyl)carbamoyl]piperidin-1-yl}methyl)phenyl]-2-methyl-7-phenylpyrazolo[1,5-a]pyrido[3,2-e]pyrimidine;

8-(4-{[4-(cyclohexylcarbamoyl)piperidin-1-yl]methyl}phenyl)-2-methyl-7-phenylpyrazolo[1,5-a]pyrido[3,2-e]pyrimidine;

8-[4-({4-[(1-methoxypropan-2-yl)carbamoyl]piperidin-1-yl}methyl)phenyl]-2-methyl-7-phenylpyrazolo[1,5-a]pyrido[3,2-e]pyrimidine;

N-({1-[4-(2-methyl-7-phenylpyrazolo[1,5-a]pyrido[3,2-e]pyrimidin-8-yl)benzyl]piperidin-4-yl}carbonyl)glycinamide;

2-methyl-7-phenyl-8-[4-({4-[(2,2,2-trifluoroethyl)carbamoyl]piperidin-1-yl}methyl)phenyl]pyrazolo[1,5-a]pyrido[3,2-e]pyrimidine;

2-methyl-8-(4-{[4-(pentan-3-ylcarbamoyl)piperidin-1-yl]methyl}phenyl)-7-phenylpyrazolo[1,5-a]pyrido[3,2-e]pyrimidine;

8-(4-{[4-(tert-butylcarbamoyl)piperidin-1-yl]methyl}phenyl)-2-methyl-7-phenylpyrazolo[1,5-a]pyrido[3,2-e]pyrimidine;

2-methyl-7-phenyl-8-(4-{[4-(propylcarbamoyl)piperidin-1-yl]methyl}phenyl)pyrazolo[1,5-a]pyrido[3,2-e]pyrimidine;

2-methyl-8-(4-{[4-(methylcarbamoyl)piperidin-1-yl]methyl}phenyl)-7-phenylpyrazolo[1,5-a]pyrido[3,2-e]pyrimidine;

8-(4-{[4-(ethylcarbamoyl)piperidin-1-yl]methyl}phenyl)-2-methyl-7-phenylpyrazolo[1,5-a]pyrido[3,2-e]pyrimidine;

8-{4-[(4-{[4-(3-hydroxyphenyl)piperazin-1-yl]carbonyl}piperidin-1-yl)methyl]phenyl}-2-methyl-7-phenylpyrazolo[1,5-a]pyrido[3,2-e]pyrimidine;

8-{4-[(4-{[(1S)-1-cyclohexylethyl]carbamoyl}piperidin-1-yl)methyl]phenyl}-2-methyl-7-phenylpyrazolo[1,5-a]pyrido[3,2-e]pyrimidine;

8-(4-{[4-(hexahydrocyclopenta[c]pyrrol-2(1H)-ylcarbonyl)piperidin-1-yl]methyl}phenyl)-2-methyl-7-phenylpyrazolo[1,5-a]pyrido[3,2-e]pyrimidine;

8-[4-({4-[ethyl(propan-2-yl)carbamoyl]piperidin-1-yl}methyl)phenyl]-2-methyl-7-phenylpyrazolo[1,5-a]pyrido[3,2-e]pyrimidine;

8-{4-[(4-{[(1S,2S)-2-hydroxycyclohexyl]carbamoyl}piperidin-1-yl)methyl]phenyl}-2-methyl-7-phenylpyrazolo[1,5-a]pyrido[3,2-e]pyrimidine;

8-[4-({4-[(2-hydroxyethyl)carbamoyl]piperidin-1-yl}methyl)phenyl]-2-methyl-7-phenylpyrazolo[1,5-a]pyrido[3,2-e]pyrimidine;

2-methyl-7-phenyl-8-[4-({4-[(tetrahydrofuran-2-ylmethyl)carbamoyl]piperidin-1-yl}methyl)phenyl]pyrazolo[1,5-a]pyrido[3,2-e]pyrimidine;

8-(4-{[4-(cyclobutylcarbamoyl)piperidin-1-yl]methyl}phenyl)-2-methyl-7-phenylpyrazolo[1,5-a]pyrido[3,2-e]pyrimidine;

2-methyl-7-phenyl-8-(4-{[4-(propan-2-ylcarbamoyl)piperidin-1-yl]methyl}phenyl)pyrazolo[1,5-a]pyrido[3,2-e]pyrimidine;

N-({1-[4-(2-methyl-7-phenylpyrazolo[1,5-a]pyrido[3,2-e]pyrimidin-8-yl)benzyl]piperidin-4-yl}carbonyl)glycine;

tert-butyl N-({1-[4-(2-methyl-7-phenylpyrazolo[1,5-a]pyrido[3,2-e]pyrimidin-8-yl)benzyl]piperidin-4-yl}carbonyl)glycinate;

8-[4-({4-[(4-hydroxyphenyl)carbamoyl]piperidin-1-yl}methyl)phenyl]-2-methyl-7-phenylpyrazolo[1,5-a]pyrido[3,2-e]pyrimidine;

8-[4-({4-[(3-carbamoylphenyl)carbamoyl]piperidin-1-yl}methyl)phenyl]-2-methyl-7-phenylpyrazolo[1,5-a]pyrido[3,2-e]pyrimidine;

8-[4-({4-[(3-methoxyphenyl)carbamoyl]piperidin-1-yl}methyl)phenyl]-2-methyl-7-phenylpyrazolo[1,5-a]pyrido[3,2-e]pyrimidine;

2-methyl-8-(4-{[4-({3-[(methylsulfonyl)amino]phenyl}carbamoyl)piperidin-1-yl]methyl}phenyl)-7-phenylpyrazolo[1,5-a]pyrido[3,2-e]pyrimidine;

8-[4-({4-[(3-cyanophenyl)carbamoyl]piperidin-1-yl}methyl)phenyl]-2-methyl-7-phenylpyrazolo[1,5-a]pyrido[3,2-e]pyrimidine;

8-[4-({4-[(3-fluorophenyl)carbamoyl]piperidin-1-yl}methyl)phenyl]-2-methyl-7-phenylpyrazolo[1,5-a]pyrido[3,2-e]pyrimidine;

8-[4-({4-[(2-hydroxyphenyl)carbamoyl]piperidin-1-yl}methyl)phenyl]-2-methyl-7-phenylpyrazolo[1,5-a]pyrido[3,2-e]pyrimidine;

8-[4-({4-[(4-carbamoylphenyl)carbamoyl]piperidin-1-yl}methyl)phenyl]-2-methyl-7-phenylpyrazolo[1,5-a]pyrido[3,2-e]pyrimidine;

2-methyl-7-phenyl-8-[4-({4-[(3-sulfamoylphenyl)carbamoyl]piperidin-1-yl}methyl)phenyl]pyrazolo[1,5-a]pyrido[3,2-e]pyrimidine;

N-(1,1-dioxido-1-benzothiophen-6-yl)-1-[4-(2-methyl-7-phenylpyrazolo[1,5-a]pyrido[3,2-e]pyrimidin-8-yl)benzyl]piperidine-4-carboxamide;

3-aminobenzyl 1-[4-(2-methyl-7-phenylpyrazolo[1,5-a]pyrido[3,2-e]pyrimidin-8-yl)benzyl]piperidine-4-carboxylate;

{1-[4-(2-methyl-7-phenylpyrazolo[1,5-a]pyrido[3,2-e]pyrimidin-8-yl)benzyl]piperidin-4-yl}(piperidin-1-yl)methanone;

(1,1-dioxidothiomorpholin-4-yl) {1-[4-(2-methyl-7-phenylpyrazolo[1,5-a]pyrido[3,2-e]pyrimidin-8-yl)benzyl]piperidin-4-yl}methanone;

1-[4-({1-[4-(2-methyl-7-phenylpyrazolo[1,5-a]pyrido[3,2-e]pyrimidin-8-yl)benzyl]piperidin-4-yl}carbonyl)piperazin-1-yl]ethanone;

N-(3-chlorophenyl)-1-[4-(2-methyl-7-phenylpyrazolo[1,5-a]pyrido[3,2-e]pyrimidin-8-yl)benzyl]piperidine-4-carboxamide;

(4-hydroxypiperidin-1-yl) {1-[4-(2-methyl-7-phenylpyrazolo[1,5-a]pyrido[3,2-e]pyrimidin-8-yl)benzyl]piperidin-4-yl}methanone;

N-cyclohexyl-N-methyl-1-[4-(2-methyl-7-phenylpyrazolo[1,5-a]pyrido[3,2-e]pyrimidin-8-yl)benzyl]piperidine-4-carboxamide;

[4-(hydroxymethyl)piperidin-1-yl] {1-[4-(2-methyl-7-phenylpyrazolo[1,5-a]pyrido[3,2-e]pyrimidin-8-yl)benzyl]piperidin-4-yl}methanone;

4-tert-butyl-N-{1-[4-(2-methyl-7-phenylpyrazolo[1,5-a]pyrido[3,2-e]pyrimidin-8-yl)benzyl]piperidin-4-yl}benzamide;

1-(4-fluorophenyl)-3-{1-[4-(2-methyl-7-phenylpyrazolo [1,5-a]pyrido[3,2-e]pyrimidin-8-yl)benzyl]piperidin-4-yl}urea;
1-(4-tert-butylphenyl)-3-{1-[4-(2-methyl-7-phenylpyrazolo[1,5-a]pyrido[3,2-e]pyrimidin-8-yl)benzyl]piperidin-4-yl}urea;
N-{1-[4-(2-methyl-7-phenylpyrazolo[1,5-a]pyrido[3,2-e]pyrimidin-8-yl)benzyl]piperidin-4-yl}benzamide;
1-{1-[4-(2-methyl-7-phenylpyrazolo[1,5-a]pyrido[3,2-e]pyrimidin-8-yl)benzyl]piperidin-4-yl}-3-phenylurea;
N-(3-aminophenyl)-1-[4-(2-methyl-7-phenylpyrazolo[1,5-a]pyrido[3,2-e]pyrimidin-8-yl)benzyl]piperidine-4-carboxamide;
N-[3-(hydroxymethyl)phenyl]-1-[4-(2-methyl-7-phenylpyrazolo[1,5-a]pyrido[3,2-e]pyrimidin-8-yl)benzyl]piperidine-4-carboxamide;
1-[4-(2-methyl-7-phenylpyrazolo[1,5-a]pyrido[3,2-e]pyrimidin-8-yl)benzyl]-N-[3-(methylsulfonyl)phenyl]piperidine-4-carboxamide;
1-[4-(2-methyl-7-phenylpyrazolo[1,5-a]pyrido[3,2-e]pyrimidin-8-yl)benzyl]-N-(3-oxo-1,3-dihydro-2-benzofuran-5-yl)piperidine-4-carboxamide;
1-[4-(2-methyl-7-phenylpyrazolo[1,5-a]pyrido[3,2-e]pyrimidin-8-yl)benzyl]-N-(1,3-thiazol-2-yl)piperidine-4-carboxamide;
1-[4-(2-methyl-7-phenylpyrazolo[1,5-a]pyrido[3,2-e]pyrimidin-8-yl)benzyl]-N-[3-(trifluoromethoxy)phenyl]piperidine-4-carboxamide;
N-(1,3-benzothiazol-5-yl)-1-[4-(2-methyl-7-phenylpyrazolo[1,5-a]pyrido[3,2-e]pyrimidin-8-yl)benzyl]piperidine-4-carboxamide;
trans-3-amino-1-cyclopropyl-3-[4-(3-bromo-2-methyl-7-phenylpyrazolo[1,5-a]pyrido[3,2-e]pyrimidin-8-yl)phenyl]cyclobutanol;
trans-3-amino-3-[4-(3-chloro-2-methyl-7-phenylpyrazolo[1,5-a]pyrido[3,2-e]pyrimidin-8-yl)phenyl]-1-cyclopropylcyclobutanol;
trans-3-amino-1-cyclopropyl-3-{4-[2-methyl-7-phenyl-3-(pyridin-3-yl)pyrazolo[1,5-a]pyrido[3,2-e]pyrimidin-8-yl]phenyl}cyclobutanol;
trans-3-amino-1-cyclopropyl-3-[4-(3-cyano-2-methyl-7-phenylpyrazolo[1,5-a]pyrido[3,2-e]pyrimidin-8-yl)phenyl]cyclobutanol;
trans-3-amino-1-cyclopropyl-3-{4-[2-methyl-7-phenyl-3-(pyridin-4-yl)pyrazolo[1,5-a]pyrido[3,2-e]pyrimidin-8-yl]phenyl}cyclobutanol;
trans-3-amino-1-cyclopropyl-3-[4-(2-methyl-3,7-diphenylpyrazolo[1,5-a]pyrido[3,2-e]pyrimidin-8-yl)phenyl]cyclobutanol;
trans-3-amino-1-cyclopropyl-3-{4-[3-(4-methoxyphenyl)-2-methyl-7-phenylpyrazolo[1,5-a]pyrido[3,2-e]pyrimidin-8-yl]phenyl}cyclobutanol;
8-[4-(trans-1-amino-3-cyclopropyl-3-hydroxycyclobutyl)phenyl]-2,3-dimethyl-7-phenylpyrazolo[1,5-a]pyrido[3,2-e]pyrimidine;
trans-3-amino-3-[4-(2,5-dimethyl-7-phenylpyrazolo[1,5-a]pyrido[3,2-e]pyrimidin-8-yl)phenyl]-1-methylcyclobutanol;
trans-3-amino-3-[4-(2,6-dimethyl-7-phenylpyrazolo[1,5-a]pyrido[3,2-e]pyrimidin-8-yl)phenyl]-1-methylcyclobutanol;
trans-3-amino-3-[4-(6-chloro-2-methyl-7-phenylpyrazolo[1,5-a]pyrido[3,2-e]pyrimidin-8-yl)phenyl]-1-methylcyclobutanol;
trans-3-Amino-1-cyclopropyl-3-[4-(2-methyl-7-phenyl-1,4,9,9b-tetraaza-cyclopenta[a]naphthalen-8-yl)-phenyl]-cyclobutanol;
1-[4-(2-methyl-7-phenyl-1,4,9,9b-tetraaza-cyclopenta[a]naphthalen-8-yl)-phenyl]-cyclobutylamine;
3,3-Difluoro-1-[4-(2-methyl-7-phenyl-1,4,9,9b-tetraaza-cyclopenta[a]naphthalen-8-yl)-phenyl]-cyclobutylamine;
trans-2-[4-(2-Methyl-7-phenyl-1,4,9,9b-tetraaza-cyclopenta[a]naphthalen-8-yl)-phenyl]-5,8-dioxa-spiro[3.4]oct-2-ylamine;
trans-3-Amino-3-[4-(2-methyl-7-phenyl-1,4,9,9b-tetraaza-cyclopenta[a]naphthalen-8-yl)-phenyl]-cyclobutanol;
trans-1-Amino-1-[4-(2-methyl-7-phenyl-1,4,9,9b-tetraaza-cyclopenta[a]naphthalen-8-yl)-phenyl]-3-methoxycyclobutane;
1-[4-(2-methyl-7-phenyl-1,4,9,9b-tetraaza-cyclopenta[a]naphthalen-8-yl)-phenyl]-ethane-1,2-diol;
trans-3-Amino-1-methyl-3-[4-(2-methyl-7-phenyl-1,4,9,9b-tetraaza-cyclopenta[a]naphthalen-8-yl)-phenyl]-cyclobutanol;
cis-3-Amino-1-methyl-3-[4-(2-methyl-7-phenyl-1,4,9,9b-tetraaza-cyclopenta[a]naphthalen-8-yl)-phenyl]-cyclobutanol;
trans-3-Amino-1-cyclopropyl-3-[4-(2-cyclopropyl-7-phenyl-1,4,9,9b-tetraaza-cyclopenta[a]naphthalen-8-yl)-phenyl]-cyclobutanol;
trans-3-Amino-1-cyclopropyl-3-[4-(7-phenyl-1,4,9,9b-tetraaza-cyclopenta[a]naphthalen-8-yl)-phenyl]-cyclobutanol;
trans-3-Amino-1-cyclopropyl-3-[4-(2-(4-fluorophenyl)-7-phenyl-1,4,9,9b-tetraaza-cyclopenta[a]naphthalen-8-yl)-phenyl]-cyclobutanol;
trans-3-Amino-1-cyclopropyl-3-[4-(2-trifluoromethyl-7-phenyl-1,4,9,9b-tetraaza-cyclopenta[a]naphthalen-8-yl)-phenyl]-cyclobutanol;
2-Methyl-8-(4-morpholin-4-ylmethyl-phenyl)-7-phenyl-1,4,9,9b-tetraaza-cyclopenta[a]naphthalene;
4-(2-Methyl-7-phenyl-1,4,9,9b-tetraaza-cyclopenta[a]naphthalen-8-yl)-phenylamine;
N-[4-(2-Methyl-7-phenyl-1,4,9,9b-tetraaza-cyclopenta[a]naphthalen-8-yl)-phenyl]-methanesulfonamide;
[4-(2-Methyl-7-phenyl-1,4,9,9b-tetraaza-cyclopenta[a]naphthalen-8-yl)-phenyl]-urea;
Morpholine-4-carboxylic acid [4-(2-methyl-7-phenyl-1,4,9,9b-tetraaza-cyclopenta[a]naphthalen-8-yl)-phenyl]-amide;
3-[4-(2-Methyl-7-phenyl-1,4,9,9b-tetraaza-cyclopenta[a]naphthalen-8-yl)-phenyl]-oxazolidin-2-one;
4-(2-Methyl-7-phenyl-1,4,9,9b-tetraaza-cyclopenta[a]naphthalen-8-yl)-benzylamine;
[4-(2-Methyl-7-phenyl-1,4,9,9b-tetraaza-cyclopenta[a]naphthalen-8-yl)-phenyl]-methanol;
1'-[4-(2-Methyl-7-phenyl-1,4,9,9b-tetraaza-cyclopenta[a]naphthalen-8-yl)-phenylmethyl]-Spiro[furo [3,4-c]pyridine-3(1H),4'-piperidine]-1-one;
1'-[4-(2-Methyl-7-phenyl-1,4,9,9b-tetraaza-cyclopenta[a]naphthalen-8-yl)-phenylmethyl]-spiro[2-methyl-2,3-dihydro-isoindole-3(1H), 4'-piperidine]-1-one;
1'-[4-(2-Methyl-7-phenyl-1,4,9,9b-tetraaza-cyclopenta[a]naphthalen-8-yl)-phenylmethyl]-spiro[furo [3,4-b]pyridine-5(7H), 4'-piperidine]-7-one;
8-[4-(4-Benzo[1,3]dioxol-5-ylmethyl-piperazin-1-ylmethyl)-phenyl]-2-methyl-7-phenyl-1,4,9,9b-tetraaza-cyclopenta[a]naphthalene;
1-[4-(2-Methyl-7-phenyl-1,4,9,9b-tetraaza-cyclopenta[a]naphthalen-8-yl)-benzyl]-piperidine-4-carboxylic acid amide;

3-[4-(2-Methyl-7-phenyl-3-pyridin-3-yl-1,4,9,9b-tetraaza-cyclopenta[a]naphthalen-8-yl)-phenyl]-oxazolidin-2-one;

trans-3-Amino-1-cyclopropyl-3-[4-(3-cyano-2-methyl-7-phenyl-1,4,9,9b-tetraaza-cyclopenta[a]naphthalen-8-yl)-phenyl]-cyclobutanol;

3-Amino-3-[4-(3-bromo-2-methyl-7-phenyl-1,4,9,9b-tetraaza-cyclopenta[a]naphthalen-8-yl)-phenyl]-cyclopropyl-cyclobutanol;

3-Amino-3-[4-(3-chloro-2-methyl-7-phenyl-1,4,9,9b-tetraaza-cyclopenta[a]naphthalen-8-yl)-phenyl]-cyclopropyl-cyclobutanol;

3-Amino-3-[4-(2,5-dimethyl-7-phenyl-1,4,9,9b-tetraaza-cyclopenta[a]naphthalen-8-yl)-phenyl]-methyl-cyclobutanol;

3-Amino-1-methyl-3-[4-(2-methyl-7-thiophen-2-yl-8,9-dihydro-1,4,9,9b-tetraaza-cyclopenta[a]naphthalene-8-yl)-phenyl]-cyclobutanol;

3-Amino-1-methyl-3-[4-(2-methyl-7-thiophen-3-yl-8,9-dihydro-1,4,9,9b-tetraaza-cyclopenta[a]naphthalene-8-yl)-phenyl]-cyclobutanol;

3-Amino-3-{4-[7-(2-fluoro-phenyl)-2-methyl-1,4,9,9b-tetraaza-cyclopenta[a]naphthalen-8-yl]-phenyl}-1-methyl-cyclobutanol;

3-Amino-1-hydroxymethyl-3-[4-(2-methyl-7-phenyl-1,4,9,9b-tetraaza-cyclopenta[a]naphthalen-8-yl)-phenyl]-cyclobutanol;

3-Methylene-1-[4-(2-methyl-7-phenyl-1,4,9,9b-tetraaza-cyclopenta[a]naphthalen-8-yl)-phenyl]-cyclobutylamine;

1-[4-(2-Methyl-7-phenyl-1,4,9,9b-tetraaza-cyclopenta[a]naphthalen-8-yl)-phenyl]-cyclobutanecarbonitrile;

Methyl-{1-[4-(2-methyl-7-phenyl-1,4,9,9b-tetraaza-cyclopenta[a]naphthalen-8-yl)-phenyl]-cyclobutyl}-amine;

1-Cyclopropyl-3-[4-(2-methyl-7-phenyl-1,4,9,9b-tetraaza-cyclopenta[a]naphthalen-8-yl)-phenyl]-cyclobutanol;

Trans-3-Amino-1-ethyl-3-[4-(2-methyl-7-phenyl-1,4,9,9b-tetraaza-cyclopenta[a]naphthalen-8-yl)-phenyl]-cyclobutanol;

Cis-3-Amino-1-ethyl-3-[4-(2-methyl-7-phenyl-1,4,9,9b-tetraaza-cyclopenta[a]naphthalen-8-yl)-phenyl]-cyclobutanol;

Trans-1-{3-Amino-1-hydroxy-3-[4-(2-methyl-7-phenyl-1,4,9,9b-tetraaza-cyclopenta[a]naphthalen-8-yl)-phenyl]-cyclobutyl}-ethane-1,2-diol;

Trans-3-Amino-3-[4-(2-methyl-7-phenyl-1,4,9,9b-tetraaza-cyclopenta[a]naphthalen-8-yl)-phenyl]-1-vinyl-cyclobutanol;

1-[4-(2-Methyl-7-phenyl-1,4,9,9b-tetraaza-cyclopenta[a]naphthalen-8-yl)-benzyl]-piperidine-4-carboxylic acid ethyl ester;

1-[4-(2-Methyl-7-phenyl-1,4,9,9b-tetraaza-cyclopenta[a]naphthalen-8-yl)-benzyl]-piperidine-4-carboxylic acid;

1-[4-(2-Methyl-7-phenyl-1,4,9,9b-tetraaza-cyclopenta[a]naphthalen-8-yl)-benzyl]-piperidine-4-carboxylic acid phenylamide;

1-[4-(2-Methyl-7-phenyl-1,4,9,9b-tetraaza-cyclopenta[a]naphthalen-8-yl)-benzyl]-piperidine-4-carboxylic acid allylamide;

1-[4-(2-Methyl-7-phenyl-1,4,9,9b-tetraaza-cyclopenta[a]naphthalen-8-yl)-benzyl]-piperidine-4-carboxylic acid (2-dimethylamino-ethyl)-amide;

1-[4-(2-Methyl-7-phenyl-1,4,9,9b-tetraaza-cyclopenta[a]naphthalen-8-yl)-benzyl]-piperidine-4-carboxylic acid (2-methoxy-ethyl)-amide;

1-[4-(2-Methyl-7-phenyl-1,4,9,9b-tetraaza-cyclopenta[a]naphthalen-8-yl)-benzyl]-piperidine-4-carboxylic acid (2-imidazol-1-yl-ethyl)-amide;

1-[4-(2-Methyl-7-phenyl-1,4,9,9b-tetraaza-cyclopenta[a]naphthalen-8-yl)-benzyl]-piperidine-4-carboxylic acid 3,4-dimethoxy-benzylamide;

1-[4-(2-Methyl-7-phenyl-1,4,9,9b-tetraaza-cyclopenta[a]naphthalen-8-yl)-benzyl]-piperidine-4-carboxylic acid [2-(1-methyl-pyrrolidin-2-yl)-ethyl]-amide;

{1-[4-(2-Methyl-7-phenyl-1,4,9,9b-tetraaza-cyclopenta[a]naphthalen-8-yl)-benzyl]-piperidin-4-yl}-morpholin-4-yl-methanone;

1-[4-(2-Methyl-7-phenyl-1,4,9,9b-tetraaza-cyclopenta[a]naphthalen-8-yl)-benzyl]-piperidine-4-carboxylic acid (1H-benzoimidazol-2-ylmethyl)-amide;

1-[4-(2-Methyl-7-phenyl-1,4,9,9b-tetraaza-cyclopenta[a]naphthalen-8-yl)-benzyl]-piperidine-4-carboxylic acid [2-(3H-imidazol-4-yl)-ethyl]-amide;

{1-[4-(2-Methyl-7-phenyl-1,4,9,9b-tetraaza-cyclopenta[a]naphthalen-8-yl)-benzyl]-piperidin-4-yl}-(4-pyrimidin-2-yl-piperazin-1-yl)-methanone;

{1-[4-(2-Methyl-7-phenyl-1,4,9,9b-tetraaza-cyclopenta[a]naphthalen-8-yl)-benzyl]-piperidin-4-yl}-[4-(5-trifluoromethyl-pyridin-2-yl)-piperazin-1-yl]-methanone;

{1-[4-(2-Methyl-7-phenyl-1,4,9,9b-tetraaza-cyclopenta[a]naphthalen-8-yl)-benzyl]-piperidin-4-yl}-(4-pyridin-2-yl-piperazin-1-yl)-methanone;

1-[4-(2-Methyl-7-phenyl-1,4,9,9b-tetraaza-cyclopenta[a]naphthalen-8-yl)-benzyl]-piperidine-4-carboxylic acid (2-pyridin-3-yl-ethyl)-amide;

1-[4-(2-Methyl-7-phenyl-1,4,9,9b-tetraaza-cyclopenta[a]naphthalen-8-yl)-benzyl]-piperidine-4-carboxylic acid (pyridin-2-ylmethyl)-amide;

1-[4-(2-Methyl-7-phenyl-1,4,9,9b-tetraaza-cyclopenta[a]naphthalen-8-yl)-benzyl]-piperidine-4-carboxylic acid (pyridin-4-ylmethyl)-amide;

1-[4-(2-Methyl-7-phenyl-1,4,9,9b-tetraaza-cyclopenta[a]naphthalen-8-yl)-benzyl]-piperidine-4-carboxylic acid (3-hydroxy-phenyl)-amide;

1-[4-(2-Methyl-7-phenyl-1,4,9,9b-tetraaza-cyclopenta[a]naphthalen-8-yl)-benzyl]-piperidine-4-carboxylic acid (4-hydroxy-cyclohexyl)-amide;

1-[4-(2-Methyl-7-phenyl-1,4,9,9b-tetraaza-cyclopenta[a]naphthalen-8-yl)-benzyl]-piperidine-4-carboxylic acid [2-hydroxy-2-(3-hydroxy-phenyl)-ethyl]-amide;

1-[4-(2-Methyl-7-phenyl-1,4,9,9b-tetraaza-cyclopenta[a]naphthalen-8-yl)-benzyl]-piperidine-4-carboxylic acid [2-(4-hydroxy-phenyl)-ethyl]-amide;

1-[4-(2-Methyl-7-phenyl-1,4,9,9b-tetraaza-cyclopenta[a]naphthalen-8-yl)-benzyl]-piperidine-4-carboxylic acid (3-hydroxy-4-methoxy-phenyl)-amide;

1-[4-(2-Methyl-7-phenyl-1,4,9,9b-tetraaza-cyclopenta[a]naphthalen-8-yl)-benzyl]-piperidine-4-carboxylic acid [2-(3,4-dihydroxy-phenyl)-ethyl]-amide;

1-[4-(2-Methyl-7-phenyl-1,4,9,9b-tetraaza-cyclopenta[a]naphthalen-8-yl)-benzyl]-piperidine-4-carboxylic acid 4-hydroxy-3-methoxy-benzylamide;

1-[4-(2-Methyl-7-phenyl-1,4,9,9b-tetraaza-cyclopenta[a]naphthalen-8-yl)-benzyl]-piperidine-4-carboxylic acid benzylamide;

1-[4-(2-Methyl-7-phenyl-1,4,9,9b-tetraaza-cyclopenta[a]naphthalen-8-yl)-benzyl]-piperidine-4-carboxylic acid benzyl-methyl-amide;

1-[4-(2-Methyl-7-phenyl-1,4,9,9b-tetraaza-cyclopenta[a]naphthalen-8-yl)-benzyl]-piperidine-4-carboxylic acid cyclohexylamide;

1-[4-(2-Methyl-7-phenyl-1,4,9,9b-tetraaza-cyclopenta[a]
  naphthalen-8-yl)-benzyl]-piperidine-4-carboxylic acid
  (2-methoxy-1-methyl-ethyl)-amide;
1-[4-(2-Methyl-7-phenyl-1,4,9,9b-tetraaza-cyclopenta[a]
  naphthalen-8-yl)-benzyl]-piperidine-4-carboxylic acid
  carbamoylmethyl-amide;
1-[4-(2-Methyl-7-phenyl-1,4,9,9b-tetraaza-cyclopenta[a]
  naphthalen-8-yl)-benzyl]-piperidine-4-carboxylic acid
  (2,2,2-trifluoro-ethyl)-amide;
1-[4-(2-Methyl-7-phenyl-1,4,9,9b-tetraaza-cyclopenta[a]
  naphthalen-8-yl)-benzyl]-piperidine-4-carboxylic acid
  (1-ethyl-propyl)-amide;
1-[4-(2-Methyl-7-phenyl-1,4,9,9b-tetraaza-cyclopenta[a]
  naphthalen-8-yl)-benzyl]-piperidine-4-carboxylic acid
  tert-butylamide;
1-[4-(2-Methyl-7-phenyl-1,4,9,9b-tetraaza-cyclopenta[a]
  naphthalen-8-yl)-benzyl]-piperidine-4-carboxylic acid
  propylamide;
1-[4-(2-Methyl-7-phenyl-1,4,9,9b-tetraaza-cyclopenta[a]
  naphthalen-8-yl)-benzyl]-piperidine-4-carboxylic acid
  methylamide;
1-[4-(2-Methyl-7-phenyl-1,4,9,9b-tetraaza-cyclopenta[a]
  naphthalen-8-yl)-benzyl]-piperidine-4-carboxylic acid
  ethylamide;
[4-(3-Hydroxy-phenyl)-piperazin-1-yl]-{1-[4-(2-methyl-
  7-phenyl-1,4,9,9b-tetraaza-cyclopenta[a]naphthalen-8-
  yl)-benzyl]-piperidin-4-yl}-methanone;
1-[4-(2-Methyl-7-phenyl-1,4,9,9b-tetraaza-cyclopenta[a]
  naphthalen-8-yl)-benzyl]-piperidine-4-carboxylic acid
  ((S)-1-cyclohexyl-ethyl)-amide;
(Hexahydro-cyclopenta[c]pyrrol-2-yl)-{1-[4-(2-methyl-
  7-phenyl-1,4,9,9b-tetraaza-cyclopenta[a]naphthalen-8-
  yl)-benzyl]-piperidin-4-yl}-methanone;
1-[4-(2-Methyl-7-phenyl-1,4,9,9b-tetraaza-cyclopenta[a]
  naphthalen-8-yl)-benzyl]-piperidine-4-carboxylic acid
  ethyl-isopropyl-amide;
1-[4-(2-Methyl-7-phenyl-1,4,9,9b-tetraaza-cyclopenta[a]
  naphthalen-8-yl)-benzyl]-piperidine-4-carboxylic acid
  ((1S,2S)-2-hydroxy-cyclohexyl)-amide;
1-[4-(2-Methyl-7-phenyl-1,4,9,9b-tetraaza-cyclopenta[a]
  naphthalen-8-yl)-benzyl]-piperidine-4-carboxylic acid
  (2-hydroxy-ethyl)-amide;
1-[4-(2-Methyl-7-phenyl-1,4,9,9b-tetraaza-cyclopenta[a]
  naphthalen-8-yl)-benzyl]-piperidine-4-carboxylic acid
  (tetrahydro-furan-2-ylmethyl)-amide;
1-[4-(2-Methyl-7-phenyl-1,4,9,9b-tetraaza-cyclopenta[a]
  naphthalen-8-yl)-benzyl]-piperidine-4-carboxylic acid
  cyclobutylamide;
1-[4-(2-Methyl-7-phenyl-1,4,9,9b-tetraaza-cyclopenta[a]
  naphthalen-8-yl)-benzyl]-piperidine-4-carboxylic acid
  isopropylamide;
({1-[4-(2-Methyl-7-phenyl-1,4,9,9b-tetraaza-cyclopenta
  [a]naphthalen-8-yl)-benzyl]-piperidine-4-carbonyl}-
  amino)-acetic acid;
1-[4-(2-Methyl-7-phenyl-1,4,9,9b-tetraaza-cyclopenta[a]
  naphthalen-8-yl)-benzyl]-piperidine-4-carboxylic acid
  (4-hydroxy-phenyl)-amide;
1-[4-(2-Methyl-7-phenyl-1,4,9,9b-tetraaza-cyclopenta[a]
  naphthalen-8-yl)-benzyl]-piperidine-4-carboxylic acid
  (3-carbamoyl-phenyl)-amide;
1-[4-(2-Methyl-7-phenyl-1,4,9,9b-tetraaza-cyclopenta[a]
  naphthalen-8-yl)-benzyl]-piperidine-4-carboxylic acid
  (3-methoxy-phenyl)-amide;
1-[4-(2-Methyl-7-phenyl-1,4,9,9b-tetraaza-cyclopenta[a]
  naphthalen-8-yl)-benzyl]-piperidine-4-carboxylic acid
  (3-methanesulfonylamino-phenyl)-amide;
1-[4-(2-Methyl-7-phenyl-1,4,9,9b-tetraaza-cyclopenta[a]
  naphthalen-8-yl)-benzyl]-piperidine-4-carboxylic acid
  (3-cyano-phenyl)-amide;
1-[4-(2-Methyl-7-phenyl-1,4,9,9b-tetraaza-cyclopenta[a]
  naphthalen-8-yl)-benzyl]-piperidine-4-carboxylic acid
  (3-fluoro-phenyl)-amide;
1-[4-(2-Methyl-7-phenyl-1,4,9,9b-tetraaza-cyclopenta[a]
  naphthalen-8-yl)-benzyl]-piperidine-4-carboxylic acid
  (2-hydroxy-phenyl)-amide;
1-[4-(2-Methyl-7-phenyl-1,4,9,9b-tetraaza-cyclopenta[a]
  naphthalen-8-yl)-benzyl]-piperidine-4-carboxylic acid
  (4-carbamoyl-phenyl)-amide;
1-[4-(2-Methyl-7-phenyl-1,4,9,9b-tetraaza-cyclopenta[a]
  naphthalen-8-yl)-benzyl]-piperidine-4-carboxylic acid
  (3-sulfamoyl-phenyl)-amide;
1-[4-(2-Methyl-7-phenyl-1,4,9,9b-tetraaza-cyclopenta[a]
  naphthalen-8-yl)-benzyl]-piperidine-4-carboxylic acid
  benzothiazol-5-ylamide;
1-[4-(2-Methyl-7-phenyl-1,4,9,9b-tetraaza-cyclopenta[a]
  naphthalen-8-yl)-benzyl]-piperidine-4-carboxylic acid
  (3-trifluoromethoxy-phenyl)-amide;
1-[4-(2-Methyl-7-phenyl-1,4,9,9b-tetraaza-cyclopenta[a]
  naphthalen-8-yl)-benzyl]-piperidine-4-carboxylic acid
  thiazol-2-ylamide;
1-[4-(2-Methyl-7-phenyl-1,4,9,9b-tetraaza-cyclopenta[a]
  naphthalen-8-yl)-benzyl]-piperidine-4-carboxylic acid
  (3-oxo-1,3-dihydro-isobenzofuran-5-yl)-amide;
1-[4-(2-Methyl-7-phenyl-1,4,9,9b-tetraaza-cyclopenta[a]
  naphthalen-8-yl)-benzyl]-piperidine-4-carboxylic acid
  (3-methanesulfonyl-phenyl)-amide;
1-[4-(2-Methyl-7-phenyl-1,4,9,9b-tetraaza-cyclopenta[a]
  naphthalen-8-yl)-benzyl]-piperidine-4-carboxylic acid
  (3-hydroxymethyl-phenyl)-amide;
1-[4-(2-Methyl-7-phenyl-1,4,9,9b-tetraaza-cyclopenta[a]
  naphthalen-8-yl)-benzyl]-piperidine-4-carboxylic acid
  3-amino-benzyl ester;
1-[4-(2-Methyl-7-phenyl-1,4,9,9b-tetraaza-cyclopenta[a]
  naphthalen-8-yl)-benzyl]-piperidine-4-carboxylic acid
  (3-amino-phenyl)-amide;
1-[4-(2-Methyl-7-phenyl-1,4,9,9b-tetraaza-cyclopenta[a]
  naphthalen-8-yl)-benzyl]-piperidine-4-carboxylic acid
  (1,1-dioxo-1H-1-benzo[b]thiophen-6-yl)amide;
3-Amino-1-methyl-3-[4-(2-methyl-7-phenyl-1,4,6,9,9b-
  pentaaza-cyclopenta[a]naphthalen-8-yl)-phenyl]-cy-
  clobutanol;
trans-3-Amino-1-methyl-3-[4-(2-t-butyl-7-phenyl-1,4,9,
  9b-tetraaza-cyclopenta[a]naphthalen-8-yl)-phenyl]-cy-
  clobutanol;
3-Amino-1-cyclopropyl-3-[4-(2,3-dimethyl-7-phenyl-1,
  4,6,9,9b-pentaaza-cyclopenta[a]naphthalen-8-yl)-phe-
  nyl]-cyclobutanol;
trans-3-Amino-1-Methyl-3-[4-(2-cyclopropyl-7-phenyl-
  1,4,9,9b-tetraaza-cyclopenta[a]naphthalen-8-yl)-phe-
  nyl]-cyclobutanol;
3-Amino-3-[4-(6-chloro-2-methyl-7-phenyl-1,4,9,9b-tet-
  raaza-cyclopenta[a]naphthalen-8-yl)-phenyl]-1-me-
  thyl-cyclobutanol;
3-Amino-3-[4-(2,6-dimethyl-7-phenyl-1,4,9,9b-tetraaza-
  cyclopenta[a]naphthalen-8-yl)-phenyl]-1-methyl-cy-
  clobutanol;
trans-3-Amino-1-methyl-3-[4-(2-(4-methoxyphenyl)-7-
  phenyl-1,4,9,9b-tetraaza-cyclopenta[a]naphthalen-8-
  yl)-phenyl]-cyclobutanol;
trans-3-Amino-1-methyl-3-[4-(2-isopropyl-7-phenyl-1,4,
  9,9b-tetraaza-cyclopenta[a]naphthalen-8-yl)-phenyl]-
  cyclobutanol;

trans-3-Amino-1-methyl-3-[4-(2-cyclobutyl-7-phenyl-1,4,9,9b-tetraaza-cyclopenta[a]naphthalen-8-yl)-phenyl]-cyclobutanol;

3-Amino-1-methyl-3-[4-(7-phenyl-1,4,9,9b-tetraaza-cyclopenta[a]naphthalen-8-yl)-phenyl]-cyclobutanol;

trans-3-Amino-1-methyl-3-[4-(2-(pyridine-4-yl)-7-phenyl-1,4,9,9b-tetraaza-cyclopenta[a]naphthalen-8-yl)-phenyl]-cyclobutanol;

trans-3-Amino-1-methyl-3-[4-(2-(thiophen-3-yl)-7-phenyl-1,4,9,9b-tetraaza-cyclopenta[a]naphthalen-8-yl)-phenyl]-cyclobutanol;

2-Methyl-7-phenyl-8-{4-[4-(5-pyridin-2-yl-4H-[1,2,4]triazol-3-yl)-piperidin-1-ylmethyl]-phenyl}-1,4,9,9b-tetraazacyclopenta[a]naphthalene;

2-Methyl-8-(4-{4-[5-(4-methylpyridin-3-yl)-4H-[1,2,4]triazol-3-yl]-piperidin-1-ylmethyl}-phenyl)-7-phenyl-1,4,9,9b-tetraazacyclopenta[a]naphthalene;

2-Methyl-7-phenyl-8-(4-{4-[5-(2-trifluoromethyl-phenyl)-4H-[1,2,4]triazol-3-yl]-piperidin-1-ylmethyl}-phenyl)-1,4,9,9b-tetraaza-cyclopenta[a]naphthalene;

4-(5-{1-[4-(2-Methyl-7-phenyl-1,4,9,9b-tetraaza-cyclopenta[a]naphthalen-8-yl)-benzyl]-piperidin-4-yl}-4H-[1,2,4]triazol-3-yl)-benzamide;

2-Methyl-7-phenyl-8-(4-{4-[5-(3-trifluoromethyl-phenyl)-4H-[1,2,4]triazol-3-yl]-piperidin-1-ylmethyl}-phenyl)-1,4,9,9b-tetraaza-cyclopenta[a]naphthalene;

2-Methyl-7-phenyl-8-{4-[4-(5-pyridin-3-yl-4H-[1,2,4]triazol-3-yl)-piperidin-1-ylmethyl]-phenyl}-1,4,9,9b-tetraaza-cyclopenta[a]naphthalene;

2-Methyl-7-phenyl-8-(4-{4-[5-(4-trifluoromethyl-phenyl)-4H-[1,2,4]triazol-3-yl]-piperidin-1-ylmethyl}-phenyl)-1,4,9,9b-tetraaza-cyclopenta[a]naphthalene;

2-Methyl-8-{4-[4-(5-phenoxymethyl-4H-[1,2,4]triazol-3-yl)-piperidin-1-ylmethyl]-phenyl}-7-phenyl-1,4,9,9b-tetraaza-cyclopenta[a]naphthalene;

2-Methyl-8-(4-{4-[5-(3-methyl-pyridin-2-yl)-4H-[1,2,4]triazol-3-yl]-piperidin-1-ylmethyl}-phenyl)-7-phenyl-1,4,9,9b-tetraaza-cyclopenta[a]naphthalene;

8-(4-{4-[5-(3-Methoxy-phenyl)-4H-[1,2,4]triazol-3-yl]-piperidin-1-ylmethyl}-phenyl)-2-methyl-7-phenyl-1,4,9,9b-tetraaza-cyclopenta[a]naphthalene;

8-(4-{4-[5-(4-Methoxy-phenyl)-4H-[1,2,4]triazol-3-yl]-piperidin-1-ylmethyl}-phenyl)-2-methyl-7-phenyl-1,4,9,9b-tetraaza-cyclopenta[a]naphthalene;

2-Methyl-7-phenyl-8-{4-[4-(6,7,8,9-tetrahydro-5H-[1,2,4]triazolo[4,3-a]azepin-3-yl)-piperidin-1-ylmethyl]-phenyl}-1,4,9,9b-tetraaza-cyclopenta[a]naphthalene;

2-Methyl-7-phenyl-8-{4-[4-(5-pyridin-2-yl-4H-[1,2,4]triazol-3-yl)-piperidin-1-ylmethyl]-phenyl}-1,4,9,9b-tetraaza-cyclopenta[a]naphthalene;

2-Methyl-7-phenyl-8-{4-[4-(5-pyridin-4-yl-4H-[1,2,4]triazol-3-yl)-piperidin-1-ylmethyl]-phenyl}-1,4,9,9b-tetraaza-cyclopenta[a]naphthalene;

2-Methyl-8-(4-{4-[5-(4-methyl-pyridin-2-yl)-4H-[1,2,4]triazol-3-yl]-piperidin-1-ylmethyl}-phenyl)-7-phenyl-1,4,9,9b-tetraaza-cyclopenta[a]naphthalene;

2-Methyl-7-phenyl-8-{4-[4-(5-pyrimidin-2-yl-4H-[1,2,4]triazol-3-yl)-piperidin-1-ylmethyl]-phenyl}-1,4,9,9b-tetraaza-cyclopenta[a]naphthalene;

2-Methyl-7-phenyl-8-(4-{4-[5-(6-trifluoromethyl-pyridin-3-yl)-4H-[1,2,4]triazol-3-yl]-piperidin-1-ylmethyl}-phenyl)-1,4,9,9b-tetraaza-cyclopenta[a]naphthalene;

2-Methyl-8-(4-{4-[5-(6-methyl-pyridin-2-yl)-4H-[1,2,4]triazol-3-yl]-piperidin-1-ylmethyl}-phenyl)-7-phenyl-1,4,9,9b-tetraaza-cyclopenta[a]naphthalene;

1-{1-[4-(2-Methyl-7-phenyl-1,4,9,9b-tetraaza-cyclopenta[a]naphthalen-8-yl)-benzyl]-piperidin-4-yl}-1,3-dihydro-benzoimidazol-2-one;

2-Methyl-8-{4-[4-(4-methyl-4H-[1,2,4]triazol-3-yl)-piperidin-1-ylmethyl]-phenyl}-7-phenyl-1,4,9,9b-tetraaza-cyclopenta[a]naphthalene;

8-[4-(2-Methyl-7-phenyl-1,4,9,9b-tetraaza-cyclopenta[a]naphthalen-8-yl)-benzyl]-1,3,8-triaza-spiro[4.5]decane-2,4-dione;

8-(4-{4-[5-(4-Chloro-phenyl)-1H-pyrazol-3-yl]-piperidin-1-ylmethyl}-phenyl)-2-methyl-7-phenyl-1,4,9,9b-tetraaza-cyclopenta[a]naphthalene;

{1-[4-(2-Methyl-7-phenyl-1,4,9,9b-tetraaza-cyclopenta[a]naphthalen-8-yl)-benzyl]-piperidin-4-yl}-carbamic acid tert-butyl ester;

1-[4-(2-Methyl-7-phenyl-1,4,9,9b-tetraaza-cyclopenta[a]naphthalen-8-yl)-benzyl]-piperidin-4-ylamine;

N-{1-[4-(2-Methyl-7-phenyl-1,4,9,9b-tetraaza-cyclopenta[a]naphthalen-8-yl)-benzyl]-piperidin-4-yl}-isonicotinamide;

N-{1-[4-(2-Methyl-7-phenyl-1,4,9,9b-tetraaza-cyclopenta[a]naphthalen-8-yl)-benzyl]-piperidin-4-yl}-phthalamic acid;

1-{1-[4-(2-Methyl-7-phenyl-1,4,9,9b-tetraaza-cyclopenta[a]naphthalen-8-yl)-benzyl]-piperidin-4-yl}-3-pyridin-4-yl-urea;

1-{1-[4-(2-Methyl-7-phenyl-1,4,9,9b-tetraaza-cyclopenta[a]naphthalen-8-yl)-benzyl]-piperidin-4-yl}-N-morpholinyl-urea;

1-[4-(2-Methyl-7-phenyl-1,4,9,9b-tetraaza-cyclopenta[a]naphthalen-8-yl)-benzyl]-piperidine-4-carboxylic acid pyridin-4-ylamide;

1-[4-(2-Methyl-7-phenyl-1,4,9,9b-tetraaza-cyclopenta[a]naphthalen-8-yl)-benzyl]-piperidine-4-carboxylic acid (2-methoxy-phenyl)-amide;

1-[4-(2-Methyl-7-phenyl-1,4,9,9b-tetraaza-cyclopenta[a]naphthalen-8-yl)-benzyl]-piperidine-4-carboxylic acid (4-carbamoyl-2-methoxy-phenyl)-amide;

1-[4-(2-Methyl-7-phenyl-1,4,9,9b-tetraaza-cyclopenta[a]naphthalen-8-yl)-benzyl]-piperidine-4-carboxylic acid hydrazide trans-3-Amino-3-[4-(2-tert-butyl-7-(thiophen-2-yl)-1,4,9,9b-tetraaza-cyclopenta[a]naphthalen-8-yl)-phenyl]-1-methyl-cyclobutanol;

trans-3-Amino-3-{4-[2-tert-butyl-7-(2-fluoro-phenyl)-1,4,9,9b-tetraaza-cyclopenta[a]naphthalen-8-yl]-phenyl}-1-methyl-cyclobutanol;

trans-3-Amino-3-[4-(2-tert-butyl-7-(thiophen-3-yl)-1,4,9,9b-tetraaza-cyclopenta[a]naphthalen-8-yl)-phenyl]-1-methyl-cyclobutanol;

trans-3-Amino-1-cyclopropyl-3-[4-(7-phenyl-4,5-dihydro-1,4,6,9,9b-pentaaza-cyclopenta[a]naphthalen-8-yl)-phenyl]-cyclobutanol;

trans-3-Amino-1-cyclopropyl-3-[4-(7-phenyl-1,4,6,9,9b-pentaaza-cyclopenta[a]naphthalen-8-yl)-phenyl]-cyclobutanol;

trans-3-Amino-1-methyl-3-[4-(7-phenyl-1,4,6,9,9b-pentaaza-cyclopenta[a]naphthalen-8-yl)-phenyl]-cyclobutanol;

trans-3-Amino-1-methyl-3-[4-(5-methyl-7-phenyl-1,4,9,9b-tetraaza-cyclopenta[a]naphthalen-8-yl)-phenyl]-cyclobutanol;

trans-3-Amino-1-methyl-3-[4-(7-thiophen-2-yl-1,4,9,9b-tetraaza-cyclopenta[a]naphthalen-8-yl)-phenyl]-cyclobutanol;

trans-3-Amino-1-cyclopropyl-3-[4-(2-methyl-3,7-diphenyl-1,4,9,9b-tetraaza-cyclopenta[a]naphthalen-8-yl)-phenyl]-cyclobutanol;

trans-3-Amino-1-cyclopropyl-3-{4-[3-(4-methoxy-phenyl)-2-methyl-7-phenyl-1,4,9,9b-tetraaza-cyclopenta[a]naphthalen-8-yl]-phenyl}-cyclobutanol;
trans-3-Amino-1-cyclopropyl-3-[4-(2-methyl-7-phenyl-3-pyridin-4-yl-1,4,9,9b-tetraaza-cyclopenta[a]naphthalen-8-yl)-phenyl]-cyclobutanol;
trans-3-Amino-1-ethyl-3-[4-(2-methyl-7-phenyl-1,4,9,9b-tetraaza-cyclopenta[a]naphthalen-8-yl)-phenyl]-cyclobutanol;
trans-3-Amino-1-cyclopropyl-3-[4-(3-bromo-2-methyl-7-phenyl-1,4,6,9,9b-pentaaza-cyclopenta[a]naphthalen-8-yl)-phenyl]-cyclobutanol;
trans-3-Amino-1-cyclopropyl-3-[4-(2,3-dimethyl-7-phenyl-1,4,6,9,9b-pentaaza-cyclopenta[a]naphthalen-8-yl)-phenyl]-cyclobutanol;
trans-3-Amino-1-methyl-3-[4-(2-methyl-6,7-diphenyl-1,4,9,9b-tetraaza-cyclopenta[a]naphthalen-8-yl)-phenyl]-cyclobutanol;
trans-8-[4-(1-Amino-3-hydroxy-3-methyl-cyclobutyl)-phenyl]-2-methyl-7-phenyl-1,4,9,9b-tetraaza-cyclopenta[a]naphthalen-6-ol;
trans-3-Amino-3-[4-(6-cyclopropyl-2-methyl-7-phenyl-1,4,9,9b-tetraaza-cyclopenta[a]naphthalen-8-yl)-phenyl]-1-methyl-cyclobutanol;
trans-3-Amino-3-[4-(2-isopropyl-7-thiophen-3-yl-1,4,9,9b-tetraaza-cyclopenta[a]naphthalen-8-yl)-phenyl]-1-methyl-cyclobutanol;
trans-3-Amino-3-[4(2-isopropyl-7-thiophen-2-yl-1,4,9,9b-tetraaza-cyclopenta[a]naphthalen-8-yl)-phenyl]-1-methyl-cyclobutanol;
trans-3-Amino-3-{4-[7-(2-fluoro-phenyl)-2-isopropyl-1,4,9,9b-tetraaza-cyclopenta[a]naphthalen-8-yl]-phenyl}-1-methyl-cyclobutanol;
trans-3-Amino-3-[4-(2-cyclopropyl-7-phenyl-1,4,9,9b-tetraaza-cyclopenta[a]naphthalen-8-yl)-phenyl]-1-isopropyl-cyclobutanol;
trans-3-Amino-1-isopropyl-3-[4-(2-methyl-7-phenyl-1,4,9,9b-tetraaza-cyclopenta[a]naphthalen-8-yl)-phenyl]-cyclobutanol;
cis-3-Amino-3-[4-(2-cyclopropyl-7-phenyl-1,4,9,9b-tetraaza-cyclopenta[a]naphthalen-8-yl)-phenyl]-1-isopropyl-cyclobutanol;
trans-2-{1-[4-(2-cyclopropyl-5-methyl-7-phenyl-1,4,9,9b-tetraaza-cyclopenta[a]naphthalen-8-yl)-phenyl]-3-hydroxy-3-methyl-cyclobutyl}-isoindole-1,3-dione;
trans-3-Amino-3-[4-(2-isopropyl-5-methyl-7-phenyl-1,4,9,9b-tetraaza-cyclopenta[a]naphthalen-8-yl)-phenyl]-1-methyl-cyclobutanol;
trans-3-Amino-3-{4-[7-(3-fluoro-phenyl)-2-methyl-1,4,9,9b-tetraaza-cyclopenta[a]naphthalen-8-yl]-phenyl}-1-methyl-cyclobutanol;
trans-3-Amino-3-{4-[7-(4-fluoro-phenyl)-2-methyl-1,4,9,9b-tetraaza-cyclopenta[a]naphthalen-8-yl]-phenyl}-1-methyl-cyclobutanol;
trans-3-Amino-3-{4-[7-(4-chloro-phenyl)-2-methyl-1,4,9,9b-tetraaza-cyclopenta[a]naphthalen-8-yl]-phenyl}-1-methyl-cyclobutanol;
trans-3-Amino-3-{4-[7-(3-chloro-phenyl)-2-methyl-1,4,9,9b-tetraaza-cyclopenta[a]naphthalen-8-yl]-phenyl}-1-methyl-cyclobutanol;
trans-3-Amino-1-methyl-3-[4-(2-methyl-7-o-tolyl-1,4,9,9b-tetraaza-cyclopenta[a]naphthalen-8-yl)-phenyl]-cyclobutanol;
trans-3-Amino-3-{4-[7-(2-methoxy-phenyl)-2-methyl-1,4,9,9b-tetraaza-cyclopenta[a]naphthalen-8-yl]-phenyl}-1-methyl-cyclobutanol;
trans-3-Amino-3-{4-[7-(3-methoxy-phenyl)-2-methyl-1,4,9,9b-tetraaza-cyclopenta[a]naphthalen-8-yl]-phenyl}-1-methyl-cyclobutanol;
trans-3-Amino-3-{4-[7-(2-chloro-phenyl)-2-methyl-1,4,9,9b-tetraaza-cyclopenta[a]naphthalen-8-yl]-phenyl}-1-methyl-cyclobutanol;
trans-3-Amino-1-methyl-3-[4-(2-methyl-7-m-tolyl-1,4,9,9b-tetraaza-cyclopenta[a]naphthalen-8-yl)-phenyl]-cyclobutanol;
trans-3-Amino-3-{4-[7-(4-methoxy-phenyl)-2-methyl-1,4,9,9b-tetraaza-cyclopenta[a]naphthalen-8-yl]-phenyl}-1-methyl-cyclobutanol;
trans-3-Amino-1-methyl-3-{4-[2-methyl-7-(2-trifluoromethyl-phenyl)-1,4,9,9b-tetraaza-cyclopenta[a]naphthalen-8-yl]-phenyl}-cyclobutanol;
trans-3-Amino-1-methyl-3-[4-(2-methyl-7-pyridin-3-yl-1,4,9,9b-tetraaza-cyclopenta[a]naphthalen-8-yl)-phenyl]-cyclobutanol;
trans-3-{8-[4-(1-Amino-3-hydroxy-3-methyl-cyclobutyl)-phenyl]-2-methyl-1,4,9,9b-tetraaza-cyclopenta[a]naphthalen-7-yl}-benzonitrile;
trans-2-{8-[4-(1-Amino-3-hydroxy-3-methyl-cyclobutyl)-phenyl]-2-methyl-1,4,9,9b-tetraaza-cyclopenta[a]naphthalen-7-yl}-benzonitrile;
trans-4-{8-[4-(1-Amino-3-hydroxy-3-methyl-cyclobutyl)-phenyl]-2-methyl-1,4,9,9b-tetraaza-cyclopenta[a]naphthalen-7-yl}-benzonitrile;
4-{8-[4-(1-amino-3-hydroxy-3-methyl-cyclobutyl)-phenyl]-2-methyl-1,4,9,9b-tetraaza-cyclopenta[a]naphthalen-7-yl}-phenyl ester;
trans-4-{8-[4-(1-Amino-3-hydroxy-3-methyl-cyclobutyl)-phenyl]-2-methyl-1,4,9,9b-tetraaza-cyclopenta[a]naphthalen-7-yl}-phenol;
trans-3-{8-[4-(1-Amino-3-hydroxy-3-methyl-cyclobutyl)-phenyl]-2-methyl-1,4,9,9b-tetraaza-cyclopenta[a]naphthalen-7-yl}-phenol;
3-{8-[4-(1-amino-3-hydroxy-3-methyl-cyclobutyl)-phenyl]-2-methyl-1,4,9,9b-tetraaza-cyclopenta[a]naphthalen-7-yl}-phenyl ester;
2-{8-[4-(1-amino-3-hydroxy-3-methyl-cyclobutyl)-phenyl]-2-methyl-1,4,9,9b-tetraaza-cyclopenta[a]naphthalen-7-yl}-phenyl ester;
trans-3-Amino-1-methyl-3-[4-(2-methyl-7-pyridin-4-yl-1,4,9,9b-tetraaza-cyclopenta[a]naphthalen-8-yl)-phenyl]-cyclobutanol;
trans-3-Amino-1-methyl-3-[4-(2-methyl-7-phenyl-6-pyridin-3-yl-1,4,9,9b-tetraaza-cyclopenta[a]naphthalen-8-yl)-phenyl]-cyclobutanol;
trans-3-Amino-1-methyl-3-[4-(2-methyl-7-phenyl-6-pyridin-4-yl-1,4,9,9b-tetraaza-cyclopenta[a]naphthalen-8-yl)-phenyl]-cyclobutanol;
trans-3-Amino-1-methyl-3-[4-(2-methyl-7-phenyl-6-pyrimidin-5-yl-1,4,9,9b-tetraaza-cyclopenta[a]naphthalen-8-yl)-phenyl]-cyclobutanol;
trans-3-Amino-1-methyl-3-{4-[2-methyl-7-phenyl-6-(1H-pyrazol-3-yl)-1,4,9,9b-tetraaza-cyclopenta[a]naphthalen-8-yl]-phenyl}-cyclobutanol;
trans-8-[4-(1-Amino-3-hydroxy-3-methyl-cyclobutyl)-phenyl]-2-methyl-7-phenyl-1,4,9,9b-tetraaza-cyclopenta[a]naphthalene-6-carbonitrile;
trans-3-Amino-3-[4-(6-methoxy-2-methyl-7-phenyl-1,4,9,9b-tetraaza-cyclopenta[a]naphthalen-8-yl)-phenyl]-1-methyl-cyclobutanol;
trans-3-Amino-3-[4-(6-amino-2-methyl-7-phenyl-1,4,9,9b-tetraaza-cyclopenta[a]naphthalen-8-yl)-phenyl]-1-methyl-cyclobutanol;

trans-3-Amino-3-[4-(3-bromo-7-phenyl-1,4,9,9b-tetraaza-cyclopenta[a]naphthalen-8-yl)-phenyl]-1-methyl-cyclobutanol;

trans-8-[4-(1-Amino-3-hydroxy-3-methyl-cyclobutyl)-phenyl]-2-methyl-7-phenyl-1,4,9,9b-tetraaza-cyclopenta[a]naphthalene-3-carbonitrile;

trans-8-[4-(1-Amino-3-hydroxy-3-methyl-cyclobutyl)-phenyl]-7-phenyl-1,4,9,9b-tetraaza-cyclopenta[a]naphthalene-3-carbonitrile;

trans-3-Amino-1-methyl-3-[4-(3-methyl-7-phenyl-1,4,9,9b-tetraaza-cyclopenta[a]naphthalen-8-yl)-phenyl]-cyclobutanol;

trans-3-Amino-3-[4(2-isopropenyl-7-phenyl-1,4,6,9,9b-pentaaza-cyclopenta[a]naphthalen-8-yl)-phenyl]-1-methyl-cyclobutanol;

trans-3-Amino-3-[4-(2-cyclopropyl-7-thiophen-2-yl-1,4,9,9b-tetraaza-cyclopenta[a]naphthalen-8-yl)-phenyl]-1-methyl-cyclobutanol;

trans-3-Amino-3-[4(2-isopropenyl-7-thiophen-2-yl-1,4,6,9,9b-pentaaza-cyclopenta[a]naphthalen-8-yl)-phenyl]-1-methyl-cyclobutanol;

3-Amino-1-methyl-3-[4-(2,5,6-trimethyl-7-phenyl-1,4,9,9b-tetraaza-cyclopenta[a]naphthalen-8-yl)-phenyl]-cyclobutanol; and 1-[4-(2-Methyl-7-phenyl-1,4,9,9b-tetraaza-cyclopenta[a]naphthalen-8-yl)-benzyl]-piperidine-4-carboxylic acid methyl ester;

or a pharmaceutically acceptable salt, stereoisomer or N-oxide derivative thereof.

5. A pharmaceutical composition comprising a pharmaceutical carrier, and dispersed therein, a therapeutically effective amount of the compound according to claim 1 or a pharmaceutically acceptable salt, stereoisomer or N-oxide derivative thereof.

* * * * *